United States Patent
Yamazaki et al.

(10) Patent No.: US 11,542,273 B2
(45) Date of Patent: Jan. 3, 2023

(54) AMIDE COMPOUND HAVING BET PROTEOLYSIS-INDUCING ACTION AND MEDICINAL APPLICATION THEREOF

(71) Applicant: MITSUBISHI TANABE PHARMA CORPORATION, Osaka (JP)

(72) Inventors: Ryuta Yamazaki, Tokyo (JP); Tatsuya Ibuki, Tokyo (JP); Yuichi Sawaguchi, Tokyo (JP); Kiyomi Ohba, Osaka (JP); Maiko Hamada, Osaka (JP); Yasuki Niwa, Osaka (JP); Yuko Ishida, Osaka (JP); Hideto Maruyama, Osaka (JP); Shiki Matsuki, Osaka (JP); Minoru Tanaka, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 17/256,633

(22) PCT Filed: Jul. 4, 2019

(86) PCT No.: PCT/JP2019/026553
§ 371 (c)(1),
(2) Date: Dec. 28, 2020

(87) PCT Pub. No.: WO2020/009176
PCT Pub. Date: Jan. 9, 2020

(65) Prior Publication Data
US 2021/0284654 A1 Sep. 16, 2021

(30) Foreign Application Priority Data
Jul. 4, 2018 (JP) .............................. JP2018-127896

(51) Int. Cl.
*C07D 495/14* (2006.01)
*A61P 35/02* (2006.01)

(52) U.S. Cl.
CPC ............ *C07D 495/14* (2013.01); *A61P 35/02* (2018.01)

(58) Field of Classification Search
CPC .............................. C07D 495/14; A61P 35/02
See application file for complete search history.

(56) References Cited

U.S. PATENT DOCUMENTS

| | | |
|---|---|---|
| 2016/0272639 A1 | 9/2016 | Crew et al. |
| 2017/0065719 A1 | 3/2017 | Qian et al. |
| 2018/0050021 A1 | 2/2018 | Ciulli et al. |

FOREIGN PATENT DOCUMENTS

WO  WO 2018/052949 A1  3/2018

OTHER PUBLICATIONS

Science (1999), vol. 286, 531-537.*
Cancer and Metastasis Reviews (1998), 17(1), 91-106.*
Crawford et al., "Bromodomain 4 activation predicts breast cancer survival," *Proc. Natl. Acad. Sci. U.S.A.*, 105(17): 6380-6385 (2008).
Dai et al., "Prostate cancer-associated SPOP mutations confer resistance to BET inhibitors through stabilization of BRD4," *Nat. Med.*, 23(9): 1063-1071 (2017).
Herrmann et al., "Small-molecule inhibition of BRD4 as a new potent approach to eliminate leukemic stem- and progenitor cells in acute myeloid leukemia (AML)," *Oncotarget*, 3(12): 1588-1599 (2012).
Hu et al., "BRD4 Inhibitor Inhibits Colorectal Cancer Growth and Metastasis," *Int. J. Mol. Sci.*, 16(1): 1928-1948 (2015).
Kanno et al., "BRD4 assists elongation of both coding and enhancer RNAs by interacting with acetylated histones," *Nat. Struct. Mol. Biol.*, 21(12): 1047-1057 (2014).
Liao et al., "High level of BRD4 promotes non-small cell lung cancer progression," *Oncotarget*, 7(8): 9491-9500 (2016).
Liu et al., "Drug Discovery Targeting Bromodomain-Containing Protein 4," *J. Med. Chem.*, 60(11): 4533-4558 (2017).
Lu et al., "Hijacking the E3 Ubiquitin Ligase Cereblon to Efficiently Target BRD4," *Chem. Biol.*, 22(6): 755-763 (2015).
Raina et al., "PROTAC-induced BET protein degradation as a therapy for castration-resistant prostate cancer," *Proc. Natl. Acad. Sci. U.S.A.*, 113(26): 7124-7129 (2016).
Segura et al., "BRD4 Sustains Melanoma Proliferation and Represents a New Target for Epigenetic Therapy," *Cancer Res.*, 73(20): 6264-6276 (2013).
Shu et al., "Response and resistance to BET bromodomain inhibitors in triple-negative breast cancer," *Nature*, 529(7586): 413-417 (2016).

(Continued)

*Primary Examiner* — Rebecca L Anderson
(74) *Attorney, Agent, or Firm* — Leydig, Voit & Mayer, Ltd.

(57) ABSTRACT

Provided are a compound superior in a cytotoxic action on cancer cells, an action inducing degradation of BET protein in cancer cells, and an inhibitory action on the binding of BET protein and acetylated histone, and useful as an anticancer agent, a BET protein degradation inducer or a BET protein inhibitor. A compound represented by the following formula (I)

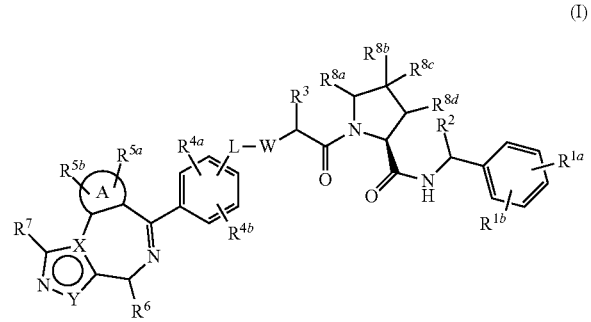

wherein each symbol is as defined in the specification, or a pharmacologically acceptable salt thereof.

25 Claims, 3 Drawing Sheets

(56) References Cited

OTHER PUBLICATIONS

Stathis et al., "Clinical Response of Carcinomas Harboring the BRD4-NUT Oncoprotein to the Targeted Bromodomain Inhibitor OTX015/MK-8628," *Cancer Discov.*, 6(5): 492-500 (2016).
Taniguchi, "The Bromodomain and Extra-Terminal Domain (BET) Family: Functional Anatomy of BET Paralogous Proteins," *Int. J. Mol. Sci.*, 17(11): 1849 (2016).
Toure et al., "Small-Molecule PROTACS: New Approaches to Protein Degradation," *Angew. Chem. Int. Ed. Engl.*, 55(6): 1966-1973 (2016).
Ucar et al., "Amplification of the bromodomain-containing protein 4 gene in ovarian high-grade serous carcinoma is associated with worse prognosis and survival," *Mol. Clin. Oncol.*, 3(6): 1291-1294 (2015).
Wurz et al., "A 'Click Chemistry Platform' for the Rapid Synthesis of Bispecific Molecules for Inducing Protein Degradation," *J. Med. Chem.*, 61(2): 453-461 (2017).
Yan et al., "Bromodomain 4 protein is a predictor of survival for urothelial carcinoma of bladder," *Int. J. Clin. Exp. Pathol.*, 7(7): 4231-4238 (2014).
Zengerle et al., "Selective Small Molecule Induced Degradation of the BET Bromodomain Protein BRD4," *ACS Chem. Biol.*, 10(8): 1770-1777 (2015).
Zhang et al., "BRD4 promotes tumor growth and epithelial-mesenchymal transition in hepatocellular carcinoma," *Int. J. Immunopathol. Pharmacol..*, 28(1): 36-44 (2015).
Zhu et al., "Bromodomain protein 4 is a novel predictor of survival for gastric carcinoma," *Oncotarget*, 8(19): 31092-31100 (2017).
Japanese Patent Office, International Search Report in International Patent Application No. PCT/JP2019/026553 (dated Oct. 1, 2019).

\* cited by examiner

AMIDE COMPOUND HAVING BET PROTEOLYSIS-INDUCING ACTION AND MEDICINAL APPLICATION THEREOF

CROSS-REFERENCE TO RELATED APPLICATIONS

This patent application is the U.S. national phase of International Patent Application No. PCT/JP2019/026553, filed on Jul. 4, 2019, which claims the benefit of Japanese Patent Application No. 2018-127896, filed on Jul. 4, 2018, which are incorporated by reference in their entireties herein.

TECHNICAL FIELD

The present invention relates to an amide compound or a pharmacologically acceptable salt thereof, which is superior in a cytotoxic action on cancer cells, an action inducing degradation of BET protein in cancer cells, and an inhibitory action on the binding of BET protein and acetylated histone, and useful as ah anticancer agent, a BET protein degradation inducer or a BET protein inhibitor.

BACKGROUND ART

Eukaryotic DNA forms a chromatin structure and is stored in the nucleus. Nucleosome which is a constituent unit thereof has a structure in which DNA is wound around histone octamer formed by 2 molecules each or 4 kinds of histones, H2A, H2E, H3, H4. Dozens of residues on the N-terminal side of histones is called a histone tale, and various post-translational modifications such as acetylation methylation, phosphorylation, ubiquitination are present therein. Post-translational modification, also called histone code, is one of the mechanisms responsible for controlling epigenetic expression, which determines when or where genetic information on DNA is expressed. Histone modification is and functionally controlled by a modifying enzyme (writer) that writes modification group histone, a de modifying enzyme (eraser) that removes modification group, and a histone reader (reader) that specifically read modified histone. It is known that such control mechanism greatly contributes to ontogenesis and cell differentiation, while epigenetics abnormalities are involved in various diseases.

The bromo domain is a reader protein consisting of about 110 amino acids that recognize acetylated lysine of histone. About 50 kinds of proteins possessing a bromo domain have been known to date, and they function as scaffold proteins for various transcription factors by binding to acetylated lysine of histone and also show various functions in the cell such as being responsible for chromatin reconstitution and transcriptional regulation through its own histone acetyltransferase activity and kinase activity and the like. BRD2, BRD3, BRD4 and BRDT contained in the BET (bromo domain and extraterminal) family protein of the bromo domain-containing protein (sometimes to be indicated as BET protein in the present specification and Claims) possess two highly conserved bromo domains on the N-terminal side and Extra C-Terminal domain on the C-terminal side within the family, and respective BET proteins are known to function both independently and cooperatively (non-patent document 1).

Among the BET family proteins, BRD4 is expected to be the target of drug discovery in cancer treatment because it regulates the expression of c-MYC which is a proto-oncogene (non-patent document 2) and has been reported to have a correlation with prognosis in various carcinomas such as gastric cancer (non-patent document 3), ovarian cancer (non-patent document 4), lung cancer (non-patent document 5), liver cancer (non-patent document 6), urothelial cancer (non-patent document 7), testicular cancer (non-patent document 8), skin cancer (non-patent document 9), prostate cancer (non-patent document 10), breast cancer (non-patent document 11), colorectal cancer (non-patent document 12) and leukemia (non-patent document 13).

To date, a BRD4 inhibitor that inhibits the binding of BRD4 to histone has been clinically developed as an anticancer agent targeting BRD4 (non-patent document 14). However, BRD4 inhibitors do not show a sufficient effect since they cause accumulation of BRD4 (non-patent document 15), and resistance is acquired by expression of proteins that stabilize BRD4 expression and proteins that enhance BRD4-mediated transcriptional activity in a bromo domain-independent manner (non-patent documents 16, 17). Thus, the development of an anticancer agent targeting BRD4 by a new means is required.

In recent years, a technology in which an artificial complex of E3 and a target protein is formed in the cell by using a compound in which a ligand for an E3 [Von Hippel-Lindau (VHL), Cereblon (CRBN), Cellular Inhibitor of Apoptosis Protein 1 (cIAP1)] having ubiquitin ligase activity and an inhibitor of the target protein are linked, and degradation of the target protein is induced by using the ubiquitin-proteasome system, which is an intracellular protein degradation mechanism (chemical knockdown) has been attracting attention as a new drug discovery technique (non-patent document 18). ARV-771, ARV-825 and the like have heretofore been reported as BRD4 protein degradation inducers utilizing this technique (non-patent documents 15, 19).

DOCUMENT LIST

Non-Patent Documents non-patent document 1: Taniguchi Y., Int J Mol Sci. 2016, 17: E1849
non-patent document 2: Kanno T., Nat Struct Mol Biol. 2014, 21: 1047-1057
non-patent document 3: Zhu Y., Oncotarget. 2017, 8: 31092-31100
non-patent document 4: Ucar D., Mol Clin Oncol. 2015, 3: 1291-1294
non-patent document 5: Liao Y F., Oncotarget. 2016, 7: 9491-9500
non-patent document 6: Zhang P., Int J Immunopathol Pharmacol. 2015, 28: 36-44
non-patent document 7: Yan Y., Int J Clin Exp Pathol. 2014, 7: 4231-4238
non-patent document 8: Stathis A., Cancer Discov. 2016, 6: 492-500
non-patent document 9: Segura M F., Cancer Res. 2013, 73: 6264-6276
non-patent document 10: Dai X., Nat Med. 2017, 23: 1063-1071
non-patent document 11: Crawford N P., Proc Natl Acad Sci USA. 2008, 105: 6380-6385
non-patent document 12: Hu Y., Int J Mol Sci. 2015, 16: 1928-1948
non-patent document 13: Herrmann H., Oncotarget. 2012, 3: 1588-1599
non-patent document 14: Liu Z., J Med Chem. 2017, 60: 4533-4558 non-patent document 15: Lu J., Chem Biol. 2015, 22: 755-763 non-patent document 16: Dai X., Nat Med. 2017, 23: 1063-1071 non-patent document 17: Shu S., Nature. 2016, 529: 413-417 non-patent document 18: Toure M., Angew Chem Int Ed Engl. 2016, 55: 1966-1973 non-patent document 19: Raina K., Proc Natl Acad Sci USA. 2016, 113: 7124-7129

SUMMARY OF THE INVENTION

Problems to be Solved by the Invention

The problem of the present invention is to provide a compound superior in a cytotoxic action on cancer cells, an action inducing degradation of BET protein in cancer cells, and an inhibitory action on the binding of BET protein and acetylated histone, and useful as an anticancer agent, a BET protein degradation inducer or a BET protein inhibitor.

Means of Solving the Problems

The present inventors have conducted intensive studies in an attempt to solve the aforementioned problem and found a compound having a cytotoxic action on cancer cells, an action inducing degradation of BET protein in cancer cells and an inhibitory action on the binding of BET protein and acetylated histone, and found that an anticancer agent, a BET protein degrader (degradation inducer) and a BET protein inhibitor can be provided, which resulted in the completion of the present invention. That is, the subject matter of the present invention is as follows.

[1] A compound represented by the following formula (I)

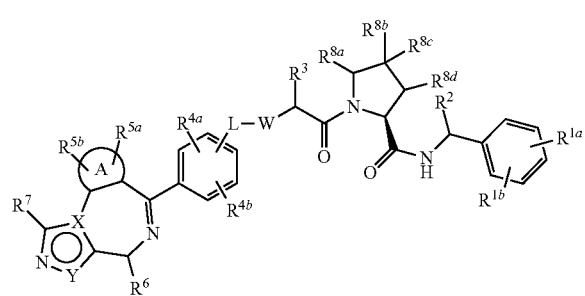

(I)

wherein

A is any of the following formula (Aa), (Ab) and (Ac)

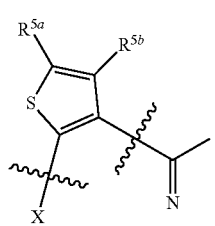

(Aa)

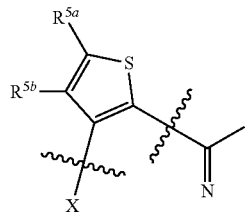

(Ab)

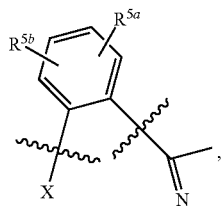

(Ac)

$R^{1a}$ and $R^{1b}$ are the same or different and each is independently a hydrogen atom,
a halogen atom,
cyano,
hydroxy,
mercapto,
nitro,
—N($R^{11}$)($R^{12}$),
—COOH,
unsubstituted or substituted alkyl having 1-6 carbon atoms,
unsubstituted or substituted cycloalkyl having 3-6 carbon atoms,
unsubstituted or substituted alkyl having 1-6 carbon atoms-O—,
unsubstituted or substituted cycloalkyl having 3-6 carbon atoms-O—,
unsubstituted or substituted alkyl having 1-6 carbon atoms-S—,
unsubstituted or substituted cycloalkyl having 3-6 carbon atoms-S—,
unsubstituted or substituted alkyl having 1-6 carbon atoms-O—CO—,
unsubstituted or substituted cycloalkyl having 3-6 carbon atoms-O—CO—,
unsubstituted or substituted alkyl having 1-6 carbon atoms-N($R^{13}$)—CO—,
unsubstituted or substituted cycloalkyl having 3-6 carbon atoms-N($R^{13}$)—CO—,
unsubstituted or substituted alkyl having 1-6 carbon atoms-CO—N($R^{13}$)—,
unsubstituted or substituted cycloalkyl having 3-6 carbon atoms-CO—N($R^{13}$)—,
unsubstituted or substituted alkyl having 1-6 carbon atoms-N($R^{13}$)—SO$_2$—,
unsubstituted or substituted cycloalkyl having 3-6 carbon atoms-N($R^{13}$)—SO$_2$—,
unsubstituted or substituted alkyl having 1-6 carbon atoms-SO$_2$—N($R^{13}$)—,
unsubstituted or substituted cycloalkyl having 3-6 carbon atoms-SO$_2$—N($R^{13}$)—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, $R^2$ is a hydrogen atom, unsubstituted or substituted alkyl having 1-6 carbon atoms or unsubstituted or substituted cycloalkyl having 3-6 carbon atoms, $R^3$ is a hydrogen atom, unsubstituted or substituted alkyl having 1-6 carbon atoms, unsubstituted or substituted cycloalkyl having 3-6 carbon atoms, unsubstituted or substituted aryl having 6-10 carbon atoms or unsubstituted or substituted heteroaryl having 1 to 6 hetero atoms selected from a nitrogen atom, an oxygen atom and a sulfur atom and containing 5 to 10 ring-constituting atoms, $R^{4a}$ and $R^{4b}$ are the same or different and each is independently a hydrogen atom, a halogen atom, cyano, hydroxy, mercapto, nitro,

—N($R^{41}$)($R^{42}$)

—COOH, unsubstituted or substituted alkyl having 1-6 carbon atoms, unsubstituted or substituted cycloalkyl having 3-6 carbon atoms, unsubstituted or substituted alkenyl having 2-6 carbon atoms, unsubstituted or substituted alkynyl having 2-6 carbon atoms, unsubstituted or substituted arylalkyl having 7-16 carbon atoms, unsubstituted or substituted alkyl having 1-6 carbon atoms-O—, unsubstituted or substituted cycloalkyl having 3-6 carbon atoms-O—, unsubstituted or substituted alkyl having 1-6 carbon atoms-S—, unsubstituted or substituted cycloalkyl having 3-6 carbon atoms-S—, unsubstituted or substituted arylalkyl having 7-16 carbon atoms-O—, unsubstituted or substituted alkyl having 1-6 carbon atoms-O—CO—, unsubstituted or substituted cycloalkyl having 3-6 carbon atoms-O—CO—, unsubstituted or substituted alkyl having 1-6 carbon atoms-N($R^{43}$)—CO—, unsubstituted or substituted cycloalkyl having 3-6 carbon atoms-N($R^{43}$)—CO—, unsubstituted or substituted alkyl having 1-6 carbon atoms-CO—N($R^{43}$)—, unsubstituted or substituted cycloalkyl having 3-6 carbon atoms-CO—N($R^{43}$)—, unsubstituted or substituted alkyl having 1-6 carbon atoms-N($R^{43}$)—SO$_2$—, unsubstituted or substituted cycloalkyl having 3-6 carbon atoms-N($R^{43}$)—SO$_2$—, unsubstituted or substituted alkyl having 1-6 carbon atoms-SO$_2$—N($R^{43}$)—, unsubstituted or substituted cycloalkyl having 3-6 carbon atoms-SO$_2$—N($R^{43}$)—, unsubstituted or substituted alkyl having 1-6 carbon atoms-CO—O—, unsubstituted or substituted cycloalkyl having 3-6 carbon atoms-CO—O—, unsubstituted or substituted alkyl having 1-6 carbon atoms-SO$_2$—, unsubstituted or substituted cycloalkyl having 3-6 carbon atoms-SO$_2$—, unsubstituted or substituted alkyl having 1-6 carbon atoms-O—CO—N($R^{43}$)—, unsubstituted or substituted cycloalkyl having 3-6 carbon atoms-O—CO—N($R^{43}$)—, unsubstituted or substituted alkyl having 1-6 carbon atoms-N($R^{43}$)—CO—N($R^{44}$)—, unsubstituted or substituted cycloalkyl having 3-6 carbon atoms-N($R^{43}$)—CO—N($R^{44}$)—, unsubstituted or substituted alkyl having 1-6 carbon atoms-N($R^{43}$)—SO$_2$—N($R^{44}$)—, unsubstituted or substituted cycloalkyl having 3-6 carbon atoms-N($R^{43}$)—SO$_2$—N($R^{44}$)—, unsubstituted or substituted aryl having 6-10 carbon atoms or an unsubstituted or substituted heterocyclic group having 1 to 6 hetero atoms selected from a nitrogen atom, an oxygen atom and a sulfur atom and containing 3 to 10 ring-constituting atoms, $R^{5a}$ and $R^{5b}$ are the same or different and each is independently a hydrogen atom, a halogen atom, cyano, unsubstituted or substituted alkyl having 1-6 carbon atoms, unsubstituted or substituted cycloalkyl having 3-6 carbon atoms, unsubstituted or substituted alkyl having 1-6 carbon atoms-O—, unsubstituted or substituted cycloalkyl having 3-6 carbon atoms-O—, unsubstituted or substituted aryl having 6-10 carbon atoms or unsubstituted or substituted heteroaryl having 1 to 6 hetero atoms selected from a nitrogen atom, an oxygen atom and a sulfur atom and containing 5 to 10 ring-constituting atoms, or $R^{5a}$ and $R^{5b}$ are joined to show

—CH$_2$—CH$_2$—CH$_2$—,

—CH$_2$—CH$_2$—CH$_2$—CH$_2$— or

—CH$_2$—CH$_2$—CH$_2$—CH$_2$—CH$_2$— and form a fused ring with adjacent ring A, $R^6$ is hydroxy, unsubstituted or substituted alkyl having 1-6 carbon atoms, unsubstituted or substituted cycloalkyl having 3-6 carbon atoms, —(CH$_2$)$_k$—CO—O$R^{61}$, —(CH$_2$)$_m$—CO—N($R^{62}$)($R^{63}$)

—(CH$_2$)$_n$—$R^{64}$,

—N($R^{65}$)—CO—O$R^{66}$,

—N($R^{65}$)—CO—N($R^{67}$)($R^{68}$)

—N($R^{65}$)—CO—$R^{69}$ or

—N($R^{610}$)($R^{611}$), k, m and n are each an integer of 1-4, $R^{62}$, $R^{63}$, $R^{67}$ and $R^{68}$ are the same or different and each is independently a hydrogen atom, unsubstituted or substituted alkyl having 1-6 carbon atoms, unsubstituted or substituted alkyl having 1-6 carbon atoms-O-unsubstituted or substituted alkyl having 1-6 carbon atoms, unsubstituted or substituted cycloalkyl having 3-6 carbon atoms, unsubstituted or substituted aryl having 6-10 carbon atoms or an unsubstituted or substituted heterocyclic group having 1 to 6 hetero atoms selected from a nitrogen atom, an oxygen atom and a sulfur atom and containing 3 to 10 ring-constituting atoms, or $R^{62}$ and $R^{63}$ or $R^{67}$ and $R^{63}$ show, together with the adjacent nitrogen atom, the following formula

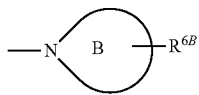

wherein ring B is an aziridine ring, an azetidine ring, a pyrrolidine ring, a piperidine ring or a morpholine ring, $R^{6B}$ is a hydrogen atom, a halogen atom, cyano, hydroxy, unsubstituted or substituted alkyl having 1-6 carbon atoms or unsubstituted or substituted alkyl having 1-6 carbon atoms-O—, $R^{64}$ is unsubstituted or substituted aryl having 6-10 carbon atoms or unsubstituted or substituted heteroaryl having 1 to 6 hetero atoms selected from a nitrogen atom, an oxygen atom and a sulfur atom and containing 5 to 10 ring-constituting atoms, $R^7$ is a hydrogen atom, unsubstituted or substituted alkyl having 1-6 carbon atoms or unsubstituted or substituted cycloalkyl having 3-6 carbon atoms, $R^{8a}$ is a hydrogen atom or unsubstituted or substituted alkyl having 1-3 carbon atoms, $R^{8b}$, $R^{8c}$ and $R^{8d}$ are the same or different and each is independently a hydrogen atom, a halogen atom, hydroxy, amino, unsubstituted or substituted alkyl having 1-3 carbon atoms or unsubstituted or substituted alkyl having 1-3 carbon atoms-O—, L is absent or a group obtained by freely selecting and combining 1-50 from $(R^{L1})(R^{L2})$—,

—$C(R^{L3})$=$C(R^{L4})$—,

—C≡C—,

—O—,

—S—,

—N($R^{L5}$)—,

—SO—,

—$SO_2$—,

—CO—O—,

—CO—N($R^{L6}$)—,

—$SO_2$—N($R^{L6}$)—,

—N($R^{L6}$)—CO—O—,

—N($R^{L6}$)—CO—N($R^{L7}$)—,

—N($R^{L6}$)—$SO_2$—N($R^{L7}$)—,

—N($R^{L6}$)—C(=N—CN)—N($R^{L7}$)—,

—N($R^{L6}$)—C(=CH—$NO_2$)—N($R^{L7}$)—, and

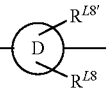

the number of ring D is 5 at maximum, and all or one part of L does not show —O—O—, —S—S—, —N($R^{L5}$)—N($R^{L5}$)—, —O—S—, —S—O—, —O—N($R^{L5}$)—N($R^{L5}$)—O—, —S—N($R^{L5}$)— or —N($R^{L5}$)—S—, ring D is cycloalkane having 3-6 carbon atoms, optionally partially reduced aromatic hydrocarbon having 6-10 carbon atoms, a hetero ring having 1-6 hetero atoms selected from a nitrogen atom, an oxygen atom and a sulfur atom and containing 3 to 10 ring-constituting atoms, a bicyclo ring having 4-12 carbon atoms, a bicyclohetero ring having 1-6 hetero atoms selected from a nitrogen atom, an oxygen atom and a sulfur atom and containing 4 to 12 ring-constituting atoms, a spiro ring having 6-12 carbon atoms, or a spirohetero ring having 1-6 hetero atoms selected from a nitrogen atom, an oxygen atom and a sulfur atom and containing 6 to 12 ring-constituting atoms, $R^{L1}$, $R^{L2}$, $R^{L8}$ and $R^{L8'}$ are the same or different and each is independently a hydrogen atom, a halogen atom, cyano, hydroxy, mercapto, nitro, —N($R^{La}$)($R^{Lb}$),

—COOH, oxo, provided that when $R^{L1}$ is oxo, then $R^{L2}$ is absent, thioxo, provided that when $R^{L1}$ is thioxo, then $R^{L2}$ is absent, unsubstituted or substituted alkyl having 1-6 carbon atoms, unsubstituted or substituted cycloalkyl having 3-6 carbon atoms, unsubstituted or substituted alkenyl having 2-6 carbon atoms, unsubstituted or substituted alkynyl having 2-6 carbon atoms, unsubstituted or substituted arylalkyl having 7-16 carbon atoms, unsubstituted or substituted alkyl having 1-6 carbon atoms-O—, unsubstituted or substituted cycloalkyl having 3-6 carbon atoms-O—, unsubstituted or substituted alkyl having 1-6 carbon atoms-S—, unsubstituted or substituted cycloalkyl having 3-6 carbon atoms-S—, unsubstituted or substituted arylalkyl having 7-16 carbon atoms-O—,
unsubstituted or substituted alkyl having 1-6 carbon atoms-O—CO—,
unsubstituted or substituted cycloalkyl having 3-6 carbon atoms-O—CO—,
unsubstituted or substituted alkyl having 1-6 carbon atoms-N($R^{Lc}$)—CO—,
unsubstituted or substituted cycloalkyl having 3-6 carbon atoms-N($R^{Lc}$)—CO—,
unsubstituted or substituted alkyl having 1-6 carbon atoms-CO—N($R^{Lc}$)—,
unsubstituted or substituted cycloalkyl having 3-6 carbon atoms-CO—N($R^{Lc}$)—,
unsubstituted or substituted alkyl having 1-6 carbon atoms-N($R^{Lc}$)—SO$_2$—,
unsubstituted or substituted cycloalkyl having 3-6 carbon atoms-N($R^{Lc}$)—SO$_2$—,
unsubstituted or substituted alkyl having 1-6 carbon atoms-SO$_2$—N($R^{Lc}$)—,
unsubstituted or substituted cycloalkyl having 3-6 carbon atoms-SO$_2$—N($R^{Lc}$)—,
unsubstituted or substituted alkyl having 1-6 carbon atoms-CO—O—,
unsubstituted or substituted cycloalkyl having 3-6 carbon atoms-CO—O—,
unsubstituted or substituted alkyl having 1-6 carbon atoms-SO$_2$—,
unsubstituted or substituted cycloalkyl having 3-6 carbon atoms-SO$_2$—,
unsubstituted or substituted alkyl having 1-6 carbon atoms-O—CO—N($R^{Lc}$)—,
unsubstituted or substituted cycloalkyl having 3-6 carbon atoms-O—CO—N($R^{Lc}$)—,
unsubstituted or substituted alkyl having 1-6 carbon atoms-N($R^{Lc}$)—CO—N($R^{Ld}$)—,
unsubstituted or substituted cycloalkyl having 3-6 carbon atoms-N($R^{Lc}$)—CO—N($R^{Ld}$)—,
unsubstituted or substituted alkyl having 1-6 carbon atoms-N($R^{Lc}$)—SO$_2$—N($R^{Ld}$)—,
unsubstituted or substituted cycloalkyl having 3-6 carbon atoms-N—($R^{Lc}$)—SO$_2$—N($R^{Ld}$)—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, and further, $R^{L1}$ and $R^{L2}$ are optionally joined to show —CH$_2$—CH$_2$—, —CH$_2$—CH$_2$—CH$_2$—, —CH$_2$—CH$_2$—CH$_2$—CH$_2$— or —CH$_2$—CH$_2$—CH$_2$—CH$_2$—CH$_2$—, $R^{L3}$ and $R^{L4}$ are the same or different and each is independently
a hydrogen atom,
a halogen atom
cyano,
—COOH,
unsubstituted or substituted alkyl having 1-6 carbon atoms,
unsubstituted or substituted cycloalkyl having 3-6 carbon atoms,
unsubstituted or substituted alkenyl having 2-6 carbon atoms,
unsubstituted or substituted arylalkyl having 7-16 carbon atoms,
unsubstituted or substituted alkyl having 1-6 carbon atoms-O—CO—,
unsubstituted or substituted cycloalkyl having 3-6 carbon atoms-O—CO—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, $R^{L5}$ is
a hydrogen atom,
unsubstituted or substituted alkyl having 1-6 carbon atoms,
unsubstituted or substituted cycloalkyl having 3-6 carbon atoms,
unsubstituted or substituted arylalkyl having 7-16 carbon atoms,
unsubstituted or substituted alkyl having 1-6 carbon atoms-O—CO—,
unsubstituted or substituted cycloalkyl having 3-6 carbon atoms-O—CO—,
unsubstituted or substituted alkyl having 1-6 carbon atoms-N($R^{Lc}$)—CO—,
unsubstituted or substituted cycloalkyl having 3-6 carbon atoms-N($R^{Lc}$)—CO—,
unsubstituted or substituted alkyl having 1-6 carbon atoms-N($R^{Lc}$)—SO$_2$—,
unsubstituted or substituted cycloalkyl having 3-6 carbon atoms-N($R^{Lc}$)—SO$_2$—,
unsubstituted or substituted alkyl having 1-6 carbon atoms-SO$_2$—,
unsubstituted or substituted cycloalkyl having 3-6 carbon atoms-SO$_2$—,
unsubstituted or substituted alkyl having 1-6 carbon atoms-CO—,
unsubstituted or substituted cycloalkyl having 3-6 carbon atoms-CO—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, W is any of the following formula (Wa), (Wb), (Wc), (Wd) and (We)

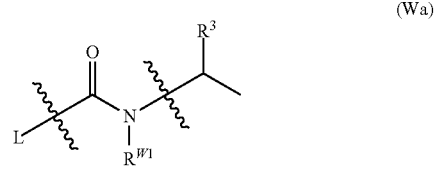

(Wa)

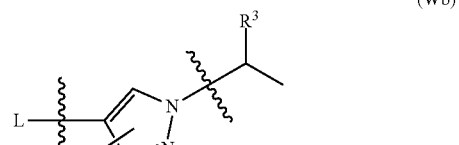

(Wb)

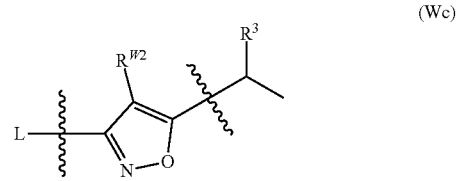

(Wc)

-continued

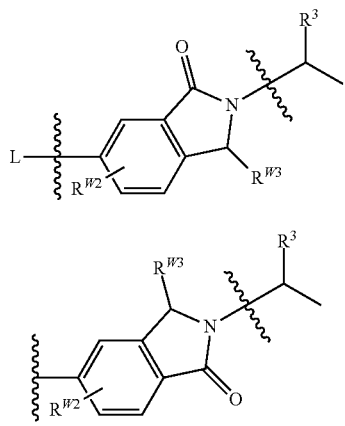

(Wd)

(We)

X and Y are:
X is a nitrogen atom and Y is a nitrogen atom, or X is a carbon atom and Y is an oxygen atom,
$R^{W2}$ is
a hydrogen atom,
a halogen atom,
cyano,
hydroxy,
unsubstituted or substituted alkyl having 1-6 carbon atoms,
unsubstituted or substituted cycloalkyl having 3-6 carbon atoms,
unsubstituted or substituted alkyl having 1-6 carbon atoms-O— or
unsubstituted or substituted cycloalkyl having 3-6 carbon atoms-O—,
$R^{11}$, $R^{12}$, $R^{13}$, $R^{41}$, $R^{42}$, $R^{43}$, $R^{44}$, $R^{61}$, $R^{65}$, $R^{66}$, $R^{610}$, $R^{611}$, $R^{L6}$, $R^{L7}$, $R^{La}$, $R^{Lb}$, $R^{Lc}$, $R^{Ld}$, $R^{W1}$ and $R^{W3}$ are the same or different and each is independently
a hydrogen atom,
unsubstituted or substituted alkyl having 1-6 carbon atoms or
unsubstituted or substituted cycloalkyl having 3-6 carbon atoms,
$R^{69}$ is
unsubstituted or substituted alkyl having 1-6 carbon atoms or
unsubstituted or substituted cycloalkyl having 3-6 carbon atoms,
when alkyl having 1-6 carbon atoms, cycloalkyl having 3-6 carbon atoms, alkenyl having 2-6 carbon atoms and alkynyl having 2-6 carbon atoms are substituted, they are substituted by one or two or more groups selected from a halogen atom, cyano, hydroxy and alkyl having 1-6 carbon atoms-O—, when aryl having 6-10 carbon atoms; a heterocyclic group having 1 to 6 hetero atoms selected from a nitrogen atom, an oxygen atom and a sulfur atom and containing 3 to 10 ring-constituting atoms; heteroaryl having 1 to 6 hetero atoms selected from a nitrogen atom, an oxygen atom and a sulfur atom and containing 5 to 10 ring-constituting atoms; and arylalkyl having 7-16 carbon atoms are substituted, they are substituted by one or two or more groups selected from a halogen atom, cyano, hydroxy, alkyl having 1-6 carbon atoms, cycloalkyl having 3-6 carbon atoms, alkyl having 1-6 carbon atoms-O— and cycloalkyl having 3-6 carbon atoms-O—, or a pharmacologically acceptable salt thereof.

[2] The compound described in [1], wherein $R^{L1}$, $R^{L2}$, $R^{L8}$ and $R^{L8'}$ are the same or different and each is independently
a hydrogen atom,
a halogen atom,
cyano,
hydroxy,
mercapto,
nitro,
—N($R^{La}$)($R^{Lb}$),
—COOH,
oxo, provided that when $R^{L1}$ is oxo, then $R^{L2}$ is absent,
thioxo, provided that when $R^{L1}$ is thioxo, then $R^{L2}$ is absent,
unsubstituted or substituted alkyl having 1-6 carbon atoms,
unsubstituted or substituted cycloalkyl having 3-6 carbon atoms,
unsubstituted or substituted alkenyl having 2-6 carbon atoms,
unsubstituted or substituted alkynyl having 2-6 carbon atoms,
unsubstituted or substituted arylalkyl having 7-16 carbon atoms,
unsubstituted or substituted alkyl having 1-6 carbon atoms-O—,
unsubstituted or substituted cycloalkyl having 3-6 carbon atoms-O—,
unsubstituted or substituted alkyl having 1-6 carbon atoms-S—,
unsubstituted or substituted cycloalkyl having 3-6 carbon atoms-S—,
unsubstituted or substituted arylalkyl having 7-16 carbon atoms-O—,
unsubstituted or substituted alkyl having 1-6 carbon atoms-O—CO—,
unsubstituted or substituted cycloalkyl having 3-6 carbon atoms-O—CO—,
unsubstituted or substituted alkyl having 1-6 carbon atoms-N($R^{Lc}$)—CO—,
unsubstituted or substituted cycloalkyl having 3-6 carbon atoms-N($R^{Lc}$)—CO—,
unsubstituted or substituted alkyl having 1-6 carbon atoms-CO—N($R^{Lc}$)—,
unsubstituted or substituted cycloalkyl having 3-6 carbon atoms-CO—N($R^{Lc}$)—,
unsubstituted or substituted alkyl having 1-6 carbon atoms-N($R^{Lc}$)—SO$_2$—,
unsubstituted or substituted cycloalkyl having 3-6 carbon atoms-N($R^{Lc}$)—SO$_2$—,
unsubstituted or substituted alkyl having 1-6 carbon atoms-SO$_2$—N($R^{Lc}$)—,
unsubstituted or substituted cycloalkyl having 3-6 carbon atoms-SO$_2$—N($R^{Lc}$)—,
unsubstituted or substituted alkyl having 1-6 carbon atoms-CO—O—,
unsubstituted or substituted cycloalkyl having 3-6 carbon atoms-CO—O—,
unsubstituted or substituted alkyl having 1-6 carbon atoms-SO$_2$—,
unsubstituted or substituted cycloalkyl having 3-6 carbon atoms-SO$_2$—,
unsubstituted or substituted alkyl having 1-6 carbon atoms-O—CO—N($R^{Lc}$)—,
unsubstituted or substituted cycloalkyl having 3-6 carbon atoms-O—CO—N($R^{Lc}$)—, unsubstituted or substituted alkyl having 1-6 carbon atoms-N($R^{Lc}$)—CO—N($R^{Ld}$)—, unsubstituted or substituted cycloalkyl having 3-6 carbon atoms-N($R^{Lc}$)—CO—N($R^{Ld}$)—, unsubstituted or substituted alkyl having 1-6 carbon atoms-N($R^{Lc}$)—SO$_2$—N($R^{Ld}$)—.

unsubstituted or substituted cycloalkyl having 3-6 carbon atoms-N($R^{Lc}$)—SO$_2$—N($R^{Ld}$)—, unsubstituted or substituted aryl having 6-10 carbon atoms or an unsubstituted or substituted heterocyclic group having 1 to 6 hetero atoms selected from a nitrogen atom, an oxygen atom and a sulfur atom and containing 3 to 10 ring-constituting atoms, or a pharmacologically acceptable salt thereof.

[3] The compound described in [1] or [2], wherein A is

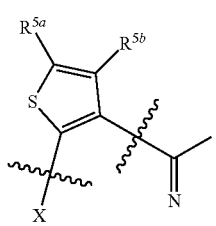

(Aa)

or a pharmacologically acceptable salt thereof.

[4] The compound described in any one of [1]-[3], wherein X and Y are nitrogen atoms, or a pharmacologically acceptable salt thereof.

[5] The compound described in any one of [1]-[4], wherein W is

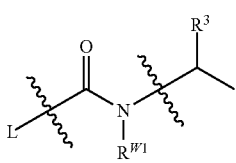

(Wa)

or a pharmacologically acceptable salt thereof.

[6] The compound described in any one of [1]-[5], wherein L is

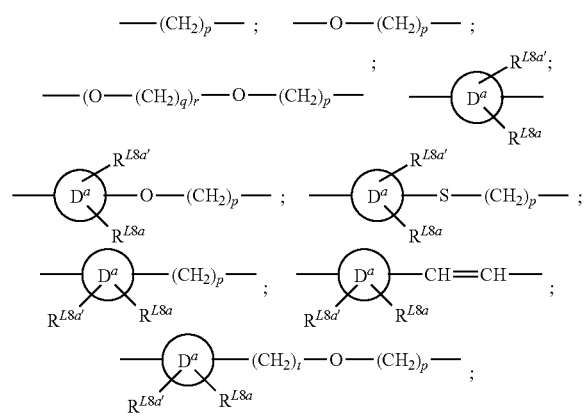

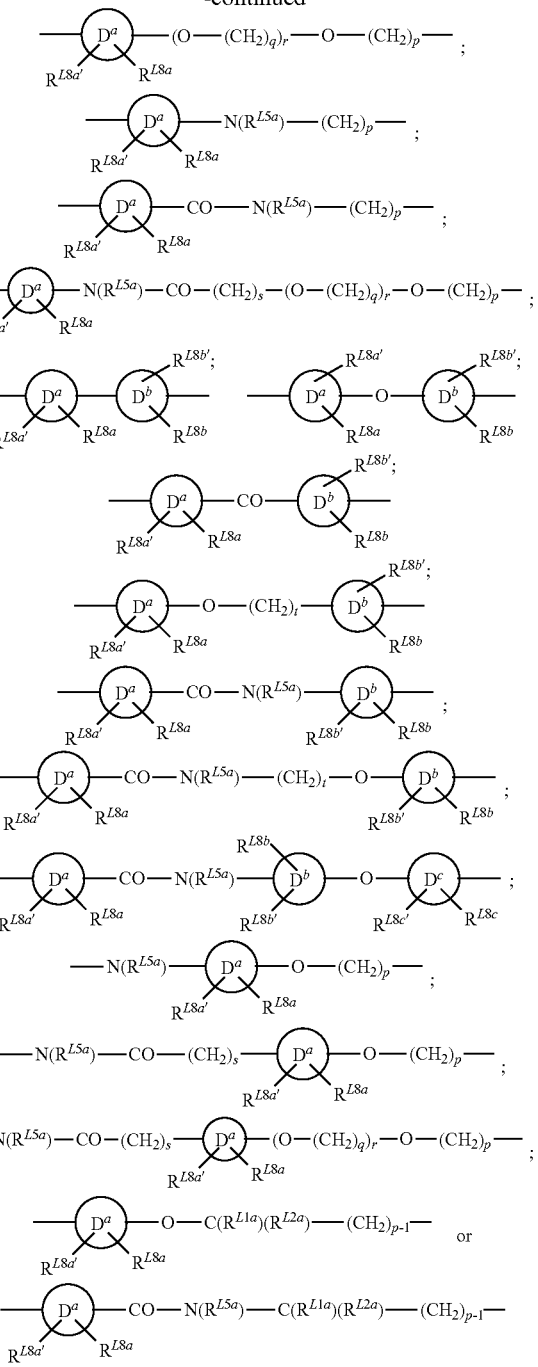

wherein p and t are each an integer of 1-6, q and s are each an integer of 1-4, r is an integer of 1-7, ring $D^a$, ring $D^b$ and ring $D^c$ are the same or different and each is independently cycloalkane having 3-6 carbon atoms, benzene, naphthalene, dihydronaphthalene, tetrahydronaphthalene, azetidine, pyrrole, dihydropyrrole, pyrrolidine, furan, dihydrofuran, tetrahydrofuran, thiophene, dihydrothiophene, tetrahydrothiophene, pyridine, dihydropyridine, tetrahydropyridine, piperidine, pyran, dihydropyran, tetrahydropyran, thiopyran, dihydrothiopyran, tetrahydrothiopyran, pyrazole, dihydropyrazole, tetrahydropyrazole, imidazole, dihydroimidazole, tetrahydroimidazole, isoxazole, dihydroisoxazole, tetrahydroisoxazole, oxazole, dihydrooxazole, tetrahydrooxazole, isothiazole, dihydroisothiazole, tetrahydroisothiazole, thiazole, dihydrothiazole, tetrahydrothiazole, pyridazine, dihydropyridazine, tetrahydropyridazine, hexahydropyridazine, pyrimidine, dihydropyrimidine, tetrahydropyrimidine, hexahydropyrimidine, pyrazine, dihydropyrazine, tetrahydropyrazine, piperazine, oxazine, dihydrooxazine, tetrahydrooxazine, thiazine, dihydrothiazine, tetrahydrothiazine, benzopyrrole, dihydrobenzopyrrole, benzopyrrolidine, benzofuran, dihydrobenzofuran, benzothiophene, dihydrobenzothiophene, benzopyridine, dihydrobenzopyridine, benzopiperidine, benzopyran, dihydrobenzopyran, benzothiopyran, dihydrobenzothiopyran, benzopyrazole, dihydrobenzopyrazole, benzimidazole, dihydrobenzimidazole, benzisoxazole, dihydrobenzisoxazole, benzoxazole, dihydrobenzoxazole, benzisothiazole, dihydrobenzisothiazole, benzothiazole, dihydrobenzothiazole, benzopyridazine, dihydrobenzopyridazine, tetrahydrobenzopyridazine, benzopyrimidine, dihydrobenzopyrimidine, tetrahydrobenzopyrimidine, benzopyrazine, dihydrobenzopyrazine, benzopiperazine, benzoxazine, dihydrobenzoxazine, benzothiazine, dihydrobenzothiazine or a bicyclo ring having 4-12 carbon atoms, $R^{L1a}$ is unsubstituted or substituted alkyl having 1-6 carbon atoms or a halogen atom, $R^{L2a}$ is a hydrogen atom, unsubstituted or substituted alkyl having 1-6 carbon atoms or a halogen atom, $R^{L5a}$ is a hydrogen atom or unsubstituted or substituted alkyl having 1-6 carbon atoms, $R^{L8a}$, $R^{L8a'}$, $R^{L8b}$, $R^{L8b'}$, $R^{L8c}$ and $R^{L8c'}$ are the same or different and each is independently a hydrogen atom, a halogen atom, cyano, oxo, unsubstituted or substituted alkyl having 1-6 carbon atoms or unsubstituted or substituted alkyl having 1-6 carbon atoms-O—, or a pharmacologically acceptable salt thereof.

[7] The compound described in any one of [1]-[6], wherein L is

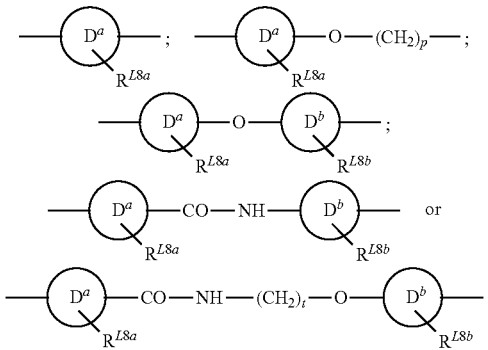

wherein
p and t are each an integer of 1-6,
ring $D^a$ and ring $D^b$ are the same or different and each is independently benzene, pyrrolidine, benzofuran, benzoxazole or benzothiazole, $R^{L8a}$ and $R^{L8b}$ are the same or different and each is independently a hydrogen atom, a halogen atom or cyano, or a pharmacologically acceptable salt thereof.

[8] The compound described in any one of [1]-[7], wherein $R^{1a}$ is unsubstituted or substituted heteroaryl having 1 to 6 hetero atoms selected from a nitrogen atom, an oxygen atom and a sulfur atom and containing 5 to 10 ring-constituting atoms, or a pharmacologically acceptable salt thereof.

[9] The compound described in any one of [1]-[8], wherein $R^{1b}$ is a hydrogen atom, or a pharmacologically acceptable salt thereof.

[10] The compound described in any one of [1]-[9], wherein $R^2$ is a hydrogen atom or unsubstituted or substituted alkyl having 1-6 carbon atoms, or a pharmacologically acceptable salt thereof.

[11] The compound described in any one of [1]-[10], wherein $R^3$ is unsubstituted or substituted alkyl having 1-6 carbon atoms, or a pharmacologically acceptable salt thereof.

[12] The compound described in any one of [1]-[11], wherein $R^{4a}$ and $R^{4b}$ are each a hydrogen atom, or a pharmacologically acceptable salt thereof.

[13] The compound described in any one of [1]-[12], wherein $R^{5a}$ and $R^{5b}$ are the same or different and each is independently unsubstituted or substituted alkyl having 1-6 carbon atoms, or a pharmacologically acceptable salt thereof.

[14] The compound described in any one of [1]-[13], wherein $R^6$ is —$(CH_2)_k$—CO—$OR^{61}$, or a pharmacologically acceptable salt thereof.

[15] The compound described in any one of [1]-[14], wherein $R^7$ is unsubstituted or substituted alkyl having 1-6 carbon atoms, or a pharmacologically acceptable salt thereof.

[16] The compound described in any one of [1]-[15], wherein $R^{8a}$, $R^{8c}$ and $R^{8d}$ are each a hydrogen atom, or a pharmacologically acceptable salt thereof.

[17] The compound described in any one of [1]-[16], wherein $R^{8b}$ is hydroxy, or a pharmacologically acceptable salt thereof.

[18] Methyl [(6S)-4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl]-2,3,9-trimethyl-6H-thieno[3,2-f][1,2,4]triazolo[4,3-a][1,4]diazepin-6-yl]acetate, methyl [(6S)-4-{4'-[2-({(2S)-1-[(2S,4R)-4-hydroxy-2-({[(4-(4-methyl-1,3-thiazol-5-yl)phenyl]methyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate, methyl {(6S)-4-[2'-fluoro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate, methyl [(6S)-4-(4-{(3R)-3-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl]-1-benzofuran-5-yl)oxy}ethyl)carbamoyl]pyrrolidin-1-yl}phenyl)-2,3,9-trimethyl-6H-thieno[3,2-f][1,2,4]triazolo[4,3-a][1,4]diazepin-6-yl]acetate, methyl {(6S)-4-[3'-fluoro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate, methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan- 2-yl}carbamoyl)-1,3-benzoxazol-5-yl]phenyl}-2,3,9-trimethyl-6H-thieno[3,2-f][1,2,4]triazolo[4,3-a][1,4]diazepin-6-yl]acetate, methyl [(6S)-4-{4-[(3S)-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]carbamoyl}pyrrolidin-1-yl]phenyl}-2,3,9-trimethyl-6H-thieno[3,2-f][1,2,4]triazolo[4,3-a][1,4]diazepin-6-yl]acetate, methyl [(6S)-4-{4-[(3R)-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}pyrrolidin-1-yl]phenyl}-2,3,9-trimethyl-6H-thieno[3,2-f][1,2,4]triazolo[4,3-a][1,4]diazepin-6-yl]acetate, methyl {(6S)-4-[3'-chloro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate, methyl [(6S)-4-{4-[7-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3,4-dihydroisoquinolin-2(1H)-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-6-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}carbamoyl)-1,3-benzoxazol-5-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzothiazol-5-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzoxazol-6-yl]phenyl}-2,3,9-trimethyl-6H-thieno[3,2-f][1,2,4]triazolo[4,3-a][1,4]diazepin-6-yl]acetate or (2S,4R)-1-{(2S)-3,3-dimethyl-2-[(3-{4-[(6S)-2,3,6,9-tetramethyl-6H-thieno[3,2-f][1,2,4]triazolo[4,3-a][1,4]diazepin-4-yl]phenyl}prop-2-ynoyl)amino]butanoyl}-4-hydroxy-N-{(1S)-1-[4-(4-methyl-1,3-thiazol-5-yl)phenyl]ethyl}pyrrolidine-2-carboxamide, or a pharmacologically acceptable salt thereof.

[19] A BET protein degrader comprising the compound described in any one of [1]-[18], or a pharmacologically acceptable salt thereof.

[20] The BET protein degrader described in [19] which is a BRD4 protein degrader.

[21] A BET protein inhibitor comprising the compound described in any one of [1]-[18] or a pharmacologically acceptable salt thereof.

[22] The BET protein inhibitor described in [19] which is a BRD4 protein inhibitor.

[23] A medicament comprising the compound described in any one of [1]-[18] or a pharmacologically acceptable salt thereof.

[24] The medicament described in [23] which is an anticancer agent.

[25] The anticancer agent described in [24] which is applicable to acute myeloid leukemia, chronic myeloid leukemia, multiple myeloma, diffuse large B-cell lymphoma, adult T-cell leukemia/lymphoma, Burkitt lymphoma, prostate cancer, ovarian cancer, bladder cancer, breast cancer, uterine sarcoma, gastric cancer, lung cancer, colorectal cancer, glioma, pancreatic cancer and liver cancer.

[26] The compound described in any one of [1]-[18] or a pharmacologically acceptable salt thereof which is used for treating cancer.

[27] The compound described in any one of [1]-[18] or a pharmacologically acceptable salt thereof which is used for degrading BET protein.

[28] The compound described in any one of [1]-[18] or a pharmacologically acceptable salt thereof which is used for degrading BRD4 protein.

[29] The compound described in any one of [1]-[18] or a pharmacologically acceptable salt thereof which is used for inhibiting BET protein.

[30] The compound described in any one of [1]-[18] or a pharmacologically acceptable salt thereof which is used for inhibiting BRD4 protein.

[31] Use of the compound described in any one of [1]-[18] or a pharmacologically acceptable salt thereof for producing an anticancer agent.

[32] Use of the compound described in any one of [1]-[18] or a pharmacologically acceptable salt thereof for producing a BET protein degrader.

[33] Use of the compound described in any one of [1]-[18] or a pharmacologically acceptable salt thereof for producing a BRD4 protein degrader.

[34] Use of the compound described in any one of [1]-[18] or a pharmacologically acceptable salt thereof for producing a BET protein inhibitor.

[35] Use of the compound described in any one of [1]-[18] or a pharmacologically acceptable salt thereof for producing a BRD4 protein inhibitor.

[36] A method for treating cancer comprising administering an effective amount of the compound described in any one of [1]-[18] or a pharmacologically acceptable salt thereof.

[37] The treatment method described in [36] wherein the cancer is acute myeloid leukemia, chronic myeloid leukemia, multiple myeloma, diffuse large B-cell lymphoma, adult T-cell leukemia/lymphoma, Burkitt lymphoma, prostate cancer, ovarian cancer, bladder cancer, breast cancer, uterine sarcoma, gastric cancer, lung cancer, colorectal cancer, glioma, pancreatic cancer or liver cancer.

[38] A method for degrading BET protein comprising administering an effective amount of the compound described in any one of [1]-[18] or a pharmacologically acceptable salt thereof.

[39] A method for degrading BRD4 protein comprising administering an effective amount of the compound described in any one of [1]-[18] or a pharmacologically acceptable salt thereof.

Effect of the Invention

The amide compound of the present invention is superior in a cytotoxic action on cancer cells, an action inducing degradation of BET protein in cancer cells, and an inhibitory action on the binding of BET protein and acetylated histone, and useful as an anticancer agent, a BET protein degrader or a BET protein inhibitor.

DESCRIPTION OF EMBODIMENTS

Figure 1:
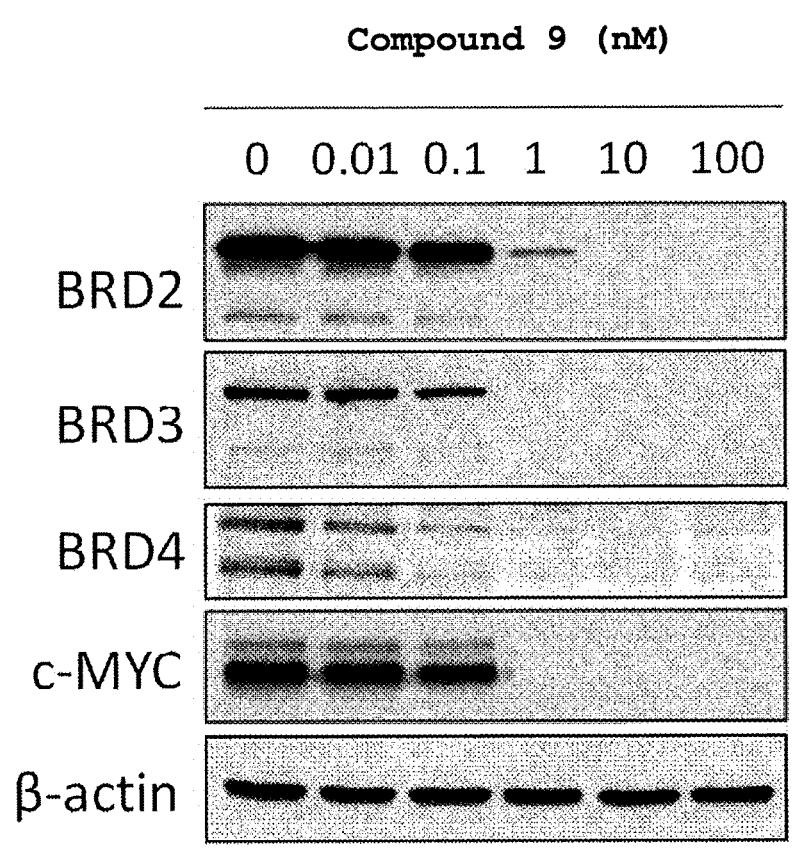
FIG. 1 shows a degradation inducing action of the compound of the present invention on each protein of BRD2, 3, 4 in human acute myeloid leukemia MV-4-11 cells.

The compound of the present invention is a compound represented by the formula (I) or a pharmacologically acceptable salt thereof. In the present specification, the "compound represented by the formula (I) or a pharmacologically acceptable salt thereof" is sometimes referred to generically as the compound of the present invention.

In the following, the meanings of the terms used in the present specification are described and the present invention is further described in detail. The following explanation of the terms does not limit the present invention in any manner.

The halogen atom is a fluorine atom, a chlorine atom, a bromine atom or an iodine atom.

The alkyl having 1-3 carbon atoms is a straight chain or branched chain saturated hydrocarbon group having 1-3 carbon atoms and specific examples thereof include methyl, ethyl, propyl, methylethyl and the like.

The alkyl having 1-6 carbon atoms is a straight chain or branched chain saturated hydrocarbon group having 1-6 carbon atoms and specific examples thereof include methyl, ethyl, propyl, methylethyl, butyl, methylpropyl, dimethylethyl, pentyl, methylbutyl, dimethylpropyl, ethylpropyl, hexyl, methylpentyl, ethylbutyl, dimethylbutyl, trimethylpropyl, ethylmethylpropyl and the like.

The cycloalkane having 3-6 carbon atoms is a saturated hydrocarbon ring having 3-6 carbon atoms and specific examples thereof include cyclopropane, cyclobutane, methylcyclopropane, cyclopentane, dimethylcyclopropane, ethylcyclopropane, methylcyclobutane, cyclohexane, trimethylcyclopropane, ethylmethylcyclopropane, dimethylcyclobutane, ethylcyclobutane, methylcyclohexane and the like.

The cycloalkyl having 3-6 carbon atoms is a monovalent group obtained by removing one hydrogen atom from the aforementioned cycloalkane having 3-6 carbon atoms and specific examples thereof include cyclopropyl, cyclobutyl, methylcyclopropyl, cyclopentyl, dimethylcyclopropyl, ethylcyclopropyl, methylcyclobutyl, cyclohexyl, trimethylcyclopropyl, ethylmethylcyclopropyl, dimethylcyclobutyl, ethylcyclobutyl, methylcyclohexyl and the like.

The alkenyl having 2-6 carbon atoms is a straight chain or branched chain hydrocarbon group having 2-6 carbon atoms and one double bond and specific examples thereof include ethenyl, propenyl, methylethenyl, butenyl, methylpropenyl, ethylethenyl, pentenyl, methylbutenyl, dimethylpropenyl, ethylpropenyl, propylethenyl, 1-(1-methylethyl)-ethenyl, hexenyl, methylpentenyl, dimethylbutenyl, ethylbutenyl, trimethylpropenyl, ethylmethylpropenyl, 1-(1-methylethyl)-propenyl and the like.

The alkynyl having 2-6 carbon atoms is a straight chain or branched chain hydrocarbon group having 2-6 carbon atoms and one triple bond and specific examples thereof include ethynyl, propynyl, butynyl, methylpropynyl, pentynyl, methylbutynyl, dimethylpropynyl, ethylpropynyl, hexynyl, methylpentynyl, dimethylbutynyl, ethylbutynyl, ethylmethylpropynyl, propylpropynyl, (1-methylethyl)propynyl and the like.

The aromatic hydrocarbon having 6-10 carbon atoms is benzene or naphthalene. The partially reduced aromatic hydrocarbon having 6-10 carbon atoms is, for example, cyclohexene, cyclohexadiene, dihydronaphthalene or tetrahydronaphthalene.

The aryl having 6-10 carbon atoms is an aromatic hydrocarbon group having 6-10 carbon atoms and specific examples thereof include phenyl and naphthyl.

The "heteroaryl having 1 to 6 hetero atoms selected from a nitrogen atom, an oxygen atom and a sulfur atom and containing 5 to 10 ring-constituting atoms" is a monovalent group obtained by removing one hydrogen atom from monocyclic aromatic heterocycle having 1 to 4 hetero atoms selected from a nitrogen atom, an oxygen atom and a sulfur atom and containing 5 or 6 ring-constituting atoms, a fused ring of the monocyclic aromatic heterocycle and benzene, or a fused ring constituted of the same or different two monocyclic aromatic heterocycles having 1 to 3 hetero atoms selected from a nitrogen atom, an oxygen atom and a sulfur atom and containing 5 or 6 ring-constituting atoms. Specific examples include pyrrolyl, furyl, thienyl, pyrazolyl, imidazolyl, triazolyl, tetrazolyl, oxazolyl, isoxazolyl, thiazolyl, isothiazolyl, furazanyl, pyridyl, pyranyl, thiopyranyl, pyridazinyl, pyrimidinyl, pyrazinyl, triazinyl, oxazinyl, thiazinyl, tetrazinyl, benzopyrrolyl, benzofuranyl, benzothienyl, benzoxazolyl, benzisoxazolyl, benzopyrazolyl, benzimidazolyl, benzothiazolyl, benzisothiazolyl, benzopyridyl, benzopyridazinyl, benzopyrimidinyl, benzopyrazinyl, benzoxazodinyl, benzothiazinyl, naphthyridinyl, thienofuranyl, pyrazolooxazolyl, imidazothiazolyl, pyrazinopyridazinyl, imidazothiazolyl and the like.

The heterocyclic group having 1 to 6 hetero atoms selected from a nitrogen atom, an oxygen atom and a sulfur atom and containing 3 to 10 ring-constituting atoms is the aforementioned heteroaryl having 1 to 6 hetero atoms selected from a nitrogen atom, an oxygen atom and a sulfur atom and containing 5 to 10 ring-constituting atoms, a group in which one part or all parts of heteroaryl are reduced or a group in which one or two or more carbon atoms of cyclopropyl and cyclobutyl are substituted by a nitrogen atom, an oxygen atom or a sulfur atom. Specific examples include the aforementioned specific examples of the heteroaryl having 1 to 6 hetero atoms selected from a nitrogen atom, an oxygen atom and a sulfur atom and containing 5 to 10 ring-constituting atoms, as well as aziridinyl, azetidinyl, dihydropyrrolyl, pyrrolidinyl, dihydrofuryl, tetrahydrofuryl, dihydrothienyl, tetrahydrothienyl, dihydropyridyl, tetrahydropyridyl, piperidinyl, dihydropyranyl, tetrahydropyranyl, thiopyranyl, dihydrothiopyranyl, tetrahydrothiopyranyl, dihydropyrazolyl, tetrahydropyrazolyl, imidazolyl, dihydroimidazolyl, tetrahydroimidazolyl, dihydroisoxazolyl, tetrahydroisoxazolyl, dihydrooxazolyl, tetrahydrooxazolyl, dihydroisothiazolyl, tetrahydroisothiazolyl, dihydrothiazolyl, tetrahydrothiazolyl, dihydropyridazinyl, tetrahydropyridazinyl, hexahydropyridazinyl, dihydropyrimidinyl, tetrahydropyrimidinyl, hexahydropyrimidinyl, dihydropyrazinyl, tetrahydropyrazinyl, piperazinyl, dihydrooxazinyl, tetrahydrooxazinyl, dihydrothiazinyl, tetrahydrothiazinyl, dihydrobenzopyrrolyl, benzopyrrolidinyl, dihydrobenzofuranyl, dihydrobenzothienyl, dihydrobenzopyridyl, benzopiperidinyl, dihydrobenzopyranyl, dihydrobenzothiopyranyl, dihydrobenzopyrazolyl, dihydrobenzimidazolyl, dihydrobenzisoxazolyl, dihydrobenzoxazolyl, dihydrobenzisothiazolyl, dihydrobenzothiazolyl, dihydrobenzopyridazinyl, tetrahydrobenzopyridazinyl, dihydrobenzopyrimidinyl, tetrahydrobenzopyrimidinyl, dihydrobenzopyrazinyl, benzopiperazinyl, dihydrobenzoxazinyl, dihydrobenzothiazinyl and the like.

The "hetero ring having 1-6 hetero atoms selected from a nitrogen atom, an oxygen atom and a sulfur atom and containing 3 to 10 ring-constituting atoms" is
1) a monocyclic aromatic heterocycle containing 1-4 hetero atoms selected from a nitrogen atom, an oxygen atom and a sulfur atom and containing 5 or 6 ring-constituting atoms
2) a fused ring of the monocyclic aromatic heterocycle of the above-mentioned 1) and benzene
3) a fused ring constituted of the same or different two monocyclic aromatic heterocycles having 1 to 3 hetero atoms selected from a nitrogen atom, an oxygen atom and a sulfur atom and containing 5 or 6 ring-constituting atoms
4) heterocycle in which one or all parts of the above-mentioned 1)-3) are reduced or
5) heterocycle in which one or two or more carbon atoms of cyclopropyl and cyclobutyl are substituted by a nitrogen atom, an oxygen atom or a sulfur atom. The aforementioned "heteroaryl having 1 to 6 hetero atoms selected from a nitrogen atom, an oxygen atom and a sulfur atom and containing 5 to 10 ring-constituting atoms" and the "heterocyclic group having 1 to 6 hetero atoms selected from a nitrogen atom, an oxygen atom and a sulfur atom and containing 3 to 10 ring-constituting atoms" are each a monovalent group obtained by removing one hydrogen atom from "a hetero ring having 1 to 6 hetero atoms selected from a nitrogen atom, an oxygen atom and a sulfur atom and containing 3 to 10 ring-constituting atoms". Therefore, recitation of specific examples of the "hetero ring having 1-6 hetero atoms selected from a nitrogen atom, an oxygen atom and a sulfur atom and containing 3 to 10 ring-constituting atoms" is omitted here. The specific examples are the same as those recited for the "heteroaryl having 1 to 6 hetero atoms selected from a nitrogen atom, an oxygen atom and a sulfur atom and containing 5 to 10 ring-constituting atoms" and the "heterocyclic group having 1 to 6 hetero atoms selected from a nitrogen atom, an oxygen atom and a sulfur atom and containing 3 to 10 ring-constituting atoms". Since the recited examples are described in a form expressing groups, it is necessary to read differently in a form expressing heterocycles as appropriate, for example, pyrrolyl as pyrrole and aziridinyl as aziridine.

The bicyclo ring having 4-12 carbon atoms is a saturated or unsaturated hydrocarbon ring having 4-12 carbon atoms in total and constituted only of two rings commonly having two or more atoms. Specific examples include bicyclobutane, bicyclopentane, bicyclohexane, bicycloheptane, bicyclooctane, bicyclononane, bicyclodecane, bicycloundecane, bicyclododecane, methylbicyclobutane, ethylbicyclopentane, bicyclobutene, bicyclopentene and the like.

The bicyclohetero ring having 1-6 hetero atoms selected from a nitrogen atom, an oxygen atom and a sulfur atom and containing 4 to 12 ring-constituting atoms is a ring in which 1-6 carbon atoms of the aforementioned bicyclo ring having 4-12 carbon atoms are substituted by a nitrogen atom, an oxygen atom or a sulfur atom. Specific examples include azabicycloheptane, oxabicycloheptane, thiabicycloheptane and the like.

The spiro ring having 6-12 carbon atoms is a saturated or unsaturated hydrocarbon ring having 6-12 carbon atoms in total in which two rings are bonded together by only one atom. Specific examples include spirohexane, spiroheptane, spirooctane, spirononane, spirodecane, spiroundecane, spirododecane, spirodecene, spirodecadiene, dispirodecane, methylspiroheptane and the like.

The spirohetero ring having 1-6 hetero atoms selected from a nitrogen atom, an oxygen atom and a sulfur atom and containing 6 to 12 ring-constituting atoms is a ring in which 1-6 carbon atoms of the aforementioned spiro ring having 6-12 carbon atoms are substituted by a nitrogen atom, an oxygen atom or a sulfur atom.

The arylalkyl having 7-16 carbon atoms is alkyl having 1-6 carbon atoms substituted by the aforementioned aryl having 6-10 carbon atoms. Specific examples include benzyl, phenethyl, naphthylmethyl and the like.

In the present specification, the number of substituents when "substituted" is one or two or more unless particularly indicated, and the kind of the substituents may be the same or different.

Preferable embodiments of the above-mentioned formula (I) are explained below.

A is preferably the following formula (Aa) or (Ab), more preferably (Aa).

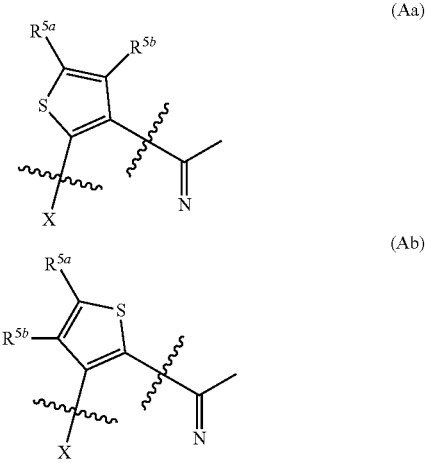

$R^{1a}$ is preferably a hydrogen atom, a halogen atom, unsubstituted or substituted alkyl having 1-6 carbon atoms or an unsubstituted or substituted heterocyclic group having 1 to 6 hetero atoms selected from a nitrogen atom, an oxygen atom and a sulfur atom and containing 3 to 10 ring-constituting atoms, and more preferably unsubstituted or substituted heteroaryl having 1 to 6 hetero atoms selected from a nitrogen atom, an oxygen atom and a sulfur atom and containing 5 to 10 ring-constituting atoms. The heterocyclic group or heteroaryl for $R^{1a}$ is preferably heteroaryl having 1 or 2 hetero atoms selected from a nitrogen atom, an oxygen atom and a sulfur atom and containing 5 ring-constituting atoms, more preferably thiazole. A preferable embodiment of $R^{1a}$ is 4-methyl-1,3-thiazol-5-yl. The bonding position of $R^{1a}$ is preferably

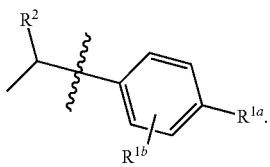

$R^{1b}$ is preferably a hydrogen atom, a halogen atom or unsubstituted or substituted alkyl having 1-6 carbon atoms, more preferably a hydrogen atom.

$R^2$ is preferably a hydrogen atom or unsubstituted or substituted alkyl having 1-6 carbon atoms, more preferably a hydrogen atom or unsubstituted or substituted alkyl having 1-3 carbon atoms, particularly preferably a hydrogen atom or methyl. The steric configuration of $R^2$ is preferably

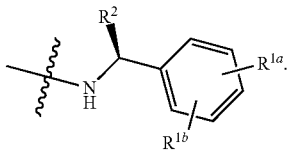

$R^3$ is preferably unsubstituted or substituted alkyl having 1-6 carbon atoms, more preferably 1,1-dimethylethyl. The steric configuration of $R^3$ is preferably

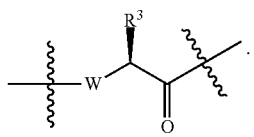

$R^{4a}$ is preferably a hydrogen atom, a halogen atom or unsubstituted or substituted alkyl having 1-6 carbon atoms, more preferably a hydrogen atom.

$R^{4b}$ is preferably a hydrogen atom.

$R^{5a}$ is preferably a hydrogen atom, a halogen atom or unsubstituted or substituted alkyl having 1-6 carbon atoms, more preferably unsubstituted or substituted alkyl having 1-6 carbon atoms, particularly preferably methyl.

$R^{5b}$ is preferably a hydrogen atom, a halogen atom or unsubstituted or substituted alkyl having 1-6 carbon atoms, more preferably unsubstituted or substituted alkyl having 1-6 carbon atoms, particularly preferably methyl.

$R^6$ is preferably hydroxy, unsubstituted or substituted alkyl having 1-6 carbon atoms, $-(CH_2)_k-CO-OR^{61}$, $-(CH_2)_m-CO-N(R^{62})(R^{63})$, $-(CH_2)_n-R^{64}$, $-N(R^{65})-CO-OR^{66}$, $-N(R^{65})-CO-N(R^{67})(R^{68})$, $-N(R^{65})-CO-R^{69}$ or $-N(R^{610})(R^{6111})$, more preferably $-(CH_2)_k-CO-OR^{61}$.

k is preferably an integer of 1-3, more preferably an integer of 1-2, particularly preferably 1.

m is preferably an integer of 1-3, more preferably an integer of 1-2, particularly preferably 1.

n is preferably an integer of 1-3, more preferably an integer of 1-2, particularly preferably 1.

$R^{61}$ is preferably unsubstituted or substituted alkyl having 1-6 carbon atoms, more preferably methyl.

$R^{62}$ is preferably a hydrogen atom, unsubstituted or substituted alkyl having 1-6 carbon atoms or unsubstituted or substituted alkyl having 1-6 carbon atoms-O-unsubstituted or substituted alkyl having 1-6 carbon atoms, more preferably unsubstituted or substituted alkyl having 1-6 carbon atoms or unsubstituted or substituted alkyl having 1-6 carbon atoms-O-unsubstituted or substituted alkyl having 1-6 carbon, particularly preferably alkyl having 1-6 carbon atoms (particularly, ethyl) substituted by hydroxy or alkyl having 1-6 carbon atoms (particularly, n-propyl) substituted by hydroxy-O-unsubstituted alkyl having 1-6 carbon atoms (particularly, ethyl).

$R^{63}$ is preferably a hydrogen atom.

$R^{64}$ is preferably unsubstituted or substituted heteroaryl having 1 to 6 hetero atoms selected from a nitrogen atom, an oxygen atom and a sulfur atom and containing 5 to 10 ring-constituting atoms, more preferably unsubstituted or substituted oxadiazolyl, particularly preferably oxadiazolyl substituted by unsubstituted alkyl having 1-6 carbon atoms (particularly, methyl).

$R^{65}$ is preferably a hydrogen atom or unsubstituted or substituted alkyl having 1-6 carbon atoms, more preferably a hydrogen atom or unsubstituted or substituted alkyl having 1-6 carbon atoms (particularly, methyl).

$R^{66}$ is preferably unsubstituted or substituted alkyl having 1-6 carbon atoms, more preferably unsubstituted alkyl having 1-6 carbon atoms, particularly preferably methyl, ethyl or tert-butyl.

$R^{67}$ is preferably a hydrogen atom or unsubstituted or substituted alkyl having 1-6 carbon atoms, more preferably unsubstituted or substituted alkyl having 1-6 carbon atoms, particularly preferably unsubstituted alkyl having 1-6 carbon atoms (particularly, methyl).

$R^{68}$ is preferably a hydrogen atom or unsubstituted or substituted alkyl having 1-6 carbon atoms, more preferably unsubstituted or substituted alkyl having 1-6 carbon atoms, particularly preferably unsubstituted alkyl having 1-6 car- bon atoms (particularly, methyl).

$R^{69}$ is preferably unsubstituted or substituted alkyl having 1-6 carbon atoms, preferably alkyl having 1-6 carbon atoms (particularly, methyl) substituted, by unsubstituted alkyl having 1-6 carbon atoms (particularly, methyl) or unsubstituted alkyl having 1-6 carbon atoms (particularly, methyl)-O—.

$R^{610}$ is preferably a hydrogen atom or unsubstituted or substituted alkyl having 1-6 carbon atoms, more preferably a hydrogen atom.

$R^{611}$ is preferably a hydrogen atom or unsubstituted or substituted alkyl having 1-6 carbon atoms, more preferably a hydrogen atom.

$R^7$ is preferably a hydrogen atom, unsubstituted or substituted alkyl having 1-6 carbon atoms, more preferably unsubstituted or substituted alkyl having 1-6 carbon atoms, particularly preferably unsubstituted alkyl having 1-6 car- bon atoms (particularly, methyl).

$R^{8a}$ is preferably a hydrogen atom.

$R^{8b}$ is preferably a halogen atom, hydroxy or unsubstituted or substituted alkyl having 1-3 carbon atoms, more preferably hydroxy.

$R^{8c}$ is preferably a hydrogen atom, a halogen atom or unsubstituted or substituted alkyl having 1-3 carbon atoms, more preferably a hydrogen atom.

$R^{8d}$ is preferably a hydrogen atom, a halogen atom or unsubstituted or substituted alkyl having 1-3 carbon atoms, more preferably a hydrogen atom.

The steric configuration of $R^{8b}$ and $R^{8c}$ is preferably

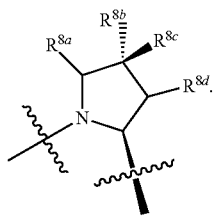

L is a group obtained by freely selecting and combining 1-50 from —C($R^{L1}$)($R^{L2}$)—, —C($R^{L3}$)=C($R^{L4}$)—, —S—, —N($R^{L5}$)—, —SO—, —SO$_2$— and

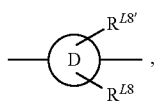

the number of ring D is preferably 5 at maximum, a group obtained by freely selecting and combining —C($R^{L1}$) ($R^{L2}$)— in the number of 0-20, —C($R^{L3}$)=C($R^{L4}$)— in the number of 0-1, —O— in the number of 0-10, —S— in the number of 0-1, —N($R^{L5}$)— in the number of 0-1, and

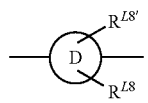

in the number of 0-3 is more preferable, and all or one part of L does not show —O—O—, —S—S—, —N($R^{L5}$)—N($R^{L5}$)—, —O—S—, —S—O—, —O—N($R^{L5}$)—, —N($R^{L5}$)—O—, —S—N($R^{L5}$)— or —N($R^{L5}$)—S—.

$R^{L1}$ is preferably a hydrogen atom, a halogen atom, hydroxy, oxo, unsubstituted or substituted alkyl having 1-6 carbon atoms or unsubstituted or substituted alkyl having 1-6 carbon atoms-O—, more preferably a hydrogen atom, a halogen atom (particularly, fluorine atom), oxo or unsubstituted alkyl having 1-6 carbon atoms (particularly, methyl).

$R^{L2}$ is preferably a hydrogen atom, a halogen atom or unsubstituted or substituted alkyl having 1-6 carbon atoms, more preferably a hydrogen atom or a halogen atom (particularly, fluorine atom).

In another preferable embodiment, $R^{L1}$ and $R^{L2}$ are joined to form —CH$_2$—CH$_2$—.

$R^{L3}$ is preferably a hydrogen atom, a halogen atom or unsubstituted or substituted alkyl having 1-6 carbon atoms, more preferably a hydrogen atom.

$R^{L4}$ is preferably a hydrogen atom, a halogen atom or unsubstituted or substituted alkyl having 1-6 carbon atoms, more preferably a hydrogen atom.

$R^{L5}$ is preferably a hydrogen atom, unsubstituted or substituted alkyl having 1-6 carbon atoms or unsubstituted or substituted alkyl having 1-6 carbon atoms-CO—, more preferably a hydrogen atom or unsubstituted or substituted alkyl having 1-6 carbon atoms, particularly preferably a hydrogen atom or unsubstituted alkyl having 1-6 carbon atoms (particularly, methyl).

$R^{L8}$ is preferably a hydrogen atom, a halogen atom, cyano, hydroxy, oxo, unsubstituted or substituted alkyl having 1-6 carbon atoms or unsubstituted or substituted alkyl having 1-6 carbon atoms-O—, more preferably a hydrogen atom, a halogen atom (particularly, fluorine atom, chlorine atom), cyano, oxo, unsubstituted or substituted alkyl having 1-6 carbon atoms (particularly, methyl, trifluoromethyl, hydroxymethyl) or unsubstituted or substituted alkyl having 1-6 carbon atoms (particularly, methyl, trifluoromethyl)-O—.

$R^{L8'}$ is preferably a hydrogen atom or a halogen atom (particularly, fluorine atom), more preferably a hydrogen atom.

Ring D is preferably cycloalkane having 3-6 carbon atoms (e.g., cyclopropane, cyclobutane), optionally partially reduced aromatic hydrocarbon having 6-10 carbon atoms (e.g., benzene), a hetero ring having 1-6 hetero atoms selected from a nitrogen atom, an oxygen atom and a sulfur atom and containing 3 to 10 ring-constituting atoms (e.g., azetidine, pyrrolidine, piperidine, piperazine, tetrahydropyridine, dihydroindole, dihydroquinoline, dihydroisoquinoline, thiophene, pyrazole, pyridine, pyrimidine, pyrazine, benzofuran, benzopyrazole, benzoxazole, benzothiazole) or a bicyclo ring having 4-12 carbon atoms (e.g., bicyclo[1.1.1]pentane), more preferably aromatic hydrocarbon having 6-10 carbon atoms or a hetero ring having 1-6 hetero atoms selected from a nitrogen atom, an oxygen atom and a sulfur atom and containing 3 to 10 ring-constituting atoms, particularly preferably benzene, pyrrolidine, benzofuran, benzoxazole or benzothiazole. Besides these, preferable examples of ring D include preferable examples of ring $D^a$, ring $D^b$ and ring $D^c$ shown below. Cycloalkane having 3-6 carbon atoms in ring D, ring $D^a$, ring $D^b$ and ring $D^c$ is preferably cycloalkane having 4-6 carbon atoms.

Preferable embodiments of L include

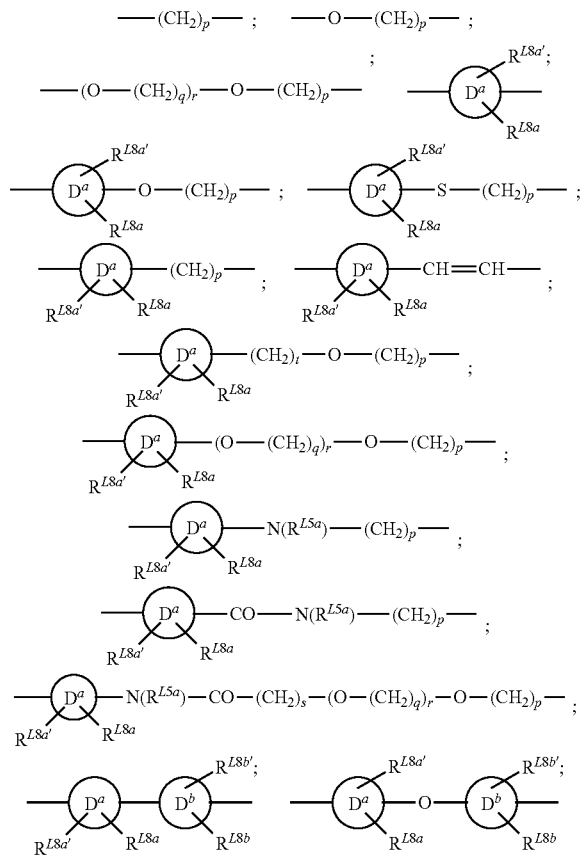

-continued

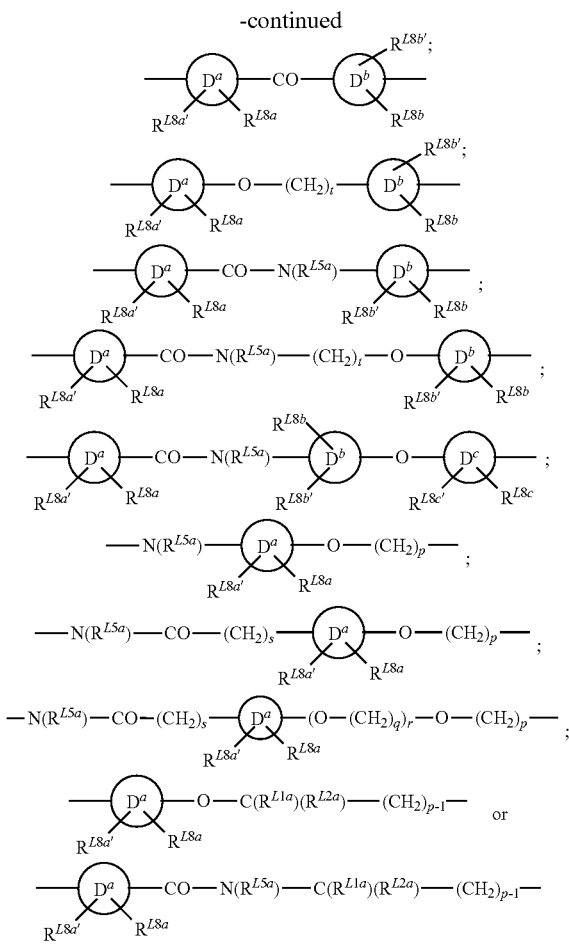

wherein a left bond is bonded to a benzene ring, and a right bond is bonded to substituent W. More preferable embodiments include

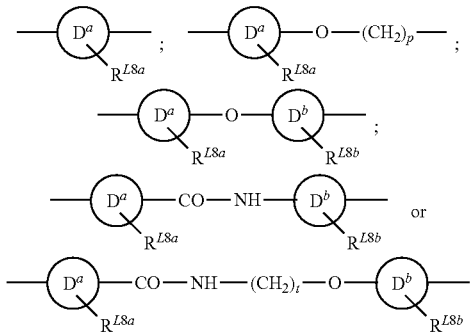

wherein a left bond is bonded to a benzene ring, and a right bond is bonded to substituent W.

p is preferably an integer of 1-3, more preferably 1.
q is preferably 2.
r is preferably 1, 2, 3, 4 or 7.
s is preferably 2.
t is preferably 1 or 2, more preferably 2.

Ring $D^a$, ring $D^b$ and ring $D^c$ are the same or different and each is independently cycloalkane having 3-6 carbon atoms, benzene, azetidine, pyrrole, dihydropyrrole, pyrrolidine, furan, dihydrofuran, tetrahydrofuran, thiophene, dihydrothiophene, tetrahydrothiophene, pyridine, dihydropyridine, tetrahydropyridine, piperidine, pyrazole, dihydropyrazole, tetrahydropyrazole, isoxazole, dihydroisoxazole, tetrahydroisoxazole, oxazole, dihydrooxazole, tetrahydrooxazole, isothiazole, dihydroisothiazole, tetrahydroisothiazole, thiazole, dihydrothiazole, tetrahydrothiazole, pyridazine, dihydropyridazine, tetrahydropyridazine, hexahydropyridazine, pyrimidine, dihydropyrimidine, tetrahydropyrimidine, hexahydropyrimidine, pyrazine, dihydropyrazine, tetrahydropyrazine, piperazine, benzopyrrole, dihydrobenzopyrrole, benzopyrrolidine, benzofuran, dihydrobenzofuran, benzothiophene, dihydrobenzothiophene, benzopyridine, dihydrobenzopyridine, benzopiperidine, benzopyrazole, dihydrobenzopyrazole, benzisoxazole, dihydrobenzisoxazole, benzoxazole, dihydrobenzoxazole, benzisothiazole, dihydrobenzisothiazole, benzothiazole, dihydrobenzothiazole, benzopyridazine, dihydrobenzopyridazine, tetrahydrobenzopyridazine, benzopyrimidine, dihydrobenzopyrimidine, tetrahydrobenzopyrimidine, benzopyrazine, dihydrobenzopyrazine, benzopiperazine or a bicyclo ring having 4-12 carbon atoms, more preferably cycloalkane having 3-6 carbon atoms, benzene, azetidine, pyrrole, dihydropyrrole, pyrrolidine, thiophene, dihydrothiophene, tetrahydrothiophene, pyridine, dihydropyridine, tetrahydropyridine, piperidine, pyrazole, dihydropyrazole, tetrahydropyrazole, pyrimidine, dihydropyrimidine, tetrahydropyrimidine, hexahydropyrimidine, pyrazine, dihydropyrazine, tetrahydropyrazine, piperazine, benzopyrrole, dihydrobenzopyrrole, benzopyrrolidine, benzofuran, dihydrobenzofuran, benzopyridine, dihydrobenzopyridine, benzopiperidine, benzopyrazole, dihydrobenzopyrazole, benzoxazole, dihydrobenzoxazole, benzothiazole, dihydrobenzothiazole or a bicyclo ring having 4-12 carbon atoms.

Ring $D^a$ is more preferably benzene, azetidine, pyrrole, dihydropyrrole, pyrrolidine, thiophene, dihydrothiophene, tetrahydrothiophene, pyridine, dihydropyridine, tetrahydropyridine, piperidine, pyrazole, dihydropyrazole, tetrahydropyrazole, pyrimidine, dihydropyrimidine, tetrahydropyrimidine, hexahydropyrimidine, pyrazine, dihydropyrazine, tetrahydropyrazine, piperazine, benzopyrrole, dihydrobenzopyrrole, benzopyrrolidine, benzofuran, dihydrobenzofuran, benzopyridine, dihydrobenzopyridine, benzopiperidine, benzopyrazole, dihydrobenzopyrazole, benzoxazole, dihydrobenzoxazole, benzothiazole or dihydrobenzothiazole, further preferably benzene, azetidine, pyrrolidine, thiophene, pyridine, tetrahydropyridine, piperidine, pyrazole, pyrimidine, pyrazine, piperazine, benzopyrrolidine, benzofuran, benzopiperidine, benzopyrazole, benzoxazole or benzothiazole, particularly preferably benzene, pyrrolidine, benzoxazole or benzothiazole.

Ring $D^b$ is more preferably cycloalkane having 3-6 carbon atoms, benzene, pyrrole, dihydropyrrole, pyrrolidine, pyridine, dihydropyridine, tetrahydropyridine, piperidine, pyrazine, dihydropyrazine, tetrahydropyrazine, piperazine, benzofuran, dihydrobenzofuran or a bicyclo ring having 4-12 carbon atoms, further preferably cycloalkane having 3-6 carbon atoms, benzene, pyrrolidine, pyridine, piperidine, pyrazine, benzofuran or a bicyclo ring having 4-12 carbon atoms, particularly preferably benzofuran.

Ring $D^c$ is more preferably benzofuran or dihydrobenzofuran, further preferably benzofuran.

In preferable embodiments, ring $D^a$ and ring $D^b$ are the same or different and each is independently benzene, pyrrolidine, benzofuran or benzoxazole.

$R^{L1a}$ is preferably unsubstituted alkyl having 1-6 carbon atoms or a halogen atom, more preferably methyl or a halogen atom.

$R^{L2a}$ is preferably a hydrogen atom or a halogen atom.

$R^{L5a}$ is preferably a hydrogen atom or unsubstituted alkyl having 1-6 carbon atoms, more preferably a hydrogen atom or methyl, particularly preferably a hydrogen atom.

$R^{L8a}$ is preferably a hydrogen atom, a halogen atom, cyano, oxo, unsubstituted or substituted alkyl having 1-3 carbon atoms or unsubstituted or substituted alkyl having 1-3 carbon atoms-O—, more preferably a hydrogen atom, a halogen atom, cyano, oxo, unsubstituted alkyl having 1-3 carbon atoms, alkyl having 1-3 carbon atoms and substituted by a halogen atom or hydroxy, unsubstituted alkyl having 1-3 carbon atoms-O— or alkyl having 1-3 carbon atoms and substituted by a halogen atom-O—, particularly preferably a hydrogen atom, a halogen atom or cyano.

$R^{L8a'}$ is preferably a hydrogen atom or a halogen atom, more preferably a hydrogen atom.

$R^{L8b}$, $R^{L8b'}$, $R^{L8c}$ and $R^{L8c'}$ are each preferably a hydrogen atom.

In addition to the above, a preferable embodiment of L is —C≡C—.

W is preferably

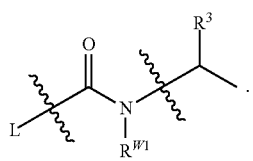

(Wa)

$R^{w1}$ is preferably a hydrogen atom or unsubstituted or substituted alkyl having 1-6 carbon atoms, more preferably a hydrogen atom.

Both X and Y are preferably nitrogen atoms.

Preferable examples of a compound represented by the formula (I) include the following compounds.

[Compound I-A]

A compound represented by the formula (I) wherein A is the following formula

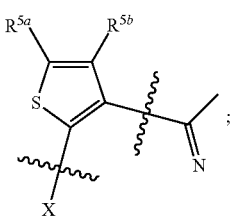

(Aa)

$R^{1a}$ and $R^{1b}$ are the same or different and each is independently
a hydrogen atom or
an unsubstituted or substituted heterocyclic group having 1 to 6 hetero atoms selected from a nitrogen atom, an oxygen atom and a sulfur atom and containing 3 to 10 ring-constituting atoms (e.g., thiazolyl);

$R^2$ is
a hydrogen atom or
unsubstituted or substituted alkyl having 1-6 carbon atoms (e.g., methyl);

$R^3$ is unsubstituted or substituted alkyl having 1-6 carbon atoms (e.g., 1,1-dimethylethyl);

$R^{4a}$ and $R^{4b}$ are each a hydrogen atom;

$R^{5a}$ and $R^{5b}$ are the same or different and each is independently unsubstituted or substituted alkyl having 1-6 carbon atoms (e.g., methyl);

$R^6$ is
hydroxy,
unsubstituted or substituted alkyl having 1-6 carbon atoms (e.g., methyl, ethyl),
—(CH$_2$)$_k$—CO—OR$^{61}$,
—(CH$_2$)$_m$—CO—N(R$^{62}$)(R$^{63}$)
—(CH$_2$)$_n$—R$^{64}$,
—N(R$^{65}$)—CO—OR$^{66}$,
—N(R$^{65}$)—CO—N(R$^{67}$)(R$^{68}$),
—N(R$^{65}$)—CO—R$^{69}$ or
—N(R$^{610}$)(R$^{611}$);

k, m and n are each is an integer of 1-4;

$R^{62}$, $R^{63}$, $R^{67}$ and $R^{68}$ are the same or different and each is independently
a hydrogen atom,
unsubstituted or substituted alkyl having 1-6 carbon atoms (e.g., methyl, ethyl) or
unsubstituted or substituted alkyl having 1-6 carbon atoms (e.g., n-propyl)-O-unsubstituted or substituted alkyl having 1-6 carbon atoms (e.g., ethyl);

$R^{64}$ is unsubstituted or substituted heteroaryl having 1 to 6 hetero atoms selected from a nitrogen atom, an oxygen atom and a sulfur atom and containing 5 to 10 ring-constituting atoms (e.g., oxadiazolyl);

$R^7$ is unsubstituted or substituted alkyl having 1-6 carbon atoms (e.g., methyl);

$R^{8a}$ is a hydrogen atom; or $R^{8b}$, $R^{8c}$ and $R^{8d}$ are the same or different and each is independently
a hydrogen atom or
hydroxy;

L is a group obtained by freely selecting and combining 1-50 from
—C(R$^{L1}$)(R$^{L2}$)—,
—C(R$^{L3}$)=C(R$^{L4}$)—,
—C≡C—,
—O—,
—S—,
—N(R$^{L5}$)—, and

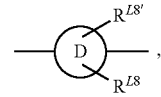

the number of ring D is 5 at maximum and all or one part of L does not show —O—O—, —S—S—, —N(R$^{L5}$)—N(R$^{L5}$)—, —O—S—, —S—O—, —O—N(R$^{L5}$)—, —N(R$^{L5}$)—O—, —S—N(R$^{L5}$)— or —N(R$^{L5}$)—S—;

ring D is
cycloalkane having 3-6 carbon atoms (e.g., cyclopropane, cyclobutane),
optionally partially reduced aromatic hydrocarbon having 6-10 carbon atoms (e.g., benzene),
a hetero ring having 1-6 hetero atoms selected from a nitrogen atom, an oxygen atom and a sulfur atom and containing 3 to 10 ring-constituting atoms (e.g., azetidine, pyrrolidine, piperidine, piperazine, tetrahydropyridine, dihydroindole, dihydroquinoline, dihydroisoquinoline, thiophene, pyrazole, pyridine, pyrimidine, pyrazine, benzofuran, benzopyrazole, benzoxazole, benzothiazole) or
a bicyclo ring having 4-12 carbon atoms (e.g., bicyclo[1.1.1]pentane);

$R^{L1}$, $R^{L2}$, $R^{L8}$ and $R^{L8'}$ are the same or different and each is independently a hydrogen atom, a halogen atom (e.g., fluorine atom, chlorine atom), cyano, oxo, provided that when $R^{L1}$ is oxo, then $R^{L2}$ is absent, unsubstituted or substituted alkyl having 1-6 carbon atoms (e.g., methyl) or unsubstituted or substituted alkyl having 1-6 carbon atoms (e.g., methyl)-O—;

$R^{L3}$ and $R^{L4}$ are each a hydrogen atom;

$R^{L5}$ is a hydrogen atom or unsubstituted or substituted alkyl having 1-6 carbon atoms (e.g., methyl);

W is the following formula (Wa)

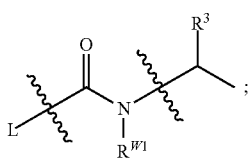

(Wa)

X is a nitrogen atom and Y is a nitrogen atom;

$R^{61}$, $R^{65}$, $R^{66}$, $R^{610}$, $R^{611}$ and $R^{w1}$ are the same or different and each is independently a hydrogen atom or unsubstituted or substituted alkyl having 1-6 carbon atoms (e.g., methyl, ethyl, tert-butyl);

$R^{69}$ is unsubstituted or substituted alkyl having 1-6 carbon atoms (e.g., methyl);

when alkyl having 1-6 carbon atoms is substituted, it is substituted by one or two or more groups selected from a halogen atom (e.g., fluorine atom), hydroxy and alkyl having 1-6 carbon atoms (e.g., methyl)-O—, when a heterocyclic group having 1 to 6 hetero atoms selected from a nitrogen atom, an oxygen atom and a sulfur atom and containing 3 to 10 ring-constituting atoms; and heteroaryl having 1 to 6 hetero atoms selected from a nitrogen atom, an oxygen atom and a sulfur atom and containing 5 to 10 ring-constituting atoms are substituted, they are substituted by one or two or more groups selected from alkyl having 1-6 carbon atoms (e.g., methyl).

[Compound I-B]

A compound represented by the formula (I) wherein A is the following formula

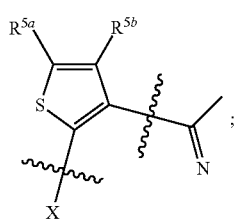

(Aa)

$R^{1a}$ is an unsubstituted or substituted heterocyclic group having 1 to 6 hetero atoms selected from a nitrogen atom, an oxygen atom and a sulfur atom and containing 3 to 10 ring-constituting atoms (e.g., thiazolyl);

$R^{1b}$ is a hydrogen atom;

$R^2$ is a hydrogen atom or unsubstituted or substituted alkyl having 1-6 carbon atoms (e.g., methyl);

$R^3$ is unsubstituted or substituted alkyl having 1-6 carbon atoms (e.g., 1,1-dimethylethyl);

$R^{4a}$ is a hydrogen atom;

$R^{4b}$ is a hydrogen atom;

$R^{5a}$ is unsubstituted or substituted alkyl having 1-6 carbon atoms (e.g., methyl);

$R^{5b}$ is unsubstituted or substituted alkyl having 1-6 carbon atoms (e.g., methyl);

$R^6$ is hydroxy, unsubstituted or substituted alkyl having 1-6 carbon atoms (e.g., methyl, ethyl), —$(CH_2)_k$—CO—$OR^{61}$, —$(CH_2)_m$—CO—$N(R^{62})(R^{63})$, —$(CH_2)_n$—$R^{64}$,

—$N(R^{65})$—CO—$OR^{66}$,

—$N(R^{65})$—CO—$N(R^{67})(R^{68})$,

—$N(R^{65})$—CO—$R^{69}$ or

—$N(R^{610})(R^{611})$;

k, m and n are each an integer of 1-4;

$R^{61}$ is unsubstituted or substituted alkyl having 1-6 carbon atoms (e.g., methyl);

$R^{62}$ is unsubstituted or substituted alkyl having 1-6 carbon atoms (e.g., ethyl) or unsubstituted or substituted alkyl having 1-6 carbon atoms (e.g., n-propyl)-O— unsubstituted or substituted alkyl having 1-6 carbon atoms (e.g., ethyl);

$R^{63}$ is a hydrogen atom;

$R^{64}$ is unsubstituted or substituted heteroaryl having 1 to 6 hetero atoms selected from a nitrogen atom, an oxygen atom and a sulfur atom and containing 5 to 10 ring-constituting atoms (e.g., oxadiazolyl);

$R^{65}$ is a hydrogen atom or unsubstituted or substituted alkyl having 1-6 carbon atoms (e.g., methyl);

$R^{66}$ is unsubstituted or substituted alkyl having 1-6 carbon atoms (e.g., methyl, ethyl, tert-butyl);

$R^{67}$ is unsubstituted or substituted alkyl having 1-6 carbon atoms (e.g., methyl);

$R^{68}$ is unsubstituted or substituted alkyl having 1-6 carbon atoms (e.g., methyl);

$R^{69}$ is unsubstituted or substituted alkyl having 1-6 carbon atoms (e.g., methyl);

$R^{610}$ is a hydrogen atom;

$R^{611}$ is a hydrogen atom;

$R^7$ is unsubstituted or substituted alkyl having 1-6 carbon atoms (e.g., methyl);

$R^{8a}$ is a hydrogen atom;

$R^{8b}$ is hydroxy;

$R^{8c}$ is a hydrogen atom;

$R^{8d}$ is a hydrogen atom;

L is a group obtained by freely selecting and combining 1-50 from

—$C(R^{L1})(R^{L2})$—,

—$C(R^{L3})$=$C(R^{L4})$—,

—C≡C—,

—O—,

—S—,

—$N(R^{L5})$—, and

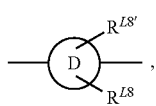

the number of ring D is 5 at maximum and all or one part of L does not show —O—O—, —S—S—, —N($R^{L5}$)—N($R^{L5}$)—, —O—S—, —S—O—, —O—N($R^{L5}$)—, —N($R^{L5}$)—O—, —S—N($R^{L5}$)— or —N($R^{L5}$)—S—;

ring D is cycloalkane having 3-6 carbon atoms (e.g., cyclopropane, cyclobutane), optionally partially reduced aromatic hydrocarbon having 6-10 carbon atoms (e.g., benzene), a hetero ring having 1-6 hetero atoms selected from a nitrogen atom, an oxygen atom and a sulfur atom and containing 3 to 10 ring-constituting atoms (e.g., azetidine, pyrrolidine, piperidine, piperazine, tetrahydropyridine, dihydroindole, dihydroquinoline, dihydroisoquinoline, thiophene, pyrazole, pyridine, pyrimidine, pyrazine, benzofuran, benzopyrazole, benzoxazole, benzothiazole) or a bicyclo ring having 4-12 carbon atoms (e.g., bicyclo [1.1.1]pentane);

$R^{L1}$ is a hydrogen atom, a halogen atom (e.g., fluorine atom), oxo, provided that when $R^{L1}$ is oxo, then $R^{L2}$ is absent, or unsubstituted or substituted alkyl having 1-6 carbon atoms (e.g., methyl);

$R^{L2}$ is a hydrogen atom or a halogen atom (e.g., fluorine atom);

$R^{L3}$ is a hydrogen atom;

$R^{L4}$ is a hydrogen atom;

$R^{L5}$ is a hydrogen atom or unsubstituted or substituted alkyl having 1-6 carbon atoms (e.g., methyl);

$R^{L8}$ is a hydrogen atom, a halogen atom (e.g., fluorine atom, chlorine atom), cyano, oxo, unsubstituted or substituted alkyl having 1-6 carbon atoms (e.g., methyl) or unsubstituted or substituted alkyl having 1-6 carbon atoms (e.g., methyl)-O—;

$R^{L8'}$ is a hydrogen atom or a halogen atom (e.g., fluorine atom);

W is the following formula (Wa)

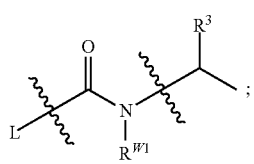
(Wa)

$R^{w1}$ is a hydrogen atom;

X is a nitrogen atom and Y is a nitrogen atom;

when alkyl having 1-6 carbon atoms is substituted, it is substituted by one or more groups selected from a halogen atom (e.g., fluorine atom), hydroxy and alkyl having 1-6 carbon atoms (e.g., methyl)-O—, when a heterocyclic group having 1 to 6 hetero atoms selected from a nitrogen atom, an oxygen atom and a sulfur atom and containing 3 to 10 ring-constituting atoms; and heteroaryl having 1 to 6 hetero atoms selected from a nitrogen atom, an oxygen atom and a sulfur atom and containing 5 to 10 ring-constituting atoms are substituted, they are substituted by one or two or more groups selected from alkyl having 1-6 carbon atoms (e.g., methyl).

[Compound I-C]

A compound represented by the formula (I) wherein A is the following formula

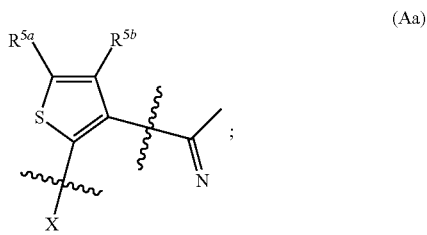
(Aa)

$R^{1a}$ and $R^{1b}$ are the same or different and each is independently a hydrogen atom or an unsubstituted or substituted heterocyclic group having 1 to 6 hetero atoms selected from a nitrogen atom, an oxygen atom and a sulfur atom and containing 3 to 10 ring-constituting atoms (e.g., thiazolyl);

$R^2$ is a hydrogen atom or unsubstituted or substituted alkyl having 1-6 carbon atoms (e.g., methyl);

$R^3$ is unsubstituted or substituted alkyl having 1-6 carbon atoms (e.g., 1,1-dimethylethyl);

$R^{4a}$ and $R^{4b}$ are each a hydrogen atom;

$R^{5a}$ and $R^{5b}$ are the same or different and each is independently unsubstituted or substituted alkyl having 1-6 carbon atoms (e.g., methyl);

$R^6$ is hydroxy, unsubstituted or substituted alkyl having 1-6 carbon atoms (e.g., methyl), —$(CH_2)_k$—CO—$OR^{61}$, —N($R^{65}$)—CO—$OR^{66}$ or

—N($R^{65}$)—CO—$R^{69}$;

k is an integer of 1-4;

$R^7$ is unsubstituted or substituted alkyl having 1-6 carbon atoms (e.g., methyl);

$R^{8a}$ is a hydrogen atom;

$R^{8b}$, $R^{8c}$ and $R^{8d}$ are the same or different and each is independently a hydrogen atom or hydroxy;

L is a group obtained by freely selecting and combining 1-50 from

—C($R^{L1}$)($R^{L2}$)—

—C($R^{L3}$)=C($R^{L4}$)—,

—C≡C—,

—O—,

—S—,

—N($R^{L5}$)—, and

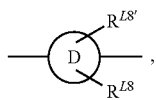

the number of ring D is 5 at maximum and all or one part of L does not show —O—O—, —S—S—, —N(R$^{L5}$)—N(R$^{L5}$)—, —O—S—, —S—O—, —O—N(R$^{L5}$)—, —N(R$^{L5}$)—O—, —S—N(R$^{L5}$)— or —N(R$^{L5}$)—S—;

ring D is optionally partially reduced aromatic hydrocarbon having 6-10 carbon atoms (e.g., benzene) or a hetero ring having 1-6 hetero atoms selected from a nitrogen atom, an oxygen atom and a sulfur atom and containing 3 to 10 ring-constituting atoms (e.g., pyrrolidine, dihydroindole, dihydroquinoline, dihydroisoquinoline, thiophene, pyridine, benzofuran, benzoxazole, benzothiazole);

R$^{L1}$, R$^{L2}$, R$^{L8}$ and R$^{L8'}$ are the same or different and each is independently a hydrogen atom, a halogen atom (e.g., fluorine atom, chlorine atom), cyano, oxo, provided that when R$^{L1}$ is oxo, then R$^{L2}$ is absent, unsubstituted or substituted alkyl having 1-6 carbon atoms (e.g., methyl) or unsubstituted or substituted alkyl having 1-6 carbon atoms (e.g., methyl)-O—;

R$^{L3}$ and R$^{L1}$ are each a hydrogen atom;

R$^{L5}$ is a hydrogen atom;

W is the following formula (Wa)

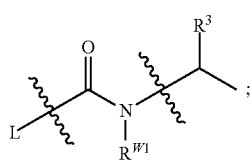

(Wa)

X is a nitrogen atom and Y is a nitrogen atom;

R$^{61}$, R$^{65}$, R$^{66}$ and R$^{w1}$ are the same or different and each is independently a hydrogen atom or unsubstituted or substituted alkyl having 1-6 carbon atoms (e.g., methyl);

R$^{69}$ is unsubstituted or substituted alkyl having 1-6 carbon atoms (e.g., methyl);

when alkyl having 1-6 carbon atoms is substituted, it is substituted by one or two or more groups selected from a halogen atom (e.g., fluorine atom) and hydroxy, when a heterocyclic group having 1 to 6 hetero atoms selected from a nitrogen atom, an oxygen atom and a sulfur atom and containing 3 to 10 ring-constituting atoms is substituted, it is substituted by one or two or more groups selected from alkyl having 1-6 carbon atoms (e.g., methyl).

[Compound I-D]

A compound represented by the formula (I) wherein A is the following formula

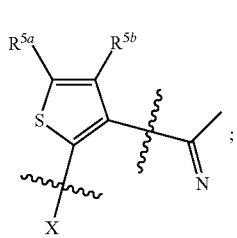

(Aa)

R$^{1a}$ is an unsubstituted or substituted heterocyclic group having 1 to 6 hetero atoms selected from a nitrogen atom, an oxygen atom and a sulfur atom and containing 3 to 10 ring-constituting atoms (e.g., thiazolyl);

R$^{1b}$ is a hydrogen atom;

R$^2$ is a hydrogen atom or unsubstituted or substituted alkyl having 1-6 carbon atoms (e.g., methyl);

R$^3$ is unsubstituted or substituted alkyl having 1-6 carbon atoms (e.g., 1,1-dimethylethyl);

R$^{4a}$ is a hydrogen atom;

R$^{4b}$ is a hydrogen atom;

R$^{5a}$ is unsubstituted or substituted alkyl having 1-6 carbon atoms (e.g., methyl);

R$^{5b}$ is unsubstituted or substituted alkyl having 1-6 carbon atoms (e.g., methyl);

R$^6$ is hydroxy, unsubstituted or substituted alkyl having 1-6 carbon atoms (e.g., methyl), —(CH$_2$)$_k$—CO—OR$^{61}$, —N(R$^{65}$)—CO—OR$^{66}$ or

—N(R$^{65}$)—CO—R$^{69}$;

k is an integer of 1-4;

R$^{61}$ is unsubstituted or substituted alkyl having 1-6 carbon atoms (e.g., methyl);

R$^{65}$ is a hydrogen atom or unsubstituted or substituted alkyl having 1-6 carbon atoms (e.g., methyl);

R$^{66}$ is unsubstituted or substituted alkyl having 1-6 carbon atoms (e.g., methyl);

R$^{69}$ is unsubstituted or substituted alkyl having 1-6 carbon atoms (e.g., methyl);

R$^7$ is unsubstituted or substituted alkyl having 1-6 carbon atoms (e.g., methyl);

R$^{8a}$ is a hydrogen atom;

R$^{8b}$ is hydroxy;

R$^{8c}$ is a hydrogen atom;

R$^{8d}$ is a hydrogen atom;

L is a group obtained by freely selecting and combining 1-50 from

—C(R$^{L1}$)(R$^{L2}$)—,

—C(R$^{L3}$)=C(R$^{L4}$)—,

—C≡C—,

—O—,

—S—,

—N(R$^{L5}$)—, and

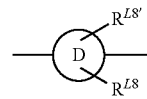

the number of ring D is 5 at maximum and all or one part of L does not show —O—O—, —S—S—, —N($R^{L5}$)—N($R^{L5}$)—, —O—S—, —S—O—, —O—N($R^{L5}$)—N($R^{L5}$)—O—, —S—N($R^{L5}$)— or —N($R^{L5}$)—S—;

ring D is optionally partially reduced aromatic hydrocarbon having 6-10 carbon atoms (e.g., benzene) or a hetero ring having 1-6 hetero atoms selected from a nitrogen atom, an oxygen atom and a sulfur atom and containing 3 to 10 ring-constituting atoms (e.g., pyrrolidine, dihydroindole, dihydroquinoline, dihydroisoquinoline, thiophene, pyridine, benzofuran, benzoxazole, benzothiazole);

$R^{L1}$ is a hydrogen atom, a halogen atom (e.g., fluorine atom), oxo, provided that when $R^{L1}$ is oxo, then $R^{L2}$ is absent, or unsubstituted or substituted alkyl having 1-6 carbon atoms (e.g., methyl);

$R^{L2}$ is a hydrogen atom or a halogen atom (e.g., fluorine atom);

$R^{L3}$ is a hydrogen atom;

$R^{L4}$ is a hydrogen atom;

$R^{L5}$ is a hydrogen atom;

$R^{L8}$ is a hydrogen atom, a halogen atom (e.g., fluorine atom, chlorine atom), cyano, oxo, unsubstituted or substituted alkyl having 1-6 carbon atoms (e.g., methyl) or unsubstituted or substituted alkyl having 1-6 carbon atoms (e.g., methyl)-O—;

$R^{L8'}$ is a hydrogen atom;

W is the following formula (Wa)

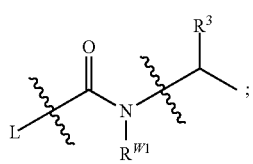

(Wa)

$R^{w1}$ is a hydrogen atom;

X is a nitrogen atom and Y is a nitrogen atom;

when alkyl having 1-6 carbon atoms is substituted, it is substituted by one or two or more groups selected from a halogen atom (e.g., fluorine atom) and hydroxy, when a heterocyclic group having 1 to 6 hetero atoms selected from a nitrogen atom, an oxygen atom and a sulfur atom and containing 3 to 10 ring-constituting atoms is substituted, it is substituted by one or two or more groups selected from alkyl having 1-6 carbon atoms (e.g., methyl).

Specific examples of a compound represented by the formula (I) include the compounds of the below-mentioned Examples 1-224, and preferred are the compounds of Examples 9, 61, 62, 67, 94, 101, 138, 142, 157, 161, 164, 171, 179, 181 and 198.

In the present invention, the "pharmacologically acceptable salt" is not particularly limited as long as it is a pharmaceutically acceptable salt, and examples include salts with inorganic acids, salts with organic acids, salts with alkali metals, salts with alkaline earth metals, salts with inorganic bases, and salts with organic bases. Furthermore, hydrates which are water-containing salts and solvates which are solvent-containing salts are also included in the pharmacologically acceptable salts in the present invention.

In the present specification, "pharmacologically acceptable" means being generally safe and harmless, possibly biologically undesirable but preferable in other aspects, and useful in preparing pharmaceutical compositions including those useful not only for application as medicament for human but also for application in veterinary medicine.

The compounds of the present invention can be produced by the following methods A-H. While these methods and steps may be combined but the production method thereof is not limited thereto.

(Method A)

(1) The production method described here is suitable for producing an intermediate of a compound represented by the formula (I) wherein ring A is represented by the aforementioned formula (Aa), X is a nitrogen atom and Y is a nitrogen atom, namely, the following compound (A-1).

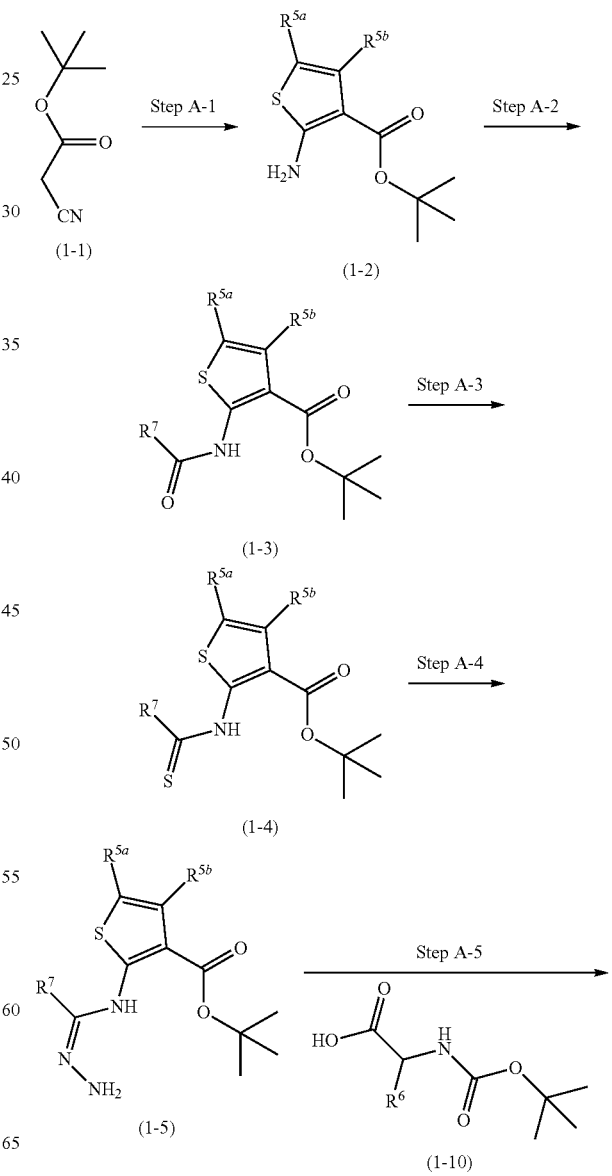

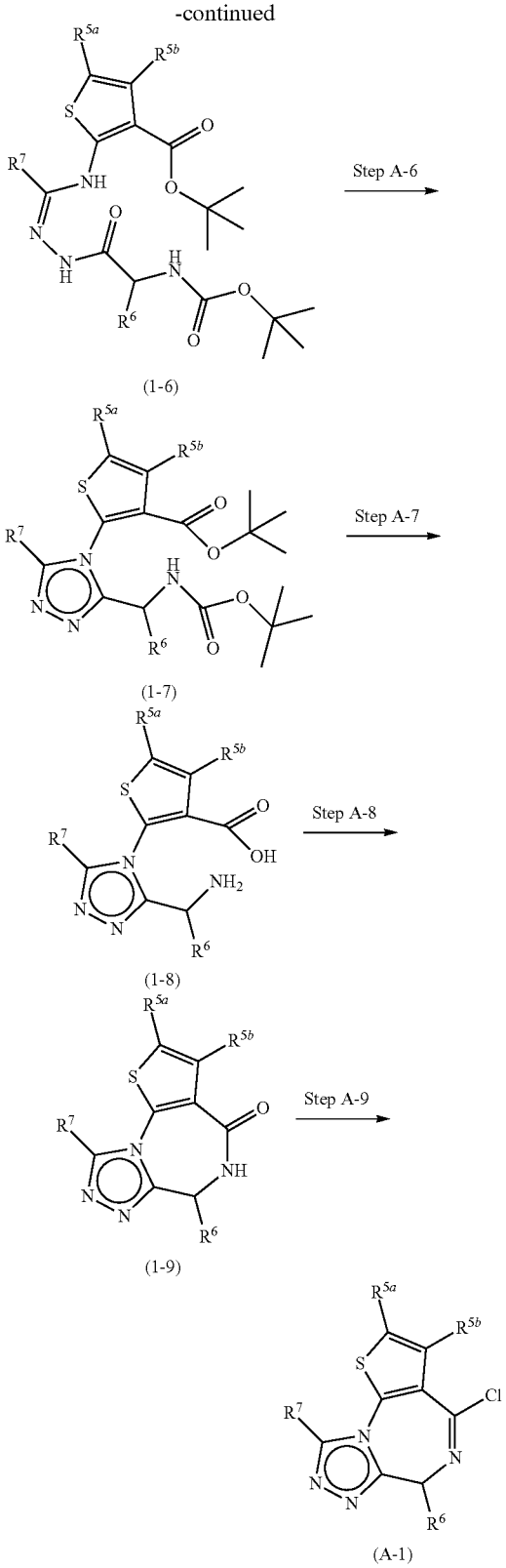

wherein each symbol is as defined above.

Step A-1

Compound (1-2) can be derived from compound (1-1) according to a known method (e.g., J. Med. Chem. 1973, 16, 214-219).

Step A-2

Compound (1-3) can be obtained by acylating compound (1-2). The reaction proceeds using a base in an appropriate solvent at generally from −20° C. to the refluxing temperature of the solvent. While the reaction time varies depending on the starting material and solvent to be used and the reaction temperature, it is generally from 0.5 hr to 24 hr. Examples the acylating agent include trifluoroacetic anhydride, acetic anhydride, propanoic anhydride, acetyl chloride and the like. Examples of the base include triethylamine, pyridine and the like. Examples of the solvent include tetrahydrofuran, dichloromethane, toluene, 1,4-dioxane and the like.

Step A-3

Compound (1-4) can be obtained by thioamidating compound (1-3). The thioamidation reaction proceeds using a sulfating agent in an appropriate solvent generally at room temperature to the refluxing temperature of the solvent. While the reaction time varies depending on the starting material and solvent to be used and the reaction temperature, it is generally from 0.5 hr to 24 hr. Examples of the sulfating agent include Lawesson reagent, diphosphorus pentasulfide and the like. Examples of the solvent include 1,2-dichloroethane, tetrahydrofuran, 1,4-dioxane and the like.

Step A-4

Compound (1-5) can be obtained by reacting compound (1-4) with hydrazine. The reaction with hydrazine proceeds using hydrazine monohydrate in an appropriate solvent generally at room temperature to the refluxing temperature of the solvent. While the reaction time varies depending on the starting material and solvent to be used and the reaction temperature, it is generally from 1 hr to 24 hr. Examples of the solvent include tetrahydrofuran, 1,4-dioxane, N,N-dimethylformamide and the like.

Step A-5

Compound (1-6) can be obtained by converting the carboxylate form (1-10) having a substituent for $R^6$ to acid halide by a halogenating agent, and reacting same with a compound represented by compound (1-5). The reaction proceeds using a base in an appropriate solvent generally from 0° C. to the refluxing temperature of the solvent. While the reaction time varies depending on the starting material and solvent to be used and the reaction temperature, it is generally from 1 hr to 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step A-6

Compound (1-7) can be obtained by a cyclization reaction of compound (1-6). It proceeds in an appropriate solvent generally at room temperature to the refluxing temperature of the solvent. While the reaction time varies depending on the starting material and solvent to be used and the reaction temperature, it is generally from 1 hr to 24 hr. Examples of the solvent include 2-propanol, 1-butanol, tetrahydrofuran and the like.

Step A-7

Compound (1-8) can be obtained by deprotection reaction of compound (1-7). The reaction proceeds using an acid in an appropriate solvent generally at room temperature to the refluxing temperature of the solvent. While the reaction time varies depending on the starting material and solvent to be used and the reaction temperature, it is generally from 1 hr to 24 hr. Examples of the acid include hydrochloric acid, trifluoroacetic acid and the like. Examples of the solvent include ethyl acetate, 1,4-dioxane, tetrahydrofuran, dichloromethane, chloroform and the like.

Step A-8

Compound (1-9) can be obtained by a cyclization reaction of compound (1-8). The reaction proceeds using a condensing agent in the presence of a suitable base in a suitable solvent at 0° C. to the refluxing temperature of the solvent. While the reaction time varies depending on the starting material and solvent to be used and the reaction temperature, it is generally from 1 hr to 24 hr. Examples of the condensing agent include 1-ethyl-3-(3-dimethylaminopropyl)carbodiimide hydrochloride (WSC.HCl), 1-[bis(dimethylamino)methylene]-1H-1,2,3-triazolo[4,5-b]pyridinium 3-oxido-hexafluorophosphate (HATU), 4-(4,6-dimethoxy[1.3.5]triazin-2-yl)-4-methylmorpholinium chloride hydrate (DMT-MM), 2-chloro-1-methylpyridinium iodide and the like. Examples of the solvent include methanol, N,N-dimethylformamide, chloroform, dichloromethane, tetrahydrofuran and the like. The reaction is sometimes accelerated by adding 1-hydroxybenzotriazole (HOBt). Examples of the base include triethylamine, N,N-diisopropylethylamine, pyridine and the like.

step A-9

Compound (A-1) can be obtained by halogenating compound (1-9). The reaction proceeds using a halogenating agent generally at room temperature to the refluxing temperature of the solvent. While the reaction time varies depending on the starting material and solvent to be used and the reaction temperature, it is generally from 1 hr to 24 hr. Examples of the halogenating agent include phosphoryl chloride and the like.

(2) The production method described here is suitable for producing an intermediate of a compound represented by the formula (I) wherein ring A is represented by the aforementioned formula (Ac), X is a nitrogen atom and Y is a nitrogen atom, namely, the following compound (A-2).

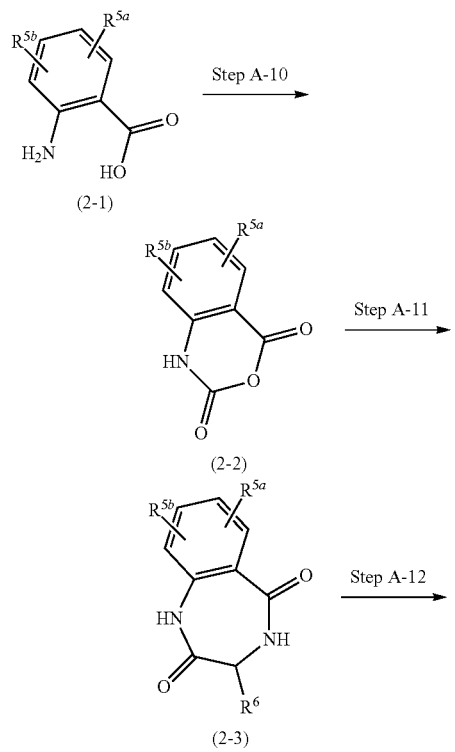

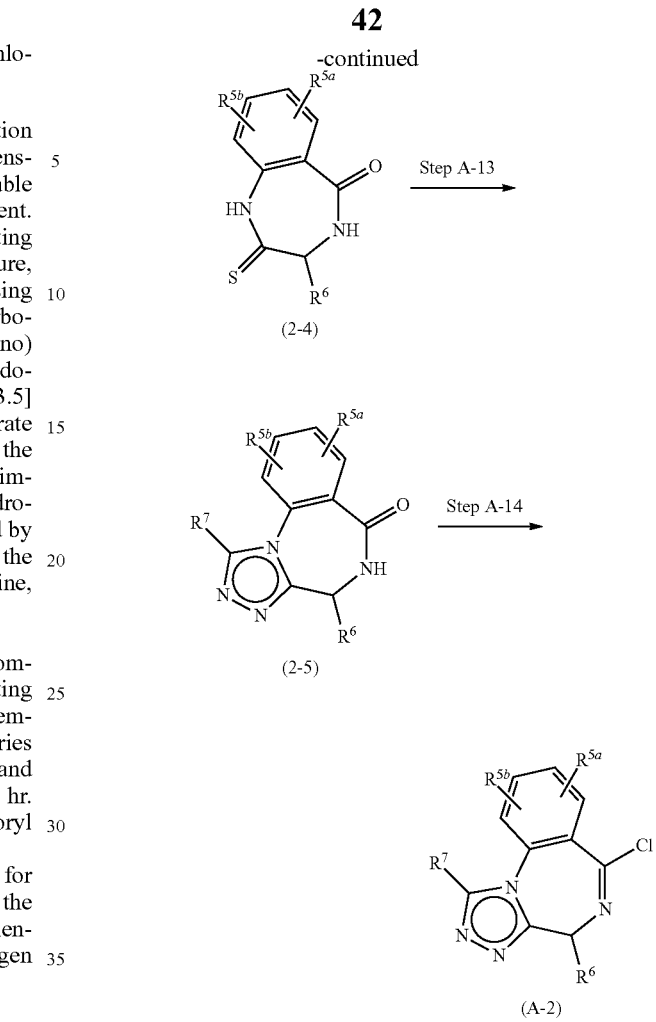

wherein each symbol is as defined above.

Compound (A-2) can be derived from compound (2-1) according to a known method (e.g., J. Med. Chem. 2016, 59, 1426).

(3) The production method described here is suitable for producing an intermediate of a compound represented by the formula (I) wherein X is a carbon atom and Y is an oxygen atom, namely, the following compound (A-3).

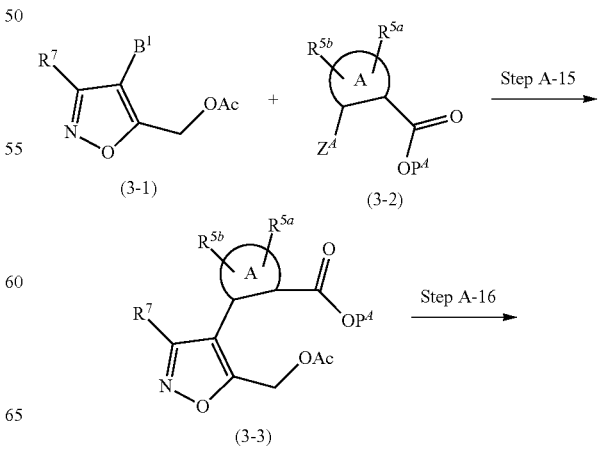

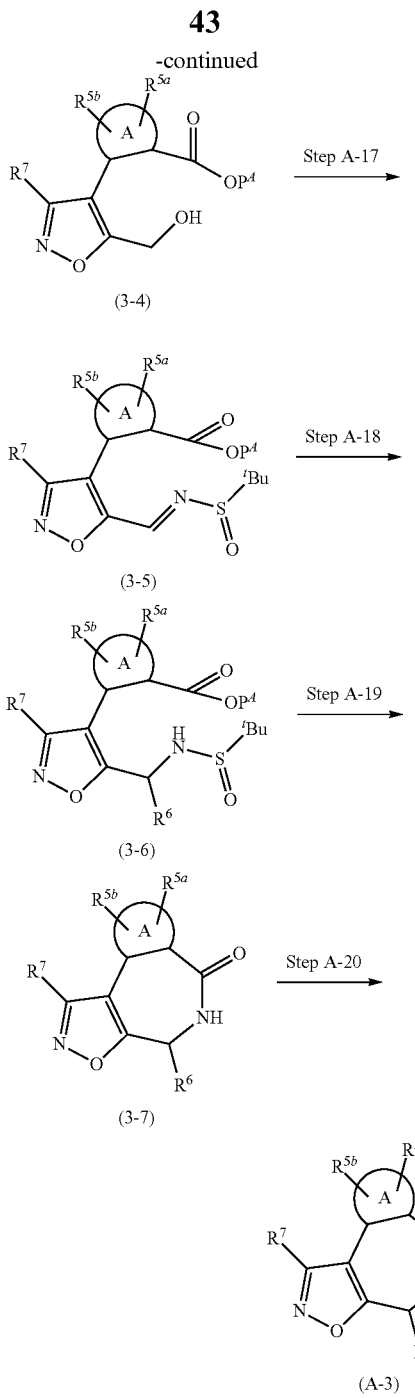

(3-4)

(3-5)

(3-6)

(3-7)

(A-3)

wherein B¹ is boronic acid or boronic acid ester optionally having substituent(s), $Z^A$ is a halogen atom, $P^4$ is a protecting group, and other symbols are as defined above.

In the formula, the boronic acid ester optionally having substituent(s) for B¹ is pinacolatoboron, neopentylglycolatoboron or the like, and the halogen atom for $Z^A$ is a chlorine atom, a bromine atom or an iodine atom. In the formula, the protecting group for $P^4$ protects carboxyl group and is not particularly limited as long as compound (3-7) is obtained. For example, alkyl (specifically methyl, ethyl) and the like can be mentioned.

Compound (A-3) can be derived from compound (3-1) according to a known method (e.g., WO 2012/075383).

(Method B)

(1)

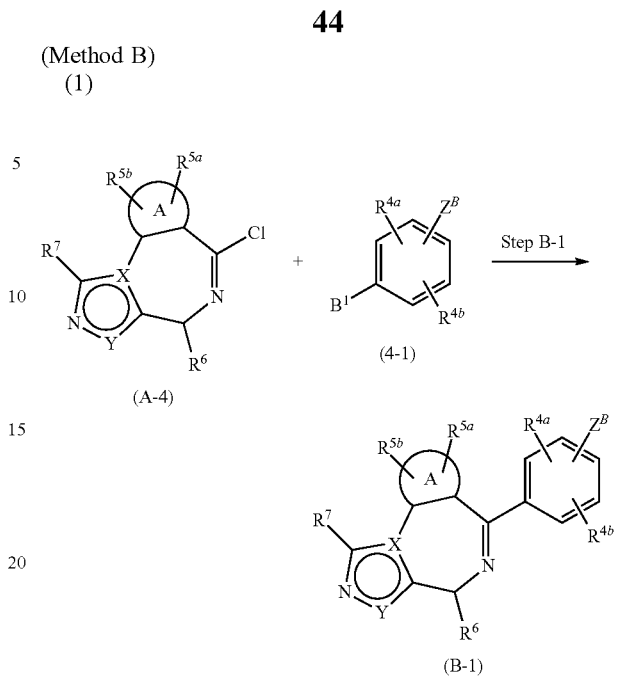

(A-4)

(4-1)

(B-1)

wherein $Z^B$ is a chlorine atom or a hydroxyl group, and other symbols are as defined above.

Step B-1

Compound (B-1) can be obtained by a coupling reaction of compound (A-4) with boronic acid derivative (4-1). The reaction preferably proceeds in the presence of a palladium catalyst, a phosphine ligand and a base in a suitable solvent at 0° C. to under heating, particularly at room temperature to the boiling point of the solvent. While the reaction time varies depending on the starting material and solvent to be used and the reaction temperature, it is generally from 1 hr to 24 hr. Examples of the palladium catalyst include palladium(II) acetate, palladium(II) chloride, tris(dibenzylideneacetone)dipalladium(0) or chloroform adduct thereof and the like. Examples of the phosphine ligand include triphenylphosphine, 2-(dicyclohexylphosphino)-2',4',6'-triisopropyl-1,1'-biphenyl, 2-(dicyclohexylphosphino)-3,6-dimethoxy-2',4',6'-triisopropyl-1,1'-biphenyl, 2-(dicyclohexyl phosphino)-2,6-diisopropoxy-1,1'-biphenyl, 2-di-tert-butylphosphino-2'-4'-6'-triisopropylbiphenyl, 2-dicyclohexylphosphino-2'-6'-dimethoxybiphenyl, 2-(dicyclohexylphosphino)-2-(N,N-dimethylamino)biphenyl, tri-orthotolylphosphine, 2-(dicyclohexylphosphino)biphenyl, 2-(di-tert-butylphosphino)biphenyl, 2-(di-tert-butylphosphino)-1, 1-binaphthyl, tri-tert-butylphosphine, tri-tert-butylphosphonium tetrafluoroborate and the like. A reagent in which a palladium catalyst and a phosphine ligand form a complex may also be used and, for example, tetrakis (triphenylphosphine)palladium(0), 1,1-bis(diphenylphosphino)ferrocene-palladium(II) dichloride, dichlorobis(triphenylphosphine)palladium(II), dichlorobis (tricyclohexylphosphine)palladium(II), bis(tri-tert-butylphosphine)palladium(0), chloro(2-dicyclohexylphosphino-2',4',6'-triisopropyl-1,1'-biphenyl) (2'-amino-1,1'-biphenyl-2-yl)palladium(II), [(2-dicyclohexylphosphino-3,6-dimethoxy-2',4',6'-triisopropyl-1,1'-biphenyl)-2-(2'-amino-1,1'-biphenyl)palladium(II) methanesulfonate, (2-dicyclohexylphosphino-2,6-diisopropoxy-1,1'-biphenyl)[2-(2'-amino-1,1'-biphenyl)]palladium(II) methanesulfonate, [(2-di-tert-butylphosphino-3,6-dimethoxy-2',4',6'-triisopropyl-1,1'-biphenyl)-2-(2'-amino-1,1'-biphenyl)palladium(II) methanesulfonate and the like. Examples of the base include tert-butoxy sodium, potassium acetate, tripotassium phosphate, cesium carbonate, potassium carbonate, sodium hydrogen carbonate, triethylamine, diisopropylethylamine, dicyclohexylethylamine, potassium fluoride, cesium fluoride and the like. Examples of the solvent include ether solvents such as tetrahydrofuran, 1,2-dimethoxyethane, 1,4-dioxane and the like, alcohol solvents such as methanol, ethanol, propanol, butanol and the like, N,N-dimethylformamide, or a mixed solvent of the organic solvent and water and the like.

(2) The production method described here is suitable for producing an intermediate of a compound represented by the formula (I) wherein X is a nitrogen atom and Y is a nitrogen atom, namely, the following compound (B-2).

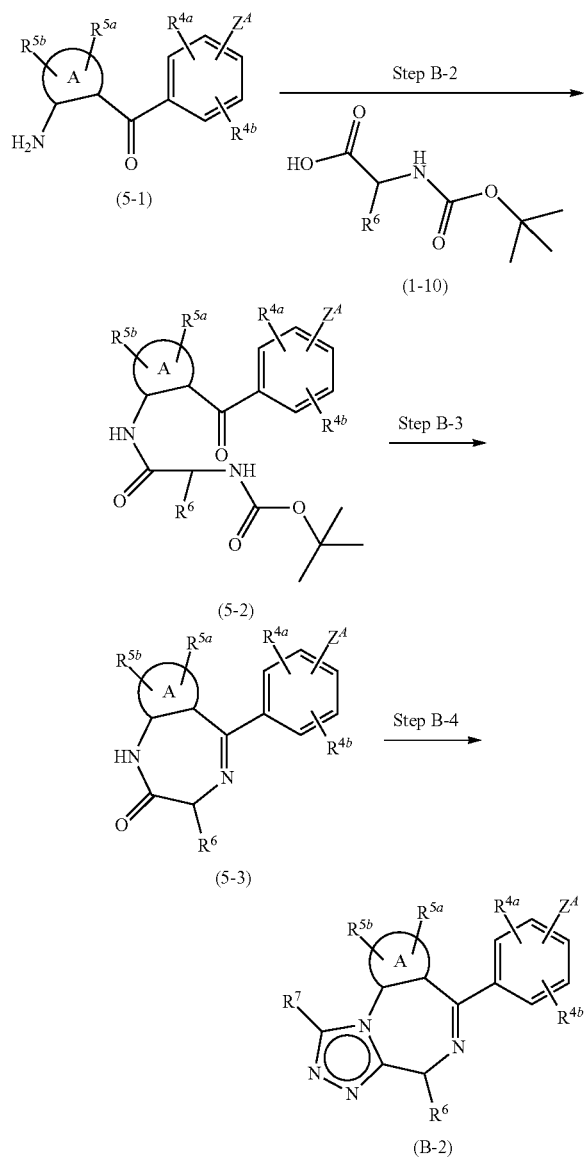

wherein each symbol is as defined above.

Step B-2

Compound (5-2) can be obtained by converting a carboxylate form having a substituent for $R^6$ to acid halide by a halogenating agent and reacting same with compound (5-1). The reaction proceeds using a base in an appropriate solvent generally at −20° C. to the refluxing temperature of the solvent. While the reaction time varies depending on the starting material and solvent to be used and the reaction temperature, it is generally from 0.5 hr to 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step B-3

Compound (5-3) can be obtained by deprotection reaction and cyclization reaction of compound (5-2). The deprotection reaction proceeds using an acid in an appropriate solvent generally at 0° C. to the refluxing temperature of the solvent. While the reaction time varies depending on the starting material and solvent to be used and the reaction temperature, it is generally from 0.5 hr to 24 hr. Examples of the acid include trifluoroacetic acid, hydrochloric acid and the like. Examples of the solvent include dichloromethane, chloroform, tetrahydrofuran and the like. This reaction can also be performed using an acid alone. The cyclization reaction proceeds using an acid in an appropriate solvent generally at room temperature to the refluxing temperature of the solvent. While the reaction time varies depending on the starting material and solvent to be used and the reaction temperature, it is generally from 0.5 hr to 24 hr. Examples of the acid include trifluoroacetic acid, acetic acid and the like. Examples of the solvent include tetrahydrofuran, N,N-dimethylformamide, 1-butanol, 2-propanol and the like.

Step B-4

Compound (B-2) can be obtained from compound (5-3) by the following two methods.

A first one can be obtained by hydrazine addition, acylation and cyclization reaction. The reaction with hydrazine proceeds using a base and hydrazine in an appropriate solvent generally at 0° C. to room temperature. Examples of the base include sodium hydride, tert-butoxy sodium, tert-butoxy potassium and the like. The acylation reaction proceeds using an acylating agent in an appropriate solvent generally at room temperature to the refluxing temperature of the solvent. While the reaction time varies depending on the starting material and solvent to be used and the reaction temperature, it is generally from 0.5 hr to 24 hr. Examples of the acylating agent include trifluoroacetic anhydride, acetic anhydride, propanoic anhydride and the like. Examples of the solvent include tetrahydrofuran, 1,4-dioxane, N,N-dimethylformamide, dichloromethane and the like. The above-mentioned reaction can also be performed using acylhydrazide instead of using hydrazine, acid chloride and acid anhydride. Examples of the acylhydrazide include acetylhydrazine and the like. The cyclization reaction proceeds using an acid in an appropriate solvent generally at room temperature to the refluxing temperature of the solvent. While the reaction time varies depending on the starting material and solvent to be used and the reaction temperature, it is generally from 0.5 hr to 24 hr. Examples of the acid include acetic acid, trifluoroacetic acid and the like. Examples of the solvent include tetrahydrofuran, N,N-dimethylformamide, 1-butanol, 2-propanol and the like. This reaction proceeds after addition of hydrazine and using the corresponding ortho ester form in an appropriate solvent generally at room temperature to the refluxing temperature of the solvent. While the reaction time varies depending on the starting material and solvent to be used and the reaction temperature, it is generally from 0.5 hr to 24 hr. Examples of the ortho ester form include 1,1,1-triethoxyethane, 1,1,1-trimethoxypentane and the like. Examples of the solvent include toluene, tetrahydrofuran and the like.

A second one can be obtained by converting amide group to thioamide group, and performing hydrazine addition, acylation and cyclization reaction. The thioamidation reaction proceeds using a sulfating agent in an appropriate solvent generally at room temperature to the refluxing temperature of the solvent. While the reaction time varies depending on the starting material and solvent to be used and the reaction temperature, it is generally from 0.5 hr to 24 hr. Examples of the sulfating agent include Lawesson reagent, diphosphorus pentasulfide and the like. Examples of the solvent include 1,2-dichloroethane, tetrahydrofuran, 1,4-dioxane and the like. The hydrazine addition reaction proceeds using hydrazine in an appropriate solvent generally at room temperature to the refluxing temperature of the solvent. While the reaction time varies depending on the starting material and solvent to be used and the reaction temperature, it is generally from 1 hr to 24 hr. Examples of the solvent include tetrahydrofuran, 1,4-dioxane, N,N-dimethylformamide and the like. The acylation reaction proceeds using an acylating agent in an appropriate solvent generally at room temperature to the refluxing temperature of the solvent. While the reaction time varies depending on the starting material and solvent to be used and the reaction temperature, it is generally from 1 hr to 24 hr. Examples of the acylating agent include trifluoroacetic anhydride, acetic anhydride, propanoic anhydride and the like. The above-mentioned reaction can also be performed using acylhydrazide instead of using hydrazine, acid chloride and acid anhydride. Examples of the acylhydrazide include acetylhydrazine and the like. Examples of the solvent include tetrahydrofuran, N,N-dimethylformamide and the like. The cyclization reaction proceeds using an acid in an appropriate solvent generally at room temperature to the refluxing temperature of the solvent. While the reaction time varies depending on the starting material and solvent to be used and the reaction temperature, it is generally from 0.5 hr to 24 hr.

Examples of the acid include acetic acid, trifluoroacetic acid and the like. Examples of the solvent include tetrahydrofuran, N,N-dimethylformamide, 1-butanol, 2-propanol and the like. This reaction proceeds after addition of hydrazine by using the corresponding ortho ester form in an appropriate solvent generally at room temperature to the refluxing temperature of the solvent. While the reaction time varies depending on the starting material and solvent to be used and the reaction temperature, it is generally from 0.5 hr to 24 hr. Examples of the ortho ester form include 1,1,1-triethoxyethane, 1,1,1-trimethoxypentane and the like. Examples of the solvent include toluene, tetrahydrofuran and the like.

(3) An intermediate of a compound represented by the formula (I) wherein X is a nitrogen atom and Y is a nitrogen atom, namely, the following compound (B-2) can also be synthesized by the following method.

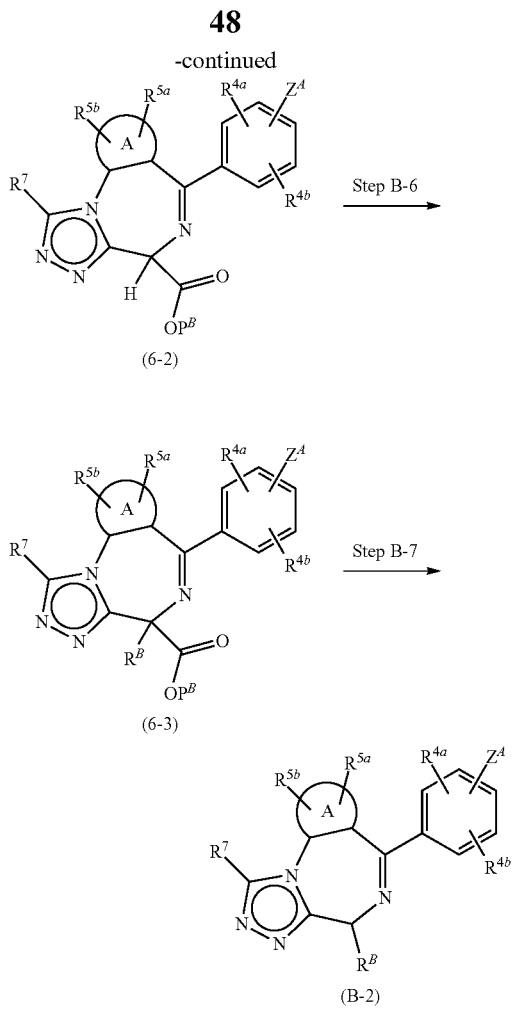

wherein $P^B$ is a protecting group, and other symbols are as defined above.

In the formula, $P^B$ is not particularly limited as long as it protects a carboxyl group. For example, alkyl (specifically methyl, ethyl, tert-butyl and the like), aralkyl (benzyl and the like) and the like can be mentioned.

Compound (B-2) can also be synthesized from compound (6-1) according to a method described in a known method (e.g., WO 1993/007129, WO 1998/011111).

(4) The production method described here is suitable for producing an intermediate of a compound represented by the formula (I) wherein $R^6$ is —N($R^{65}$)—CO—O$R^{66}$, —N($R^{65}$)—CO—N($R^{67}$)($R^{68}$) or —N($R^{65}$)—CO—$R^{69}$, namely, the following compound (B-3), compound (B-4).

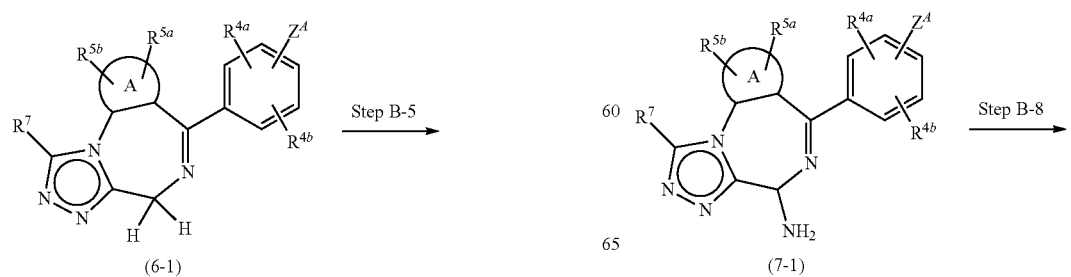

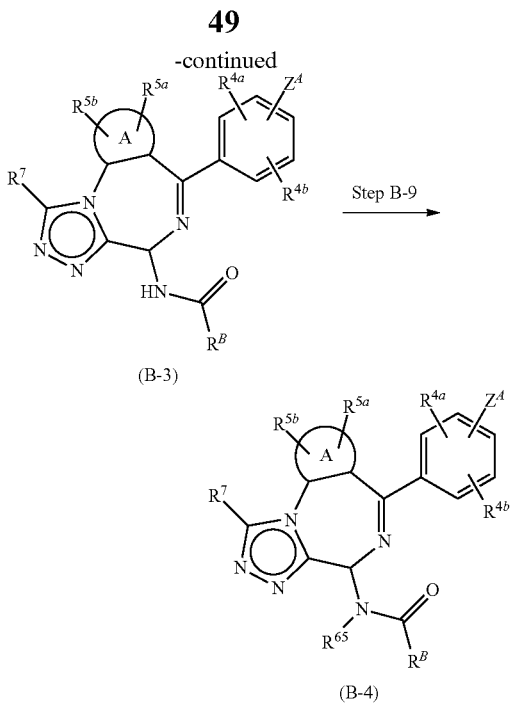

(B-3)

(B-4)

wherein $R^B$ is —$OR^{66}$, —$N(R^{67})(R^{68})$ or —$R^{69}$, and other respective symbols $R^{66}$, $R^{67}$, $R^{68}$ and $R^{69}$ are as defined above.

Step B-8

Compound (B-3) can be obtained by the following three methods from compound (7-1) synthesized according to a known method (e.g., JP-A-7-17941).

A first one is a method including reacting compound (7-1) with the corresponding acid halide (e.g., Cl—CO—$OR^{66}$, Cl—CO—$N(R^{67})(R^{68})$, or Cl—CO—$R^{69}$) or acid anhydride (e.g., $R^{66}$O—CO—O—CO—$OR^{66}$, or $R^{69}$—CO—O—CO—$R^{69}$). The reaction proceeds using a base in a suitable solvent generally at −20° C. to the refluxing temperature of the solvent. While the reaction time varies depending on the starting material and solvent to be used, the reaction temperature and the like, it is generally from 30 min to 24 hr. Examples of the base include triethylamine, N,N-diisopropylethylamine, pyridine and the like. Examples of the solvent include dichloromethane, 1,2-dichloroethane, chloroform, N-methylpyrrolidone, pyridine, toluene and the like. In this reaction, the base to be used can also be used as a solvent.

A second one is a method including condensing compound (7-1) and the corresponding carboxylate form (HO—CO—$R^{69}$) in the presence of a condensing agent. The reaction proceeds using a condensing agent in the presence of a suitable base in a suitable solvent at 0° C. to the refluxing temperature of the solvent. The reaction time and the condensing agent, solvent, reaction promoter and base to be used are the same as those in step A-8.

A third one is a method including converting the corresponding carboxylate form (HO—CO—$R^{69}$) to a mixed acid anhydride with methyl chlorocarbonate, ethyl chlorocarbonate, isobutyloxycarbonyl chloride, pivaloyl chloride or the like, and reacting same with compound (7-1) in a solvent in the presence of a base or in the base serving as a solvent. Examples of the solvent include methanol, ethanol, isopropyl alcohol, butanol, ethylene glycol, tetrahydrofuran, chloroform, N,N-dimethylformamide, toluene and the like. Examples of the base include triethylamine, pyridine, N-methylmorpholine and the like. The reaction temperature is generally 0° C.-100° C. While the reaction time varies depending on the starting material and solvent to be used, the reaction temperature and the like, it is generally from 30 min to 24 hr.

Step B-9

Compound (B-4) can be obtained by alkylating compound (B-3). The alkylation reaction proceeds using a base and an alkylating agent such as alkyl halide and the like in an appropriate solvent at generally 0° C. to the refluxing temperature of the solvent. While the reaction time varies depending on the starting material and solvent to be used and the reaction temperature, it is generally from 10 min to 24 hr. Examples of the base include inorganic bases such as sodium hydride, potassium hydroxide, potassium carbonate and the like, alkoxides such as potassium t-butoxide and the like, and the like. Examples of the solvent include N,N-dimethylformamide, tetrahydrofuran, dimethyl sulfoxide and the like.

(5) The production method described here is suitable for producing an intermediate of a compound represented by the formula (I) wherein $R^6$ is a hydroxyl group, namely, the following compound (B-5).

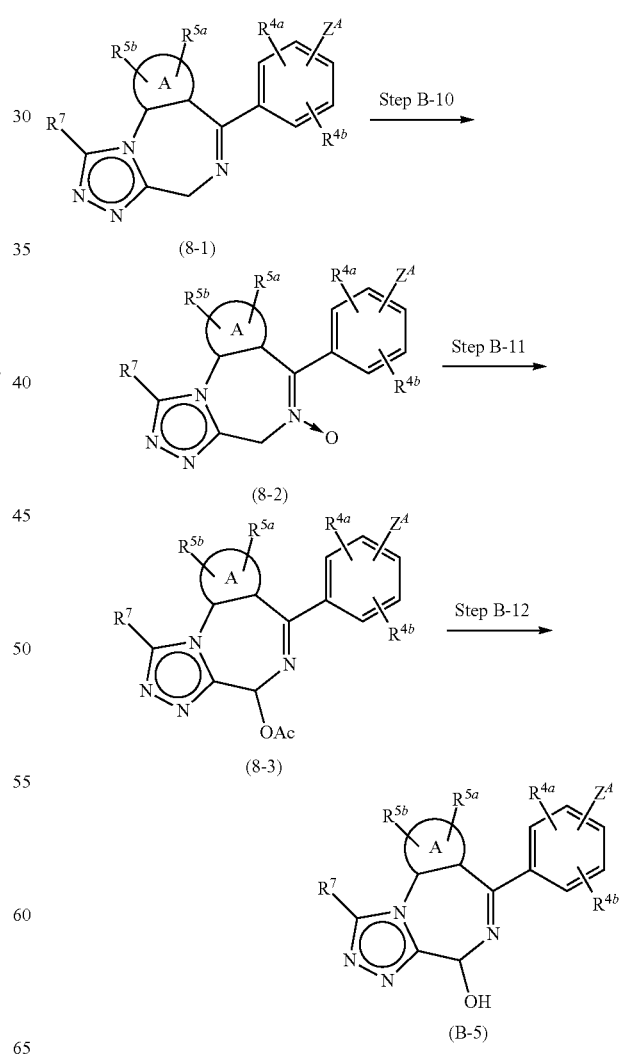

wherein each symbol is as defined above.

Compound (B-5) can be derived from compound (8-1) according to a known method (e.g., U.S. Pat. No. 4,959,361).

(6) The production method described here is suitable for producing an intermediate of a compound represented by the formula (I) wherein $R^6$ is —$(CH_2)_m$—CO—N($R^{62}$)($R^{63}$), namely, the following compound (B-6).

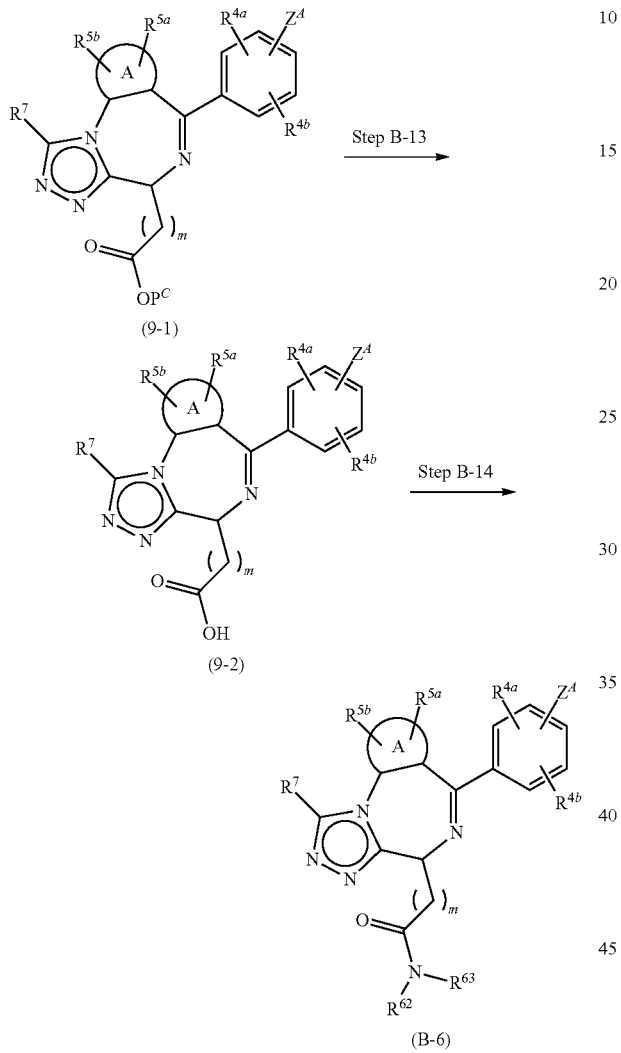

wherein $P^C$ is a hydrogen atom or a protecting group, and other symbols are as defined above.

In the formula, the protecting group for $P^C$ is not particularly limited as long as it protects a carboxyl group.

For example, alkyl (specifically methyl, ethyl, tert-butyl and the like), aralkyl (benzyl and the like) and the like can be mentioned.

Step B-13

Compound (9-2) can be obtained by removing the protecting group $P^C$ of compound (9-1). When $P^C$ is a hydrogen atom, this step can be omitted. The conditions of deprotection are not particularly limited as long as they are used for deprotection of $P^C$. For example, when $P^C$ is methyl or ethyl, a method including using an inorganic base such as sodium hydroxide or the like in a mixed solvent of an alcohol solvent and water can be mentioned. When it is tert-butyl, a method including using an acid such as hydrochloric acid, trifluoroacetic acid or the like, and the like can be mentioned. When $P^C$ is benzyl or substituted benzyl, benzyloxymethyl or the like, a method including using a catalytic hydrogenation reaction can be mentioned.

Step B-14

Compound (B-6) is obtained by condensing compound (9-2) and the corresponding amine having $R^{62}$, $R^{63}$. The reaction proceeds using a condensing agent in the presence of a suitable base in a suitable solvent at 0° C. to the refluxing temperature of the solvent. The reaction time and the condensing agent, solvent, reaction promoter and base to be used are the same as those in step A-8.

(7) The production method described here is suitable for producing an intermediate of a compound represented by the formula (I) wherein ring A is represented by the aforementioned formula (Ab), X is a nitrogen atom and Y is a nitrogen atom, namely, the following compound (B-7).

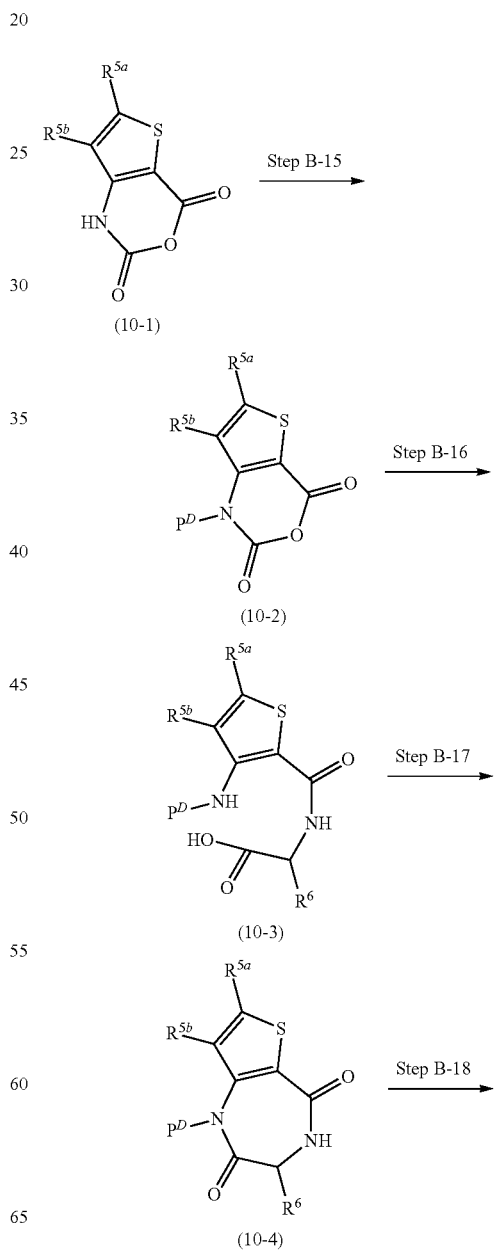

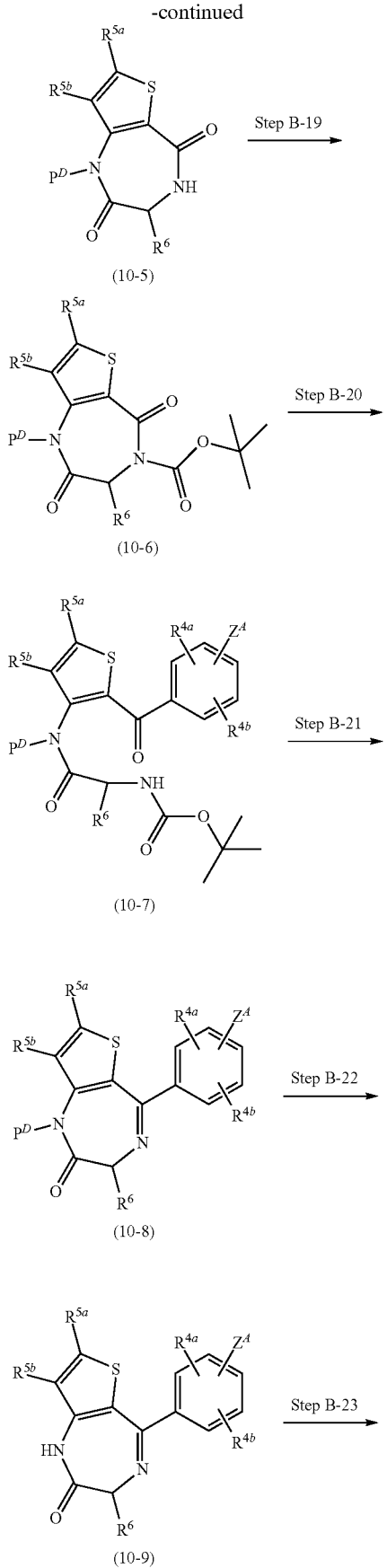

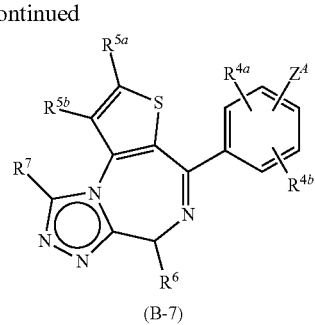

wherein $P^D$ is a protecting group, and other symbols are as defined above.

In the formula, $P^D$ is not particularly limited as long as it protects an amide group to produce compound (10-9). For example, 4-methoxybenzyl group, 2,4-dimethoxybenzyl group and the like can be mentioned.

Compound (B-7) can be synthesized from compound (10-1) according to the method described in SYNLETT, 2008, 15, 2360-2364 and J. Org. Chem., 2009, 74, 4975-4981.

(8) An intermediate of a compound represented by the formula (I) wherein ring A is represented by the aforementioned formula (Aa), X is a nitrogen atom, Y is a nitrogen atom, and $R^{5a}$ is cyanomethyl, namely, the following compound (B-8) can also be synthesized by the following production method.

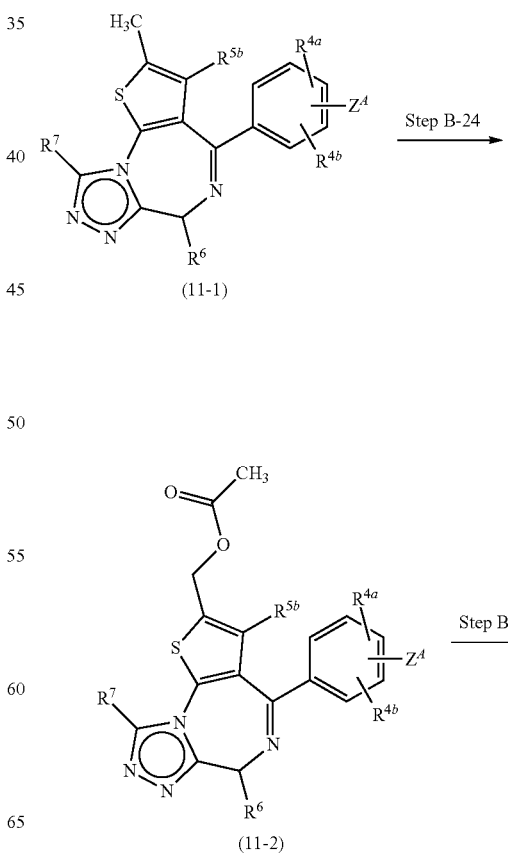

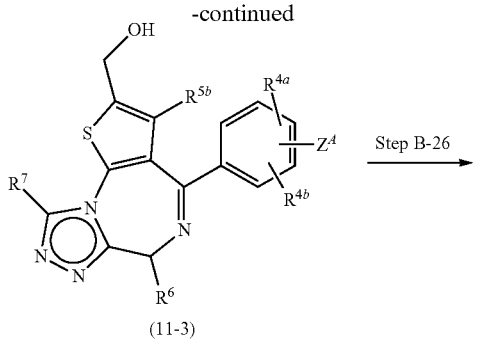

(11-3)

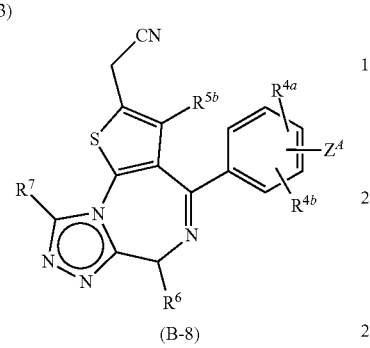

(B-8)

wherein each symbol is as defined above.

Step B-24

Compound (11-2) can be obtained by reacting compound (11-1) with a mixture of magnesium acetate dihydrate, acetic acid, acetic anhydride and concentrated sulfuric acid at room temperature for a suitable time.

Step B-25

Compound (11-3) is obtained by reacting compound (11-2) with a base. The reaction proceeds in an appropriate solvent generally at 0° C. to room temperature. While the reaction time varies depending on the starting material and solvent to be used, the reaction temperature, and the like, it is generally from 0.5 hr to 24 hr. Examples of the base include aqueous sodium hydroxide solution, aqueous potassium hydroxide solution and the like. Examples of the solvent include methanol, ethanol, tetrahydrofuran, 1,4-dioxane and the like.

Step B-26

Compound (B-8) can be obtained by converting a hydroxyl group of compound (11-3) to a leaving group and substituting same with cyano (cyanated). The conversion to the leaving group proceeds using a protecting agent and a base in an appropriate solvent generally at 0° C. to at room temperature. Examples of the protecting agent include p-toluenesulfonyl chloride, mesyl chloride and the like. While the reaction time varies depending on the starting material and solvent to be used, the reaction temperature, and the like, it is generally from 1 hr to 24 hr. Examples of the base include triethylamine, N,N-diisopropylethylamine and the like. Examples of the solvent include dichloromethane, tetrahydrofuran and the like. The cyanation reaction proceeds using a cyanating agent in an appropriate solvent generally at 0° C. to the refluxing temperature of the solvent. While the reaction time varies depending on the starting material and solvent to be used, the reaction temperature, and the like, it is generally from 1 hr to 24 hr. Examples of the cyanating agent include sodium cyanide, trimethylsilyl cyanide and the like. Examples of the solvent include dimethyl sulfoxide, acetonitrile, tetrahydrofuran and the like. When trimethylsilyl cyanide is used, tetrabutylammonium fluoride is used.

(9) An intermediate of a compound represented by the formula (I) wherein ring A is represented by the aforementioned formula (Aa), X is a nitrogen atom, Y is a nitrogen atom, and $R^{5a}$ is alkyl having 1-6 carbon atoms and substituted by cyano, namely, the following compound (B-9) can also be synthesized by the following production method.

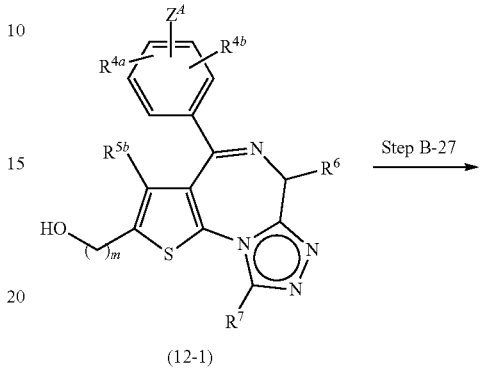

(12-1)

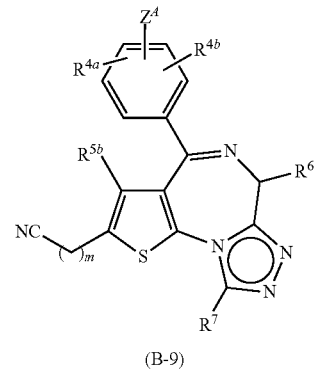

(B-9)

wherein m is any of 1-6, and other symbols are as defined above.

Step B-27

Compound (B-9) can be obtained by cyanating compound (12-1). As the reaction conditions, the conditions similar to those of the aforementioned Step B-26 can be mentioned.

(10) An intermediate of a compound represented by the formula (I) wherein ring A is represented by the aforementioned formula (Aa), X is a nitrogen atom, Y is a nitrogen atom, and $R^{5a}$ is cyano, namely, the following compound (B-10) can be synthesized by the following production method.

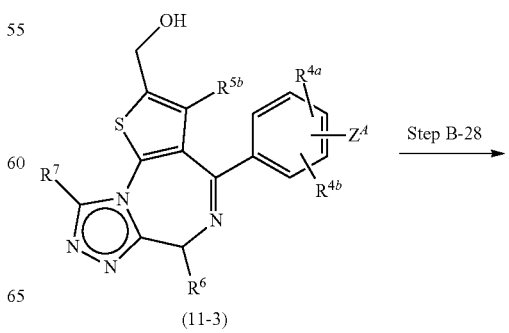

(11-3)

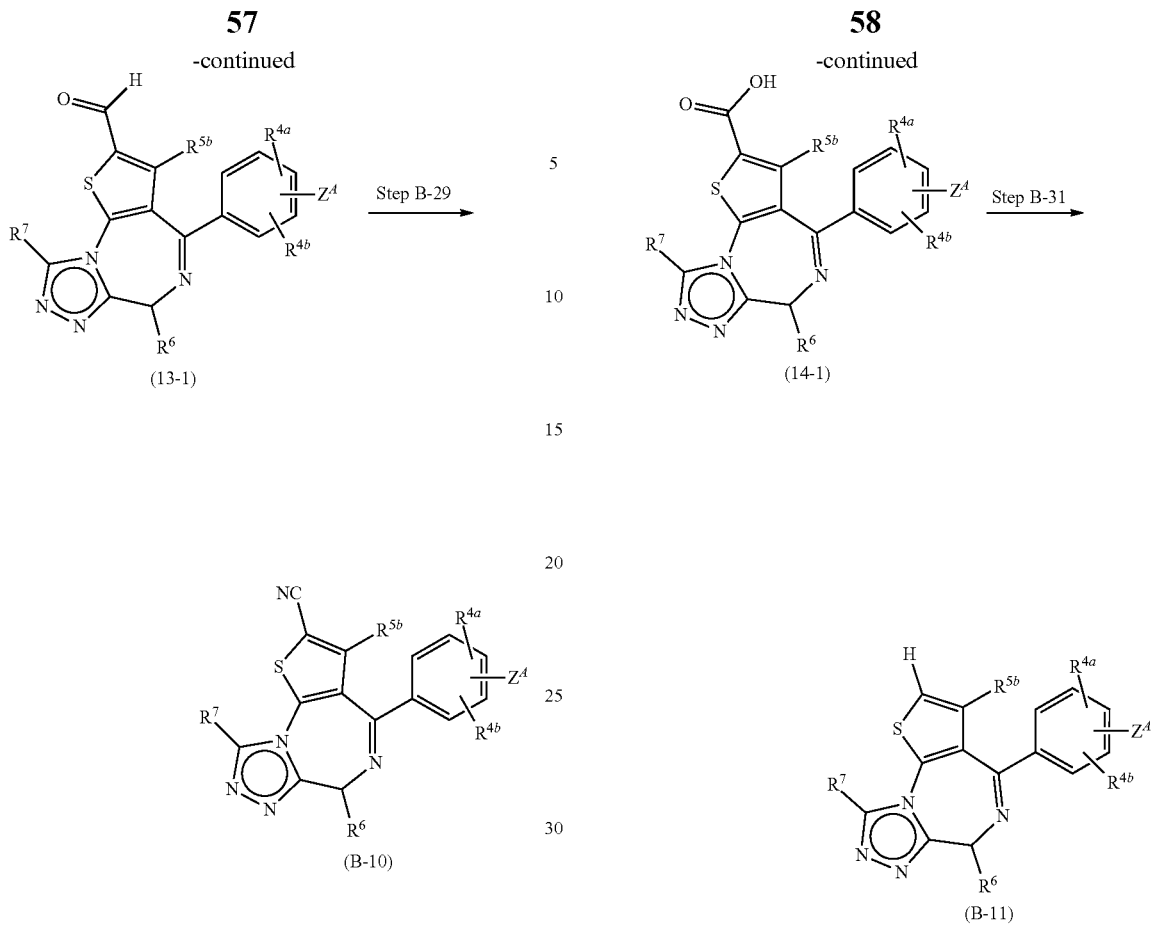

wherein each symbol is as defined above.

Step B-28

Compound (13-1) can be obtained by oxidizing compound (11-3). The reaction conditions are, for example, those for reacting a mixture of manganese dioxide and dichloromethane for a suitable time at room temperature.

Step B-29

Compound (B-10) can be obtained by cyanating compound (13-1). The reaction conditions are, for example, those for reacting a mixture of hydroxylamine hydrochloride and dimethyl sulfoxide for a suitable time under heating.

(11) An intermediate of a compound represented by the formula (I) wherein ring A is represented by the aforementioned formula (Aa), X is a nitrogen atom, Y is a nitrogen atom, and $R^{5a}$ is a hydrogen atom, namely, the following compound (B-11) can be synthesized by the following production method.

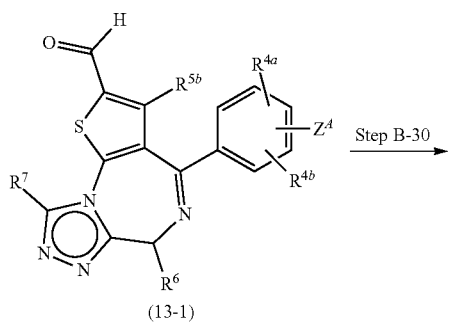

wherein each symbol is as defined above.

Step B-30

Compound (14-1) can be obtained by oxidizing compound (13-1). The reaction proceeds using an oxidant in an appropriate solvent generally at 0° C. to the refluxing temperature of the solvent. While the reaction time varies depending on the starting material and solvent to be used and the reaction temperature, it is generally from 0.5 hr to 24 hr. Examples of the oxidant include hydrogen peroxide, tert-butyl hydroperoxide, sodium chlorite, potassium permanganate and the like. Examples of the solvent include methanol, acetonitrile, water and the like. The reaction proceeds, for example, by adding 35% hydrogen peroxide water, aqueous sodium chlorite solution to a mixture of acetonitrile and aqueous sodium dihydrogen phosphate solution at 0° C. to room temperature.

Step B-31

Compound (B-11) can be obtained by decarboxylating compound (14-1). The reaction conditions are, for example, those for reacting in quinoline in the presence of copper at 150° C.

(Method C)

(1) An intermediate of a compound represented by the formula (I) wherein W is represented by the aforementioned formula (Wa), namely, the following compound (C-1) can also be synthesized by the following method.

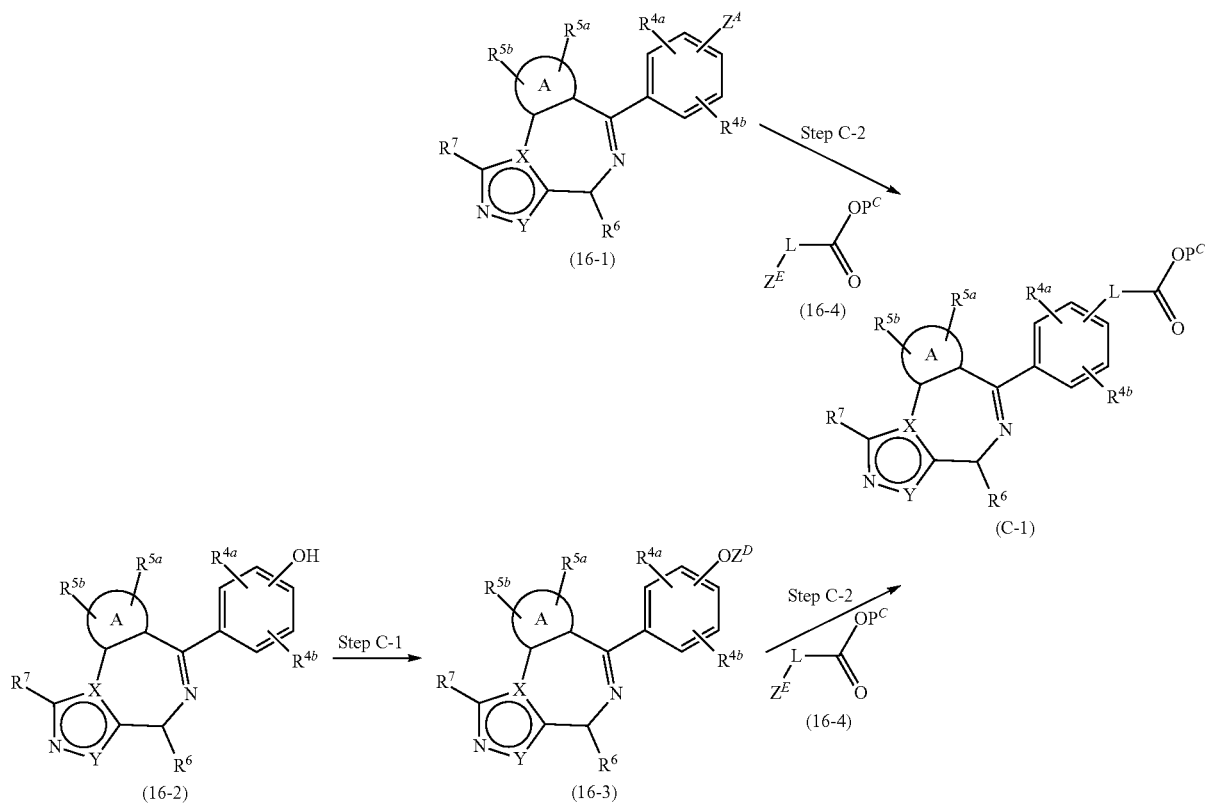

wherein $Z^D$ is a hydroxyl group-activating group, $Z^E$ is a hydrogen atom, a halogen atom, boronic acid or boronic acid ester optionally having substituent(s), and other symbols are as defined above.

In the formula, the halogen atom for $Z^E$ is a chlorine atom, a bromine atom or an iodine atom, and the hydroxyl group-activating group for $Z^D$ is a sulfonyl group such as trifluoromethanesulfonyl, toluenesulfonyl and the like. In the formula, the boronic acid ester optionally having substituent(s) for $Z^E$ is pinacolatoboron, neopentylglycolatoboron or the like.

Step C-1

In this step, the hydroxyl group of compound (16-2) is converted to an activating group $OZ^D$. The reaction proceeds in the presence of a base in a suitable solvent at about −50 to 50° C., particularly preferably 0° C. to room temperature. As the activating reagent, an activated sulfonic acid derivative such as trifluoromethanesulfonic acid anhydride, 1-(trifluoromethanesulfonyl)imidazole or toluenesulfonyl chloride is used. This reaction can also be performed by using sulfonic acid and a condensing agent in combination. Examples of the base include triethylamine, pyridine, lutidine and the like. Examples of the solvent include dichloromethane, 1,2-dichloroethane, chloroform, pyridine, toluene and the like.

Step C-2

Compound (C-1) can be obtained by reacting a compound represented by compound (16-1) or compound (16-3) with compound (16-4).

Compound (C-1) is obtained by a coupling reaction of compound (16-1) or compound (16-3) and amine, olefin, acetylene, thiol or alcohol represented by $P^COC(O)$-L-H (wherein L and $P^C$ are as defined above), an arylboronic acid derivative represented by L-B(OH)$_2$ or an ester thereof (wherein L is as defined above). The palladium catalyst, phosphine ligand, reagent in which a palladium catalyst and a phosphine ligand form a complex, base and solvent to be used are the same as those in Step B-1.

When L is aryl having 6-12 carbon atoms, heteroaryl containing 5-12 ring-constituting atoms, olefin or acetylene, compound (C-1) can also be obtained by a coupling reaction of an organic metal salt (e.g., tin, zinc, copper and the like) for L or an alkylmetal derivative (e.g., alkylaluminum derivative, alkyltin derivative, alkylborane derivative and the like) for L or the like, and compound (16-1) or compound (16-3).

(2) An intermediate of a compound represented by the formula (I) wherein W is represented by the aforementioned formula (Wa), namely, the following compound (C-1) can also be produced by the following method.

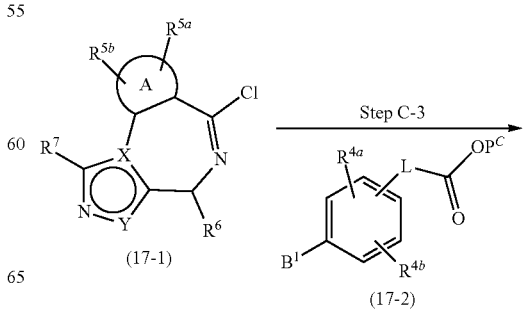

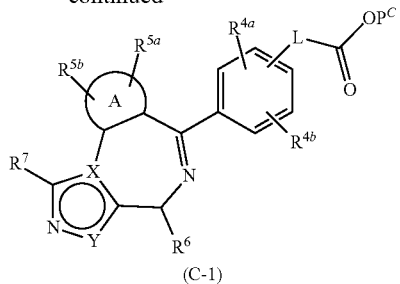

wherein each symbol is as defined above.

Compound (C-1) can be obtained by a coupling reaction of compound (17-1) and boronic acid derivative (17-2). The reaction conditions are the same as those in the aforementioned Step B-1.

(3) The production method described here is suitable for producing a compound (C-1) wherein W is the aforementioned formula (Wa) and L can be introduced by a reaction with boronic acid (18-1) (e.g., L is unsubstituted or substituted aryl having 6-10 carbon atoms, unsubstituted or substituted heteroaryl having 1 to 5 hetero atoms selected from a nitrogen atom, an oxygen atom and a sulfur atom and containing 3 to 10 ring-constituting atoms, olefin, acetylene etc.).

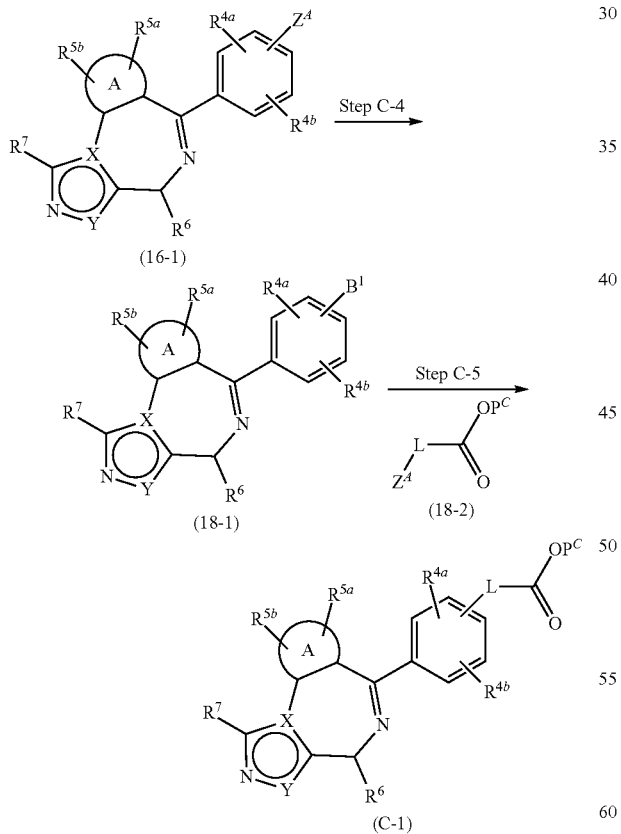

wherein each symbol is as defined above.
Step C-4

Boronic acid (18-1) is obtained by reacting compound (16-1) with a boronic acid derivative (e.g., bispinacolatodiboron, bisneopentylglycolatodiboron and the like). The reaction proceeds in the presence of a palladium catalyst, a phosphine ligand and a base in a suitable solvent at 0° C. to under heating, particularly preferably at room temperature to the boiling point of the solvent. As the palladium catalyst, phosphine ligand, base and solvent, those recited in Step B-1 can be used.

Step C-5

Compound (C-1) is obtained by reacting boronic acid (18-1) with compound (18-2). The reaction proceeds in the presence of a palladium catalyst, a phosphine ligand and a base in a suitable solvent at 0° C. to under heating, particularly preferably at room temperature to the boiling point of the solvent. As the palladium catalyst, phosphine ligand, base and solvent, those recited in Step B-1 can be used.

(3) An intermediate of a compound represented by the formula (I) wherein ring A is represented by the aforementioned formula (Aa), X is a nitrogen atom, Y is a nitrogen atom, and $R^{5a}$ is substituted by a halogen atom, namely, the following compound (C-2) can also be produced by the following method.

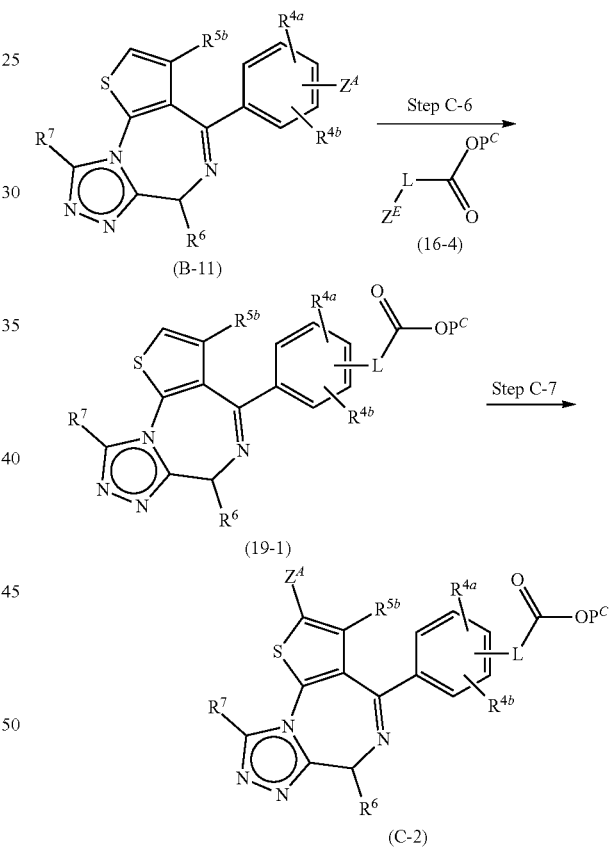

wherein each symbol is as defined above.
Step C-6

Compound (19-1) can be obtained by reacting compound (B-11) with compound (16-4). The reaction conditions are the same as those in Step C-2.

Step 0-7

Compound (C-2) is obtained by reacting compound (19-1) with sulfuryl chloride, N-bromosuccinimide and the like in acetic acid or a mixture of acetic acid and chloroform at room temperature to 50° C.

(Method D)

(1) A compound represented by the formula (I) wherein W is represented by the aforementioned formula (Wa), namely, the following compound (I-1) can be produced by the following method.

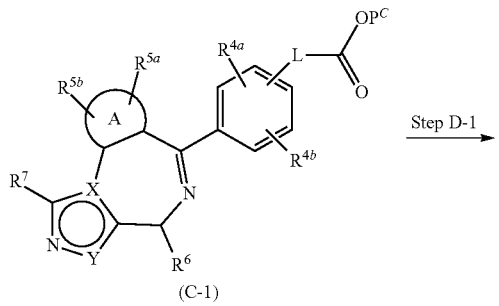

(C-1)

Step D-1

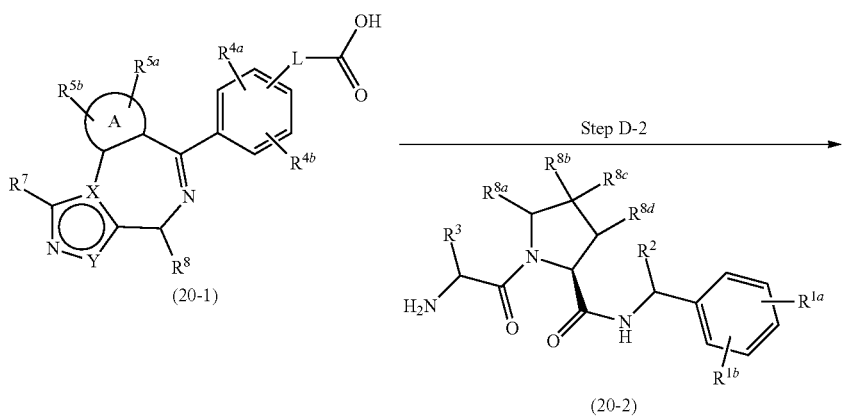

(20-1)

Step D-2

(20-2)

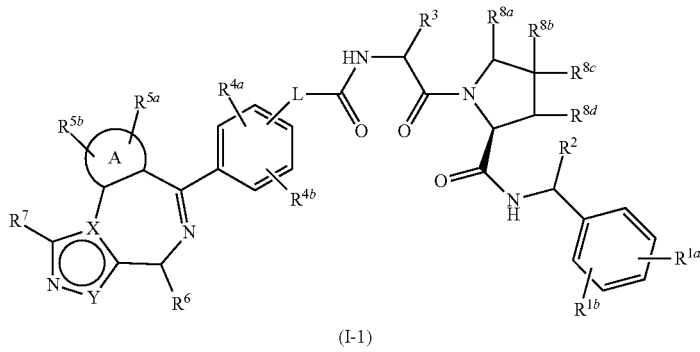

(I-1)

wherein each symbol is as defined above.

Step D-1

Compound (20-1) can be obtained by removing protecting group $P^C$ from compound (C-1). When $P^C$ is a hydrogen atom, this step can be omitted. The condition for removing protecting group $P^C$ is not particularly limited as long as it is used for deprotection of $P^C$. For example, when $P^C$ is methyl, a method using Lewis acid such as boron tribromide and the like in a methylene chloride solvent and a method using an inorganic base such as sodium hydroxide and the like in a mixed solvent of alcohol solvent and water can be mentioned. When it is ethyl, a method using an inorganic base such as sodium hydroxide and the like in a mixed solvent of alcohol solvent and water can be mentioned. When it is t-butyl, a method using an acid such as hydrochloric acid, trifluoroacetic acid and the like can be mentioned. When $P^C$ is benzyl or substituted benzyl, benzyloxymethyl or the like, a method using catalytic hydrogenation reaction can be mentioned.

Step D-2

Compound (I-1) can be obtained by a condensation reaction of carboxylic acid derivative (20-1) and amine derivative (20-2). The reaction conditions are the same as those in the aforementioned Step B-14.

(2)

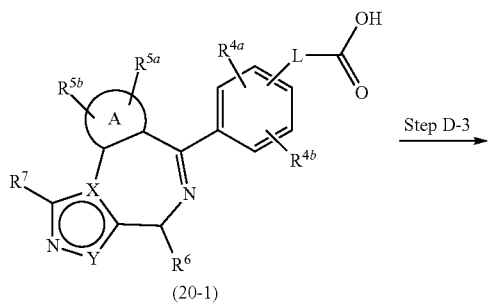

(20-1)

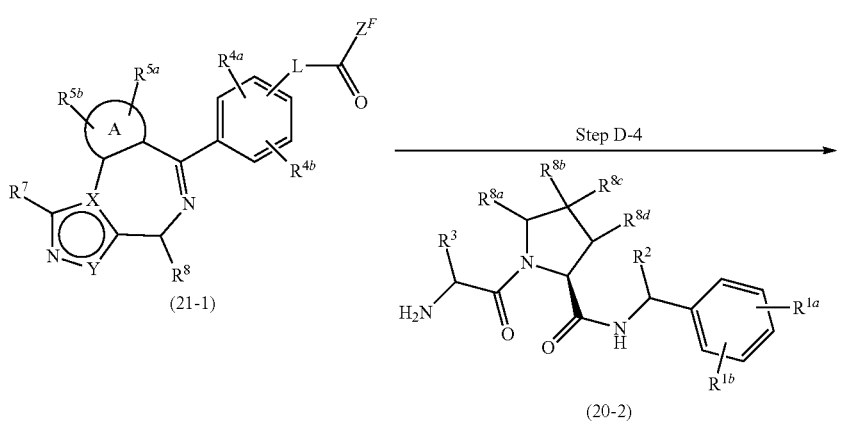

(21-1)       (20-2)

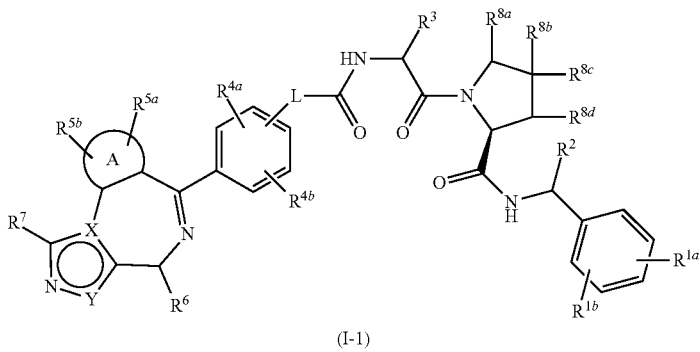

(I-1)

wherein $Z^F$ is a chlorine atom or a bromine atom, and other symbols are as defined above.

Step D-3

In this step, compound (20-1) is converted to acid halide (21-1). The reaction proceeds in an appropriate solvent generally at 0° C. to the refluxing temperature of the solvent for generally from 1 hr to 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step D-4

Compound (I-1) can be obtained by reacting acid halide (21-1) with amine derivative (20-2). The reaction proceeds using a base in a suitable solvent generally at 0° C. to the refluxing temperature of the solvent. While the reaction time varies depending on the starting material and solvent to be used and the reaction temperature and the like, it is generally from 30 min to 12 hr. Examples of the base include triethylamine, pyridine and the like. Examples of the solvent include dichloromethane, dichloroethane, chloroform, N-methylpyrrolidone, pyridine, toluene and the like.

(Method E)

(1) A compound represented by the formula (I) wherein W is represented by the aforementioned formula (Wa), namely, the following compound (I-1) can also be produced by the following method.

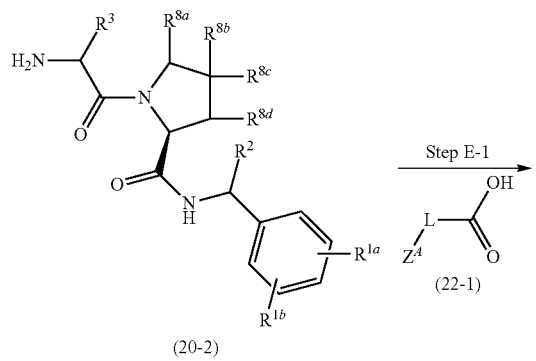

(20-2) (22-1)

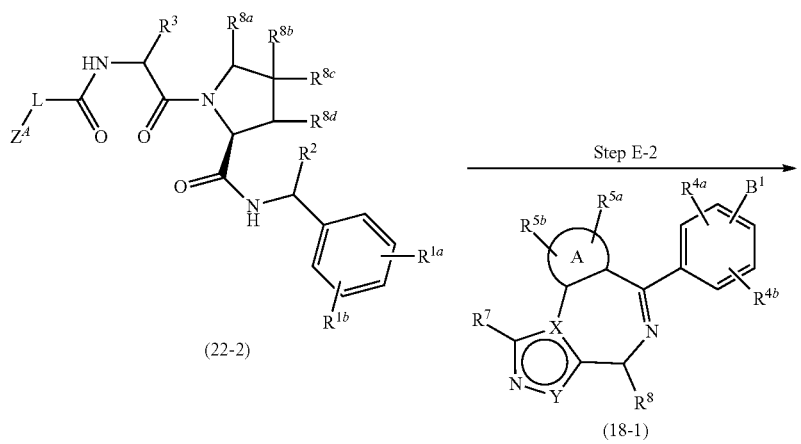

(22-2) (18-1)

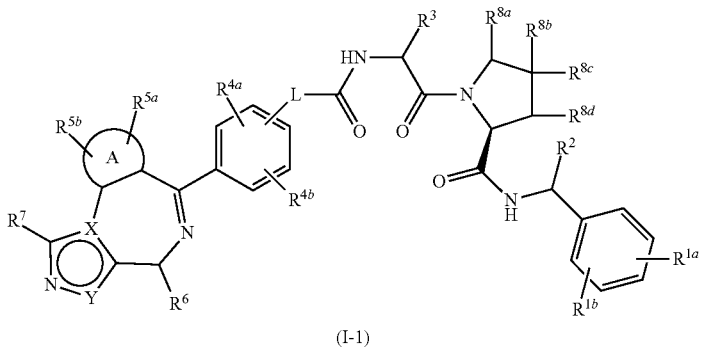

(I-1)

wherein each symbol is as defined above.

Step E-1

Compound (22-2) can be obtained by reacting amine (20-2) with carboxylic acid (22-1) represented by HOC(O)-L-$Z^A$ (wherein $Z^A$ is as defined above). The reaction conditions are the same as those in the aforementioned Step B-14.

Step E-2

In this step, compound (I-1) is obtained by reacting compound (22-2) with boronic acid (18-1). The reaction conditions are the same as those in Step B-1.

(2) A compound represented by the formula (I) wherein W is represented by the aforementioned formula (Wa), namely, the following compound (I-1) can also be produced by the following method.

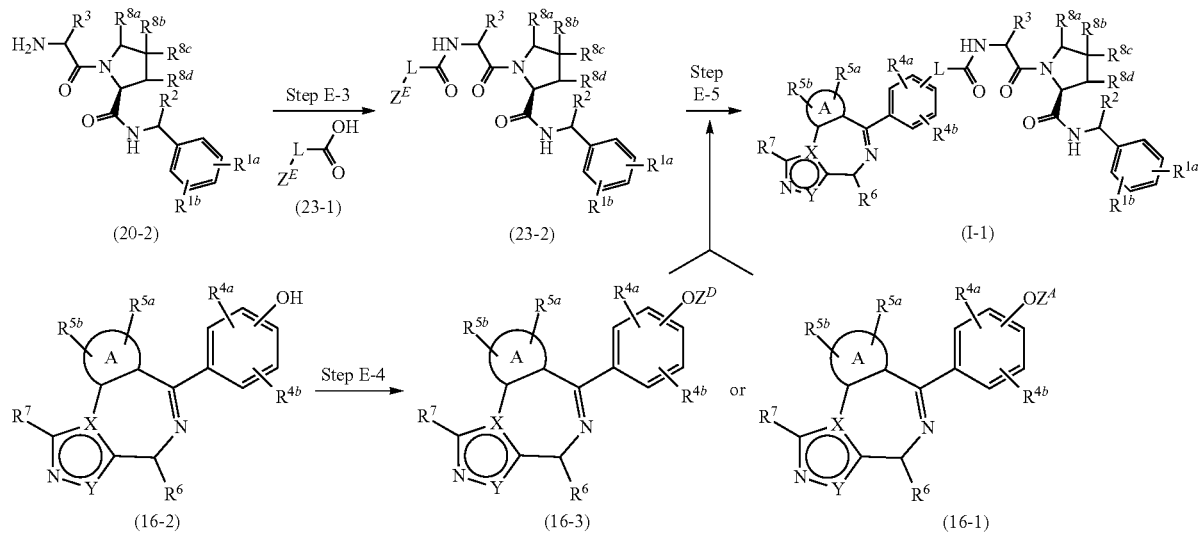

wherein each symbol is as defined above.

Step E-3

Compound (23-2) can be obtained by reacting amine (20-2) with carboxylic acid (23-1). The reaction conditions are the same as those in the aforementioned Step B-14.

Step E-4

In this step, a hydroxyl group of compound (16-2) is converted to activated group $OZ^D$. The reaction conditions are the same as those in the aforementioned Step C-1.

Step E-5

In this step, compound (I-1) is obtained by reacting compound (16-1) or compound (16-3) obtained in Step E-4 with compound (23-2). The reaction conditions are the same as those in the aforementioned Step C-2.

(3) A compound represented by the formula (I) wherein W is represented by the aforementioned formula (Wa), namely, compound (I-1) can also be produced by the following method.

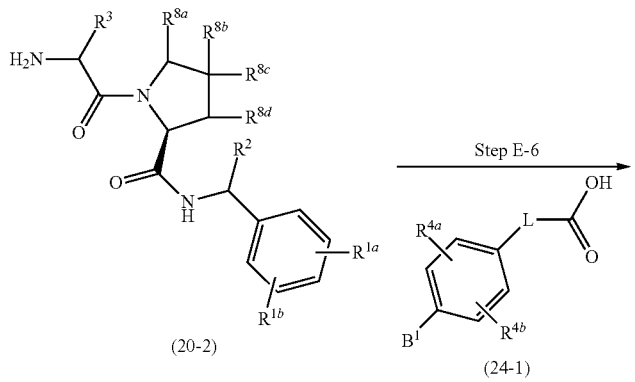

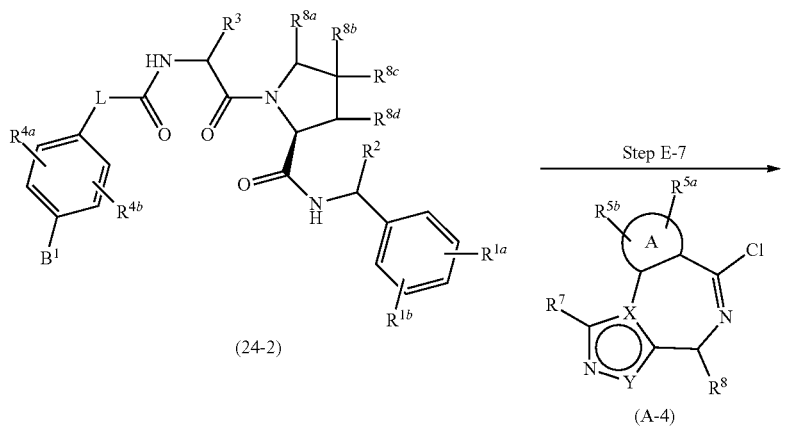

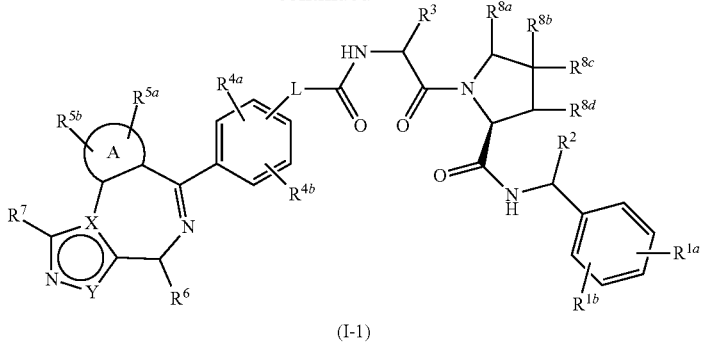

(I-1)

wherein each symbol is as defined above.

In the aforementioned method E (2), boronic acid (24-2) is obtained using compound (24-1) instead of compound (23-1) which is reacted with iminochloride (A-4) to give compound (I-1).

The reaction conditions of Step E-6 are the same as those in Step B-14.

The reaction conditions of Step E-7 are the same as those in Step B-1.

(Method F)

(1) A compound represented by the formula (I) wherein W is represented by the aforementioned formula (Wd) or (We), namely, the following compound (I-2) can be produced by the following method.

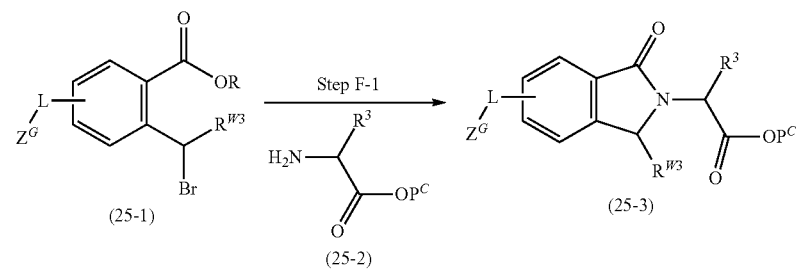

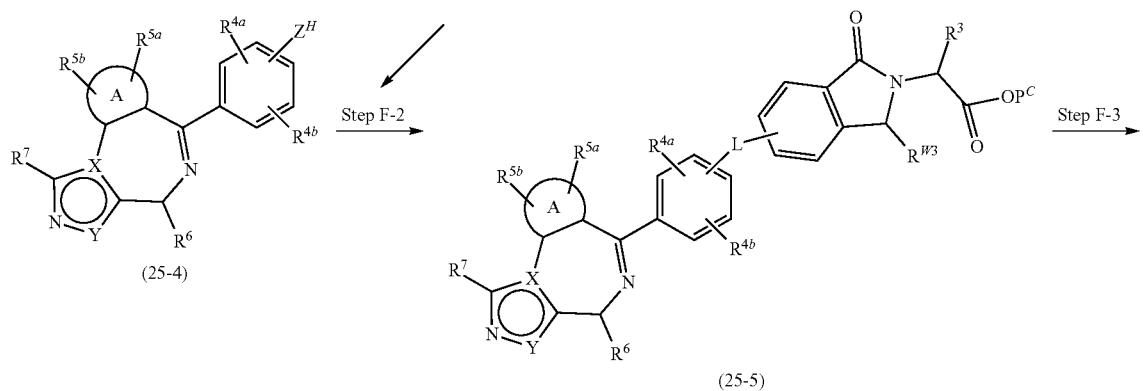

-continued

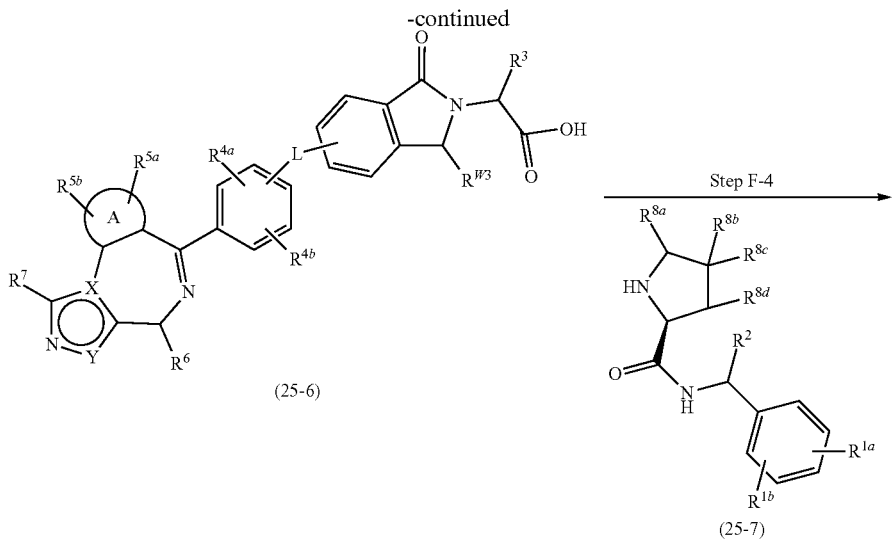

(25-6)

(25-7)

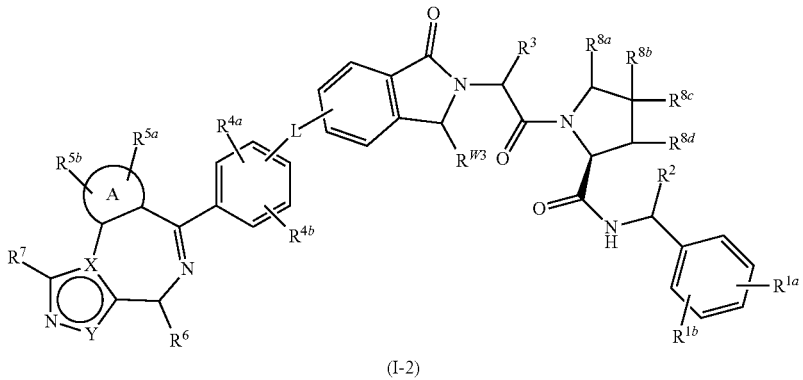

(I-2)

wherein $Z^G$ is a hydrogen atom or a halogen atom, $Z^H$ is a halogen atom, boronic acid or boronic acid ester optionally having substituent(s), and other symbols are as defined above.

In the formula, the halogen atom for $Z^G$ or $Z^H$ is a chlorine atom, a bromine atom or an iodine atom, and boronic acid ester optionally having substituent(s) for $Z^H$ is pinacolatoboron, neopentylglycolatoboron or the like.

Step F-1

Compound (25-3) can be synthesized from compound (25-1) according to a method described in a known method (e.g., WO 2011/080718).

Step F-2

In this step, compound (25-5) is obtained by reacting compound (25-4) with compound (25-3). When $Z^G$ is a hydrogen atom, compound (25-5) can be obtained by reacting with compound (25-4) wherein $Z^H$ is a halogen atom. The reaction conditions are the same as those in Step C-2.

When $Z^G$ is a halogen atom and compound (25-3) is alkenyl halide, alkynyl halide, aryl halide, heteroaryl halide or the like, compound (25-5) can be obtained by reacting with compound (25-4) wherein $Z^H$ is boronic acid or boronic acid ester optionally having substituent(s). The reaction proceeds in the presence of a palladium catalyst, a phosphine ligand and a base in a suitable solvent at 0° C. to under heating, particularly preferably at room temperature to the boiling point of the solvent. As the palladium catalyst, phosphine ligand, base and solvent, those recited in Step B-1 can be used.

Step F-3

Compound (25-6) can be obtained by deprotecting compound (25-5). The reaction conditions are the same as those in Step B-13.

Step F-4

Compound (I-2) can be obtained by a condensation reaction of carboxylic acid (25-6) and amine (25-7). The reaction conditions are the same as those in Step B-14.

(Method G)

A compound represented by the formula (I) wherein W is represented by the aforementioned formula (Wb), namely, the following compound (I-3) can be produced by the following method.

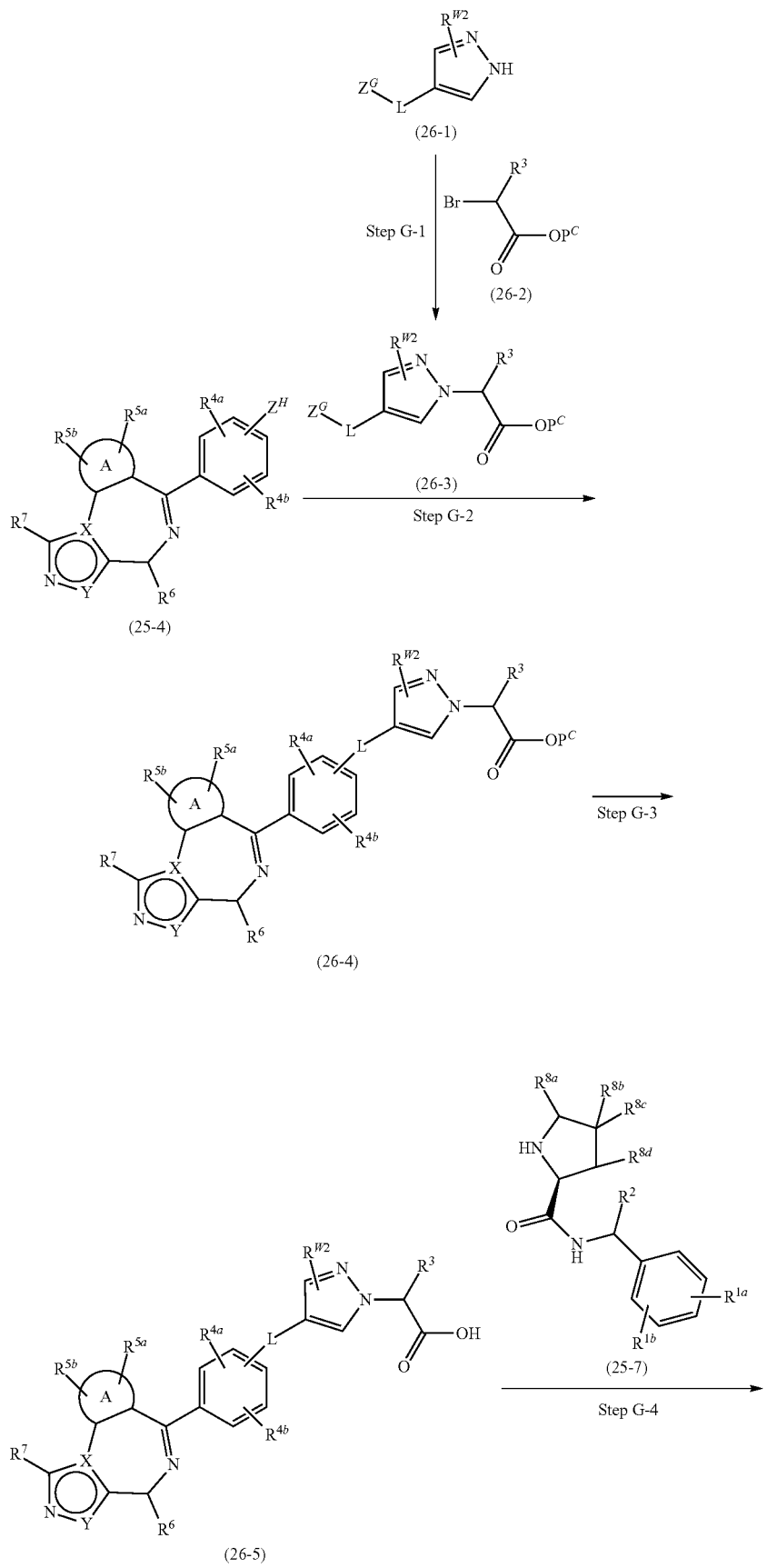

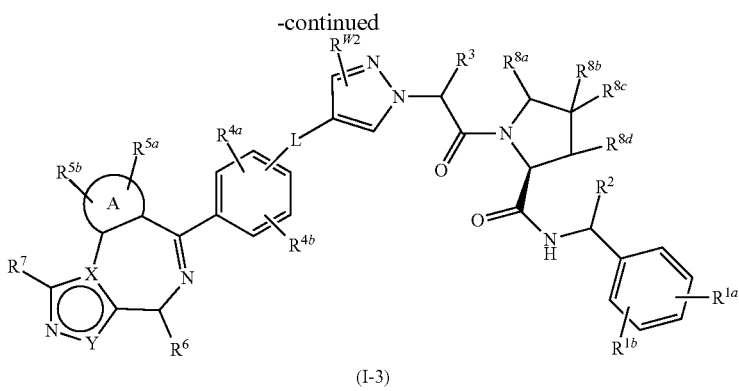

(I-3)

wherein each symbol is as defined above.

Step G-1

Compound (26-3) can be synthesized from compound (26-1) according to a known method (e.g., method described in WO 2013/006738, US20160272651).

Step G-2 to Step G-4

In this step, compound (25-4) is reacted with compound (26-3) to give compound (26-4) which is deprotected and condensed with amine to give compound (I-3). The reaction conditions are the same as those in step F-2 to Step F-4.

(Method H)

A compound represented by the formula (I) wherein W is represented by the aforementioned formula (Wc), namely, compound (I-4) can be produced by the following method.

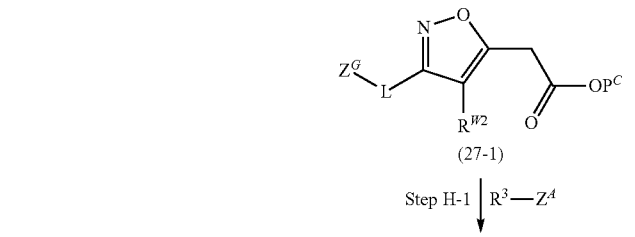

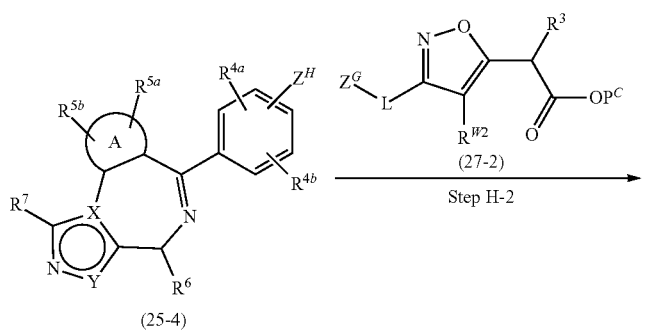

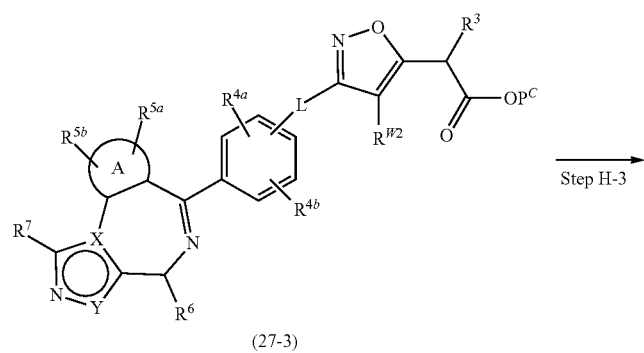

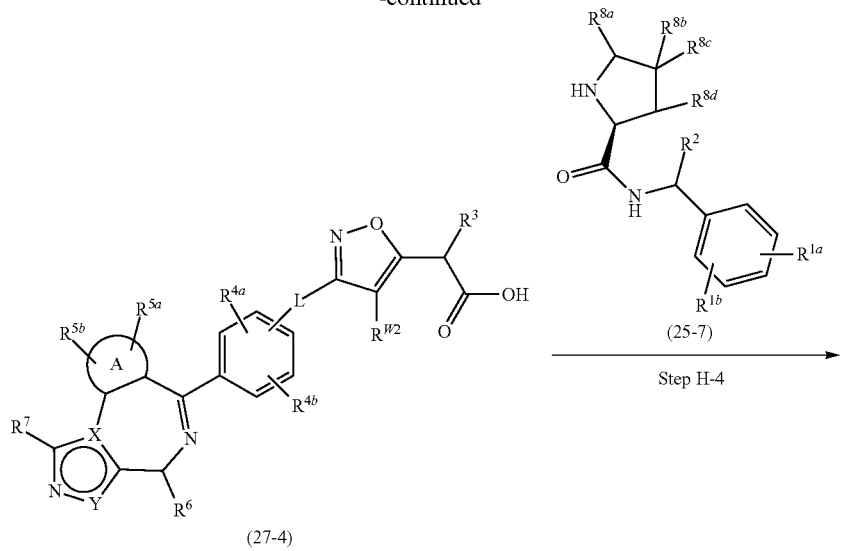

(27-4)

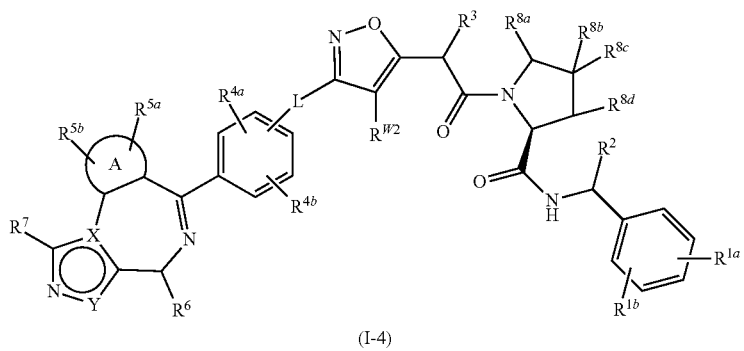

(I-4)

wherein each symbol is as defined above.

Step H-1

Compound (27-2) is obtained by enolating compound (27-1) in a suitable solvent using a base and alkylating same by reacting with $R^3$—$Z^A$ (wherein $R^3$, $Z^A$ are as defined above). The temperature of reaction with the base is −80° C. to room temperature, and the reaction time is from 30 min to about 10 hr. Examples of the base include metal reagents such as butyllithium, lithium diisopropylamide, lithium bis(trimethylsilyl)amide, sodium hydride and the like, metal alkoxides such as tert-butoxy potassium, sodium methoxide and the like, and the like. Examples of the alkylating agent include alkyl halide and the reaction temperature is 0° C. to the refluxing temperature of the solvent. While the reaction time varies depending on the starting material and solvent to be used, the reaction temperature, and the like, it is generally from 30 min to 24 hr. The solvent to be used for the reaction includes, for example, tetrahydrofuran, toluene, 1,4-dioxane and the like.

Step H-2 to Step H-4

In this step, compound (25-4) is reacted with compound (27-2) to give compound (27-3), which is deprotected and condensed with amine to give compound (I-4). The reaction conditions are the same as those in step F-2 to step F-4.

(Method I)

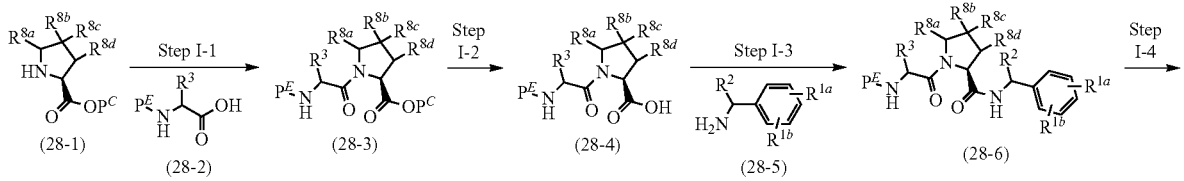

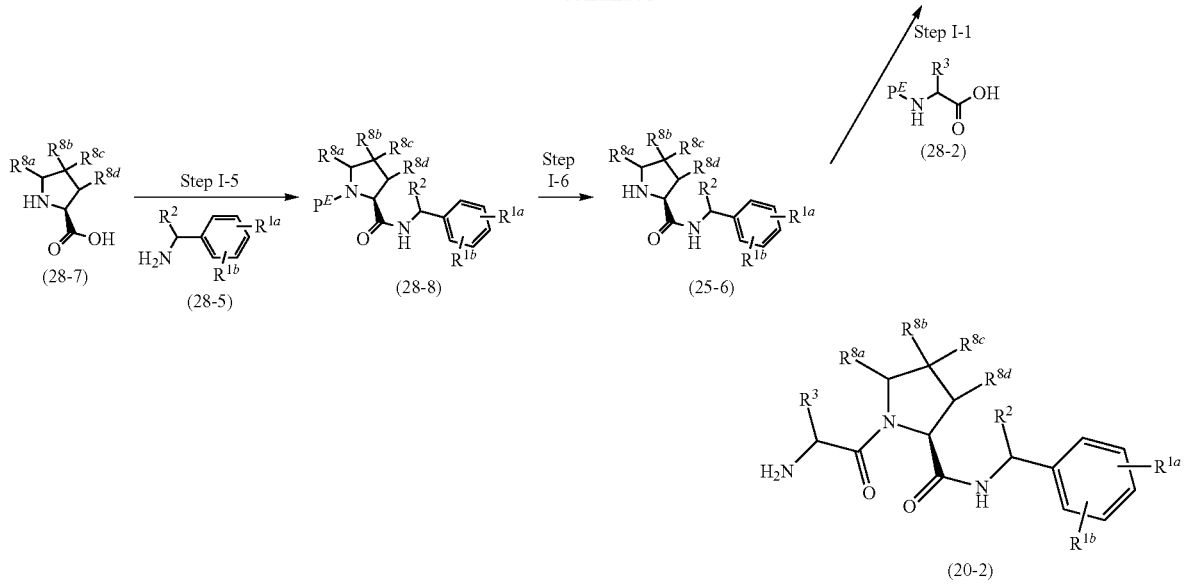

wherein $P^E$ is a protecting group, and other symbols are as defined above.

$P^E$ protects amino group and, for example, carbamate group (specifically tert-butyloxycarbonyl, benzyloxycarbonyl and the like) and the like can be mentioned. The combination of $P^C$ and $P^E$ is not particularly limited as long as the combination can selectively remove $P^C$ in Step I-2. For example, $P^C$ is tert-butyloxycarbonyl and $P^E$ is ethyl, or $P^C$ is benzyloxycarbonyl and $P^E$ is tert-butyl and the like.

Step I-1

In this step, amide (28-3) is obtained by condensation of amine (28-1) and carboxylic acid (28-2). The reaction conditions are the same as those in the aforementioned Step B-14.

Step I-2

Compound (28-4) can be obtained by removing protecting group $P^C$ from compound (28-3). The deprotection condition is not particularly limited as long as it is used for deprotection of $P^C$. For example, when $P^C$ is methyl or ethyl, a method using an inorganic base such as sodium hydroxide and the like in a mixed solvent of alcohol solvent and water can be mentioned. When it is tert-butyl, a method using an acid such as hydrochloric acid, trifluoroacetic acid and the like can be mentioned. When $P^C$ is benzyl or substituted benzyl, benzyloxymethyl or the like, a method using a catalytic hydrogenation reaction can be mentioned.

Step I-3

In this step, amide (28-6) is obtained by condensation of carboxylic acid (28-4) and amine (28-5). The reaction conditions are the same as those in the aforementioned Step B-14.

Step I-4

Compound (20-2) can be obtained by removing protecting group $P^E$ from compound (28-6). The deprotection condition is not particularly limited as long as it is used for deprotection of $P^E$. For example, when $P^E$ is tert-butyloxycarbonyl, simultaneous deprotection can be performed using an acid. As the acid, inorganic acids such as hydrochloric acid and the like, trifluoroacetic acid and the like can be mentioned. As the reaction conditions, a reaction in an alcoholic solvent such as ethanol and the like, ether solvent such as tetrahydrofuran and the like, water or a mixed solvent thereof under ice-cooling to 80° C. for 10 min to about 12 hr can be mentioned. When $P^E$ is benzyloxycarbonyl, deprotection can be performed by reduction by catalytic hydrogenation. Examples of the catalyst include palladium carbon and the like. The reaction temperature is generally room temperature to the refluxing temperature of the solvent and the hydrogen pressure is 1 to 20 atm. While the reaction time varies depending on the starting material and solvent to be used, the reaction temperature, and the like, it is generally from 1 hr to 48 hr.

Step I-5 to Step I-7

A synthesis pathway is provided in which proline derivative (28-7) is reacted with amine (28-5), $P^E$ is removed, and the side chain of the formula (28-2) having $R^3$ is introduced. The reaction conditions of step I-5 are the same as those in step I-3, the reaction conditions of step I-6 are the same as those in step I-4, and the reaction conditions of step I-7 are the same as those in step B-14.

A compound represented by the formula (I), which is produced by the aforementioned method, can be purified to any purity by a conventionally used purification means, for example, concentration, extraction, chromatography, reprecipitation, recrystallization and the like. It can be converted to a pharmacologically acceptable salt as necessary by treating with an acid or a base etc. in a suitable solvent (water, alcohol, ether etc.). Furthermore, the obtained compound of the present invention or a pharmacologically acceptable salt thereof can be converted to hydrate or solvate by treating with water, water-containing solvent or other solvent.

The compound and a pharmacologically acceptable salt thereof of the present invention include racemic compounds, stereoisomers, and mixture of these compounds, and includes isotope-labeled and radioactive-labeled compounds. Such isomers can be isolated by a standard separation technique including fractional crystallization and chiral column chromatography. In addition, the compound of the present invention has an asymmetric carbon atom. Therefore, it includes enantiomer and diastereomer. A diastereomer mixture can be separated into each diastereomer based on their physical/chemical differences by a method well known in the art, for example, chromatography and/or fractional crystallization. Enantiomer can be separated by chiral column chromatography or by reacting an enantiomer compound with an appropriate optically active compound to give a diastereomer mixture, separating each diastereomer and converting each diastereomer to a corresponding enantiomer. The compound of the present invention may be any of such isomers including diastereomer, enantiomer and a mixture thereof.

The compound or a pharmacologically acceptable salt thereof of the present invention has a cytotoxic action on cancer cells. Furthermore, it also has an action to induce degradation of BET protein in cancer cells and an inhibitory action on the binding of BET protein and acetylated histone. Therefore, the compound or a pharmacologically acceptable salt thereof of the present invention can also be used as an anticancer agent, and further can be used as a BET protein degrader or a BET protein inhibitor. According to the present invention, a cancer treatment method using the compound or a pharmacologically acceptable salt thereof of the present invention, a BET protein degrading method and a BET protein inhibitory method can also be provided.

In the present invention, the type of cancer does not matter. Concrete examples thereof include oral cancer, pharyngeal cancer, laryngeal cancer, thyroid cancer, esophageal cancer, gastric cancer, duodenum cancer, small intestine cancer, colorectal cancer, anal cancer, liver cancer, biliary tract cancer, pancreatic cancer, gastrointestinal stromal tumor, lung cancer, skin cancer, breast cancer, uterine cancer, ovarian cancer, prostate cancer, testicular cancer, bladder cancer, kidney cancer, urothelial cancer, brain tumor, bone and soft tissue tumor, leukemia, malignant lymphoma, multiple myeloma, sarcoma (e.g., Ewing sarcoma, rhabdomyosarcoma, bone and soft tissue sarcoma) and the like.

In the medical field, colorectal cancer is sometimes called colon cancer or rectal cancer, liver cancer is sometimes called hepatocyte cancer, biliary tract cancer is sometimes called bile duct cancer or gallbladder cancer, pancreatic cancer is sometimes called pancreatic duct cancer or pancreatic endocrine tumor, lung cancer is sometimes called non-small cell lung cancer, small cell lung cancer, large cell lung cancer, malignant pleural mesothelioma or thymus tumor, skin cancer is sometimes called skin malignancy or skin lymphoma, uterine cancer is sometimes called cervix cancer, uterine body cancer or uterine sarcoma, kidney cancer is sometimes called renal cell cancer, urothelial cancer is sometimes called renal pelvis cancer or ureter cancer, and brain tumor is sometimes called glioma. In addition, breast cancer includes subtypes called triple-negative breast cancer, HER2 positive breast cancer, luminal A type breast cancer, luminal B type breast cancer and the like, prostate cancer includes subtypes called hormone dependency prostate cancer, hormone independent prostate cancer, castration-resistant prostate cancer and the like, leukemia includes subtypes called acute myeloid leukemia (AML), acute promyelocytic leukemia (APL), acute lymphoblastic leukemia (ALL), lymphoblastic lymphoma (LBL), chronic myeloid leukemia (CML), myeloproliferative neoplasm (MPN), chronic lymphocytic leukemia (CLL), small lymphocytic lymphoma (SLL), myelodysplastic syndrome (MDS) and the like, and malignant lymphoma includes subtypes called follicular lymphoma (FL), MALT lymphoma, marginal zone lymphoma, lymphoplasmacytic lymphoma (LPL), Waldenstrom's macroglobulinemia (Wm), mantle cell lymphoma (MCL), diffuse large B-cell lymphoma (DLBCL, NOS), Burkitt lymphoma (BL), peripheral T-cell lymphoma (PTCL), adult T cell leukemia/lymphoma (ATL), extranodal NK/T-cell lymphoma, nasal type (ENKL), Hodgkin lymphoma (HL) and the like.

In the present specification, the anticancer agent is a concept including carcinostatic agent, antitumor agent and the like. It has the effect of damaging, killing or weakening cancer cells and tumor cells, and reducing or eliminating or preventing an increase in the clump of cells that grew abnormally for the purpose of treating cancer. In addition, treatment means an act of administering the compound of the present invention or a pharmacologically acceptable salt thereof or a pharmaceutical composition containing same to an individual who has developed an illness, disease or symptom. Therefore, an act of administration to an individual who has developed an illness, disease or symptom, for the prevention of aggravation of the symptom and the like, and for the prevention of recurrence is one embodiment of the treatment.

When the compound of the present invention is used as a medicament, the compound of the present invention is mixed with a pharmaceutically acceptable additive (excipient, binder, disintegrant, corrigent, flavor, emulsifier, diluent, solubilizing agents and the like) to give a pharmaceutical composition which can be orally or parenterally administered. A pharmaceutical composition can be formulated by a general method.

While the subject to which the compound or pharmaceutical composition of the present invention is to be administered is not particularly limited, mammal is preferable. Examples of the mammal include primates (e.g., human, monkey, chimpanzee), rodents (e.g., mouse, rat, guinea pig), pets (e.g., dog, cat, rabbit), working animals or domestic animals (e.g., bovine, horse, swine, sheep, goat), and human is preferable.

In the present specification, parenteral includes subcutaneous injection, intravenous injection, intramuscular injection, intraperitoneal injection, drip or topical administration (intraarticular administration, transdermal administration, transocular administration, transpulmonary or bronchial administration, transnasal administration, transrectal administration and the like) and the like.

The dose of the compound of the present invention is determined according to the age, body weight, general health condition, sex, diet, administration time, administration method, clearance rate, and the level of symptom for which patients are undergoing treatments at that time, or further in consideration of other factors. While the daily dose of the compound of the present invention varies depending on the condition and body weight of patient, the kind of the compound, administration route and the like, it is parenterally administered at, for example, about 0.001 to 100 mg/patient/day by subcutaneous, intravenous, intramuscular, intraarticular, transdermal, transocular, transpulmonary or bronchial, transnasal or rectal administration, or about 0.01 to 1000 mg/patient/day by oral administration.

EXAMPLES

The present invention is explained in detail in the following by referring to Reference Examples, Examples and Experimental Examples, which are not to be construed as limitative.

Reference Example 1 methyl [(6S)-4-(4-chlorophenyl)-2,3,9-trimethyl-6H-thieno[3,2-f][1,2,4]triazolo[4,3-a][1,4]diazepin-6-yl]acetate (Reference Example Compound 1)

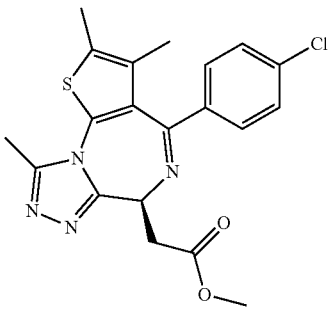 [SMILES: COC(=O)C[C@@H]1N=C(c2ccc(Cl)cc2)c2c(sc(C)c2C)-n2c(C)nnc21]

To a suspension of (6S)-4-(4-chlorophenyl)-2,3,9-trimethyl-6H-thieno[3,2-f][1,2,4]triazolo[4,3-a][1,4]diazepine-6-acetic acid (300 g) in methanol (1.5 L) was added dropwise (10-25° C.) under ice-cooling thionyl chloride (320 g) over 1 hr, and the mixture was stirred at room temperature for 4 hr. After completion of the reaction, the solvent was evaporated under reduced pressure, chloroform (1.5 L) and water (1 L) were added for partitioning, and the mixture was further extracted with chloroform (500 mL). The organic layer was washed with saturated aqueous sodium hydrogen carbonate (500 mL), dried over anhydrous sodium sulfate, and the solvent was evaporated under reduced pressure (azeotropically distilled twice with methanol). The residue was washed with methanol/water (300 mL/300 mL) to give the title compound (250 g).
MS (ESI) m/z: 415.2 [M+H]$^+$

Reference Example 2 methyl {(6S)-4-[4-(5,5-dimethyl-1,3,2-dioxaborinan-2-yl)phenyl]-2,3,9-trimethyl-6H-thieno[3,2-f][1,2,4]triazolo[4,3-a][1,4]diazepin-6-yl}acetate (Reference Example Compound 2)

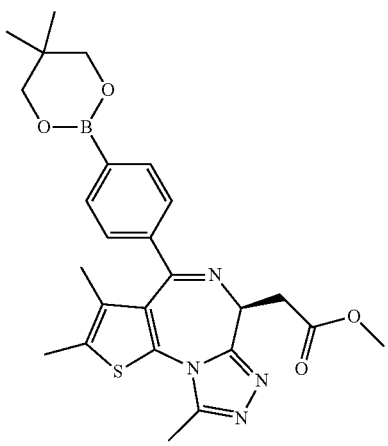

A mixture of Reference Example compound 1 (12.4 g), dichlorobis(tricyclohexylphosphine)palladium (1.1 g) and potassium acetate (4.42 g) was stirred in dioxane at 100° C. for 5 hr. After cooling, water and chloroform were added for partitioning, and the chloroform layer was washed with saturated brine and dried over anhydrous sodium sulfate. The solvent was evaporated and the residue was purified by silica gel column chromatography (chloroform:methanol=100:1) to give the title compound (14.8 g). MS (ESI) m/z: 425 [M+H−68]$^+$ (hydrolysis of boronic acid ester)

Reference Example 3 methyl {(6S)-2,3,9-trimethyl-4-[4-(4,4,5,5-tetramethyl-1,3,2-dioxaboronan-2-yl)phenyl]-6H-thieno[3,2-f][1,2,4]triazolo[4,3-a][1,4]diazepin-6-yl}acetate (Reference Example Compound 3)

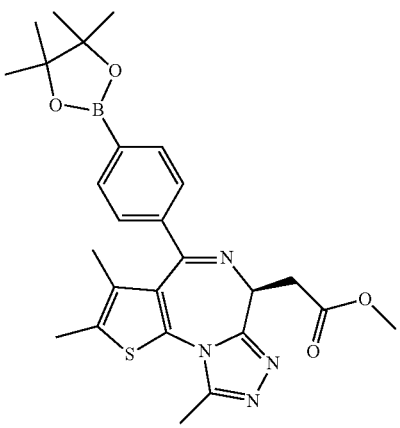

Under an argon stream, Reference Example compound 1 (5.00 g), bis(pinacolato)diboron (4.59 g), potassium acetate (2.37 g) and dichlorobis(tricyclohexylphosphine)palladium (445 mg) were heated under reflux in a tetrahydrofuran solvent for 25 hr. Furthermore, dichlorobis(tricyclohexylphosphine)palladium (445 mg), bis(pinacolato)diboron (1.53 g) were added and the mixture was heated under reflux for 7 hr. Bis(pinacolato)diboron (1.53 g), potassium acetate (1.18 g) and dichlorobis(tricyclohexylphosphine)palladium (445 mg) were added and the mixture was heated under reflux for 16 hr. After cooling to room temperature, the reaction mixture was filtered through celite using ethyl acetate. The filtrate was washed twice with saturated brine, and the organic layer was concentrated under reduced pressure. The residue was purified by silica gel column chromatography (chloroform/methanol=100:0-97:3) and then by silica gel column chromatography (ethyl acetate/methanol=100:0-95:5) to give the title compound (5.27 g) as a pale-yellow solid. MS (ESI) m/z: 507.2 [M+H]$^+$

Reference Example 4

(4-1) 3-(4-bromophenyl)-3-oxopropanenitrile (Reference Example Compound 4-1)

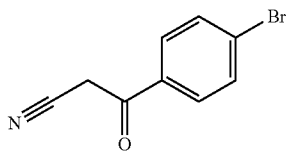 [SMILES: N#CCC(=O)c1ccc(Br)cc1]

At room temperature, to a suspension of sodium methoxide (12.4 g) in dimethylsulfoxide (23 mL) was added acetonitrile (12.3 g), and the mixture was stirred at room temperature for 2 hr. A solution of ethyl 4-bromobenzoate (22.9 g) in dimethyl sulfoxide (23 mL) was slowly added, and the mixture was stirred at 45° C. for 3 hr. The reaction solution was cooled under ice-cooling, water and concentrated hydrochloric acid were added and the mixture was stirred for 0.5 hr. The precipitate was collected by filtration and the obtained residue was dried to give the title compound (22.4 g) as a pale-brown solid. $^1$H NMR (400 MHz, DMSO-d6) δ4.75 (brs, 2H), 7.87-7.70 (m, 4H)

(4-2) (2-amino-4,5-dimethylthiophen-3-yl) (4-bromophenyl)methanone (Reference Example Compound 4-2)

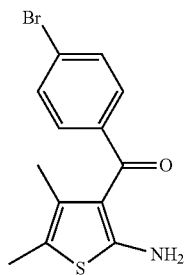 [SMILES: Cc1sc(N)c(C(=O)c2ccc(Br)cc2)c1C]

A mixture of Reference Example compound 4-1 (25.0 g), ethyl methyl ketone (8.0 g), sulfur (3.6 g), morpholine (9.7 mL) and ethanol (325 mL) was stirred at 70° C. for 7 hr. After evaporation of the solvent, ethyl acetate was added. The organic layer was washed with 1N hydrochloric acid, 1N aqueous sodium hydroxide solution and saturated brine, dried over anhydrous sodium sulfate and filtered. The filtrate was concentrated under reduced pressure. To the obtained solid was added ethanol, and the mixture was stirred at room temperature for 2 hr. The precipitate was collected by filtration to give the title compound (13.5 g) as a yellow solid.
MS (ESI) m/z: 310.2, 312.1 [M+H]$^+$ (4-3) (3S)-5-(4-bromophenyl)-3,6,7-trimethyl-1,3-dihydro-2H-thieno[2,3-e][1,4]diazepin-2-one (Reference Example Compound 4-3)

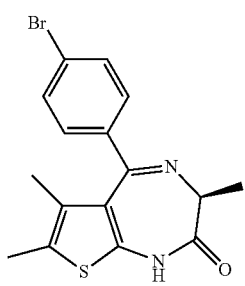

Under ice-cooling, to Reference Example compound 4-2 (43.0 g) were added (2S)-2-(t-butoxycarbonylamino)propanoic acid (27.6 g) and pyridine (200 mL), and phenylphosphonyl dichloride (29.7 g) was slowly added dropwise, and the mixture was stirred under ice-cooling for 1 hr. After evaporation of the solvent, ethyl acetate was added, and the organic layer was washed with saturated aqueous sodium hydrogen carbonate and water, dried over anhydrous sodium sulfate and filtered. The filtrate was concentrated under reduced pressure. To a solution of the obtained residue in dichloromethane (70 mL) was added trifluoroacetic acid (53 mL), and the mixture was stirred at room temperature for 2 hr. Trifluoroacetic acid (53 mL) was added and the mixture was stirred at room temperature for 2 hr. The reaction solution was concentrated and azeotropically distilled with toluene. To the obtained mixture was added saturated aqueous sodium hydrogen carbonate, and the mixture was extracted with ethyl acetate. The organic layer was dried over anhydrous sodium sulfate and filtered. The filtrate was concentrated under reduced pressure. To a suspension of the obtained residue in 2-propanol (200 mL) was added acetic acid (12 mL), and the mixture was stirred at 90° C. for 1 hr. To the reaction mixture was added saturated aqueous sodium hydrogen carbonate and the mixture was extracted with ethyl acetate. The organic layer was washed with saturated aqueous sodium hydrogen carbonate, dried over anhydrous sodium sulfate and filtered. The filtrate was concentrated under reduced pressure. To the obtained residue was added ethyl acetate (43 mL) and the mixture was stirred at 45° C. for 1 hr. The insoluble material was collected by filtration. The obtained solid was dried under reduced pressure to give the title compound (25.7 g) as a yellow solid. MS (ESI) m/z: 363.2, 365.2 [M+H]$^+$ (4-4) (6S)-4-(4-bromophenyl)-2,3,6,9-tetramethyl-6H-thieno[3,2-f][1,2,4]triazolo[4,3-a][1,4]diazepine (Reference Example Compound 4)

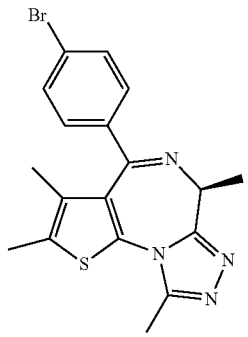

Under ice-cooling, to a solution of Reference Example compound 4-3 (9.6 g) in tetrahydrofuran (65 mL) was added sodium hydride (60%, 1.1 g) and the mixture was stirred for 0.5 hr. Diethylphosphonyl chloride (5.5 g) was added and the mixture was stirred at room temperature for 0.25 hr. Acetohydrazide (2.9 g) and n-butanol (10 mL) were added and the mixture was stirred at 70° C. for 0.5 hr. To the reaction mixture was added saturated aqueous sodium hydrogen carbonate, and the mixture was extracted with ethyl acetate. The organic layer was washed with saturated brine, dried over anhydrous sodium sulfate, filtered, and the filtrate was concentrated under reduced pressure. The obtained residue was purified by NH silica gel column chromatography (n-hexane:ethyl acetate) to give the title compound (8.9 g) as a yellow powder.
MS (ESI) m/z: 401.1, 403.1 [M+H]$^+$

Reference Example 5

(5-1) t-butyl [(1S)-1-(4-bromophenyl)ethyl]carbamate (Reference Example Compound 5-1)

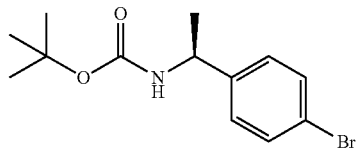 [SMILES: C[C@H](NC(=O)OC(C)(C)C)c1ccc(Br)cc1]

(S)-1-(4-bromophenyl)ethanamine (21.0 g), ethyl acetate (53 mL) and water (53 mL) were mixed, under ice-cooling, sodium hydrogen carbonate (6.61 g) and di-t-butyl carbonate (27.5 g) were added, and the mixture was stirred at room temperature overnight. The reaction mixture was filtered. The obtained crude crystal was suspended in hexane/water and washed to give the title compound (31.3 g) as a colorless solid. $^1$H NMR (400 MHz, CDCl$_3$) δ1.41 (brs, 12H), 4.74 (brs, 2H), 7.16-7.18 (m, 2H), 7.43-7.46 (m, 2H)

(5-2) t-butyl {(1S)-1-[4-(4-methyl-1,3-thiazol-5-yl)phenyl]ethyl}carbamate (Reference Example Compound 5-2)

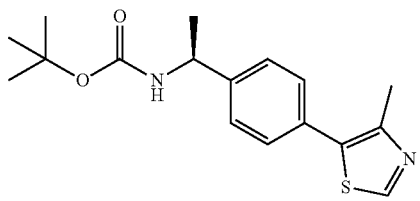 [SMILES: Cc1ncsc1-c1ccc([C@H](C)NC(=O)OC(C)(C)C)cc1]

A mixture of Reference Example compound 5-1 (32.2 g), dimethylacetamide (80 mL), 4-methylthiazole 21.3 g), palladium acetate (482 mg) and potassium acetate (21.0 g) was stirred under a nitrogen atmosphere at 90° C. for 7 hr. Water was added to the reaction mixture, and the mixture was extracted with ethyl acetate. The organic layer was washed successively with water and saturated brine, dried over anhydrous sodium sulfate, filtered and concentrated. The obtained residue was purified by silica gel column chromatography (hexane:ethyl acetate=7:3) to give the title compound (23.4 g) as a colorless solid.
MS (ESI) m/z: 319.4 [M+H]$^+$

(5-3) (1S)-1-[4-(4-methyl-1,3-thiazol-5-yl)phenyl]ethan-1-amine hydrochloride (Reference Example Compound 5-3)

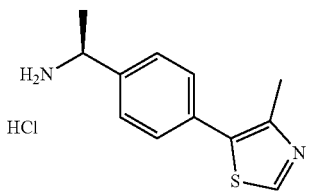

To a mixture of Reference Example compound 5-2 (24.3 g) and 1,4-dioxane was added 4 M hydrogen chloride/dioxane solution, and the mixture was stirred at room temperature for 5 hr. The reaction mixture was concentrated and suspension washed with isopropyl ether to give the title compound (20.5 g) as a yellow solid. MS (ESI) m/z: 219.2 [M+H]$^+$

(5-4) methyl (2S,4R)-1-{(2S)-2-[(t-butoxycarbonyl)amino]-3,3-dimethylbutanoyl}-4-hydroxypyrrolidine-2-carboxylate (Reference Example Compound 5-4)

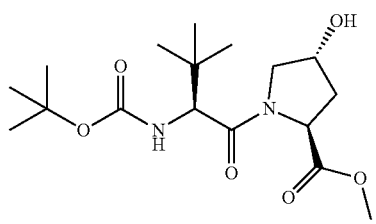 [SMILES: COC(=O)[C@@H]1C[C@@H](O)CN1C(=O)[C@@H](NC(=O)OC(C)(C)C)C(C)(C)C]

(2S)-2-(t-butoxycarbonylamino)-3,3-dimethyl-butanoic acid (27.0 g), N,N-dimethylformamide (220 mL) were mixed, N,N-diisopropylethylamine (60 mL), methyl (2S, 4R)-4-hydroxypyrrolidine-2-carboxylate hydrochloride (21.2 g) and 1-[bis(dimethylamino)methylene]-1H-1,2,3-triazolo[4,5-b]pyridinium 3-oxide hexafluorophosphate (48.8 g, hereinafter indicated as HATU) were added under ice-cooling, and the mixture was stirred at room temperature overnight. Water was added to the reaction mixture, the mixture was extracted with ethyl acetate. The organic layer was washed successively with 10% aqueous citric acid solution, saturated aqueous sodium hydrogen carbonate and saturated brine, dried over anhydrous sodium sulfate, filtered and concentrated. The obtained residue was purified by silica gel column chromatography (chloroform:methanol=100:0-10:1) to give the title compound (41.0 g) as a pale-yellow oil. MS (ESI) m/z: 259.2 [M−Boc+2H]$^+$

(5-5) (2S,4R)-1-{(2S)-2-[(t-butoxycarbonyl)amino]-3,3-dimethylbutanoyl}-4-hydroxypyrrolidine-2-carboxylic acid (Reference Example Compound 5-5)

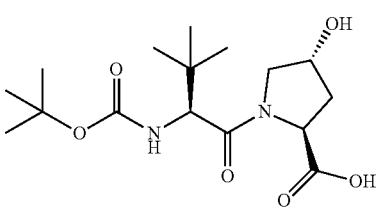 [SMILES: CC(C)(C)OC(=O)N[C@H](C(=O)N1C[C@H](O)C[C@H]1C(=O)O)C(C)(C)C]

To a mixture of Reference Example compound 5-4 (41.0 g), tetrahydrofuran (380 mL) and water (190 mL) was added lithium hydroxide (8.21 g) and the mixture was stirred at room temperature overnight. The reaction mixture was concentrated, 1N hydrochloric acid was added under ice-cooling, and the precipitated solid was collected by filtration to give the title compound (27.4 g) as a colorless solid.
MS (ESI) m/z: 245.2 [M−Boc+2H]$^+$ (5-6) t-butyl {(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamate (Reference Example Compound 5-6)

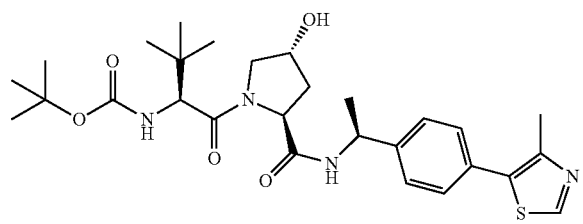 [SMILES: Cc1ncsc1-c1ccc([C@H](C)NC(=O)[C@@H]2C[C@@H](O)CN2C(=O)[C@@H](NC(=O)OC(C)(C)C)C(C)(C)C)cc1]

To a mixture of Reference Example compound 5-3 (20.5 g), Reference Example compound 5-5 (27.8 g) and N,N-dimethylformamide (350 mL) were added, under ice-cooling, N,N-diisopropylethylamine (42.2 mL), HATU (36.8 g), and the mixture was stirred at room temperature overnight. Water was added to the reaction mixture, and the mixture was extracted with ethyl acetate. The organic layer was washed successively with saturated brine, dried over anhydrous sodium sulfate, filtered and concentrated. The obtained residue was dissolved in chloroform, hexane was added and the precipitated solid was collected by filtration to give the title compound (36.9 g) as a colorless solid. MS (ESI) m/z: 445.3 [M−Boc+2H]$^+$ (5-7) (2S,4R)-1-[(2S)-2-amino-3,3-dimethylbutanoyl]-4-hydroxy-N-{(1S)-1-[4-(4-methyl-1,3-thiazol-5-yl)phenyl]ethyl}pyrrolidine-2-carboxamide hydrochloride (Reference Example Compound 5)

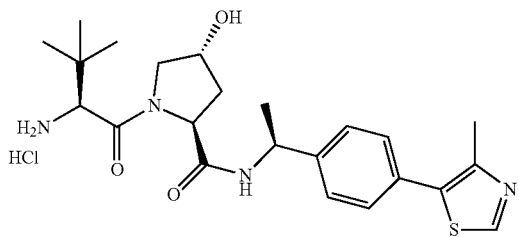 [SMILES: Cl ; Cc1ncsc1-c1ccc([C@H](C)NC(=O)[C@@H]2C[C@@H](O)CN2C(=O)[C@@H](N)C(C)(C)C)cc1]

To a mixture of Reference Example compound 5-6 (34.8 g), chloroform (160 mL) and 1,4-dioxane (500 mL) was added dropwise under ice-cooling 4 M hydrogen chloride/dioxane solution, and the mixture was stirred at room temperature overnight. The reaction mixture was concentrated, acetonitrile was added and the mixture was concentrated to give the title compound (30.0 g) as a pale-yellow solid. MS (ESI) m/z: 445.5 [M+H]$^+$ Reference Example 6

(6-1) 4-(4-methyl-1,3-thiazol-5-yl)benzonitrile (Reference Example Compound 6-1)

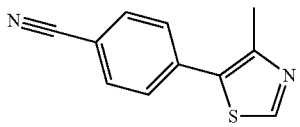

To a solution of 4-methylthiazole 10.9 g) in dimethylacetamide (55 mL) were added 4-bromobenzonitrile (10.0 g), potassium acetate (10.8 g) and palladium acetate (25 mg), and the mixture was stirred with heating at an outer temperature of 150° C. for 18 hr. The reaction mixture was cooled to room temperature, diluted with ethyl acetate and the insoluble material was filtered off through diatomaceous earth. Water was added to the filtrate and the mixture was extracted twice with ethyl acetate. The organic layer was washed 3 times with saturated brine, dried over anhydrous sodium sulfate, filtered, and the filtrate was concentrated under reduced pressure. The obtained residue was purified by silica gel column chromatography (hexane:ethyl acetate=80:20-50:50) to give the title compound (8.93 g) as a pale-yellow solid.

MS (ESI) m/z: 201.1 [M+H]$^+$ (6-2) 1-[4-(4-methyl-1,3-thiazol-5-yl)phenyl]methanamine (Reference Example Compound 6-2)

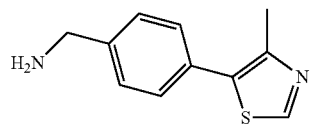

To a solution of Reference Example compound 6-1 (8.00 g) in methanol (400 mL) was added cobalt(II) chloride (7.80 g) at an inside temperature of 5° C. Under a nitrogen atmosphere, sodium borohydride (7.56 g) was slowly added over 45 min while keeping the inside temperature at 5-8° C., and the mixture was stirred at inside temperature 5° C. for 90 min. To the reaction mixture were added aqueous ammonia, water and the mixture was stirred at room temperature for 15 min. The mixture was extracted 3 times with chloroform. The precipitated insoluble material was removed using diatomaceous earth, and the organic layer was washed with saturated brine, dried over magnesium sulfate, filtered and concentrated. The obtained residue was purified twice by NH silica gel column chromatography (ethyl acetate:methanol=100:0-93:7, hexane:ethyl acetate=50:50-0:100) to give the title compound (3.78 g) as a pale-yellow oil. $^1$H NMR (400 MHz, CDCl$_3$) δ2.54 (s, 3H), 3.92 (s, 2H), 7.35-7.45 (4H, m), 8.67 (s, 1H)

(6-3) t-butyl (2S,4R)-4-hydroxy-2-({[4-(4-methyl-1,3-thiazol-5-yl)phenyl]methyl}carbamoyl)pyrrolidine-1-carboxylate (Reference Example Compound 6-3)

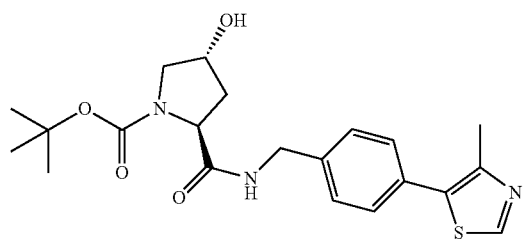 [SMILES: Cc1ncsc1-c1ccc(CNC(=O)[C@@H]2C[C@@H](O)CN2C(=O)OC(C)(C)C)cc1]

To a solution of Reference Example compound 6-2 (3.77 g) in N,N-dimethylformamide (46 mL) were added (2S,4R)-1-(t-butoxycarbonyl)-4-hydroxyproline 4.27 g) and N,N-diisopropylethylamine (12.8 mL). N,N-dimethylformamide (46 mL) was added and the mixture was stirred for 5 min. HATU (7.73 g) was added and the mixture was stirred for 30 min. Water was added to the reaction mixture and the mixture was extracted with ethyl acetate. The organic layer was washed twice with saturated brine, dried over anhydrous sodium sulfate, filtered and concentrated. The obtained residue was purified by silica gel column chromatography (ethyl acetate:methanol=100:0-90:10) to give the title compound (9.15 g) as an orange oil.
MS (ESI) m/z: 418.4 [M+H]+

(6-4) t-butyl {(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}carbamate (Reference Example Compound 6-4)

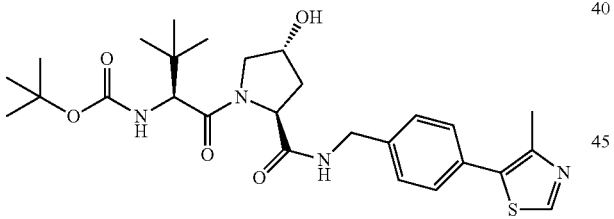

A solution of Reference Example compound 6-3 (9.15 g) in dichloromethane (50 mL) and trifluoroacetic acid (50 mL) was stirred at room temperature for 30 min. The reaction mixture was concentrated under reduced pressure, toluene was added to the residue and the mixture was concentrated under reduced pressure. This operation was performed 3 times. To a solution of the obtained residue in N,N-dimethylformamide (10 mL) was added N,N-diisopropylethylamine (19.0 mL). The solution was added to a solution of separately prepared (2S)-2-(t-butoxycarbonylamino)-3,3-dimethyl-butanoic acid (5.10 g), N,N-dimethylformamide (43.8 mL), HATU (9.17 g) with a pipette, and the reaction mixture was stirred at room temperature for 15 min. HATU (4.17 g), N,N-diisopropylethylamine (7.58 mL) were further added and the mixture was stirred at room temperature for 1 hr. Water was added to the reaction mixture and the mixture was extracted 4 times with ethyl acetate. The organic layer was washed twice with saturated brine, dried over anhydrous sodium sulfate, filtered and concentrated. The obtained residue was purified by NH silica gel column chromatography (ethyl acetate:methanol=100:0-90:0) and silica gel column chromatography (chloroform:methanol=100:0-90:10) to give the title compound (5.51 g) as a pale-yellow powder.
MS (ESI) m/z: 531.4 [M+H]+

(6-5) (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (Reference Example Compound 6)

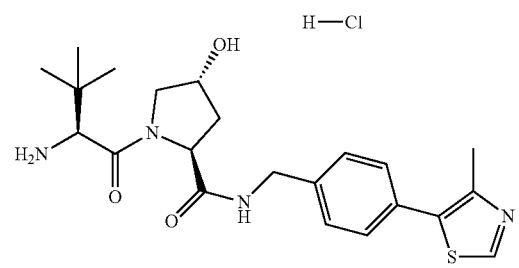 [SMILES: Cl ; Cc1ncsc1-c1ccc(CNC(=O)[C@@H]2C[C@@H](O)CN2C(=O)[C@@H](N)C(C)(C)C)cc1]

To a solution of Reference Example compound 6-4 (4.50 g) in dichloromethane (21.2 mL) was added 4 M hydrogen chloride/dioxane solution, and the mixture was stirred at room temperature for 1 hr. The reaction mixture was concentrated and the precipitated solid was suspension washed with diethyl ether to give the title compound (5.04 g) as a white solid.
MS (ESI) m/z: 431.3 [M+H]+

Reference Example 7

2-hydroxy-5-(4,4,5,5-tetramethyl-1,3,2-dioxaboronan-2-yl)benzonitrile (Reference Example Compound 7)

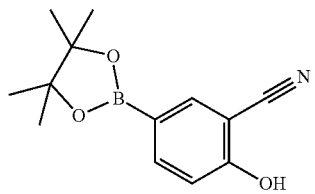 [SMILES: CC1(C)OB(c2ccc(O)c(C#N)c2)OC1(C)C]

A mixture of 5-bromo-2-hydroxybenzonitrile (5.15 g), bis(pinacolato)diboron (9.90 g), potassium acetate (7.66 g), 1,1'-bis(diphenylphosphino)ferrocene-palladium(II) dichloride dichloromethane complex (4.25 g) and 1,4-dioxane (260 mL) was stirred at 60° C. for 32 hr. 1,1'-Bis(diphenylphosphino)ferrocene-palladium(II) dichloride dichloromethane complex (4.20 g) and bis(pinacolato)diboron (5.20 g) were added, and the mixture was further stirred for 8 hr. The reaction mixture was concentrated, ethyl acetate was added to the residue and the precipitate was collected by filtration from the reaction mixture. The filtrate was partitioned by adding water. The organic layer was washed with saturated brine and dried over anhydrous sodium sulfate, and the solvent was evaporated under reduced pressure. The obtained residue was purified by silica gel column chromatography (hexane:ethyl acetate=100:0-65:35). The precipitated solid was suspension washed with ethyl acetate:hexane (10:1) solution and collected by filtration to give the title compound (3.27 g) as a white solid. The filtrate was further purified by silica gel column chromatography (hexane:ethyl acetate=70:30) to give the title compound (925 mg) as a white solid. MS (ESI) m/z: 244.3 [M−H]⁻

Reference Example 8 t-butyl [4-(4,4,5,5-tetramethyl-1,3,2-dioxaboronan-2-yl)phenoxy]acetate (Reference Example Compound 8)

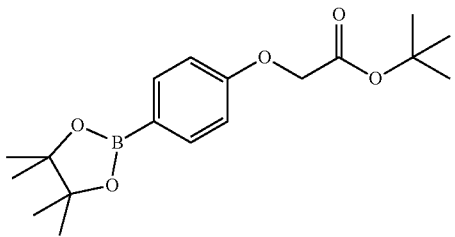 [SMILES: CC(C)(C)OC(=O)COc1ccc(B2OC(C)(C)C(C)(C)O2)cc1]

To a suspension of 4-(4,4,5,5-tetramethyl-1,3,2-dioxaborolan-2-yl)phenol (5.26 g) in acetonitrile (50 mL) were added at room temperature t-butyl bromoacetate (3.86 mL) and cesium carbonate (9.35 g) and the mixture was stirred at 60° C. for 30 min. Water was added to the reaction mixture, and the mixture was extracted with chloroform. The organic layer was mixed, dried over anhydrous sodium sulfate and filtered. The solvent was evaporated under reduced pressure. The residue was purified by silica gel column chromatography (hexane:ethyl acetate=100:0-90:10) to give the title compound (6.83 g) as a white solid. ¹H NMR (400 MHz, CDCl₃) δppm 1.33 (12H, s), 1.48 (9H, s), 4.53 (2H, s), 6.88 (2H, d, J=8.2 Hz), 7.74 (2H, d, J=8.7 Hz)

Reference Example 9

(2S,4R)-1-[(2S)-3,3-dimethyl-2-{2-[4-(4,4,5,5-tetramethyl-1,3,2-dioxaboronan-2-yl)phenoxy]acetamido}butanoyl]-4-hydroxy-N-{(1S)-1-[4-(4-methyl-1,3-thiazol-5-yl)phenyl]ethyl}pyrrolidine-2-carboxamide (Reference Example Compound 9)

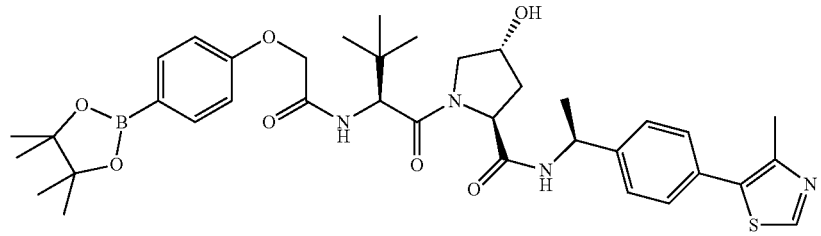 [SMILES: Cc1ncsc1-c1ccc([C@H](C)NC(=O)[C@@H]2C[C@@H](O)CN2C(=O)[C@@H](NC(=O)COc2ccc(B3OC(C)(C)C(C)(C)O3)cc2)C(C)(C)C)cc1]

To a solution of Reference Example compound 8 (110 mg) in dichloromethane (1 mL) was added at room temperature trifluoroacetic acid (1 mL), and the mixture was stirred at the same temperature for 1 hr. The reaction mixture was concentrated under reduced pressure and toluene was added to the residue. The solvent was evaporated under reduced pressure and the obtained residue was dissolved by adding Reference Example compound 5 (190 mg) and N,N-dimethylformamide (3.3 mL) at room temperature. N,N-diisopropylethylamine (0.57 mL) and HATU (175 mg) were added at the same temperature and the mixture was stirred at the same temperature for 1 hr. Water was added to the reaction mixture, and the mixture was extracted twice with ethyl acetate, and the extract was washed with water and saturated brine, dried over anhydrous sodium sulfate and filtered. The solvent was evaporated under reduced pressure. The residue was purified by silica gel column chromatography (chloroform:methanol=100:0-97:3) to give the title compound (217 mg) as a white powder.
MS (ESI) m/z: 705.5 [M+H]⁺

Reference Example 10 methyl [(6S)-4-(4-aminophenyl)-2,3,9-trimethyl-6H-thieno[3,2-f][1,2,4]triazolo[4,3-a][1,4]diazepin-6-yl]acetate (Reference Example Compound 10)

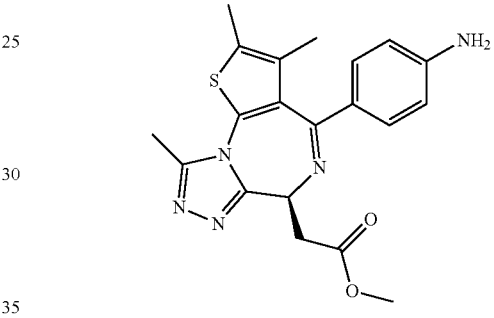

A mixed solution of Reference Example compound 1 (500 mg), 2-di-t-butylphosphino-2'-4'-6'-triisopropylbiphenyl (t-BuXphos, 77 mg), tris(dibenzylideneacetone)dipalladium (55 mg), tripotassium phosphate (640 mg) and benzophenonimine (262 mg) in 1,2-dimethoxyethane (2.4 mL) was stirred at 60° C. for 4 hr. To the reaction solution were added t-BuXphos (31 mg), tris(dibenzylideneacetone)dipalladium (22 mg) and the mixture was further stirred at 60° C. for 16 hr. Water was added to the reaction solution and the mixture was extracted with ethyl acetate. The organic layer was washed with saturated brine and dried over anhydrous sodium sulfate and the solvent was evaporated under reduced pressure. The obtained residue was dissolved in tetrahydrofuran (10 mL), 1N hydrochloric acid was added and the mixture was stirred at room temperature for 2 hr. The reaction solution was partitioned between ethyl acetate and 1N aqueous sodium hydroxide solution, and the aqueous layer was extracted again twice with ethyl acetate. The organic layers were combined, washed with saturated brine and dried over anhydrous sodium sulfate, and the solvent was evaporated under reduced pressure. The obtained residue was purified by NH silica gel column chromatography (hexane:ethyl acetate=70:30-40:60-0:100) to give the title compound (249 mg) as a yellow powder. MS (ESI) m/z: 396.3 [M+H]+

Reference Example 11 t-butyl 4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylate (Reference Example Compound 11)

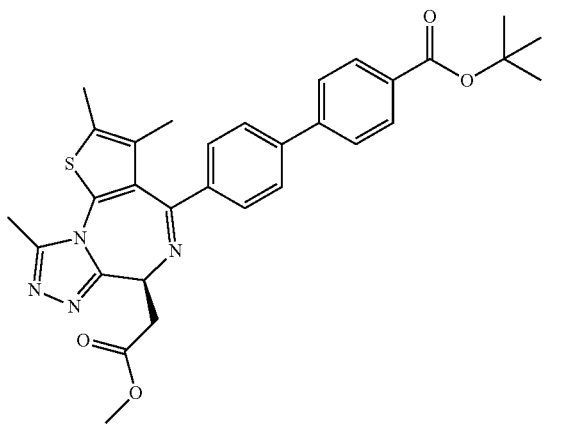 [SMILES: COC(=O)C[C@@H]1N=C(c2ccc(-c3ccc(C(=O)OC(C)(C)C)cc3)cc2)c2c(sc(C)c2C)-n2c(C)nnc21]

A mixture of Reference Example compound 1 (5.00 g), t-butyl 4-(4,4,5,5-tetramethyl-1,3,2-dioxaborolan-2-yl)benzoate (4.03 g), potassium fluoride (2.10 g), 2-dicyclohexylphosphino-2'-6'-dimethoxybiphenyl (hereinafter to be indicated as S-phos, 495 mg), palladium acetate (271 mg), tetrahydrofuran (40.2 mL) and water (0.78 mL) was stirred with heating under reflux for 40 hr. Furthermore, (4-t-butoxycarbonylphenyl)boronic acid (803 mg), S-phos (247 mg), palladium acetate (135 mg), water (0.78 mL) were added and the mixture was stirred for 20 hr. To the reaction mixture was added ethyl acetate, the insoluble material in the reaction mixture was filtered off through diatomaceous earth, and the filtrate was concentrated under reduced pressure. To the residue were added chloroform, water to extract the organic layer, and the aqueous layer was extracted again with chloroform. The organic layer was collected, dried over anhydrous sodium sulfate, and the solvent was evaporated under reduced pressure. The residue was purified by silica gel column chromatography (chloroform:methanol=98:2-95:5). It was further purified by silica gel column chromatography (chloroform:methanol=100:0-95:5) to give the title compound (6.55 g) as a crudely purified yellow solid. MS (ESI) m/z: 557.3 [M+H]+

Reference Example 12

(12-1) t-butyl [(2S)-1-{[3-(4-chlorobenzoyl)-4,5-dimethylthiophen-2-yl]amino}-1-oxopropan-2-yl] carbamate (Reference Example Compound 12-1)

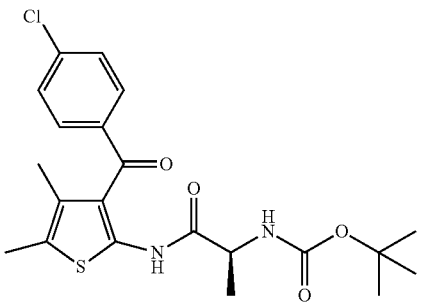 [SMILES: Cc1sc(NC(=O)[C@H](C)NC(=O)OC(C)(C)C)c(C(=O)c2ccc(Cl)cc2)c1C]

Under ice-cooling, to (2-amino-4,5-dimethyl-3-thienyl)-(4-chlorophenyl)methanone (10 g) described in J. Med. Chem. 1973, 16, 214 were added (2S)-2-(t-butoxycarbonylamino)propanoic acid (7.5 g) and pyridine (75 mL), phenylphosphonyl dichloride (28 g) was slowly added dropwise and the mixture was stirred under ice-cooling for 1 hr. After evaporation of the solvent, ethyl acetate was added, and the organic layer was washed with saturated aqueous sodium hydrogen carbonate, dried over anhydrous sodium sulfate, filtered, and the filtrate was concentrated under reduced pressure. The obtained residue was purified by silica gel column chromatography (hexane:ethyl acetate) to give the title compound (13 g) as a yellow powder. MS (ESI) m/z: 337.1 [M−Boc+2H]+

(12-2) (3S)-5-(4-chlorophenyl)-3,6,7-trimethyl-1,3-dihydro-2H-thieno[2,3-e][1,4]diazepin-2-one (Reference Example Compound 12-2)

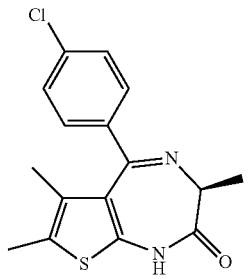

At room temperature, to a solution of Reference Example compound 12-1 (13 g) in dichloromethane (26 mL) was added trifluoroacetic acid (26 mL), the mixture was stirred for 1 hr, and the solvent was evaporated. To the obtained residue was added saturated aqueous sodium hydrogen carbonate, and the mixture was extracted with chloroform.

The organic layer was dried over anhydrous sodium sulfate, filtered, and the filtrate was concentrated under reduced pressure. To the obtained residue were added 2-propanol (53 mL) and acetic acid (2.6 mL), and the mixture was stirred at 90° C. for 1 hr. To the reaction mixture was added saturated aqueous sodium hydrogen carbonate, and the mixture was extracted with chloroform. The organic layer was dried over anhydrous sodium sulfate, filtered, and the filtrate was concentrated under reduced pressure. The obtained residue was suspension washed with ethyl acetate, and the insoluble material was collected by filtration. The obtained solid was dried under reduced pressure to give the title compound (8.1 g) as a white solid.

MS (ESI) m/z: 319.1 [M+H]$^+$ (12-3) (3S)-5-(4-chlorophenyl)-3,6,7-trimethyl-1,3-dihydro-2H-thieno[2,3-e][1,4]diazepine-2-thione (Reference Example Compound 12-3)

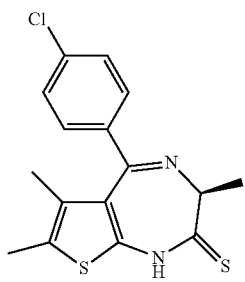

At room temperature, to Reference Example compound 12-2 (8.0 g) were added Lawesson reagent (10 g) and 1,2-dimethoxyethane (159 mL), and the mixture was stirred at 80° C. for 1.25 hr. The solvent was evaporated and the obtained residue was purified by NH silica gel column chromatography (chloroform:methanol) to give the title compound (6.9 g) as a pale-yellow solid. MS (ESI) m/z: 335.1 [M+H]$^+$ (12-4) (6S)-4-(4-chlorophenyl)-2,3,6,9-tetramethyl-6H-thieno[3,2-f][1,2,4]triazolo[4,3-a][1,4]diazepine (Reference Example Compound 12)

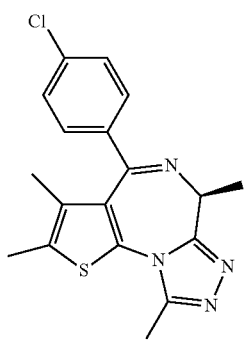

At room temperature, to a suspension of Reference Example compound 12-3 (6.9 g) in tetrahydrofuran (51 mL) was added hydrazine monohydrate (3.1 g), and the mixture was stirred for 3 hr. To the reaction mixture was added saturated brine, and the mixture was extracted with chloroform. The organic layer was dried over anhydrous sodium sulfate, filtered, and the filtrate was concentrated under reduced pressure. To the obtained residue were added 1,1,1-triethoxyethane (7.5 mL) and toluene (51 mL) and the mixture was stirred at 120° C. for 1 hr. The solvent was evaporated and the obtained residue was purified by silica gel column chromatography (ethyl acetate:methanol) to give the title compound (7.3 g) as a pale-red amorphous compound. MS (ESI) m/z: 357.2 [M+H]$^+$ Reference Example 13 methyl [4-(4-chlorophenyl)-2,3,9-trimethyl-6H-thieno[3,2-f][1,2,4]triazolo[4,3-a][1,4]diazepin-6-yl]acetate (Reference Example Compound 13)

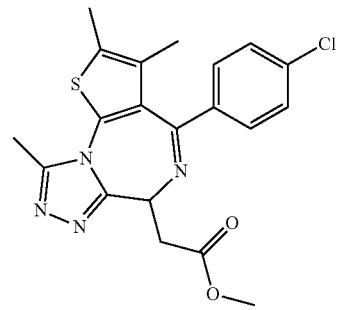 [SMILES: COC(=O)CC1N=C(c2ccc(Cl)cc2)c2c(sc(C)c2C)-n2c(C)nnc21]

By an operation in the same manner as in (1-1) in Reference Example 1 and using 4-(4-chlorophenyl)-2,3,9-trimethyl-6H-thieno[3,2-f][1,2,4]triazolo[4,3-a][1,4]diazepine-6-acetic acid instead of (S)-4-(4-chlorophenyl)-2,3,9-trimethyl-6H-thieno[3,2-f][1,2,4]triazolo[4,3-a][1,4]diazepine-6-acetic acid, the title compound was obtained as a white solid.

MS (ESI) m/z: 415.3 [M+H]$^+$

Example 1

(1-1) t-butyl {2-[2-(2-benzyloxyethoxy)ethoxy]ethoxy}acetate (Example Compound 1-1)

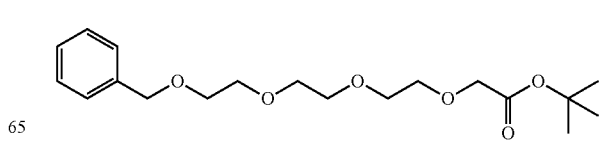

To a solution of 2-[2-(2-benzyloxyethoxy)ethoxy]ethanol (5.00 g) in t-butyl alcohol (69.4 mL) was added potassium t-butoxide (2.57 g) and the mixture was stirred at room temperature for 2 hr. After cooling to 0° C., t-butyl bromoacetate (5.62 mL) was added and the mixture was stirred at room temperature for 20 hr. To the reaction mixture were added methylene chloride, water for partitioning. The organic layer was washed with saturated brine, dried over anhydrous sodium sulfate, filtered and the filtrate was concentrated under reduced pressure. The obtained residue was purified by silica gel column chromatography (hexane:ethyl acetate=90:10-70:30) to give the title compound (6.02 g) as a colorless oil.

MS (ESI) m/z: 355.4 [M+H]$^+$ (1-2) t-butyl {2-[2-(2-hydroxyethoxy)ethoxy]ethoxy}acetate (Example Compound 1-2)

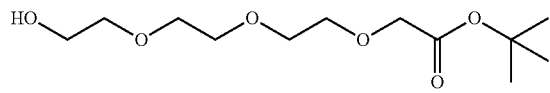 [SMILES: CC(C)(C)OC(=O)COCCOCCOCCO]

To a solution of Example compound 1-1 (4.50 g) in ethanol (42.3 mL) was added 10% palladium carbon (PH, 450 mg), and the mixture was vigorously stirred under a hydrogen atmosphere at room temperature for 3 hr. The reaction mixture was diluted with chloroform-ethanol (1:1), the insoluble material was filtered off through diatomaceous earth, and the filtrate was concentrated under reduced pressure. The obtained residue was dried under reduced pressure to give the title compound (3.15 g) as a yellow oil. MS (APCI) m/z: 264.9 [M+H]$^+$ (1-3) t-butyl [2-(2-{2-[(4-methylbenzene-1-sulfonyl)oxy]ethoxy}ethoxy)ethoxy]acetate (Example Compound 1-3)

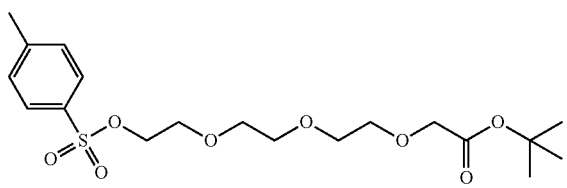 [SMILES: Cc1ccc(S(=O)(=O)OCCOCCOCCOCC(=O)OC(C)(C)C)cc1]

To a solution of Example compound 1-2 (2.00 g) in pyridine (30 mL) was added, under ice-cooling, p-toluenesulfonyl chloride (2.43 mL) and the mixture was stirred for 4 hr, and further stirred at room temperature for 4 hr. The reaction mixture was concentrated under reduced pressure at 30° C., and the residue was diluted with ethyl acetate, washed twice with 5% aqueous potassium sulfite solution and further with saturated brine, dried over anhydrous sodium sulfate and filtered. The solvent was evaporated under reduced pressure. The obtained residue was purified by silica gel chromatography (hexane:ethyl acetate=80:20-40:60) to give the title compound (2.76 g) as a pale-orange oil. MS (ESI) m/z: 363.2 [M−tBu+2H]$^+$ (1-4) methyl 3-{4-[(13,13-dimethyl-11-oxo-3,6,9,12-tetraoxatetradecan-1-yl)oxy]phenyl}propanoate (Example Compound 1-4)

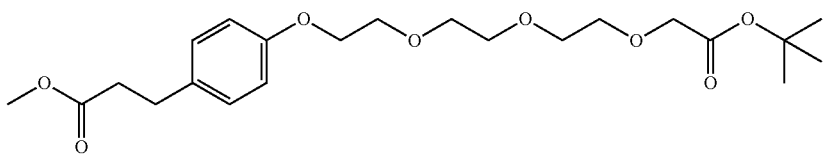 [SMILES: COC(=O)CCc1ccc(OCCOCCOCCOCC(=O)OC(C)(C)C)cc1]

To a solution of methyl 3-(4-hydroxyphenyl)propanoate (300 mg), Example compound 1-3 (836 mg) in N,N-dimethylformamide (8.3 mL) was added cesium carbonate (10.8 g), and the mixture was stirred at 80° C. for 1 hr. The reaction mixture was diluted with ethyl acetate, washed successively with water and saturated brine, dried over anhydrous sodium sulfate and filtered. The solvent was evaporated under reduced pressure. The obtained residue was purified by silica gel chromatography (hexane:ethyl acetate=90:10-50:50) to give the title compound (698 mg) as a colorless oil.

MS (ESI) m/z: 371.3 [M−tBu+2H]$^+$ (1-5) [2-(2-{2-[4-(3-methoxy-3-oxypropyl)phenoxy]ethoxy}ethoxy)ethoxy]acetic acid (Example Compound 1-5)

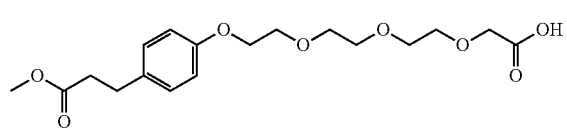 [SMILES: COC(=O)CCc1ccc(OCCOCCOCCOCC(=O)O)cc1]

To a solution of Example compound 1-4 (682 mg) in dichloromethane (4.0 mL) was added trifluoroacetic acid (2.0 mL), and the mixture was stirred at room temperature for 3 hr. The reaction mixture was concentrated under reduced pressure, and an operation to added toluene to the residue and concentrate was performed 3 times to give the title compound (647 mg) as an unpurified pale-yellow oil.

MS (ESI) m/z: 371.3 [M+H]$^+$ (1-6) methyl 3-[4-({(13S)-13-[(2S,4R)-4-hydroxy-2-({(1S)-1-[4-(4-methyl-1,3-thiazol-5-yl)phenyl]ethyl}carbamoyl)pyrrolidine-1-carbonyl]-14,14-dimethyl-11-oxo-3,6,9-trioxa-12-azapentadecan-1-yl}oxy)phenyl]propanoate (Example Compound 1-6)

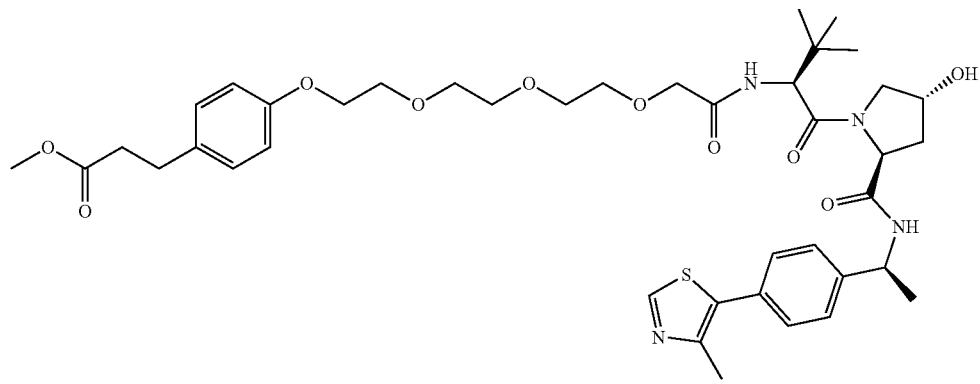 [SMILES: COC(=O)CCc1ccc(OCCOCCOCCOCC(=O)N[C@H](C(=O)N2C[C@H](O)C[C@H]2C(=O)N[C@@H](C)c2ccc(-c3scnc3C)cc2)C(C)(C)C)cc1]

To a solution of Reference Example compound 5 (200 mg), Example compound 1-5 (186 mg) in N,N-dimethylformamide (2.0 mL) were added, under ice-cooling, N,N-diisopropylethylamine (0.360 mL) and HATU (221 mg) and the mixture was stirred at room temperature for 1 hr. The reaction mixture was diluted with ethyl acetate, washed successively with saturated aqueous sodium hydrogen carbonate, water and saturated brine, dried over anhydrous sodium sulfate and filtered. The solvent was evaporated under reduced pressure. The obtained residue was purified by silica gel chromatography (hexane:ethyl acetate=100:0-95:5) to give the title compound (222 mg) as a colorless oil.
MS (ESI) m/z: 797.6 [M+H]$^+$ (1-7) 3-[4-({(13S)-13-[(2S,4R)-4-hydroxy-2-({(1S)-1-[4-(4-methyl-1,3-thiazol-5-yl)phenyl]ethyl}carbamoyl)pyrrolidine-1-carbonyl]-14,14-dimethyl-11-oxo-3,6,9-trioxa-12-azapentadecan-1-yl}oxy)phenyl]propanoic acid (Example Compound 1-7)

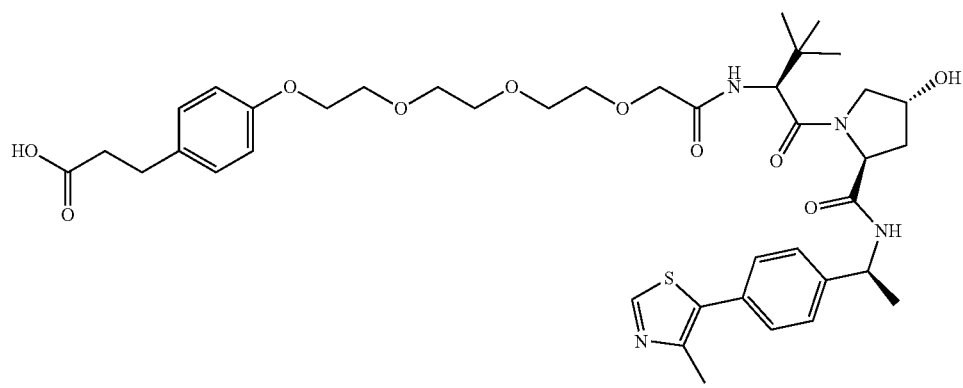 [SMILES: Cc1ncsc1-c1ccc([C@H](C)NC(=O)[C@@H]2C[C@@H](O)CN2C(=O)[C@@H](NC(=O)COCCOCCOCCOc2ccc(CCC(=O)O)cc2)C(C)(C)C)cc1]

To a solution of Example compound 1-6 (212 mg) in tetrahydrofuran (4.2 mL), water (1.1 mL) and methanol (1.1 mL) was added, under ice-cooling, lithium hydroxide monohydrate (22 mg) and the mixture was stirred for 4 hr and then at room temperature for 2 hr. The reaction mixture was diluted with ethyl acetate, washed successively with 5% aqueous potassium bisulfite solution and saturated brine, dried over anhydrous sodium sulfate, filtered and the solvent was evaporated under reduced pressure to give the title compound (232 mg) as a colorless oil. MS (ESI) m/z: 783.7 [M+H]$^+$ (1-8) methyl [(6S)-4-(4-{3-[4-({(13S)-13-[(2S,4R)-4-hydroxy-2-({(1S)-1-[4-(4-methyl-1,3-thiazol-5-yl)phenyl]ethyl}carbamoyl)pyrrolidine-1-carbonyl]-14,14-dimethyl-11-oxo-3,6,9-trioxa-12-azapentadecan-1-yl}oxy)phenyl]propanamido}phenyl)-2,3,9-trimethyl-6H-thieno[3,2-f][1,2,4]triazolo[4,3-a][1,4]diazepin-6-yl]acetate (Example Compound 1)

Example 2

(2-1) methyl [(6S)-4-(3'-cyano-4'-hydroxy[1,1'-biphenyl]-4-yl)-2,3,9-trimethyl-6H-thieno[3,2-f][1,2,4]triazolo[4,3-a][1,4]diazepin-6-yl]acetate (Example Compound 2-1)

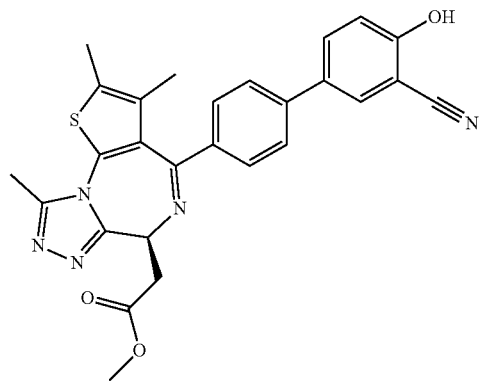

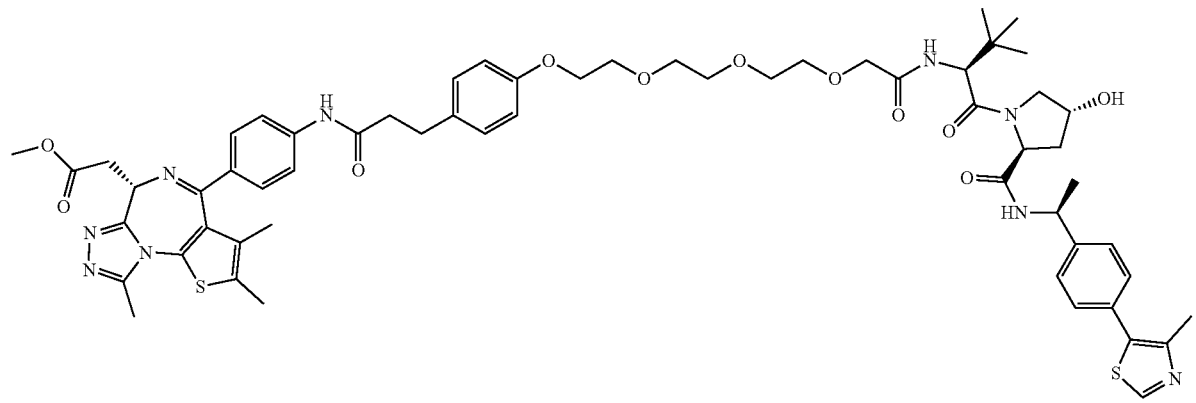

To a solution of Reference Example compound 10 (68 mg), Example compound 1-7 (149 mg) in N,N-dimethylformamide (1.7 mL) were added N,N-diisopropylethylamine (0.119 mL) and HATU (78 mg), and the mixture was stirred at room temperature for 14 hr. Water was added to the reaction mixture, and the mixture was extracted twice with ethyl acetate, and the extract was washed with water, saturated aqueous sodium hydrogen carbonate, dried over anhydrous sodium sulfate, and the solvent was evaporated. The obtained residue was purified by preparative HPLC (10 mM aqueous ammonium carbonate solution-acetonitrile) to give the title compound (129 mg) as a white solid.

MS (ESI) m/z: 1160.6 [M+H]$^+$

A mixture of Reference Example compound 7 (5.25 g), Reference Example compound 1 (4.80 g), potassium fluoride (2.02 g), tetrahydrofuran (58 mL), S-phos (950 mg), palladium acetate (260 mg) and water (0.75 mL) was stirred with heating under reflux for 24 hr, S-phos (950 mg) and palladium acetate (260 mg) were added and the mixture was stirred for 24 hr. Reference Example compound 7 (1.05 g), S-phos (950 mg), palladium acetate (260 mg) were added, and the mixture was further stirred for 24 hr, the reaction mixture was concentrated, water was added, extracted 3 times with ethyl acetate, and the extract was dried over anhydrous sodium sulfate and filtered. The solvent was evaporated under reduced pressure. The obtained residue was purified by silica gel column chromatography twice (chloroform:methanol=98:2-92:8) (hexane:ethyl acetate=20:80, chloroform:methanol=100:0-90:10) to give the title compound (2.64 g) as a crudely purified pale-yellow solid. MS (ESI) m/z: 498.4 [M+H]+

(2-2) methyl [(6S)-4-{3'-cyano-4'-[(13,13-dimethyl-11-oxo-3,6,9,12-tetraoxatetradecan-1-yl)oxy][1,1'-biphenyl]-4-yl}-2,3,9-trimethyl-6H-thieno[3,2-f][1,2,4]triazolo[4,3-a][1,4]diazepin-6-yl]acetate (Example Compound 2-2)

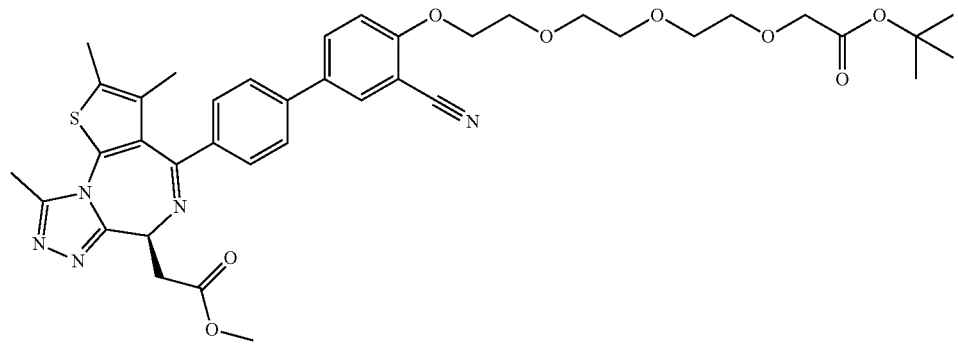 [SMILES: COC(=O)C[C@@H]1N=C(c2ccc(-c3ccc(OCCOCCOCCOCC(=O)OC(C)(C)C)c(C#N)c3)cc2)c2c(sc(C)c2C)-n2c(C)nnc21]

To a mixture of Example compound 2-1 (83 mg), potassium carbonate (46 mg) and N,N-dimethylformamide (1.1 mL) was added Example compound 1-3 (70 mg) and the mixture was stirred at 60° C. for 1 hr. Water was added to the reaction mixture and the mixture was extracted with ethyl acetate. The organic layer was washed with water-saturated brine (1:1), dried over anhydrous sodium sulfate, filtered, and the filtrate was concentrated under reduced pressure. The obtained residue was purified by silica gel column chromatography (chloroform:methanol=100:0-90:10) to give the title compound (121 mg) as a colorless oil. MS (ESI) m/z: 744.4 [M+H]$^+$ (2-3) (2-{2-[2-({3-cyano-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)ethoxy]ethoxy}ethoxy)acetic acid (Example Compound 2-3)

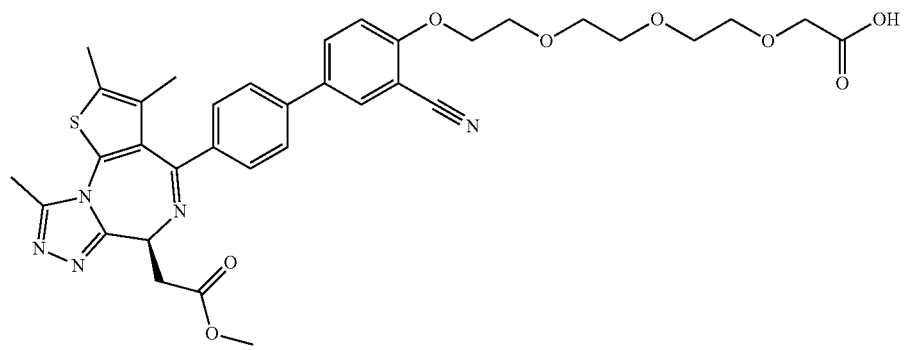 [SMILES: COC(=O)C[C@@H]1N=C(c2ccc(-c3ccc(OCCOCCOCCOCC(=O)O)c(C#N)c3)cc2)c2c(sc(C)c2C)-n2c(C)nnc21]

To a solution of Example compound 2-2 (121 mg) in dichloromethane (4.0 mL) was added trifluoroacetic acid (0.30 mL), and the mixture was stirred at room temperature for 5 hr. To the reaction mixture was added water and the mixture was extracted with ethyl acetate. The organic layer was washed with water and saturated brine, dried over anhydrous sodium sulfate, filtered and the filtrate was concentrated under reduced pressure. The obtained residue was purified by silica gel column chromatography (chloroform:methanol=100:0-80:20) to give the title compound (146 mg) as a crudely purified yellow oil. MS (ESI) m/z: 688.3 [M+H]$^+$ (2-4) methyl {(6S)-4-[3'-cyano-4'-({(13S)-13-[(2S,4R)-4-hydroxy-2-({(1S)-1-[4-(4-methyl-1,3-thiazol-5-yl)phenyl]ethyl}carbamoyl)pyrrolidine-1-carbonyl]-14,14-dimethyl-11-oxo-3,6,9-trioxa-12-azapentadecan-1-yl}oxy)[1,1'-biphenyl]-4-yl]-2,3,9-trimethyl-6H-thieno[3,2-f][1,2,4]triazolo[4,3-a][1,4]diazepin-6-yl}acetate (Example Compound 2)

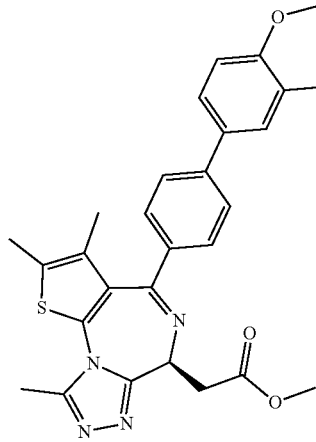
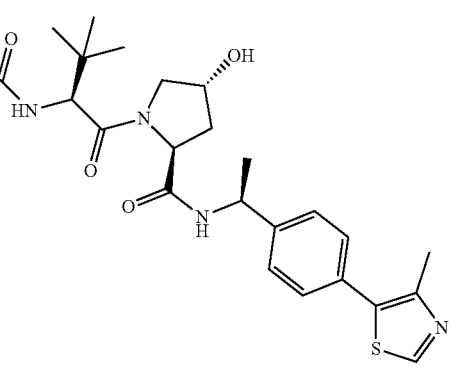

To a solution of Example compound 2-3 (17 mg), Reference Example compound 5 (13 mg) in N,N-dimethylformamide (0.5 mL) and N,N-diisopropylethylamine (0.013 mL) was added, under ice-cooling, HATU (14 mg), and the mixture was stirred at room temperature for 3.5 hr. To the reaction mixture was added saturated aqueous sodium hydrogen carbonate and the mixture was extracted with chloroform. The solvent was evaporated under reduced pressure. The obtained residue was purified by preparative HPLC (10 mM aqueous ammonium carbonate solution-acetonitrile) to give the title compound (9.6 mg) as a colorless oil. MS (ESI) m/z: 558.3[(M+2H)/2]$^+$ Example 3

(3-1) 2-amino-5-(4,4,5,5-tetramethyl-1,3,2-dioxaboronan-2-yl)benzonitrile (Example Compound 3-1)

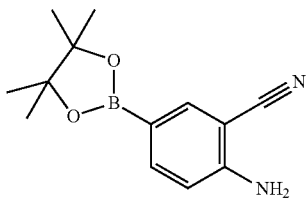 [SMILES: CC1(C)OB(c2ccc(N)c(C#N)c2)OC1(C)C]

A mixture of 2-amino-5-bromo-benzonitrile (1.00 g), bis(pinacolato)diboron (1.95 g), potassium acetate (1.50 g), 1,1'-bis(diphenylphosphino)ferrocene-palladium(II) dichloride dichloromethane complex (207 mg) and 1,4-dioxane (15 mL) was stirred under a nitrogen atmosphere at 80° C. for 20 hr. The insoluble material in the reaction mixture was filtered off through diatomaceous earth, and the filtrate was concentrated under reduced pressure. The obtained residue was purified by silica gel column chromatography (hexane:ethyl acetate=91:9-66:34) to give the title compound (1.65 g) as a white solid.

MS (ESI) m/z: 245.1 [M+H]$^+$ (3-2) methyl [(6S)-4-(4'-amino-3'-cyano[1,1'-biphenyl]-4-yl)-2,3,9-trimethyl-6H-thieno[3,2-f][1,2,4]triazolo[4,3-a][1,4]diazepin-6-yl]acetate (Example Compound 3-2)

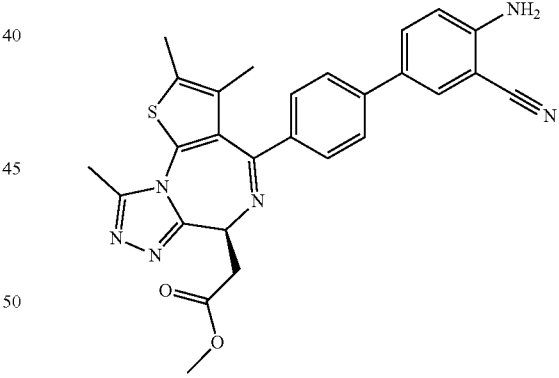

A mixture of Example compound 3-1 (262 mg), Reference Example compound 1 (300 mg), tripotassium phosphate (460 mg), tetrahydrofuran (3.6 mL), S-phos (119 mg), palladium acetate (65 mg) and water (0.047 mL) was stirred with heating under reflux for 4.5 hr. The insoluble material in the reaction mixture was filtered off through diatomaceous earth and the solvent was evaporated under reduced pressure. The obtained residue was purified by silica gel column chromatography (chloroform:methanol=100:0-94:6) and NH silica gel column chromatography (chloroform:methanol=100:0-94:6) to give the title compound (393 mg) as an orange solid.

MS (ESI) m/z: 497.4 [M+H]$^+$ (3-3) (2-{2-[2-({3-cyano-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}amino)-2-oxoethoxy]ethoxy}ethoxy)acetic acid (Example Compound 3-3)

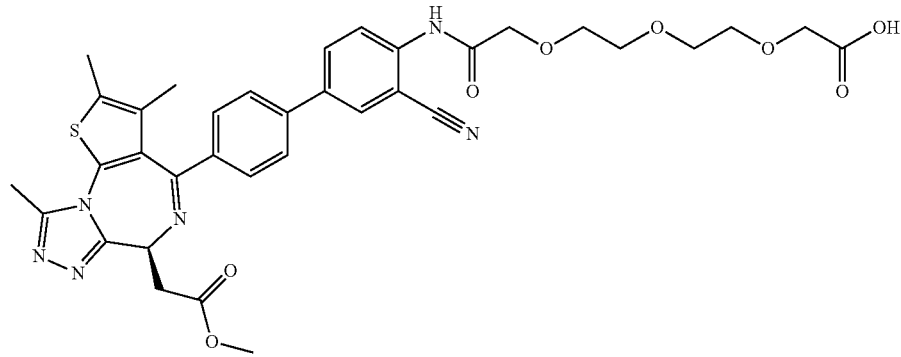 [SMILES: COC(=O)C[C@@H]1N=C(c2ccc(-c3ccc(NC(=O)COCCOCCOCC(=O)O)c(C#N)c3)cc2)c2c(sc(C)c2C)-n2c(C)nnc21]

To a mixture of 2-{2-[2-(carbomethoxy)ethoxy]ethoxy}acetic acid (230 mg), dichloromethane (6.6 mL) and oxalyl chloride (0.526 mL) was added, under ice-cooling, N,N-dimethylformamide (1 drop), and the mixture was stirred at room temperature for 1 hr and concentrated. The residue was dissolved in N,N-dimethylformamide (1.0 mL) under ice-cooling, Example compound 3-2 (50 mg), N,N-diisopropylethylamine (0.026 mL) were added and the mixture was stirred for 10 min. The reaction mixture was diluted with toluene, and the solvent was evaporated under reduced pressure. The obtained residue was purified by preparative HPLC (10 mM aqueous ammonium carbonate solution-acetonitrile) to give the title compound (37 mg) as a yellow oil. MS (ESI) m/z: 701.5 [M+H]$^+$ (3-4) methyl {(6S)-4-[3'-cyano-4'-({(13S)-13-[(2S,4R)-4-hydroxy-2-({(1S)-1-[4-(4-methyl-1,3-thiazol-5-yl)phenyl]ethyl}carbamoyl)pyrrolidine-1-carbonyl]-14,14-dimethyl-11-oxo-3,6,9-trioxa-12-azapentadecanan-1-oyl}amino)[1,1'-biphenyl]-4-yl]-2,3,9-trimethyl-6H-thieno[3,2-f][1,2,4]triazolo[4,3-a][1,4]diazepin-6-yl}acetate (Example Compound 3)

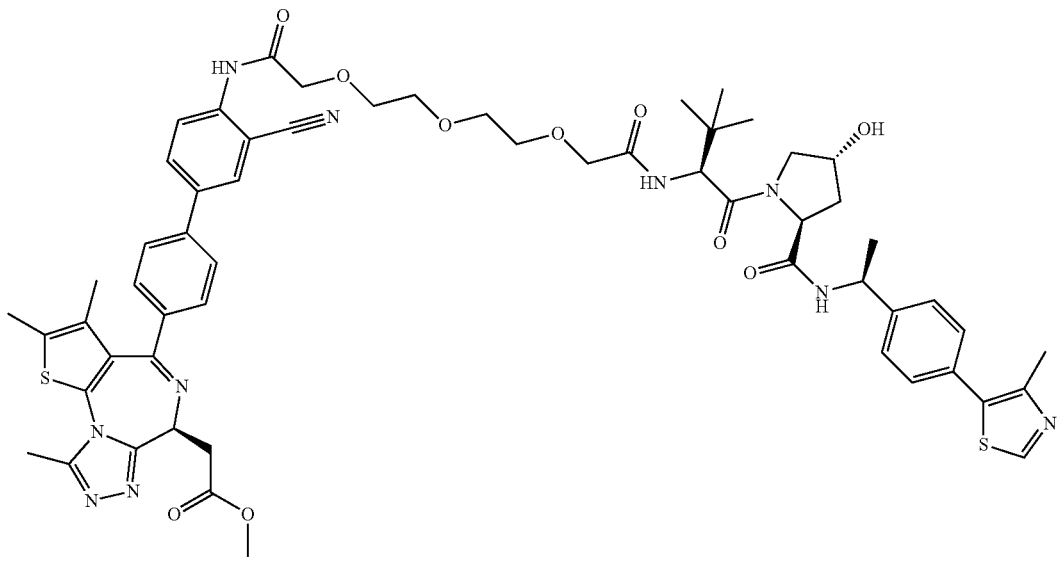 [SMILES: COC(=O)C[C@@H]1N=C(c2ccc(-c3ccc(NC(=O)COCCOCCOCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

To a solution of Example compound 3-3 (37 mg) and Reference Example compound 5 (28 mg) in N,N-dimethylformamide (1.1 mL), N,N-diisopropylethylamine (0.022 mL) was added, under ice-cooling, HATU (30 mg), and the mixture was stirred at room temperature for 1 hr. To the reaction mixture was added saturated aqueous sodium hydrogen carbonate and the mixture was extracted with chloroform. The solvent was evaporated under reduced pressure. The obtained residue was purified by silica gel column chromatography (chloroform:methanol=100:0-95:5) to give the title compound (30 mg) as a white solid.

MS (ESI) m/z: 1127.5 [M+H]$^+$

Example 4

(4-1) methyl 3-[4-(2-t-butoxy-2-oxoethoxy)phenyl]propanoate (Example Compound 4-1)

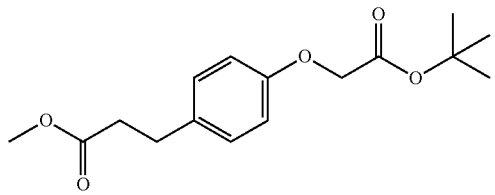 [SMILES: COC(=O)CCc1ccc(OCC(=O)OC(C)(C)C)cc1]

To a solution of methyl 3-(4-hydroxyphenyl)propanoate (500 mg) and t-butyl 2-bromoacetate (649 mg) in N,N-dimethylformamide (5.0 mL) was added cesium carbonate (1.36 g), and the mixture was stirred at room temperature for 1 hr. The reaction mixture was diluted with ethyl acetate, washed successively with water and saturated brine, dried over anhydrous sodium sulfate and filtered. The solvent was evaporated under reduced pressure. The obtained residue was purified by silica gel chromatography (hexane:ethyl acetate=90:10-80:20) to give the title compound (786 mg) as a colorless oil. MS (ESI) m/z: 239.2 [M–tBu+2H]$^+$ (4-2) [4-(3-methoxy-3-oxypropyl)phenoxy]acetic acid (Example Compound 4-2)

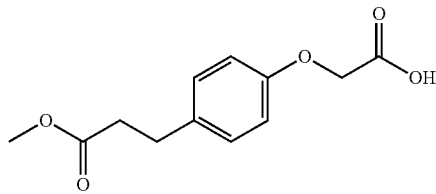 [SMILES: COC(=O)CCc1ccc(OCC(=O)O)cc1]

To a solution of Example compound 4-1 (780 mg) in dichloromethane (3.9 mL) was added trifluoroacetic acid (3.9 mL), and the mixture was stirred at room temperature for 1 hr. The reaction mixture was concentrated, toluene was added and the solvent was evaporated. This operation was performed 3 times to give the title compound (625 mg) as an unpurified colorless solid. MS (ESI) m/z: 237.3 [M–H]$^-$ (4-3) methyl 3-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]phenyl}propanoate (Example Compound 4-3)

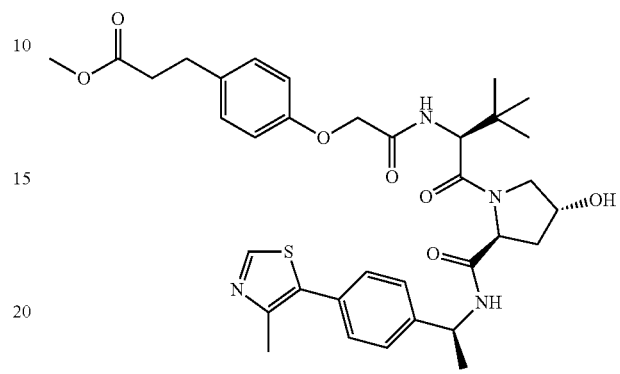

To a solution of Reference Example compound 5 (500 mg), Example compound 4-2 (272 mg) in N,N-dimethylformamide (5.2 mL) were added, under ice-cooling, N,N-diisopropylethylamine (0.899 mL) and HATU (553 mg) and the mixture was stirred at room temperature for 18 hr. The reaction mixture was diluted with ethyl acetate, washed successively with saturated aqueous sodium hydrogen carbonate, water and saturated brine, dried over anhydrous sodium sulfate and filtered. The solvent was evaporated under reduced pressure. The obtained residue was purified by silica gel chromatography (chloroform:methanol=100:0-95:5) to give the title compound (548 mg) as a pale-yellow oil. MS (ESI) m/z: 665.6 [M+H]$^+$ (4-4) 3-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]phenyl}propanoic acid (Example Compound 4-4)

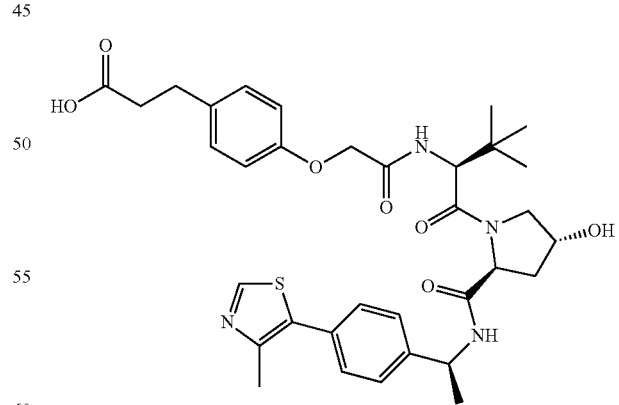

To a solution of Example compound 4-3 (542 mg) in tetrahydrofuran (11 mL), water (2.7 mL) and methanol (2.7 mL) was added, under ice-cooling, lithium hydroxide monohydrate (103 mg) and the mixture was stirred at room temperature for 3 hr. The reaction mixture was diluted with ethyl acetate, washed successively with 5% aqueous potassium bisulfite solution and saturated brine, dried over anhydrous sodium sulfate, filtered and the solvent was evaporated under reduced pressure to give the title compound (521 mg) as a colorless solid. MS (ESI) m/z: 651.6 [M+H]⁺

(4-5) methyl {(6S)-4-[4-(3-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]phenyl}propanamido)phenyl]-2,3,9-trimethyl-6H-thieno[3,2-f][1,2,4]triazolo[4,3-a][1,4]diazepin-6-yl}acetate (Example Compound 4)

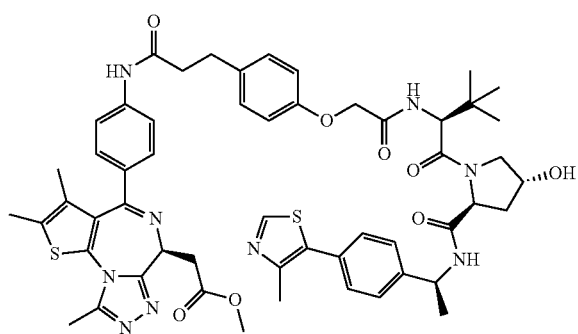 [SMILES: COC(=O)C[C@@H]1N=C(c2ccc(NC(=O)CCc3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 4-4 (428 mg) and Reference Example compound 10 (200 mg) in N,N-dimethylformamide (5.0 mL) were added, under ice-cooling, N,N-diisopropylethylamine (0.262 mL) and HATU (385 mg), and the mixture was stirred at room temperature for 16 hr. To the reaction mixture was added saturated aqueous sodium hydrogen carbonate and the mixture was extracted with ethyl acetate, and the extract was washed successively with saturated aqueous sodium hydrogen carbonate and saturated brine, dried over anhydrous sodium sulfate and filtered. The solvent was evaporated under reduced pressure. The obtained residue was purified by preparative HPLC (10 mM aqueous ammonium carbonate solution-acetonitrile) to give the title compound (220 mg) as a colorless solid. MS (ESI) m/z: 1028.8 [M+H]⁺

Example 5

(5-1) methyl [(6S)-4-{4-[3-(4-hydroxyphenyl)propanamido]phenyl}-2,3,9-trimethyl-6H-thieno[3,2-f][1,2,4]triazolo[4,3-a][1,4]diazepin-6-yl]acetate (Example Compound 5-1)

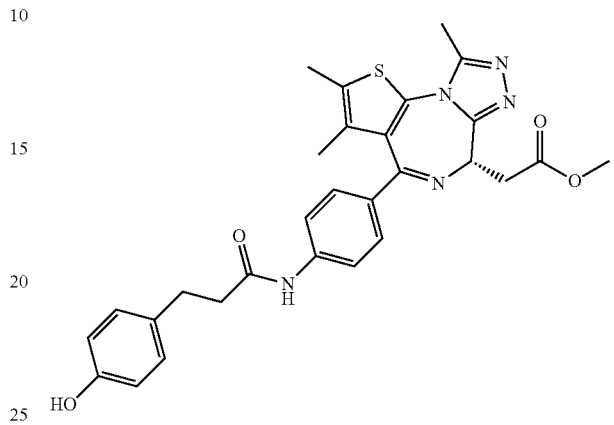

A mixture of Reference Example compound 10 (153 mg), 3-(4-hydroxyphenyl)propanoic acid (77 mg), dichloromethane (1.9 mL) and 1-(3-dimethylaminopropyl)-3-ethylcarbodiimide hydrochloride (WSCI, 148 mg) was stirred at room temperature for 20 hr, 3-(4-hydroxyphenyl)propanoic acid (38 mg) and WSCI (74 mg) were added, and the mixture was further stirred for 35 hr. Water was added to the reaction mixture for partitioning, and the organic layer was concentrated. The obtained residue was purified by silica gel column chromatography (chloroform:methanol=100:0-95:5) to give the title compound (197 mg) as a pale-yellow solid. MS (ESI) m/z: 544.2 [M+H]⁺

(5-2) 23-[(4-methylbenzene-1-sulfonyl)oxy]-3,6,9,12,15,18,21-heptaoxatricosanoic acid (Example Compound 5-2)

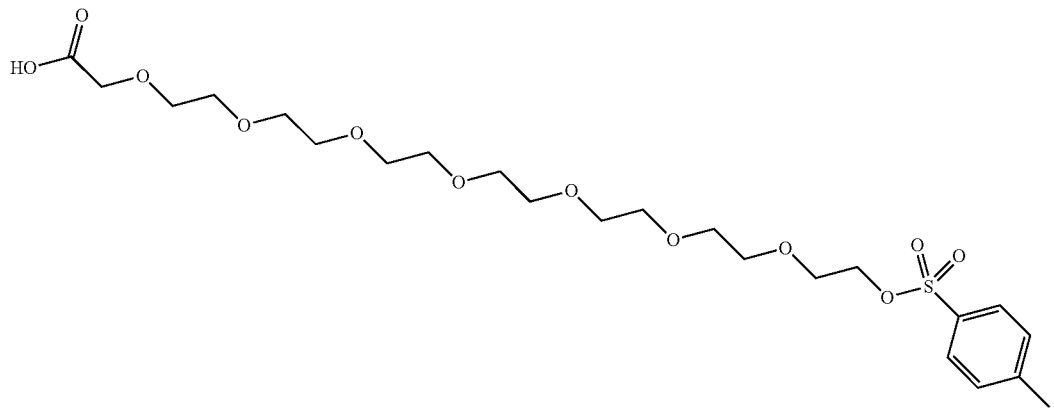 [SMILES: Cc1ccc(S(=O)(=O)OCCOCCOCCOCCOCCOCCOCCOCC(=O)O)cc1]

To a solution of 2-(2-{2-[2-(2-{2-[2-(2-hydroxyethoxy)ethoxy]ethoxy}ethoxy)ethoxy]ethoxy}ethoxy)ethyl 4-methylbenzenesulfonate (150 mg), carbon tetrachloride (0.57 mL), acetonitrile (0.57 mL) and water (0.38 mL) were added sodium periodate (86 mg) and trichlororuthenium (5.9 mg), and the mixture was stirred at room temperature for 3 hr. The insoluble material in the reaction mixture was filtered off through diatomaceous earth and the filtrate was concentrated under reduced pressure to give the title compound (151 mg) as a yellow oil. MS (ESI) m/z: 537.3 [M−H]⁻

(5-3) (25S)-25-[(2S,4R)-4-hydroxy-2-({(1S)-1-[4-(4-methyl-1,3-thiazol-5-yl)phenyl]ethyl}carbamoyl)pyrrolidine-1-carbonyl]-26,26-dimethyl-23-oxo-3,6,9,12,15,18,21-heptaoxa-24-azaheptacosan-1-yl 4-methylbenzene-1-sulfonate (Example Compound 5-3)

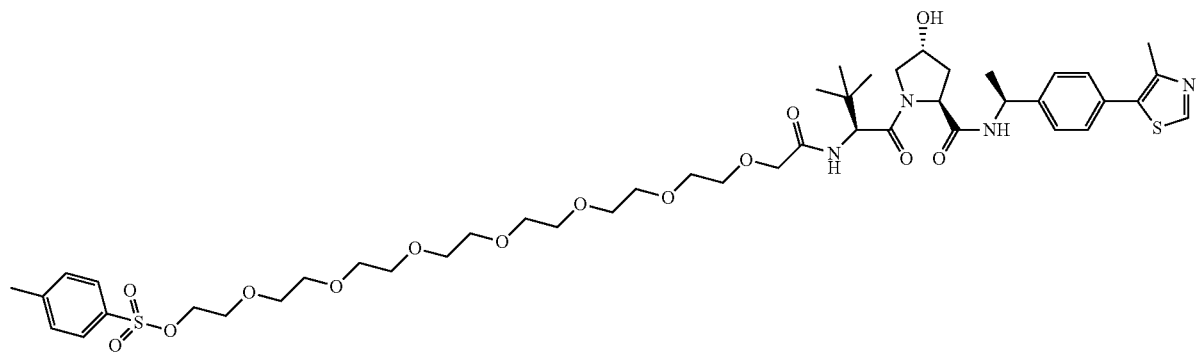 [SMILES: Cc1ccc(S(=O)(=O)OCCOCCOCCOCCOCCOCCOCCOCC(=O)N[C@H](C(=O)N2C[C@H](O)C[C@H]2C(=O)N[C@@H](C)c2ccc(-c3scnc3C)cc2)C(C)(C)C)cc1]

To a solution of Reference Example compound 5 (135 mg) and Example compound 5-2 (151 mg) in N,N-dimethylformamide (4.5 mL) and N,N-diisopropylethylamine (0.146 mL) was added, under ice-cooling, HATU (160 mg) and the mixture was stirred at room temperature for 40 min. To the reaction mixture was added saturated aqueous sodium hydrogen carbonate and the mixture was extracted twice with ethyl acetate, and the extract was washed twice with water-saturated brine (1:1), dried over anhydrous sodium sulfate and filtered. The solvent was evaporated under reduced pressure. The obtained residue was purified by silica gel chromatography (hexane:ethyl acetate=100:0-94:6) to give the title compound (192 mg) as a colorless oil. MS (ESI) m/z: 965.7 [M+H]⁺

(5-4) methyl [(6S)-4-(4-{3-[4-({(25S)-25-[(2S,4R)-4-hydroxy-2-({(1S)-1-[4-(4-methyl-1,3-thiazol-5-yl)phenyl]ethyl}carbamoyl)pyrrolidine-1-carbonyl]-26,26-dimethyl-23-oxo-3,6,9,12,15,18,21-heptaoxa-24-azaheptacosan-1-yl}oxy)phenyl]propanamido}phenyl)-2,3,9-trimethyl-6H-thieno[3,2-f][1,2,4]triazolo[4,3-a][1,4]diazepin-6-yl]acetate (Example Compound 5)

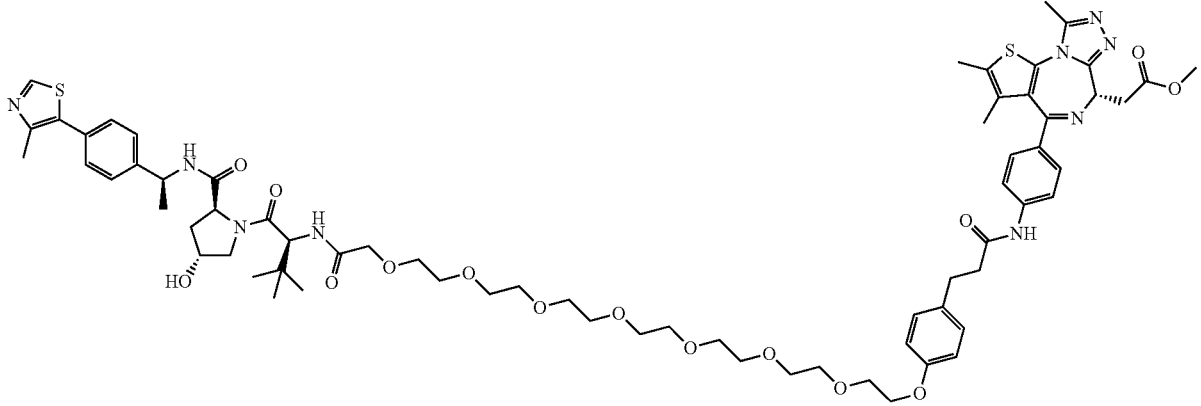 [SMILES: COC(=O)C[C@@H]1N=C(c2ccc(NC(=O)CCc3ccc(OCCOCCOCCOCCOCCOCCOCCOCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

A mixture of Example compound 5-1 (35 mg), Example compound 5-3 (62 mg), potassium carbonate (13 mg) and N,N-dimethylformamide (0.64 mL) was stirred at 60° C. for 23 hr. To the reaction mixture were added water and chloroform and the mixture was stirred. The organic layer was separated and concentrated under reduced pressure. The obtained residue was purified by preparative HPLC (10 mM aqueous ammonium carbonate solution-acetonitrile) to give the title compound (16 mg) as a white solid. MS (ESI) m/z: 1336.6 [M+H]⁺

Example 6

(6-1) t-butyl {2-[(4-methylbenzene-1-sulfonyl)oxy]ethoxy}acetate (Example Compound 6-1)

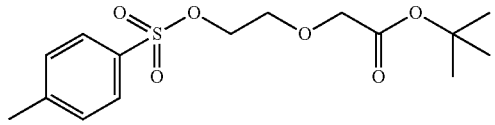 [SMILES: Cc1ccc(S(=O)(=O)OCCOCC(=O)OC(C)(C)C)cc1]

To a solution of t-butyl 2-(2-hydroxyethoxy)acetate (1.09 g) in pyridine (10.9 mL) was added, under ice-cooling, p-toluenesulfonyl chloride (1.76 g) and the mixture was stirred at room temperature for 2.5 hr. The reaction mixture was diluted with ethyl acetate and acidified with 1N hydrochloric acid under ice-cooling. The organic layer was separated, washed again with 1N hydrochloric acid and successively washed with saturated brine, saturated saline. The obtained residue was purified by silica gel column chromatography twice (chloroform:methanol=100:0-90:10) (hexane:ethyl acetate=100:0-70:30) to give the title compound (1.39 g) as a colorless oil.
MS (ESI) m/z: 661.2 [2 M+H]⁺

(6-2) methyl 3-{4-[2-(2-t-butoxy-2-oxoethoxy)ethoxy]phenyl}propanoate (Example Compound 6-2)

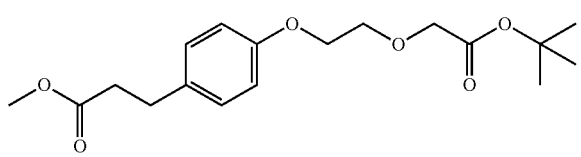 [SMILES: COC(=O)CCc1ccc(OCCOCC(=O)OC(C)(C)C)cc1]

To a solution of Example compound 6-1 (323 mg) and t-butyl 2-{2-[2-(2-hydroxyethoxy)ethoxy]ethoxy}acetate (160 mg) in N,N-dimethylformamide (4.4 mL) was added cesium carbonate (434 mg), and the mixture was stirred at 80° C. for 1 hr. The reaction mixture was diluted with ethyl acetate, washed successively with water and saturated brine, dried over anhydrous sodium sulfate and filtered. The solvent was evaporated under reduced pressure. The obtained residue was purified by silica gel column chromatography (hexane:ethyl acetate=90:0-67:33) to give the title compound (1.39 g) as a colorless oil. MS (ESI) m/z: 283.2 [M−tBu+2H]⁺

(6-3) {2-[4-(3-methoxy-3-oxypropyl)phenoxy]ethoxy}acetic acid (Example Compound 6-3)

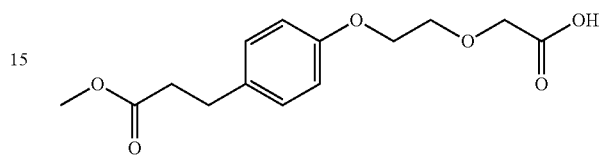

To a solution of Example compound 6-2 (294 mg) in dichloromethane (2.0 mL) was added trifluoroacetic acid (2.0 mL), and the mixture was stirred at room temperature for 1 hr. The reaction mixture was concentrated, toluene was added and the solvent was evaporated. This operation was performed 3 times to give the title compound (245 mg) as an unpurified colorless solid. MS (ESI) m/z: 283.3 [M+H]⁺

(6-4) methyl 3-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]ethoxy}phenyl)propanoate (Example Compound 6-4)

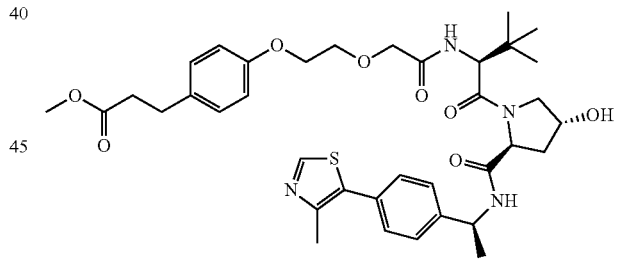

To a solution of Reference Example compound 5 (360 mg) and Example compound 6-3 (232 mg) in N,N-dimethylformamide (3.7 mL) were added, under ice-cooling, N,N-diisopropylethylamine (0.647 mL) and HATU (398 mg) and the mixture was stirred at room temperature for 14 hr. The reaction mixture was diluted with ethyl acetate, washed successively with saturated aqueous sodium hydrogen carbonate, water and saturated brine, dried over anhydrous sodium sulfate and filtered. The solvent was evaporated under reduced pressure. The obtained residue was purified by silica gel chromatography (chloroform:methanol=100:0-90:10) to give the title compound (458 mg) as a pale-yellow solid. MS (ESI) m/z: 709.5 [M+H]⁺

(6-5) 3-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]ethoxy}phenyl)propanoic acid (Example Compound 6-5)

(6-6) methyl [(6S)-4-{4-[3-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]ethoxy}phenyl)propanamido]phenyl}-2,3,9-trimethyl-6H-thieno[3,2-f][1,2,4]triazolo[4,3-a][1,4]diazepin-6-yl]acetate (Example Compound 6)

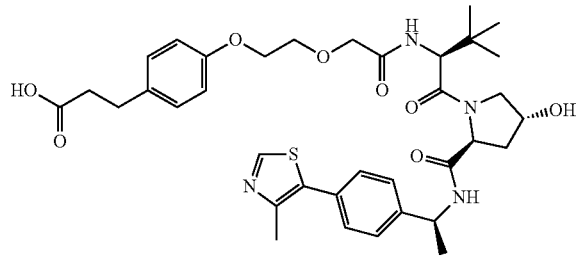 [SMILES: Cc1ncsc1-c1ccc([C@H](C)NC(=O)[C@@H]2C[C@@H](O)CN2C(=O)[C@@H](NC(=O)COCCOc2ccc(CCC(=O)O)cc2)C(C)(C)C)cc1]

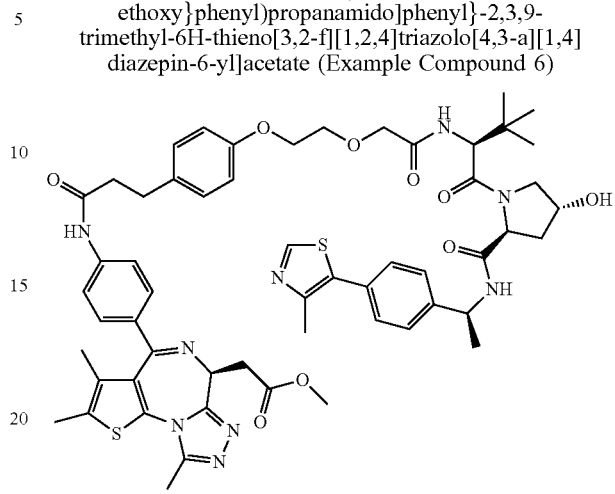

To a solution of Example compound 6-5 (211 mg) and Reference Example compound 11 (100 mg) in N,N-dimethylformamide (2.5 mL) were added N,N-diisopropylethylamine (0.131 mL) and HATU (144 mg), and the mixture was stirred at room temperature for 16 hr. The reaction mixture was diluted with ethyl acetate, washed successively with saturated aqueous sodium hydrogen carbonate, 5% aqueous potassium bisulfite solution, saturated aqueous sodium hydrogen carbonate and saturated brine, dried over anhydrous sodium sulfate and filtered. The solvent was evaporated under reduced pressure. The obtained residue was purified by silica gel chromatography (chloroform:methanol=100:0-95:5) to give the title compound (97 mg) as a colorless solid. MS (ESI) m/z: 1072.8 [M+H]⁺

Example 7

(7-1) methyl [(6S)-4-(4-{3-[4-({(16S)-16-[(2S,4R)-4-hydroxy-2-({(1S)-1-[4-(4-methyl-1,3-thiazol-5-yl)phenyl]ethyl}carbamoyl)pyrrolidine-1-carbonyl]-17,17-dimethyl-14-oxo-3,6,9,12-tetraoxa-15-azaoctadecan-1-yl}oxy)phenyl]propanamido]phenyl)-2,3,9-trimethyl-6H-thieno[3,2-f][1,2,4]triazolo[4,3-a][1,4]diazepin-6-yl]acetate (Example Compound 7)

To a solution of Example compound 6-4 (450 mg) in tetrahydrofuran (9.0 mL), water (2.2 mL) and methanol (2.2 mL) was added, under ice-cooling, lithium hydroxide monohydrate (80 mg) and the mixture was stirred at room temperature for 2 hr. The reaction mixture was diluted with ethyl acetate, washed successively with 5% aqueous potassium bisulfite solution and saturated brine, dried over anhydrous sodium sulfate, filtered and the solvent was evaporated under reduced pressure to give the title compound (394 mg) as a colorless solid.

MS (ESI) m/z: 695.6 [M+H]⁺

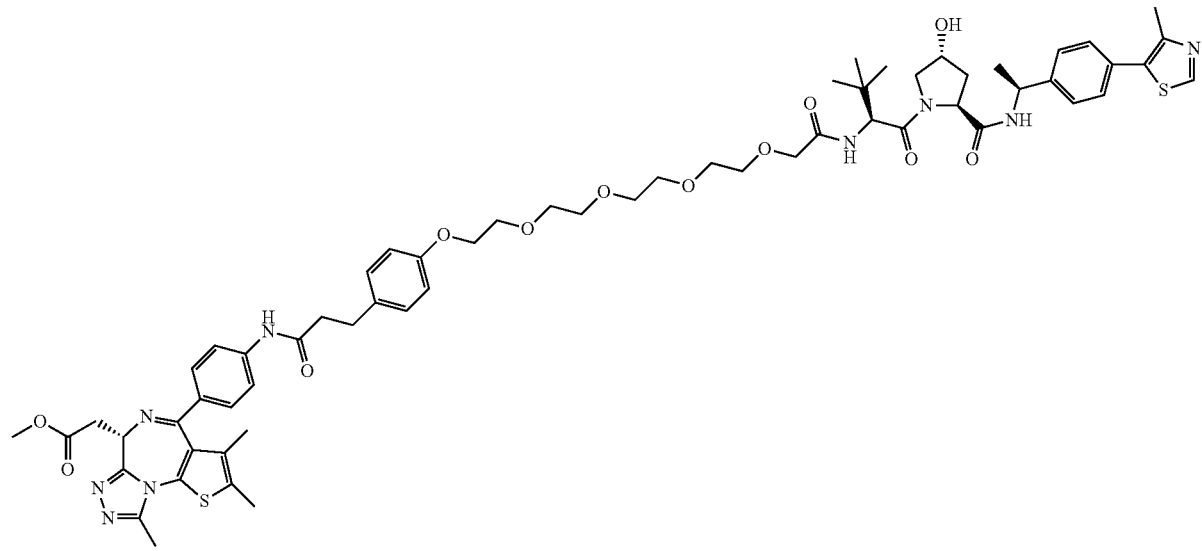 [SMILES: COC(=O)C[C@@H]1N=C(c2ccc(NC(=O)CCc3ccc(OCCOCCOCCOCCOCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

123

By reaction and treatment in the same manner as in Example 6 (6-1)-(6-6) and using t-butyl 2-[2-[2-[2-(2-hydroxyethoxy)ethoxy]ethoxy]ethoxy]acetate instead of t-butyl 2-2-hydroxyethoxy)acetate, the title compound was obtained.

MS (ESI) m/z: 1204.9 [M+H]+

Example 8

(8-1) methyl [(6S)-4-{4'-[2-(2-t-butoxy-2-oxoethoxy)ethoxy]-3'-cyano[1,1'-biphenyl]-4-yl}-2,3,9-trimethyl-6H-thieno[3,2-f][1,2,4]triazolo[4,3-a][1,4]diazepin-6-yl]acetate (Example Compound 8-1)

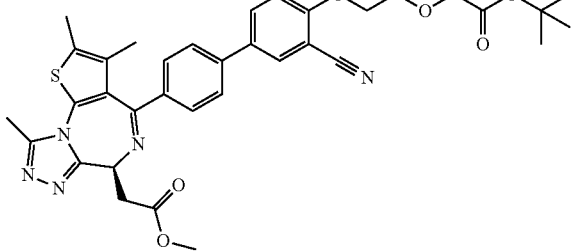

To a mixture of Example compound 2-1 (400 mg), potassium carbonate (222 mg) N,N-dimethylformamide (8.0 mL) was added Example compound 6-1 (292 mg) and the mixture was stirred at 60° C. for 7.5 hr. Water was added to the reaction mixture and the precipitated solid was collected by filtration to give the title compound (495 mg) as a pale-yellow solid.

MS (ESI) m/z: 656.6 [M+H]+

124

(8-2) [2-({3-cyano-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)ethoxy]acetic acid (Example Compound 8-2)

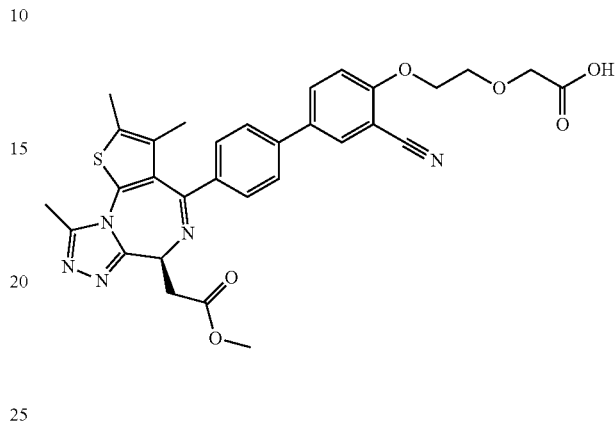

To a solution of Example compound 8-1 (490 mg) in dichloromethane (5.0 mL) was added, under ice-cooling, trifluoroacetic acid (2.5 mL) and the mixture was stirred at room temperature for 2 hr. The reaction mixture was concentrated, the residue was extracted with water, chloroform and dried over anhydrous sodium sulfate. The solvent was evaporated under reduced pressure. The obtained residue was purified by silica gel column chromatography (chloroform:methanol=98:2-90:10) to give the title compound (390 mg) as a pale-yellow solid. MS (ESI) m/z: 600.5 [M+H]+

(8-3) methyl [(6S)-4-(3'-cyano-4'-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]ethoxy}[1,1'-biphenyl]-4-yl)-2,3,9-trimethyl-6H-thieno[3,2-f][1,2,4]triazolo[4,3-a][1,4]diazepin-6-yl]acetate (Example Compound 8)

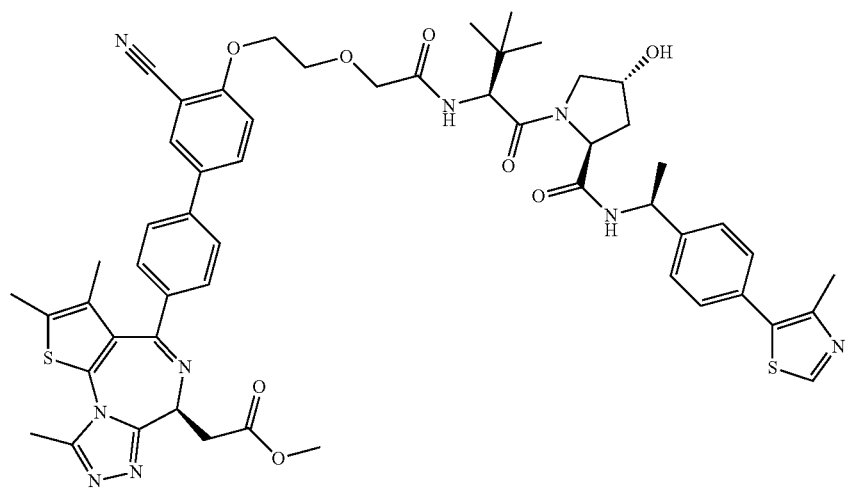 [SMILES: COC(=O)C[C@@H]1N=C(c2ccc(-c3ccc(OCCOCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

To a solution of Example compound 8-2 (200 mg) and Reference Example compound 5 (160 mg) in N,N-dimethylformamide (2.2 mL) and N,N-diisopropylethylamine (0.173 mL) was added, under ice-cooling, HATU (190 mg), and the mixture was stirred at room temperature for 2 hr. Water was added to the reaction mixture, and the mixture was extracted with ethyl acetate, extracted with chloroform, and the extract was washed with water and saturated brine, dried over anhydrous sodium sulfate and filtered. The solvent was evaporated under reduced pressure. The obtained residue was purified by preparative HPLC (10 mM aqueous ammonium carbonate solution-acetonitrile) to give the title compound (208 mg) as a white solid.

MS (ESI) m/z: 1026.8 [M+H]$^+$

Example 9

(9-1) t-butyl (4-bromo-2-cyanophenoxy)acetate (Example Compound 9-1)

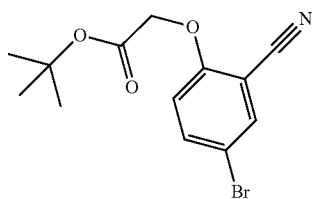 [SMILES: CC(C)(C)OC(=O)COc1ccc(Br)cc1C#N]

To a suspension of 5-bromo-2-hydroxy-benzonitrile (10.0 g) and potassium carbonate (14.0 g) in acetone (168 mL) was added at room temperature t-butyl bromoacetate (8.15 mL) and the mixture was stirred at 60° C. for 3.5 hr. t-Butyl bromoacetate (1.48 mL) was added and the mixture was stirred for 2 hr. The insoluble material in the reaction mixture was filtered off, washed with acetone and the filtrate was concentrated under reduced pressure. To the residue were added water and the mixture was extracted with ethyl acetate. The organic layer was washed with saturated brine, dried over anhydrous magnesium sulfate, filtered and the filtrate was concentrated under reduced pressure. Hexane was added to the obtained solid, ultrasonicated, suspension washed and the solid was collected by filtration. The solid precipitated in the filtrate was also collected by filtration to give the title compound (14.8 g) as a white solid. MS (ESI) m/z: 312.2 [M+H]$^+$ (9-2) t-butyl [2-cyano-4-(4,4,5,5-tetramethyl-1,3,2-dioxaboronan-2-yl)phenoxy]acetate (Example Compound 9-2)

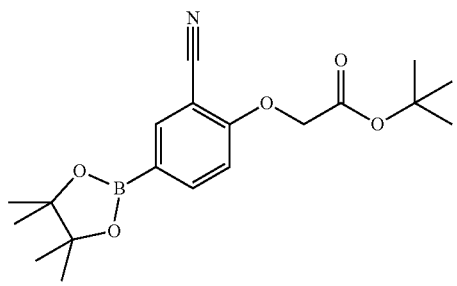 [SMILES: CC(C)(C)OC(=O)COc1ccc(B2OC(C)(C)C(C)(C)O2)cc1C#N]

A mixture of Example compound 9-1 (3.00 g), bis(pinacolato)diboron (2.68 g), 1,1'-bis(diphenylphosphino)ferrocene-palladium(II) dichloride dichloromethane complex (392 mg), potassium acetate (1.89 g) and 1,4-dioxane (32 mL) was stirred at 130° C. for 4 hr. The insoluble material in the reaction mixture was filtered off through diatomaceous earth, washed with ethyl acetate, and the filtrate was concentrated under reduced pressure. To the obtained residue was added water, and the mixture was extracted with ethyl acetate, and the extract was washed with saturated brine, dried over anhydrous sodium sulfate and filtered. The solvent was evaporated under reduced pressure. The obtained residue was purified by silica gel column chromatography (hexane:ethyl acetate=90:10-70:30), hexane was added to the obtained solid. The solid was ultrasonicated, suspension washed, collected by filtration, and washed with hexane to give the title compound (2.63 g) as a white solid.

MS (ESI) m/z: 360.4 [M+H]$^+$ (9-3) methyl {(6S)-4-[4'-(2-t-butoxy-2-oxoethoxy)-3'-cyano[1,1'-biphenyl]-4-yl]-2,3,9-trimethyl-6H-thieno[3,2-f][1,2,4]triazolo[4,3-a][1,4]diazepin-6-yl}acetate (Example Compound 9-3)

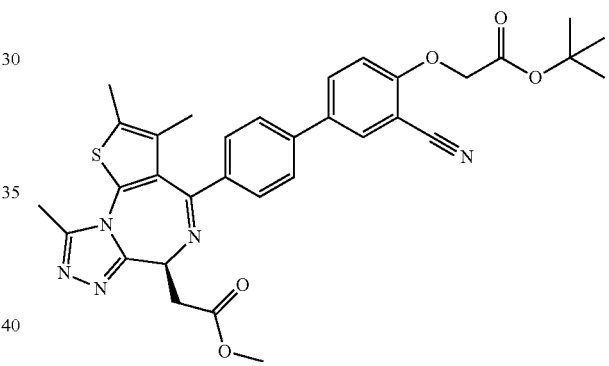

A mixture of Example compound 9-2 (2.60 g), Reference Example compound 1 (3.00 g), potassium fluoride (1.26 g), tetrahydrofuran (14.5 mL), palladium acetate (162 mg), S-phos (594 mg) and water (0.47 mL) was stirred with heating under reflux for 6 hr. Palladium acetate (32 mg) and S-phos (119 mg) were added, and the mixture was further stirred for 8 hr. Potassium fluoride (420 mg), palladium acetate (32 mg), S-phos (119 mg), water (0.16 mL) were added, and the mixture was stirred for 6 hr. The insoluble material in the reaction mixture was filtered off through diatomaceous earth, washed with ethyl acetate, and the filtrate was concentrated under reduced pressure. To the reaction mixture were added water and saturated brine, and the mixture was extracted with ethyl acetate, and the extract was dried over anhydrous sodium sulfate and filtered. The filtrate was passed through NH silica gel, washed with ethyl acetate, and the filtrate was concentrated under reduced pressure to give the title compound (4.92 g) as a crudely purified pale-yellow solid.

MS (ESI) m/z: 612.4 [M+H]$^+$ (9-4) ({3-cyano-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetic acid (Example Compound 9-4)

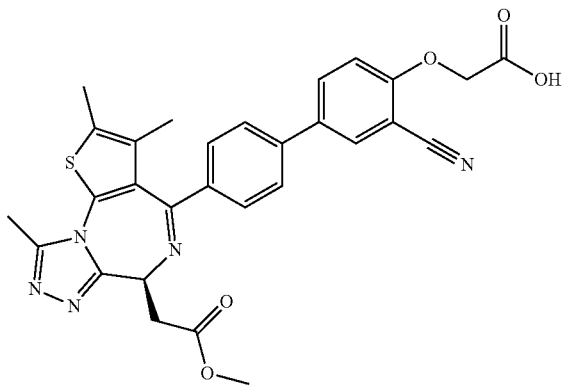 [SMILES: COC(=O)C[C@@H]1N=C(c2ccc(-c3ccc(OCC(=O)O)c(C#N)c3)cc2)c2c(sc(C)c2C)-n2c(C)nnc21]

acid was slowly added with stirring until foaming ceased. After partitioning, the aqueous layer was extracted again with chloroform, and the extract was washed with saturated brine, dried over anhydrous sodium sulfate, filtered and the solvent was evaporated under reduced pressure to give the title compound (4.90 g) as a yellow solid.

MS (ESI) m/z: 556.3 [M+H]$^+$ (9-5) methyl [(6S)-4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 9)

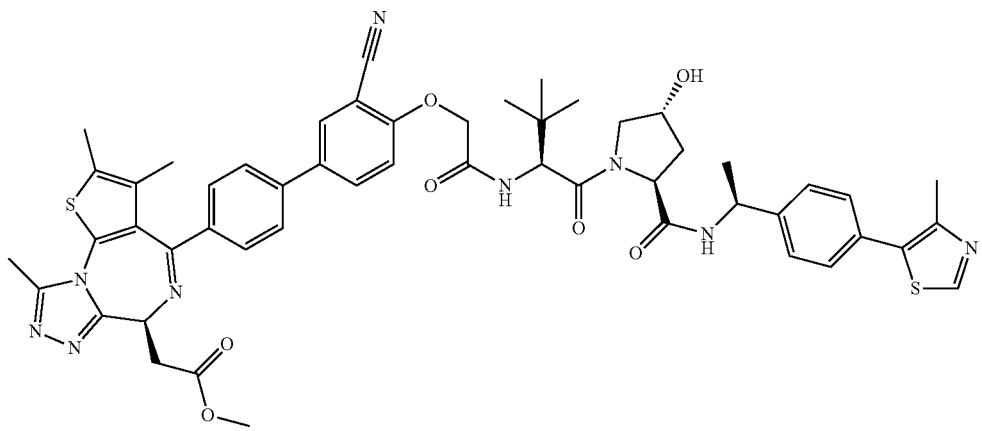 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

To a solution of Example compound 9-3 (4.92 g) in dichloromethane (25 mL) was added, under ice-cooling, trifluoroacetic acid (25 mL) and the mixture was stirred at room temperature for 4 hr. To the reaction mixture was added dichloromethane and the solvent was evaporated under reduced pressure. To the obtained residue was added ethyl acetate and, under ice-cooling, saturated aqueous sodium hydrogen carbonate was added with stirring until foaming ceased. After partitioning, the aqueous layer was washed again with ethyl acetate. Chloroform was added to the aqueous layer and, under ice-cooling, 1N hydrochloric To a solution of Example compound 9-4 (4.02 g), N,N-dimethylformamide (24 mL) and N,N-diisopropylethylamine (6.25 mL) were added, under ice-cooling, HATU (4.12 g) and Reference Example compound 5 (3.48 g), and the mixture was stirred at room temperature for 4 hr. Water was added to the reaction mixture, and the mixture was extracted with ethyl acetate, and the extract was washed with water and saturated brine, dried over anhydrous sodium sulfate and filtered. The solvent was evaporated under reduced pressure. The obtained residue was purified by NH silica gel column chromatography (ethyl acetate:methanol=98:2-85:15) and silica gel column chromatography (chloroform:methanol=98:2-93:7) to give the title compound (3.85 g) as a pale-yellow solid.

MS (ESI) m/z: 982.4 [M+H]$^+$

Example 10

(10-1) t-butyl 14-[(4-methylbenzene-1-sulfonyl)oxy]-3,6,9,12-tetraoxatetradecanoate (Example Compound 10-1)

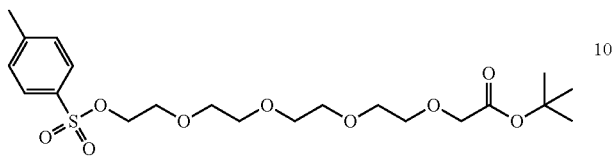

By reaction and treatment in the same manner as in Example 6 (6-1) and using t-butyl 2-[2-[2-[2-(2-hydroxyethoxy)ethoxy]ethoxy]ethoxy]acetate instead of t-butyl 2-(2-hydroxyethoxy)acetate, the title compound was obtained.

MS (ESI) m/z: 463.3 [M+H]$^+$ (10-2) methyl {(6S)-4-[3'-cyano-4'-({(16S)-16-[(2S,4R)-4-hydroxy-2-({(1S)-1-[4-(4-methyl-1,3-thiazol-5-yl)phenyl]ethyl}carbamoyl)pyrrolidine-1-carbonyl]-17,17-dimethyl-14-oxo-3,6,9,12-tetraoxa-15-azaoctadecan-1-yl}oxy)[1,1'-biphenyl]-4-yl]-2,3,9-trimethyl-6H-thieno[3,2-f][1,2,4]triazolo[4,3-a][1,4]diazepin-6-yl}acetate (Example Compound 10)

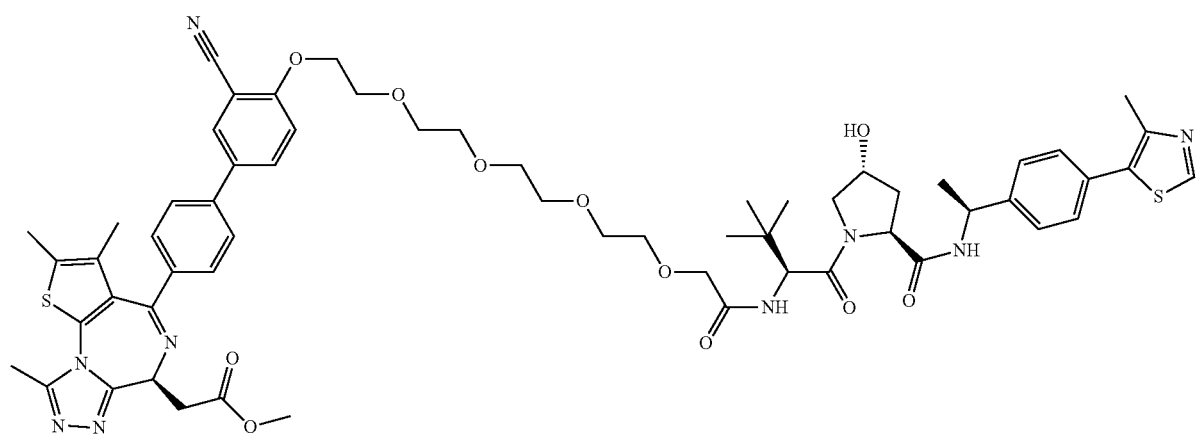 [SMILES: COC(=O)C[C@@H]1N=C(c2ccc(-c3ccc(OCCOCCOCCOCCOCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

By reaction and treatment in the same manner as in Example 2 (2-2)-(2-4) and using Example compound 10-1 instead of Example compound 1-3, the title compound was obtained.

MS (ESI) m/z: 1158.8 [M+H]$^+$

Example 12

(11-1) methyl {[(6S)-4-{3'-cyano-4'-[2-({(25S)-25-[(2S,4R)-4-hydroxy-2-({[(1S)-1-[4-(4-methyl-1,3-thiazol-5-yl)phenyl]ethyl}carbamoyl)pyrrolidin-1-carbonyl]-26,26-dimethyl-23-oxo-3.6.9.12.15.18.21-heptaoxa-24-azaheptacosan-1-yl}oxy)][1,1'-biphenyl]-4-yl}-2,3,9-trimethyl-6H-thieno[3,2-f][1,2,4]triazolo[4,3-a][1,4]diazepin-6-yl]acetate
(Example Compound 11)

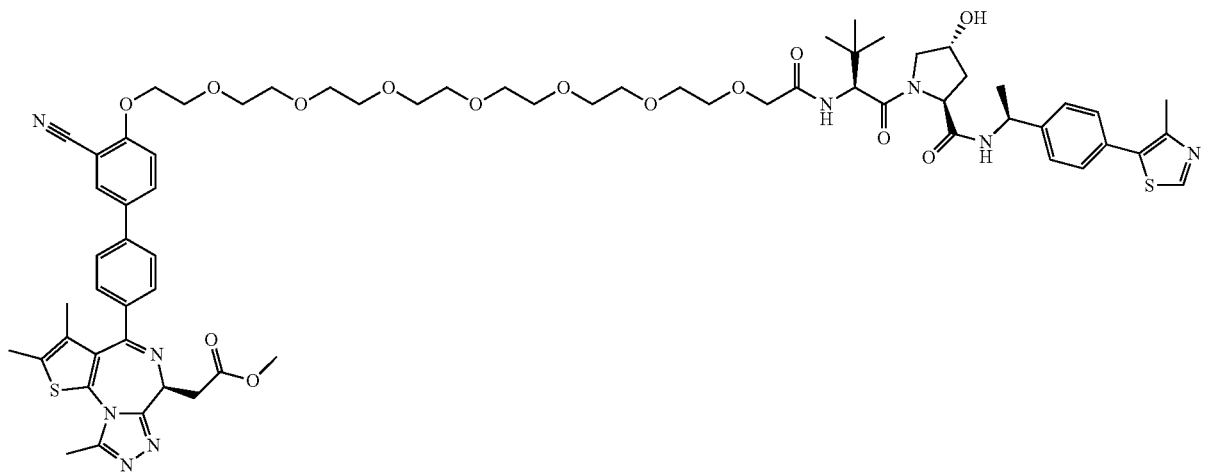 [SMILES: COC(=O)C[C@@H]1N=C(c2ccc(-c3ccc(OCCOCCOCCOCCOCCOCCOCCOCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

By reaction and treatment in the same manner as in Example 5 (5-4) and using Example compound 2-1 instead of Example compound 5-1, the title compound was obtained.

MS (ESI) m/z: 646.3[(M+2H)/2]$^+$

Example 12

(12-1) methyl [(6S)-4-{3'-cyano-4'-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate
(Example Compound 12)

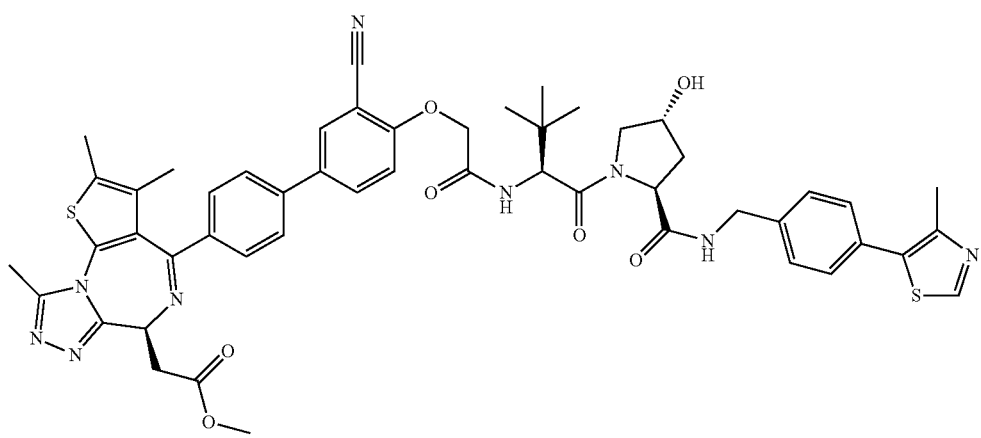 [SMILES: COC(=O)C[C@@H]1N=C(c2ccc(-c3ccc(OCC(=O)N[C@H](C(=O)N4C[C@H](O)C[C@H]4C(=O)NCc4ccc(-c5scnc5C)cc4)C(C)(C)C)c(C#N)c3)cc2)c2c(sc(C)c2C)-n2c(C)nnc21]

To a solution of Example compound 9-4 (73 mg), N,N-dimethylformamide (0.90 mL), N,N-diisopropylethylamine (0.070 mL) and Reference Example compound 6 (63 mg) was added HATU (77 mg), and the mixture was stirred at room temperature for 18 hr. Under ice-cooling, water was added to the reaction mixture, and the mixture was extracted with chloroform. The solvent was evaporated under reduced pressure. The obtained residue was diluted with ethyl acetate, washed with water, dried over anhydrous sodium sulfate and filtered. The solvent was evaporated under reduced pressure. The obtained residue was purified by preparative HPLC (10 mM aqueous ammonium carbonate solution-acetonitrile) to give the title compound (81 mg) as a white solid. MS (ESI) m/z: 968.7 [M+H]$^+$ Example 13

(13-1) [(6S)-4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetic acid (Example Compound 13-1)

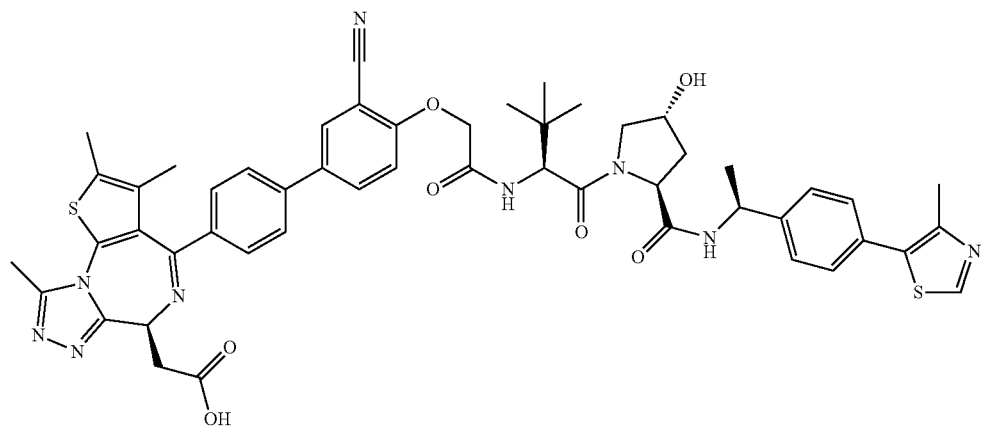 [SMILES: Cc1ncsc1-c1ccc([C@H](C)NC(=O)[C@@H]2C[C@@H](O)CN2C(=O)[C@@H](NC(=O)COc2ccc(-c3ccc(C4=N[C@@H](CC(=O)O)c5nnc(C)n5-c5sc(C)c(C)c54)cc3)cc2C#N)C(C)(C)C)cc1]

A solution of Example compound 9 (700 mg), tetrahydrofuran (7.13 mL), water (2 mL), methanol (2 mL) and lithium hydroxide monohydrate (90 mg) was stirred at room temperature for 5 hr. To the reaction mixture were added ice water and chloroform, adjusted to pH3-4 with 1N hydrochloric acid and stirred. The aqueous layer was extracted with chloroform, and the organic layers were combined, dried over anhydrous sodium sulfate, filtered and the solvent was evaporated under reduced pressure to give the title compound (700 mg) as a yellow solid. MS (ESI) m/z: 966.5 [M−H]$^-$ (13-2) (2S,4R)-1-{(2S)-2-[2-({3-cyano-4'-[(6S)-6-{2-[(2-hydroxyethyl)amino]-2-oxoethyl}-2,3,9-trimethyl-6H-thieno[3,2-f][1,2,4]triazolo[4,3-a][1,4]diazepin-4-yl][1,1'-biphenyl]-4-yl}oxy)acetamido]-3,3-dimethylbutanoyl}-4-hydroxy-N-1(1S)-1-[4-(4-methyl-1,3-thiazol-5-yl)phenyl]ethyl}pyrrolidine-2-carboxamide (Example Compound 13)

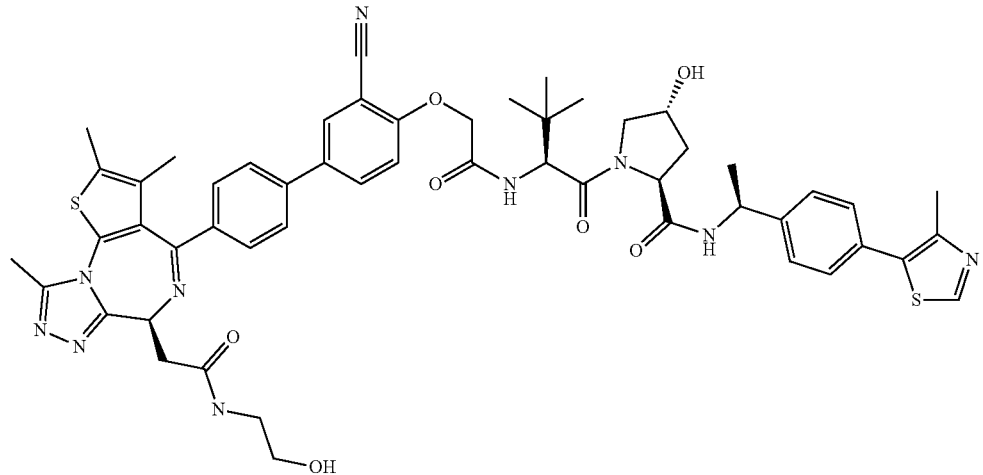 [SMILES: Cc1ncsc1-c1ccc([C@H](C)NC(=O)[C@@H]2C[C@@H](O)CN2C(=O)[C@@H](NC(=O)COc2ccc(-c3ccc(C4=N[C@@H](CC(=O)NCCO)c5nnc(C)n5-c5sc(C)c(C)c54)cc3)cc2C#N)C(C)(C)C)cc1]

To a solution of Example compound 13-1 (55 mg), N,N-dimethylformamide (1.1 mL), N,N-diisopropylethylamine (0.030 mL) and 2-aminoethanol (5.2 mg) was added, under ice-cooling, HATU (32 mg), and the mixture was stirred at room temperature for 15 hr. Under ice-cooling, water was added to the reaction mixture, and the mixture was extracted with chloroform. The solvent was evaporated under reduced pressure. The obtained residue was diluted with ethyl acetate, washed with water, dried over anhydrous sodium sulfate and filtered. The solvent was evaporated under reduced pressure. The obtained residue was purified by preparative HPLC (10 mM aqueous ammonium carbonate solution-acetonitrile) to give the title compound (37 mg) as a pale-yellow solid. MS (ESI) m/z: 1011.8 [M+H]$^+$ Example 14

(14-1) (2S,4R)-1-{(2S)-2-[2-({3-cyano-4'-[(6S)-6-(2-{[2-(3-hydroxypropoxy)ethyl]amino}-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 14)

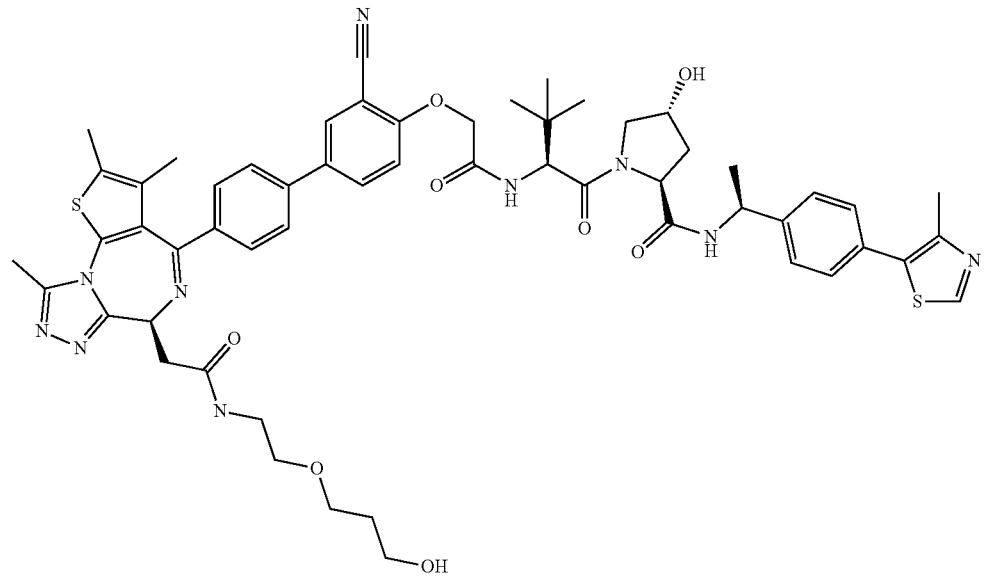 [SMILES: Cc1ncsc1-c1ccc([C@H](C)NC(=O)[C@@H]2C[C@@H](O)CN2C(=O)[C@@H](NC(=O)COc2ccc(-c3ccc(C4=N[C@@H](CC(=O)NCCOCCCO)c5nnc(C)n5-c5sc(C)c(C)c54)cc3)cc2C#N)C(C)(C)C)cc1]

By reaction and treatment in the same manner as in Example 13 (13-2) and using 3-(2-aminoethoxy)propan-1-ol instead of 2-aminoethanol, the title compound was obtained as a pale-orange solid. MS (ESI) m/z: 1069.9 [M+H]+

Example 15

(15-1) methyl {(6S)-4-[4'-(2-t-butoxy-2-oxoethoxy)[1,1'-biphenyl]-4-yl]-2,3,9-trimethyl-6H-thieno[3,2-f][1,2,4]triazolo[4,3-a][1,4]diazepin-6-yl}acetate (Example Compound 15-1)

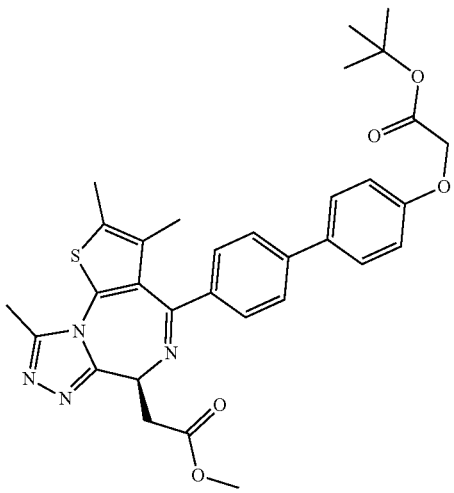 [SMILES: COC(=O)C[C@@H]1N=C(c2ccc(-c3ccc(OCC(=O)OC(C)(C)C)cc3)cc2)c2c(sc(C)c2C)-n2c(C)nnc21]

A mixture of Reference Example compound 8 (2.66 g), Reference Example compound 1 (3.00 g), potassium fluoride (1.26 g), tetrahydrofuran (24.1 mL), S-phos (594 mg), palladium acetate (162 mg) and water (0.47 mL) was stirred with heating under reflux for 6 hr. The insoluble material in the reaction mixture was filtered off through diatomaceous earth, washed with ethyl acetate, and the filtrate was concentrated under reduced pressure. To the obtained residue was added water, and the mixture was extracted with ethyl acetate, and the extract was washed with saturated brine, dried over anhydrous sodium sulfate and filtered. The solvent was evaporated under reduced pressure. The reaction mixture was concentrated, water was added, and the mixture was extracted 3 times with ethyl acetate, and the extract was dried over anhydrous sodium sulfate and filtered. The solvent was evaporated under reduced pressure. The obtained residue was diluted with ethyl acetate, passed through NH silica gel and washed with ethyl acetate. The solvent was evaporated under reduced pressure to give the title compound (4.59 g) as an unpurified white solid.
MS (ESI) m/z: 587.5 [M+H]+

(15-2) ({4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetic acid (Example Compound 15-2)

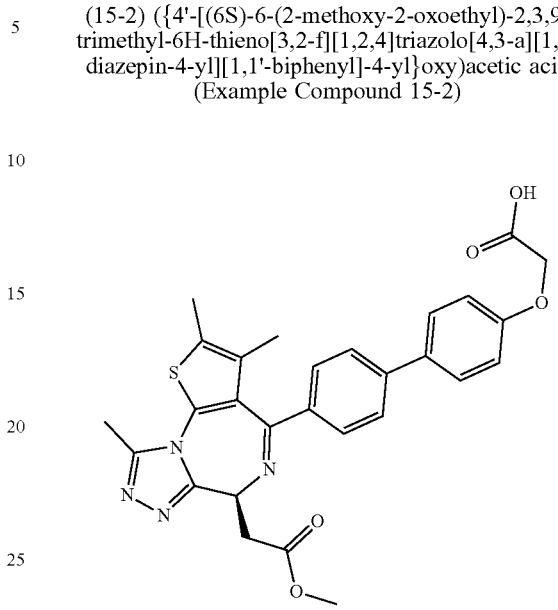

To a solution of Example compound 15-1 (4.59 g) in dichloromethane (21 mL) was added, under ice-cooling, trifluoroacetic acid (21 mL) and the mixture was stirred at room temperature for 3 hr. The reaction mixture was diluted with dichloromethane and the solvent was evaporated under reduced pressure. To the obtained residue were added ethyl acetate and saturated aqueous sodium hydrogen carbonate for partitioning. The aqueous layer was washed again with ethyl acetate and, after partitioning, the obtained aqueous layer was adjusted to less than pH3 by adding 1N hydrochloric acid. The mixture was extracted with ethyl acetate, and the extract was washed with saturated brine, dried over anhydrous sodium sulfate, filtered and the solvent was evaporated under reduced pressure to give the title compound (4.20 g) as an unpurified yellow solid. MS (ESI) m/z: 531.4 [M+H]+

(15-3) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 15)

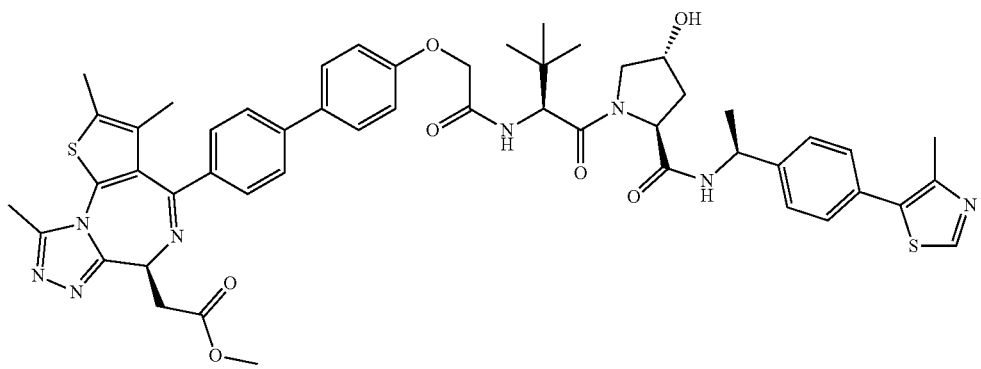 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 15-2 (4.20 g), N,N-dimethylformamide (24.1 mL) and N,N-diisopropylethylamine (6.25 mL) was added, under ice-cooling, HATU (4.12 g) and the mixture was stirred for 10 min, Reference Example compound 5 (3.48 g) was added, and the mixture was stirred at room temperature for 14 hr. Water was added to the reaction mixture, and the mixture was extracted with ethyl acetate, and the extract was washed with water and saturated brine, dried over anhydrous sodium sulfate and filtered. The solvent was evaporated under reduced pressure. The obtained residue was purified by silica gel column chromatography twice (ethyl acetate:methanol=98:2-92:8, chloroform:methanol=98:2-95:5) (chloroform:methanol=98:2-95:5), concentrated, and diethyl ether was added to the obtained residue and the precipitated solid was collected by filtration to give the title compound (2.45 g) as a pale-yellow solid. MS (ESI) m/z: 957.4 [M+H]$^+$ Example 16

(16-1) (2S,4R)-1-[(2S)-2-(2-bromoacetamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 16-1)

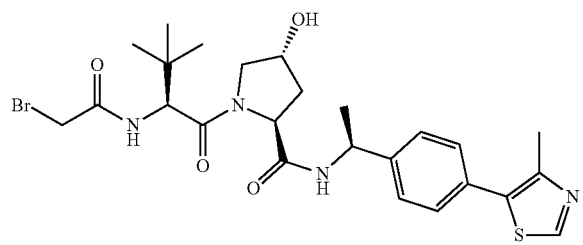 [SMILES: Cc1ncsc1-c1ccc([C@H](C)NC(=O)[C@@H]2C[C@@H](O)CN2C(=O)[C@@H](NC(=O)CBr)C(C)(C)C)cc1]

To a solution of Reference Example compound 5 (1.0 g), acetonitrile (20.8 mL) and triethylamine (0.867 mL) were added, under ice-cooling, bromoacetic acid (0.15 mL) and then HATU (1.19 g), and the mixture was stirred at room temperature for 16 hr. Triethylamine (0.289 mL), bromoacetic acid (0.045 mL), HATU (237 mg) were added, and the mixture was further stirred for 4 hr. To the reaction mixture were added, under ice-cooling chloroform, saturated aqueous ammonium chloride solution, water. After partitioning, the aqueous layer was extracted twice with chloroform. The organic layers were combined, dried over anhydrous sodium sulfate and filtered. The solvent was evaporated under reduced pressure. The obtained residue was purified by silica gel column chromatography (ethyl acetate:methanol=100:0-90:10) to give the title compound (930 mg) as a crudely purified white solid.

MS (ESI) m/z: 565.5 [M+H]$^+$ (16-2) 4-hydroxy-4'-[(6S)-2,3,6,9-tetramethyl-6H-thieno[3,2-f] [1,2,4]triazolo[4,3-a][1,4]diazepin-4-yl][1,1'-biphenyl]-3-carbonitrile (Example Compound 16-2)

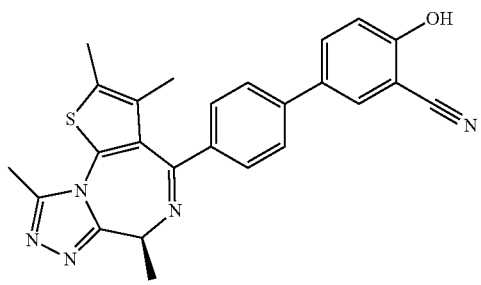 [SMILES: Cc1sc2c(c1C)C(c1ccc(-c3ccc(O)c(C#N)c3)cc1)=N[C@@H](C)c1nnc(C)n1-2]

A mixture of Reference Example compound 4 (300 mg), Reference Example compound 7 (220 mg), sodium carbonate (238 mg), 1,4-dioxane (3.0 mL), water (1.0 mL) and 2-dicyclohexylphosphino-2',4',6'-triisopropylbiphenyl aminobiphenyl palladium chloride precatalyst (59 mg) was stirred in a microwave reaction apparatus (Initiator, manufactured by Biotage) at 100° C. for 1 hr. 2-Dicyclohexylphosphino-2',4',6'-triisopropylbiphenyl aminobiphenyl palladium chloride precatalyst (29 mg) was added, and the mixture was stirred again in a microwave reaction apparatus at 100° C. for 1.5 hr, 2-dicyclohexylphosphino-2',4',6'-triisopropylbiphenyl aminobiphenyl palladium chloride precatalyst (29 mg), Reference Example compound 7 (55 mg), sodium carbonate (79 mg) were added, and the mixture was stirred again in a microwave reaction apparatus at 100° C. for 1.5 hr. The insoluble material in the reaction mixture was filtered off through diatomaceous earth, water was added to the filtrate and the mixture was extracted with chloroform, and the extract was dried over anhydrous sodium sulfate and filtered. The solvent was evaporated under reduced pressure. The obtained residue was purified by silica gel column chromatography (chloroform:methanol=98:2-93:7) to give the title compound (359 mg) as an orange solid.

MS (ESI) m/z: 440.4 [M+H]$^+$ (16-3) (2S,4R)-1-{(2S)-2-[2-({3-cyano-4'-[(6S)-2,3,6,9-tetramethyl-6H-thieno[3,2-f][1,2,4]triazolo[4,3-a] [1,4]diazepin-4-yl][1,1'-biphenyl]-4-yl}oxy)acetamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 16)

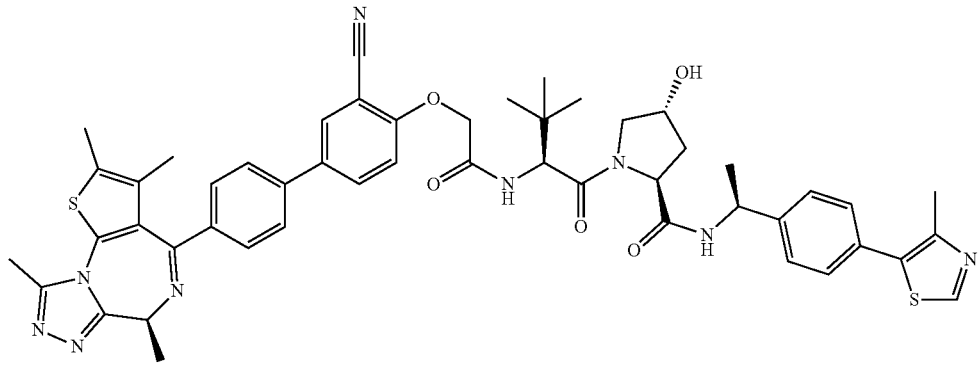 [SMILES: Cc1ncsc1-c1ccc([C@H](C)NC(=O)[C@@H]2C[C@@H](O)CN2C(=O)[C@@H](NC(=O)COc2ccc(-c3ccc(C4=N[C@@H](C)c5nnc(C)n5-c5sc(C)c(C)c54)cc3)cc2C#N)C(C)(C)C)cc1]

A mixture of Example compound 16-2 (100 mg), potassium carbonate (63 mg), N,N-dimethylformamide (2.3 mL) and Example compound 16-1 (154 mg) was stirred at 60° C. for 2 hr and at 80° C. for 4 hr. Example compound 16-1 (64 mg), potassium carbonate (31 mg) were added and the mixture was stirred for 3.5 hr. Example compound 16-1 (64 mg), potassium carbonate (31 mg) were added again and the mixture was stirred for 2 hr. To the reaction mixture was added ice water, and the mixture was extracted with chloroform, and the extract was dried over anhydrous sodium sulfate and filtered. The solvent was evaporated under reduced pressure. The residue was diluted with ethyl acetate, washed with water, dried again over anhydrous sodium sulfate and filtered. The solvent was evaporated under reduced pressure. The obtained residue was purified by preparative HPLC (10 mM aqueous ammonium carbonate solution-acetonitrile) to give the title compound (120 mg) as a yellow solid. MS (ESI) m/z: 924.4 [M+H]$^+$ Example 17

(17-1) methyl [(6S)-4-(4'-hydroxy-3'-methoxy[1,1'-biphenyl]-4-yl)-2,3,9-trimethyl-6H-thieno[3,2-f][1,2,4]triazolo[4,3-a] [1,4]diazepin-6-yl]acetate (Example Compound 17-1)

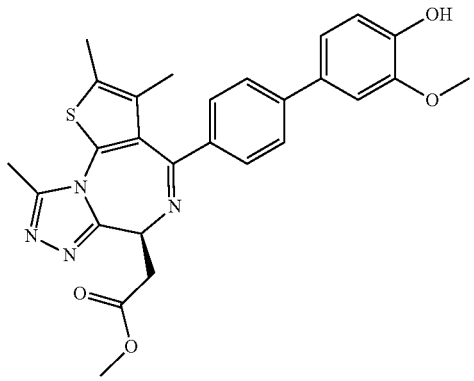

A mixture of 2-methoxy-4-(4,4,5,5-tetramethyl-1,3,2-dioxaboran-2-yl)phenol (271 mg), Reference Example compound 1 (300 mg), potassium fluoride (126 mg), tetrahydrofuran (2.4 mL), palladium acetate (16 mg), S-phos (59 mg) and water (0.47 mL) was stirred with heating under reflux for 6 hr. The insoluble material in the reaction mixture was filtered off through diatomaceous earth, water was added to the filtrate and the mixture was extracted with chloroform, and the extract was dried over anhydrous sodium sulfate and filtered. The solvent was evaporated under reduced pressure. The obtained residue was purified by silica gel column chromatography (chloroform:methanol=98:2-93:7) and NH silica gel column chromatography (chloroform:methanol=98:2-95:5) to give the title compound (350 mg) as a pale-yellow solid.

MS (ESI) m/z: 503.4 [M+H]$^+$ (17-2) methyl {(6S)-4-[4'-(2-t-butoxy-2-oxoethoxy)-3'-methoxy[1,1'-biphenyl]-4-yl]-2,3,9-trimethyl-6H-thieno[3,2-f] [1,2,4]triazolo[4,3-a][1,4]diazepin-6-yl}acetate (Example 15 compound 17-2)

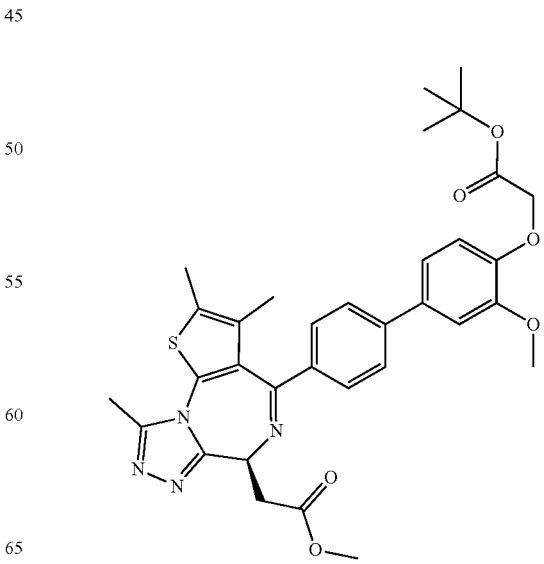

A mixture of Example compound 17-1 (150 mg), potassium carbonate (82 mg), N,N-dimethylformamide (3.0 mL) and t-butyl bromoacetate (0.049 mL) was stirred at 60° C. for 2 hr. Water was added to the reaction mixture, and the mixture was extracted with chloroform. The solvent was evaporated under reduced pressure. To the residue was added ethyl acetate, and the mixture was washed with water, dried over anhydrous sodium sulfate and filtered. The solvent was evaporated under reduced pressure. The obtained residue was purified by silica gel column chromatography (chloroform:methanol=98:2-93:7) to give the title compound (154 mg) as a pale-red solid.

MS (ESI) m/z: 617.7 [M+H]$^+$ (17-3) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-3'-methoxy[1,1'-biphenyl]-4-yl}-2,3,9-trimethyl-6H-thieno[3,2-f][1,2,4]triazolo[4,3-a] [1,4]diazepin-6-yl]acetate (Example Compound 17)

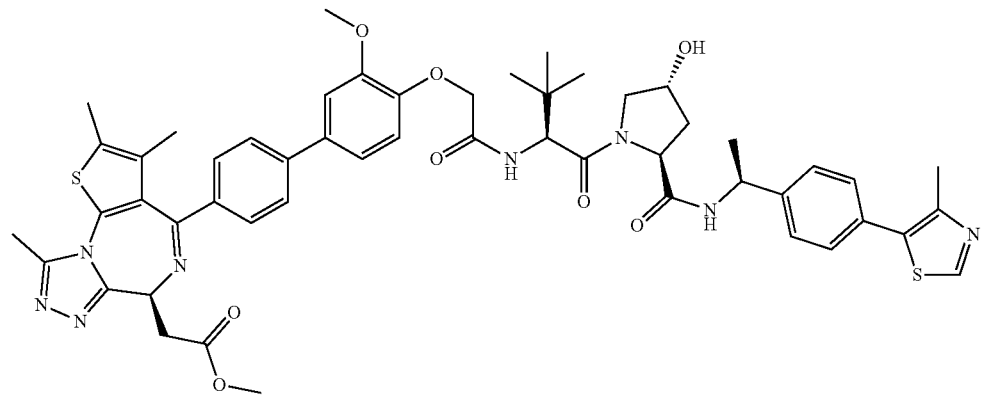 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(OC)c3)cc2)c2c(sc(C)c2C)-n2c(C)nnc21]

To a solution of Example compound 17-2 (154 mg) in dichloromethane (1.5 mL) was added, under ice-cooling, trifluoroacetic acid (0.77 mL) and the mixture was stirred at room temperature for 2 hr. The reaction mixture was diluted with dichloromethane and the solvent was evaporated under reduced pressure. To the obtained residue was added toluene and the solvent was evaporated under reduced pressure. This operation was performed twice. To a solution of the obtained residue, N,N-dimethylformamide (2.5 mL), N,N-diisopropylethylamine (0.216 mL), Reference Example compound 5 (120 mg) was added, under ice-cooling, HATU (142 mg), and the mixture was stirred at room temperature for 15 hr. Furthermore, N,N-diisopropylethylamine (0.022 mL), Reference Example compound 5 (36 mg), HATU (47 mg) were added, and the mixture was stirred at room temperature for 2 hr. To the reaction mixture was added ice water, and the mixture was extracted with chloroform, and the extract was dried over anhydrous sodium sulfate and filtered. The solvent was evaporated under reduced pressure. The residue was diluted with ethyl acetate, washed with water, and dried over anhydrous sodium sulfate. The solvent was evaporated under reduced pressure. The obtained residue was purified by preparative HPLC (10 mM aqueous ammonium carbonate solution-acetonitrile) to give the title compound (149 mg) as a white solid. MS (ESI) m/z: 987.8 [M+H]$^+$ Example 18

(18-1) t-butyl [4-(4-chlorophenyl)-2,3,9-trimethyl-6H-thieno[3,2-f][1,2,4]triazolo[4,3-a][1,4]diazepin-6-yl]carbamate (Example Compound 18-1)

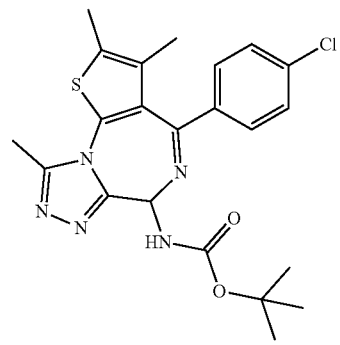 [SMILES: Cc1sc2c(c1C)C(c1ccc(Cl)cc1)=NC(NC(=O)OC(C)(C)C)c1nnc(C)n1-2]

To a suspension of 6-amino-4-(4-chlorophenyl)-2,3,9-trimethyl-6H-thieno[3,2-f][1,2,4]triazolo[4,3-a][1,4]diazepine described in JP-A-7-17941, Starting Material Preparation Example 1 (670 mg) in dichloromethane (9.4 mL) were added di-t-butyl dicarbonate (490 mg) and triethylamine (0.39 mi) at room temperature, and the mixture was stirred at the same temperature for 15 hr. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) and silica gel column chromatography (hexane:ethyl acetate=50:50-33:67) to give the title compound (648 mg) as a white solid. MS (ESI) m/z: 458.3 [M+H]$^+$ (18-2) t-butyl [4-(3'-cyano-4'-hydroxy[1,1'-biphenyl]-4-yl)-2,3,9-trimethyl-6H-thieno[3,2-f][1,2,4]triazolo[4,3-a][1,4]diazepin-6-yl]carbamate (Example Compound 18-2)

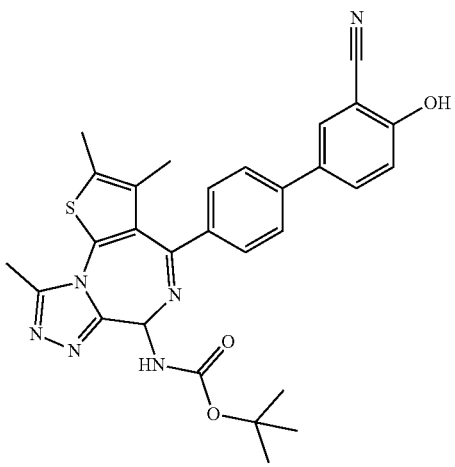 [SMILES: Cc1sc2c(c1C)C(c1ccc(-c3ccc(O)c(C#N)c3)cc1)=NC(NC(=O)OC(C)(C)C)c1nnc(C)n1-2]

To a mixture of Example compound 18-1 (630 mg), Reference Example compound 7 (506 mg) and 2-dicyclohexylphosphino-2',4',6'-triisopropylbiphenyl aminobiphenyl palladium chloride precatalyst (55 mg) were added 1,4-dioxane (8 mL) and 2 M aqueous cesium carbonate solution (2.1 mL). After nitrogen substitution, the mixture was stirred under microwave irradiation with heating at 150° C. for 15 min. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:ethyl acetate=50:50-0:100) to give the title compound (561 mg) as a white solid.
MS (ESI) m/z: 541.4 [M+H]$^+$ (18-3) methyl [(4'-{6-[(t-butoxycarbonyl)amino]-2,3,9-trimethyl-6H-thieno[3,2-f][1,2,4]triazolo[4,3-a][1,4]diazepin-4-yl}-3-cyano[1,1'-biphenyl]-4-yl)oxy]acetate (Example Compound 18-3)

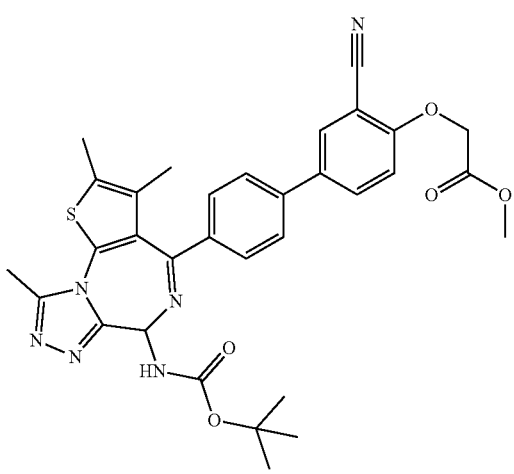

To a solution of Example compound 18-2 (555 mg) and methyl bromoacetate (0.12 mL) in N,N-dimethylformamide (5 mL) was added at room temperature cesium carbonate (670 mg), and the mixture was stirred at the same temperature for 15 hr. Water was added to the reaction mixture, and the mixture was extracted twice with ethyl acetate, and the extract was washed with water and saturated brine, dried over anhydrous sodium sulfate and filtered. The solvent was evaporated under reduced pressure. The residue was purified by silica gel column chromatography (chloroform:ethyl acetate=50:50-0:100) to give a crudely purified title compound (474 mg) as a pale-yellow powder. MS (ESI) m/z: 613.5 [M+H]$^+$ (18-4) [(4'-{6-[(t-butoxycarbonyl)amino]-2,3,9-trimethyl-6H-thieno[3,2-f][1,2,4]triazolo[4,3-a][1,4]diazepin-4-yl}-3-cyano[1,1'-biphenyl]-4-yl)oxy]acetic acid (Example Compound 18-4)

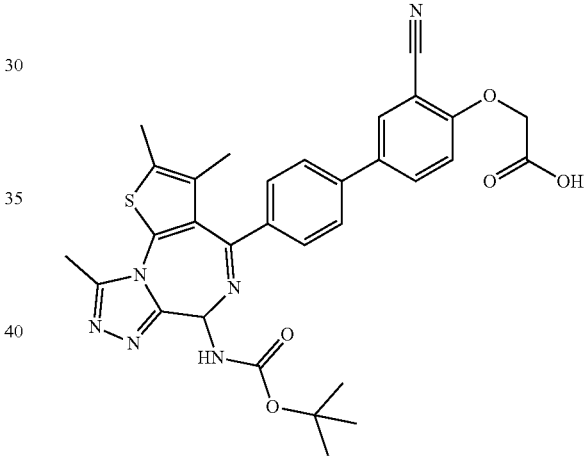

To a solution of Example compound 18-3 (470 mg) in tetrahydrofuran (4 mL), methanol (2 mL) and water (2 mL) was added lithium hydroxide monohydrate (130 mg) at room temperature, and the mixture was stirred at the same temperature for 30 min. To the reaction mixture was added 5% aqueous potassium hydrogensulfate solution, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-80:20) and carboxylic acid-supported silica gel column chromatography (chloroform:methanol-100:0-50:50) to give the title compound (261 mg) as a white solid.

MS (ESI) m/z: 599.5 [M+H]$^+$ (18-5) t-butyl (4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl}pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)carbamate (Example Compound 18)

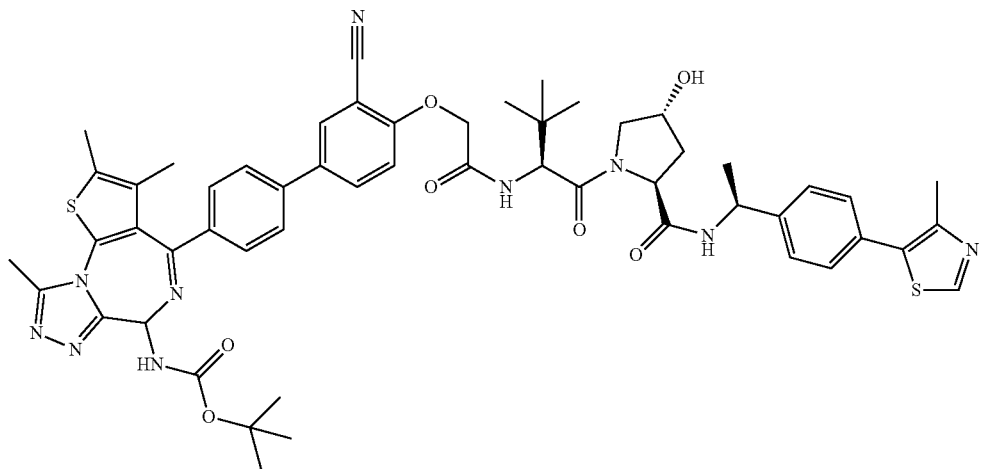 [SMILES: Cc1ncsc1-c1ccc([C@H](C)NC(=O)[C@@H]2C[C@@H](O)CN2C(=O)[C@@H](NC(=O)COc2ccc(-c3ccc(C4=NC(NC(=O)OC(C)(C)C)c5nnc(C)n5-c5sc(C)c(C)c54)cc3)cc2C#N)C(C)(C)C)cc1]

To a solution of Example compound 18-4 (255 mg) and Reference Example compound 5 (246 mg) in N,N-dimethylformamide (4.3 mL) were added at room temperature N,N-diisopropylethylamine (0.22 mL) and HATU (227 mg), and the mixture was stirred at the same temperature for 15 hr. To the reaction mixture was added saturated aqueous sodium hydrogen carbonate, and the mixture was extracted once with ethyl acetate, and the extract was washed with water and saturated brine, dried over anhydrous sodium sulfate and filtered. The solvent was evaporated under reduced pressure. The residue was purified by silica gel column chromatography (chloroform:methanol=100:0-97:3) to give the title compound (337 mg) as a white powder.
MS (ESI) m/z: 1025.9 [M+H]$^+$ Example 19

(19-1) (2S,4R)-1-[(2S)-2-(2-{[4'-(6-amino-2,3,9-trimethyl-6H-thieno[3,2-f][1,2,4]triazolo[4,3-a][1,4]diazepin-4-yl)-3-cyano[1,1'-biphenyl]-4-yl]oxy}acetamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 19)

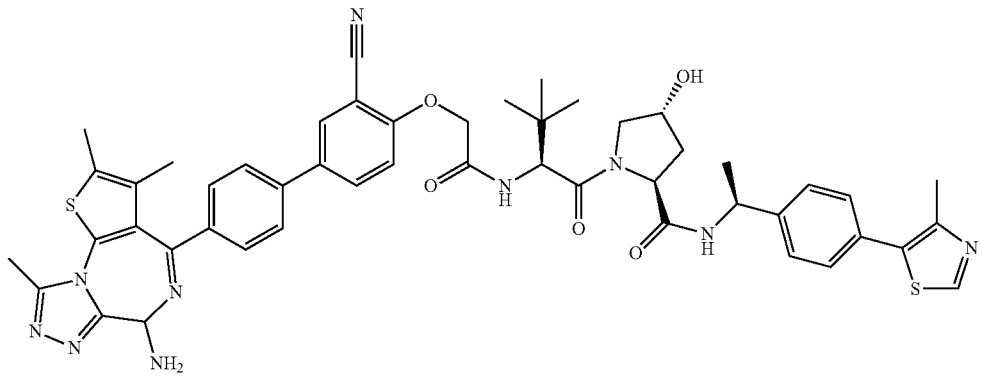 [SMILES: Cc1ncsc1-c1ccc([C@H](C)NC(=O)[C@@H]2C[C@@H](O)CN2C(=O)[C@@H](NC(=O)COc2ccc(-c3ccc(C4=NC(N)c5nnc(C)n5-c5sc(C)c(C)c54)cc3)cc2C#N)C(C)(C)C)cc1]

To a solution of Example compound 18 (270 mg) in dichloromethane (1.5 mL) was added trifluoroacetic acid (1.5 mL) at room temperature, and the mixture was stirred at the same temperature for 2 hr. The reaction mixture was concentrated under reduced pressure, and saturated aqueous sodium hydrogen carbonate (30 mL), chloroform (30 mL), methanol (5 mL) were added to the residue for partitioning. The aqueous layer was extracted once with chloroform (30 mL), and the organic layer was mixed, dried over anhydrous sodium sulfate and filtered. The solvent was evaporated under reduced pressure. The residue was purified by NH silica gel column chromatography (chloroform:methanol=100:0-97:3) and silica gel column chromatography (chloroform:methanol=100:0-95:5) to give the title compound (196 mg) as a white powder.

MS (ESI) m/z: 925.7 [M+1-1]$^+$

Example 20

(20-1) methyl (4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)carbamate (Example Compound 20)

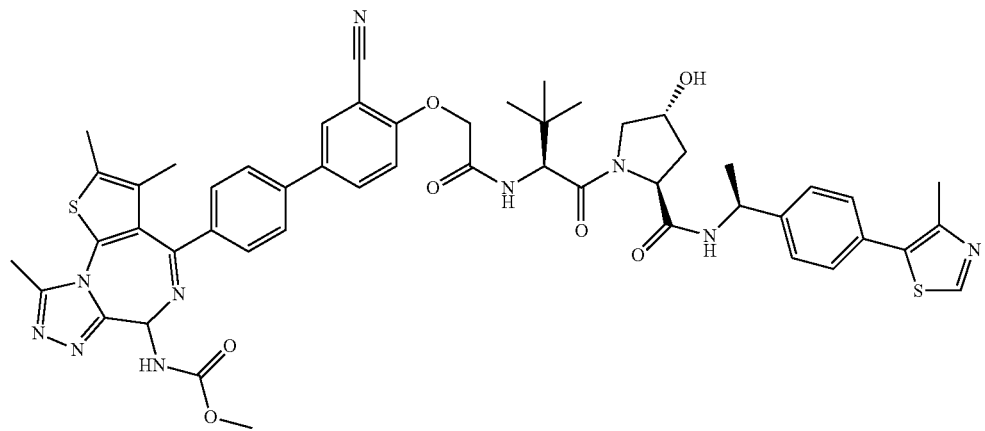 [SMILES: COC(=O)NC1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

To a solution of Example compound 19 (47 mg) in dichloromethane (0.5 mL) were added N,N-diisopropylethylamine (0.013 mL) and methyl chloroformate (5.3 mg) at room temperature, and the mixture was stirred at the same temperature for 1 hr. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-95:5) to give the title compound (38 mg) as a white powder. MS (ESI) m/z: 983.6 [M+H]$^+$ Example 21

(21-1) t-butyl 5-bromo-1-benzofuran-2-carboxylate (Example Compound 21-1)

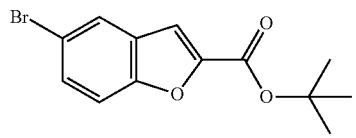 [SMILES: CC(C)(C)OC(=O)c1cc2cc(Br)ccc2o1]

To a solution of 5-bromosalicylaldehyde (5.0 g) in N,N-dimethylformamide (50 mL) were added t-butyl bromoacetate (5.34 g) and potassium carbonate (6.90 g) at room temperature, and the mixture was stirred at 80° C. for 24 hr. The insoluble material in the reaction mixture was filtered off through diatomaceous earth, and the filtration residue was washed with ethyl acetate. The filtrate was concentrated under reduced pressure, water was added to the residue and the mixture was extracted twice with hexane. The organic layers were mixed, washed with saturated brine, dried over anhydrous sodium sulfate and filtered. The solvent was evaporated under reduced pressure. The residue was purified by silica gel column chromatography (hexane:ethyl acetate=100:0-90:10) to give the title compound (6.37 g) as a pale-yellow oil. $^1$H NMR (400 MHz, CDCl$_3$) δppm 1.62 (9H, s), 7.35 (1H, s), 7.46 (1H, d, J=9.2 Hz), 7.51 (1H, dd, J=8.7, 2.1 Hz), 7.79 (1H, d, J=2.1 Hz)

(21-2) t-butyl 5-(4,4,5,5-tetramethyl-1,3,2-dioxaboronan-2-yl)-1-benzofuran-2-carboxylate (Example Compound 21-2)

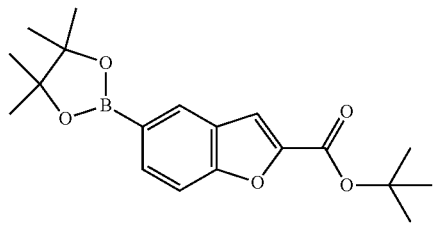 [SMILES: CC(C)(C)OC(=O)c1cc2cc(B3OC(C)(C)C(C)(C)O3)ccc2o1]

To a mixture of Example compound 21-1 (1.50 g), bis(pinacolato)diboron (1.41 g), 1,1'-bis(diphenylphosphino)ferrocene-palladium(II) dichloride dichloromethane complex (206 mg) and potassium acetate (991 mg) was added 1,4-dioxane (17 mL). After nitrogen substitution, the mixture was stirred with heating under microwave irradiation at 130° C. for 30 min. To the reaction mixture were added water, ethyl acetate and activated carbon, the insoluble material was filtered off through diatomaceous earth, and the filtration residue was washed with ethyl acetate. The filtrate was partitioned, and the organic layer was washed with saturated brine, dried over anhydrous sodium sulfate and filtered. The solvent was evaporated under reduced pressure. The residue was purified by silica gel column chromatography (hexane:ethyl acetate=100:0-90:10) to give the title compound (1.38 g) as a pale-yellow solid. ¹H NMR (400 MHz, CDCl₃) δppm 1.37 (12H, s), 1.63 (9H, s), 7.40 (1H, d, J=1.0 Hz), 7.56 (1H, d, J=8.7 Hz), 7.87 (1H, dd, J=1.3, 8.5 Hz), 8.15 (1H, s)

heating under microwave irradiation at 70° C. for 30 min. After cooling to room temperature, Example compound 21-2 (249 mg), palladium acetate (22 mg), S-phos (40 mg), potassium fluoride (84 mg) and water (0.031 mL) were added. After nitrogen substitution, the mixture was stirred with heating under microwave irradiation at 70° C. for 30 min. The reaction mixture was diluted with ethyl acetate, activated carbon was added, insoluble material was filtered off through diatomaceous earth, and the filtration residue was washed with ethyl acetate. The filtrate was concentrated under reduced pressure, and the residue was purified by silica gel column chromatography (chloroform:methanol=100:0-97:3) to give a crudely purified title compound (390 mg) as a brown powder.
MS (ESI) m/z: 597.5 [M+H]⁺

(21-4) methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]phenyl}-2,3,9-trimethyl-6H-thieno[3,2-f][1,2,4]triazolo[4,3-a][1,4]diazepin-6-yl]acetate (Example Compound 21)

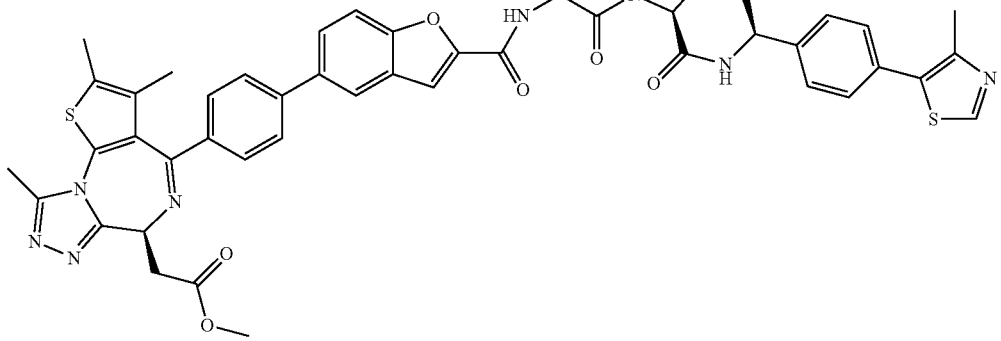

(21-3) t-butyl 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1-benzofuran-2-carboxylate (Example Compound 21-3)

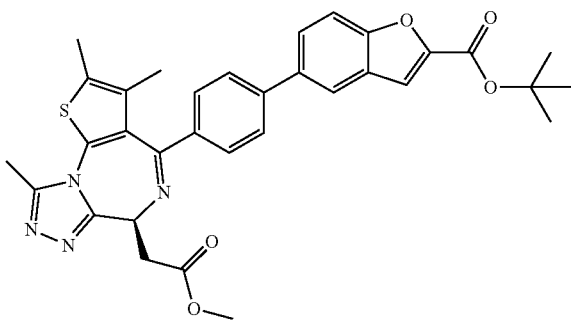 [SMILES: COC(=O)C[C@@H]1N=C(c2ccc(-c3ccc4oc(C(=O)OC(C)(C)C)cc4c3)cc2)c2c(sc(C)c2C)-n2c(C)nnc21]

To a mixture of Reference Example compound 1 (200 mg), Example compound 21-2 (249 mg), palladium acetate (22 mg), S-phos (40 mg) and potassium fluoride (84 mg) were added tetrahydrofuran (2.4 mL) and water (0.031 mL). After nitrogen substitution, the mixture was stirred with To a solution of Example compound 21-3 (385 mg) in dichloromethane (3 mL) was added trifluoroacetic acid (3 mL) at room temperature, and the mixture was stirred at the same temperature for 30 min. The reaction mixture was concentrated under reduced pressure, and toluene was added to the residue.

The solvent was evaporated under reduced pressure and the obtained residue was dissolved in Reference Example compound 5 (272 mg) and N,N-dimethylformamide (4.7 mL) at room temperature. N,N-diisopropylethylamine (0.82 mL) and HATU (250 mg) were added at the same temperature, and the mixture was stirred at the same temperature for 1 hr. To the reaction mixture was added saturated aqueous sodium hydrogen carbonate, and the mixture was extracted twice with ethyl acetate, and the extract was washed with saturated aqueous sodium hydrogen carbonate and saturated brine, dried over anhydrous sodium sulfate and filtered. The solvent was evaporated under reduced pressure. The residue was purified by NH silica gel column chromatography (ethyl acetate:methanol=100:0-90:10) and silica gel column chromatography (chloroform:methanol=100:0-97:3), and the obtained solid was suspension washed with diethyl ether and collected by filtration to give the title compound (307 mg) as a white powder. MS (ESI) m/z: 484.6[(M+2H)/2]⁺

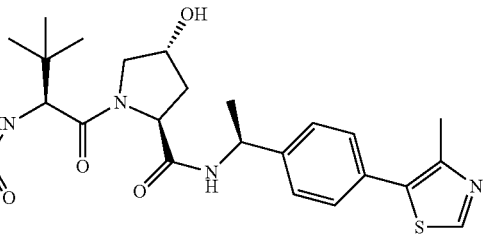

Example 22

(22-1) 2-[(6S)-4-(4-chlorophenyl)-2,3,9-trimethyl-6H-thieno[3,2-f][1,2,4]triazolo[4,3-a][1,4]diazepin-6-yl]ethan-1-ol (Example Compound 22-1)

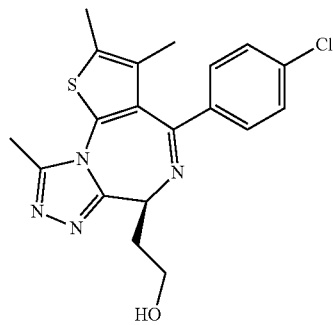 [SMILES: Cc1sc2c(c1C)C(c1ccc(Cl)cc1)=N[C@@H](CCO)c1nnc(C)n1-2]

To a solution of lithium aluminum hydride (550 mg) in tetrahydrofuran (40 mL) was slowly added dropwise under ice-cooling a solution of Reference Example compound 1 (4.0 g) in tetrahydrofuran (60 mL). After completion of the dropwise addition, ice water was added, 1N hydrochloric acid was added, and the mixture was extracted with ethyl acetate. The extract was washed with saturated aqueous sodium hydrogen carbonate and saturated brine, dried over anhydrous sodium sulfate and filtered. The solvent was evaporated under reduced pressure.

The obtained residue was purified by NH silica gel column chromatography (hexane:ethyl acetate=10:90-0:100) to give the title compound (1.39 g) as a pale-orange solid. The fractions that could not be purified were collected and purified again by silica gel column chromatography (chloroform:methanol=100:0-88:12) to give the title compound (1.19 g) as a crudely purified pale-orange solid. MS (ESI) m/z: 387.2 [M+H]$^+$ (22-2) (6S)-4-(4-chlorophenyl)-6-(2-methoxyethyl)-2,3,9-trimethyl-6H-thieno[3,2-f][1,2,4]triazolo[4,3-a][1,4]diazepine (Example Compound 22-2)

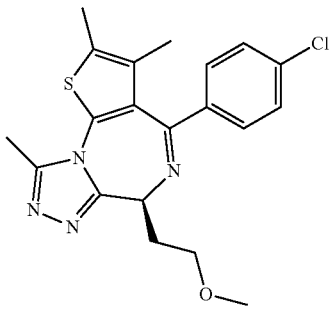 [SMILES: COCC[C@@H]1N=C(c2ccc(Cl)cc2)c2c(sc(C)c2C)-n2c(C)nnc21]

A mixture of Example compound 22-1 (500 mg), dichloromethane (4.3 mL), triethylamine (0.539 mL) and 4-methylbenzenesulfonyl chloride (370 mg) was stirred at room temperature for 15 hr. Triethylamine (0.180 mL), 4-methylbenzenesulfonyl chloride (123 mg) were added, and the mixture was further stirred for 2 hr and at 40° C. for 1 hr. To the reaction mixture were added ice water, saturated aqueous sodium hydrogen carbonate, and the mixture was extracted with chloroform, and the extract was dried over anhydrous sodium sulfate and filtered. The solvent was evaporated under reduced pressure. To the obtained residue were added methanol (10 mL), sodium methoxide (10 mL), and the mixture was stirred at room temperature for 15 hr. Water was added to the reaction mixture, and the mixture was extracted with chloroform and the extract was washed with water. The solvent was evaporated under reduced pressure. The obtained residue was purified by silica gel column chromatography (chloroform:methanol=98:2-93:7) to give the title compound (432 mg) as a yellow oil.

MS (ESI) m/z: 401.4 [M+H]$^+$ (22-3) (2S,4R)-1-{(2S)-2-[2-({3-cyano-4'-[(6S)-6-(2-methoxyethyl)-2,3,9-trimethyl-6H-thieno[3,2-f][1,2,4]triazolo[4,3-a][1,4]diazepin-4-yl][1,1'-biphenyl]-4-yl}oxy)acetamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 22)

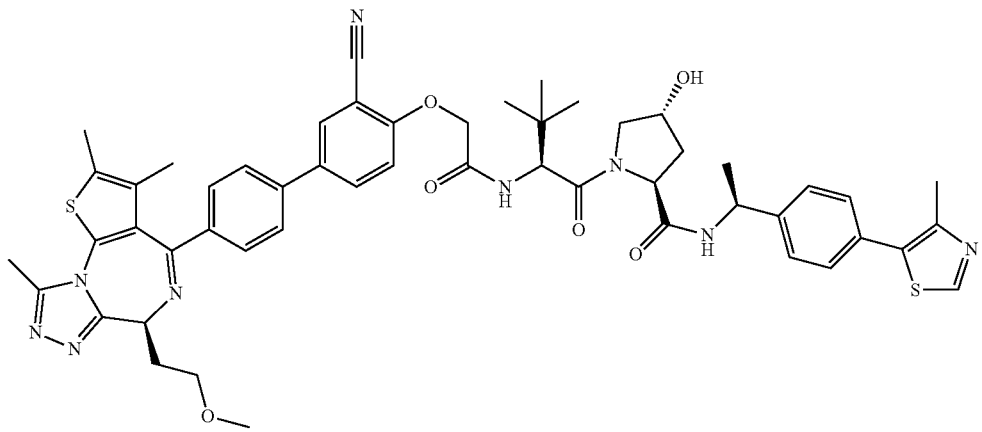 [SMILES: COCC[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

By reaction and treatment in the same manner as in Example 6 (16-2)-(16-3) and using Example compound 22-2 instead of Reference Example compound 4, the title compound was obtained as a white solid. MS (ESI) m/z: 968.8 [M+H]⁺

Example 23

(23-1) methyl [(6S)-4-{3'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 23)

To a solution of 4-(4,4,5,5-tetramethyl-1,3,2-dioxaborolan-2-yl)pyrazole (2.0 g) in acetonitrile (50 mL) were added t-butyl bromoacetate (3.02 g) and potassium carbonate (6.72 g) at room temperature and the mixture was stirred at 60° C. for 1 hr. Water was added to the reaction mixture and the mixture was extracted twice with ethyl acetate, and the extract was washed with water and saturated brine, dried over anhydrous sodium sulfate and filtered. The solvent was evaporated under reduced pressure. The residue was purified by silica gel column chromatography (hexane:ethyl acetate=90:10-75:25) to give the title compound (2.09 g) as a colorless oil. MS (ESI) m/z: 309.4 [M+H]⁺

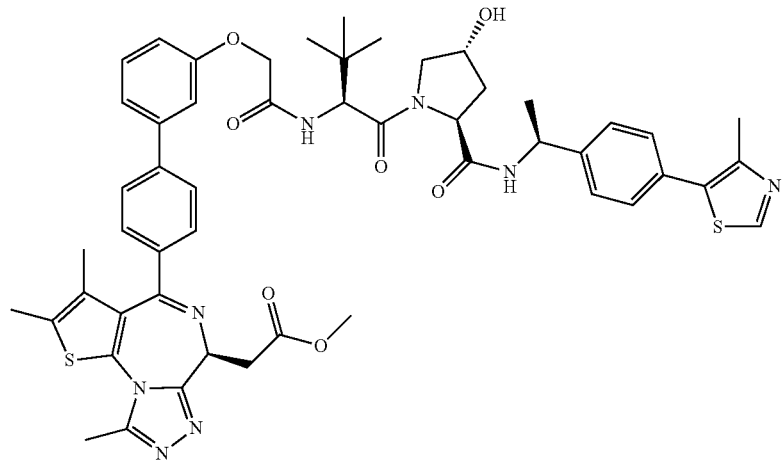 [SMILES: COC(=O)C[C@@H]1N=C(c2ccc(-c3cccc(OCC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

By reaction and treatment in the same manner as in Example 6 (16-2)-(16-3) and using Example compound 1-1 instead of Reference Example compound 4, 3-(4,4,5,5-tetramethyl-1,3,2-dioxaborolan-2-yl)phenol instead of Reference Example compound 7, the title compound was obtained as a white solid.

MS (ESI) m/z: 957.7 [M+H]⁺

Example 24

(24-1) t-butyl [4-(4,4,5,5-tetramethyl-1,3,2-dioxaboronan-2-yl)-1H-pyrazol-1-yl]acetate (Example Compound 24-1)

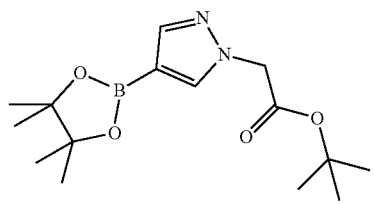 [SMILES: CC(C)(C)OC(=O)Cn1cc(B2OC(C)(C)C(C)(C)O2)cn1]

(24-2) methyl [(6S)-4-{4-[1-(2-t-butoxy-2-oxoethyl)-1H-pyrazol-4-yl]phenyl}-2,3,9-trimethyl-6H-thieno[3,2-f][1,2,4]triazolo[4,3-a][1,4]diazepin-6-yl]acetate (Example Compound 24-2)

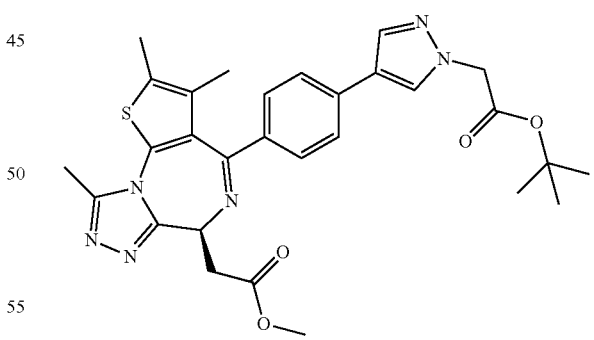

To a mixture of Reference Example compound 1 (200 mg), Example compound 24-1 (297 mg), palladium acetate (33 mg), S-phos (60 mg) and potassium fluoride (140 mg) were added tetrahydrofuran (2.4 mL) and water (0.052 mL). After nitrogen substitution, under microwave irradiation, the mixture was stirred with heating at 70° C. for 1.5 hr. The mixture was cooled to room temperature and Example compound 24-1 (75 mg), palladium acetate (11 mg), S-phos (20 mg) were added. After nitrogen substitution, the mixture was stirred with heating under microwave irradiation at 70° C. for 30 min. The reaction mixture was diluted with ethyl acetate, activated carbon was added, insoluble material was filtered off through diatomaceous earth, and the filtration residue was washed with ethyl acetate. The filtrate was concentrated under reduced pressure, and the residue was purified twice by silica gel column chromatography (chloroform:methanol=100:0-97:3) to give the title compound (158 mg) as a pale-yellow viscous compound.

MS (ESI) m/z: 561.4 [M+H]+

(24-3) methyl [(6S)-4-(4-{1-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1H-pyrazol-4-yl}phenyl)-2,3,9-trimethyl-6H-thieno[3,2-f][1,2,4]triazolo[4,3-a][1,4]diazepin-6-yl]acetate (Example Compound 24)

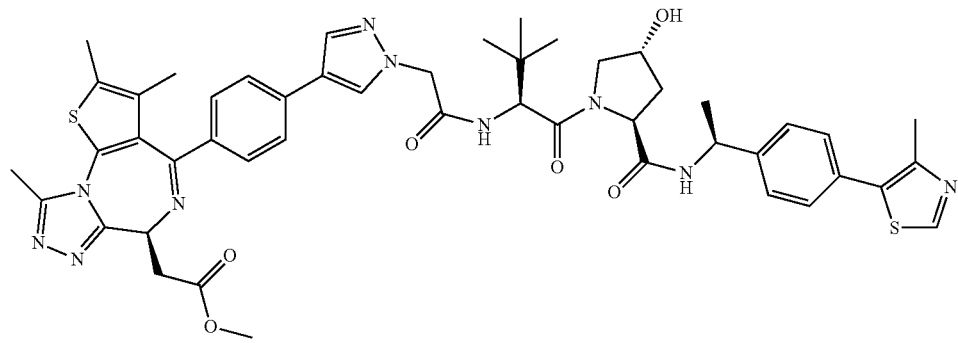 [SMILES: COC(=O)C[C@@H]1N=C(c2ccc(-c3cnn(CC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 24-2 (152 mg) in dichloromethane (2 mL) was added at room temperature trifluoroacetic acid (2 mL), and the mixture was stirred at the same temperature for 1.5 hr. The reaction mixture was concentrated under reduced pressure, and toluene was added to the residue. The solvent was evaporated under reduced pressure. The obtained residue was dissolve in Reference Example compound 5 (157 mg) and N,N-dimethylformamide (2.7 mL) at room temperature, N,N-diisopropylethylamine (0.47 mL) and HATU (145 mg) were added at the same temperature, and the mixture was, stirred at the same temperature for 1 hr. To the reaction mixture was added saturated aqueous sodium hydrogen carbonate, and the mixture was extracted twice with ethyl acetate, and the extract was washed with saturated aqueous sodium hydrogen carbonate and saturated brine, dried over anhydrous sodium sulfate and filtered. The solvent was evaporated under reduced pressure. The residue was purified by silica gel column chromatography (chloroform:methanol=100:0-97:3, precolumn:NH silica gel) and the obtained solid was suspension washed with diethyl ether and collected by filtration to give the title compound (107 mg) as a white powder. MS (ESI) m/z: 931.8 [M+H]+

Example 25

(25-1) methyl 5-methoxy-1-benzofuran-2-carboxylate (Example Compound 25-1)

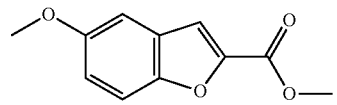

To a solution of 2-hydroxy-5-methoxy-benzaldehyde (5.00 g) in N,N-dimethylformamide (30 mL) were added potassium carbonate (8.63 g) and methyl 2-bromoacetate (3.16 mL) and the mixture was stirred at 80° C. for 19 hr. Water was added to the reaction mixture, and the precipitate was collected by filtration. The filtrate was extracted 3 times with ethyl acetate, and the extract was dried over anhydrous sodium sulfate and filtered. The solvent was evaporated under reduced pressure. The residue as a solid was combined with the solid which was previously collected by filtration to give the title compound (3.6 g) as a pale-yellow solid.

MS (ESI) m/z: 207.0 [M+H]+

(25-2) methyl 5-hydroxy-1-benzofuran-2-carboxylate (Example Compound 25-2)

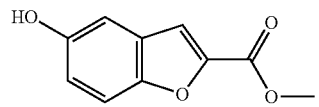

To a solution of Example compound 25-1 (2.84 g) in dichloromethane (70 mL) was added tribromoborane (14.5 mL) at −78° C. and the mixture was stirred for 10 min, and stirred for 2 hr while raising the temperature to room temperature. Methanol was added and the mixture was washed with saturated brine. The organic layer was extracted with ethyl acetate, and the extract was dried over anhydrous sodium sulfate and filtered. The solvent was evaporated under reduced pressure. The obtained residue was purified by silica gel column chromatography (hexane:ethyl acetate=90:10-75:25) to give the title compound (1.74 g) as a colorless solid. MS (ESI) m/z: 193.1 [M+H]+

(25-3) methyl 5-{2-[(t-butoxycarbonyl)amino]ethoxy}-1-benzofuran-2-carboxylate (Example Compound 25-3)

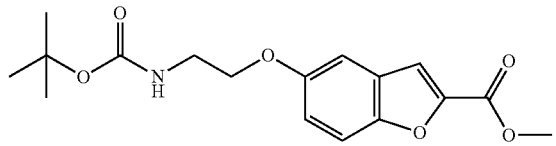 [SMILES: COC(=O)c1cc2cc(OCCNC(=O)OC(C)(C)C)ccc2o1]

A mixture of Example compound 25-2 (300 mg), potassium carbonate (431 mg), N,N-dimethylformamide (3.1 mL) and t-butyl N-(2-bromoethyl)carbamate (350 mg) was stirred at 50° C. for 24 hr. Potassium carbonate (431 mg) and t-butyl N-(2-bromoethyl)carbamate (350 mg) were added, and the mixture was stirred for 8 hr. Furthermore, t-butyl N-(2-bromoethyl)carbamate (174 mg) was added and the mixture was is stirred for 3 hr. Potassium carbonate (431 mg) and t-butyl N-(2-bromoethyl)carbamate (174 mg) were added and the mixture was stirred for 2 hr. To the reaction mixture was added water, and the mixture was extracted with ethyl acetate, and the extract was washed with water and saturated brine, dried over anhydrous sodium sulfate and filtered. The solvent was evaporated under reduced pressure. Water-ethanol was added to the precipitated solid, ultrasonicated, suspension washed and the solid was collected by filtration to give the title compound (415 mg).
MS (ESI) m/z: 671.6 [2 M+H]⁺

(25-4) 5-{2-[(t-butoxycarbonyl)amino]ethoxy}-1-benzofuran-2-carboxylic acid (Example Compound 25-4)

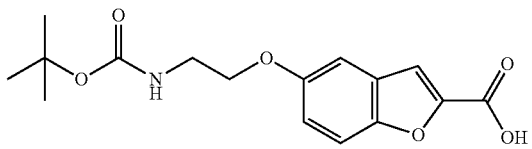 [SMILES: CC(C)(C)OC(=O)NCCOc1ccc2oc(C(=O)O)cc2c1]

To a solution of Example compound 25-3 (412 mg) in tetrahydrofuran (5.0 mL), water (1.0 mL) and methanol (1.0 mL) was added lithium hydroxide monohydrate (154 mg) under ice-cooling and the mixture was stirred for 3 hr. Under ice-cooling, ethyl acetate and water were added to the reaction mixture and the mixture was acidified (pH 4) by adding 1N hydrochloric acid with stirring. After partitioning, the aqueous layer was extracted with ethyl acetate. The organic layers were combined, washed with saturated brine, and dried over anhydrous sodium sulfate. The solvent was evaporated m under reduced pressure and the residue was dried to give the title compound (360 mg) as a white solid.
MS (ESI) m/z: 320.4 [M−H]⁻

(25-5) t-butyl (2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamate (Example Compound 25-5)

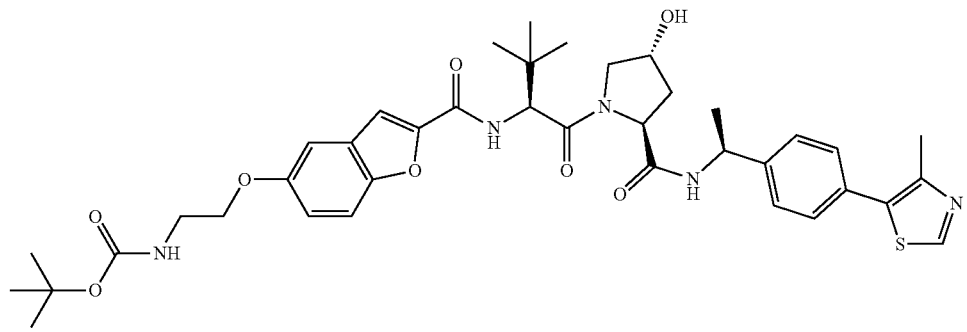 [SMILES: Cc1ncsc1-c1ccc([C@H](C)NC(=O)[C@@H]2C[C@@H](O)CN2C(=O)[C@@H](NC(=O)c2cc3cc(OCCNC(=O)OC(C)(C)C)ccc3o2)C(C)(C)C)cc1]

To a solution of Example compound 25-4 (245 mg), Reference Example compound 5 (385 mg) in N,N-dimethylformamide (5.0 mL) were added, under ice-cooling, N,N-diisopropylethylamine (0.264 mL) and HATU (580 mg), and the mixture was stirred at room temperature for 24 hr. Furthermore, N,N-diisopropylethylamine (0.264 mL), HATU (145 mg) were added and the mixture was stirred at room temperature for 24 hr. Water was added to the reaction mixture and the mixture was extracted with chloroform. The solvent was evaporated under reduced pressure. To the residue was added ethyl acetate, the mixture was washed 3 times with water and the solvent was evaporated under reduced pressure. The obtained residue was purified by silica gel column chromatography (ethyl acetate:methanol=100:0-93:7) to give the title compound (560 mg) as a white solid.
MS (ESI) m/z: 748.7 [M+H]⁺

(25-6) methyl [(6S)-4-{4'-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 25)

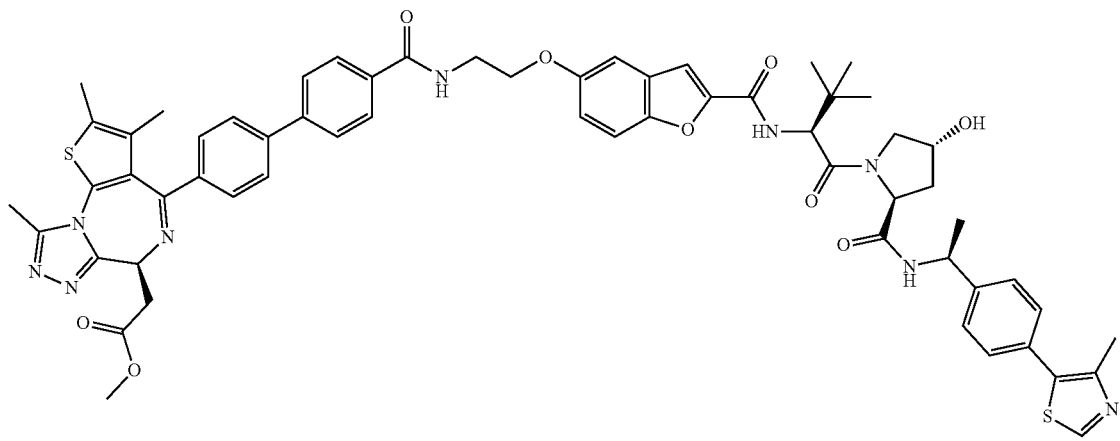

To a solution of Example compound 25-5 (110 mg) and dichloromethane (1.1 mL) was added trifluoroacetic acid (1.1 mL), and the mixture was stirred at room temperature for 2 hr. To the reaction mixture was added dichloromethane and the solvent was evaporated under reduced pressure. To the residue was added toluene and the mixture was concentrated under reduced pressure. This operation was performed twice and the mixture was dried by heating. To the obtained residue were added N,N-dimethylformamide (1.5 mL), N,N-diisopropylethylamine (0.256 mL), Example compound 90-1 (99 mg) and HATU (84 mg) was added under ice-cooling and the mixture was stirred at room temperature for 19 hr. To the reaction mixture was added ice water and the mixture was extracted with chloroform and the extract was washed 3 times with water. The solvent was evaporated under reduced pressure. The obtained residue was purified by silica gel column chromatography (chloroform:methanol=100:0-93:7) to give the title compound (79 mg) as a white solid. MS (ESI) m/z: 1129.8 [M+H]$^+$ Example 26

(26-1) (6S)-4-(4-chlorophenyl)-2,3,9-trimethyl-6-[(5-methyl-1,3,4-oxadiazol-2-yl)methyl]-6H-thieno[3,2-f] [1,2,4]triazolo[4,3-a][1,4]diazepine (Example Compound 26-1)

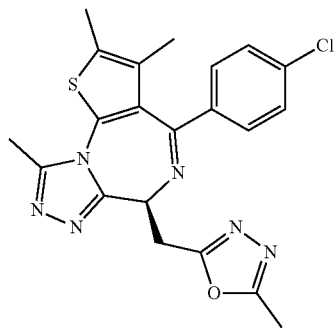 [SMILES: Cc1nnc(C[C@@H]2N=C(c3ccc(Cl)cc3)c3c(sc(C)c3C)-n3c(C)nnc32)o1]

To a solution of (S)-4-(4-chlorophenyl)-2,3,9-trimethyl-6H-thieno[3,2-f][1,2,4]triazolo[4,3-a][1,4]diazepine-6-acetic acid (2.0 g) in tetrahydrofuran were added triethylamine (0.69 mL), pivaloyl chloride (0.61 mL) and hydrazine monohydrate (0.61 mL), and the mixture was stirred at room temperature for 1 hr. The reaction mixture was concentrated, the obtained residue was purified by silica gel column chromatography (chloroform:methanol=50:1) to give a white solid (1.30 g). To a solution of the obtained solid (1.30) in tetrahydrofuran (50 mL) and ethyl acetate (50 mL) was added acetic anhydride (0.35 mL), and the mixture was stirred at room temperature for 1 hr. The reaction mixture was concentrated and the obtained residue was purified by silica gel column chromatography (chloroform:methanol=20:1) to give a white solid (1.51 g). To a solution of the obtained solid (0.80 g) in 1,2-dimethoxyethane (20 mL) was added phosphorus oxychloride (2.21 mL) and the mixture was stirred at 100° C. for 2 hr. The reaction mixture was added to ice water and the mixture was stirred at room temperature for 1 hr. 1N Aqueous sodium hydroxide solution was added and the mixture was extracted with ethyl acetate, and the extract was washed with saturated brine, dried over anhydrous sodium sulfate and filtered. The solvent was evaporated under reduced pressure. The obtained residue was purified by silica gel column chromatography (chloroform:methanol=50:1) to give the title compound (0.59 g) as a white solid. MS (ESI) m/z: 439.3 [M+H]$^+$ (26-2) (2S,4R)-1-[(2S)-2-{2-[(3-cyano-4'-{(6S)-2,3,9-trimethyl-6-[(5-methyl-1,3,4-oxadiazol-2-yl)methyl]-6H-thieno[3,2-f] [1,2,4]triazolo[4,3-a][1,4]diazepin-4-yl}[1,1'-biphenyl]-4-yl)oxy]acetamido}-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 26)

was washed with hexane. The filtrate was concentrated under reduced pressure to give a crudely purified title compound (1.52 g) as a pale-yellow solid. $^1$H NMR (400 MHz, CDCl$_3$) δppm 1.53 (9H, s), 6.35 (1H, d, J=15.9 Hz), 7.31-7.41 (2H, m), 7.46-7.55 (3H, m)

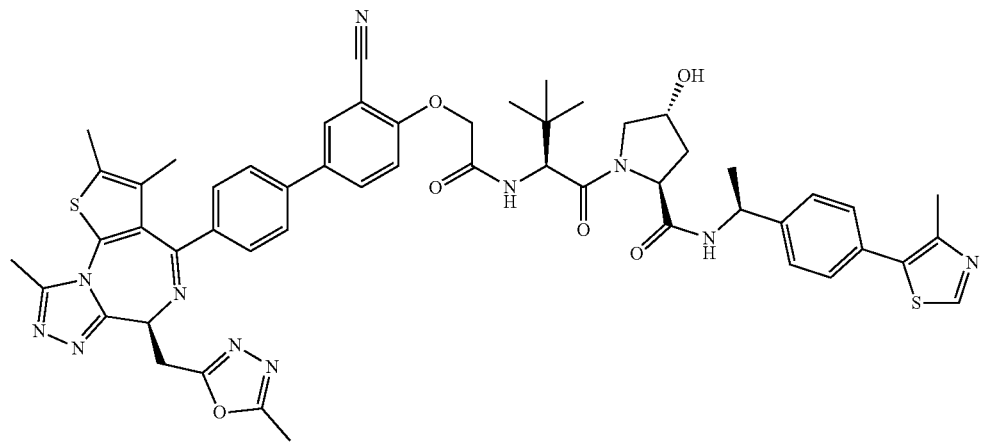 [SMILES: Cc1nnc(C[C@@H]2N=C(c3ccc(-c4ccc(OCC(=O)N[C@H](C(=O)N5C[C@H](O)C[C@H]5C(=O)N[C@@H](C)c5ccc(-c6scnc6C)cc5)C(C)(C)C)c(C#N)c4)cc3)c3c(sc(C)c3C)-n3c(C)nnc32)o1]

By reaction and treatment in the same manner as in Example 17 (17-1)-(17-3) and using Reference Example compound 7 instead of 2-methoxy-4-(4,4,5,5-tetramethyl-1,3,2-dioxaboran-2-yl)phenol, and Example compound 26-1 instead of Reference Example compound 1, the title compound was obtained as a pale-yellow solid. MS (ESI) m/z: 1006.9 [M+H]$^+$ Example 27

(27-1) t-butyl (2E)-3-(4-bromophenyl)-2-propenoate (Example compound 27-1)

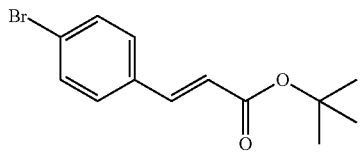 [SMILES: CC(C)(C)OC(=O)/C=C/c1ccc(Br)cc1]

To a suspension of 4-bromocinnamic acid (2.0 g) in t-butanol (22 mL) were added at room temperature di-t-butyl dicarbonate (2.50 g) and 4-dimethylaminopyridine (1.40 g), and the mixture was stirred at 80° C. for 4 hr. The reaction mixture was concentrated under reduced pressure, to the residue was added ethyl acetate, and the mixture was successively washed with saturated aqueous sodium hydrogen carbonate, saturated aqueous ammonium chloride solution and saturated brine, dried over anhydrous sodium sulfate and filtered. The solvent was evaporated under reduced pressure. To the residue were added is hexane, and the insoluble material was filtered off and the filtration residue (27-2) t-butyl (2E)-3-[4-(4,4,5,5-tetramethyl-1,3,2-dioxaboronan-2-yl)phenyl]-2-propenoate (Example Compound 27-2)

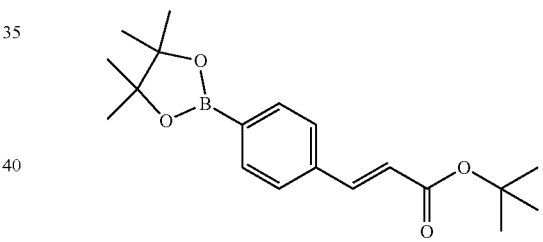

To a mixture of Example compound 27-1 (1.51 g), bis(pinacolato)diboron (1.49 g), 1,1'-bis(diphenylphosphino)ferrocene-palladium(II) dichloride dichloromethane complex (218 mg) and potassium acetate (1.05 g) was added 1,4-dioxane (14 mL). After nitrogen substitution, under microwave irradiation, the mixture was stirred with heating at 130° C. for 30 min. To the reaction mixture was added ethyl acetate and the insoluble material was filtered off through diatomaceous earth-activated carbon, and the filtration residue was washed with ethyl acetate. The filtrate was concentrated under reduced pressure, and the residue was purified by silica gel column chromatography (hexane:ethyl acetate=100:0-90:10) to give the title compound (1.40 g) as a white solid. $^1$H NMR (400 MHz, CDCl$_3$) δppm 1.35 (12H, s), 1.53 (9H, s), 6.42 (1H, d, J=16.4 Hz), 7.50 (2H, d, J=8.2 Hz), 7.58 (1H, d, J=16.4 Hz), 7.80 (2H, d, J=8.2 Hz)

(27-3) t-butyl (2E)-3-{4'-[(6S)-6-(2-methoxy-2-oxo-ethyl)-2,3,9-trimethyl-6H-thieno[3,2-f][1,2,4]tri-azolo[4,3-a][1,4]diazepin-4-yl][1,1'-biphenyl]-4-yl}-2-propenoate (Example Compound 27-3)

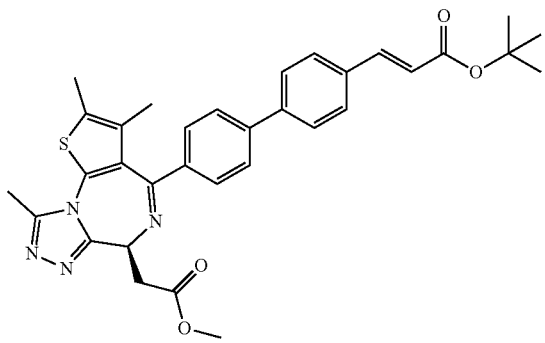 [SMILES: COC(=O)C[C@@H]1N=C(c2ccc(-c3ccc(/C=C/C(=O)OC(C)(C)C)cc3)cc2)c2c(sc(C)c2C)-n2c(C)nnc21]

To a mixture of Reference Example compound 1 (400 mg), Example compound 27-2 (414 mg), 2-dicyclohexylphosphino-2'-6'-dimethoxybiphenyl aminobiphenyl palladium chloride precatalyst (70 mg) and potassium fluoride (168 mg) were added tetrahydrofuran (4.8 mL) and water (0.063 mL). After nitrogen substitution, the mixture was stirred with heating under microwave irradiation at 70° C. for 30 min, cooled to room temperature, and palladium acetate (44 mg), S-phos (80 mg), potassium fluoride (168 mg) and water (0.063 mL) were added. After nitrogen substitution, under microwave irradiation, the mixture was stirred with heating at 70° C. for 2 hr. The mixture was cooled to room temperature again, Example compound 27-2 (414 mg), palladium acetate (87 mg), S-phos (158 mg), potassium fluoride (168 mg), water (0.063 mL) were added. After nitrogen substitution, under microwave irradiation, the mixture was stirred with heating at 70° C. for 1.5 hr. The reaction mixture was diluted with ethyl acetate, activated carbon was added, the insoluble material was filtered off through diatomaceous earth, and the filtration residue was washed with ethyl acetate. The filtrate was concentrated under reduced pressure, and the residue was purified by silica gel column chromatography (chloroform:methanol=100:0-97:3, precolumn:NH silica gel) to give a crudely purified title compound (616 mg) as a pale-yellow powder. MS (ESI) m/z: 583.5 [M+H]+

(27-4) methyl [(6S)-4-{4'-[(1E)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropen-1-yl][1,1'-biphenyl]-4-yl}-2,3,9-trimethyl-6H-thieno[3,2-f][1,2,4]triazolo[4,3-a] [1,4]diazepin-6-yl]acetate (Example Compound 27)

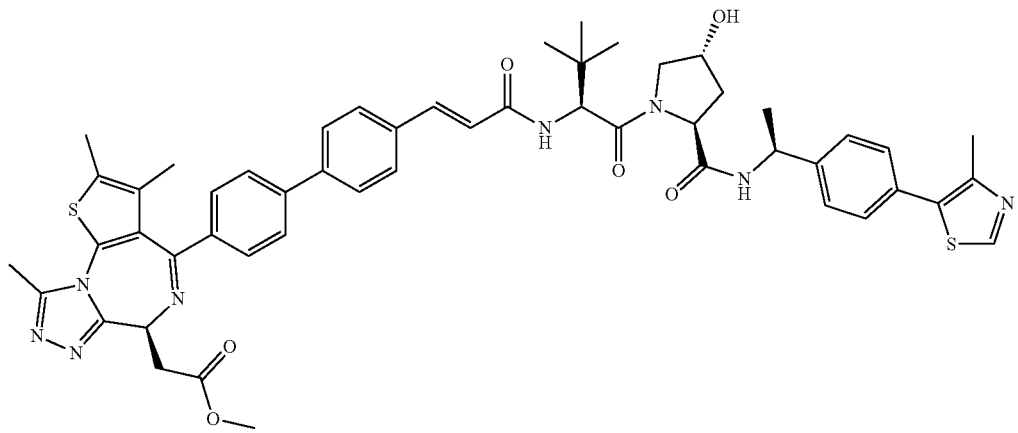 [SMILES: COC(=O)C[C@@H]1N=C(c2ccc(-c3ccc(/C=C/C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 27-3 (200 mg) in dichloromethane (2 mL) was added at room temperature trifluoroacetic acid (2 mL), and the mixture was stirred at the same temperature for 1 hr. The reaction mixture was concentrated under reduced pressure and toluene was added to the residue. The solvent was evaporated under reduced pressure. The obtained residue was dissolved in Reference Example compound 5 (181 mg) and N,N-dimethylformamide (3 mL) at room temperature, N,N-diisopropylethylamine (0.54 mL) and HATU (167 mg) were added at the same temperature, and the mixture was stirred at the same temperature for 1 hr. To the reaction mixture was added saturated aqueous sodium hydrogen carbonate, and the mixture was extracted twice with ethyl acetate, and the extract was washed with saturated aqueous sodium hydrogen carbonate and saturated brine, dried over anhydrous sodium sulfate and filtered. The solvent was evaporated under reduced pressure. The residue was purified by NH silica gel column chromatography (ethyl acetate:methanol=100:0-90:10) and the obtained solid was suspension washed with diethyl ether and collected by filtration to give the title compound (177 mg) as a white powder. MS (ESI) m/z: 953.8 [M+H]+

Example 28

(28-1) t-butyl 3-{4'-[(6S)-6-(2-methoxy-2-oxo-ethyl)-2,3,9-trimethyl-6H-thieno[3,2-f][1,2,4]tri-azolo[4,3-a][1,4]diazepin-4-yl][1,1'-biphenyl]-4-yl}propanoate (Example Compound 28-1)

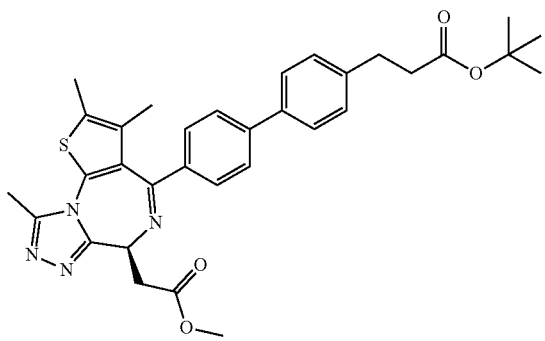 [SMILES: COC(=O)C[C@@H]1N=C(c2ccc(-c3ccc(CCC(=O)OC(C)(C)C)cc3)cc2)c2c(sc(C)c2C)-n2c(C)nnc21]

Example compound 27-3 (410 mg) was dissolved in methanol (6.4 mL), and 10% palladium carbon (273 mg) was added. The reaction container was substituted with hydrogen and the mixture was stirred at room temperature for 1 hr. The reaction container was substituted with nitrogen and the reaction mixture was filtered. The filtrate was concentrated, methanol (12 mL) and 20% palladium hydroxide carbon (180 mg) were added to the residue and the reaction container was substituted with hydrogen. After stirring at room temperature for 15 hr, the reaction container was substituted with nitrogen. The reaction mixture was filtered, and the solvent was concentrated under reduced pressure to give a crudely purified title compound (334 mg) as a pale-yellow powder. MS (ESI) m/z: 585.5 [M+H]$^+$ (28-2) methyl [(6S)-4-{4'-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl][1,1'-biphenyl]-4-yl}-2,3,9-trimethyl-6H-thieno[3,2-f][1,2,4]triazolo[4,3-a][1,4]diazepin-6-yl]acetate (Example Compound 28)

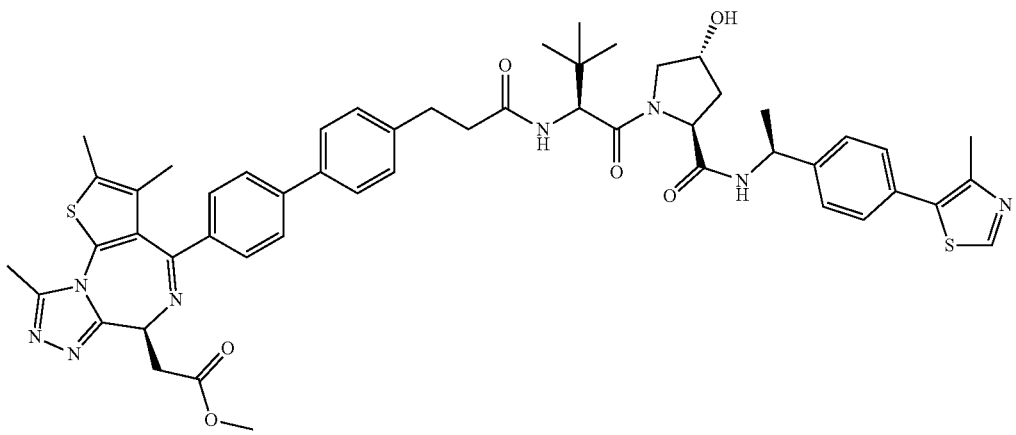

To a solution of Example compound 28-1 (334 mg) in dichloromethane (3 mL) was added trifluoroacetic acid (3 mL) at room temperature, and the mixture was stirred at the same temperature for 1 hr. The reaction mixture was concentrated under reduced pressure, and toluene was added to the residue. The solvent was evaporated under reduced pressure and the obtained residue was dissolved in Reference Example compound 5 (330 mg) and N,N-dimethylformamide (5.7 mL) at room temperature. To this solution were added at room temperature N,N-diisopropylethylamine (1.0 mL) and HATU (304 mg), and the mixture was stirred at the same temperature for 1 hr. To the reaction mixture was added saturated aqueous sodium hydrogen carbonate, and the mixture was extracted twice with ethyl acetate, and the extract was washed with saturated aqueous sodium hydrogen carbonate and saturated brine, dried over anhydrous sodium sulfate and filtered. The solvent was evaporated under reduced pressure. The residue was purified by NH silica gel column chromatography (ethyl acetate:methanol=100:0-90:10) and silica gel column chromatography (chloroform:methanol=100:0-97:3, precolumn:NH silica gel). The obtained solid was suspension washed with diethyl ether and collected by filtration to give the title compound (248 mg) as a white powder. MS (ESI) m/z: 955.8 [M+H]$^+$

Example 29

(29-1) t-butyl [4-(4'-hydroxy[1,1'-biphenyl]-4-yl)-2,3,9-trimethyl-6H-thieno[3,2-f][1,2,4]triazolo[4,3-a][1,4]diazepin-6-yl]carbamate (Example Compound 29-1)

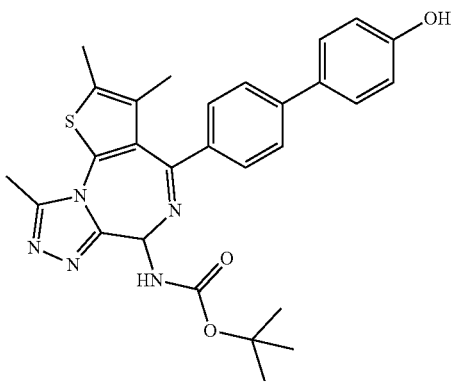 [SMILES: Cc1sc2c(c1C)C(c1ccc(-c3ccc(O)cc3)cc1)=NC(NC(=O)OC(C)(C)C)c1nnc(C)n1-2]

To a mixture of Example compound 18-1 (760 mg), 4-(4,4,5,5-tetramethyl-1,3,2-dioxaborolan-2-yl)phenol (550 mg), 2-dicyclohexylphosphino-2',4',6'-triisopropylbiphenyl aminobiphenyl palladium chloride precatalyst (65 mg) were added 1,4-dioxane (8.3 mL) and 2 M aqueous cesium carbonate solution (2.5 mL). After nitrogen substitution, under microwave irradiation, the mixture was stirred with heating at 150° C. for 15 min. The aqueous layer in the reaction mixture was removed by a pipette operation, the insoluble material was filtered off through diatomaceous earth-activated carbon, and the filtration residue was washed with chloroform. The filtrate was concentrated under reduced pressure, and the residue was purified by silica gel column chromatography (chloroform:ethyl acetate=50:50-0:100) to give a crudely purified title compound (998 mg) as a white powder. MS (ESI) m/z: 516.4 [M+H]$^+$

(29-2) methyl [(4'-{6-[(t-butoxycarbonyl)amino]-2,3,9-trimethyl-6H-thieno[3,2-f][1,2,4]triazolo[4,3-a][1,4]diazepin-4-yl}[1,1'-biphenyl]-4-yl)oxy]acetate (Example Compound 29-2)

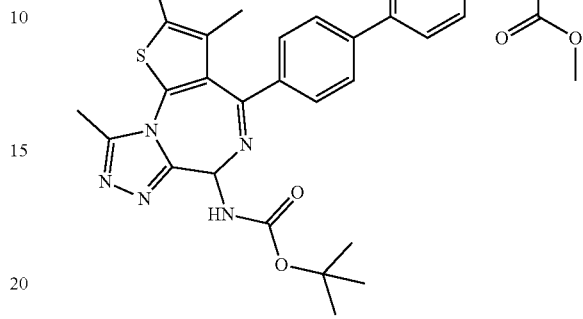

To a solution of Example compound 29-1 (994 mg) and methyl bromoacetate (0.18 mL) in N,N-dimethylformamide (8.2 mL) was added at room temperature cesium carbonate (800 mg), and the mixture was stirred at 60° C. for 15 min. Water was added to the reaction mixture, and the mixture was extracted twice with ethyl acetate, and the extract was washed with water and saturated brine, dried over anhydrous sodium sulfate and filtered. The solvent was evaporated under reduced pressure. The residue was purified by silica gel column chromatography (chloroform:methanol=100:0-97:3) to give the title compound (876 mg) as a pale-yellow powder. MS (ESI) m/z: 588.5 [M+H]$^+$

(29-3) t-butyl (4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)carbamate (compound 29-3)

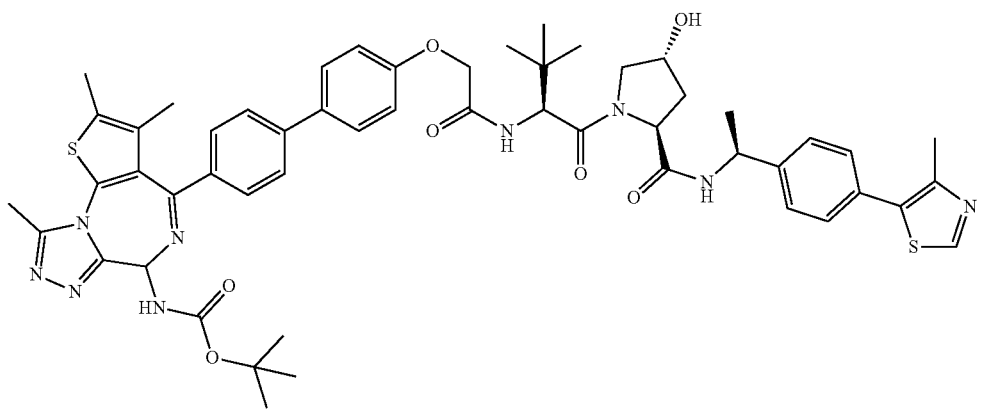 [SMILES: Cc1ncsc1-c1ccc([C@H](C)NC(=O)[C@@H]2C[C@@H](O)CN2C(=O)[C@@H](NC(=O)COc2ccc(-c3ccc(C4=NC(NC(=O)OC(C)(C)C)c5nnc(C)n5-c5sc(C)c(C)c54)cc3)cc2)C(C)(C)C)cc1]

To a solution of Example compound 29-2 (870 mg) in tetrahydrofuran (8 mL), methanol (4 mL) and water (4 mL) was added at room temperature lithium hydroxide monohydrate (250 mg), and the mixture was stirred at the same temperature for 1 hr. To the reaction mixture was added 5% aqueous potassium hydrogensulfate solution, and the mixture was extracted twice with chloroform, and the extract was dried over anhydrous sodium sulfate and filtered. The solvent was evaporated under reduced pressure. To the residue were added at room temperature Reference Example compound 5 (855 mg) and N,N-dimethylformamide (15 mL) to give a solution, N,N-diisopropylethylamine (0.77 mL) and HATU (788 mg) were added at the same temperature, and the mixture was stirred at the same temperature for 30 min. To the reaction mixture was added saturated aqueous sodium hydrogen carbonate, and the mixture was extracted once with ethyl acetate, and the extract was washed with water and saturated brine, dried over anhydrous sodium sulfate and filtered. The solvent was evaporated under reduced pressure. The residue was purified by silica gel column chromatography (chloroform:methanol=100:0-97:3) to give a crudely purified title compound (1.56 g) as a white powder. MS (ESI) m/z: 1000.7 [M+H]$^+$ (29-4) (2S,4R)-1-[(2S)-2-(2-{[4'-(6-amino-2,3,9-trimethyl-6H-thieno[3,2-f][1,2,4]triazolo[4,3-a][1,4]diazepin-4-yl)[1,1'-biphenyl]-4-yl]oxy}acetamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 29-4)

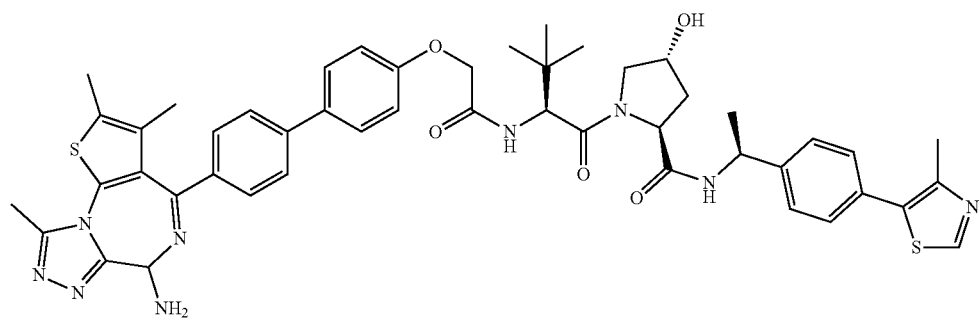 [SMILES: Cc1ncsc1-c1ccc([C@H](C)NC(=O)[C@@H]2C[C@@H](O)CN2C(=O)[C@@H](NC(=O)COc2ccc(-c3ccc(C4=NC(N)c5nnc(C)n5-c5sc(C)c(C)c54)cc3)cc2)C(C)(C)C)cc1]

To a solution of Example compound 29-3 (1.55 g) in dichloromethane (8 mL) was added at room temperature trifluoroacetic acid (8 mL), and the mixture was stirred at the same temperature for 1 hr. The reaction mixture was concentrated under reduced pressure, toluene was added to the residue and the mixture was concentrated again under reduced pressure. The residue was dissolved in methanol (10 mL), potassium carbonate was added at room temperature to alkalify the reaction mixture. After stirring at the same temperature for 5 min, saturated aqueous sodium hydrogen carbonate was added and the mixture was extracted twice with chloroform. The organic layers were mixed, dried over anhydrous sodium sulfate and filtered. The solvent was evaporated under reduced pressure. The residue was purified by silica gel column chromatography (chloroform:methanol=95:5-90:10) to give the title compound (1.24 g) as a white powder.

MS (ESI) m/z: 451.1[(M+2H)/2]$^+$ (29-5) methyl (4-{4'-[2-({(2S)-1-[(2S,4R)-4-hy-droxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)carbamate (Example Compound 29)

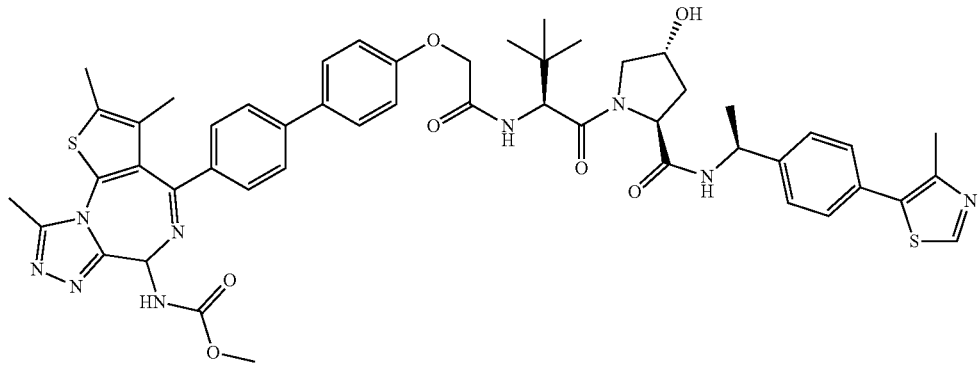

To a solution of Example compound 29-4 (630 mg) in dichloromethane (3.5 mL) were added N,N-diisopropylethylamine (0.18 mL) and methyl chloroformate (73 mg) at room temperature, and the mixture was stirred at the same temperature for 1 hr. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) to give the title compound (265 mg) as a white powder.
MS (ESI) m/z: 958.6 [M+H]$^+$ Example 30

(30-1) 4-(4-chlorophenyl)-2,3,9-trimethyl-6H-thieno[3,2-f] [1,2,4]triazolo[4,3-a][1,4]diazepin-6-ol (Example Compound 30-1)

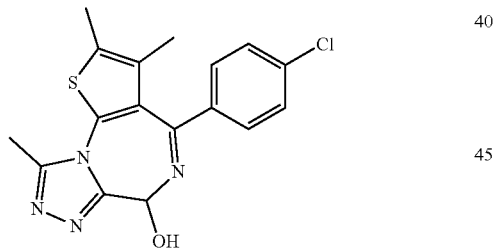

To a suspension of ethyl (6-amino-4-(4-chlorophenyl)-2,3,9-trimethyl-6H-thieno[3,2-f][1,2,4]triazolo[4,3-a] [1,4]diazepin-6-yl)carboxylate (4.0 g) (described in JP-A-7-17941, Starting Material Preparation Example 1) in ethanol (60 mL), water (20 mL) was added barium hydroxide (19.1 g) at room temperature, and the mixture was stirred at same temperature for 3 hr. At room temperature, concentrated hydrochloric acid was added to the reaction mixture to adjust to pH=1-2 and the mixture was stirred for 30 min. The reaction mixture was diluted with chloroform (100 mL), saturated aqueous sodium hydrogen carbonate (150 mL) was added and the mixture was stirred at the same temperature for 10 min. The insoluble material was filtered off, and the filtrate was partitioned. The aqueous layer was extracted with chloroform (100 mL), the mixed organic layer was dried over anhydrous sodium sulfate and filtered. The solvent was evaporated under reduced pressure. The residue was purified by NH silica gel column chromatography (chloroform:methanol=97:3) to give the title compound (527 mg) as a white solid. MS (ESI) m/z: 359.2 [M+H]$^+$ (30-2) (2S,4R)-4-hydroxy-1-[(2S)-2-(2-{[4'-(6-hydroxy-2,3,9-trimethyl-6H-thieno[3,2-f][1,2,4]triazolo[4,3-a][1,4]diazepin-4-yl)[1,1'-biphenyl]-4-yl]oxy}acetamido)-3,3-dimethylbutanoyl]-N-{(1S)-1-[4-(4-methyl-1,3-thiazol-5-yl)phenyl]ethyl}pyrrolidine-2-carboxamide (Example Compound 30)

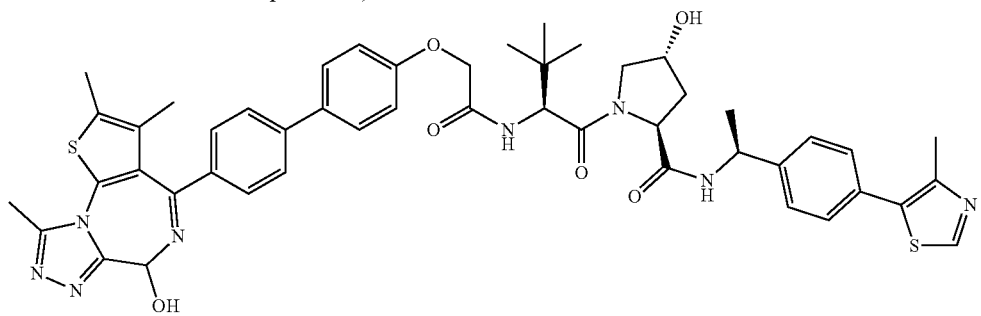

To a mixture of compound 30-1 (50 mg), Reference Example compound 9 (108 mg) and 2-dicyclohexylphosphino-2',4',6'-triisopropylbiphenyl aminobiphenyl palladium chloride precatalyst (11 mg) were added 1,4-dioxane (1.4 mL) and 2 M aqueous cesium carbonate solution (0.21 mL). After nitrogen substitution, under microwave irradiation, the mixture was stirred with heating at 120° C. for 1 hr. Water was added to the reaction mixture, and the mixture was extracted 3 times with chloroform, and the extract was dried over anhydrous sodium sulfate and filtered. The solvent was evaporated under reduced pressure. The residue was purified by silica gel column chromatography (chloroform:methanol=100:0-95:5) and NH silica gel column chromatography (chloroform:methanol=100:0-97:3) to give the title compound (14 mg) as a white powder.

MS (ESI) m/z: 901.5 [M+H]$^+$

Example 31 and Example 32

(31-1) and (32-1) methyl [(6R)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]carbamate, methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]carbamate)

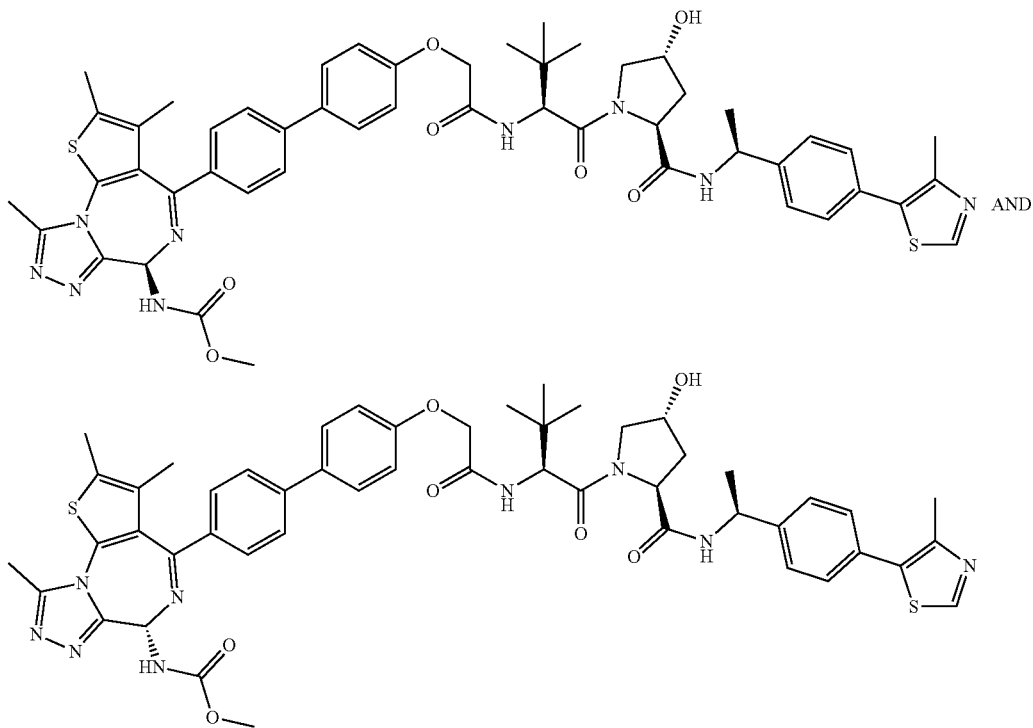

Example compound 29 (250 mg) was resolved by chiral column [CHIRALPAK ID (30×250 mm), methanol:tetrahydrofuran:normal butylamine=70:30:0.5] and the fraction was purified by silica gel column chromatography (chloroform:methanol=100:0-97:3) to give both the title compounds (compound having shorter retention time, 105 mg (MS (ESI) m/z: 958.8 [M+H]+, Example compound 31) and compound having longer retention time, 105 mg (MS (ESI) m/z: 958.8 [M+H]+, Example compound 32)) as white solids.

Example 33

(33-1) t-butyl ({4'-[(6S)-2,3,6,9-tetramethyl-6H-thieno[3,2-f] [1,2,4]triazolo[4,3-a][1,4]diazepin-4-yl][1,1'-biphenyl]-4-yl}oxy)acetate (Example Compound 33-1)

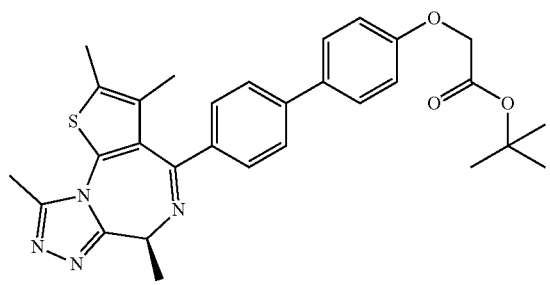 [SMILES: Cc1sc2c(c1C)C(c1ccc(-c3ccc(OCC(=O)OC(C)(C)C)cc3)cc1)=N[C@@H](C)c1nnc(C)n1-2]

To a mixture of Reference Example compound 4 (300 mg), Reference Example compound 8 (300 mg) and 2-dicyclohexylphosphino-2',4',6'-triisopropylbiphenyl aminobiphenyl palladium chloride precatalyst (30 mg) were added 1,4-dioxane (3.8 mL) and 2 M aqueous cesium carbonate solution (1.1 mL). After nitrogen substitution, under microwave irradiation, the mixture was stirred with heating at 120° C. for 20 min. Water was added to the reaction mixture, and the mixture was extracted twice with ethyl acetate. The insoluble material was filtered off through diatomaceous earth-activated carbon, and the filtration residue was washed with ethyl acetate. The filtrate was concentrated under reduced pressure, and the residue was purified by silica gel column chromatography (chloroform:methanol=100:0-97:3) to give the title compound (340 mg) as a pale-yellow powder.

MS (ESI) m/z: 529.4 [M+H]+

(33-2) (2S,4R)-1-{(2S)-3,3-dimethyl-2-[2-({4'-[(6S)-2,3,6,9-tetramethyl-6H-thieno[3,2-f][1,2,4] triazolo[4,3-a] [1,4] diazepin-4-yl][1,1'-biphenyl]-4-yl}oxy)acetamido]butanoyl}-4-hydroxy-N-{(1S)-1-[4-(4-methyl-1,3-thiazol-5-yl)phenyl] ethyl}pyrrolidine-2-carboxamide (Example Compound 33)

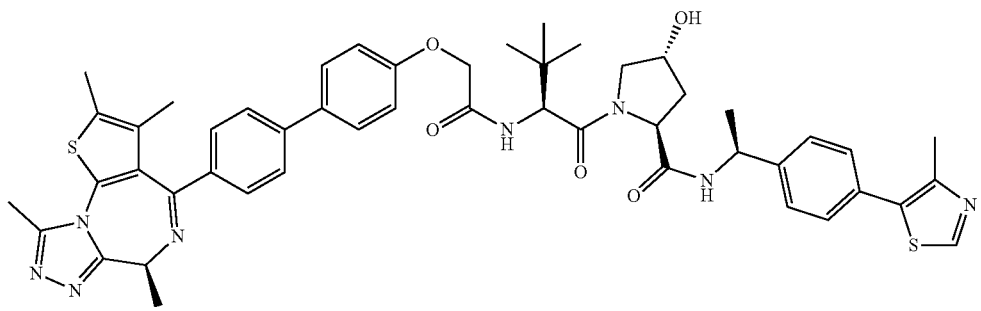 [SMILES: Cc1ncsc1-c1ccc([C@H](C)NC(=O)[C@@H]2C[C@@H](O)CN2C(=O)[C@@H](NC(=O)COc2ccc(-c3ccc(C4=N[C@@H](C)c5nnc(C)n5-c5sc(C)c(C)c54)cc3)cc2)C(C)(C)C)cc1]

To a solution of Example compound 33-1 (335 mg) in dichloromethane (2 mL) was added at room temperature trifluoroacetic acid (2 mL), and the mixture was stirred at the same temperature for 1 hr. The reaction mixture was concentrated under reduced pressure, and toluene was added to the residue. The solvent was evaporated under reduced pressure, the obtained residue was dissolved in Reference Example compound 5 (366 mg) and N,N-dimethylformamide (6.4 mL) at room temperature, N,N-diisopropylethylamine (1.1 mL) and HATU (338 mg) were added at the same temperature, and the mixture was stirred at the same temperature for 30 min. Water was added to the reaction mixture, and the mixture was extracted twice with ethyl acetate, and the extract was washed with saturated aqueous sodium hydrogen carbonate, water and saturated brine, dried over anhydrous sodium sulfate and filtered. The solvent was evaporated under reduced pressure. The residue was purified by silica gel column chromatography (chloroform:methanol=100:0-97:3, precolumn:NH silica gel) and the obtained solid was suspension washed with diethyl ether and collected by filtration to give the title compound (391 mg) as a white powder. MS (ESI) m/z: 899.7 [M+H]+

Example 34

(34-1) (2S,4R)-1-[(2S)-2-(2-{[4'-(6-acetamido-2,3,9-trimethyl-6H-thieno[3,2-f][1,2,4]triazolo[4,3-a][1,4]diazepin-4-yl) [1,1'-biphenyl]-4-yl]oxy}acetamido)-3,3-dimethylbutanoyl]-4-hydroxy-N-{(1S)-1-[4-(4-methyl-1,3-thiazol-5-yl) phenyl] ethyl}pyrrolidine-2-carboxamide (Example Compound 34)

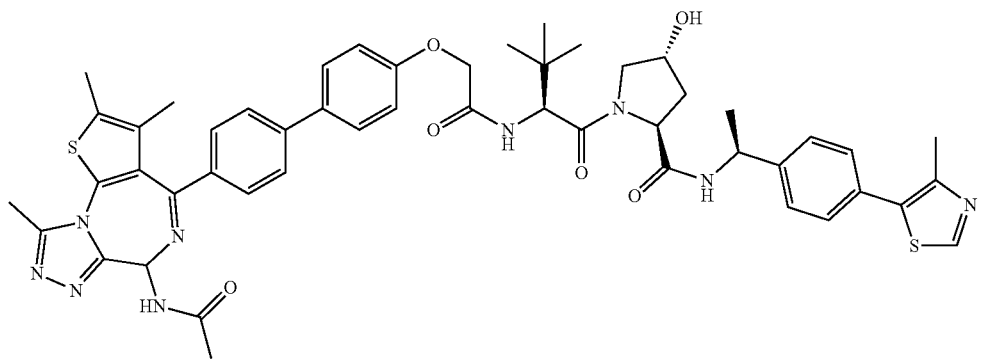 [SMILES: CC(=O)NC1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 29-4 (40 mg) in dichloromethane (1 mL) were added at room temperature N,N-diisopropylethylamine (0.012 mL) and acetic anhydride (0.007 mL), and the mixture was stirred at the same temperature for 1 hr. Water was added to the reaction mixture, and the mixture was extracted twice with chloroform. The organic layer was mixed, dried over anhydrous sodium sulfate and filtered. The solvent was evaporated under reduced pressure. The residue was purified by silica gel column chromatography (chloroform:methanol=100:0-97:3) to give the title compound (24 mg) as a white powder. MS (ESI) m/z: 472.1[(M+2H)/2]$^+$

Example 35

(35-1) methyl [4-(4-chlorophenyl)-2,3,9-trimethyl-6H-thieno[3,2-f][1,2,4]triazolo[4,3-a][1,4]diazepin-6-yl]carbamate (Example Compound 35-1)

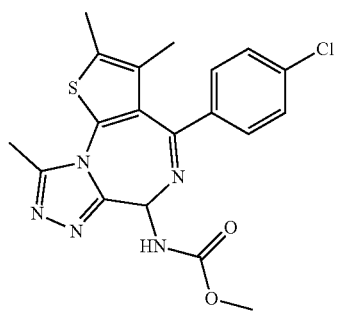 [SMILES: COC(=O)NC1N=C(c2ccc(Cl)cc2)c2c(sc(C)c2C)-n2c(C)nnc21]

To a solution of 6-amino-4-(4-chlorophenyl)-2,3,9-trimethyl-6H-thieno[3,2-f][1,2,4]triazolo[4,3-a][1,4]diazepine (200 mg) (described in JP-A-7-17941, Starting Material Preparation Example 1) in dichloromethane (6 mL) were added at 0° C. N,N-diisopropylethylamine (0.15 mL) and methyl chloroformate (0.05 mL), and the mixture was stirred at the same temperature for 30 min. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) to give the title compound (233 mg) as a pale-orange powder. MS (ESI) m/z: 416.3 [M+H]$^+$ (35-2) methyl [4-(4-chlorophenyl)-2,3,9-trimethyl-6H-thieno[3,2-f][1,2,4]triazolo[4,3-a][1,4]diazepin-6-yl]methylcarbamate (Example Compound 35-2)

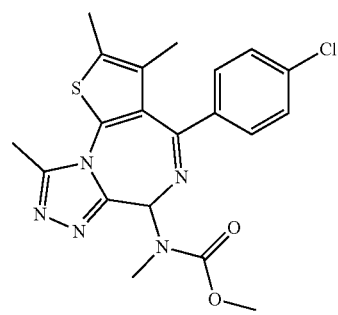 [SMILES: COC(=O)N(C)C1N=C(c2ccc(Cl)cc2)c2c(sc(C)c2C)-n2c(C)nnc21]

To a solution of Example compound 35-1 (230 mg) in N,N-dimethylformamide (5.5 mL) was added at room temperature sodium hydride (45 mg, 60%, dispersion in liquid paraffin) and the mixture was stirred for 5 min. Methyl iodide (0.069 mL) was added and the mixture was stirred at the same temperature for 2 hr. To the reaction mixture was added saturated aqueous ammonium chloride solution, and the mixture was extracted twice with ethyl acetate, and the extract was washed with water and saturated brine, dried over anhydrous sodium sulfate and filtered. The solvent was evaporated under reduced pressure. The residue was purified by silica gel column chromatography (chloroform:methanol=100:0-97:3, precolumn:NH silica gel) to give the title compound (137 mg) as a pale-yellow powder.

MS (ESI) m/z: 430.3 [M+H]$^+$ (35-3) methyl (4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)methylcarbamate (Example Compound 35)

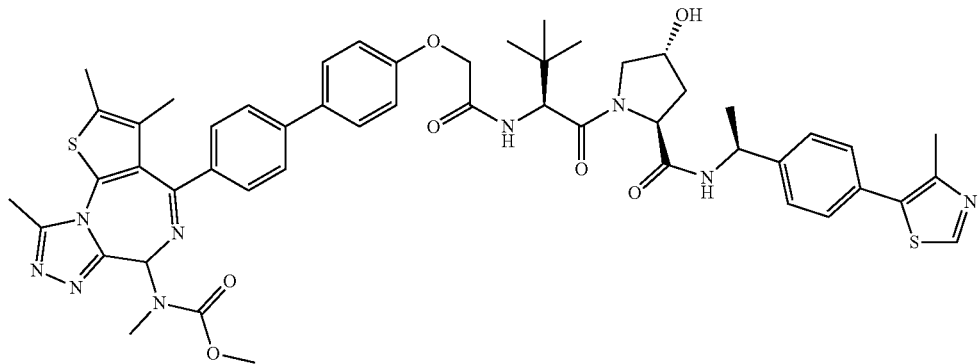 [SMILES: COC(=O)N(C)C1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a mixture of Example compound 35-2 (60 mg), Reference Example compound 9 (108 mg) and 2-dicyclohexylphosphino-2',4',6'-triisopropylbiphenyl aminobiphenyl palladium chloride precatalyst (11 mg) were added 1,4-dioxane (1.4 mL) and 2 M aqueous cesium carbonate solution (0.21 mL). After nitrogen substitution, under microwave irradiation, the mixture was stirred with heating at 150° C. for 30 min. Water was added to the reaction mixture, the mixture was extracted 4 times with ethyl acetate, the organic layers were combined, and the insoluble material was filtered off through diatomaceous earth-activated carbon. The filtrate was dried over anhydrous sodium sulfate and filtered. The solvent was evaporated under reduced pressure. To the residue were added 2-dicyclohexylphosphino-2',4',6'-triisopropylbiphenyl aminobiphenyl palladium chloride precatalyst (11 mg), 1,4-dioxane (1.4 mL) and 2 M aqueous cesium carbonate solution (0.21 mL). After nitrogen substitution, under microwave irradiation, the mixture was stirred with heating at 120° C. for 30 min. The reaction mixture was cooled to room temperature, 2-dicyclohexylphosphino-2',4',6'-triisopropylbiphenyl aminobiphenyl palladium chloride precatalyst (11 mg) and 2 M aqueous cesium carbonate solution (0.21 mL) were added. After nitrogen substitution, under microwave irradiation, the mixture was stirred again with heating at 150° C. for 30 min. Water was added to the reaction mixture, and the mixture was extracted 3 times with chloroform, and the extract was dried over anhydrous sodium sulfate and filtered. The solvent was evaporated under reduced pressure. The residue was purified by silica gel column chromatography (chloroform:methanol=100:0-97:3, precolumn:NH silica gel) and purified again by silica gel column chromatography (chloroform:methanol=100:0-90:10, precolumn:NH silica gel) to give the title compound (30 mg) as a pale-yellow powder.

MS (ESI) m/z: 972.7 [M+H]+

Example 36

(36-1) ethyl (4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)carbamate (Example Compound 36)

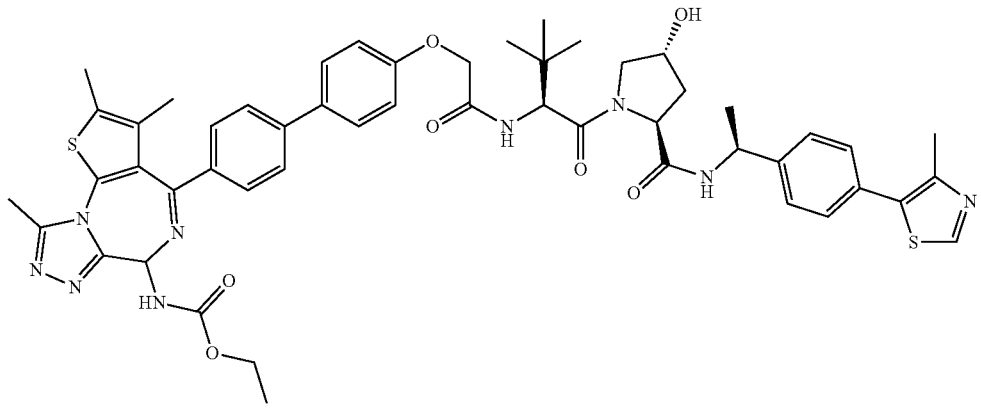 [SMILES: CCOC(=O)NC1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 29-4 (50 mg) in dichloromethane (2 mL) were added, under ice-cooling, N,N-diisopropylethylamine (0.015 mL) and ethyl chloroformate (0.006 mL), and the mixture was stirred at the same temperature for 30 min. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) to give the title compound (35 mg) as a white powder.
MS (ESI) m/z: 972.6 [M+H]$^+$ Example 37

(37-1) (2S,4R)-4-hydroxy-1-{(2S)-2-[2-({4'-[6-(2-methoxyacetamido)-2,3,9-trimethyl-6H-thieno[3,2-f][1,2,4]triazolo[4,3-a][1,4]diazepin-4-yl][1,1'-biphenyl]-4-yl}oxy)acetamido]-3,3-dimethylbutanoyl}-N-{(1S)-1-[4-(4-methyl-1,3-thiazol-5-yl)phenyl]ethyl}pyrrolidine-2-carboxamide (Example Compound 37)

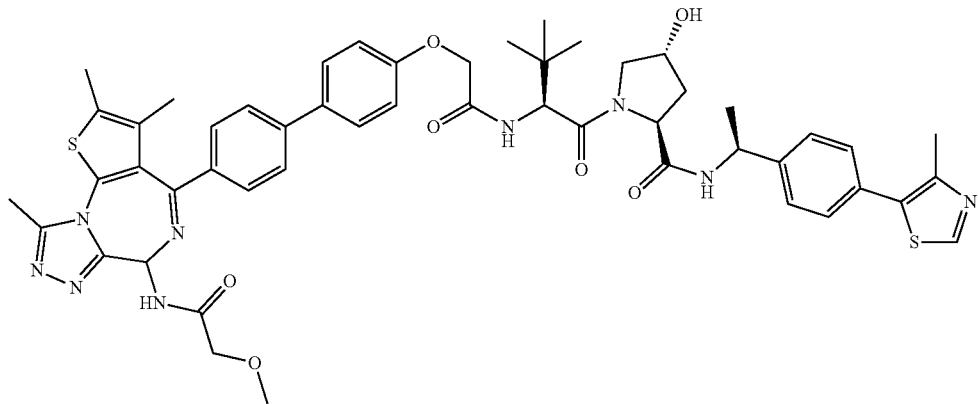 [SMILES: COCC(=O)NC1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 29-4 (50 mg) in dichloromethane (2 mL) were added, under ice-cooling, N,N-diisopropylethylamine (0.015 mL) and methoxyacetyl chloride (0.007 mL), and the mixture was stirred at the same temperature for 30 min. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) to give the title compound (39 mg) as a pale-yellow powder. MS (ESI) m/z: 487.1[(M+2H)/2]$^+$ Example 38

(38-1) (2S,4R)-1-[(2S)-2-{2-[(4'-{6-[(dimethylcarbamoyl)amino]-2,3,9-trimethyl-6H-thieno[3,2-f][1,2,4]triazolo[4,3-a][1,4]diazepin-4-yl}[1,1'-biphenyl]-4-yl)oxy]acetamido}-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 38)

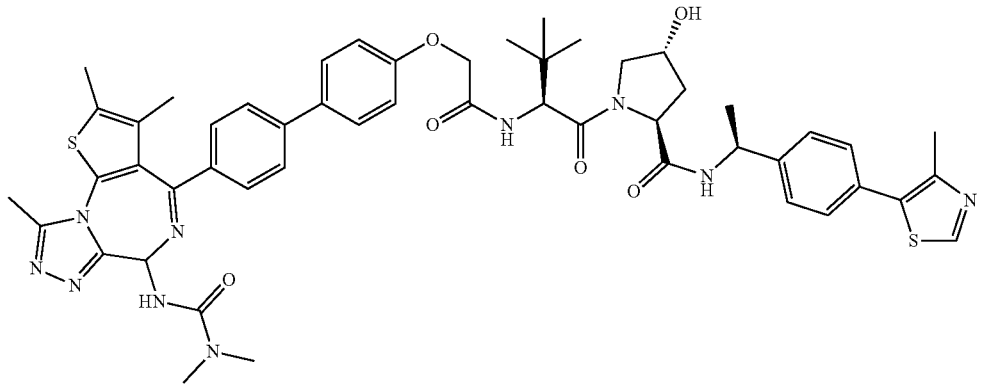 [SMILES: Cc1ncsc1-c1ccc([C@H](C)NC(=O)[C@@H]2C[C@@H](O)CN2C(=O)[C@@H](NC(=O)COc2ccc(-c3ccc(C4=NC(NC(=O)N(C)C)c5nnc(C)n5-c5sc(C)c(C)c54)cc3)cc2)C(C)(C)C)cc1]

To a solution of Example compound 29-4 (50 mg) in acetonitrile (2 mL) and chloroform (2 mL) were added at room temperature N,N-diisopropylethylamine (0.03 mL) and dimethylcarbamoyl chloride (0.01 mL), and the mixture was stirred at 60° C. for 3 hr. The reaction mixture was cooled to room temperature, N,N-diisopropylethylamine (0.10 mL) and dimethylcarbamoyl chloride (0.052 mL) were added, and the mixture was further stirred at 60° C. for 6 hr. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) to give the title compound (20 mg) as a white powder.

MS (ESI) m/z: 486.5[(M+2H)/2]$^+$

Example 39

(39-1) t-butyl [(4-bromophenyl)methoxy]acetate (Example compound 39-1)

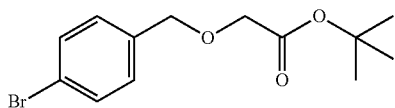

To a solution of 4-bromobenzyl alcohol (3.0 g) in N,N-dimethylformamide (100 mL) were added at room temperature cesium carbonate (5.7 g) and t-butyl bromoacetate (2.4 mL), and the mixture was stirred at the same temperature for 15 hr (white suspension). Saturated aqueous ammonium chloride solution and water were added to the reaction solution, and the mixture was extracted with ethyl acetate, and the extract was dried over anhydrous sodium sulfate and the solvent was evaporated under reduced pressure. The residue was purified by silica gel column chromatography (hexane:ethyl acetate=98:2-90:10) to give the title compound (3.62 g) as a colorless oil. $^1$H NMR (400 MHz, DMSO-d6) δppm 1.42 (9H, s), 4.03 (2H, s), 4.49 (2H, s), 7.30 (2H, d, J=7.3 Hz), 7.55 (2H, d, J=7.5 Hz)

(39-2) methyl [(6S)-4-{4'-[(2-t-butoxy-2-oxoethoxy)methyl] [1,1'-biphenyl]-4-yl}-2,3,9-trimethyl-6H-thieno[3,2-f][1,2,4]triazolo[4,3-a][1,4]diazepin-6-yl]acetate (Example Compound 39-2)

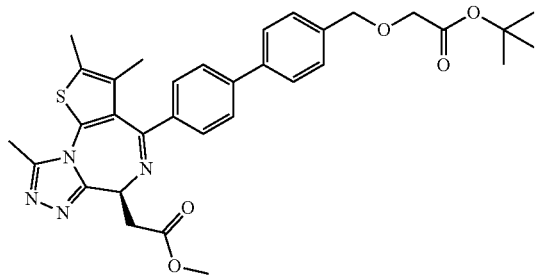 [SMILES: COC(=O)C[C@@H]1N=C(c2ccc(-c3ccc(COCC(=O)OC(C)(C)C)cc3)cc2)c2c(sc(C)c2C)-n2c(C)nnc21]

Reference Example compound 3 (500 mg) and Example compound 39-1 (357 mg) were dissolved in tetrahydrofuran (4.9 mL), palladium acetate (22 mg), S-phos (81 mg), potassium fluoride (172 mg) and water (0.062 mL) were added and the mixture was stirred at 85° C. for 86.5 hr. The insoluble material in the reaction solution was filtered off through diatomaceous earth, water was added to the filtrate, and the mixture was extracted with chloroform and the organic layer was dried over anhydrous sodium sulfate. The solvent was evaporated under reduced pressure. The residue was purified by silica gel column chromatography (chloroform:methanol=98:2-93:7) to give the title compound (404 mg) as a pale-yellow powder. MS (ESI) m/z: 601.5 [M+H]$^+$ (39-3) ({4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}methoxy)acetic acid trifluoroacetate (Example Compound 39-3)

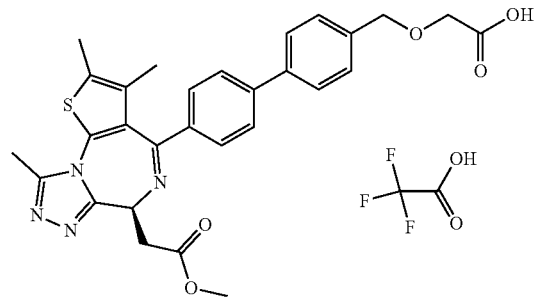 [SMILES: COC(=O)C[C@@H]1N=C(c2ccc(-c3ccc(COCC(=O)O)cc3)cc2)c2c(sc(C)c2C)-n2c(C)nnc21 ; O=C(O)C(F)(F)F]

To a solution of Example compound 39-2 (400 mg) in dichloromethane (2.0 mL) was added dropwise under ice-cooling trifluoroacetic acid (2.0 mL), and the mixture was allowed to naturally warm to room temperature and stirred for 17 hr. The reaction solution was diluted with ethyl acetate, and the solvent was evaporated under reduced pressure. The mixture was further azeotropically concentrated with toluene and the operation was performed twice to give the title compound (609 mg) as a crudely purified pale-yellow oil.

MS (ESI) m/z: 545.5 [M+H]$^+$ (39-4) methyl [(6S)-4-(4'-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]methyl}[1,1'-biphenyl]-4-yl)-2,3,9-trimethyl-6H-thieno[3,2-f][1,2,4]triazolo[4,3-a] [1,4]diazepin-6-yl]acetate (Example Compound 39)

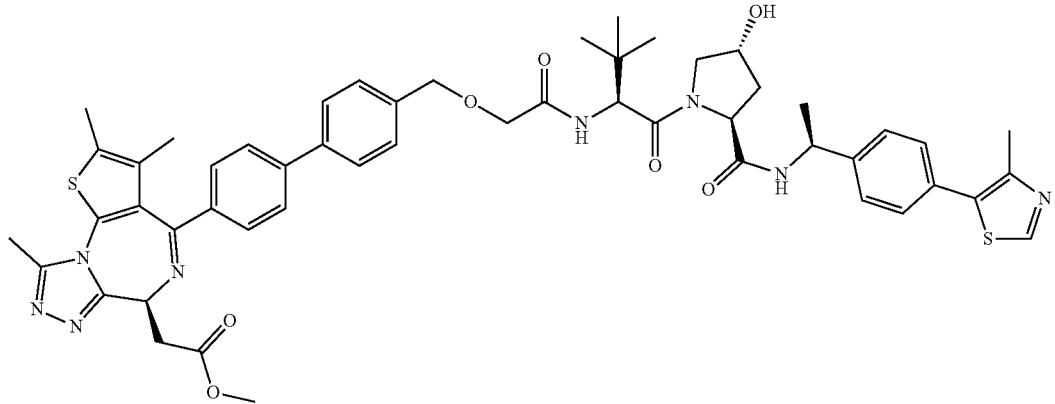 [SMILES: COC(=O)C[C@@H]1N=C(c2ccc(-c3ccc(COCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 39-3 (605 mg), Reference Example compound 5 (320 mg) in N,N-dimethylformamide (4.4 mL) was added N,N-diisopropylethylamine (0.691 mL), HATU (759 mg) was added under ice-cooling, and the mixture was allowed to naturally warm to room temperature and stirred for 15 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-95:5) (repurified with chloroform:methanol=100:0-96:4) to give the title compound (319 mg) as a pale-yellow solid. MS (ESI) m/z: 1015.8 [M+HCOO]⁻

Example 40

(40-1) methyl [(6S)-4-(3'-fluoro-4'-hydroxy[1,1'-biphenyl]-4-yl)-2,3,9-trimethyl-6H-thieno[3,2-f][1,2,4]triazolo[4,3-a] [1,4]diazepin-6-yl]acetate (Example Compound 40-1)

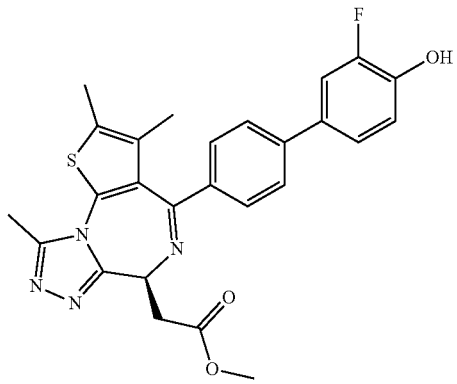 [SMILES: COC(=O)C[C@@H]1N=C(c2ccc(-c3ccc(O)c(F)c3)cc2)c2c(sc(C)c2C)-n2c(C)nnc21]

To a solution of Reference Example compound 1 (500 mg) in tetrahydrofuran (5.0 mL) were added bispinacolatoboron (459 mg), dichlorobis(tricyclohexylphosphine)palladium (89 mg) and potassium acetate (237 mg) and the mixture was stirred with heating at 85° C. for 4 hr. To the reaction solution was added dichlorobis(tricyclohexylphosphine)palladium (89 mg), and the mixture was further stirred with heating at 85° C. for 4 hr. To the reaction solution were added 4-bromo-2-fluorophenol (276 mg), palladium acetate (27 mg), S-phos (99 mg), potassium fluoride (210 mg) and water (0.076 mL) in one pot, and the mixture was stirred at 85° C. for 23 hr. The insoluble material in the reaction solution was filtered off through diatomaceous earth, water was added to the filtrate and the mixture was extracted with chloroform. The organic layer was dried over anhydrous sodium sulfate and the solvent was evaporated under reduced pressure. The residue was purified by silica gel column chromatography (chloroform:methanol=98:2-93:7) to give the title compound (576 mg) as a pale-yellow viscous compound.

MS (ESI) m/z: 491.4 [M+H]⁺

(40-2) methyl {(6S)-4-[4'-(2-t-butoxy-2-oxoethoxy)-3'-fluoro[1,1'-biphenyl]-4-yl]-2,3,9-trimethyl-6H-thieno[3,2-f] [1,2,4]triazolo[4,3-a][1,4]diazepin-6-yl}acetate (Example Compound 40-2)

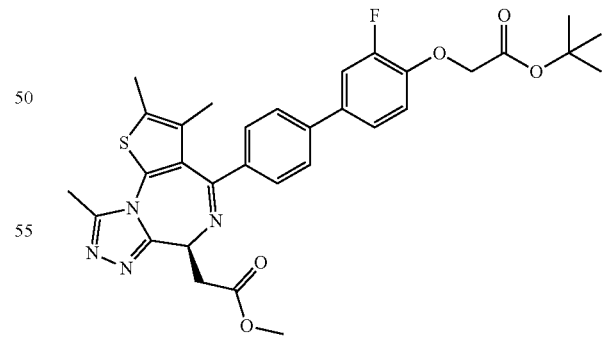

To a solution of Example compound 40-1 (574 mg) in N,N-dimethylformamide (5.9 mL) were added t-butyl bromoacetate (251 mg) and potassium carbonate (469 mg) and the mixture was stirred with heating at 60° C. for 30 min. Ice water was added to the reaction solution and the mixture was extracted with chloroform. The organic layer was washed with water and saturated brine, and dried over anhydrous sodium sulfate. The solvent was evaporated under reduced pressure. The residue was purified twice by silica gel column chromatography (chloroform:methanol=100:0-95:5) to give the title compound (293 mg) as a pale-brown viscous compound.
MS (ESI) m/z: 605.5 [M+H]+

(40-3) ({3-fluoro-4'-[(6S)-6-(2-methoxy-2-oxo-ethyl)-2,3,9-trimethyl-6H-thieno[3,2-f][1,2,4]tri-azolo[4,3-a][1,4]diazepin-4-yl][1,1'-biphenyl]-4-yl}oxy)acetic acid trifluoroacetate (Example Compound 40-3)

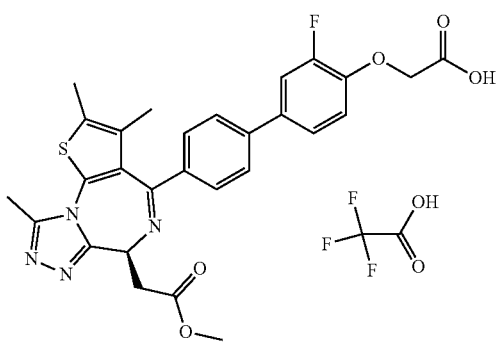 [SMILES: COC(=O)C[C@@H]1N=C(c2ccc(-c3ccc(OCC(=O)O)c(F)c3)cc2)c2c(sc(C)c2C)-n2c(C)nnc21 ; O=C(O)C(F)(F)F]

To a solution of Example compound 40-2 (290 mg) in dichloromethane (3.0 mL) was added dropwise under ice-cooling trifluoroacetic acid (3.0 mL), and the mixture was allowed to naturally warm to room temperature and stirred for 2 hr. The reaction solution was diluted with ethyl acetate, and the solvent was evaporated under reduced pressure, and the mixture was further concentrated azeotropically with toluene. This operation was performed two times to give the title compound (456 mg) as a pale-brown crudely purified oil.
MS (ESI) m/z: 549.4 [M+H]+

(40-4) methyl [(6S)-4-{3'-fluoro-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 40)

To a solution of Example compound 40-3 (456 mg), Reference Example compound 5 (320 mg) in N,N-dimethylformamide (4.5 mL) was added N,N-diisopropylethylamine (0.714 mL), then HATU (760 mg) was added under ice-cooling, and the mixture was allowed to naturally warm to room temperature and stirred for 15 hr. Water was added to the reaction solution and the mixture was extracted with chloroform, and the organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-96:4) to give the title compound (231 mg) as a pale-yellow solid. MS (ESI) m/z: 1019.8 [M+HCOO]−

Example 41

(41-1) methyl [(6S)-4-(2'-fluoro-4'-hydroxy[1,1'-biphenyl]-4-yl)-2,3,9-trimethyl-6H-thieno[3,2-f][1,2,4]triazolo[4,3-a][1,4]diazepin-6-yl]acetate (Example Compound 41-1)

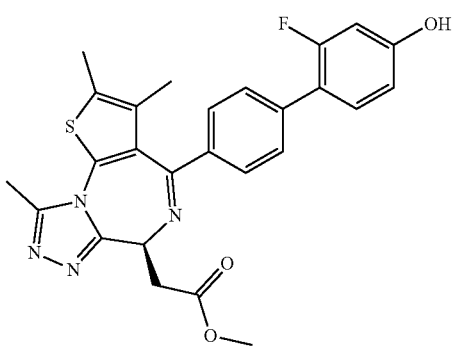

To a solution of Reference Example compound 1 (500 mg) in tetrahydrofuran (5.0 mL) were added bispinacolatoboron (459 mg), dichlorobis(tricyclohexylphosphine)palladium (89 mg) and potassium acetate (237 mg) and the mixture was stirred with heating at 85° C. for 4 hr. To the reaction solution was added dichlorobis(tricyclohexylphosphine)palladium (89 mg), and the mixture was further stirred with heating at 85° C. for 4 hr. To the reaction solution were added 4-bromo-3-fluorophenol (276 mg), palladium acetate

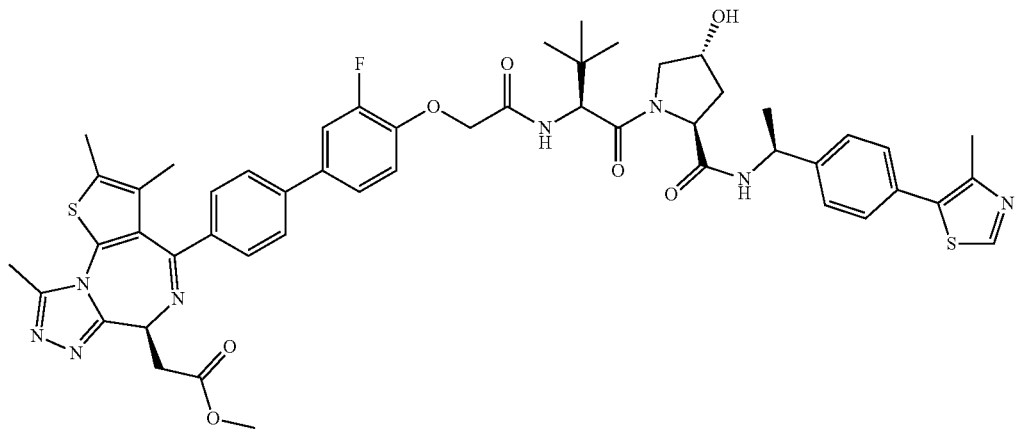 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(F)c3)cc2)c2c(sc(C)c2C)-n2c(C)nnc21]

(27 mg), S-phos (99 mg), potassium fluoride (210 mg) and water (0.076 mL) in one pot, and the mixture was stirred at 85° C. for 23 hr. The insoluble material in the reaction solution was filtered off through diatomaceous earth, water was added to the filtrate and the mixture was extracted with chloroform. The organic layer was dried over anhydrous sodium sulfate and the solvent was evaporated under reduced pressure. The residue was purified by silica gel column chromatography (chloroform:methanol=98:2-93:7) to give the title compound (720 mg) as a pale-yellow crudely purified viscous compound. MS (ESI) m/z: 491.4 [M+H]+

(41-2) methyl {(6S)-4-[4'-(2-t-butoxy-2-oxoethoxy)-2'-fluoro[1,1'-biphenyl]-4-yl]-2,3,9-trimethyl-6H-thieno[3,2-f] [1,2,4]triazolo[4,3-a][1,4]diazepin-6-yl}acetate (Example Compound 41-2)

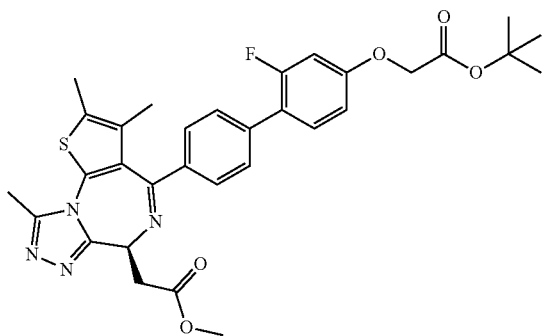 [SMILES: COC(=O)C[C@@H]1N=C(c2ccc(-c3ccc(OCC(=O)OC(C)(C)C)cc3F)cc2)c2c(sc(C)c2C)-n2c(C)nnc21]

To a solution of Example compound 41-1 (715 mg, crudely purified) in N,N-dimethylformamide (6.0 mL) were added t-butyl bromoacetate (259 mg) and potassium carbonate (333 mg) and the mixture was stirred with heating at 60° C. for 30 min. Ice water was added to the reaction solution and the mixture was extracted with chloroform. The organic layer was washed with water and saturated brine, and dried over anhydrous sodium sulfate. The solvent was evaporated under reduced pressure. The residue was purified by silica gel column chromatography twice (chloroform:methanol=100:0-95:5) to give the title compound (330 mg) as a pale-brown viscous compound.
MS (ESI) m/z: 605.5 [M+H]+

(41-3) ({2-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetic acid trifluoroacetate (Example Compound 41-3)

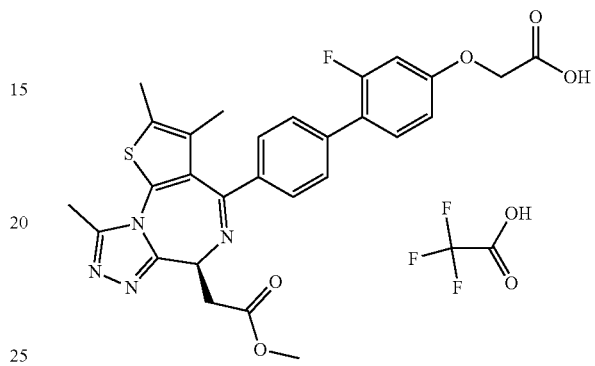

To a solution of Example compound 41-2 (325 mg) in dichloromethane (3.0 mL) was added dropwise under ice-cooling trifluoroacetic acid (3.0 mL), and the mixture was allowed to naturally warm to room temperature and stirred for 2 hr. The reaction solution was diluted with ethyl acetate, and the solvent was evaporated under reduced pressure. The residue was further concentrated azeotropically with toluene and this operation was performed two times to give the title compound (526 mg) as a pale-brown crudely purified oil.
MS (ESI) m/z: 549.4 [M+H]+

(41-4) methyl [(6S)-4-{2'-fluoro-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 41)

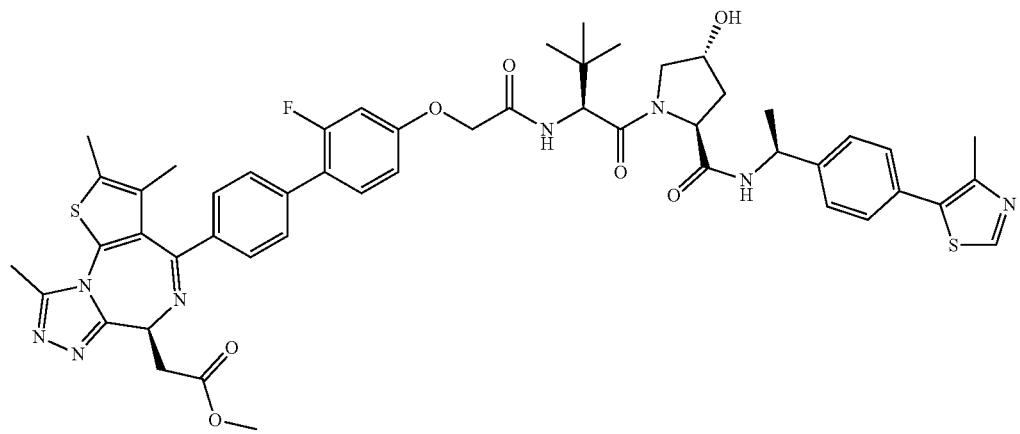 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3F)cc2)c2c(sc(C)c2C)-n2c(C)nnc21]

To a solution of Example compound 41-3 (526 mg), Reference Example compound 5 (382 mg) in N,N-dimethylformamide (5.3 mL) was added N,N-diisopropylethylamine (0.823 mL), and HATU (905 mg) was added under ice-cooling, and the mixture was allowed to naturally warm to room temperature and stirred for 15 hr. Water was added to the reaction solution and the mixture was extracted with chloroform, and the organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-96:4) to give the title compound (199 mg) as a yellow solid. MS (ESI) m/z: 1019.9 [M+HCOO]$^-$ Example 42

(42-1) (2S,4R)-1-[(2S)-2-{[5-(2-aminoethoxy)-1-benzofuran-2-carbonyl]amino}-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 42-1)

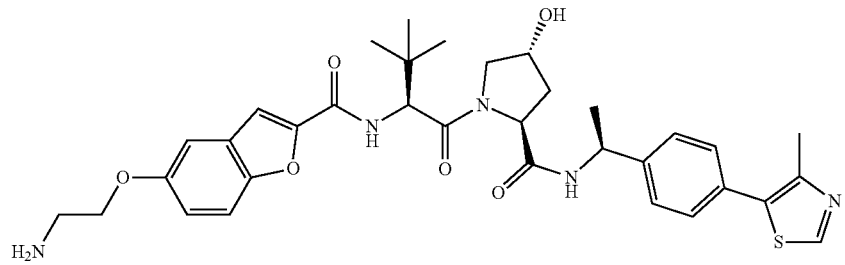 [SMILES: Cc1ncsc1-c1ccc([C@H](C)NC(=O)[C@@H]2C[C@@H](O)CN2C(=O)[C@@H](NC(=O)c2cc3cc(OCCN)ccc3o2)C(C)(C)C)cc1]

To a solution of Example compound 25-5 (560 mg) in dichloromethane (3.0 mL) was added, under ice-cooling, trifluoroacetic acid (3.0 mL), and the mixture was stirred at room temperature for 1.5 hr. The reaction mixture was diluted with dichloromethane, and the solvent was evaporated under reduced pressure. The residue was diluted with chloroform, saturated aqueous sodium hydrogen carbonate was added under ice-cooling and the mixture was stirred. After partitioning, the aqueous layer was extracted with chloroform again, and the organic layers were combined, dried over anhydrous sodium sulfate, filtered and the solvent was evaporated under reduced pressure to give the title compound (547 mg) as a pale-brown solid. MS (ESI) m/z: 648.7 [M+H]$^+$ (42-2) methyl [(6S)-4-(4-{3-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamoyl]pyrrolidin-1-yl}phenyl)-2,3,9-trimethyl-6H-thieno[3,2-f][1,2,4]triazolo[4,3-a][1,4]diazepin-6-yl]acetate (Example Compound 42)

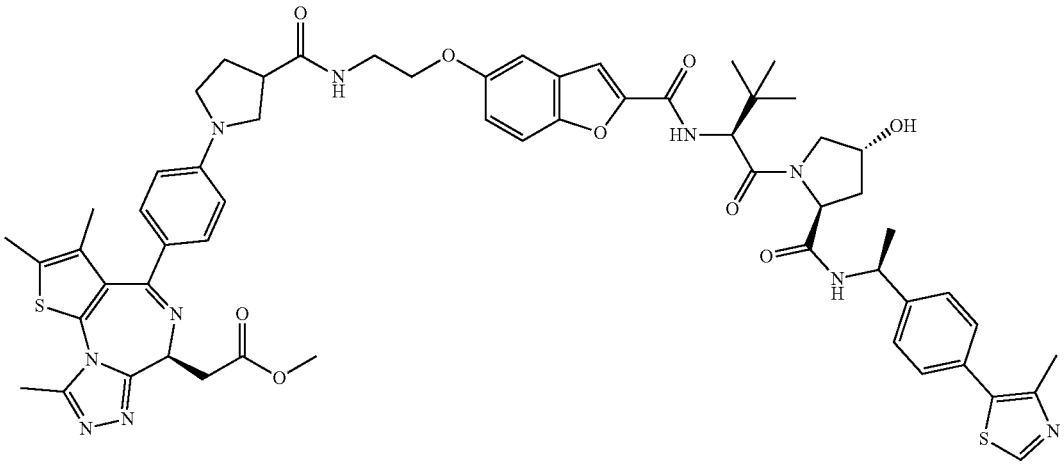

To a solution of Example compound 81-1 (205 mg) in dichloromethane (2.0 mL) was added, under ice-cooling, trifluoroacetic acid (2.0 mL), and the mixture was stirred at room temperature for 2 hr. The reaction mixture was diluted with dichloromethane, and the solvent was evaporated under reduced pressure. To the residue were added toluene and the mixture was concentrated under reduced pressure. This operation was performed twice. To a solution of the obtained residue, Example compound 42-1 (241 mg), N,N-dimethylformamide (3.7 mL), N,N-diisopropylethylamine (0.645 mL) was added, under ice-cooling, HATU (263 mg) and the mixture was stirred at room temperature for 2 hr. Under ice-cooling, to the reaction mixture was added saturated aqueous sodium hydrogen carbonate, and the mixture was extracted with chloroform, and the extract was washed with water, dried over anhydrous sodium sulfate and filtered. The solvent was evaporated under reduced pressure. The obtained residue was purified by silica gel chromatography (hexane:ethyl acetate=100:0-90:0) to give the title compound (263 mg) as an orange solid. MS (ESI) m/z: 1123.9 [M+H]⁻

Example 43

(43-1) methyl {(6S)-4-[4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 43)

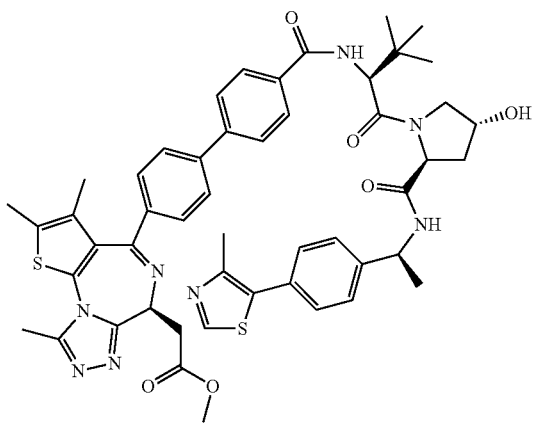 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

Reference Example compound 11 (350 mg) was dissolved in dichloromethane (3.5 mL), trifluoroacetic acid (3.5 mL) was added under ice-cooling, and the mixture was stirred at room temperature for 1.5 hr. The reaction mixture was diluted with dichloromethane and the solvent was evaporated under reduced pressure. Toluene was added to the residue and evaporated under reduced pressure twice. The residue was dried under reduced pressure to give a yellow solid (450 mg). The obtained solid (330 mg) was dissolved in N,N-dimethylformamide (5.4 mL), N,N-diisopropylethylamine (0.46 mL), Reference Example compound 5 (277 mg), HATU (308 mg) were added under ice-cooling and the mixture was stirred at room temperature for 17 hr. To the reaction mixture were added, under ice-cooling, saturated aqueous sodium hydrogen carbonate, water and the mixture was extracted twice with chloroform, and the organic layers were collected, washed with water, dried over anhydrous sodium sulfate, and the solvent was evaporated under reduced pressure. The residue was purified by silica gel column chromatography (chloroform:methanol=100:0-50:50). Successively, it was purified by preparative HPLC (10 mM aqueous ammonium carbonate solution-acetonitrile) twice. Furthermore, it was purified by NH silica gel column chromatography (ethyl acetate:methanol=100:0-85:15) and silica gel column chromatography (ethyl acetate:methanol=100:0-85:15) to give the title compound (122 mg) as a yellow-white solid.

MS (ESI) m/z: 927.5 [M+H]⁺

Example 44

(44-1) t-butyl [(pyrrolidin-3-yl)oxy]acetate (Example Compound 44-1)

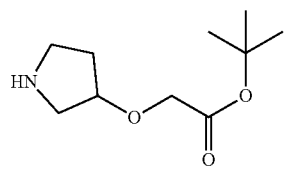

To a solution of N-(benzyloxycarbonyl)-3-hydroxypyrrolidine (1.0 g) in tetrahydrofuran (22.6 mL) was added, under ice-cooling, sodium hydride (60%, 199 mg) and the mixture was stirred for 30 min. t-Butyl bromoacetate (0.663 mL) was added and the mixture was stirred at room temperature for 2 hr. Sodium hydride (60%, 54 mg) and t-butyl bromoacetate (0.331 mL) were added and the mixture was further stirred for 4 hr. The reaction mixture was partitioned between ethyl acetate and ice water, and the aqueous layer was again extracted twice with ethyl acetate, and the organic layers were combined, dried over anhydrous sodium sulfate and filtered. The solvent was evaporated under reduced pressure. The obtained residue was purified by silica gel column chromatography (hexane:ethyl acetate=100:0-65:35) to give a pale-yellow oil (663 mg). To a solution of the obtained oil (660 mg) in ethanol (6.6 mL) was added 7.5% palladium carbon (PH, 120 mg) and the mixture was stirred under a hydrogen atmosphere at room temperature for 2 hr. To the reaction mixture was added ethanol and the mixture was passed through a syringe filter (chromatodisc) to remove palladium carbon and washed with ethanol, and the filtrate was concentrated to give the title compound (420 mg) as an unpurified orange solid. MS (ESI) m/z: 202.3 [M+H]⁺

(44-2) methyl [(6S)-4-{4-[3-(2-t-butoxy-2-oxoethoxy)pyrrolidin-1-yl]phenyl}-2,3,9-trimethyl-6H-thieno[3,2-f][1,2,4]triazolo[4,3-a][1,4]diazepin-6-yl]acetate (Example compound 44-2)

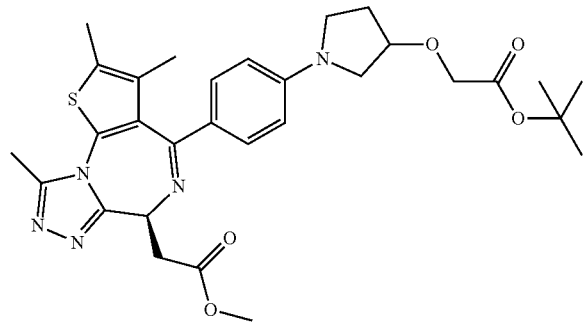 [SMILES: COC(=O)C[C@@H]1N=C(c2ccc(N3CCC(OCC(=O)OC(C)(C)C)C3)cc2)c2c(sc(C)c2C)-n2c(C)nnc21]

A mixture of Example compound 44-1 (175 mg), Reference Example compound 1 (300 mg), tris(dibenzylideneacetone)dipalladium(0) (33 mg), t-BuXphos (31 mg), potassium phosphate (460 mg) and tetrahydrofuran (7.2 mL) was stirred in a microwave reaction apparatus (Initiator, manufactured by Biotage) at 70° C. for 3 hr. Tris(dibenzylideneacetone)dipalladium(0) (33 mg) and t-BuXphos (31 mg) were added and the mixture was stirred at 70° C. for 3 hr. Tris(dibenzylideneacetone)dipalladium(0) (33 mg), t-BuXphos (31 mg), potassium phosphate (230 mg) were added and the mixture was further stirred at 70° C. for 3 hr. The mixture was stirred with heating under reflux for 18 hr in an oil bath. Water was added to the reaction mixture, and the mixture was extracted with chloroform, and the extract was dried over anhydrous sodium sulfate and filtered. The solvent was evaporated under reduced pressure. The obtained residue was purified by silica gel column chromatography (chloroform:methanol=100:0-93:7) to give the title compound (315 mg) as a crudely purified orange solid. MS (ESI) m/z: 580.5 [M+H]$^+$ (44-3) methyl [(6S)-4-(4-{3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyrrolidin-1-yl}phenyl)-2,3,9-trimethyl-6H-thieno[3,2-f][1,2,4]triazolo[4,3-a][1,4]diazepin-6-yl]acetate (Example Compound 44)

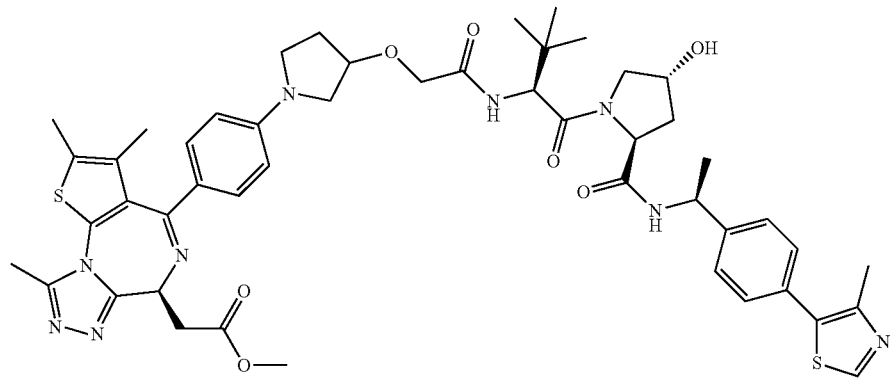 [SMILES: COC(=O)C[C@@H]1N=C(c2ccc(N3CCC(OCC(=O)N[C@H](C(=O)N4C[C@H](O)C[C@H]4C(=O)N[C@@H](C)c4ccc(-c5scnc5C)cc4)C(C)(C)C)C3)cc2)c2c(sc(C)c2C)-n2c(C)nnc21]

To a solution of Example compound 44-2 (315 mg) in dichloromethane (3.1 mL) was added, under ice-cooling, trifluoroacetic acid (3.1 mL), and the mixture was stirred at room temperature for 4 hr. The reaction mixture was concentrated, toluene was added to the residue, the mixture was concentrated under reduced pressure, and the residue was dried under reduced pressure. To a solution of the obtained residue, Reference Example compound 5 (288 mg), N,N-dimethylformamide (5.4 mL), N,N-diisopropylethylamine (0.940 mL) was added HATU (372 mg) under ice-cooling and the mixture was stirred at room temperature for 3 hr. Under ice-cooling, water was added to the reaction mixture, and the mixture was extracted with chloroform. The solvent was evaporated under reduced pressure. The obtained residue was diluted with chloroform, washed with water, dried over anhydrous sodium sulfate and filtered. The solvent was evaporated under reduced pressure. The obtained residue was purified by silica gel chromatography (ethyl acetate:methanol=100:0-95:5) to give the title compound (244 mg) as a yellow solid. MS (ESI) m/z: 950.8 [M+H]$^+$ Example 45

(45-1) methyl [(6S)-4-(4'-amino[1,1'-biphenyl]-4-yl)-2,3,9-trimethyl-6H-thieno[3,2-f][1,2,4]triazolo[4,3-a][1,4]diazepin-6-yl]acetate (Example Compound 45-1)

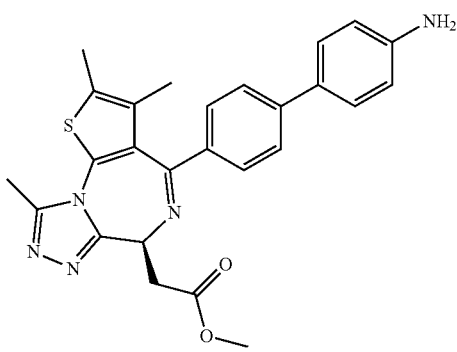 [SMILES: COC(=O)C[C@@H]1N=C(c2ccc(-c3ccc(N)cc3)cc2)c2c(sc(C)c2C)-n2c(C)nnc21]

To a solution of Reference Example compound 1 (500 mg) in tetrahydrofuran (4.0 mL) were added 4-(4,4,5,5-tetramethyl-1,3,2-dioxaborolan-2-yl)aniline (290 mg), palladium acetate (27 mg), S-phos (99 mg), potassium fluoride (210 mg) and water (0.076 mL) and the mixture was stirred at 85° C. for 16.5 hr. To the reaction solution were added 4-(4,4,5,5-tetramethyl-1,3,2-dioxaborolan-2-yl)aniline (264 mg), palladium acetate (27 mg), S-phos (99 mg) and the mixture was further stirred at 85° C. for 3 hr. The insoluble material in the reaction solution was filtered off through diatomaceous earth, water was added to the filtrate and the mixture was extracted with ethyl acetate. The organic layer was dried over anhydrous sodium sulfate. The solvent was evaporated under reduced pressure. The residue was purified by silica gel column chromatography (chloroform:methanol=99:1-95:5) to give the title compound (432 mg) as a pale-brown viscous compound.

MS (ESI) m/z: 472.4 [M+H]$^+$ (45-2) methyl [(6S)-4-{4'-[(2-t-butoxy-2-oxoethyl)amino][1,1'-biphenyl]-4-yl}-2,3,9-trimethyl-6H-thieno[3,2-f] [1,2,4]triazolo[4,3-a][1,4]diazepin-6-yl]acetate (Example Compound 45-2)

(45-3) ({4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}amino)acetic acid trifluoroacetate (Example Compound 45-3)

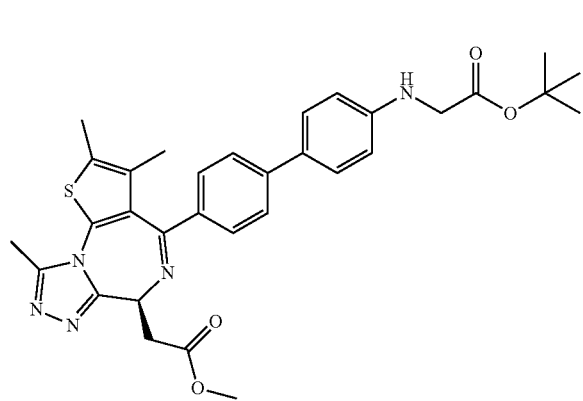 [SMILES: COC(=O)C[C@@H]1N=C(c2ccc(-c3ccc(NCC(=O)OC(C)(C)C)cc3)cc2)c2c(sc(C)c2C)-n2c(C)nnc21]

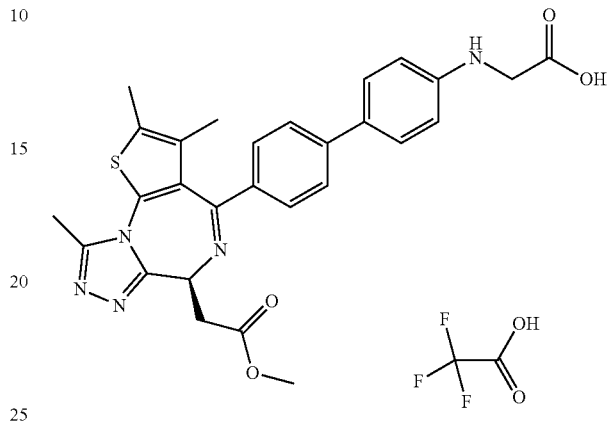

To a solution of Example compound 45-1 (430 mg) in N,N-dimethylformamide (0.92 mL) were added t-butyl bromoacetate (178 mg) and potassium carbonate (139 mg) and the mixture was stirred at room temperature for 28 hr. Ice water was added to the reaction solution and the mixture was extracted with ethyl acetate. The organic layer was washed with saturated brine and dried over anhydrous sodium sulfate. The solvent was evaporated under reduced pressure. The residue was purified by silica gel column chromatography (chloroform:methanol=100:0-96:4) to give the title compound (304 mg) as a red-brown solid.

MS (ESI) m/z: 586.5 [M+H]$^+$

To a solution of Example compound 45-2 (300 mg) in dichloromethane (1.0 mL) was added dropwise under ice-cooling trifluoroacetic acid (0.5 mL), and the mixture was allowed to naturally warm to room temperature and stirred for 8 hr. The reaction solution was diluted with ethyl acetate, the solvent was evaporated under reduced pressure, and the residue was further concentrated azeotropically with toluene. This operation was performed twice and the residue was dried by heating under reduced pressure to give the title compound (410 mg) as a red-brown crudely purified viscous compound.

MS (ESI) m/z: 530.4 [M+H]$^+$ (45-4) methyl [(6S)-4-(4'-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]amino}[1,1'-biphenyl]-4-yl)-2,3,9-trimethyl-6H-thieno[3,2-f] [1,2,4]triazolo[4,3-a] [1,4]diazepin-6-yl]acetate (Example Compound 45)

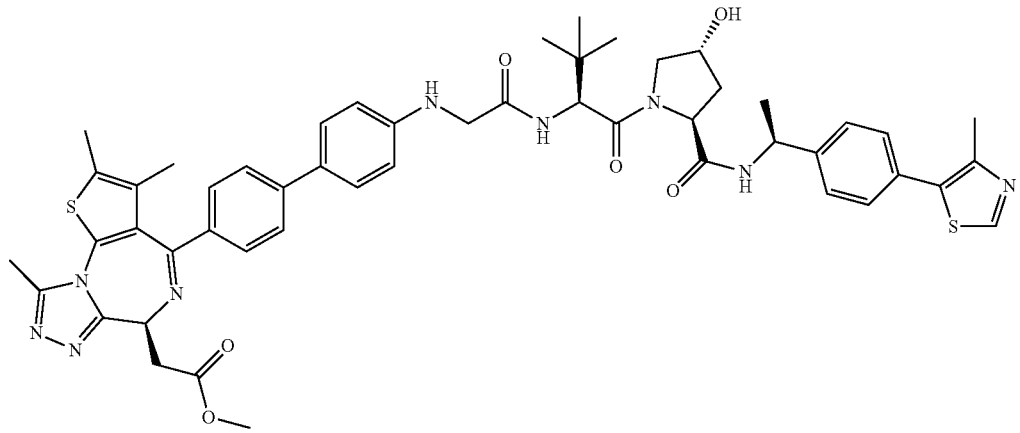 [SMILES: COC(=O)C[C@@H]1N=C(c2ccc(-c3ccc(NCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 45-3 (330 mg), Reference Example compound 5 (264 mg) in N,N-dimethylformamide (3.4 mL) was added N,N-diisopropylethylamine (0.886 mL), and HATU (584 mg) was added under ice-cooling, and the mixture was allowed to naturally warm to room temperature and stirred for 15 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-90:10-85:15) and further purified by silica gel column chromatography (chloroform:methanol=99:1-95:5). The obtained solid was suspension washed with diethyl ether, collected by filtration and dried under reduced pressure to give the title compound (113 mg) as an orange solid.

MS (ESI) m/z: 479.2[(M+2H)/2]$^+$

Example 46

(46-1) t-butyl (4-bromophenoxy)acetate (Example Compound 46-1)

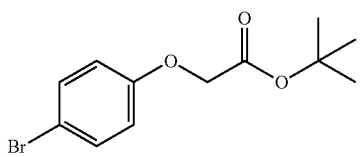 [SMILES: CC(C)(C)OC(=O)COc1ccc(Br)cc1]

To a solution of 4-bromophenol (3.0 g) in N,N-dimethylformamide (26 mL) was added cesium carbonate (6.21 g) and the mixture was stirred for 10 min. t-Butyl bromoacetate (3.43 g) was added dropwise over 5 min and the mixture was stirred at room temperature for 3 hr. To the reaction solution were added saturated aqueous ammonium chloride solution and water, and the mixture was extracted with ethyl acetate. The organic layer was washed with water and saturated brine, dried over anhydrous sodium sulfate and the solvent was evaporated under reduced pressure. The obtained residue was purified by silica gel column chromatography (hexane:ethyl acetate=98:2-93:7) to give the title compound (5.61 g) as colorless crudely purified liquid. $^1$H NMR (400 MHz, CDCl$_3$) δppm 1.48 (9H, s), 4.48 (2H, s), 6.75-6.78 (2H, m), 7.35-7.40 (2H, m)

(46-2) methyl [(6S)-4-{4-[4-(2-t-butoxy-2-oxoethoxy)anilino]phenyl}-2,3,9-trimethyl-6H-thieno[3,2-f][1,2,4]triazolo[4,3-a][1,4]diazepin-6-yl]acetate (Example Compound 46-2)

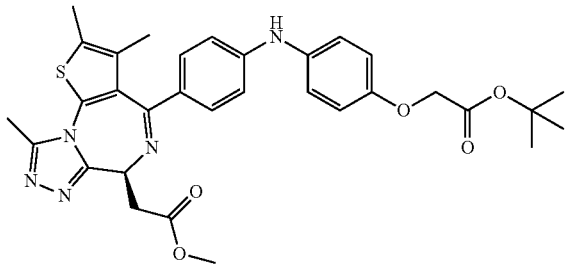 [SMILES: COC(=O)C[C@@H]1N=C(c2ccc(Nc3ccc(OCC(=O)OC(C)(C)C)cc3)cc2)c2c(sc(C)c2C)-n2c(C)nnc21]

To a solution of Reference Example compound 10 (150 mg) in tetrahydrofuran (3.8 mL) were added Example compound 46-1 (163 mg), palladium acetate (8.5 mg), t-BuXphos (32 mg) and tripotassium phosphate (242 mg) and the mixture was stirred at 70° C. for 66.5 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (hexane:ethyl acetate=99:1-95:5) to give the title compound (130 mg) as a pale-yellow crudely purified viscous compound.

MS (ESI) m/z: 602.5 [M+H]$^+$ (46-3) (4-{4-[(6S)-6-(2-methoxy-2-oxoethyl)-2,3,9-trimethyl-6H-thieno[3,2-f][1,2,4]triazolo[4,3-a][1,4]diazepin-4-yl]anilino}phenoxy)acetic acid trifluoroacetate (Example Compound 46-3)

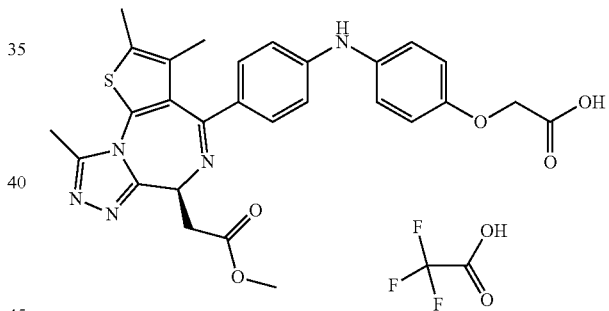

To a solution of Example compound 46-2 (125 mg) in dichloromethane (1.0 mL) was added dropwise under ice-cooling trifluoroacetic acid (0.5 mL), and the mixture was allowed to naturally warm to room temperature and stirred for 5 hr. The reaction solution was diluted with ethyl acetate, the solvent was evaporated under reduced pressure, and the residue was further concentrated azeotropically with toluene. This operation was performed twice and the residue was dried by heating under reduced pressure to give the title compound (207 mg) as a red-brown crudely purified viscous compound.

MS (ESI) m/z: 546.5 [M+H]$^+$

(46-4) methyl [(6S)-4-(4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]anilino}phenyl)-2,3,9-trimethyl-6H-thieno[3,2-f][1,2,4]triazolo[4,3-a][1,4]diazepin-6-yl]acetate (Example Compound 46)

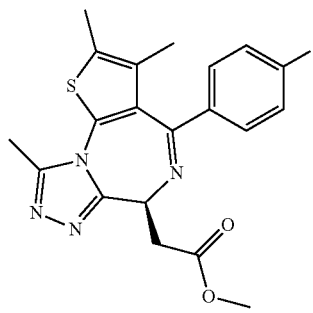
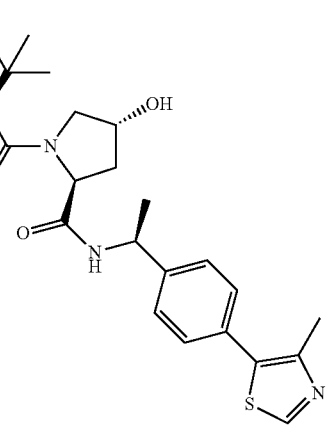

To a solution of Example compound 46-3 (200 mg), Reference Example compound 5 (150 mg) in N,N-dimethylformamide (2.1 mL) was added N,N-diisopropylethylamine (0.359 mL), and HATU (237 mg) was added under ice-cooling, and the mixture was allowed to naturally warm to room temperature and stirred for 18 hr. Water was added to the reaction solution and the mixture was extracted with chloroform, and the organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-90:10-85:15) and further purified by silica gel column chromatography (chloroform:methanol=99:1-95:5). The obtained solid was suspension washed with diethyl ether, collected by filtration and dried under reduced pressure to give the title compound (58 mg) as an orange solid. MS (ESI) m/z: 487.2[(M+2H)/2]$^+$

Example 47

(47-1) t-butyl (3-bromophenoxy)acetate (Example Compound 47-1)

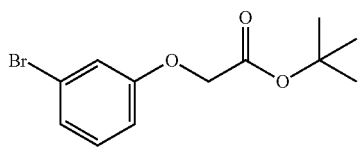 [SMILES: CC(C)(C)OC(=O)COc1cccc(Br)c1]

To a solution of 3-bromophenol (3.0 g) in N,N-dimethylformamide (25.9 mL) was added cesium carbonate (6.21 g) and the mixture was stirred for 10 min. t-Butyl bromoacetate (3.38 g) was added dropwise over 5 min, and the mixture was stirred at room temperature for 3 hr. To the reaction solution were added saturated aqueous ammonium chloride solution and water, and the mixture was extracted with ethyl acetate. The organic layer was washed with water and saturated brine, dried over anhydrous sodium sulfate and the solvent was evaporated under reduced pressure. The obtained residue was purified by silica gel column chromatography (hexane:ethyl acetate=98:2-93:7) to give the title compound (5.64 g) as a colorless crudely purified liquid. $^1$H NMR (400 MHz, CDCl$_3$) δppm 1.48 (9H, s), 4.94 (2H, s), 6.80-6.86 (1H, m), 7.03-7.07 (1H, m), 7.09-7.17 (2H, m)

(47-2) methyl [(6S)-4-{4-[3-(2-t-butoxy-2-oxoethoxy)anilino]phenyl}-2,3,9-trimethyl-6H-thieno[3,2-f] [1,2,4]triazolo[4,3-a][1,4]diazepin-6-yl]acetate (Example Compound 47-2)

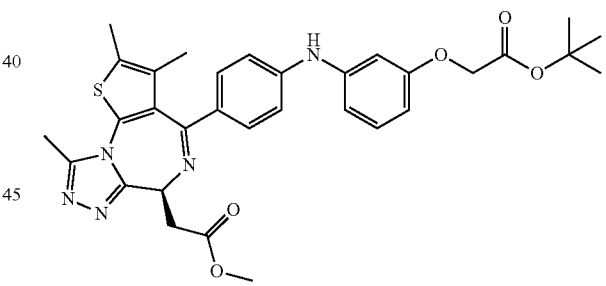

To a solution of Reference Example compound 10 (150 mg) in tetrahydrofuran (3.8 mL) was added tripotassium phosphate (242 mg) and the mixture was stirred for about 10 min. Example compound 47-1 (131 mg), palladium acetate (8.5 mg), t-BuXphos (32 mg) were added and the mixture was stirred at 70° C. for 66.5 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (hexane:ethyl acetate=99:1-95:5) to give the title compound (110 mg) as a pale-yellow viscous compound. MS (ESI) m/z: 602.5 [M+H]$^+$ (47-3) (3-{4-[(6S)-6-(2-methoxy-2-oxoethyl)-2,3,9-trimethyl-6H-thieno[3,2-f][1,2,4]triazolo[4,3-a][1,4]diazepin-4-yl]anilino}phenoxy)acetic acid trifluoroacetate (Example Compound 47-3)

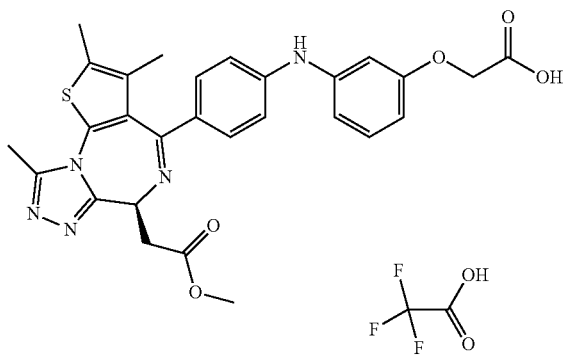 [SMILES: COC(=O)C[C@@H]1N=C(c2ccc(Nc3cccc(OCC(=O)O)c3)cc2)c2c(sc(C)c2C)-n2c(C)nnc21 ; O=C(O)C(F)(F)F]

To a solution of Example compound 47-2 (105 mg) in dichloromethane (1.0 mL) was added dropwise under ice-cooling trifluoroacetic acid (0.5 mL), and the mixture was allowed to naturally warm to room temperature and stirred for 5 hr. The reaction solution was diluted with ethyl acetate, the solvent was evaporated under reduced pressure, and the residue was further concentrated azeotropically with toluene. This operation was performed twice and the residue was dried by heating under reduced pressure to give the title compound (132 mg) as a red-brown crudely purified viscous compound.

MS (ESI) m/z: 546.5 [M+H]$^+$ (47-4) methyl [(6S)-4-(4-{3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]anilino}phenyl)-2,3,9-trimethyl-6H-thieno[3,2-f][1,2,4]triazolo[4,3-a][1,4]diazepin-6-yl]acetate (Example Compound 47)

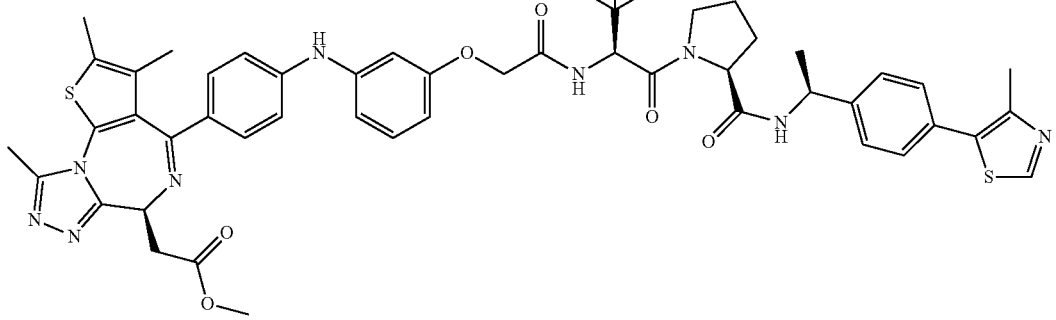

To a solution of Example compound 47-3 (125 mg), Reference Example compound 5 (84 mg) in N,N-dimethylformamide (1.8 mL) was added N,N-diisopropylethylamine (0.302 mL), and HATU (199 mg) was added under ice-cooling, and the mixture was allowed to naturally warm to room temperature and stirred for 18 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-90:10-85:15) and further purified by silica gel column chromatography (chloroform:methanol=99:1-95:5). The obtained solid was suspension washed with diethyl ether, collected by filtration and dried under reduced pressure to give the title compound (50 mg) as an orange solid.

MS (ESI) m/z: 487.2[(M+2H)/2]$^+$

Example 48

(48-1) (2S,4R)-1-{(2S)-2-[2-(4-bromophenyl)acetamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 48-1)

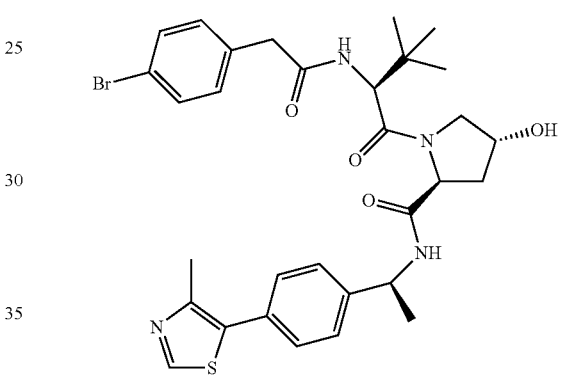

Reference Example compound 5 (400 mg), 2-(4-bromophenyl)acetic acid (220 mg) were dissolved in N,N-dimethylformamide (8.3 mL), and N,N-diisopropylethylamine (0.43 mL) and HATU (474 mg) were added under ice-cooling and the mixture was stirred for 10 min and at room temperature for 16 hr. To the reaction mixture were added saturated aqueous sodium hydrogen carbonate, water and the mixture was stirred. The mixture was extracted with chloroform, and the extract was washed twice with water. After drying over anhydrous sodium sulfate, the solvent was evaporated under reduced pressure, and the residue was (48-2) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl][1,1'-biphenyl]-4-yl}-2,3,9-trimethyl-6H-thieno[3,2-f][1,2,4]triazolo[4,3-a][1,4]diazepin-6-yl]acetate (Example Compound 48)

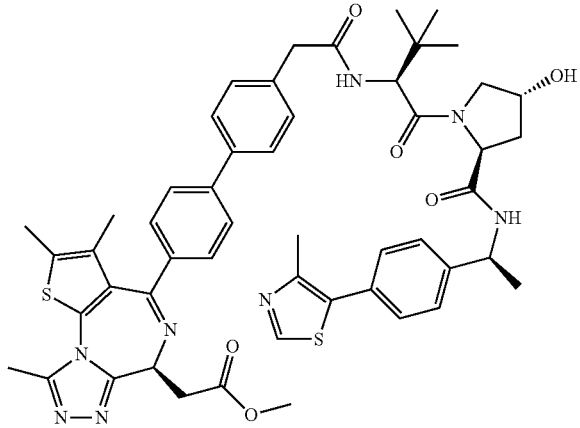 [SMILES: COC(=O)C[C@@H]1N=C(c2ccc(-c3ccc(CC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

Example compound 48-1 (400 mg) was dissolved in tetrahydrofuran (3.1 mL), Reference Example compound 3 (380 mg), palladium acetate (14 mg), S-phos (55 mg), potassium fluoride (110 mg) and water (40 μL) were added and the mixture was stirred at 75° C. for 16 hr. The reaction mixture was filtered through diatomaceous earth, chloroform and water were added to the filtrate, and the organic layer was extracted and washed with saturated brine, dried over anhydrous sodium sulfate, and the solvent was evaporated under reduced pressure. The residue was purified by silica gel column chromatography (chloroform:methanol=100:0-92:8), successively purified by NH silica gel column chromatography (chloroform:methanol=100:0-92:8) and silica gel column chromatography (chloroform:methanol=100:0-92:8) and purified by preparative HPLC (10 mM aqueous ammonium carbonate solution-acetonitrile). It was purified again by silica gel column chromatography (ethyl acetate:methanol=100:0-90:10) to give the title compound (148 mg) as a yellow-white solid.

MS (ESI) m/z: 941.8 [M+H]+

Example 49

(49-1) methyl [(6S)-4-(4'-hydroxy-2'-methyl[1,1'-biphenyl]-4-yl)-2,3,9-trimethyl-6H-thieno[3,2-f][1,2,4]triazolo[4,3-a] [1,4]diazepin-6-yl]acetate (Example Compound 49-1)

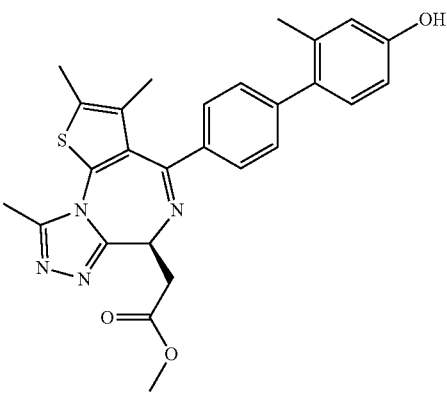 [SMILES: COC(=O)C[C@@H]1N=C(c2ccc(-c3ccc(O)cc3C)cc2)c2c(sc(C)c2C)-n2c(C)nnc21]

To a mixture of Reference Example compound 1 (500 mg), (4-hydroxy-2-methyl-phenyl)boronic acid (274 mg), potassium fluoride (210 mg), S-phos (99 mg) and palladium acetate (27 mg) were added tetrahydrofuran (4.0 mL) and water (78 μL) and the mixture was stirred at 70° C. for 110 hr. Tetrahydrofuran, ethyl acetate and water were added, the insoluble material was filtered through diatomaceous earth, and the filtrate was passed through a phase separator. The solvent was evaporated under reduced pressure. The residue was dissolved in tetrahydrofuran (4.0 mL), and (4-hydroxy-2-methyl-phenyl)boronic acid (274 mg), potassium fluoride (210 mg), S-phos (99 mg), palladium acetate (27 mg) were added and the mixture was stirred at 80° C. for 15 hr. The reaction mixture was filtered through diatomaceous earth, water was added to the filtrate and the mixture was extracted with chloroform, and the extract was dried over anhydrous sodium sulfate. The solvent was evaporated under reduced pressure. The residue was purified by silica gel column chromatography (chloroform:methanol=100:0-93:7) to give the title compound (560 mg) as a crudely purified brown solid.

MS (ESI) m/z: 487.4 [M+H]+

(49-2) methyl {(6S)-4-[4'-(2-t-butoxy-2-oxoethoxy)-2'-methyl[1,1'-biphenyl]-4-yl]-2,3,9-trimethyl-6H-thieno[3,2-f] [1,2,4]triazolo[4,3-a][1,4]diazepin-6-yl}acetate (Example compound 49-2)

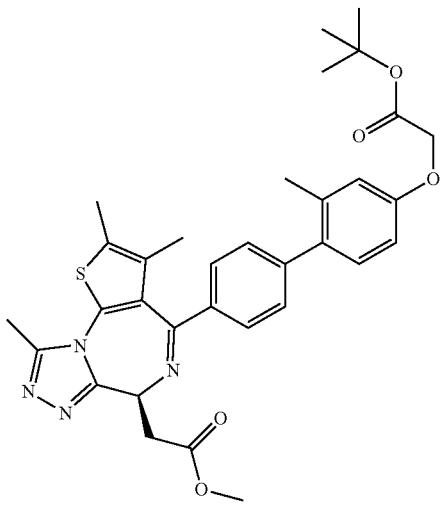 [SMILES: COC(=O)C[C@@H]1N=C(c2ccc(-c3ccc(OCC(=O)OC(C)(C)C)cc3C)cc2)c2c(sc(C)c2C)-n2c(C)nnc21]

Example compound 49-1 (560 mg) was dissolved in N,N-dimethylformamide (11.5 mL), t-butyl bromoacetate (0.26 mL) and potassium carbonate (318 mg) were added and the mixture was stirred at 60° C. for 1.5 hr. Furthermore, t-butyl bromoacetate (0.26 mL) was added and the mixture was stirred at 60° C. for 1.5 hr. To the reaction mixture was added ice water and the mixture was extracted with ethyl acetate, and the extract was washed with water and saturated brine, dried over anhydrous sodium sulfate, and the solvent was evaporated under reduced pressure. The residue was purified by silica gel column chromatography (chloroform:methanol=100:0-96:4) to give the title compound (435 mg) as a crudely purified brown solid.
MS (ESI) m/z: 601.5 [M+H]+

(49-3) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-2'-methyl[1,1'-biphenyl]-4-yl}-2,3,9-trimethyl-6H-thieno[3,2-f][1,2,4]triazolo[4,3-a] [1,4]diazepin-6-yl]acetate (Example Compound 49)

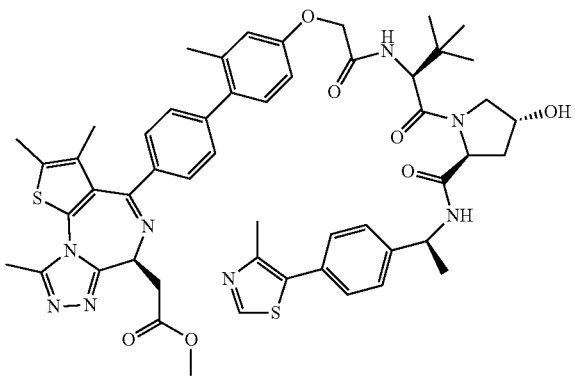 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3C)cc2)c2c(sc(C)c2C)-n2c(C)nnc21]

Example compound 49-2 (430 mg) was dissolved in dichloromethane (5.0 mL), trifluoroacetic acid (5.0 mL) was added under ice-cooling and the mixture was stirred at room temperature for 4 hr. The solvent was evaporated under reduced pressure. Toluene was added and the mixture was concentrated under reduced pressure, and this operation was performed twice. The residue was dissolved in N,N-dimethylformamide (14 mL), and N,N-diisopropylethylamine (0.93 mL), Reference Example compound 5 (516 mg), HATU (408 mg) were added under ice-cooling and the mixture was stirred at room temperature for 16 hr. To the reaction mixture was added ice water and the mixture was stirred. Saturated aqueous sodium hydrogen carbonate was added and the mixture was extracted with chloroform. The aqueous layer was extracted again with chloroform, and the organic layers were collected and washed twice with water. After drying over anhydrous sodium sulfate, the solvent was evaporated under reduced pressure. To the residue were added ethyl acetate:tetrahydrofuran=1:1, water and the organic layer was extracted. The organic layer was washed twice with water and washed with saturated brine. The aqueous layer was extracted again with ethyl acetate, and the extract was washed twice with water and washed with saturated brine. The earlier organic layer was combined and dried over anhydrous sodium sulfate. The solvent was evaporated under reduced pressure, and the residue was purified by NH silica gel column chromatography (ethyl acetate:methanol=100:0-85:15), silica gel column chromatography (ethyl acetate:methanol=100:0-85:15) to give the title compound (265 mg) as a yellow-white solid. MS (ESI) m/z: 971.5 [M+H]+

Example 50

(50-1) methyl [(6S)-4-(4'-hydroxy[1,1'-biphenyl]-4-yl)-2,3,9-trimethyl-6H-thieno[3,2-f][1,2,4]triazolo[4,3-a][1,4]diazepin-6-yl]acetate (Example Compound 50-1)

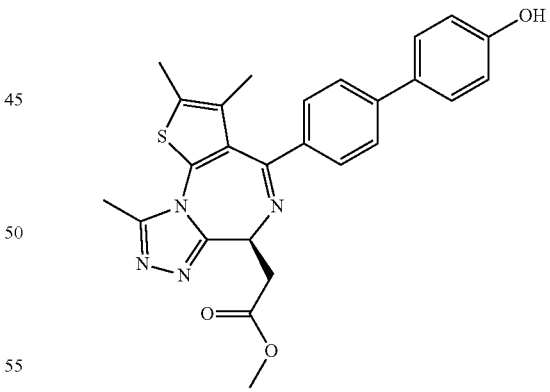

Reference Example compound 1 (2.00 g) was dissolved in tetrahydrofuran (16 mL), 4-(4,4,5,5-tetramethyl-1,3,2-dioxaborolan-2-yl)phenol (1.60 g), potassium fluoride (840 mg), S-phos (400 mg), palladium acetate (110 mg) and water (0.31 mL) were added and the mixture was stirred at 75° C. for 10 hr. Furthermore, 4-(4,4,5,5-tetramethyl-1,3,2-dioxaborolan-2-yl)phenol (800 mg), potassium fluoride (420 mg), S-phos (200 mg), palladium acetate (55 mg), water (0.31 mL) were added and the mixture was stirred at 75° C. for 15 hr. The reaction mixture was filtered through diatomaceous earth, water was added to the filtrate and the mixture was extracted with chloroform. The aqueous layer was extracted again with chloroform, and the organic layers were collected and dried over anhydrous sodium sulfate. The solvent was evaporated under reduced pressure. The residue was purified by silica gel column chromatography (chloroform:methanol=100:0-92:8) to give the title compound (2.60 g) as a crudely purified purple solid. MS (ESI) m/z: 473.4 [M+H]$^+$ (50-2) methyl [(6S)-4-(4'-{[1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]oxy}[1,1'-biphenyl]-4-yl)-2,3,9-trimethyl-6H-thieno[3,2-f][1,2,4]triazolo[4,3-a] [1,4]diazepin-6-yl] acetate (Example Compound 50)

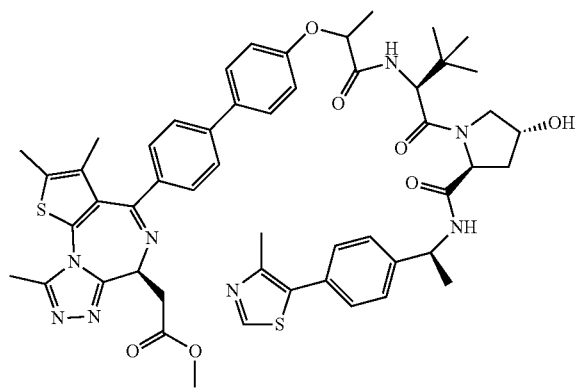 [SMILES: COC(=O)C[C@@H]1N=C(c2ccc(-c3ccc(OC(C)C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

By reaction and treatment in the same manner as in Example 52(52-2)-(52-3) and using t-butyl 2-bromopropionate instead of t-butyl bromoacetate, the title compound was obtained as a yellow-white solid. MS (ESI) m/z: 971.5 [M+H]$^+$ Example 51

(51-1) t-butyl [(3-bromophenyl)methoxy]acetate (Example Compound 51-1)

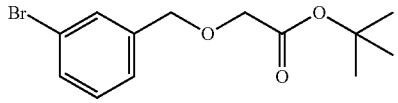 [SMILES: CC(C)(C)OC(=O)COCc1cccc(Br)c1]

To a solution of 3-bromobenzyl alcohol (3.0 g) in N,N-dimethylformamide (24.0 mL) was added at room temperature cesium carbonate (5.74 g), and t-butyl bromoacetate (2.4 mL) was added dropwise over 5 min, and the mixture was stirred at the same temperature for 24 hr. To the reaction solution were added saturated aqueous ammonium chloride solution and water, and the mixture was extracted with ethyl acetate, and the extract was dried over anhydrous sodium sulfate. The solvent was evaporated under reduced pressure. The residue was purified by silica gel column chromatography (hexane:ethyl acetate=99:1-95:5) to give the title compound (2.78 g) as a colorless liquid. $^1$H NMR (400 MHz, CDCl$_3$) δppm 1.49 (9H, s), 3.99 (2H, s), 4.58 (2H, s), 7.22 (1H, t, J=7.7 Hz), 7.29 (1H, d, J=7.7 Hz), 7.39 (1H, dt, J=1.5, 8.2 Hz), 7.54 (1H, m)

(51-2) methyl [(6S)-4-{3'-[(2-t-butoxy-2-oxoethoxy)methyl] [1,1'-biphenyl]-4-yl}-2,3,9-trimethyl-6H-thieno[3,2-f][1,2,4]triazolo[4,3-a][1,4]diazepin-6-yl] acetate (Example Compound 51-2)

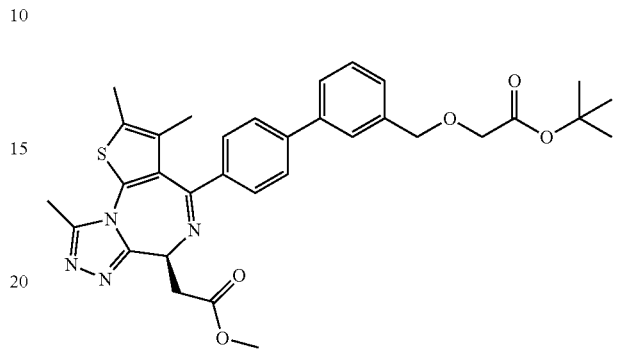

Reference Example compound 3 (800 mg) and Example compound 51-1 (464 mg) were dissolved in tetrahydrofuran (5.1 mL), palladium acetate (23 mg), S-phos (84 mg), potassium fluoride (179 mg) and water (0.065 mL) were added and the mixture was stirred at 70° C. for 6 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=98:2-90:10) to give the title compound (792 mg) as a yellow viscous compound.
MS (ESI) m/z: 601.5 [M+H]$^+$ (51-3) ({4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-3-yl}methoxy)acetic acid trifluoroacetate (Example Compound 51-3)

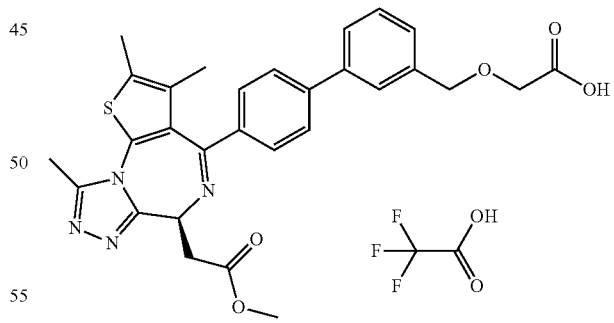

To a solution of Example compound 51-2 (785 mg) in dichloromethane (2.0 mL) was added dropwise under ice-cooling trifluoroacetic acid (2.0 mL), and the mixture was allowed to naturally warm to room temperature and stirred for 4 hr. The reaction solution was diluted with ethyl acetate, the solvent was evaporated under reduced pressure, and the residue was further concentrated azeotropically with toluene. This operation was performed two times to give the title compound (1.13 g) as a crudely purified orange oil.
MS (ESI) m/z: 545.5 [M+H]$^+$

(51-4) methyl [(6S)-4-(3'-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]methyl}[1,1'-biphenyl]-4-yl)-2,3,9-trimethyl-6H-thieno[3,2-f][1,2,4]triazolo[4,3-a] [1,4]diazepin-6-yl]acetate (Example Compound 51)

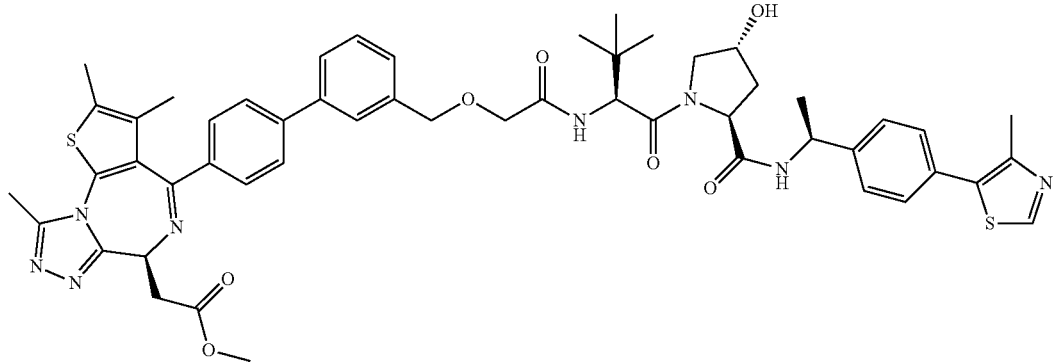 [SMILES: COC(=O)C[C@@H]1N=C(c2ccc(-c3cccc(COCC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 51-3 (1.13 g), Reference Example compound 5 (629 mg) in N,N-dimethylformamide (8.7 mL) was added N,N-diisopropylethylamine (0.905 mL), and HATU (994 mg) was added under ice-cooling, and the mixture was allowed to naturally warm to room temperature and stirred for 16 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=97:3-90:10-85:15) and further purified by silica gel column chromatography (chloroform:methanol=98:2-92:8). The obtained solid was suspension washed with diethyl ether, collected by filtration and dried under reduced pressure to give the title compound (501 mg) as a white solid.

MS (ESI) m/z: 971.8 [M+H]$^+$

Example 52

(52-1) methyl [(6S)-4-(2'-chloro-4'-hydroxy[1,1'-biphenyl]-4-yl)-2,3,9-trimethyl-6H-thieno[3,2-f][1,2,4]triazolo[4,3-a] [1,4]diazepin-6-yl]acetate (Example Compound 52-1)

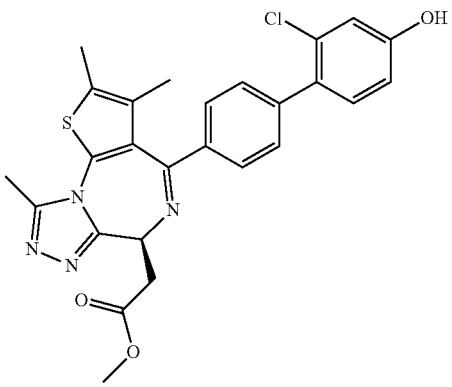 [SMILES: COC(=O)C[C@@H]1N=C(c2ccc(-c3ccc(O)cc3Cl)cc2)c2c(sc(C)c2C)-n2c(C)nnc21]

To a mixture of Reference Example compound 3 (400 mg), 4-bromo-3-chlorophenol (200 mg), potassium fluoride (139 mg), S-phos (66 mg) and palladium acetate (18 mg) in tetrahydrofuran (7.9 mL) was added water (51 μL), and the mixture was stirred at 75° C. for 8 hr. Water was added to the reaction mixture and the mixture was extracted twice with chloroform, and the organic layers were collected and washed with saturated brine, dried over anhydrous sodium sulfate, and the solvent was evaporated under reduced pressure. The residue was purified by silica gel column chromatography (ethyl acetate:methanol=100:0-90:10) to give a crudely purified title compound (283 mg) as a yellow-white solid. MS (ESI) m/z: 507.4 [M+H]$^+$

(52-2) methyl {(6S)-4-[4'-(2-t-butoxy-2-oxoethoxy)-2'-chloro[1,1'-biphenyl]-4-yl]-2,3,9-trimethyl-6H-thieno[3,2-f] [1,2,4]triazolo[4,3-a][1,4]diazepin-6-yl}acetate (Example Compound 52-2)

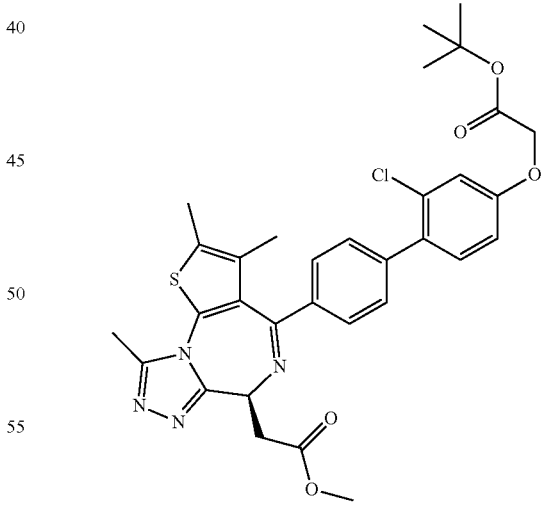

Example compound 52-1 (280 mg) was dissolved in N,N-dimethylformamide (5.5 mL), t-butyl bromoacetate (0.12 mL) and potassium carbonate (110 mg) were added and the mixture was stirred at 60° C. for 2 hr. To the reaction mixture was added ice water and the mixture was extracted with ethyl acetate, and the extract was washed twice with water, and washed with saturated brine. The aqueous layer was extracted again with ethyl acetate, and the extract was washed twice with water, washed with saturated brine, and the organic layers were collected and dried over anhydrous sodium sulfate. The solvent was evaporated under reduced pressure, and the residue was purified by silica gel column chromatography (chloroform:methanol=100:0-95:5) to give the title compound as a crudely purified orange oil (323 mg).

MS (ESI) m/z: 621.4 [M+H]+

(52-3) methyl [(6S)-4-{2'-chloro-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl] acetate (Example Compound 52)

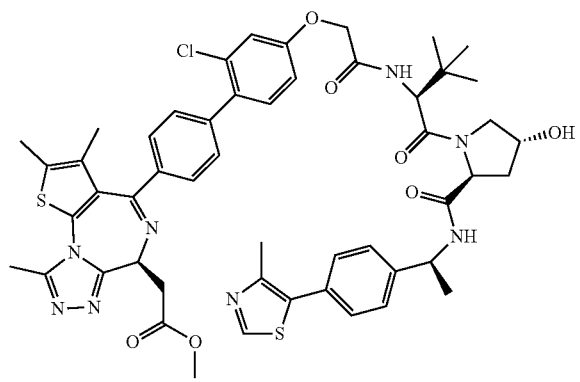 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3Cl)cc2)c2c(sc(C)c2C)-n2c(C)nnc21]

Example compound 52-2 (320 mg) was dissolved in dichloromethane (3.2 mL), trifluoroacetic acid (3.2 mL) was added under ice-cooling and the mixture was stirred at room temperature for 3 hr. To the reaction mixture was added toluene and toluene was evaporated under reduced pressure. This was repeated 3 times, and the mixture was dried under reduced pressure at 60° C. The residue was dissolved in N,N-dimethylformamide (10.3 mL), and N,N-diisopropylethylamine (0.45 mL), Reference Example compound 5 (297 mg), HATU (294 mg) were added under ice-cooling and the mixture was stirred at room temperature for 6 hr. To the reaction mixture were added ice water and saturated brine and the mixture was extracted with ethyl acetate, and the extract was washed twice with water:saturated brine=1:1 and washed with saturated brine. After drying over anhydrous sodium sulfate, the solvent was evaporated under reduced pressure, and the residue was purified by NH silica gel column chromatography (ethyl acetate:methanol=100:0-85:15), silica gel column chromatography (ethyl acetate:methanol=100:0-85:15) to give the title compound (217 mg) as a yellow-white solid.

MS (ESI) m/z: 991.5 [M+H]+

Example 53

(53-1) methyl [(6S)-4-{4'-[(2-t-butoxy-2-oxoethyl)sulfanyl] [1,1'-biphenyl]-4-yl}-2,3,9-trimethyl-6H-thieno[3,2-f][1,2,4]triazolo[4,3-a][1,4]diazepin-6-yl] acetate (Example Compound 53-1)

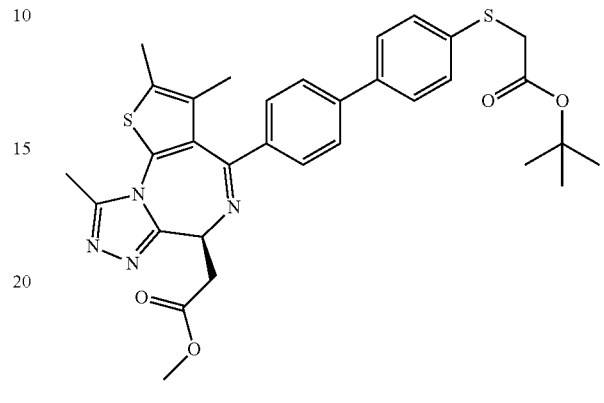

To a mixture of Reference Example compound 3 (400 mg), t-butyl 2-(4-bromophenyl)sulfanylacetate (288 mg), palladium acetate (18 mg), S-phos (65 mg) and potassium fluoride (140 mg) in tetrahydrofuran (7.9 mL) was added water (51 μL), and the mixture was stirred at 75° C. for 8 hr. Water was added to the reaction mixture and the mixture was extracted twice with chloroform. The organic layers were collected and washed with saturated brine, dried over anhydrous sodium sulfate, and the solvent was evaporated under reduced pressure. The residue was purified by silica gel column chromatography (ethyl acetate:methanol=100:0-90:10) to give the title compound (400 mg) as a yellow oil. MS (ESI) m/z: 603.5 [M+H]+

(53-2) methyl [(6S)-4-(4'-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]sulfanyl} [1,1'-biphenyl]-4-yl)-2,3,9-trimethyl-6H-thieno[3,2-f][1,2,4]triazolo[4,3-a] [1,4]diazepin-6-yl]acetate (Example Compound 53)

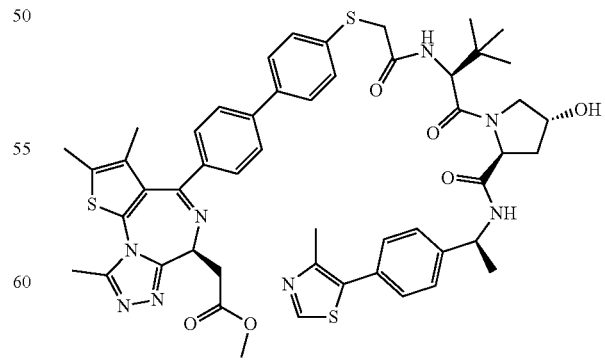

Example compound 53-1 (400 mg) was dissolved in dichloromethane (4.0 mL), trifluoroacetic acid (4.0 mL) was added under ice-cooling and the mixture was stirred at room temperature for 3 hr. To the reaction mixture was added toluene and toluene was evaporated under reduced pressure. This was repeated 3 times and the mixture was dried under reduced pressure at 60° C. The residue was dissolved in N,N-dimethylformamide (10.3 mL), N,N-diisopropylethylamine (0.57 mL), Reference Example compound 5 (383 mg), HATU (378 mg) were added under ice-cooling and the mixture was stirred at room temperature for 6 hr. To the reaction mixture were added ice water and saturated brine and the mixture was extracted with ethyl acetate, and the aqueous layer was extracted again with ethyl acetate. The organic layers were collected, washed twice with water: saturated brine=1:1, and washed with saturated brine. After drying over anhydrous sodium sulfate, the solvent was evaporated under reduced pressure, and the residue was purified by NH silica gel column chromatography (ethyl acetate:methanol=100:0-85:15), silica gel column chromatography (ethyl acetate:methanol=100:0-85:15) to give the title compound (317 mg) as a yellow-white solid.

MS (ESI) m/z: 973.5 [M+H]$^+$

Example 54

(54-1) 3-(4-iodophenoxy)propanoic acid (Example Compound 54-1)

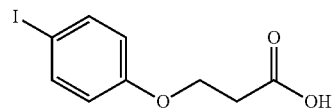 [SMILES: O=C(O)CCOc1ccc(I)cc1]

A mixed solution of 4-iodophenol (3.0 g), 3-bromopropionic acid (1.4 mL), 10N aqueous sodium hydroxide solution (2.73 mL) and water (6.81 mL) was stirred with heating under reflux overnight. Under ice-cooling, concentrated hydrochloric acid was added to the reaction solution, and the mixture was extracted with ethyl acetate. The organic layer was dried over, anhydrous sodium sulfate. The solvent was evaporated under reduced pressure to give the title compound (750 mg) as a flesh-colored crudely purified solid.

MS (ESI) m/z: 290.8 [M−H]$^-$ (54-2) (2S,4R)-4-hydroxy-1-{(2S)-2-[3-(4-iodophenoxy)propanamido]-3,3-dimethylbutanoyl}-N-{(1S)-1-[4-(4-methyl-1,3-thiazol-5-yl)phenyl]ethyl}pyrrolidine-2-carboxamide (Example Compound 54-2)

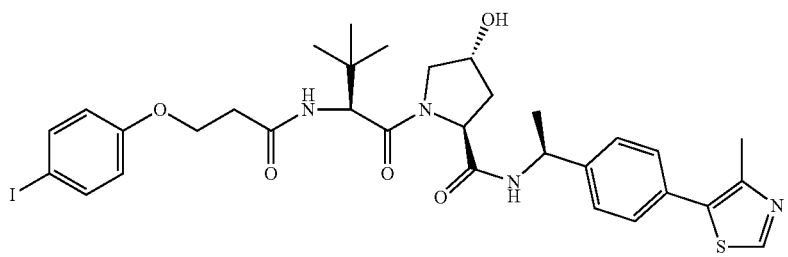 [SMILES: Cc1ncsc1-c1ccc([C@H](C)NC(=O)[C@@H]2C[C@@H](O)CN2C(=O)[C@@H](NC(=O)CCOc2ccc(I)cc2)C(C)(C)C)cc1]

To a solution of Example compound 54-1 (300 mg), Reference Example compound 5 (494 mg) in N,N-dimethylformamide (6.9 mL) was added N,N-diisopropylethylamine (0.711 mL), and HATU (781 mg) was added under ice-cooling, and the mixture was allowed to naturally warm to room temperature and stirred for 6.5 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (604 mg) as a white powder. MS (ESI) m/z: 719.5 [M+H]$^+$ (54-3) methyl [(6S)-4-{4'-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropoxy][1,1'-biphenyl]-4-yl}-2,3,9-trimethyl-6H-thieno[3,2-f][1,2,4]triazolo[4,3-a][1,4]diazepin-6-yl]acetate (Example Compound 54)

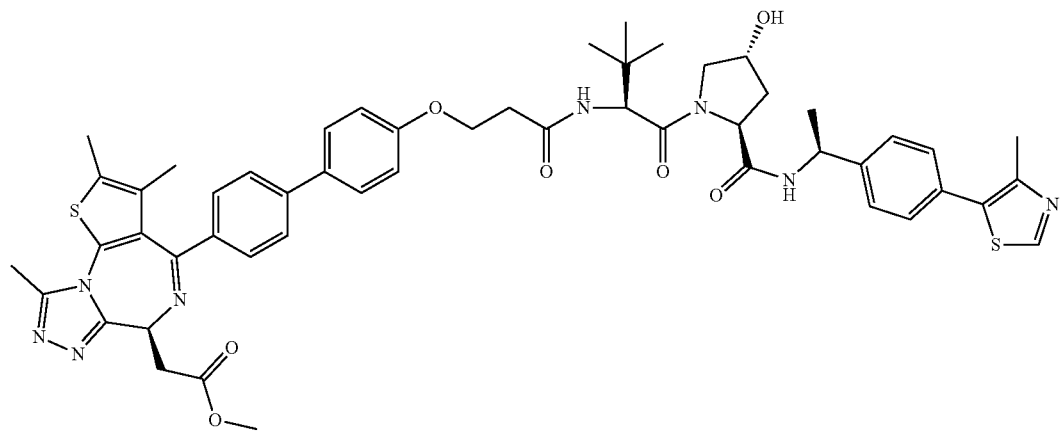 [SMILES: COC(=O)C[C@@H]1N=C(c2ccc(-c3ccc(OCCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 54-2 (226 mg) in tetrahydrofuran (4.2 mL) were added Reference Example compound 2 (300 mg), palladium acetate (9.4 mg), S-phos (34 mg), potassium fluoride (73 mg) and water (0.027 mL) and the mixture was stirred at 70° C. for 16.5 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=97:3-90:10) and further purified by silica gel column chromatography (chloroform:methanol=99:1-95:5) to give the title compound (128 mg) as a white solid. MS (ESI) m/z: 971.8 [M+H]$^+$ Example 55

(55-1) (2S,4R)-1-{(2S)-2-[2-(3-bromophenyl)acetamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 55-1)

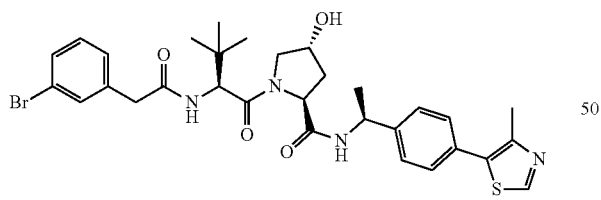

To a solution of 3-bromophenylacetic acid (300 mg), Reference Example compound 5 (671 mg) in N,N-dimethylformamide (9.3 mL) was added N,N-diisopropylethylamine (0.965 mL), and HATU (1.06 g) was added under ice-cooling, and the mixture was allowed to naturally warm to room temperature and stirred for 16 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-90:10) to give the title compound (751 mg) as a yellow viscous compound.
MS (ESI) m/z: 639.5, 641.5 [M+H]$^+$ (55-2) methyl [(6S)-4-{3'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl][1,1'-biphenyl]-4-yl}-2,3,9-trimethyl-6H-thieno[3,2-f][1,2,4]triazolo[4,3-a][1,4]diazepin-6-yl]acetate (Example Compound 55)

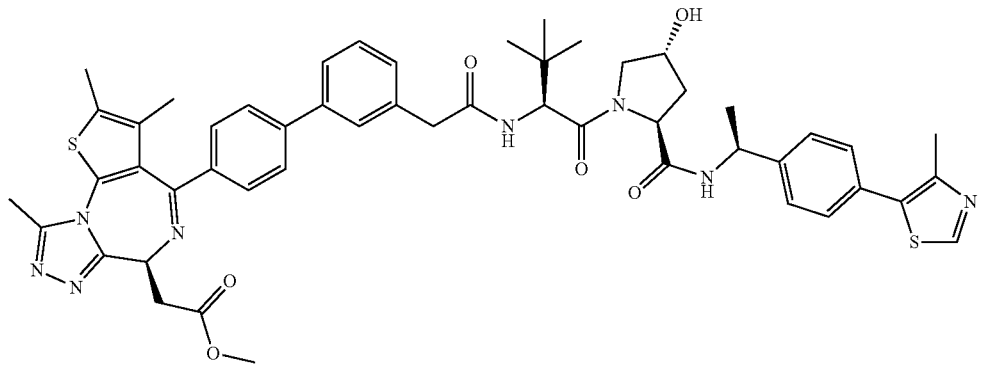 [SMILES: COC(=O)C[C@@H]1N=C(c2ccc(-c3cccc(CC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 55-1 (745 mg) in tetrahydrofuran (11.6 mL) were added Reference Example compound 2 (629 mg), palladium acetate (26 mg), S-phos (95 mg), potassium fluoride (202 mg) and water (0.075 mL) and the mixture was stirred at 70° C. for 16.5 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=97:3-90:10) and further purified by silica gel column chromatography (chloroform:methanol=99:1-95:5). The obtained solid was suspension washed with diethyl ether, collected by filtration and dried under reduced pressure to give the title compound (563 mg) as a white solid.

MS (ESI) m/z: 941.8 [M+H]$^+$

Example 56

(56-1) methyl [(6S)-4-(3'-fluoro-5'-hydroxy[1,1'-biphenyl]-4-yl)-2,3,9-trimethyl-6H-thieno[3,2-f][1,2,4]triazolo[4,3-a] [1,4]diazepin-6-yl]acetate (Example Compound 56-1)

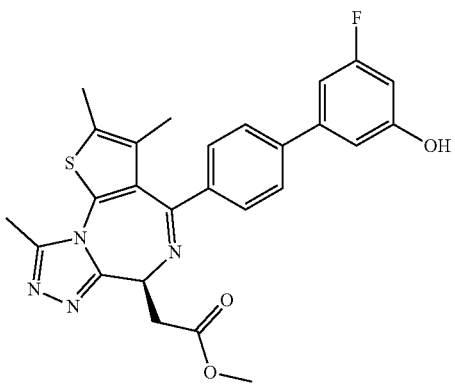 [SMILES: COC(=O)C[C@@H]1N=C(c2ccc(-c3cc(O)cc(F)c3)cc2)c2c(sc(C)c2C)-n2c(C)nnc21]

To a solution of Reference Example compound 2 (500 mg) in tetrahydrofuran (1.0 mL) were added 5-bromo-3-fluorophenol (233 mg), palladium acetate (23 mg), S-phos (83 mg), potassium fluoride (177 mg) and water (0.066 mL) and the mixture was stirred at 70° C. for 6 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=98:2-93:7) to give the title compound (361 mg) as a yellow viscous compound.

MS (ESI) m/z: 491.4 [M+H]$^+$ (56-2) methyl {(6S)-4-[3'-(2-t-butoxy-2-oxoethoxy)-3'-fluoro[1,1'-biphenyl]-4-yl]-2,3,9-trimethyl-6H-thieno[3,2-f] [1,2,4]triazolo[4,3-a][1,4]diazepin-6-yl}acetate (Example Compound 56-2)

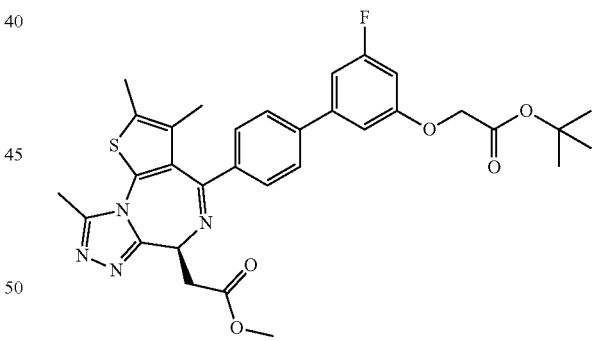

To a solution of Example compound 56-1 (355 mg) in N,N-dimethylformamide (3.6 mL) was added cesium carbonate (472 mg) and the mixture was stirred for 10 min. t-Butyl bromoacetate (155 mg) was added dropwise over 5 min and the mixture was stirred at the same temperature for 1 hr. To the reaction solution were added saturated aqueous ammonium chloride solution and water and the mixture was extracted with ethyl acetate. The organic layer was washed with saturated brine and dried over anhydrous sodium sulfate. The solvent was evaporated under reduced pressure. The residue was purified by silica gel column chromatography (chloroform:methanol=100:0-97:3) to give the title compound (337 mg) as an orange powder.

MS (ESI) m/z: 605.5 [M+H]$^+$ (56-3) ({5-fluoro-4'-[(6S)-6-(2-methoxy-2-oxo-ethyl)-2,3,9-trimethyl-6H-thieno[3,2-f][1,2,4]tri-azolo[4,3-a][1,4]diazepin-4-yl][1,1'-biphenyl]-3-yl}oxy)acetic acid trifluoroacetate (Example Compound 56-3)

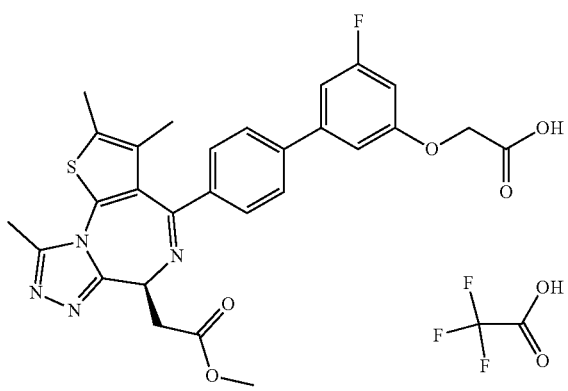 [SMILES: COC(=O)C[C@@H]1N=C(c2ccc(-c3cc(F)cc(OCC(=O)O)c3)cc2)c2c(sc(C)c2C)-n2c(C)nnc21 ; O=C(O)C(F)(F)F]

To a solution of Example compound 56-2 (330 mg) in dichloromethane (1.5 mL) was added dropwise under ice-cooling trifluoroacetic acid (1.5 mL) and the mixture was allowed to naturally warm to room temperature and stirred for 4 hr. The reaction solution was diluted with ethyl acetate, and the solvent was evaporated under reduced pressure. The residue was further concentrated azeotropically with toluene and this operation was performed two times to give the title compound (522 mg) as a crudely purified orange viscous compound.

MS (ESI) m/z: 549.4 [M+H]$^+$ (56-4) methyl [(6S)-4-{3'-fluoro-5'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 56)

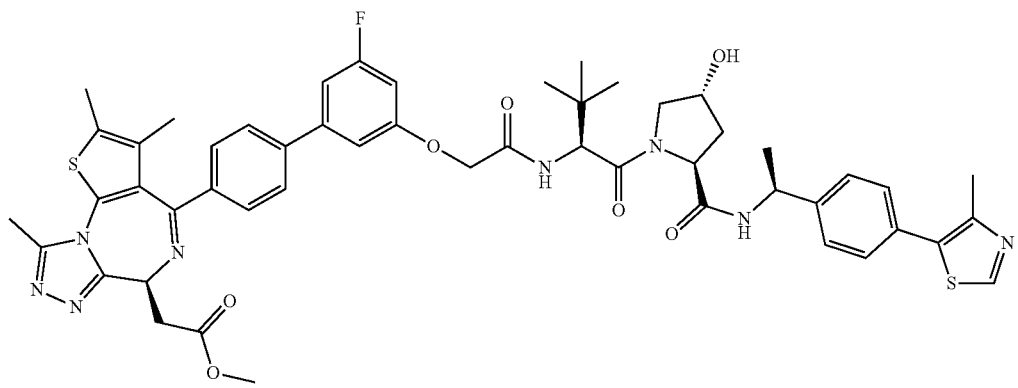 [SMILES: COC(=O)C[C@@H]1N=C(c2ccc(-c3cc(F)cc(OCC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 56-3 (520 mg), Reference Example compound 5 (263 mg) in N,N-dimethylformamide (3.6 mL) was added N,N-diisopropylethylamine (0.378 mL), and HATU (415 mg) was added under ice-cooling, and the mixture was allowed to naturally warm to room temperature and stirred for 40 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=97:3-90:10-88:12) and further purified by silica gel column chromatography (chloroform:methanol=100:0-97:3). The obtained solid was suspension washed with diethyl ether, collected by filtration and dried under reduced pressure to give the title compound (278 mg) as a white solid.

MS (ESI) m/z: 975.7 [M+H]$^+$

Example 57

(57-1) (2S,4R)-1-{(2S)-2-[3-(3-bromophenoxy)propanamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 57-1)

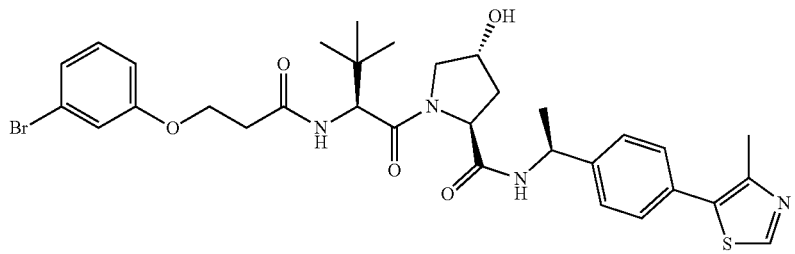 [SMILES: Cc1ncsc1-c1ccc([C@H](C)NC(=O)[C@@H]2C[C@@H](O)CN2C(=O)[C@@H](NC(=O)CCOc2cccc(Br)c2)C(C)(C)C)cc1]

To a solution of 3-(3-bromophenoxy)propionic acid (300 mg), Reference Example compound 5 (589 mg) in N,N-dimethylformamide (8.2 mL) was added N,N-diisopropylethylamine (0.847 mL), and HATU (931 mg) was added under ice-cooling, and the mixture was allowed to naturally warm to room temperature and stirred for 15 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-95:5) to give the title compound (628 mg) as a pale-yellow powder.

MS (ESI) m/z: 671.4, 673.4 [M+H]$^+$ (57-2) methyl [(6S)-4-{3'-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropoxy][1,1'-biphenyl]-4-yl}-2,3,9-trimethyl-6H-thieno[3,2-f][1,2,4]triazolo[4,3-a][1,4]diazepin-6-yl]acetate (Example Compound 57)

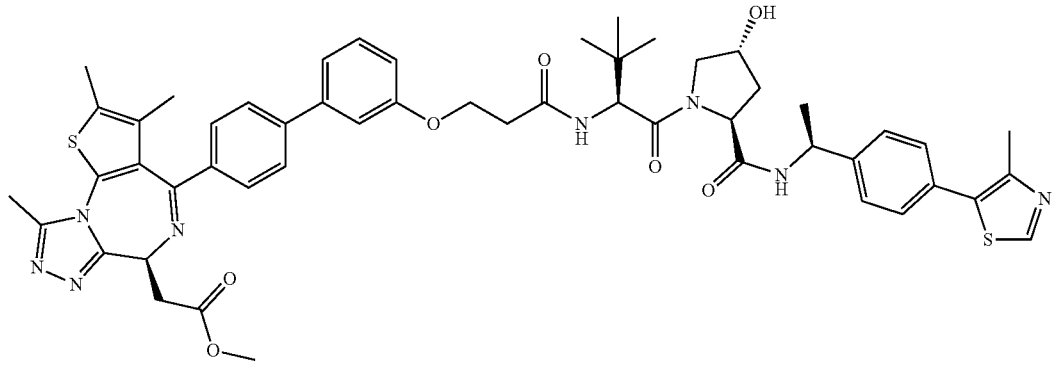 [SMILES: COC(=O)C[C@@H]1N=C(c2ccc(-c3cccc(OCCC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 57-1 (312 mg) in tetrahydrofuran (4.7 mL) were added Reference Example compound 2 (217 mg), palladium acetate (11 mg), S-phos (38 mg), potassium fluoride (81 mg) and water (0.030 mL) and the mixture was stirred at 70° C. for 4 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-90:10-88:12) and further purified by silica gel column chromatography (chloroform:methanol=100:0-97:3). The obtained solid was suspension washed with diethyl ether, collected by filtration and dried under reduced pressure to give the title compound (180 mg) as a white solid. MS (ESI) m/z: 971.8 [M+H]$^+$

Example 58

(58-1) (2S,4R)-1-{(2S)-2-[3-(3-bromophenyl)propanamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 58-1)

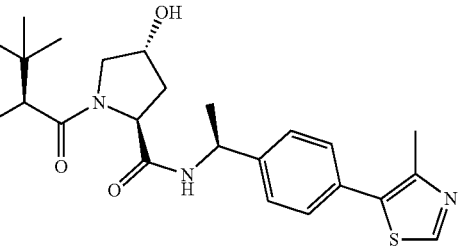

To a solution of 3-(3-bromophenyl)propionic acid (300 mg), Reference Example compound 5 (630 mg) in N,N-dimethylformamide (8.7 mL) was added N,N-diisopropylethylamine (0.906 mL), and HATU (996 mg) was added under ice-cooling, and the mixture was allowed to naturally warm to room temperature and stirred for 15 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-95:5) to give the title compound (680 mg) as a pale-yellow viscous compound. MS (ESI) m/z: 655.4, 657.4 [M+H]⁺

(58-2) methyl [(6S)-4-{3'-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl][1,1'-biphenyl]-4-yl}-2,3,9-trimethyl-6H-thieno[3,2-f][1,2,4]triazolo[4,3-a][1,4]diazepin-6-yl]acetate (Example Compound 58)

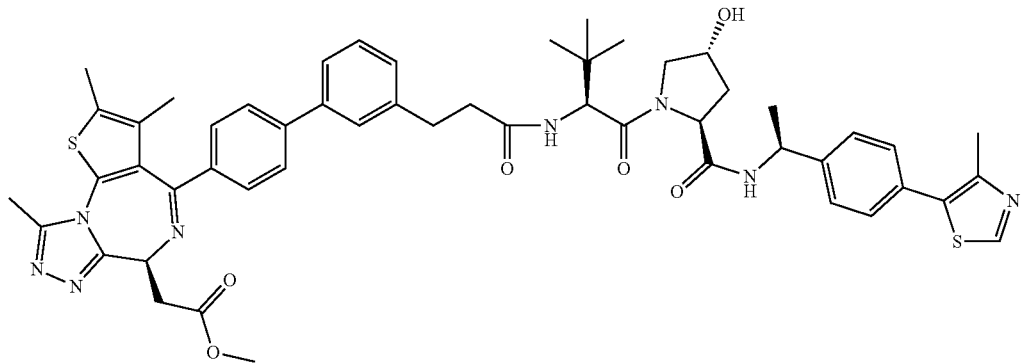 [SMILES: COC(=O)C[C@@H]1N=C(c2ccc(-c3cccc(CCC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 58-1 (340 mg) in tetrahydrofuran (5.2 mL) were added Reference Example compound 2 (243 mg), palladium acetate (12 mg), S-phos (43 mg), potassium fluoride (90 mg) and water (0.034 mL) and the mixture was stirred at 70° C. for 4 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-90:10-88:12) and further purified by silica gel column chromatography (chloroform:methanol=100:0-97:3). The obtained solid was suspension washed with diethyl ether, collected by filtration and dried under reduced pressure to give the title compound (265 mg) as a white solid. MS (ESI) m/z: 955.7 [M+H]⁺

Example 59

(59-1) t-butyl (5-bromo-1H-indazol-1-yl)acetate (Example Compound 59-1A) and t-butyl (5-bromo-2H-indazol-2-yl)acetate (Example Compound 59-1B)

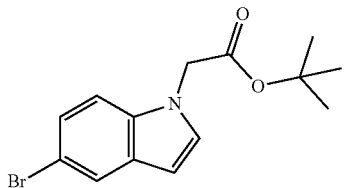

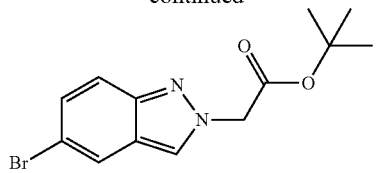

5-Bromo-1H-indazole (1.01 g) was dissolved in N,N-dimethylformamide (25 mL), and t-butyl bromoacetate (0.89 mL) and potassium carbonate (1.11 g) were added and the mixture was stirred at 80° C. for 1 hr. The mixture was heated to 100° C. and further stirred for 3 hr. Ice water was added to the reaction mixture, the mixture was stirred, hexane:ethyl acetate=1:1 and water were added and the organic layer was extracted. The aqueous layer was extracted again with hexane:ethyl acetate=1:1, and the organic layers were collected and washed twice with water and washed with saturated brine, dried over anhydrous sodium sulfate, and the solvent was evaporated under reduced pressure. The residue was purified by silica gel column chromatography (hexane:ethyl acetate=90:10-65:35) to give the title compounds (Example compound 59-1A, 983 mg), (Example compound 59-1B, 440 mg) each as a yellow solid.

MS (ESI) m/z: 311.2 [M+H]⁺ (Example compound 59-1A), MS (ESI) m/z: 311.2 [M+H]⁺ (Example compound 59-1B)

(59-2) methyl [(6S)-4-(4-{1-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1H-indazol-5-yl}phenyl)-2,3,9-trimethyl-6H-thieno[3,2-f][1,2,4]triazolo[4,3-a][1,4]diazepin-6-yl]acetate (Example Compound 59)

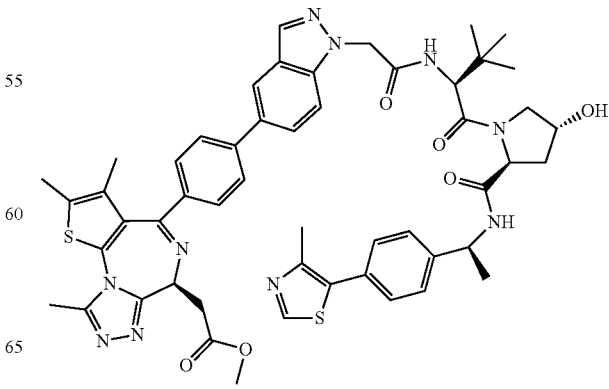

By reaction and treatment in the same manner as in Example 62 (62-1)-(62-2) and using Example compound 59-1A instead of t-butyl 4-bromo-3-fluoro-benzoate, the title compound was obtained as a white solid. MS (ESI) m/z: 981.5 [M+H]+

Example 60

(60-1) (2S,4R)-1-[(2S)-2-(3-bromobenzamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 60-1)

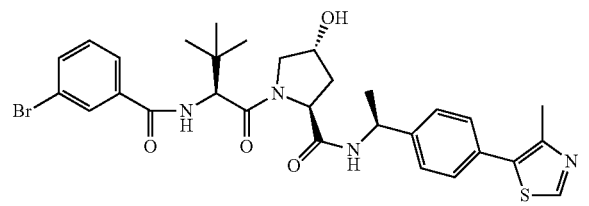 [SMILES: Cc1ncsc1-c1ccc([C@H](C)NC(=O)[C@@H]2C[C@@H](O)CN2C(=O)[C@@H](NC(=O)c2cccc(Br)c2)C(C)(C)C)cc1]

To a solution of 3-bromobenzoic acid (350 mg), Reference Example compound 5 (838 mg) in N,N-dimethylformamide (11.6 mL) was added N,N-diisopropylethylamine (1.2 mL), and HATU (1.32 g) was added under ice-cooling, and the mixture was allowed to naturally warm to room temperature and stirred for 14.5 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=99:1-94:6) to give the title compound (937 mg) as a pale-yellow solid. MS (ESI) m/z: 625.4, 627.4 [M+H]+

(60-2) methyl {(6S)-4-[3'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 60)

To a solution of Example compound 60-1 (327 mg) in tetrahydrofuran (5.2 mL) were added Reference Example compound 2 (244 mg), palladium acetate (12 mg), S-phos (43 mg), potassium fluoride (91 mg) and water (0.034 mL) and the mixture was stirred at 70° C. for 5 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-93:7) and further purified by silica gel column chromatography (chloroform:methanol=100:0-97:3). The obtained solid was suspension washed with diethyl ether, collected by filtration and dried under reduced pressure to give the title compound (245 mg) as a white solid. MS (ESI) m/z: 927.7 [M+H]+

Example 61

(61-1) methyl [(6S)-4-(4'-hydroxy[1,1'-biphenyl]-4-yl)-2,3,9-trimethyl-6H-thieno[3,2-f][1,2,4]triazolo[4,3-a][1,4]diazepin-6-yl]acetate (Example Compound 61-1)

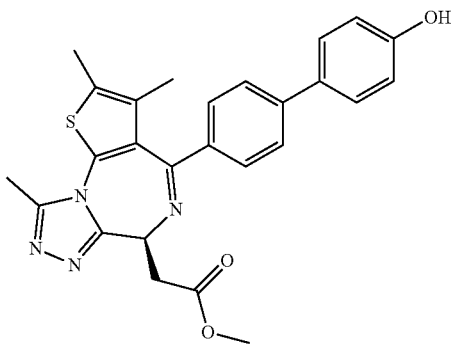

To a solution of Reference Example compound 1 (500 mg) in tetrahydrofuran (4.0 mL) were added 4-(4,4,5,5-tetramethyl-1,3,2-dioxaborolan-2-yl)phenol (292 mg), palladium acetate (27 mg), S-phos (99 mg), potassium fluoride (210 mg) and water (0.076 mL), and the mixture was stirred at 85° C. for 16.5 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under

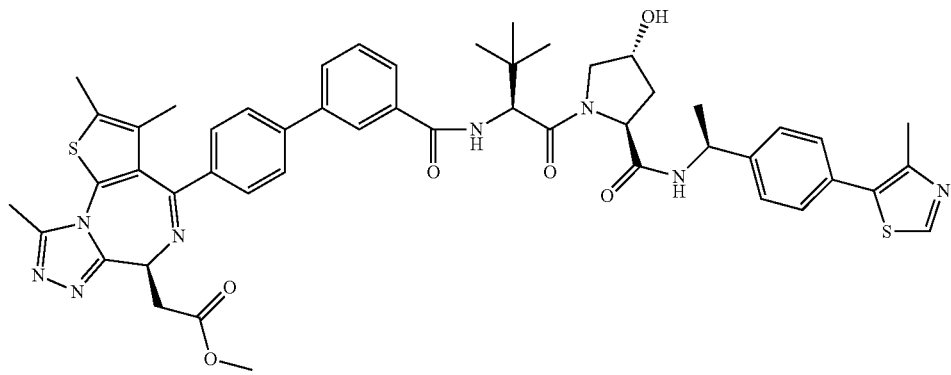 [SMILES: COC(=O)C[C@@H]1N=C(c2ccc(-c3cccc(C(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

(61-2) methyl {(6S)-4-[4'-(2-t-butoxy-2-oxoethoxy)[1,1'-biphenyl]-4-yl]-2,3,9-trimethyl-6H-thieno[3,2-f][1,2,4]triazolo[4,3-a][1,4]diazepin-6-yl}acetate (Example Compound 61-2)

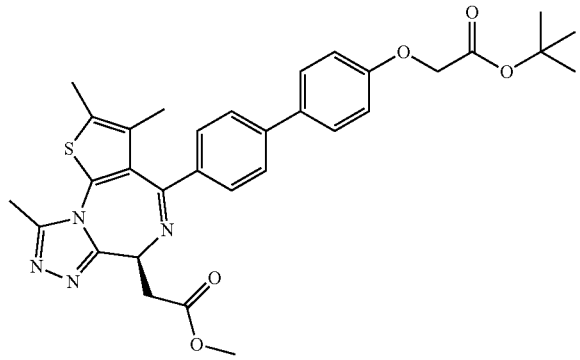 [SMILES: COC(=O)C[C@@H]1N=C(c2ccc(-c3ccc(OCC(=O)OC(C)(C)C)cc3)cc2)c2c(sc(C)c2C)-n2c(C)nnc21]

To a solution of Example compound 61-1 (430 mg) in N,N-dimethylformamide (5.5 mL) were added potassium carbonate (252 mg) and t-butyl bromoacetate (231 mg), and the mixture was stirred at 60° C. for 1 hr. Ice water was added to the reaction solution and the mixture was extracted with ethyl acetate. The organic layer was washed with water and saturated brine, and dried over anhydrous sodium sulfate. The solvent was evaporated under reduced pressure. The residue was purified by silica gel column chromatography (chloroform:methanol=100:0-97:3) to give the title compound (412 mg) as an orange powder.

MS (ESI) m/z: 587.5 [M+H]⁺

(61-3) ({4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetic acid trifluoroacetate (Example Compound 61-3)

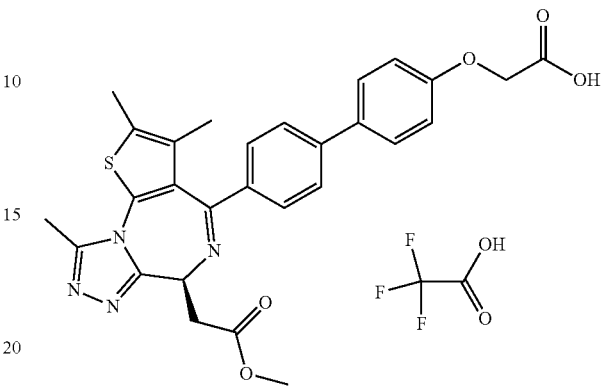

To a solution of Example compound 61-2 (405 mg) in dichloromethane (1.5 mL) was added dropwise under ice-cooling trifluoroacetic acid (1.5 mL), and the mixture was allowed to naturally warm to room temperature and stirred for 2 hr. The reaction solution was diluted with ethyl acetate, and the solvent was evaporated under reduced pressure. The residue was further concentrated azeotropically with toluene and this operation was performed two times to give the title compound (633 mg) as a crudely purified orange viscous compound.

MS (ESI) m/z: 531.4 [M+H]⁺

(61-4) methyl [(6S)-4-{4'-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 61)

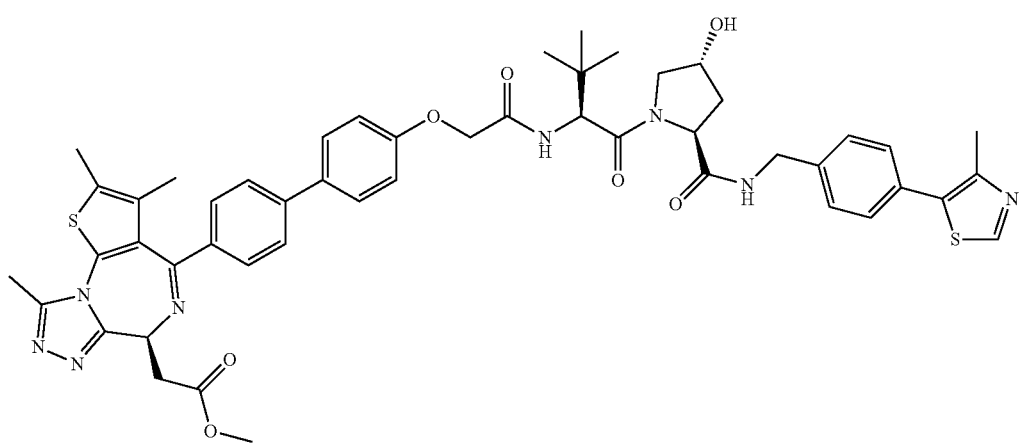 [SMILES: COC(=O)C[C@@H]1N=C(c2ccc(-c3ccc(OCC(=O)N[C@H](C(=O)N4C[C@H](O)C[C@H]4C(=O)NCc4ccc(-c5scnc5C)cc4)C(C)(C)C)cc3)cc2)c2c(sc(C)c2C)-n2c(C)nnc21]

To a solution of Example compound 61-3 (630 mg), Reference Example compound 6 (263 mg) in N,N-dimethylformamide (4.6 mL) was added N,N-diisopropylethylamine (0.478 mL), and HATU (525 mg) was added under ice-cooling, and the mixture was allowed to naturally warm to room temperature and stirred for 16 hr. To the reaction solution were added N,N-diisopropylethylamine (0.478 mL), HATU (525 mg), and the mixture was further stirred at room temperature for 1 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=98:2-90:10) and further purified by silica gel column chromatography (chloroform:methanol=100:0-97:3). The obtained solid was suspension washed with diethyl ether, collected by filtration and dried under reduced pressure to give the title compound (371 mg) as a white solid.

MS (ESI) m/z: 943.7 [M+H]$^+$

Example 62

(62-1) t-butyl 2-fluoro-4'-[(6S)-6-(2-methoxy-2-oxoethyl)-2,3,9-trimethyl-6H-thieno[3,2-f][1,2,4]triazolo[4,3-a] [1,4]diazepin-4-yl][1,1'-biphenyl]-4-carboxylate (Example Compound 62-1)

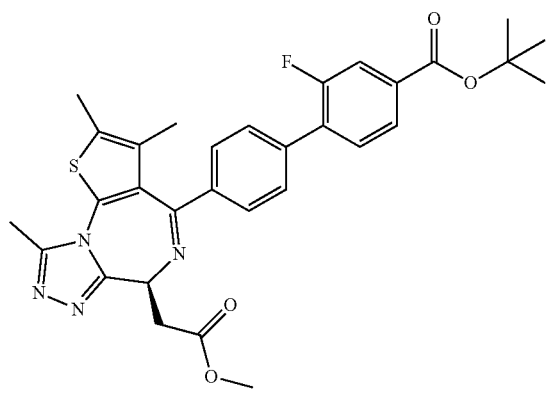 [SMILES: COC(=O)C[C@@H]1N=C(c2ccc(-c3ccc(C(=O)OC(C)(C)C)cc3F)cc2)c2c(sc(C)c2C)-n2c(C)nnc21]

Reference Example compound 2 (435 mg) was dissolved in tetrahydrofuran (2.9 mL), t-butyl 4-bromo-3-fluoro-benzoate (291 mg), palladium acetate (20 mg), S-phos (72 mg), potassium fluoride (154 mg) and water (0.057 mL) were added and the mixture was stirred at 70° C. for 15 hr. The insoluble material in the reaction mixture was filtered off through diatomaceous earth. Water was added to the filtrate and the mixture was extracted 3 times with ethyl acetate, and the extract was dried over anhydrous sodium sulfate, and the solvent was evaporated under reduced pressure. The residue was purified by silica gel column chromatography (chloroform:methanol=100:0-97:3) to give the title compound (375 mg) as a pale-yellow powder.

MS (ESI) m/z: 575.4 [M+H]$^+$ (62-2) methyl {(6S)-4-[2'-fluoro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl) [1,1'-biphenyl]-4-yl]-2,3,9-trimethyl-6H-thieno[3,2-f][1,2,4]triazolo[4,3-a][1,4]diazepin-6-yl}acetate (Example Compound 62)

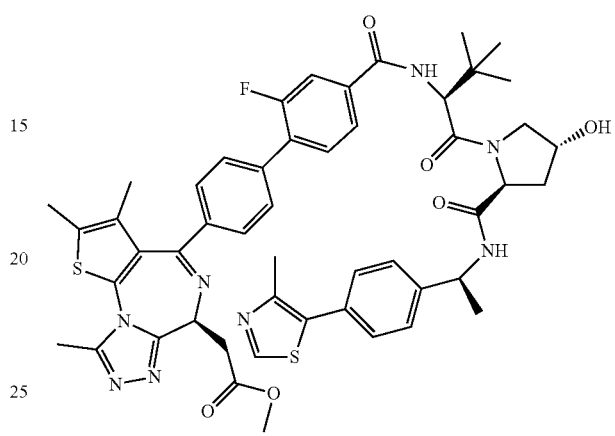

Example compound 62-1 (180 mg) was dissolved in dichloromethane (2.0 mL), trifluoroacetic acid (2.0 mL) was added under ice-cooling and the mixture was stirred at room temperature for 3 hr. To the reaction mixture was added toluene and toluene was evaporated under reduced pressure. This was repeated 3 times, and the residue was dried under reduced pressure at 60° C. The residue was dissolved in N,N-dimethylformamide (6.3 mL), N,N-diisopropylethylamine (0.20 mL), Reference Example compound 5 (183 mg), HATU (180 mg) were added under ice-cooling and the mixture was stirred at room temperature for 16 hr. To the reaction mixture was added ice water to quench the reaction, ethyl acetate and saturated brine and water were added and the organic layer was extracted. The aqueous layer was extracted again twice with ethyl acetate, and the organic layers were collected and washed with saturated brine. After drying over anhydrous sodium sulfate, the solvent was evaporated under reduced pressure, and the residue was purified by NH silica gel column chromatography (ethyl acetate:methanol=100:0-85:15), silica gel column chromatography (ethyl acetate:methanol=100:0-85:15) to give the title compound (188 mg) as a yellow solid.

MS (ESI) m/z: 945.5 [M+H]$^+$

Example 63

(63-1) t-butyl [(5-bromopyridin-2-yl)oxy]acetate (Example Compound 63-1)

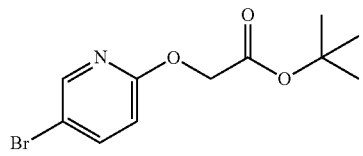 [SMILES: CC(C)(C)OC(=O)COc1ccc(Br)cn1]

Under an argon stream, a solution of 5-bromo-2-fluoropyridine (353 mg), t-butyl glycolate (291 mg) in N,N-dimethylformamide (5 mL) was cooled to 0° C., sodium hydride (60%, 120 mg) was added by small portions, and the mixture was stirred while allowing the mixture to naturally warm to room temperature for 5 hr. Water was added to the reaction mixture and the mixture was stirred and extracted twice with ethyl acetate. The organic layer was washed twice with water and concentrated under reduced pressure. The residue was purified by silica gel column chromatography (ethyl acetate:hexane=0:100-10:90) to give the title compound (343 mg) as a colorless viscous compound. MS (ESI) m/z: 231.9, 233.9 [M−tBu+2H]⁺

(63-2) methyl [(6S)-4-{4-[6-(2-t-butoxy-2-oxoethoxy)pyridin-3-yl]phenyl}-2,3,9-trimethyl-6H-thieno[3,2-f][1,2,4]triazolo[4,3-a] [1,4]diazepin-6-yl]acetate (Example Compound 63-2)

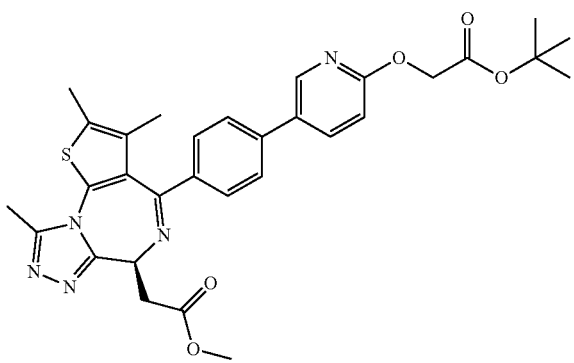 [SMILES: COC(=O)C[C@@H]1N=C(c2ccc(-c3ccc(OCC(=O)OC(C)(C)C)nc3)cc2)c2c(sc(C)c2C)-n2c(C)nnc21]

Under an argon stream, Example compound 63-1 (340 mg), Reference Example compound 2 (400 mg), palladium acetate (18 mg), S-phos (67 mg), potassium fluoride (142 mg) and water (0.053 L) were heated under reflux in a tetrahydrofuran (5 mL) solvent for 7 hr. Using ethyl acetate, the reaction mixture was filtered through diatomaceous earth, and the filtrate was concentrated under reduced pressure. The residue was purified by NH silica gel column chromatography (ethyl acetate:hexane=50:50-95:5) to give the title compound (326 mg) as a white solid. MS (ESI) m/z: 588.2 [M+H]⁺

(63-3) methyl [(6S)-4-(4-{6-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyridin-3-yl}phenyl)-2,3,9-trimethyl-6H-thieno[3,2-f][1,2,4]triazolo[4,3-a][1,4]diazepin-6-yl]acetate (Example Compound 63)

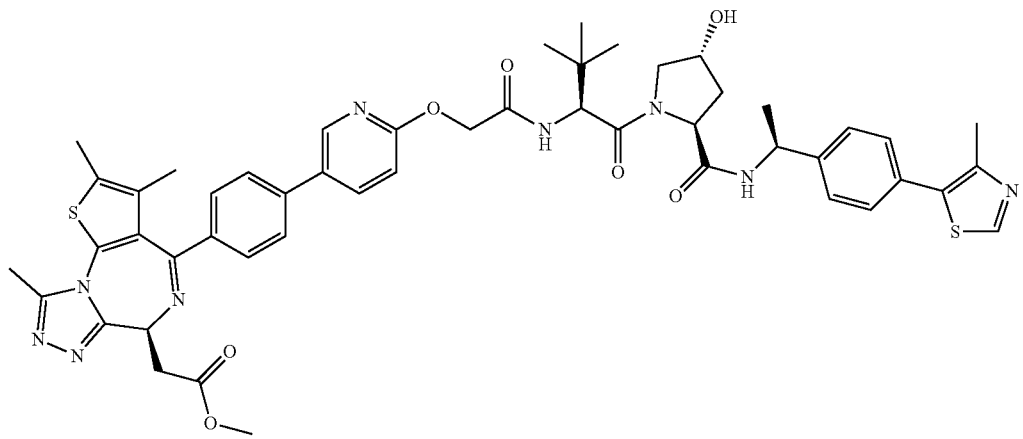 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)nc3)cc2)c2c(sc(C)c2C)-n2c(C)nnc21]

To a solution of Example compound 63-2 (326 mg) in chloroform (1 mL) was added trifluoroacetic acid (1 mL) and the mixture was stirred at room temperature for 5 hr. The reaction mixture was concentrated under reduced pressure, and azeotropically distilled twice with toluene. The residue was dissolved in N,N-dimethylformamide (5 mL), and Reference Example compound 5 (320 mg), N,N-diisopropylethylamine (0.479 mL), HATU (253 mg) were added and the mixture was stirred at room temperature for 18 hr. To the reaction mixture was added saturated aqueous sodium hydrogen carbonate and the mixture was stirred and extracted 3 times with ethyl acetate. The organic layer was washed twice with saturated brine and concentrated under reduced pressure. The residue was purified by silica gel column chromatography (methanol:chloroform=0:100-5:95) to give the title compound (411 mg) as a white solid. MS (ESI) m/z: 958.9 [M+H]⁺

Example 64

(64-1) t-butyl 3-(4-bromo-1H-pyrazol-1-yl)propanoate (Example Compound 64-1)

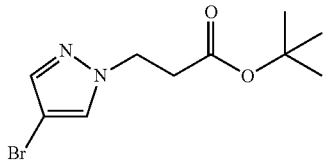

To a solution of 4-bromopyrazole (294 mg) in acetonitrile (5 mL) were added t-butyl acrylate (0.584 mL) and 1,8-diazabicyclo[5.4.0]-7-undecene (0.149 mL) and the mixture was stirred at room temperature for 6 hr. Water was added to the reaction mixture and the mixture was stirred and extracted twice with ethyl acetate. The organic layer was washed twice with 1N hydrochloric acid and concentrated under reduced pressure. The residue was purified by silica gel column chromatography (ethyl acetate:hexane=0:100-20:80) to give the title compound (536 mg) as a colorless liquid.
MS (ESI) m/z: 218.9, 220.9 [M−tBu+2H]$^+$ (64-2) methyl [(6S)-4-(4-{1-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl]-1H-pyrazol-4-yl}phenyl)-2,3,9-trimethyl-6H-thieno[3,2-f][1,2,4]triazolo[4,3-a] [1,4]diazepin-6-yl]acetate
(Example Compound 64)

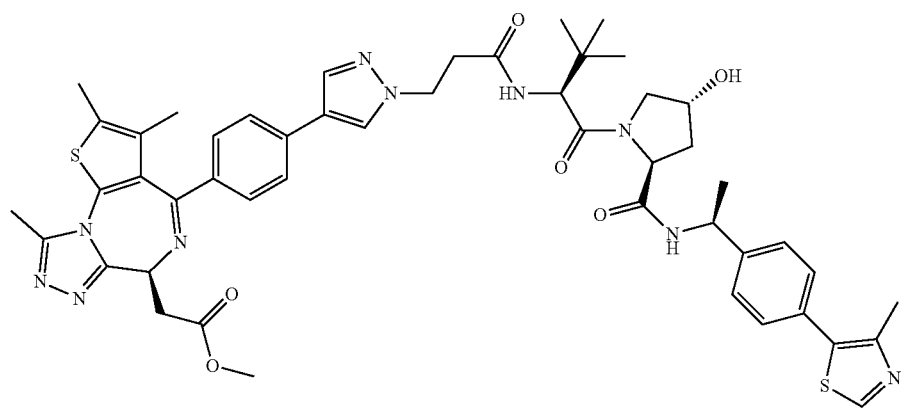

By reaction and treatment in the same manner as in Example 63 (63-2)-(63-3) and using Example compound 64-1 instead of Example compound 63-1, the title compound was obtained as a white solid. MS (ESI) m/z: 945.4 [M+H]$^+$ Example 65

(65-1) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-2H-indazol-5-yl}phenyl)-2,3,9-trimethyl-6H-thieno[3,2-f][1,2,4]triazolo[4,3-a][1,4]diazepin-6-yl]acetate
(Example Compound 65)

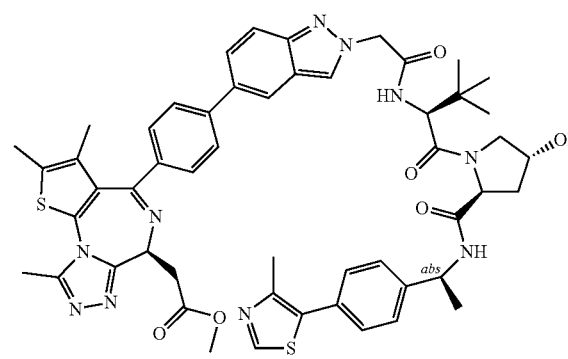

By reaction and treatment in the same manner as in Example 62 (62-1)-(62-2) and using Example compound 59-1B instead of t-butyl 4-bromo-3-fluoro-benzoate, the title compound was obtained as a yellow solid.
MS (ESI) m/z: 981.5 [M+H]$^+$ Example 66

(66-1) t-butyl (6-bromo-2H-indazol-2-yl)acetate
(Example Compound 66-1)

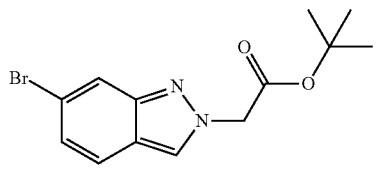 [SMILES: CC(C)(C)OC(=O)Cn1cc2ccc(Br)cc2n1]

By reaction and treatment in the same manner as in Example 59 (59-1) and using 6-bromo-1H-indazole instead of 5-bromo-1H-indazole, the title compound was obtained as a white solid. MS (ESI) m/z: 311.1 [M+H]$^+$ (66-2) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-2H-indazol-6-yl}phenyl)-2,3,9-trimethyl-6H-thieno[3,2-f][1,2,4]triazolo[4,3-a][1,4]diazepin-6-yl]acetate
(Example Compound 66)

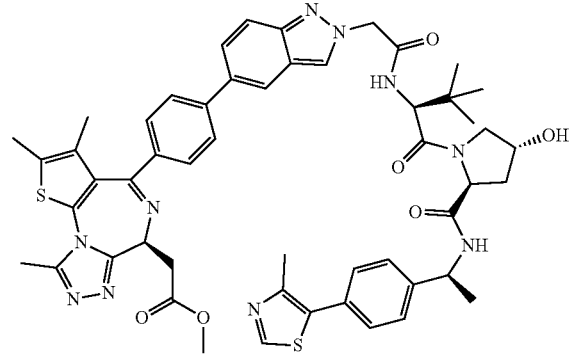 [SMILES: COC(=O)C[C@@H]1N=C(c2ccc(-c3ccc4nn(CC(=O)N[C@H](C(=O)N5C[C@H](O)C[C@H]5C(=O)N[C@@H](C)c5ccc(-c6scnc6C)cc5)C(C)(C)C)cc4c3)cc2)c2c(sc(C)c2C)-n2c(C)nnc21]

By reaction and treatment in the same manner as in Example 62 (62-1)-(62-2) and using Example compound 66-1 instead of t-butyl 4-bromo-3-fluoro-benzoate, the title compound was obtained as a pale-yellow solid.
MS (ESI) m/z: 981.5 [M+H]$^+$

Example 67

(67-1) methyl [(6S)-4-(4-{(3R)-3-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamoyl]pyrrolidin-1-yl}phenyl)-2,3,9-trimethyl-6H-thieno[3,2-f][1,2,4]triazolo[4,3-a][1,4]diazepin-6-yl]acetate (Example Compound 67)

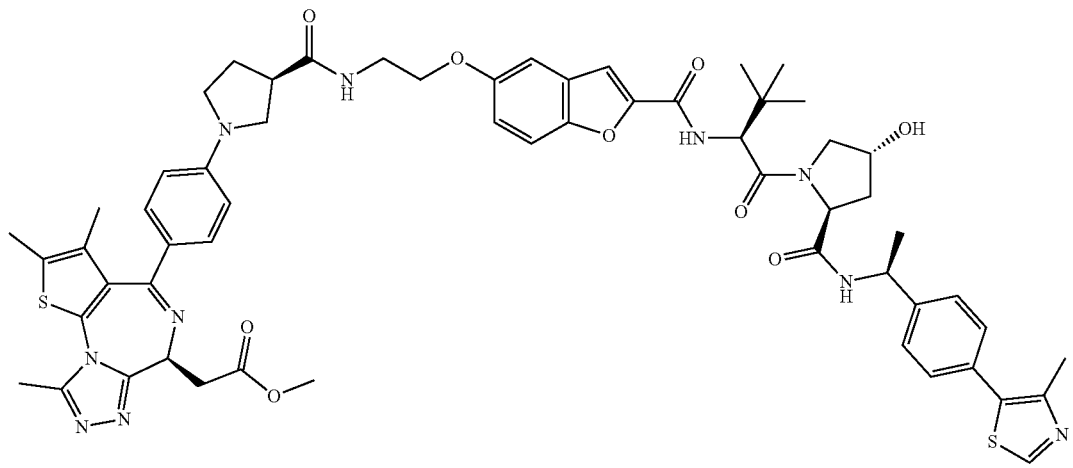

Example compound 42 (263 mg) was resolved by chiral column [CHIRALPAK IF (30*250), ethanol:tetrahydrofuran:diethylamine=60:40:0.1]. The fraction obtained first was recovered, concentrated, and purified by silica gel column chromatography (methanol:chloroform=0:100-10:90) to give the title compound (93 mg) as a pale-yellow solid. MS (ESI) m/z: 1123.5 [M+H]$^+$

Example 68

(68-1) methyl [(6S)-4-(4-{(3S)-3-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamoyl]pyrrolidin-1-yl}phenyl)-2,3,9-trimethyl-6H-thieno[3,2-f][1,2,4]triazolo[4,3-a][1,4]diazepin-6-yl]acetate (Example Compound 68)

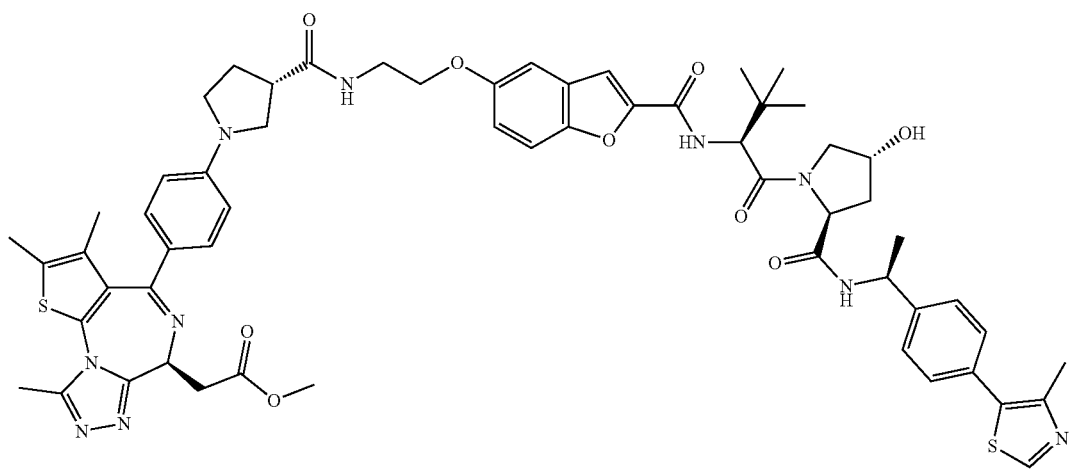

Example compound 42 (263 mg) was resolved by chiral column [CHIRALPAK IF (30*250), ethanol:tetrahydrofuran:diethylamine=60:40:0.1]. The fraction obtained later was recovered, concentrated, and purified by silica gel column chromatography (methanol:chloroform=0:100-10:90) to give the title compound (93 mg) as a pale-yellow solid. MS (ESI) m/z: 1123.5 [M+H]+

Example 69 and Example 70

(69-1) and (70-1) methyl [(6S)-4-(4-{(3R)-3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyrrolidin-1-yl}phenyl)-2,3,9-trimethyl-6H-thieno[3,2-f][1,2,4]triazolo[4,3-a][1,4]diazepin-6-yl]acetate and methyl [(6S)-4-(4-{(3S)-3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyrrolidin-1-yl}phenyl)-2,3,9-trimethyl-6H-thieno[3,2-f][1,2,4]triazolo[4,3-a][1,4]diazepin-6-yl]acetate)

Example compound 44 (230 mg) was separated by chiral column [CHIRALPAK IF (30*250), ethanol:tetrahydrofuran:diethylamine=60:40:0.1] to give both the title compounds (compound having shorter retention time, 74 mg (MS (ESI) m/z: 950.7 [M+H]+, Example compound 69) and compound having longer retention time, 74 mg (MS (ESI) m/z: 950.7 [M+H]+, Example compound 70)).

Example 71

(71-1) t-butyl [(2-chloropyrimidin-5-yl)oxy]acetate (Example Compound 71-1)

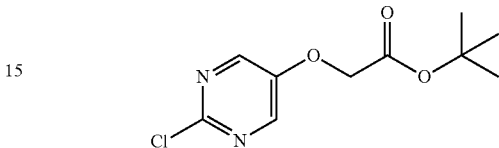

To a solution of 2-chloro-5-hydroxypyrimidine (261 mg) in N,N-dimethylformamide (5 mL) were added cesium carbonate (1.95 g), t-butyl bromoacetate (0.323 mL) and the mixture was stirred at room temperature for 20 hr. Water was added to the reaction mixture and the mixture was stirred and the resulting solid was filtered off. The precipitate was suspended in water, washed and dried to give the title compound (422 mg) as a white solid.
MS (ESI) m/z: 245.2, 247.2 [M+H]+

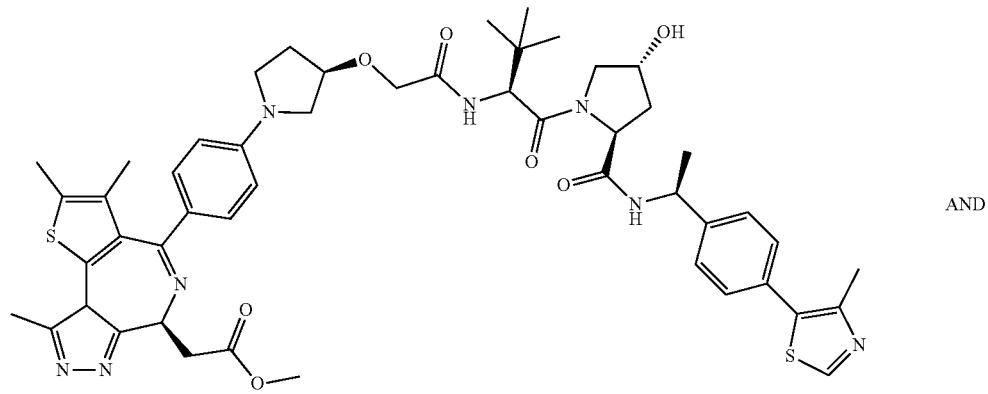

AND

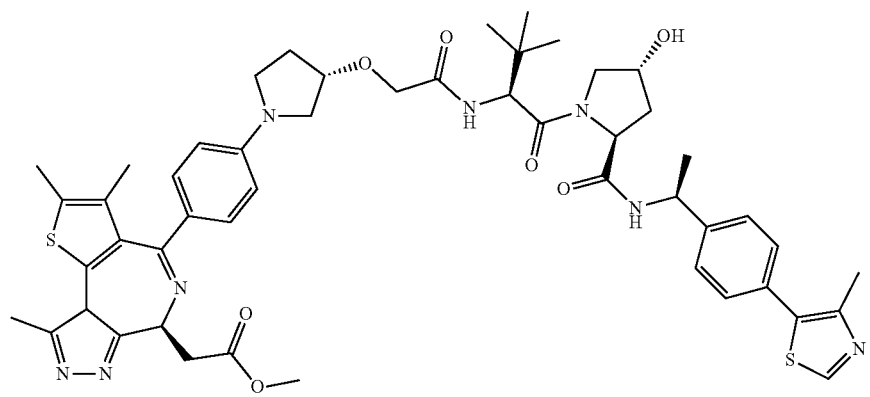

(71-2) [(2-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrimidin-5-yl)oxy]acetic acid hydrochloride (Example Compound 71-2)

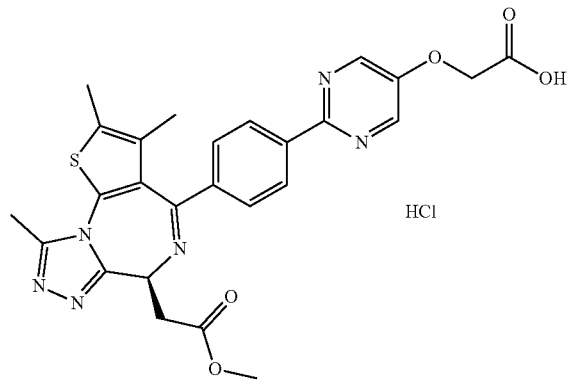 [SMILES: COC(=O)C[C@@H]1N=C(c2ccc(-c3ncc(OCC(=O)O)cn3)cc2)c2c(sc(C)c2C)-n2c(C)nnc21 ; Cl]

Under an argon stream, Example compound 71-1 (239 mg), Reference Example compound 2 (400 mg), palladium acetate (18 mg), S-phos (67 mg), potassium fluoride (142 mg) and water (0.053 mL) were heated under reflux in a tetrahydrofuran (5 mL) solvent for 7 hr. Palladium acetate (18 mg), S-phos (67 mg) were added and the mixture was further heated under reflux for 16 hr. Using ethyl acetate, the reaction mixture was filtered through diatomaceous earth, and the filtrate was concentrated under reduced pressure. The residue was purified by NH silica gel column chromatography (ethyl acetate:hexane=50:50-100:0) and silica gel column chromatography (methanol:chloroform=0:100-3:97) to give a white solid. The obtained solid was dissolved in chloroform (1 mL), trifluoroacetic acid (1 mL) was added and the mixture was stirred at room temperature for 15 hr. The reaction mixture was concentrated under reduced pressure, and the residue was dissolved in ethyl acetate, and saturated aqueous sodium hydrogen carbonate was slowly added to adjust to pH9. The mixture was washed twice with ethyl acetate, the aqueous layer was acidified with 1N hydrochloric acid and extracted 3 times with ethyl acetate. The organic layer was concentrated under reduced pressure to give the title compound (282 mg) as a yellow viscous compound. MS (ESI) m/z: 533.1 [M+H]$^+$ (71-3) methyl [(6S)-4-(4-{5-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyrimidin-2-yl}phenyl)-2,3,9-trimethyl-6H-thieno[3,2-f][1,2,4]triazolo[4,3-a][1,4]diazepin-6-yl]acetate (Example Compound 71)

By reaction and treatment in the same manner as in Example 97 (97-2) and using Example compound 71-2 instead of Example compound 97-1, the title compound was obtained as a white solid. MS (ESI) m/z: 959.9 [M+H]$^+$ Example 72

(72-1) t-butyl [(6-bromopyridin-3-yl)oxy]acetate (Example Compound 72-1)

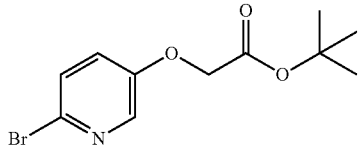

To a solution of 2-bromo-5-hydroxypyridine (348 mg) in acetonitrile (5 mL) were added cesium carbonate (1.96 g) and t-butyl bromoacetate (0.323 mL) and the mixture was stirred at room temperature for 4 hr. Using ethyl acetate, the reaction mixture was filtered, and the filtrate was concentrated under reduced pressure. The residue was purified by silica gel column chromatography (ethyl acetate:hexane=0:100-25:75) to give the title compound (566 mg) as a white solid.

MS (ESI) m/z: 288.0, 290.0 [M+H]$^+$ (72-2) [(6-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyridin-3-yl)oxy]acetic acid hydrochloride (Example Compound 72-2)

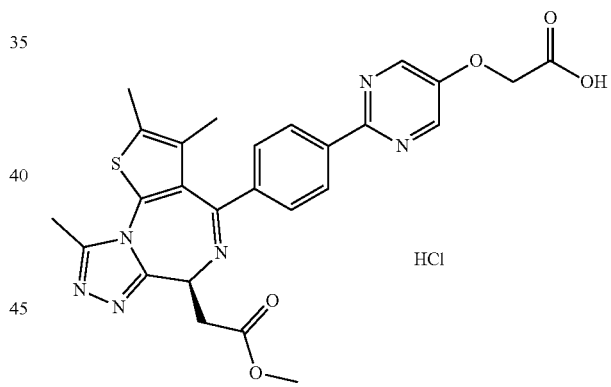

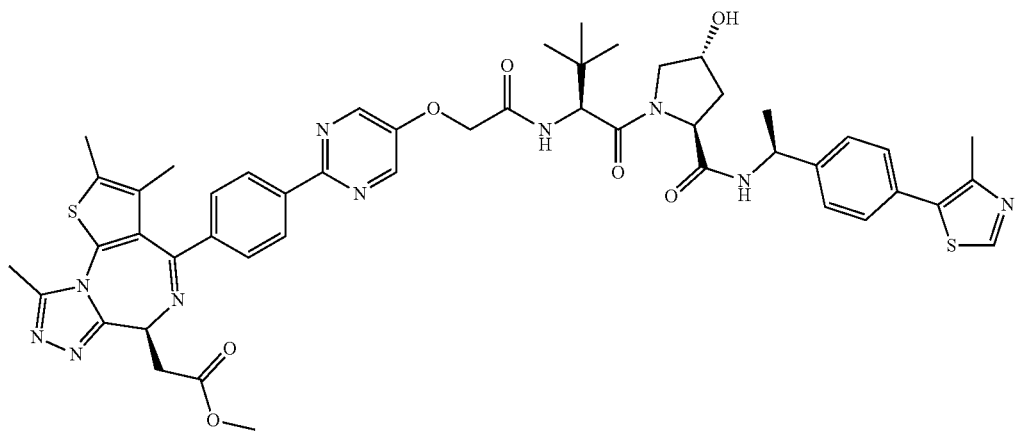 [SMILES: COC(=O)C[C@@H]1N=C(c2ccc(-c3ncc(OCC(=O)N[C@H](C(=O)N4C[C@H](O)C[C@H]4C(=O)N[C@@H](C)c4ccc(-c5scnc5C)cc4)C(C)(C)C)cn3)cc2)c2c(sc(C)c2C)-n2c(C)nnc21]

By reaction and treatment in the same manner as in Example 71 (71-2) and using Example compound 72-1 instead of Example compound 71-1, the title compound was obtained as a yellow viscous compound. MS (ESI) m/z: 532.1 [M+H]+

(72-3) methyl [(6S)-4-(4-{5-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyridin-2-yl}phenyl)-2,3,9-trimethyl-6H-thieno[3,2-f][1,2,4]triazolo[4,3-a][1,4]diazepin-6-yl]acetate (Example Compound 72)

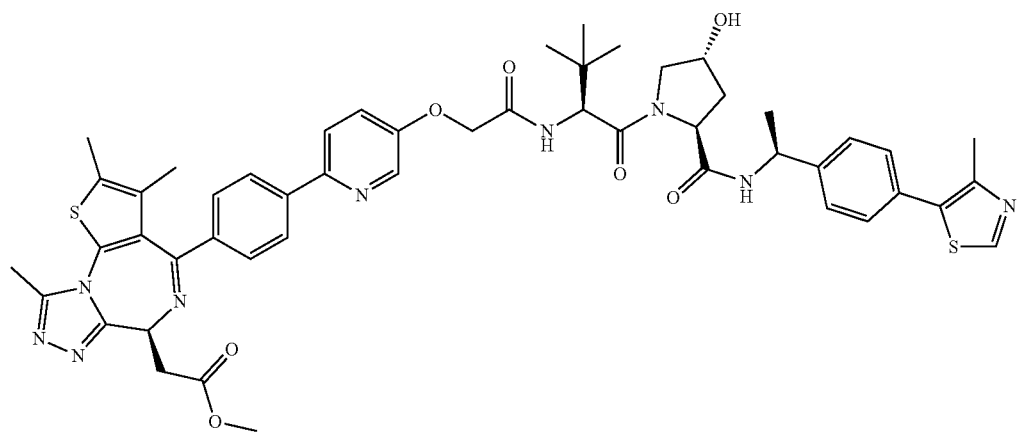 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cn3)cc2)c2c(sc(C)c2C)-n2c(C)nnc21]

By reaction and treatment in the same manner as in Example 97 (97-2) and using Example compound 72-2 instead of Example compound 97-1, the title compound was obtained as a white solid. MS (ESI) m/z: 958.4 [M+H]+

Example 73

(73-1) t-butyl [(5-bromopyrimidin-2-yl)amino]acetate (Example Compound 73-1)

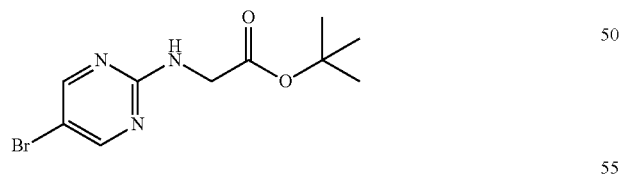

5-Bromo-2-chloropyrimidine (500 mg), t-butyl glycinate hydrochloride (520 mg) and triethylamine (0.898 mL) were stirred in N,N-dimethylformamide (5 mL) solvent at 50° C. for 6 hr. Water was added to the reaction mixture and the mixture was stirred and the resulting solid was filtered off. The precipitate was suspended in water, washed and dried to give the title compound (474 mg) as a white solid.

MS (ESI) m/z: 231.9, 233.9 [M−tBu+2H]+

(73-2) methyl {(6S)-4-[4-(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]amino}pyrimidin-5-yl)phenyl]-2,3,9-trimethyl-6H-thieno[3,2-f][1,2,4]triazolo[4,3-a] [1,4]diazepin-6-yl}acetate (Example Compound 73)

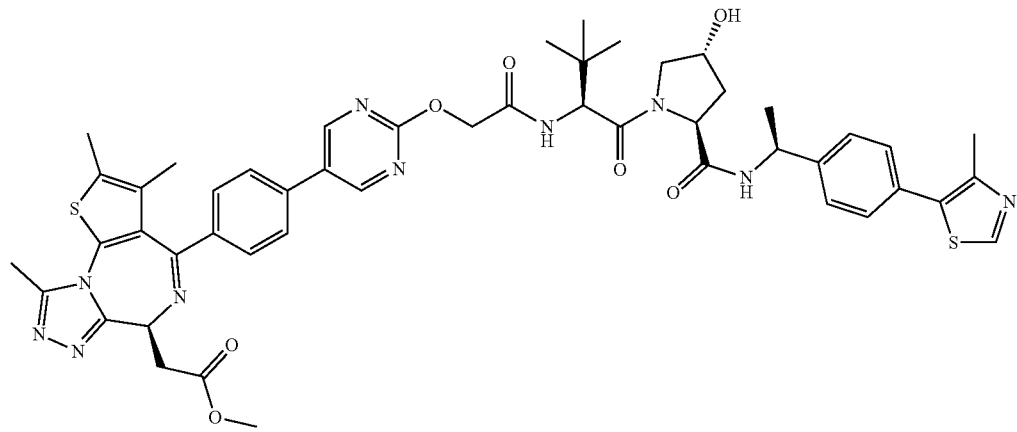 [SMILES: COC(=O)C[C@@H]1N=C(c2ccc(-c3cnc(OCC(=O)N[C@H](C(=O)N4C[C@H](O)C[C@H]4C(=O)N[C@@H](C)c4ccc(-c5scnc5C)cc4)C(C)(C)C)nc3)cc2)c2c(sc(C)c2C)-n2c(C)nnc21]

By reaction and treatment in the same manner as in Example 63 (63-2)-(63-3) and using Example compound 73-1 instead of Example compound 63-1, the title compound was obtained as a pale-yellow solid. MS (ESI) m/z: 958.4 [M+H]$^+$ Example 74

(74-1) methyl [(6S)-4-(4'-hydroxy-2'-methoxy[1,1'-biphenyl]-4-yl)-2,3,9-trimethyl-6H-thieno[3,2-f][1,2,4]triazolo[4,3-a] [1,4]diazepin-6-yl]acetate (Example Compound 74-1)

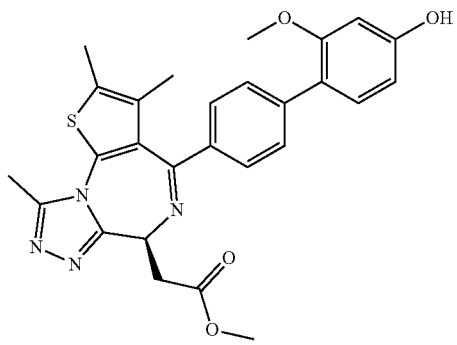 [SMILES: COC(=O)C[C@@H]1N=C(c2ccc(-c3ccc(O)cc3OC)cc2)c2c(sc(C)c2C)-n2c(C)nnc21]

To a solution of Reference Example compound 2 (300 mg) in tetrahydrofuran (6.1 mL) were added 4-bromo-3-methoxyphenol (136 mg), palladium acetate (14 mg), S-phos (50 mg), potassium fluoride (106 mg) and water (0.040 mL) and the mixture was stirred at 70° C. for 7 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=98:2-93:7) to give the title compound (189 mg) as a pale-yellow powder.

MS (ESI) m/z: 503.4 [M+H]$^+$ (74-2) methyl {(6S)-4-[4'-(2-t-butoxy-2-oxoethoxy)-2'-methoxy[1,1'-biphenyl]-4-yl]-2,3,9-trimethyl-6H-thieno[3,2-f] [1,2,4]triazolo[4,3-a][1,4]diazepin-6-yl}acetate (Example Compound 74-2)

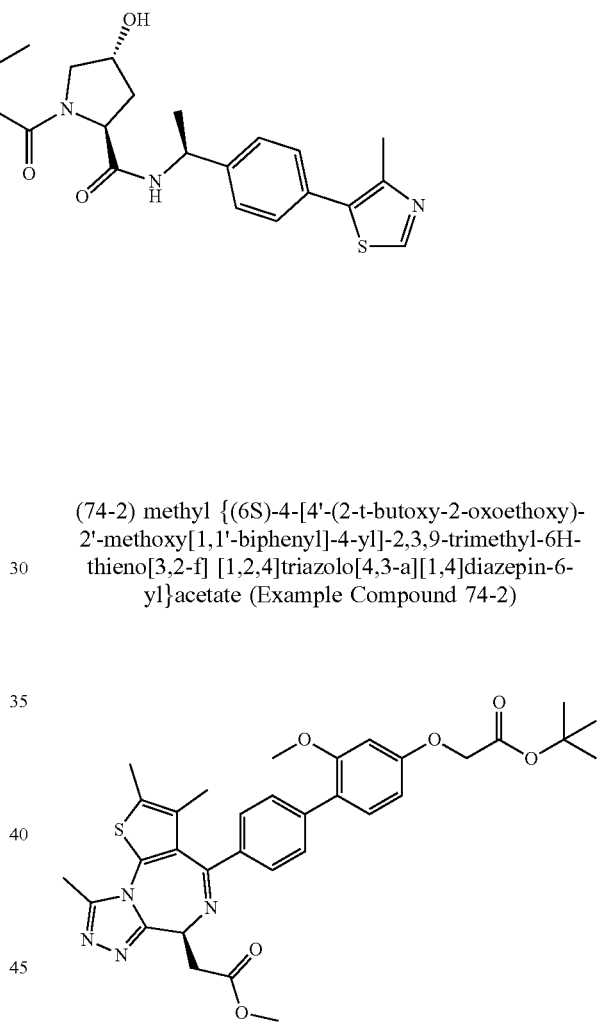

To a solution of Example compound 74-1 (185 mg) in N,N-dimethylformamide (3.7 mL) were added cesium carbonate (240 mg) and t-butyl bromoacetate (93 mg), and the mixture was stirred at 60° C. for 4 hr. Ice water was added to the reaction solution and the mixture was extracted with ethyl acetate. The organic layer was washed with water and saturated brine, and dried over anhydrous sodium sulfate. The solvent was evaporated under reduced pressure. The residue was purified by silica gel column chromatography (chloroform:methanol=98:2-93:7) to give the title compound (209 mg) as a yellow powder.

MS (ESI) m/z: 617.5 [M+H]$^+$ (74-3) ({2-methoxy-4'-[(6S)-6-(2-methoxy-2-oxo-ethyl)-2,3,9-trimethyl-6H-thieno[3,2-f][1,2,4]triazolo[4,3-a][1,4]diazepin-4-yl][1,1'-biphenyl]-4-yl}oxy)acetic acid trifluoroacetate (Example Compound 74-3)

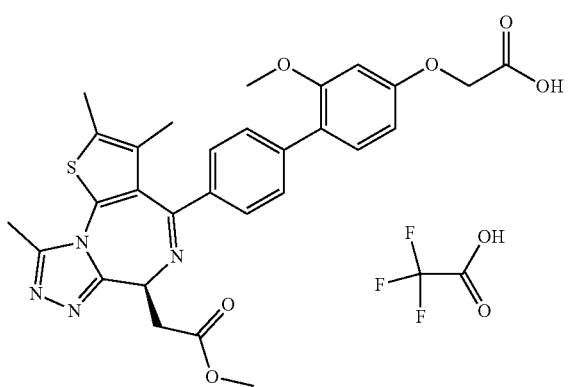 [SMILES: COC(=O)C[C@@H]1N=C(c2ccc(-c3ccc(OCC(=O)O)cc3OC)cc2)c2c(sc(C)c2C)-n2c(C)nnc21 ; O=C(O)C(F)(F)F]

To a solution of Example compound 74-2 (205 mg) in dichloromethane (2.0 mL) was added dropwise under ice-cooling trifluoroacetic acid (2.0 mL), and the mixture was allowed to naturally warm to room temperature and stirred for 2 hr. The reaction solution was diluted with ethyl acetate, the solvent was evaporated under reduced pressure, and the residue was further concentrated azeotropically with toluene. This operation was performed two times to give the title compound (321 mg) as a crudely purified orange viscous compound.

MS (ESI) m/z: 561.4 [M+H]+

(74-4) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-2'-methoxy[1,1'-biphenyl]-4-yl}-2,3,9-trimethyl-6H-thieno[3,2-f][1,2,4]triazolo[4,3-a] [1,4]diazepin-6-yl]acetate (Example Compound 74)

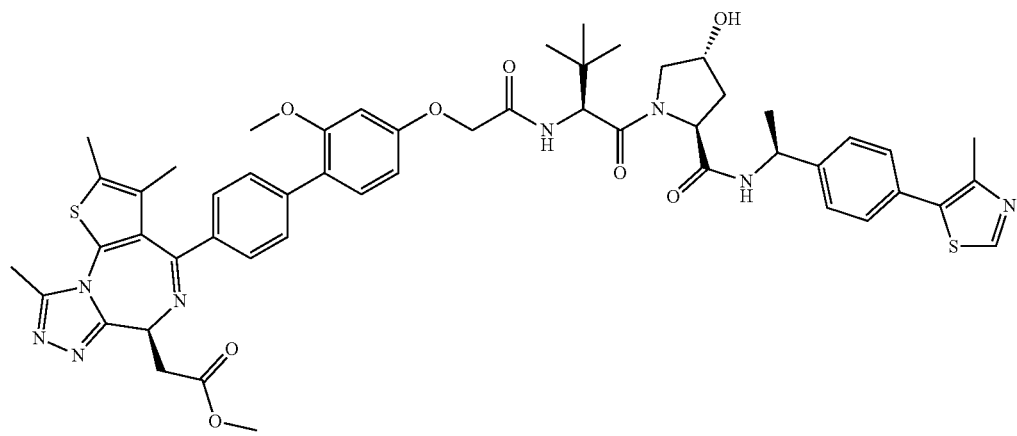 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3OC)cc2)c2c(sc(C)c2C)-n2c(C)nnc21]

To a solution of Example compound 74-3 (315 mg), Reference Example compound 5 (160 mg) in N,N-dimethylformamide (3.3 mL) was added N,N-diisopropylethylamine (0.345 mL), and HATU (379 mg) was added under ice-cooling, and the mixture was allowed to naturally warm to room temperature and stirred for 5 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-85:15) and further purified by silica gel column chromatography (chloroform:methanol=100:0-97:3). The obtained solid was suspension washed with diethyl ether, collected by filtration and dried under reduced pressure to give the title compound (199 mg) as a white solid.

MS (ESI) m/z: 987.9 [M+H]+

Example 75

(75-1) methyl {(6S)-4-[4'-hydroxy-2'-(trifluoromethoxy)[1,1'-biphenyl]-4-yl]-2,3,9-trimethyl-6H-thieno[3,2-f] [1,2,4]triazolo[4,3-a][1,4]diazepin-6-yl}acetate (Example Compound 75-1)

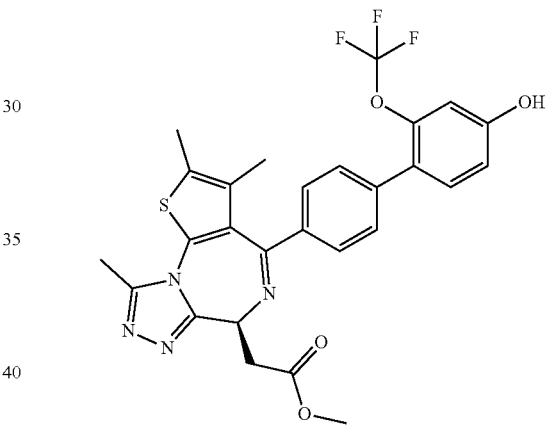

To a solution of Reference Example compound 2 (300 mg) in tetrahydrofuran (6.1 mL) were added 4-bromo-3-trifluoromethoxyphenol (172 mg), palladium acetate (14 mg), S-phos (50 mg), potassium fluoride (106 mg) and water (0.040 mL) and the mixture was stirred at 70° C. for 7 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=98:2-93:7) to give the title compound (309 mg) as a pale-yellow powder. MS (ESI) m/z: 557.3 [M+H]⁺, 555.4 [M–H]⁻

(75-2) methyl {(6S)-4-[4'-(2-t-butoxy-2-oxoethoxy)-2'-(trifluoromethoxy)[1,1'-biphenyl]-4-yl]-2,3,9-trimethyl-6H-thieno[3,2-f][1,2,4]triazolo[4,3-a][1,4]diazepin-6-yl}acetate (Example Compound 75-2)

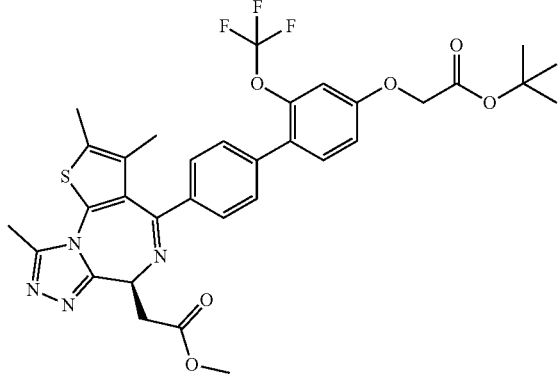 [SMILES: COC(=O)C[C@@H]1N=C(c2ccc(-c3ccc(OCC(=O)OC(C)(C)C)cc3OC(F)(F)F)cc2)c2c(sc(C)c2C)-n2c(C)nnc21]

To a solution of Example compound 75-1 (305 mg) in N,N-dimethylformamide (5.5 mL) was added cesium carbonate (357 mg) and the mixture was stirred for about 10 min. t-Butyl bromoacetate (139 mg) was added, and the mixture was stirred at 60° C. for 4 hr. To the reaction solution were added saturated aqueous ammonium chloride solution and water and the mixture was extracted with ethyl acetate. The organic layer was washed with saturated brine and dried over anhydrous sodium sulfate. The solvent was evaporated under reduced pressure. The residue was purified by silica gel column chromatography (chloroform:methanol=98:2-93:7) to give the title compound (215 mg) as a yellow powder. MS (ESI) m/z: 671.5 [M+H]⁺

(75-3) ({4'-[(6S)-6-(2-methoxy-2-oxoethyl)-2,3,9-trimethyl-6H-thieno[3,2-f][1,2,4]triazolo[4,3-a][1,4]diazepin-4-yl]-2-(trifluoromethoxy)[1,1'-biphenyl]-4-yl}oxy)acetic acid trifluoroacetate (Example Compound 75-3)

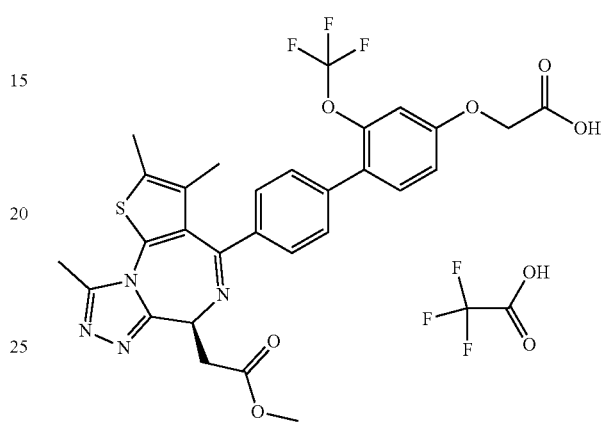

To a solution of Example compound 75-2 (210 mg) in dichloromethane (2.0 mL) was added dropwise under ice-cooling trifluoroacetic acid (2.0 mL), and the mixture was allowed to naturally warm to room temperature and stirred for 2 hr. The reaction solution was diluted with ethyl acetate, the solvent was evaporated under reduced pressure, and the residue was further concentrated azeotropically with toluene. This operation was performed two times to give the title compound (337 mg) as a crudely purified orange viscous compound.
MS (ESI) m/z: 615.4 [M+H]⁺

(75-4) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-2'-(trifluoromethoxy)[1,1'-biphenyl]-4-yl}-2,3,9-trimethyl-6H-thieno[3,2-f][1,2,4]triazolo[4,3-a][1,4]diazepin-6-yl]acetate (Example Compound 75)

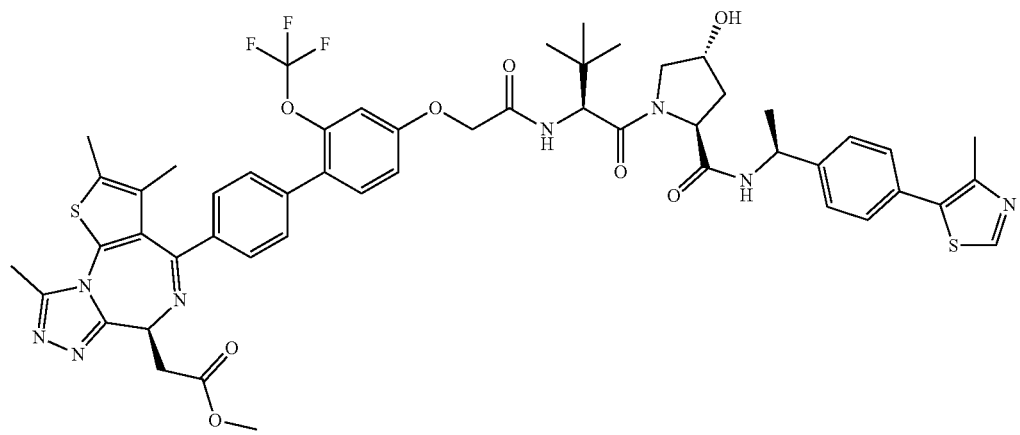 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3OC(F)(F)F)cc2)c2c(sc(C)c2C)-n2c(C)nnc21]

To a solution of Example compound 75-3 (330 mg), Reference Example compound 5 (151 mg) in N,N-dimethylformamide (3.1 mL) was added N,N-diisopropylethylamine (0.325 mL), and HATU (357 mg) was added under ice-cooling, and the mixture was allowed to naturally warm to room temperature and stirred for 5 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=97:3-88:12) and further purified by silica gel column chromatography (chloroform:methanol=100:0-97:3). The obtained solid was suspension washed with diethyl ether, collected by filtration and dried under reduced pressure to give the title compound (19 mg) as a white solid.

MS (ESI) m/z: 1041.7 [M+H]$^+$

Example 76

(76-1) methyl {(6S)-4-[4'-hydroxy-2'-(trifluoromethyl)[1,1'-biphenyl]-4-yl]-2,3,9-trimethyl-6H-thieno[3,2-f][1,2,4]triazolo[4,3-a][1,4]diazepin-6-yl}acetate (Example Compound 76-1)

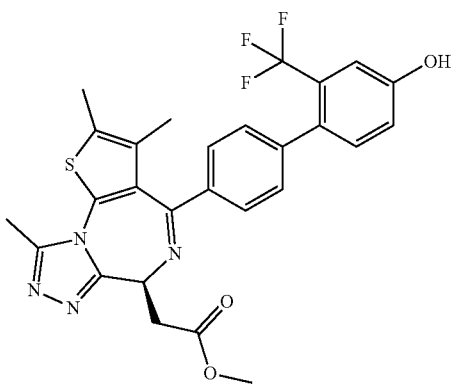 [SMILES: COC(=O)C[C@@H]1N=C(c2ccc(-c3ccc(O)cc3C(F)(F)F)cc2)c2c(sc(C)c2C)-n2c(C)nnc21]

To a solution of Reference Example compound 2 (300 mg) in tetrahydrofuran (6.1 mL) were added 4-bromo-3-trifluoromethylphenol (162 mg), palladium acetate (14 mg), S-phos (50 mg), potassium fluoride (106 mg) and water (0.040 mL) and the mixture was stirred at 70° C. for 7 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=98:2-93:7) to give the title compound (279 mg) as a pale-yellow solid. MS (ESI) m/z: 541.3 [M+H]$^+$ (76-2) methyl {(6S)-4-[4'-(2-t-butoxy-2-oxoethoxy)-2'-(trifluoromethyl)[1,1'-biphenyl]-4-yl]-2,3,9-trimethyl-6H-thieno[3,2-f][1,2,4]triazolo[4,3-a][1,4]diazepin-6-yl}acetate (Example Compound 76-2)

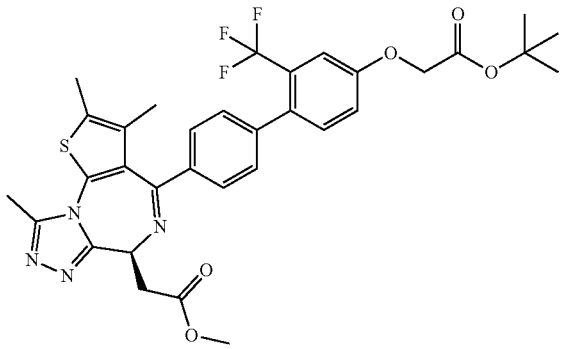 [SMILES: COC(=O)C[C@@H]1N=C(c2ccc(-c3ccc(OCC(=O)OC(C)(C)C)cc3C(F)(F)F)cc2)c2c(sc(C)c2C)-n2c(C)nnc21]

To a solution of Example compound 76-1 (275 mg) in N,N-dimethylformamide (5.1 mL) was added cesium carbonate (332 mg) and the mixture was stirred for 10 min. t-Butyl bromoacetate (129 mg) was added, and the mixture was stirred at 60° C. for 4 hr. To the reaction solution were added saturated aqueous ammonium chloride solution and water and the mixture was extracted with ethyl acetate. The organic layer was washed with saturated brine and dried over anhydrous sodium sulfate. The solvent was evaporated under reduced pressure. The residue was purified by silica gel column chromatography (chloroform:methanol=98:2-93:7) to give the title compound (272 mg) as a yellow powder. MS (ESI) m/z: 655.5 [M+H]$^+$ (76-3) ({4'-[(6S)-6-(2-methoxy-2-oxoethyl)-2,3,9-trimethyl-6H-thieno[3,2-f][1,2,4]triazolo[4,3-a][1,4]diazepin-4-yl]-2-(trifluoromethyl)[1,1'-biphenyl]-4-yl}oxy)acetic acid trifluoroacetate (Example Compound 76-3)

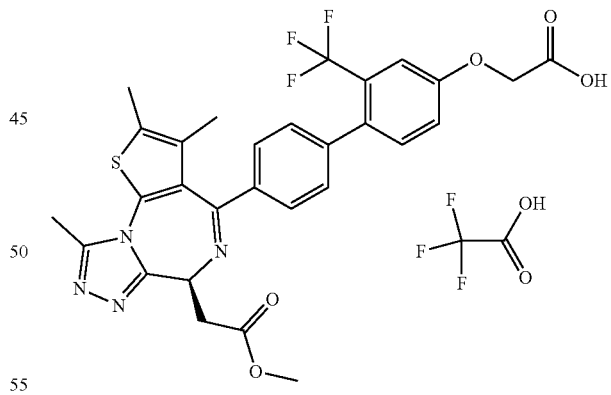

To a solution of Example compound 76-2 (268 mg) in dichloromethane (2.0 mL) was added dropwise under ice-cooling trifluoroacetic acid (2.0 mL), and the mixture was allowed to naturally warm to room temperature and stirred for 2 hr. The reaction solution was diluted with ethyl acetate, and the solvent was evaporated under reduced pressure. The residue was further concentrated azeotropically with toluene and this operation was performed two times to give the title compound (404 mg) as a crudely purified orange viscous compound.

MS (ESI) m/z: 599.4 [M+H]$^+$ (76-4) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-2'-(trifluoromethyl)[1,1'-biphenyl]-4-yl}-2,3,9-trimethyl-6H-thieno[3,2-f] [1,2,4]triazolo[4,3-a][1,4]diazepin-6-yl]acetate (Example Compound 76)

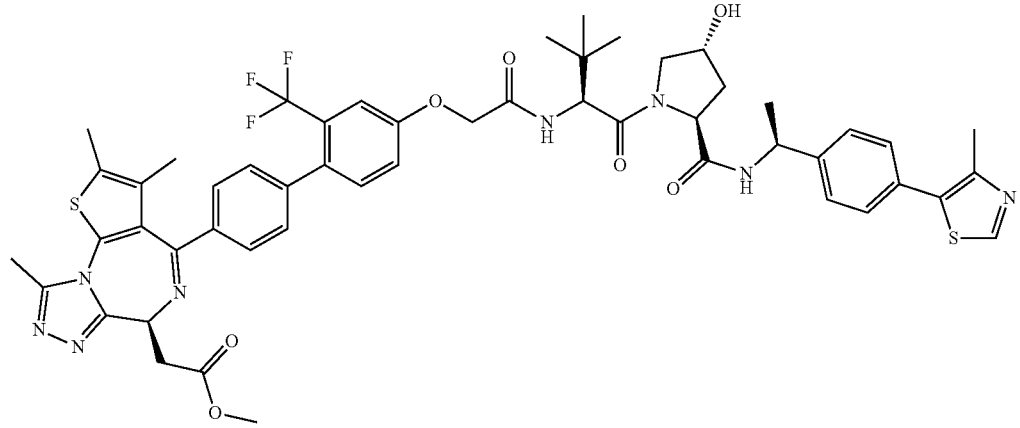 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3C(F)(F)F)cc2)c2c(sc(C)c2C)-n2c(C)nnc21]

To a solution of Example compound 76-3 (400 mg), Reference Example compound 5 (197 mg) in N,N-dimethylformamide (4.1 mL) was added N,N-diisopropylethylamine (0.425 mL), and HATU (467 mg) was added under ice-cooling, and the mixture was allowed to naturally warm to room temperature and stirred for 5 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=97:3-88:12) and further purified by silica gel column chromatography (chloroform:methanol=100:0-97:3). The obtained solid was suspension washed with diethyl ether, collected by filtration and dried under reduced pressure to give the title compound (219 mg) as a white solid.
MS (ESI) m/z: 1025.8 [M+H]$^+$ Example 77

(77-1) methyl [(6S)-4-(2'-cyano-4'-hydroxy[1,1'-biphenyl]-4-yl)-2,3,9-trimethyl-6H-thieno[3,2-f][1,2,4]triazolo[4,3-a] [1,4]diazepin-6-yl]acetate (Example Compound 77-1)

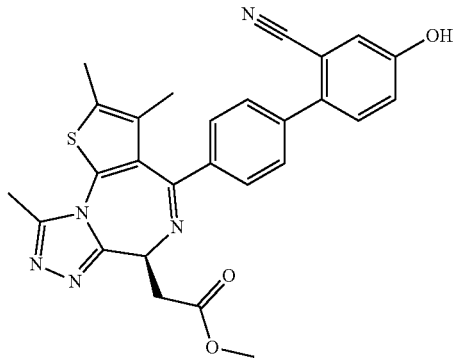 [SMILES: COC(=O)C[C@@H]1N=C(c2ccc(-c3ccc(O)cc3C#N)cc2)c2c(sc(C)c2C)-n2c(C)nnc21]

To a solution of Reference Example compound 2 (300 mg) in tetrahydrofuran (6.1 mL) were added 2-bromo-5-hydroxybenzonitrile (133 mg), palladium acetate (14 mg), S-phos (50 mg), potassium fluoride (106 mg) and water (0.040 mL) and the mixture was stirred at 70° C. for 7 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=98:2-93:7) to give the title compound (250 mg) as a pale-yellow powder. MS (ESI) m/z: 498.3 [M+H]$^+$ (77-2) methyl {(6S)-4-[4'-(2-t-butoxy-2-oxoethoxy)-2'-cyano[1,1'-biphenyl]-4-yl]-2,3,9-trimethyl-6H-thieno[3,2-f] [1,2,4]triazolo[4,3-a][1,4]diazepin-6-yl}acetate (Example Compound 77-2)

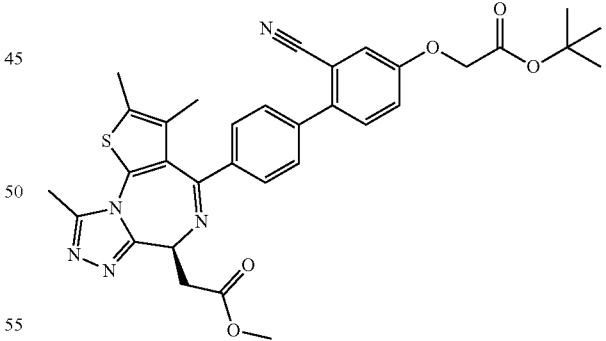

To a solution of Example compound 77-1 (245 mg) in N,N-dimethylformamide (4.9 mL) was added cesium carbonate (321 mg) and the mixture was stirred for 10 min. t-Butyl bromoacetate (125 mg) was added, and the mixture was stirred at 60° C. for 4 hr. To the reaction solution were added saturated aqueous ammonium chloride solution and water and the mixture was extracted with ethyl acetate. The organic layer was washed with saturated brine and dried over anhydrous sodium sulfate. The solvent was evaporated under reduced pressure. The residue was purified by silica gel column chromatography (chloroform:methanol=98:2-93:7) to give the title compound (273 mg) as a yellow powder. MS (ESI) m/z: 612.5 [M+H]⁺

(77-3) ({2-cyano-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetic acid trifluoroacetate (Example Compound 77-3)

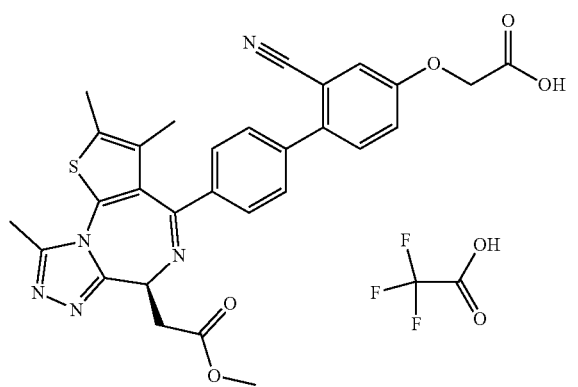 [SMILES: COC(=O)C[C@@H]1N=C(c2ccc(-c3ccc(OCC(=O)O)cc3C#N)cc2)c2c(sc(C)c2C)-n2c(C)nnc21 ; O=C(O)C(F)(F)F]

To a solution of Example compound 77-2 (268 mg) in dichloromethane (2.0 mL) was added dropwise under ice-cooling trifluoroacetic acid (2.0 mL), and the mixture was allowed to naturally warm to room temperature and stirred for 2 hr. The reaction solution was diluted with ethyl acetate, the solvent was evaporated under reduced pressure, and the residue was further concentrated azeotropically with toluene. This operation was performed two times to give the title compound (407 mg) as a crudely purified orange viscous compound. MS (ESI) m/z: 556.4 [M+H]⁺

(77-4) methyl [(6S)-4-{2'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 77)

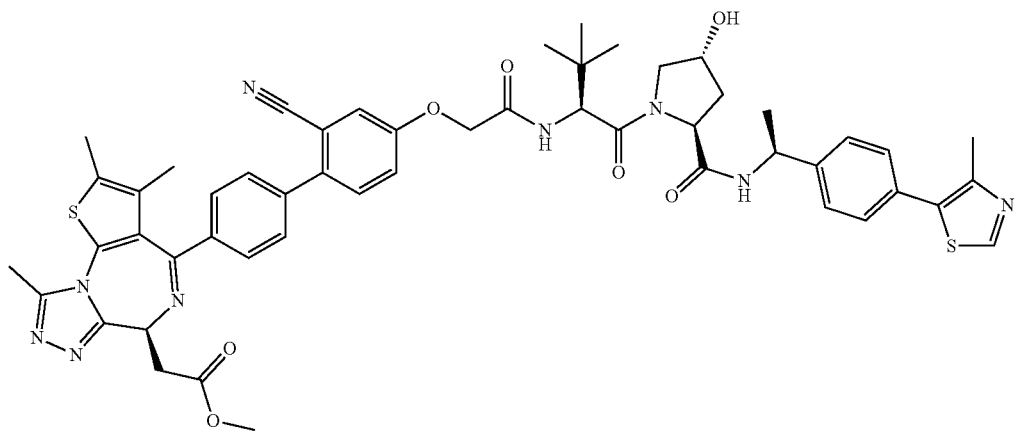 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3C#N)cc2)c2c(sc(C)c2C)-n2c(C)nnc21]

To a solution of Example compound 77-3 (400 mg), Reference Example compound 5 (211 mg) in N,N-dimethylformamide (4.4 mL) was added N,N-diisopropylethylamine (0.455 mL), and HATU (500 mg) was added under ice-cooling, and the mixture was allowed to naturally warm to room temperature and stirred for 5 hr. Water was added to the reaction solution and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-85:15) and further purified by silica gel column chromatography (chloroform:methanol=100:0-97:3). The obtained solid was suspension washed with diethyl ether, collected by filtration and dried under reduced pressure to give the title compound (216 mg) as a white solid.

MS (ESI) m/z: 982.7 [M+H]⁺

Example 78 and Example 79

(78-1), (79-1) methyl [(6S)-4-(4'-{[(2S)-1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]oxy}[1,1'-biphenyl]-4-yl)-2,3,9-trimethyl-6H-thieno[3,2-f][1,2,4]triazolo[4,3-a] [1,4]diazepin-6-yl]acetate and methyl [(6S)-4-(4'-{[(2R)-1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]oxy}[1,1'-biphenyl]-4-yl)-2,3,9-trimethyl-6H-thieno[3,2-f] [1,2,4]triazolo [4,3-a][1,4]diazepin-6-yl]acetate (Example Compound 78 and Example compound 79)

Example 80

(80-1) 1,2,3,4-tetrahydroisoquinolin-7-ol hydrochloride (Example Compound 80-1)

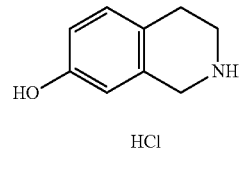 [SMILES: Oc1ccc2c(c1)CNCC2 ; Cl]

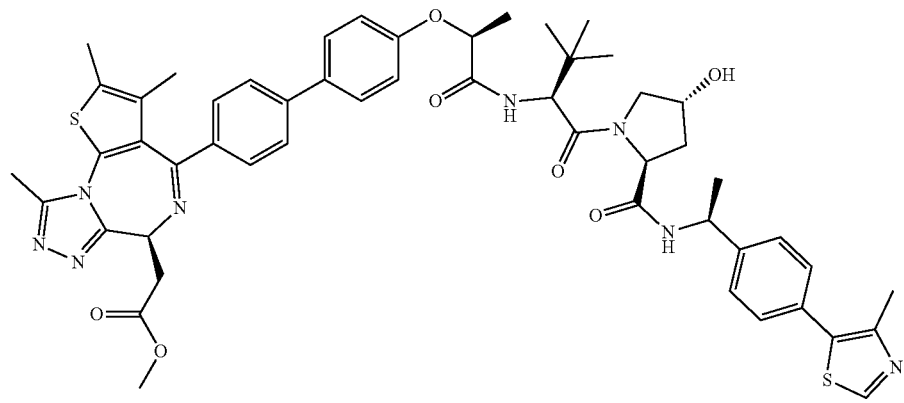

AND

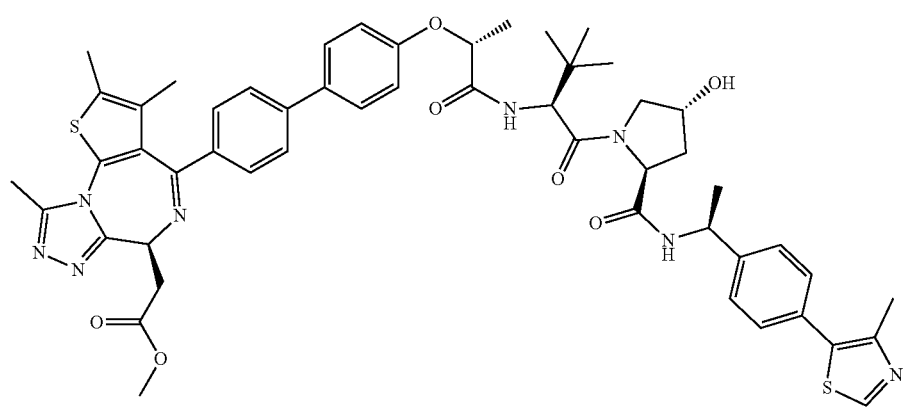

Example compound 50 (300 mg) was purified by preparative HPLC (10 mM aqueous ammonium carbonate solution-acetonitrile) to give both the title compounds (compound having shorter retention time, 128 mg (MS (ESI) m/z: 971.5 [M+H]⁺, Example compound 78) and compound having longer retention time, 132 mg (MS (ESI) m/z: 971.5 [M+H]⁺, Example compound 79)) as pale-yellow solids.

To a solution of 7-hydroxy-2-N-(t-butoxycarbonyl)-3,4-dihydroisoquinoline (1 g) in t-butanol (27 mL) was added 4 M hydrogen chloride/ethyl acetate solution (30 mL) and the mixture was stirred for 2 hr. The reaction mixture was concentrated under reduced pressure to give the title compound (665 mg) as a white solid. MS (ESI) m/z: 150.0 [M+H]⁺

(80-2) t-butyl [(1,2,3,4-tetrahydroisoquinolin-7-yl)oxy]acetate (Example Compound 80-2)

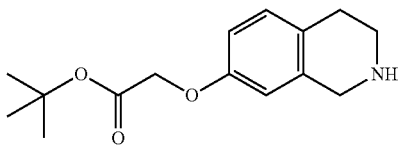 [SMILES: CC(C)(C)OC(=O)COc1ccc2c(c1)CNCC2]

To a solution of Example compound 80-1 (665 mg) in N,N-dimethylformamide (36 mL) were added potassium carbonate (990 mg), t-butyl bromoacetate (0.591 mL) and the mixture was stirred at 40° C. for 2 hr. Water was added to the reaction mixture and the mixture was stirred and the precipitate was collected by filtration to give the title compound (841 mg) as a white solid. MS (ESI) m/z: 264.1 [M+H]$^+$ (80-3) methyl [(6S)-4-{4-[7-(2-t-butoxy-2-oxoethoxy)-3,4-dihydroisoquinolin-2(1H)-yl]phenyl}-2,3,9-trimethyl-6H-thieno[3,2-f][1,2,4]triazolo[4,3-a][1,4]diazepin-6-yl]acetate (Example Compound 80-3)

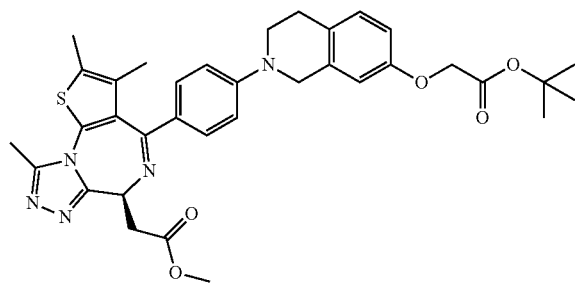 [SMILES: COC(=O)C[C@@H]1N=C(c2ccc(N3CCc4ccc(OCC(=O)OC(C)(C)C)cc4C3)cc2)c2c(sc(C)c2C)-n2c(C)nnc21]

Under an argon stream, Reference Example compound 1 (500 mg), Example compound 80-2 (381 mg), tris(dibenzylideneacetone)dipalladium(0) (55 mg), t-BuXphos (51 mg) and potassium phosphate (767 mg) were stirred in 1,2-dimethoxyethane (8 mL) solvent at 80° C. for 3 hr. Water was added to the reaction mixture and the mixture was stirred and extracted twice with ethyl acetate. Using ethyl acetate, the extract was filtered through celite. The filtrate was concentrated under reduced pressure, and the residue was purified by NH silica gel column chromatography (ethyl acetate:hexane=30:70-75:25) to give the title compound (841 mg) as an orange viscous compound. MS (ESI) m/z: 642.3 [M+H]$^+$ (80-4) [(2-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1,2,3,4-tetrahydroisoquinolin-7-yl)oxy]acetic acid trifluoroacetate (Example Compound 80-4)

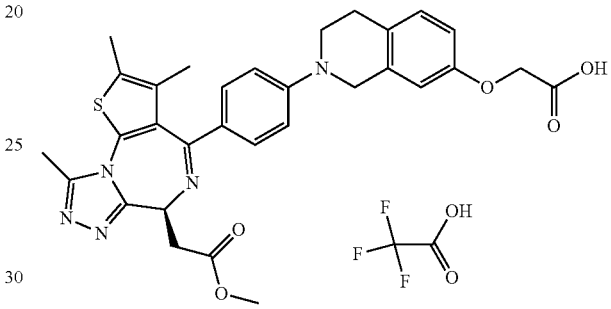

To a solution of Example compound 80-3 (619 mg) in chloroform (4 mL) was added trifluoroacetic acid (2 mL) and the mixture was stirred at room temperature for 24 hr. The reaction mixture was concentrated under reduced pressure, and azeotropically distilled 3 times with toluene to give the title compound (1.10 g) as a yellow viscous compound. MS (ESI) m/z: 586.6 [M+H]$^+$ (80-5) methyl [(6S)-4-(4-{7-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-3,4-dihydroisoquinolin-2(1H)-yl}phenyl)-2,3,9-trimethyl-6H-thieno[3,2-f][1,2,4]triazolo[4,3-a][1,4]diazepin-6-yl]acetate (Example Compound 80)

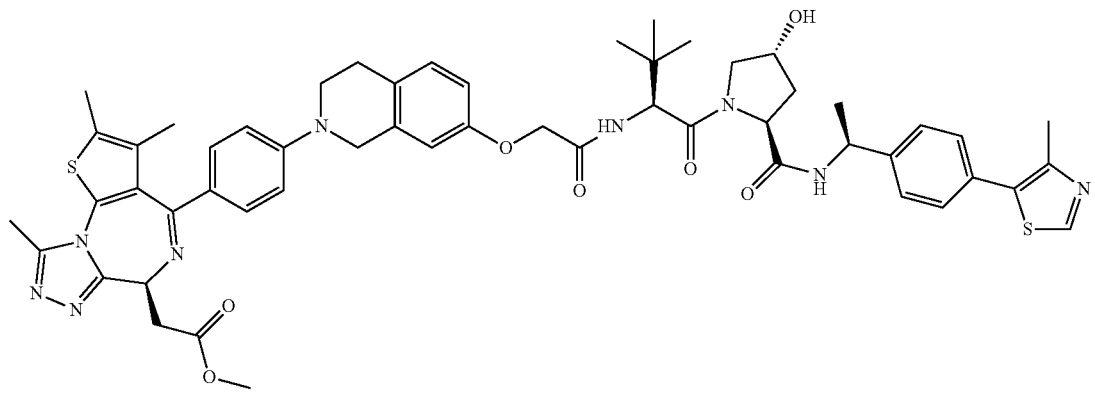 [SMILES: COC(=O)C[C@@H]1N=C(c2ccc(N3CCc4ccc(OCC(=O)N[C@H](C(=O)N5C[C@H](O)C[C@H]5C(=O)N[C@@H](C)c5ccc(-c6scnc6C)cc5)C(C)(C)C)cc4C3)cc2)c2c(sc(C)c2C)-n2c(C)nnc21]

Example compound 80-4 (210 mg) was dissolved in N,N-dimethylformamide (5 mL), and Reference Example compound 5 (173 mg), N,N-diisopropylethylamine (0.519 mL) and HATU (171 mg) m were added and the mixture was stirred at room temperature for 1 hr. Water was added to the reaction mixture and the mixture was stirred. The precipitate was collected by filtration. The solid was purified by silica gel column chromatography (methanol:ethyl acetate=0:100-5:95) to give the title compound (85 mg) as a yellow powder. MS (ESI) m/z: 1012.3 [M+H]$^+$ Example 81

(81-1) t-butyl 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrrolidine-3-carboxylate (Example Compound 81-1)

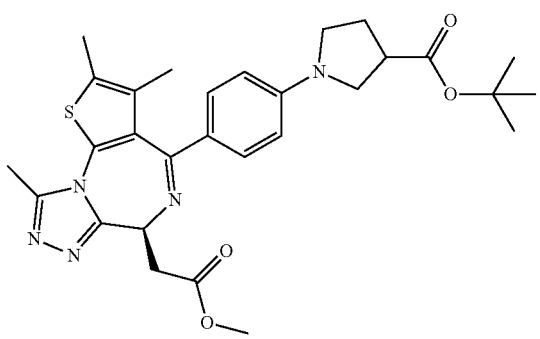 [SMILES: COC(=O)C[C@@H]1N=C(c2ccc(N3CCC(C(=O)OC(C)(C)C)C3)cc2)c2c(sc(C)c2C)-n2c(C)nnc21]

3-(t-Butoxycarbonyl)pyrrolidine (2.1 g), Reference Example compound 1 (5.0 g), tris(dibenzylideneacetone)dipalladium(0) (552 mg), t-BuXphos (512 mg) and potassium phosphate (7.67 g) were heated under reflux in tetrahydrofuran (40 mL) solvent for 6 hr. Tris(dibenzylideneacetone)dipalladium(0) (110 mg) and t-BuXphos (102 mg) were added, and the mixture was further stirred with heating under reflux for 18 hr. Using chloroform, the reaction mixture was filtered through celite, and the filtrate was concentrated under reduced pressure. The residue was purified by silica gel column chromatography (methanol:chloroform=2:98-7:93) twice to give the title compound (4.86 g) as an orange solid. MS (ESI) m/z: 550.3 [M+H]$^+$ (81-2) methyl [(6S)-4-{4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrrolidin-1-yl]phenyl}-2,3,9-trimethyl-6H-thieno[3,2-f][1,2,4]triazolo[4,3-a][1,4]diazepin-6-yl]acetate (Example Compound 81)

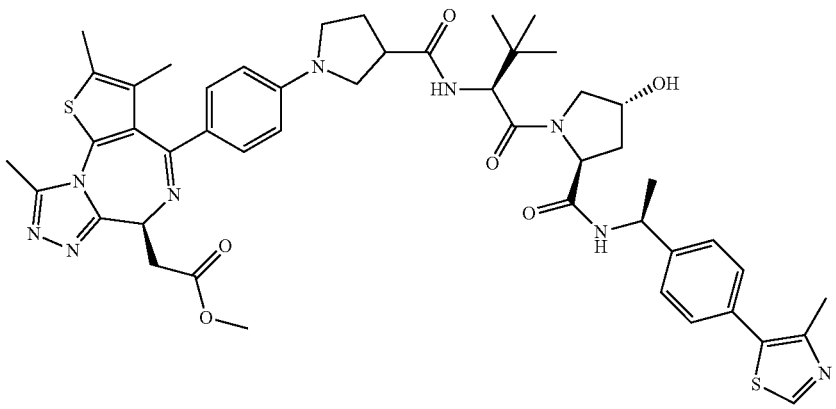

By reaction and treatment in the same manner as in Example 80 (80-4)-(80-5) and using Example compound 81-1 instead of Example compound 80-3, the title compound was obtained as a yellow powder. MS (ESI) m/z: 920.3 [M+H]$^+$ Example 82

(82-1) benzyl 4-(3-t-butoxy-3-oxypropyl)piperazine-1-carboxylate (Example Compound 82-1)

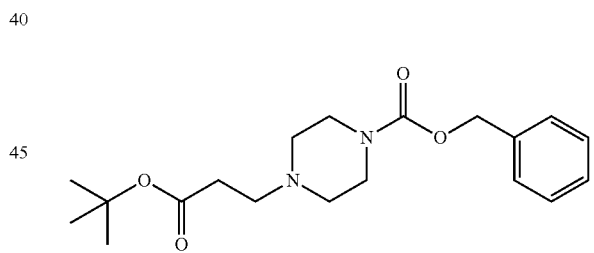

By reaction and treatment in the same manner as in Example 64 (64-1) and using 1-(benzyloxycarbonyl)-piperazine instead of 4-bromopyrazole, the title compound was obtained as a white solid. MS (ESI) m/z: 349.4 [M+H]$^+$ (82-2) t-butyl 3-(piperazin-1-yl)propanoate (Example Compound 82-2)

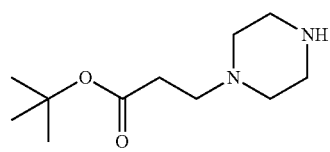

To a solution of Example compound 82-1 (2.6 g) in ethanol (15 mL), methanol (20 mL) was added 10% palladium carbon (500 mg) and, after hydrogen substitution, the mixture was stirred at room temperature for 5 hr. Using methanol, the reaction mixture was filtered through celite and the filtrate was concentrated under reduced pressure to give the title compound (2.1 g) as an orange oil. MS (ESI) m/z: 215.1 [M+H]+

(82-3) methyl [(6S)-4-(4-{4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl]piperazin-1-yl}phenyl)-2,3,9-trimethyl-6H-thieno[3,2-f][1,2,4]triazolo[4,3-a][1,4]diazepin-6-yl]acetate (Example Compound 82)

Under an argon stream, to a solution of trans-t-butyl 3-hydroxycyclobutylcarbamate (2 g) and triethylamine (2.2 mL) in dichloromethane (54 mL) was added methanesulfonyl chloride (1 mL) at −30° C. and the mixture was stirred for 30 min. Water was added to the reaction mixture, and the mixture was extracted twice with chloroform. The organic layer was dried over sodium sulfate, filtered and concentrated under reduced pressure. The residue was purified by silica gel column chromatography (ethyl acetate:hexane=33:67-50:50) to give the title compound (2820 mg) as a white solid. $^1$H NMR (400 MHz, CDCl$_3$) δppm 1.44 (9H, s), 2.43 (2H, ddd, J=6.3, 6.3, 12.7 Hz), 2.62-2.73 (2H, m), 2.99 (3H, s), 4.18-4.33 (1H, m), 4.56-4.79 (1H, m), 5.12-5.21 (1H, m)

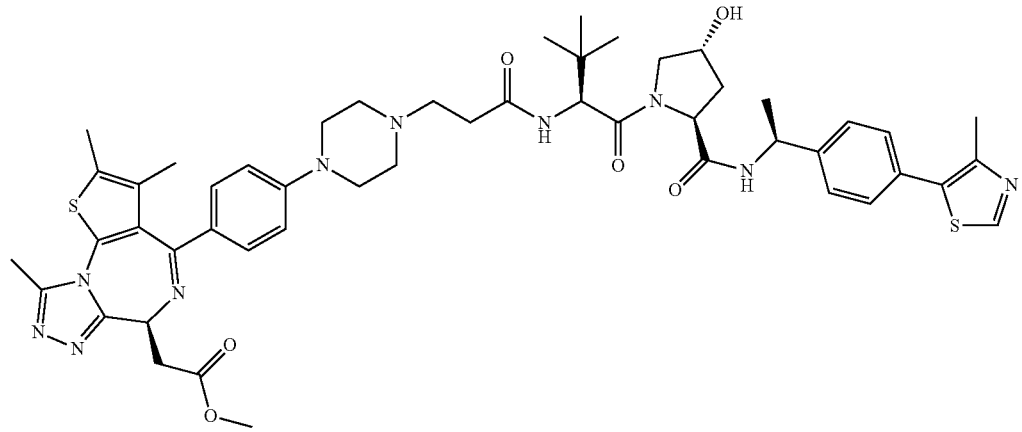 [SMILES: COC(=O)C[C@@H]1N=C(c2ccc(N3CCN(CCC(=O)N[C@H](C(=O)N4C[C@H](O)C[C@H]4C(=O)N[C@@H](C)c4ccc(-c5scnc5C)cc4)C(C)(C)C)CC3)cc2)c2c(sc(C)c2C)-n2c(C)nnc21]

By reaction and treatment in the same manner as in Example 80 (80-3)-(80-5) and using Example compound 82-2 instead of Example compound 80-2, the title compound was obtained as a yellow powder. MS (ESI) m/z: 963.3 [M+H]+

Example 83

(83-1) trans-3-[(t-butoxycarbonyl)amino]cyclobutyl methanesulfonate (Example Compound 83-1)

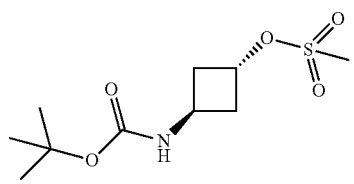 [SMILES: CC(C)(C)OC(=O)N[C@H]1C[C@H](OS(C)(=O)=O)C1]

(83-2) methyl 5-({cis-3-[(t-butoxycarbonyl)amino]cyclobutyl}oxy)-1-benzofuran-2-carboxylate (Example Compound 83-2)

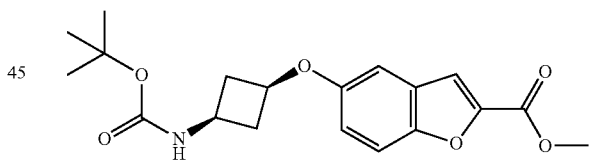

To a solution of Example compound 25-2 (500 mg) and Example compound 83-1 (1382 mg) in N,N-dimethylformamide (13 mL) was added cesium carbonate (2544 mg) and the mixture was stirred at 70° C. for 3 hr. Water was added to the reaction mixture and the mixture was stirred and extracted twice with ethyl acetate. The organic layers were collected, washed withed 3 times with saturated brine, and the organic layer was dried over sodium sulfate and filtered. The filtrate was concentrated under reduced pressure, and the residue was purified by silica gel column chromatography (ethyl acetate:chloroform=2:98) to give the title compound (306 mg) as a pale-yellow solid. MS (ESI) m/z: 262.2 [M−Boc+2H]+

(83-3) 5-({cis-3-[(t-butoxycarbonyl)amino]cyclobutyl}oxy)-1-benzofuran-2-carboxylic acid (Example Compound 83-3)

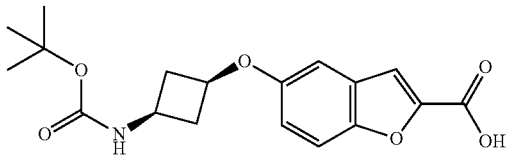 [SMILES: CC(C)(C)OC(=O)N[C@H]1C[C@@H](Oc2ccc3oc(C(=O)O)cc3c2)C1]

To a solution of Example compound 83-2 (300 mg) in tetrahydrofuran (4 mL), methanol (1 mL) and water (1 mL) was added lithium hydroxide monohydrate (140 mg) and the mixture was stirred at room temperature for 30 min. To the reaction mixture was added ethyl acetate, and the mixture was washed with 5% aqueous potassium hydrogensulfate solution and saturated brine. The aqueous layer was extracted with ethyl acetate. The organic layers were collected and dried over sodium sulfate, filtered and concentrated under reduced pressure to give the title compound (288 mg) as a white solid.

MS (ESI) m/z: 348.3 [M+H]$^+$

(83-4) t-butyl [cis-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamate (Example Compound 83-4)

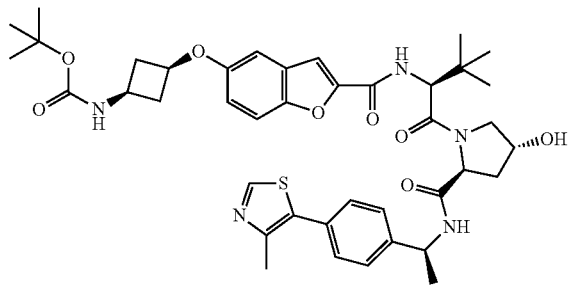 [SMILES: Cc1ncsc1-c1ccc([C@H](C)NC(=O)[C@@H]2C[C@@H](O)CN2C(=O)[C@@H](NC(=O)c2cc3cc(O[C@H]4C[C@@H](NC(=O)OC(C)(C)C)C4)ccc3o2)C(C)(C)C)cc1]

By reaction and treatment in the same manner as in Example 97 (97-2) and using Example compound 83-3 instead of Example compound 97-1, the title compound was obtained as a white powder. MS (ESI) m/z: 774.6 [M+H]$^+$

(83-5) (2S,4R)-1-{(2S)-2-[(5-{[cis-3-aminocyclobutyl]oxy}-1-benzofuran-2-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide hydrochloride (Example Compound 83-5)

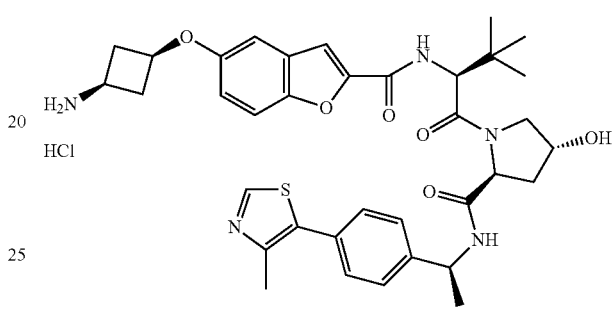

To a solution of Example compound 83-4 (630 mg) in 1,4-diaoxane (6.3 mL) was added 4 M hydrogen chloride/dioxane solution (6.3 mL) and the mixture was stirred for 14 hr. To the reaction mixture was added methanol and the mixture was concentrated under reduced pressure. The residue was suspension washed with diethyl ether and collected by filtration to give the title compound (488 mg) as a pale-yellow solid. MS (ESI) m/z: 674.6 [M+H]$^+$

(83-6) methyl {(6S)-4-[4-(3-{[cis-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamoyl}pyrrolidin-1-yl)phenyl]-2,3,9-trimethyl-6H-thieno[3,2-f][1,2,4]triazolo[4,3-a][1,4]diazepin-6-yl}acetate (Example Compound 83)

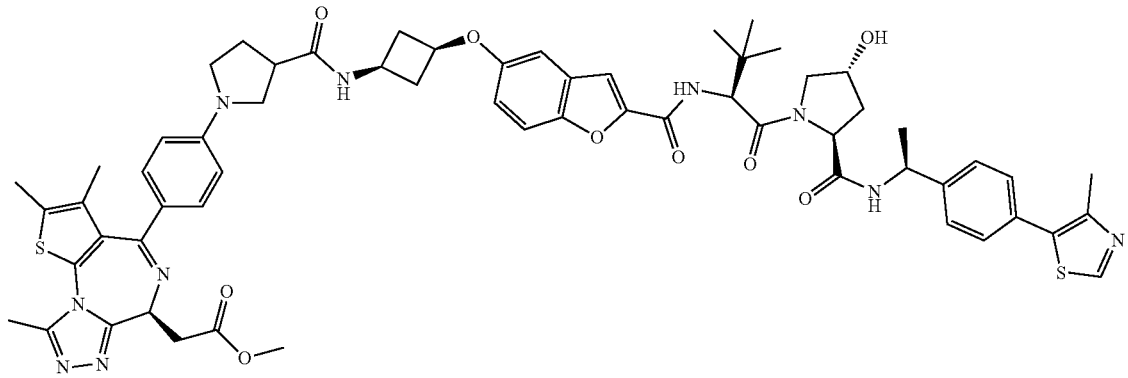 [SMILES: COC(=O)C[C@@H]1N=C(c2ccc(N3CCC(C(=O)N[C@H]4C[C@@H](Oc5ccc6oc(C(=O)N[C@H](C(=O)N7C[C@H](O)C[C@H]7C(=O)N[C@@H](C)c7ccc(-c8scnc8C)cc7)C(C)(C)C)cc6c5)C4)C3)cc2)c2c(sc(C)c2C)-n2c(C)nnc21]

By reaction and treatment in the same manner as in Example 80 (80-4)-(80-5) and using Example compound 81-1 instead of Example compound 80-3 and Reference Example compound 83-5 instead of Example compound 5, the title compound was obtained as a yellow solid. MS (ESI) m/z: 1149.3 [M+H]$^+$ Example 84

(84-1) methyl [(6S)-4-(4'-{[cis-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 84)

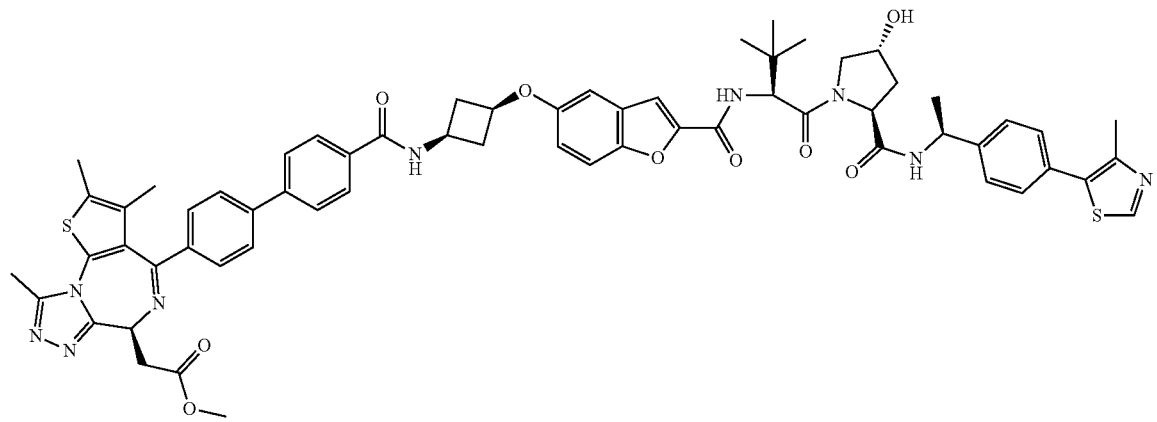 [SMILES: COC(=O)C[C@@H]1N=C(c2ccc(-c3ccc(C(=O)N[C@H]4C[C@@H](Oc5ccc6oc(C(=O)N[C@H](C(=O)N7C[C@H](O)C[C@H]7C(=O)N[C@@H](C)c7ccc(-c8scnc8C)cc7)C(C)(C)C)cc6c5)C4)cc3)cc2)c2c(sc(C)c2C)-n2c(C)nnc21]

By reaction and treatment in the same manner as in Example 43 (43-1) and using Reference Example compound 83-5 instead of Reference Example compound 5, the title compound was obtained as a white powder. MS (ESI) m/z: 1156.3 [M+H]$^+$ Example 85

(85-1) methyl [(6S)-4-{4-[(3S)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrrolidin-1-yl]phenyl}-2,3,9-trimethyl-6H-thieno[3,2-f][1,2,4]triazolo[4,3-a][1,4]diazepin-6-yl]acetate, or methyl [(6S)-4-{4-[(3R)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrrolidin-1-yl]phenyl}-2,3,9-trimethyl-6H-thieno[3,2-f][1,2,4]triazolo[4,3-a][1,4]diazepin-6-yl]acetate (Example Compound 85)

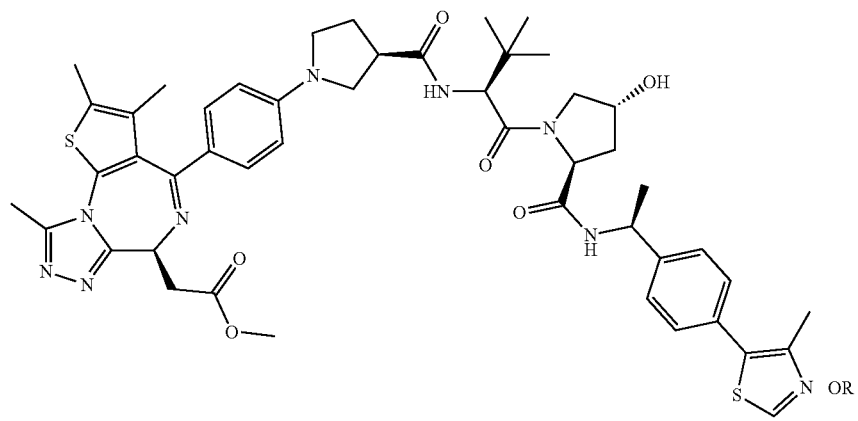

OR

-continued

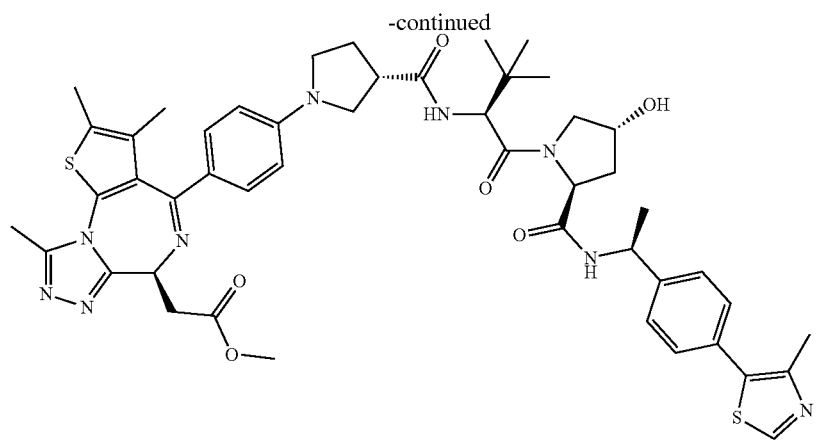

Example compound 81 (176 mg) was passed through a chiral column [CHIRALPAK ID (30*250), ethanol:acetonitrile:diethylamine=85:15:0.1, flow 20 mL/min, recycle once] to find peaks at retention time 28 min and 37 min. Of these, compounds having a peak at retention time 37 min were collected and concentrated to give the title compound (74 mg) as a pale-yellow powder. MS (ESI) m/z: 920.3 [M+H]$^+$ Example 86 and Example 87

(86-1) and (87-1) methyl [(6S)-4-{4-[(3R)-3-{[cis-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamoyl}pyrrolidin-1-yl]phenyl}-2,3,9-trimethyl-6H-thieno[3,2-f][1,2,4]triazolo[4,3-a][1,4]diazepin-6-yl]acetate and methyl [(6S)-4-{4-[(3S)-3-{[cis-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamoyl}pyrrolidin-1-yl]phenyl}-2,3,9-trimethyl-6H-thieno[3,2-f][1,2,4]triazolo[4,3-a][1,4]diazepin-6-yl]acetate

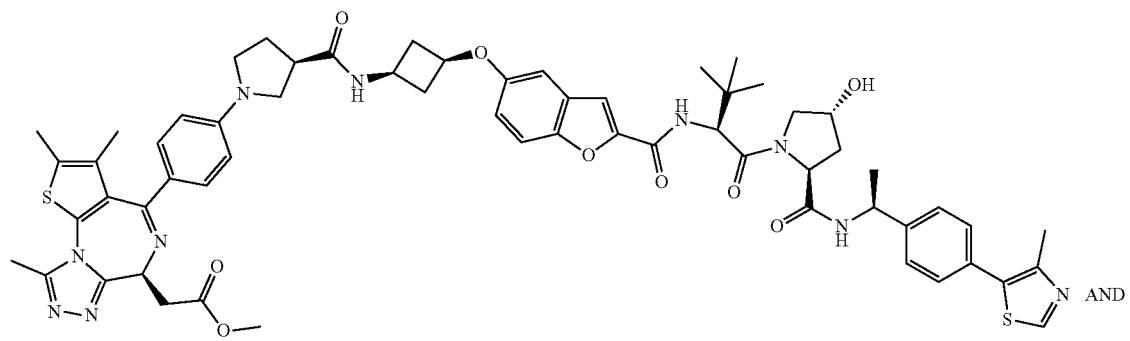

AND

-continued

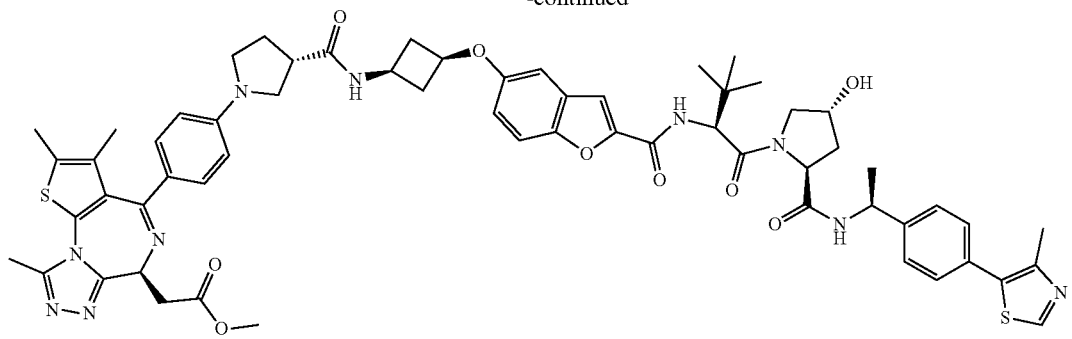

Example compound 83 (66 mg) was separated by chiral column [CHIRALPAK IF (30*250), ethanol:methanol:tetrahydrofuran:butylamine=30:40:30:0.1] to give both the title compounds (compound having shorter retention time, 23 mg (MS (ESI) m/z: 1149.3 [M+H]+, Example compound 86) and compound having longer retention time, 23 mg (MS (ESI) m/z: 1149.3 [M+H]+, Example compound 87)) as yellow solids.

Example 88

(88-1) t-butyl 4-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-3,6-dihydropyridine-1(2H)-carboxylate (Example Compound 88-1)

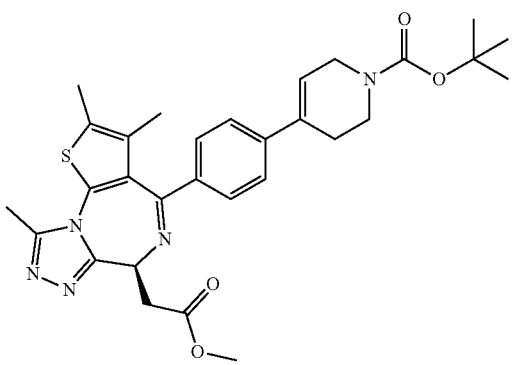 [SMILES: COC(=O)C[C@@H]1N=C(c2ccc(C3=CCN(C(=O)OC(C)(C)C)CC3)cc2)c2c(sc(C)c2C)-n2c(C)nnc21]

Under an argon stream, Reference Example compound 1 (500 mg), N-(t-butoxycarbonyl)-1,2,3,6-tetrahydropyridine-4-boronic acid pinacol ester (447 mg), palladium acetate (7.1 mg), S-phos (99 mg), potassium fluoride (210 mg) and water (78 μL) were heated under reflux in tetrahydrofuran (5 mL) solvent for 7 hr. Using ethyl acetate, the reaction mixture was filtered through diatomaceous earth, and the filtrate was concentrated under reduced pressure. The residue was purified by NH silica gel column chromatography (ethyl acetate:hexane=30:70-80:20) to give the title compound (680 mg) as a pale-yellow solid.

MS (ESI) m/z: 562.5 [M+H]+

(88-2) t-butyl 3-[4-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-3,6-dihydropyridin-1(2H)-yl]propanoate (Example Compound 88-2)

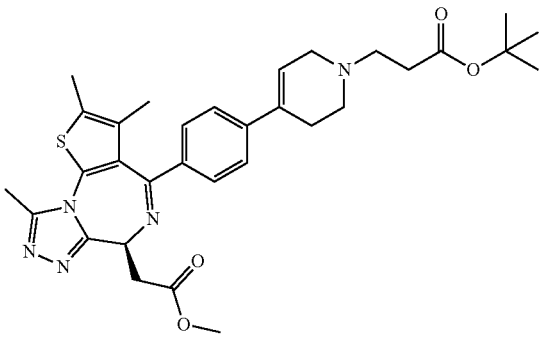 [SMILES: COC(=O)C[C@@H]1N=C(c2ccc(C3=CCN(CCC(=O)OC(C)(C)C)CC3)cc2)c2c(sc(C)c2C)-n2c(C)nnc21]

[0986]

To a solution of Example compound 88-1 (330 mg) in chloroform (1 mL) was added trifluoroacetic acid (1 mL) and the mixture was stirred at room temperature for 5 hr. The reaction mixture was concentrated under reduced pressure, and azeotropically distilled 2 times with toluene. To a solution of the residue in acetonitrile (5 mL) were added potassium carbonate (244 mg), t-butyl acrylate (0.129 mL) and the mixture was stirred at room temperature for 16 hr and at 50° C. for 8 hr. Using ethyl acetate, the reaction mixture was filtered, and the filtrate was concentrated under reduced pressure. The residue was purified by NH silica gel column chromatography (ethyl acetate:hexane=0:100-10:90) to give the title compound (226 mg) as a pale-yellow solid. MS (ESI) m/z: 590.4 [M+H]+

(88-3) methyl [(6S)-4-(4-{1-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl]-1,2,3,6-tetrahydropyridin-4-yl}phenyl)-2,3,9-trimethyl-6H-thieno[3,2-f][1,2,4]triazolo[4,3-a] [1,4]diazepin-6-yl]acetate (Example Compound 88)

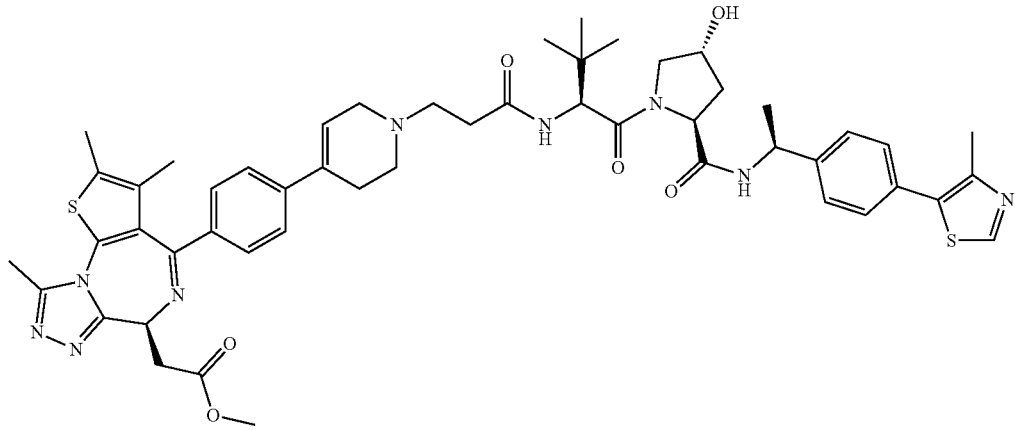 [SMILES: COC(=O)C[C@@H]1N=C(c2ccc(C3=CCN(CCC(=O)N[C@H](C(=O)N4C[C@H](O)C[C@H]4C(=O)N[C@@H](C)c4ccc(-c5scnc5C)cc4)C(C)(C)C)CC3)cc2)c2c(sc(C)c2C)-n2c(C)nnc21]

To a solution of Example compound 88-2 (226 mg) in chloroform (1 mL) was added trifluoroacetic acid (1 mL) and the mixture was stirred at room temperature for 4 hr. The reaction mixture was concentrated under reduced pressure and azeotropically distilled 2 times with toluene. The residue was dissolved in N,N-dimethylformamide (5 mL), and Reference Example compound 5 (222 mg), N,N-diisopropylethylamine (0.332 mL), HATU (175 mg) were added and the mixture was stirred at room temperature for 3 hr. To the reaction mixture was added saturated aqueous sodium hydrogen carbonate and the mixture was stirred and extracted twice with ethyl acetate. The organic layer was washed twice with saturated brine and concentrated under reduced pressure. The residue was purified by silica gel column chromatography (methanol:chloroform=0:100-7:93) and NH silica gel column chromatography (methanol:chloroform=0:100-2:98) to give the title compound (182 mg) as a white solid.

MS (ESI) m/z: 960.9 [M+H]$^+$

Example 89

(89-1) t-butyl 3-fluoro-4'-[(6S)-6-(2-methoxy-2-oxoethyl)-2,3,9-trimethyl-6H-thieno[3,2-f][1,2,4]triazolo[4,3-a] [1,4]diazepin-4-yl][1,1'-biphenyl]-4-carboxylate (Example Compound 89-1)

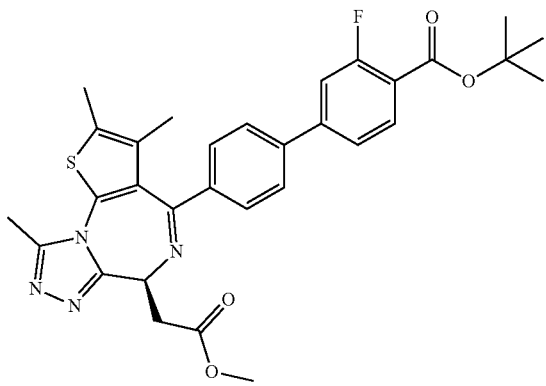 [SMILES: COC(=O)C[C@@H]1N=C(c2ccc(-c3ccc(C(=O)OC(C)(C)C)c(F)c3)cc2)c2c(sc(C)c2C)-n2c(C)nnc21]

To a solution of Reference Example compound 2 (526 mg) in tetrahydrofuran (10.7 mL) were added t-butyl 4-bromo-2-fluorobenzoate (323 mg), palladium acetate (24 mg), S-phos (88 mg), potassium fluoride (186 mg) and water (0.069 mL) and the mixture was stirred at 70° C. for 15 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by silica gel column chromatography (chloroform:methanol=100:0-97:3) to give the title compound (489 mg) as a yellow powder.

MS (ESI) m/z: 575.4 [M+H]$^+$ (89-2) 3-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Example Compound 89-2)

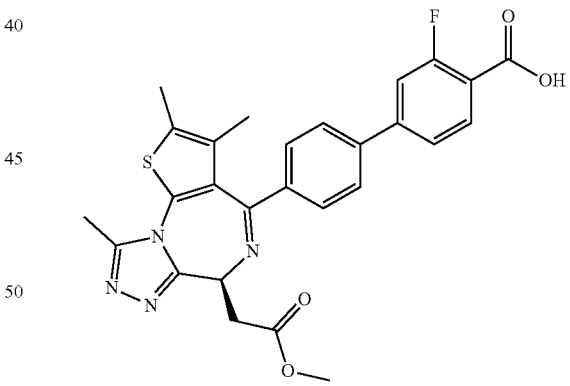

To a solution of Example compound 89-1 (485 mg) in dichloromethane (2.0 mL) was added dropwise under ice-cooling trifluoroacetic acid (2.0 mL), and the mixture was allowed to naturally warm to room temperature and stirred for 2 hr. The reaction solution was diluted with ethyl acetate, the solvent was evaporated under reduced pressure, and the residue was further concentrated azeotropically with toluene. This operation was performed two times. To the obtained residue were added ethyl acetate, saturated aqueous sodium hydrogen carbonate for partitioning, and the aqueous layer was acidified with 1N hydrochloric acid and extracted 3 times with ethyl acetate. The organic layer was concentrated under reduced pressure and dried to give the title compound (361 mg) as a yellow crudely purified powder. MS (ESI) m/z: 519.4 [M+H]$^+$ (89-3) methyl [(6S)-4-{3'-fluoro-4'-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate
(Example Compound 89)

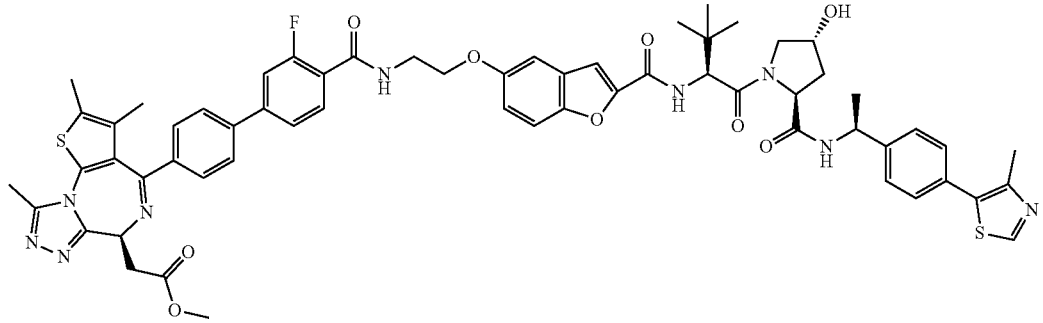 [SMILES: COC(=O)C[C@@H]1N=C(c2ccc(-c3ccc(C(=O)NCCOc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)c(F)c3)cc2)c2c(sc(C)c2C)-n2c(C)nnc21]

To a solution of Example compound 25-5 70 mg) in dichloromethane (1.0 mL) was added dropwise under ice-cooling trifluoroacetic acid (1.0 mL), and the mixture was allowed to naturally warm to room temperature and stirred for 2 hr. The reaction solution was diluted with ethyl acetate, the solvent was evaporated under reduced pressure, and the residue was further concentrated azeotropically with toluene. This operation was performed two times. To a solution of the obtained residue (155 mg) and Example compound 89-2 (49 mg) in N,N-dimethylformamide (0.936 mL) was added N,N-diisopropylethylamine (0.097 mL), and HATU (107 mg) was added under ice-cooling, and the mixture was allowed to naturally warm to room temperature and stirred for 5 hr. Water was added to the reaction solution and the mixture was extracted with ethyl acetate. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-97:3). The obtained solid was suspension washed with diethyl ether, collected by filtration and dried under reduced pressure to give the title compound (42 mg) as a white solid.
MS (ESI) m/z: 1146.5 [M−H]⁺

Example 90

(90-1) 4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Example Compound 90-1)

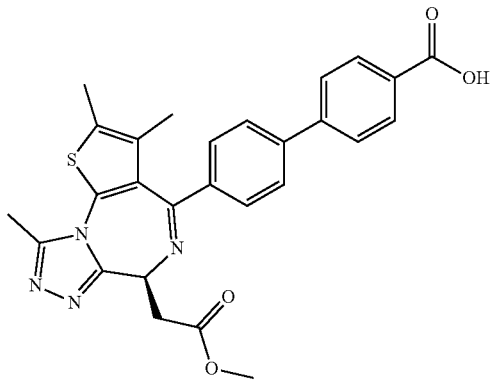 [SMILES: COC(=O)C[C@@H]1N=C(c2ccc(-c3ccc(C(=O)O)cc3)cc2)c2c(sc(C)c2C)-n2c(C)nnc21]

To a solution of Reference Example compound 11 (6.55 g) in dichloromethane (32.8 mL) was added dropwise under ice-cooling trifluoroacetic acid (19.7 mL), and the mixture was allowed to naturally warm to room temperature and stirred for 4 hr. The reaction solution was diluted with chloroform, and the solvent was evaporated under reduced pressure. To the obtained residue was added ethyl acetate and, under ice-cooling, saturated aqueous sodium hydrogen carbonate was added until foaming ceased to perform partitioning. The aqueous layer was washed with ethyl acetate, acidified with 1N hydrochloric acid under ice-cooling and extracted 3 times with chloroform. The organic layer was washed with water and saturated brine, dried over anhydrous sodium sulfate, concentrated under reduced pressure and dried to give the title compound (5.11 g) as a yellow crudely purified solid. MS (ESI) m/z: 501.3 [M+H]⁺

(90-2) t-butyl [2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]carbamate (Example Compound 90-2)

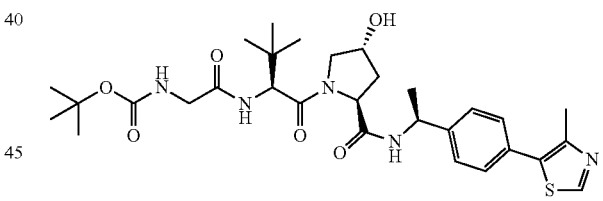

To a solution of N-(t-butoxycarbonyl)-glycine (131 mg), Reference Example compound 5 (300 mg) in N,N-dimethylformamide (6.2 mL) was added N,N-diisopropylethylamine (0.647 mL), and HATU (711 mg) was added under ice-cooling, and the mixture was allowed to naturally warm to room temperature and stirred for 14 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (250 mg) as a pale-yellow solid. MS (ESI) m/z: 646.5 [M+HCOO]⁻

(90-3) methyl [(6S)-4-(4'-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]carbamoyl}[1,1'-biphenyl]-4-yl)-2,3,9-trimethyl-6H-thieno[3,2-f][1,2,4]triazolo[4,3-a] [1,4]diazepin-6-yl]acetate (Example Compound 90)

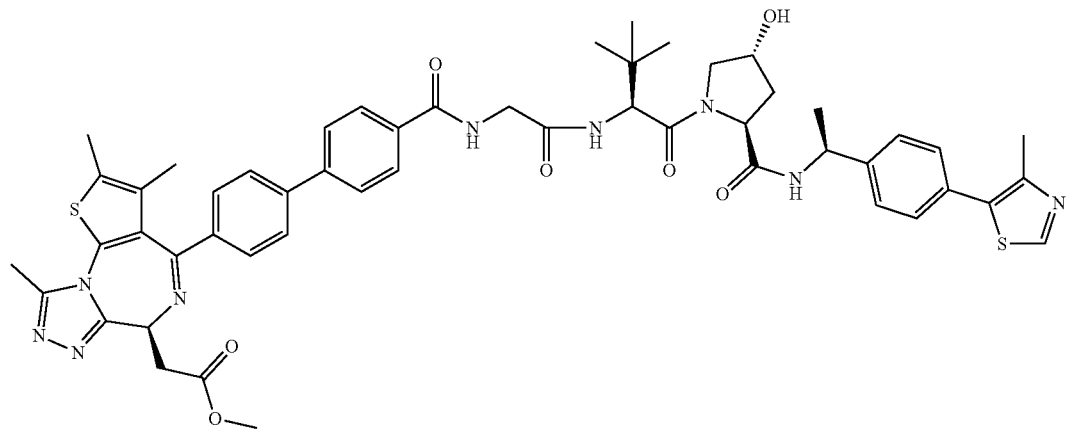 [SMILES: COC(=O)C[C@@H]1N=C(c2ccc(-c3ccc(C(=O)NCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 90-2 (125 mg) in dichloromethane (2.0 mL) was added dropwise under ice-cooling trifluoroacetic acid (2.0 mL), and the mixture was allowed to naturally warm to room temperature and stirred for 3 hr. The reaction solution was diluted with ethyl acetate, the solvent was evaporated under reduced pressure, and the residue was further concentrated azeotropically with toluene. This operation was performed two times. To a solution of the obtained residue (216 mg) and Example compound 90-1 (104.0 mg) in N,N-dimethylformamide (2.1 mL) was added N,N-diisopropylethylamine (0.216 mL), and HATU (237 mg) was added under ice-cooling, and the mixture was allowed to naturally warm to room temperature and stirred for 18 hr. To the reaction solution were added saturated aqueous sodium hydrogen carbonate and ethyl acetate and the mixture was vigorously stirred at room temperature for 1 hr. After partitioning, the organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=100:0-97:3-95:5-93:7). The obtained solid was suspension washed with diethyl ether, collected by filtration and dried under reduced pressure to give the title compound (130 mg) as a white solid.

MS (ESI) m/z: 984.7 [M+H]+

Example 91

(91-1) t-butyl [(2S)-1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]carbamate (Example Compound 91-1)

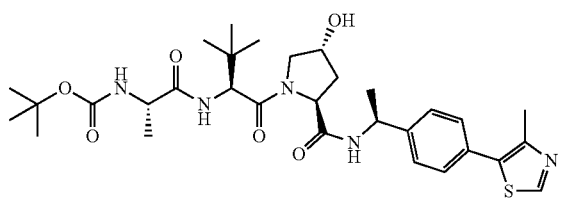 [SMILES: Cc1ncsc1-c1ccc([C@H](C)NC(=O)[C@@H]2C[C@@H](O)CN2C(=O)[C@@H](NC(=O)[C@H](C)NC(=O)OC(C)(C)C)C(C)(C)C)cc1]

To a solution of N-(t-butoxycarbonyl)-alanine (142 mg), Reference Example compound 5 (300 mg) in N,N-dimethylformamide (6.2 mL) was added N,N-diisopropylethylamine (0.647 mL), and HATU (711 mg) was added under ice-cooling, and the mixture was allowed to naturally warm to room temperature and stirred for 14 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (296 mg) as a pale-yellow solid. MS (ESI) m/z: 660.6 [M+HCOO]−

(91-2) methyl [(6S)-4-(4'-{[(2S)-1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 91)

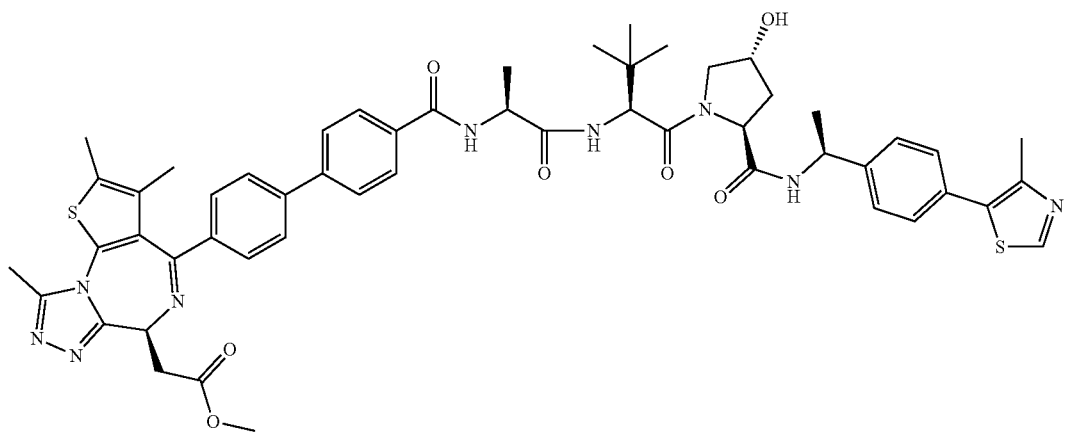 [SMILES: COC(=O)C[C@@H]1N=C(c2ccc(-c3ccc(C(=O)N[C@@H](C)C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 91-1 (145 mg) in dichloromethane (2.0 mL) was added dropwise under ice-cooling trifluoroacetic acid (2.0 mL), and the mixture was allowed to naturally warm to room temperature and stirred for 3 hr. The reaction solution was diluted with ethyl acetate, the solvent was evaporated under reduced pressure, and the residue was further concentrated azeotropically with toluene. This operation was performed two times. To a solution of the obtained residue (250 mg) and Example compound 90-1 (118 mg) in N,N-dimethylformamide (2.4 mL) was added N,N-diisopropylethylamine (0.244 mL), and HATU (269 mg) was added under ice-cooling, and the mixture was allowed to naturally warm to room temperature and stirred for 18 hr. To the reaction solution were added saturated aqueous sodium hydrogen carbonate and ethyl acetate and the mixture was vigorously stirred at room temperature for 1 hr. After partitioning, the organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7). The obtained solid was suspension washed with diethyl ether, collected by filtration and dried under reduced pressure to give the title compound (165 mg) as a white solid.

MS (ESI) m/z: 998.7 [M+H]$^+$

Example 92

(92-1) t-butyl [(2R)-1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]carbamate (Example Compound 92-1)

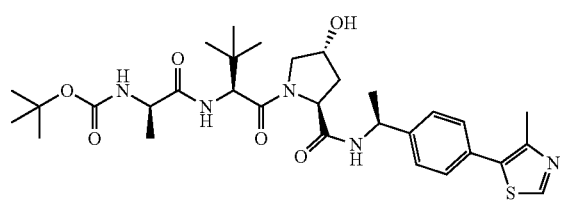 [SMILES: Cc1ncsc1-c1ccc([C@H](C)NC(=O)[C@@H]2C[C@@H](O)CN2C(=O)[C@@H](NC(=O)[C@@H](C)NC(=O)OC(C)(C)C)C(C)(C)C)cc1]

To a solution of N-(t-butoxycarbonyl)-D-alanine (142 mg), Reference Example compound 5 (300 mg) in N,N-dimethylformamide (6.2 mL) was added N,N-diisopropylethylamine (0.647 mL), and HATU (711 mg) was added under ice-cooling, and the mixture was allowed to naturally warm to room temperature and stirred for 14 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (326 mg) as a pale-yellow solid. MS (ESI) m/z: 660.6 [M+HCOO]$^-$ (92-2) methyl [(6S)-4-(4'-{[(2R)-1-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-1-oxopropan-2-yl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 92)

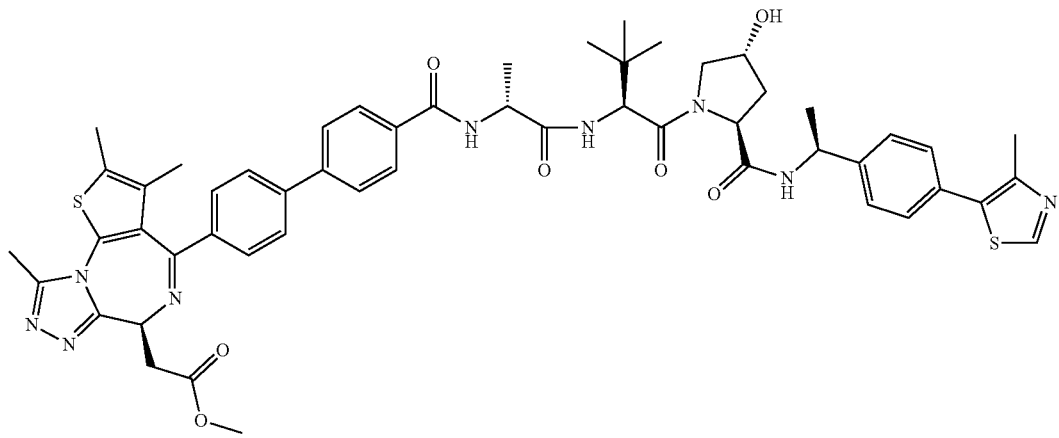 [SMILES: COC(=O)C[C@@H]1N=C(c2ccc(-c3ccc(C(=O)N[C@H](C)C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

To a solution of Example compound 92-1 (160 mg) in dichloromethane (2.0 mL) was added dropwise under ice-cooling trifluoroacetic acid (2.0 mL), and the mixture was allowed to naturally warm to room temperature and stirred for 3 hr. The reaction solution was diluted with ethyl acetate, the solvent was evaporated under reduced pressure, and the residue was further concentrated azeotropically with toluene. This operation was performed two times. To a solution of the obtained residue (278 mg) and Example compound 90-1 (130 mg) in N,N-dimethylformamide (2.6 mL) was added N,N-diisopropylethylamine (0.270 mL), and HATU (296 mg) was added under ice-cooling, and the mixture was allowed to naturally warm to room temperature and stirred for 18 hr. To the reaction solution were added saturated aqueous sodium hydrogen carbonate and ethyl acetate and the mixture was vigorously stirred at room temperature for 1 hr. After partitioning, the organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7). The obtained solid was suspension washed with diethyl ether, collected by filtration and dried under reduced pressure to give the title compound (187 mg) as a white solid.

MS (ESI) m/z: 996.5 [M−H]−

Example 93

(93-1) (6S)-4-(4-iodophenyl)-2,3,6,9-tetramethyl-6H-thieno[3,2-f][1,2,4]triazolo[4,3-a][1,4]diazepine (Example Compound 93-1)

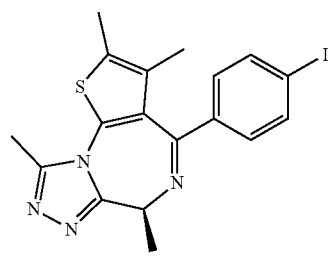 [SMILES: Cc1sc2c(c1C)C(c1ccc(I)cc1)=N[C@@H](C)c1nnc(C)n1-2]

To a solution of Reference Example compound 4 (500 mg), trans-N,N'-dimethylcyclohexane-1,2-diamine (106 mg) in dioxane (2.4 mL) was added copper iodide (48 mg), then sodium iodide (560 mg) was added and the mixture was stirred at 110° C. overnight. To the reaction solution were added ethyl acetate and water, and the mixture was filtered using Kimwipes. Partitioning operation was performed to separate the organic layer. The aqueous layer was extracted with ethyl acetate. The organic layers were collected and washed successively with water and saturated brine, and dried over anhydrous sodium sulfate. The solvent was evaporated under reduced pressure. The residue was purified by silica gel column chromatography (chloroform:methanol=95:5-80:20), then NH silica gel column chromatography (hexane:ethyl acetate=40:60-0:100) to give the title compound (422 mg) as a white solid.

MS (ESI) m/z: 449.0 [M+H]+

(93-2) (3E)-4-{4-[(6S)-2,3,6,9-tetramethyl-6H-thieno[3,2-f] [1,2,4]triazolo[4,3-a][1,4]diazepin-4-yl]phenyl}-3-butenoic acid (Example Compound 93-2)

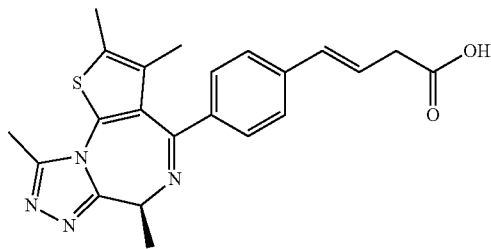 [SMILES: Cc1sc2c(c1C)C(c1ccc(/C=C/CC(=O)O)cc1)=N[C@@H](C)c1nnc(C)n1-2]

To a solution of Example compound 93-1 (150 mg) in tetrahydrofuran (1.1 mL) were added 3-butenoic acid (72 mg), palladium acetate (8.0 mg), tri(o-tolyl)phosphine (22 mg) and triethylamine (0.273 mL) and the mixture was stirred at 70° C. for 66 hr. The reaction solution was diluted with ethyl acetate, the solvent was evaporated under reduced pressure, and the residue was further concentrated azeotropically with toluene. This operation was performed two times. To the obtained residue were added saturated aqueous sodium hydrogen carbonate and ethyl acetate. After partitioning, the aqueous layer was acidified with 1N hydrochloric acid and the mixture was extracted with chloroform. The organic layer was dried over anhydrous sodium sulfate, and the solvent was evaporated under reduced pressure and dried to give the title compound (184 mg) as a crudely purified orange viscous compound.
MS (ESI) m/z: 407.2 [M+H]$^+$ (93-3) 4-{4-[(6S)-2,3,6,9-tetramethyl-6H-thieno[3,2-f] [1,2,4]triazolo[4,3-a][1,4]diazepin-4-yl] phenyl}butanoic acid (Example Compound 93-3)

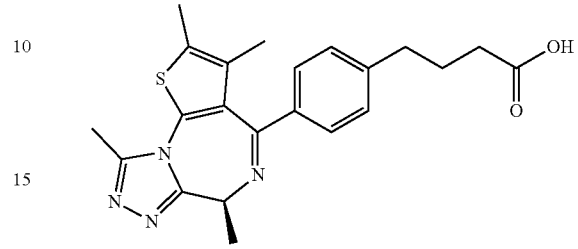

To a solution of Example compound 93-2 (180 mg) in methanol (4.4 mL) was added 10% palladium carbon (190 mg) and, after hydrogen substitution, the mixture was stirred at room temperature for 30 min. The reaction solution was filtered through diatomaceous earth using methanol, and the filtrate was concentrated under reduced pressure and dried to give the title compound (152 mg) as a brown crudely purified viscous compound.
MS (ESI) m/z: 409.3 [M+H]$^+$ (93-4) (2S,4R)-1-[(2S)-3,3-dimethyl-2-(4-{4-[(6S)-2,3,6,9-tetramethyl-6H-thieno[3,2-f][1,2,4]triazolo [4,3-a] [1,4]diazepin-4-yl]phenyl}butanamido)butanoyl]-4-hydroxy-N-{(1S)-1-[4-(4-methyl-1,3-thiazol-5-yl)phenyl]ethyl}pyrrolidine-2-carboxamide (Example Compound 93)

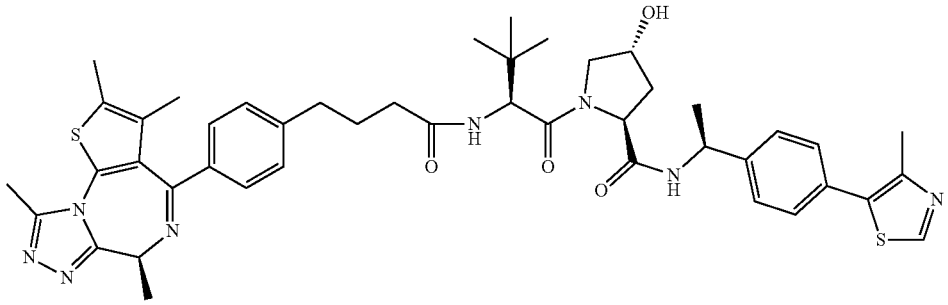 [SMILES: Cc1ncsc1-c1ccc([C@H](C)NC(=O)[C@@H]2C[C@@H](O)CN2C(=O)[C@@H](NC(=O)CCCc2ccc(C3=N[C@@H](C)c4nnc(C)n4-c4sc(C)c(C)c43)cc2)C(C)(C)C)cc1]

To a solution of Example compound 93-3 (150 mg) and Reference Example compound 5 (194 mg) in N,N-dimethylformamide (3.7 mL) was added N,N-diisopropylethylamine (0.286 mL), and HATU (209 mg) was added under ice-cooling, and the mixture was allowed to naturally warm to room temperature and stirred for 66.5 hr. To the reaction solution was added water and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-85:15), then silica gel column chromatography (chloroform:methanol=99:1-95:5). The obtained solid was suspension washed with diethyl ether, collected by filtration and dried under reduced pressure to give the title compound (42 mg) as a white solid. MS (ESI) m/z: 835.6 [M+H]$^+$

Example 94

(94-1) t-butyl 3-fluoro-4'-[(6S)-6-(2-methoxy-2-oxoethyl)-2,3,9-trimethyl-6H-thieno[3,2-f][1,2,4]triazolo[4,3-a] [1,4]diazepin-4-yl][1,1'-biphenyl]-4-carboxylate (Example Compound 94-1)

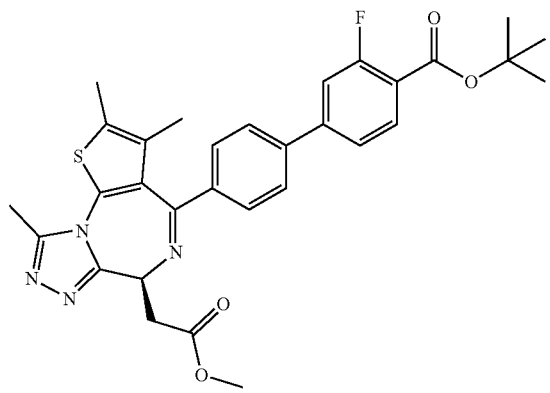 [SMILES: COC(=O)C[C@@H]1N=C(c2ccc(-c3ccc(C(=O)OC(C)(C)C)c(F)c3)cc2)c2c(sc(C)c2C)-n2c(C)nnc21]

Reference Example compound 2 (526 mg), t-butyl 4-bromo-2-fluoro-benzoate (323 mg) were dissolved in tetrahydrofuran (10.7 mL), palladium acetate (24 mg), S-phos (87 mg), potassium fluoride (186 mg) and water (69 μL) were added and the mixture was stirred at 70° C. for 15 hr. The insoluble material in the reaction mixture was filtered off through diatomaceous earth, water was added to the filtrate and the mixture was extracted 3 times with ethyl acetate, and the extract was dried over anhydrous sodium sulfate, and the solvent was evaporated under reduced pressure. The residue was purified by silica gel column chromatography (chloroform:methanol=100:0-97:3) to give the title compound (489 mg) as a yellow powder.

MS (ESI) m/z: 575.4 [M+H]$^+$ (94-2) 3-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Example Compound 94-2)

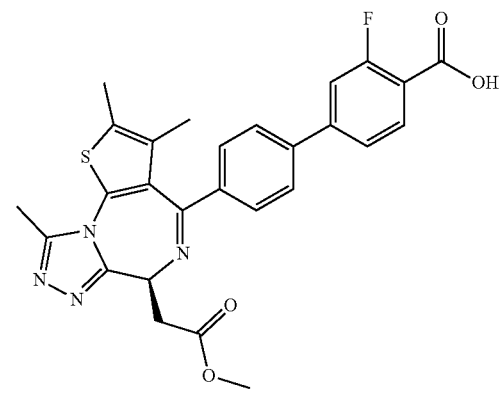 [SMILES: COC(=O)C[C@@H]1N=C(c2ccc(-c3ccc(C(=O)O)c(F)c3)cc2)c2c(sc(C)c2C)-n2c(C)nnc21]

Example compound 94-1 (120 mg) was dissolved in dichloromethane (2.0 mL), trifluoroacetic acid (2.0 mL) was added under ice-cooling and the mixture was stirred at room temperature for 2 hr. To the reaction mixture was added ethyl acetate and the solvent was evaporated under reduced pressure. To the residue was added toluene and toluene was evaporated under reduced pressure. This was repeated two times. To the residue was added saturated aqueous sodium hydrogen carbonate and the mixture was washed twice with ethyl acetate. The aqueous layer was adjusted to less than pH3.0 with 1N hydrochloric acid and extracted 3 times with ethyl acetate. The organic layer was concentrated under reduced pressure and dried to give the title compound (361 mg) as a yellow powder.

MS (ESI) m/z: 519.3 [M+H]$^+$ (94-3) methyl {(6S)-4-[3'-fluoro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 94)

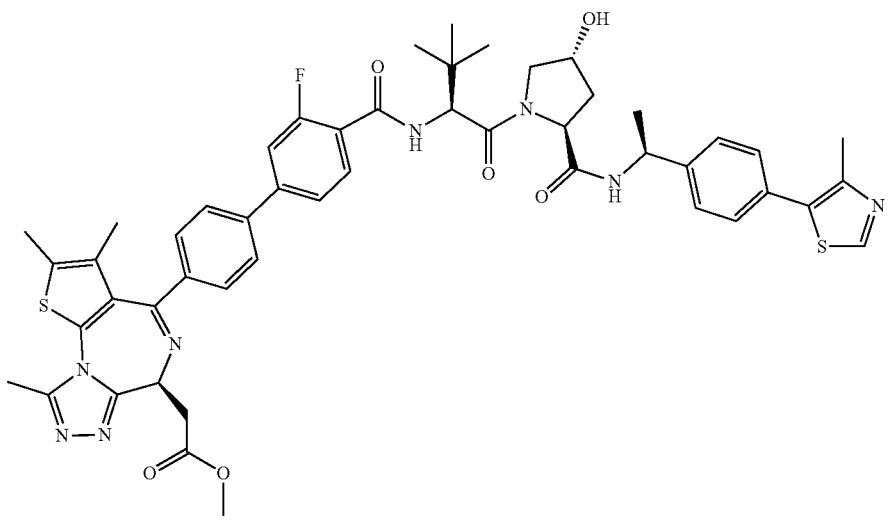 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(F)c3)cc2)c2c(sc(C)c2C)-n2c(C)nnc21]

Example compound 94-2 (120 mg) was dissolved in N,N-dimethylformamide (2.4 mL), and N,N-diisopropylethylamine (0.12 mL), Reference Example compound 5 (136 mg) and HATU (139 mg) were added under ice-cooling and the mixture was stirred at room temperature for 3 hr. To the reaction mixture was added ice water to quench the reaction, ethyl acetate and saturated brine were added and the organic layer was extracted. The aqueous layer was extracted again two times with ethyl acetate, and the organic layers were collected and washed twice with saturated brine:water=1:1 and washed with saturated brine. After drying over anhydrous sodium sulfate, the solvent was evaporated under reduced pressure, and the residue was purified by NH silica gel column chromatography (ethyl acetate:methanol=100:0-85:15), silica gel column chromatography (ethyl acetate:methanol=100:0-85:15) to give the title compound (129 mg) as a white solid.

MS (ESI) m/z: 945.4 [M+H]+

Example 95

(95-1) (2S,4R)-4-hydroxy-1-{(2S)-2-[2-({4'-[(6S)-6-(2-{[2-(3-hydroxypropoxy)ethyl]amino}-2-oxoethyl)-2,3,9-trimethyl-6H-thieno[3,2-f][1,2,4]triazolo[4,3-a][1,4]diazepin-4-yl][1,1'-biphenyl]-4-yl}oxy)acetamido]-3,3-dimethylbutanoyl}-N-{(1S)-1-[4-(4-methyl-1,3-thiazol-5-yl)phenyl]ethyl}pyrrolidine-2-carboxamide (Example Compound 95)

By reaction and treatment in the same manner as in Example 13, (13-1)-(13-2) and using Example compound 15 instead of Example compound 9, and 3-(2-aminoethoxy)propan-1-ol instead of 2-aminoethanol, the title compound was obtained as a yellow solid. MS (ESI) m/z: 1044.5 [M+H]+

Example 96

(96-1) t-butyl 4-(4-bromo-1H-pyrazol-1-yl)butanoate (Example Compound 96-1)

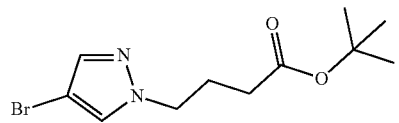

4-Bromopyrazole (500 mg), t-butyl bromobutyrate (911 mg) and potassium carbonate (705 mg) were stirred in N,N-dimethylformamide (5 mL) solvent at 50° C. for 7 hr. Water was added to the reaction mixture and the mixture was stirred and extracted twice with ethyl acetate. The organic layer was washed twice with water, and concentrated under reduced pressure. The residue was purified by silica gel column chromatography (ethyl acetate:hexane=0:100-20:80) to give the title compound (940 mg) as a white solid.

MS (ESI) m/z: 289.0, 291.0 [M+H]+

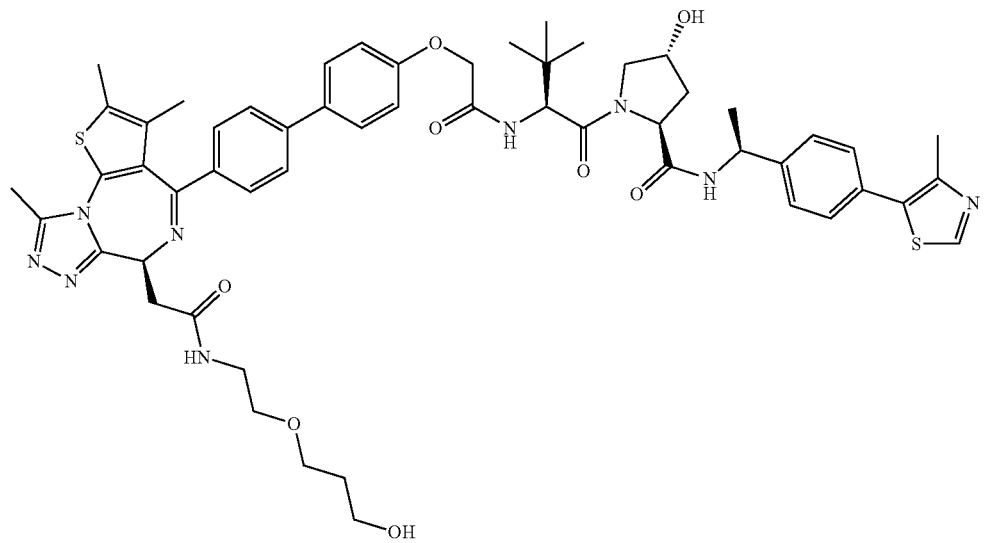 [SMILES: Cc1ncsc1-c1ccc([C@H](C)NC(=O)[C@@H]2C[C@@H](O)CN2C(=O)[C@@H](NC(=O)COc2ccc(-c3ccc(C4=N[C@@H](CC(=O)NCCOCCCO)c5nnc(C)n5-c5sc(C)c(C)c54)cc3)cc2)C(C)(C)C)cc1]

(96-2) methyl [(6S)-4-(4-{1-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-4-oxobutyl]-1H-pyrazol-4-yl}phenyl)-2,3,9-trimethyl-6H-thieno[3,2-f][1,2,4]triazolo[4,3-a][1,4]diazepin-6-yl]acetate (Example Compound 96)

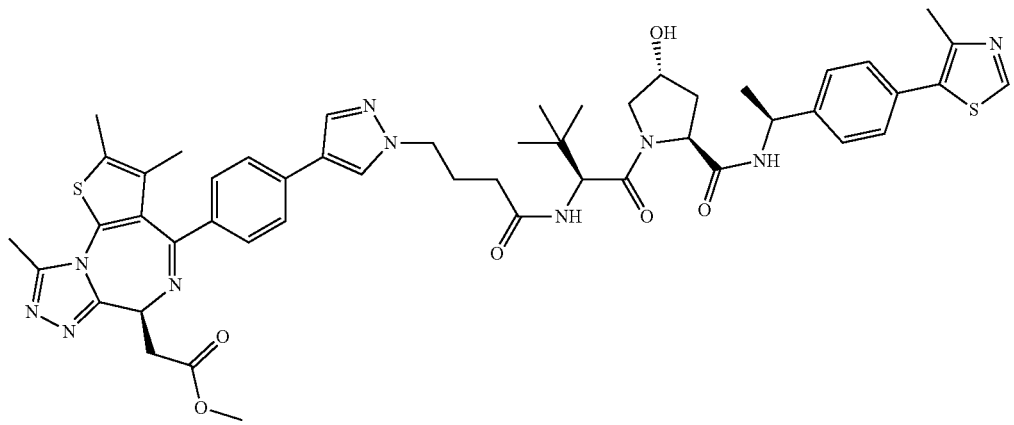 [SMILES: COC(=O)C[C@@H]1N=C(c2ccc(-c3cnn(CCCC(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

By reaction and treatment in the same manner as in Example 63 (63-2)-(63-3) and using Example compound 96-1 instead of Example compound 63-1, the title compound was obtained as a white solid. MS (ESI) m/z: 959.4 [M+H]+

Example 97

(97-1) (1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}piperidin-4-yl)acetic acid hydrochloride (Example compound 97-1)

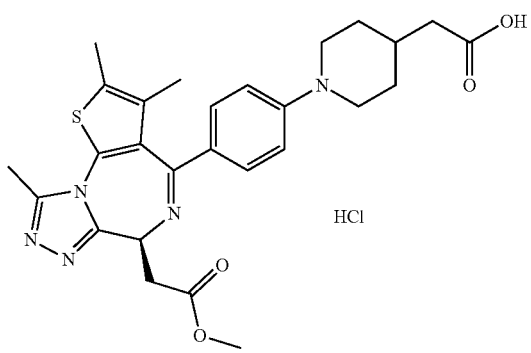 [SMILES: COC(=O)C[C@@H]1N=C(c2ccc(N3CCC(CC(=O)O)CC3)cc2)c2c(sc(C)c2C)-n2c(C)nnc21 ; Cl]

Under an argon stream, Reference Example compound 1 (400 mg), t-butyl 2-(4-piperidyl)acetate (231 mg), tris(dibenzylideneacetone)dipalladium(0) (44 mg), t-BuXphos (41 mg) and potassium phosphate (614 mg) were stirred in 1,2-dimethoxyethane (5 mL) solvent at 70° C. for 20 hr. Using ethyl acetate, the reaction mixture was filtered through diatomaceous earth, and the filtrate was concentrated under reduced pressure. The residue was purified by silica gel column chromatography (methanol:chloroform=0:100-5:95) to give a yellow viscous compound. The viscous compound was dissolved in chloroform (1 mL), trifluoroacetic acid (1 mL) was added and the mixture was stirred at room temperature for 4 hr. The reaction mixture was concentrated under reduced pressure and azeotropically distilled with toluene. The residue was dissolved in ethyl acetate, and saturated aqueous sodium hydrogen carbonate was slowly added to adjust to pH9. The organic layer was removed by partitioning, and the aqueous layer was adjusted to pH4 with 1N hydrochloric acid. It was extracted two times with ethyl acetate and two times with chloroform, and the organic layer was concentrated under reduced pressure to give the title compound (376 mg) as an orange solid. MS (ESI) m/z: 522.2 [M+H]+

(97-2) methyl [(6S)-4-(4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]piperidin-1-yl}phenyl)-2,3,9-trimethyl-6H-thieno[3,2-f][1,2,4]triazolo[4,3-a][1,4]diazepin-6-yl]acetate (Example Compound 97)

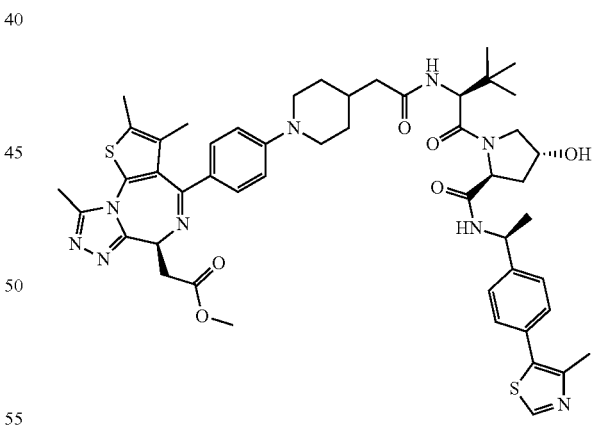

Example compound 97-1 (376 mg) and Reference Example compound 5 (389 mg), N,N-diisopropylethylamine (0.349 mL) and HATU (307 mg) were stirred in N,N-dimethylformamide (5 mL) at room temperature for 6 hr. To the reaction mixture was added saturated aqueous sodium hydrogen carbonate and the mixture was stirred and extracted twice with ethyl acetate. The organic layer was washed twice with water, and concentrated under reduced pressure. The residue was purified by silica gel column chromatography (methanol:chloroform=0:100-5:95) to give the title compound (205 mg) as a yellow solid.

MS (ESI) m/z: 948.9 [M+H]+

Example 98

(98-1) benzyl 4-(2-t-butoxy-2-oxoethoxy)piperidine-1-carboxylate (Example Compound 98-1)

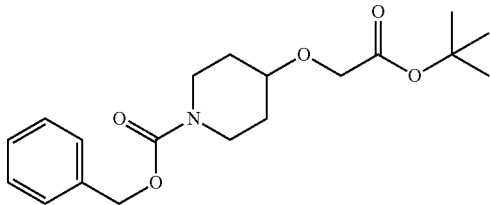 [SMILES: CC(C)(C)OC(=O)COC1CCN(C(=O)OCc2ccccc2)CC1]

Under an argon stream, a suspension of sodium hydride (60%, 221 mg) in N,N-dimethylformamide (5 mL) was cooled to 0° C., benzyl 4-hydroxy-1-piperidinecarboxylate (1.18 g) was added and the mixture was stirred for 15 min. Then t-butyl bromoacetate (0.883 mL) was added and the mixture was stirred for 3 hr while warming to room temperature. Water was added to the reaction mixture and the mixture was stirred and extracted twice with ethyl acetate. The organic layer was washed twice with water and concentrated under reduced pressure. The residue was purified by silica gel column chromatography (ethyl acetate:hexane=0:100-30:70) to give the title compound (930 mg) as a colorless viscous compound. MS (ESI) m/z: 350.2 [M+H]$^+$

(98-2) t-butyl [(piperidin-4-yl)oxy]acetate (Example Compound 98-2)

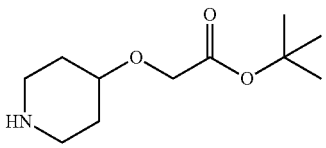

To a solution of Example compound 98-1 (930 mg) in ethanol (5 mL) was added 10% palladium carbon (300 mg) and, after hydrogen substitution, the mixture was stirred at room temperature for 7 hr. Using ethyl acetate, the reaction mixture was filtered through celite, and the filtrate was concentrated under reduced pressure to give the title compound (569 mg) as a pale-yellow viscous compound.
MS (ESI) m/z: 216.3 [M+H]$^+$

(98-3) methyl [(6S)-4-{4-[4-(2-t-butoxy-2-oxoethoxy)piperidin-1-yl]phenyl}-2,3,9-trimethyl-6H-thieno[3,2-f][1,2,4]triazolo[4,3-a][1,4]diazepin-6-yl]acetate (Example Compound 98-3)

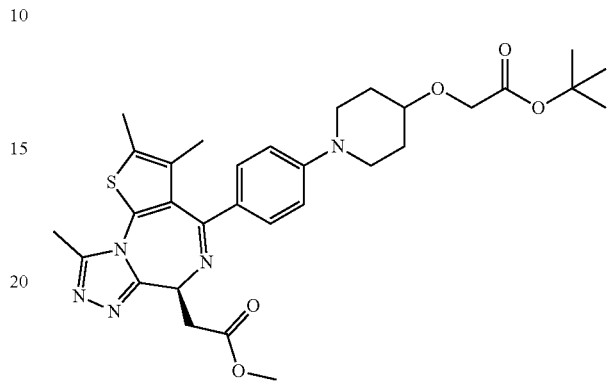

Under an argon stream, Reference Example compound 1 (400 mg), Example compound 98-2 (249 mg), tris(dibenzylideneacetone)dipalladium(0) (44 mg), t-BuXphos (41 mg) and potassium phosphate (614 mg) were stirred in 1,2-dimethoxyethane (5 mL) solvent at 70° C. for 24 hr. Compound 98-2 (249 mg), tris(dibenzylideneacetone)dipalladium(0) (44 mg), t-BuXphos (41 mg) were added and the mixture was stirred at 70° C. for 7 hr. Furthermore, tris(dibenzylideneacetone)dipalladium(0) (44 mg), t-BuXphos (41 mg) were added and the mixture was stirred at 70° C. for 15 hr. Using ethyl acetate, the reaction mixture was filtered through diatomaceous earth, and the filtrate was concentrated under reduced pressure. The residue was purified by silica gel column chromatography (methanol:chloroform=0:100-4:96) to give the title compound (374 mg) as a yellow solid.
MS (ESI) m/z: 594.3 [M+H]$^+$

(98-4) methyl [(6S)-4-(4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]piperidin-1-yl}phenyl)-2,3,9-trimethyl-6H-thieno[3,2-f][1,2,4]triazolo[4,3-a][1,4]diazepin-6-yl]acetate (Example Compound 98)

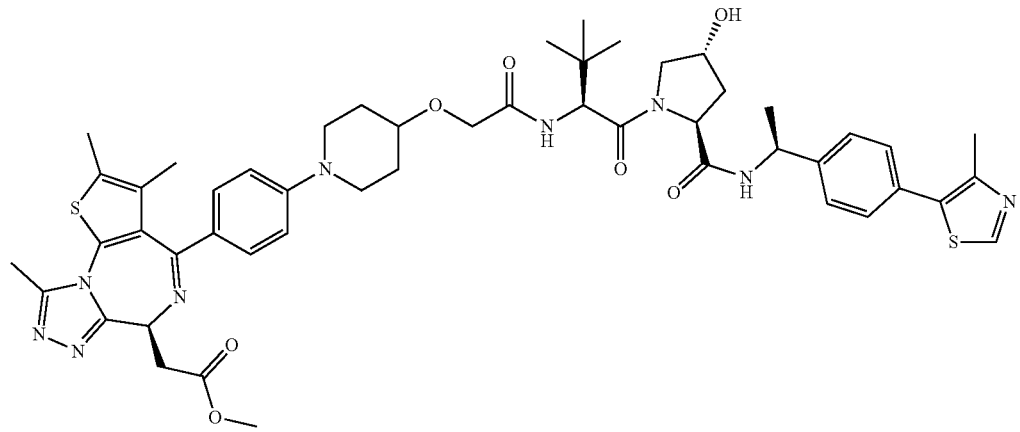 [SMILES: COC(=O)C[C@@H]1N=C(c2ccc(N3CCC(OCC(=O)N[C@H](C(=O)N4C[C@H](O)C[C@H]4C(=O)N[C@@H](C)c4ccc(-c5scnc5C)cc4)C(C)(C)C)CC3)cc2)c2c(sc(C)c2C)-n2c(C)nnc21]

To a solution of Example compound 98-3 (374 mg) in chloroform (1 mL) was added trifluoroacetic acid (1 mL) and the mixture was stirred at room temperature for 4 hr. The reaction mixture was concentrated under reduced pressure and azeotropically distilled 2 times with toluene. The residue was dissolved in N,N-dimethylformamide (5 mL), Reference Example compound 5 (364 mg), HATU (287 mg), N,N-diisopropylethylamine (0.545 mL) were added and the mixture was stirred at room temperature for 3 hr. To the reaction mixture was added saturated aqueous sodium hydrogen carbonate and the mixture was stirred and extracted twice with ethyl acetate. The organic layer was washed twice with water, and concentrated under reduced pressure. The residue was purified by silica gel column chromatography (methanol:chloroform=0:100-7:93) and silica gel column chromatography (methanol:chloroform=8:92) and then preparative HPLC (10 mM aqueous ammonium carbonate solution-acetonitrile) to give the title compound (155 mg) as a pale-yellow solid. MS (ESI) m/z: 964.9 [M+H]$^+$ Example 99

(99-1) t-butyl 3-methylpyrrolidine-1-carboxylato-(2S,4R)-1-[(2S)-2-acetamido-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 99-1)

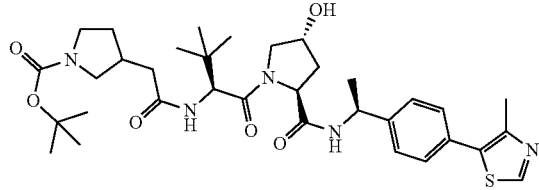 [SMILES: Cc1ncsc1-c1ccc([C@H](C)NC(=O)[C@@H]2C[C@@H](O)CN2C(=O)[C@@H](NC(=O)CC2CCN(C(=O)OC(C)(C)C)C2)C(C)(C)C)cc1]

To a solution of 2-(1-t-butoxycarbonylpyrrolidin-3-yl)acetic acid (300 mg), N,N-dimethylformamide (6.5 mL), N,N-diisopropylethylamine (0.679 mL) and Reference Example compound 5 (630 mg) was added HATU (746 mg), and the mixture was stirred at room temperature for 16 hr. Under ice-cooling, water was added to the reaction mixture, and the mixture was extracted with chloroform. The solvent was evaporated under reduced pressure. The obtained residue was diluted with ethyl acetate, washed with water, dried over anhydrous sodium sulfate, filtered and the solvent was evaporated under reduced pressure to give the title compound (875 mg) as an unpurified yellow solid. MS (ESI) m/z: 654.7 [M−H]$^-$ (99-2) (2S,4R)-1-{(2S)-3,3-dimethyl-2-[2-(pyrrolidin-3-yl)acetamido]butanoyl}-4-hydroxy-N-{(1S)-1-[4-(4-methyl-1,3-thiazol-5-yl)phenyl]ethyl}pyrrolidine-2-carboxamide (Example Compound 99-2)

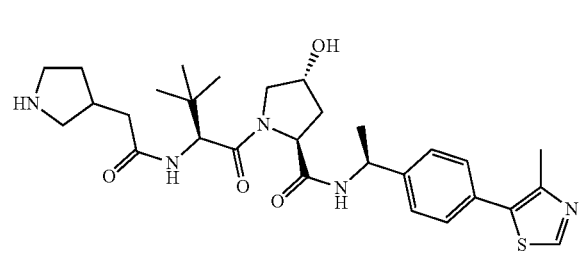 [SMILES: Cc1ncsc1-c1ccc([C@H](C)NC(=O)[C@@H]2C[C@@H](O)CN2C(=O)[C@@H](NC(=O)CC2CCNC2)C(C)(C)C)cc1]

To a solution of Example compound 99-1 (875 mg) in dichloromethane (8.8 mL) was added, under ice-cooling, trifluoroacetic acid (4.4 mL), and the mixture was stirred at room temperature for 2.5 hr. The reaction mixture was concentrated, diluted with chloroform, and saturated aqueous sodium hydrogen carbonate was added under ice-cooling. The chloroform layer was extracted, 1N aqueous sodium hydroxide solution was added to the aqueous layer, and the mixture was extracted twice with chloroform-methanol (10:1). The organic layers were combined, washed with saturated brine, dried over anhydrous sodium sulfate and filtered. The solvent was evaporated under reduced pressure. The obtained residue was purified by preparative HPLC (10 mM aqueous ammonium carbonate solution-acetonitrile) to give the title compound (410 mg) as a pale-yellow solid. MS (ESI) m/z: 556.4 [M+H]$^+$ (99-3) methyl [(6S)-4-(4-{3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]pyrrolidin-1-yl}phenyl)-2,3,9-trimethyl-6H-thieno[3,2-f][1,2,4]triazolo[4,3-a][1,4]diazepin-6-yl]acetate (Example Compound 99)

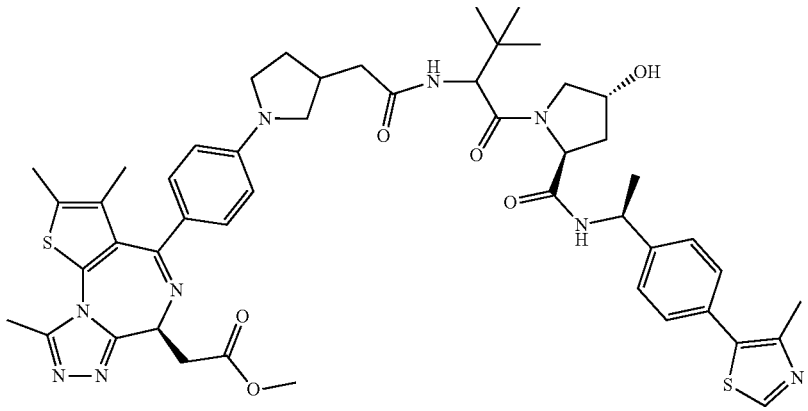

A mixture of Example compound 99-2 (165 mg), Reference Example compound 1 (123 mg), tris(dibenzylideneacetone)dipalladium(0) (14 mg), t-BuXphos (13 mg), potassium phosphate (189 mg) and tetrahydrofuran (1.5 mL) was stirred in a microwave reaction apparatus (Initiator, manufactured by Biotage) at 80° C. for 2 hr. Tris(dibenzylideneacetone)dipalladium(0) (14 mg), t-BuXphos (13 mg) were added, and the mixture was stirred in an oil bath at 90° C. for 5 hr, tris(dibenzylideneacetone)dipalladium(0) (14 mg), t-BuXphos (13 mg) were added and the mixture was further stirred for 5 hr. To the reaction mixture was added chloroform, the insoluble material in the reaction mixture was filtered off through diatomaceous earth, and the filtrate was concentrated under reduced pressure. The obtained residue was purified by NH silica gel column chromatography (ethyl acetate:methanol=100:0-93:7) to give the title compound (46 mg) as an orange solid. MS (ESI) m/z: 934.5 [M+H]$^+$ Example 100

(100-1) t-butyl [4-bromo-2-(trifluoromethyl)phenoxy]acetate (Example Compound 100-1)

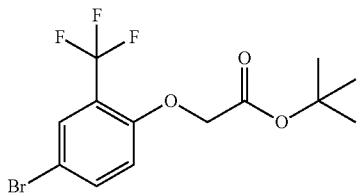 [SMILES: CC(C)(C)OC(=O)COc1ccc(Br)cc1C(F)(F)F]

To a solution of 4-bromo-2-trifluoromethylphenol (600 mg) in N,N-dimethylformamide (10 mL) were added potassium carbonate (688 mg) and t-butyl bromoacetate (0.411 mL) and the mixture was stirred at room temperature for 20 hr. Water was added to the reaction mixture and the mixture was stirred and extracted twice with ethyl acetate. The organic layers were collected and washed twice with water and passed through Phase Separator using ethyl acetate. The filtrate was concentrated under reduced pressure to give the title compound (923 mg) as a colorless oil. MS (ESI) m/z: 298.8, 300.8 [M−tBu+2H]$^+$ (100-2) methyl {(6S)-4-[4'-(2-t-butoxy-2-oxoethoxy)-3'-(trifluoromethyl)[1,1'-biphenyl]-4-yl]-2,3,9-trimethyl-6H-thieno[3,2-f][1,2,4]triazolo[4,3-a][1,4]diazepin-6-yl}acetate (Example Compound 100-2)

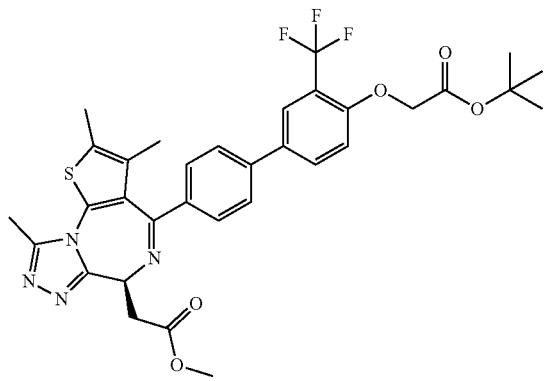 [SMILES: COC(=O)C[C@@H]1N=C(c2ccc(-c3ccc(OCC(=O)OC(C)(C)C)c(C(F)(F)F)c3)cc2)c2c(sc(C)c2C)-n2c(C)nnc21]

Under an argon stream, Example compound 100-1 (232 mg), Reference Example compound 3 (300 mg), palladium acetate (13 mg), S-phos (49 mg), potassium fluoride (103 mg) and water (38 μL) were heated under reflux in tetrahydrofuran (3 mL) solvent for 7 hr. Using ethyl acetate, the reaction mixture was filtered through diatomaceous earth, and the filtrate was concentrated under reduced pressure. The residue was purified by silica gel column chromatography (methanol:ethyl acetate=0:100-10:90) to give the title compound (309 mg) as a white solid. MS (ESI) m/z: 655.2 [M+H]$^+$ (100-3) methyl [(6S)-4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-3'-(trifluoromethyl)[1,1'-biphenyl]-4-yl}-2,3,9-trimethyl-6H-thieno[3,2-f][1,2,4]triazolo[4,3-a][1,4]diazepin-6-yl]acetate (Example Compound 100)

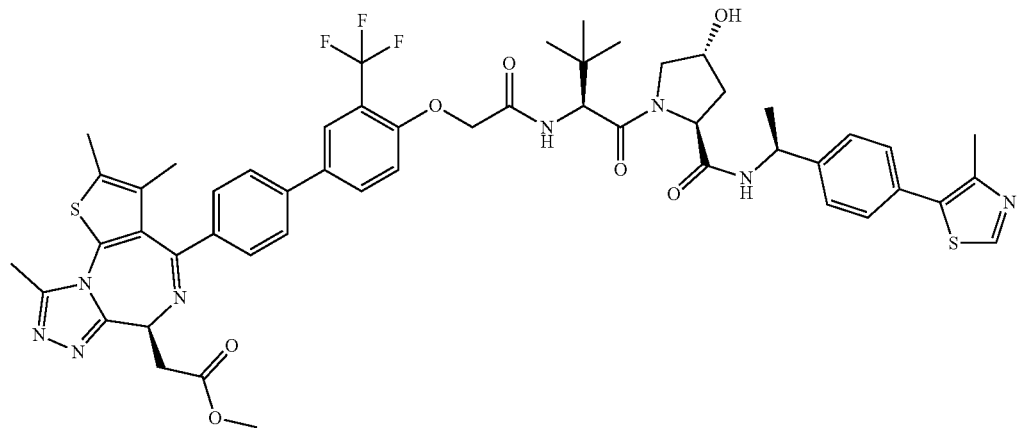 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(C(F)(F)F)c3)cc2)c2c(sc(C)c2C)-n2c(C)nnc21]

To a solution of Example compound 100-2 (309 mg) in chloroform (4 mL) was added trifluoroacetic acid (2 mL) and the mixture was stirred at room temperature for 16 hr. The reaction mixture was concentrated under reduced pressure and axeotropically distilled 2 times with toluene. The residue was dissolved in N,N-dimethylformamide (5 mL). Reference Example compound 5 (251 mg), N,N-diisopropylethylamine (0.821 mL), HATU (198 mg) were added and the mixture was stirred at room temperature for 2 hr. Water was added to the reaction mixture and the mixture was stirred. The precipitate was collected by filtration and the solid was purified by silica gel column chromatography (methanol:chloroform=0:100-3:97) to give the title compound (144 mg) as a white solid.

MS (ESI) m/z: 1025.3 [M+H]$^+$

Example 101

(101-1) 5-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-1,3-benzoxazole-2-carboxamide (Example Compound 101-1)

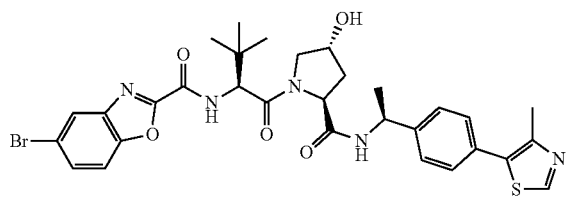 [SMILES: Cc1ncsc1-c1ccc([C@H](C)NC(=O)[C@@H]2C[C@@H](O)CN2C(=O)[C@@H](NC(=O)c2nc3cc(Br)ccc3o2)C(C)(C)C)cc1]

To a suspension of methyl 5-bromobenzoxazole-2-carboxylate (300 mg) in 1,2-dimethoxyethane (5 mL) was added 4 M aqueous lithium hydroxide solution (0.879 mL) and the mixture was stirred at room temperature for 2 hr. To the reaction mixture were added 1N hydrochloric acid and chloroform and the mixture was stirred. A small amount of tetrahydrofuran was added and the mixture was stirred. The aqueous layer was removed by Phase Separator and the organic layer was concentrated under reduced pressure. The residue was dissolved in N,N-dimethylformamide (5 mL), and Reference Example compound 5 (564 mg), HATU (535 mg), N,N-diisopropylethylamine (0.608 mL) were added and the mixture was stirred at room temperature. Water was added to the reaction mixture and the mixture was stirred and extracted twice with ethyl acetate. The organic layer was washed twice with water and concentrated under reduced pressure. The residue was purified by NH silica gel column chromatography (methanol:chloroform=0:100-2:98) to give the title compound (402 mg) as a white solid.

MS (ESI) m/z: 668.1, 670.1 [M+H]$^+$ (101-2) methyl [(6S)-4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzoxazol-5-yl]phenyl}-2,3,9-trimethyl-6H-thieno[3,2-f][1,2,4]triazolo[4,3-a][1,4]diazepin-6-yl]acetate (Example Compound 101)

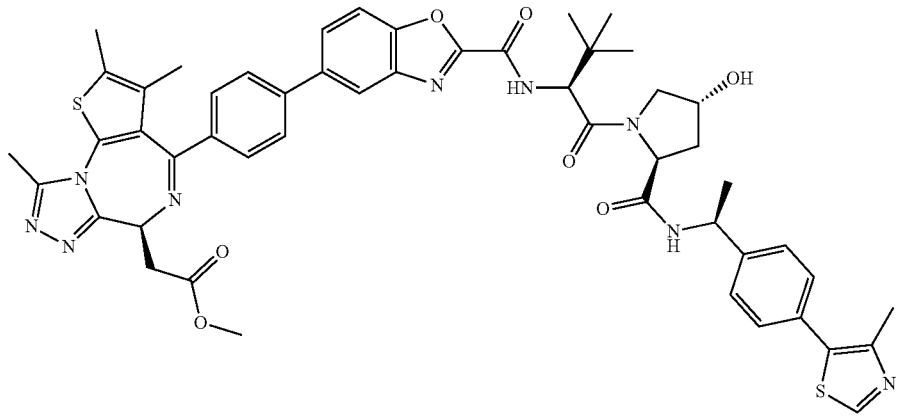

Under an argon stream, Reference Example compound 3 (200 mg), Example compound 101-1 (317 mg), palladium acetate (8.9 mg), S-phos (32 mg), potassium fluoride (69 mg) and water (26 µL) were heated under reflux in tetrahydrofuran (5 mL) solvent for 7 hr. Using ethyl acetate, the reaction mixture was filtered through diatomaceous earth, and the filtrate was concentrated under reduced pressure. The residue was purified by NH silica gel column chromatography (methanol:chloroform=0:100-2:98) and silica gel column chromatography (methanol:chloroform=0:100-5:95) to give the title compound (225 mg) as a white solid.

MS (ESI) m/z: 968.3 [M+H]$^+$

Example 102

(102-1) 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1H-pyrazole-4-carboxylic acid hydrochloride (Example Compound 102-1)

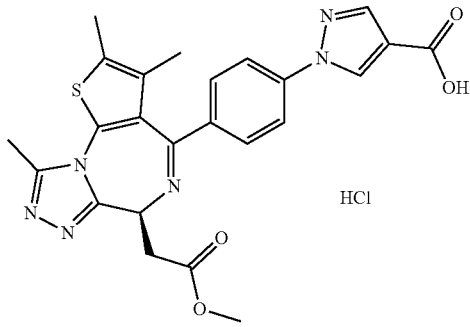 [SMILES: COC(=O)C[C@@H]1N=C(c2ccc(-n3cc(C(=O)O)cn3)cc2)c2c(sc(C)c2C)-n2c(C)nnc21 ; Cl]

Reference Example compound 2 (400 mg), copper(I) oxide (23 mg) and t-butyl pyrazole-4-carboxylate (164 mg) were stirred in methanol (5 mL) solvent at room temperature for 20 hr. The mixture was heated at 50° C. and stirred for 8 hr and then heated under reflux for 9 hr. Using ethyl acetate, the reaction mixture was filtered through diatomaceous earth, and the filtrate was concentrated under reduced pressure. The residue was purified by NH silica gel column chromatography (ethyl acetate:hexane=30:70-70:30) to give a white solid. The obtained solid was dissolved in chloroform (1 mL), trifluoroacetic acid (1 mL) was added and the mixture was stirred at room temperature for 5 hr. The reaction mixture was concentrated under reduced pressure, and azeotropically distilled 2 times with toluene. Saturated aqueous sodium hydrogen carbonate was added to set to pH9, and the mixture was washed twice with ethyl acetate. The aqueous layer was set to pH4 with 1N hydrochloric acid and extracted 3 times with chloroform. The organic layer was concentrated under reduced pressure to give the title compound (49 mg) as a white solid.
MS (ESI) m/z: 491.1 [M+H]$^+$ (102-2) methyl [(6S)-4-{4-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1H-pyrazol-1-yl]phenyl}-2,3,9-trimethyl-6H-thieno[3,2-f][1,2,4]triazolo[4,3-a][1,4]diazepin-6-yl]acetate (Example Compound 102)

By reaction and treatment in the same manner as in Example 97 (97-2) and using Example compound 102-1 instead of Example compound 97-1, the title compound was obtained as a white solid. MS (ESI) m/z: 917.3 [M+H]$^+$

Example 103

(103-1) 2-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyridine-4-carboxamide (Example Compound 103-1)

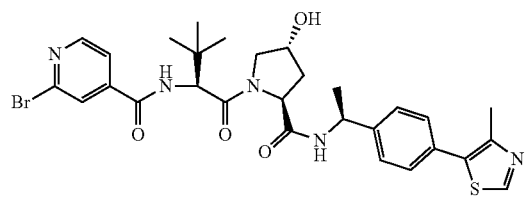

To a solution of 2-bromoisonicotinic acid (139 mg) and Reference Example compound 5 (300 mg) in N,N-dimethylformamide (4.2 mL) was added N,N-diisopropylethylamine (0.539 mL), and HATU (356 mg) was added under ice-cooling, and the mixture was allowed to naturally warm to room temperature and stirred for 65 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (287 mg) as a white solid. MS (ESI) m/z: 626.5, 628.5 [M−H]$^−$

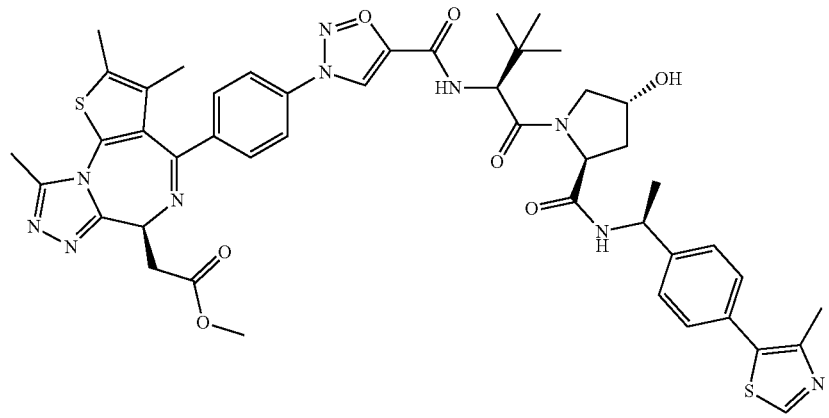

(103-2) methyl [(6S)-4-{4-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-2-yl]phenyl}-2,3,9-trimethyl-6H-thieno[3,2-f][1,2,4]triazolo[4,3-a][1,4]diazepin-6-yl]acetate (Example Compound 103)

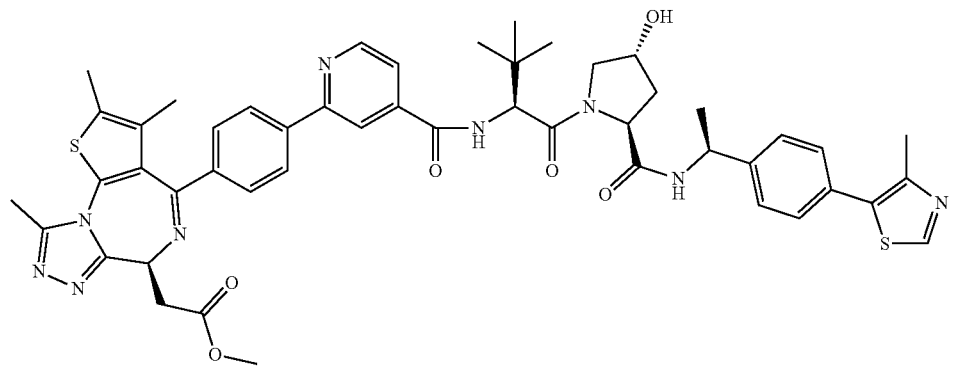 [SMILES: COC(=O)C[C@@H]1N=C(c2ccc(-c3cc(C(=O)N[C@H](C(=O)N4C[C@H](O)C[C@H]4C(=O)N[C@@H](C)c4ccc(-c5scnc5C)cc4)C(C)(C)C)ccn3)cc2)c2c(sc(C)c2C)-n2c(C)nnc21]

To a solution of Example compound 103-1 (280 mg) and Reference Example compound 3 (248 mg) in tetrahydrofuran (4.454 mL) were added palladium acetate (10 mg), S-phos (37 mg), potassium fluoride (78 mg) and water (0.029 mL) and the mixture was stirred at 70° C. for 21 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-93:7), and then by silica gel column chromatography (chloroform:methanol=98:2-93:7). The obtained solid was suspension washed with diethyl ether, collected by filtration and dried under reduced pressure to give the title compound (35 mg) as a white solid.
MS (ESI) m/z: 926.7 [M−H]−

Example 104

(104-1) 5-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyridine-3-carboxamide (Example Compound 104-1)

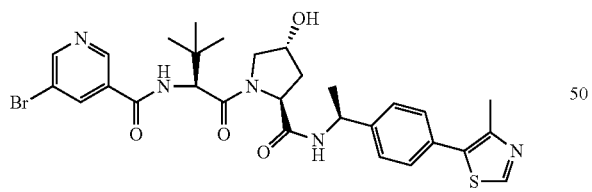

To a solution of 5-bromonicotinic acid (231 mg) and Reference Example compound 5 (500 mg) in N,N-dimethylformamide (6.9 mL) was added N,N-diisopropylethylamine (0.899 mL), and HATU (593 mg) was added under ice-cooling, and the mixture was allowed to naturally warm to room temperature and stirred for 6 hr. Water was added to the reaction solution and the mixture was extracted with chloroform, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (520 mg) as a white solid. MS (ESI) m/z: 626.4, 628.4 [M−H]−

(104-2) methyl [(6S)-4-{4-[5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-3-yl]phenyl}-2,3,9-trimethyl-6H-thieno[3,2-f][1,2,4]triazolo[4,3-a][1,4]diazepin-6-yl]acetate (Example Compound 104)

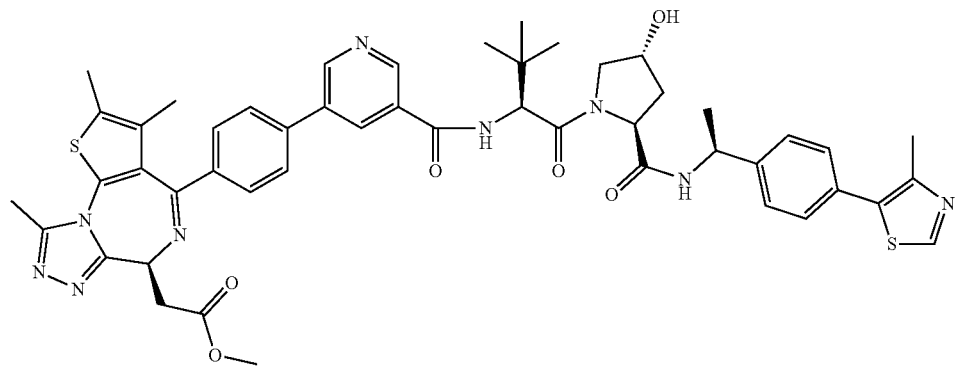 [SMILES: COC(=O)C[C@@H]1N=C(c2ccc(-c3cncc(C(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 104-1 (515 mg) and Reference Example compound 3 (456 mg) in tetrahydrofuran (8.2 mL) were added palladium acetate (18 mg), S-phos (67 mg), potassium fluoride (143 mg) and water (0.053 mL) and the mixture was stirred at 70° C. for 64 hr. The insoluble material in the reaction solution was filtered off through diatomaceous earth, water was added to the filtrate and the mixture was extracted with chloroform. The organic layer was dried over anhydrous sodium sulfate and the solvent was evaporated under reduced pressure. The residue was purified by NH silica gel column chromatography (ethyl acetate:methanol=98:2-93:7), and then by silica gel column chromatography (chloroform:methanol=98:2-93:7). The obtained solid was suspension washed with diethyl ether, collected by filtration and dried under reduced pressure to give the title compound (475 mg) as a white solid. MS (ESI) m/z: 928.5 [M+H]$^+$ Example 105

(105-1) 4-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyridine-4-carboxamide (Example Compound 105-1)

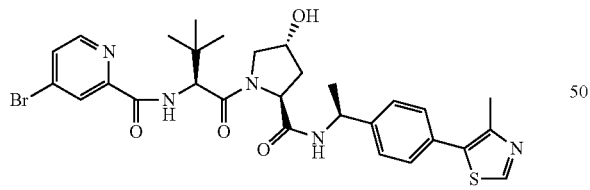

To a solution of 4-bromopicolinic acid (139 mg) and Reference Example compound 5 (300 mg) in N,N-dimethylformamide (4.2 mL) was added N,N-diisopropylethylamine (0.539 mL), and HATU (356 mg) was added under ice-cooling, and the mixture was allowed to naturally warm to room temperature and stirred for 65 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (338 mg) as a white solid. MS (ESI) m/z: 626.4, 628.5 [M−H]$^-$ (105-2) methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-4-yl]phenyl}-2,3,9-trimethyl-6H-thieno[3,2-f][1,2,4]triazolo[4,3-a][1,4]diazepin-6-yl]acetate (Example Compound 105)

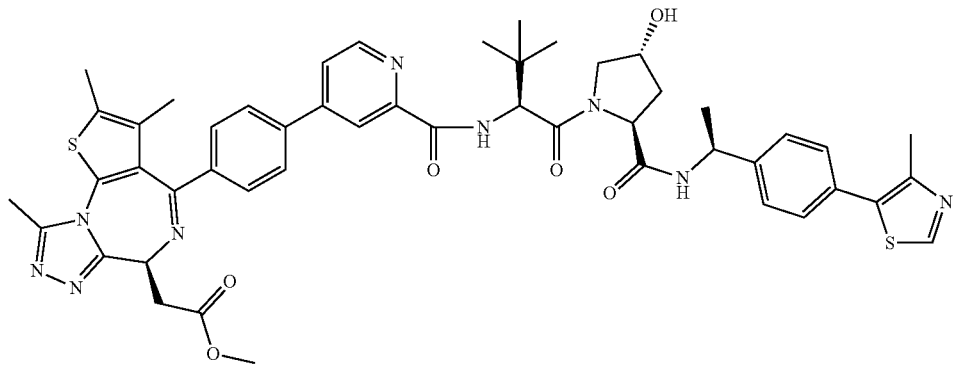 [SMILES: COC(=O)C[C@@H]1N=C(c2ccc(-c3ccnc(C(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 105-1 (335 mg) and Reference Example compound 3 (297 mg) in tetrahydrofuran (5.3 mL) were added palladium acetate (12 mg), S-phos (44 mg), potassium fluoride (93 mg) and water (0.035 mL) and the mixture was stirred at 70° C. for 21 hr. The insoluble material in the reaction solution was filtered off through diatomaceous earth, water was added to the filtrate, and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-93:7), and then by silica gel column chromatography (chloroform:methanol=98:2-93:7). The obtained solid was suspension washed with diethyl ether, collected by filtration and dried under reduced pressure to give the title compound (475 mg) as a white solid.

MS (ESI) m/z: 465.1[(M+2H)/2]$^+$

Example 106

(106-1) (2S,4R)-1-[(2S)-2-(3-bromo-4-fluorobenzamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 106-1)

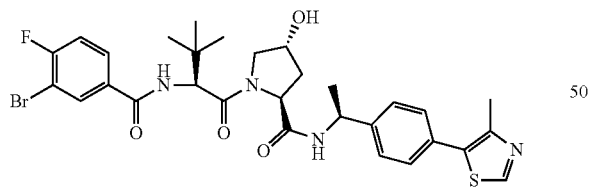

To a solution of 3-bromo-4-fluorobenzoic acid (150 mg), Reference Example compound 5 (300 mg) in N,N-dimethylformamide (4.2 mL) was added N,N-diisopropylethylamine (0.539 mL), and HATU (356 mg) was added under ice-cooling, and the mixture was allowed to naturally warm to room temperature and stirred for 65 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (360 mg) as a white solid. MS (ESI) m/z: 645.4, 647.5 [M+H]$^+$ (106-2) methyl {(6S)-4-[2'-fluoro-5'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 106)

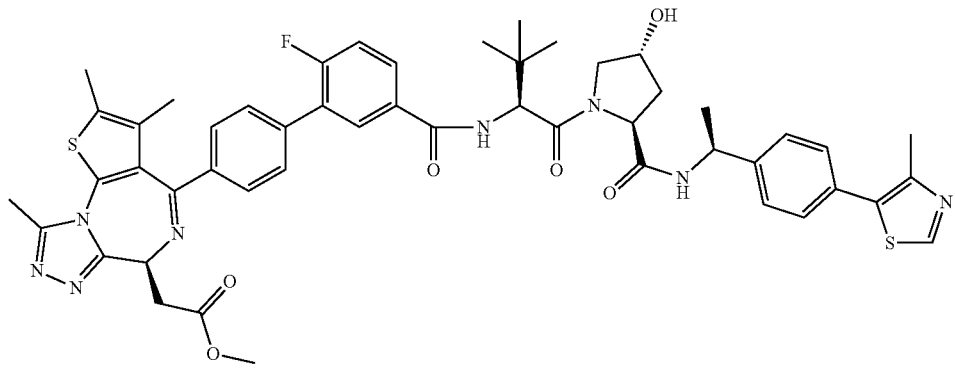 [SMILES: COC(=O)C[C@@H]1N=C(c2ccc(-c3cc(C(=O)N[C@H](C(=O)N4C[C@H](O)C[C@H]4C(=O)N[C@@H](C)c4ccc(-c5scnc5C)cc4)C(C)(C)C)ccc3F)cc2)c2c(sc(C)c2C)-n2c(C)nnc21]

To a solution of Example compound 106-1 (355 mg) and Reference Example compound 3 (306 mg) in tetrahydrofuran (5.5 mL) were added palladium acetate (12 mg), S-phos (45 mg), potassium fluoride (96 mg) and water (0.036 mL) and the mixture was stirred at 70° C. for 21 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-93:7), and then by silica gel column chromatography (chloroform:methanol=99:1-94:6). The obtained solid was suspension washed with diethyl ether, collected by filtration and dried under reduced pressure to give the title compound (241 mg) as a white solid.

MS (ESI) m/z: 945.7 [M+H]$^+$

Example 107

(107-1) (2S,4R)-1-[(2S)-2-(3-bromo-5-fluorobenzamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 107-1)

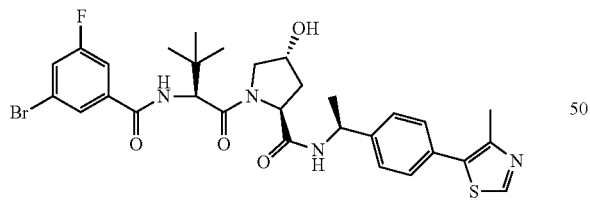

To a solution of 2-bromo-5-fluorobenzoic acid (150 mg) and Reference Example compound 5 (300 mg) in N,N-dimethylformamide (4.2 mL) was added N,N-diisopropylethylamine (0.539 mL), and HATU (356 mg) was added under ice-cooling, and the mixture was allowed to naturally warm to room temperature and stirred for 65 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (341 mg) as a pale-yellow solid.

MS (ESI) m/z: 645.3, 647.3 [M+H]$^+$ (107-2) methyl {(6S)-4-[3'-fluoro-5'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 107)

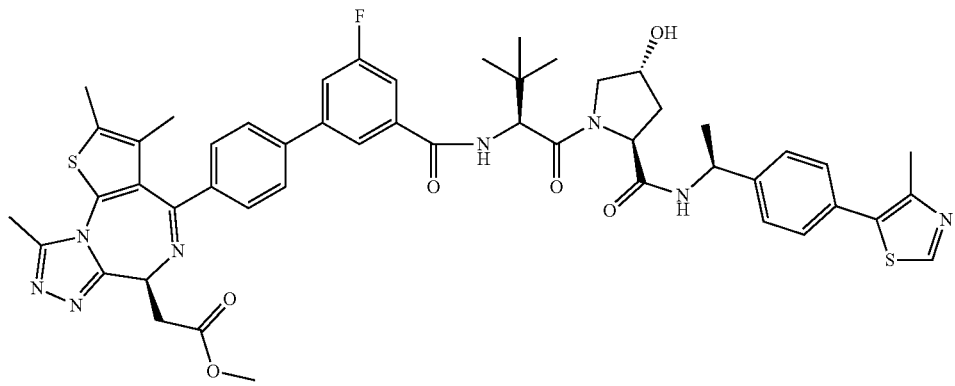 [SMILES: COC(=O)C[C@@H]1N=C(c2ccc(-c3cc(F)cc(C(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 107-1 (335 mg) and Reference Example compound 3 (289 mg) in tetrahydrofuran (5.2 mL) were added palladium acetate (12 mg), S-phos (43 mg), potassium fluoride (90 mg) and water (0.034 mL) and the mixture was stirred at 70° C. for 21 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-93:7), and then by silica gel column chromatography (chloroform:methanol=99:1-94:6). The obtained solid was suspension washed with diethyl ether, collected by filtration and dried under reduced pressure is to give the title compound (182 mg) as a white solid.

MS (ESI) m/z: 945.8 [M+H]$^+$

Example 108

(108-1) (2S,4R)-1-[(2S)-2-(5-bromo-2-fluorobenzamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 108-1)

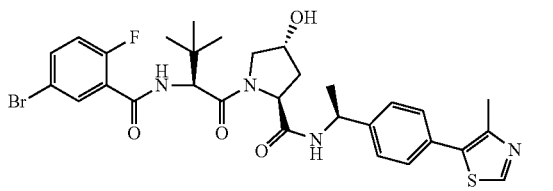 [SMILES: Cc1ncsc1-c1ccc([C@H](C)NC(=O)[C@@H]2C[C@@H](O)CN2C(=O)[C@@H](NC(=O)c2cc(Br)ccc2F)C(C)(C)C)cc1]

To a solution of 5-bromo-2-fluorobenzoic acid (150 mg), Reference Example compound 5 (300 mg) in N,N-dimethylformamide (4.2 mL) was added N,N-diisopropylethylamine (0.539 mL), and HATU (356 mg) was added under ice-cooling, and the mixture was allowed to naturally warm to room temperature and stirred for 65 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (416 mg) as a pale-yellow solid. MS (ESI) m/z: 645.3, 647.3 [M+H]$^+$ (108-2) methyl {(6S)-4-[4'-fluoro-3'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 108)

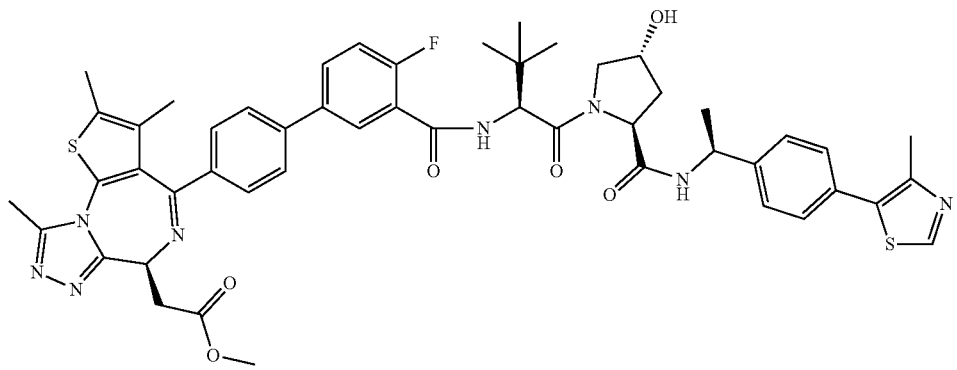 [SMILES: COC(=O)C[C@@H]1N=C(c2ccc(-c3ccc(F)c(C(=O)N[C@H](C(=O)N4C[C@H](O)C[C@H]4C(=O)N[C@@H](C)c4ccc(-c5scnc5C)cc4)C(C)(C)C)c3)cc2)c2c(sc(C)c2C)-n2c(C)nnc21]

To a solution of Example compound 108-1 (410 mg) and Reference Example compound 3 (354 mg) in tetrahydrofuran (6.4 mL) were added palladium acetate (14 mg), S-phos (52 mg), potassium fluoride (111 mg) and water (0.041 mL) and the mixture was stirred at 70° C. for 21 hr. The insoluble material in the reaction solution was filtered off through diatomaceous earth, water was added to the filtrate and the mixture was extracted with ethyl acetate. The organic layer was dried over anhydrous sodium sulfate and the solvent was evaporated under reduced pressure. The residue was purified by NH silica gel column chromatography (ethyl acetate:methanol=98:2-93:7), and then by silica gel column chromatography (chloroform:methanol=99:1-94:6). The obtained solid was suspension washed with diethyl ether, collected by filtration and dried under reduced pressure to give the title compound (316 mg) as a white solid. MS (ESI) m/z: 945.6 [M+H]$^+$ Example 109

(109-1) t-butyl (3R)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrrolidine-1-carboxylate (Example Compound 109-1)

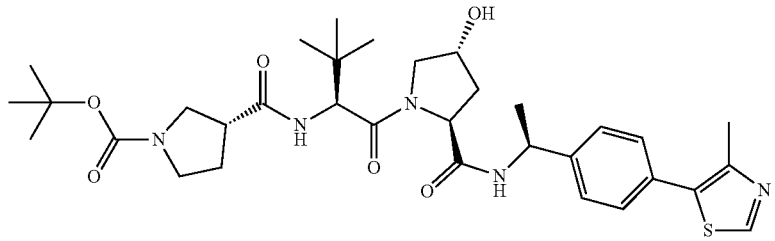 [SMILES: Cc1ncsc1-c1ccc([C@H](C)NC(=O)[C@@H]2C[C@@H](O)CN2C(=O)[C@@H](NC(=O)[C@@H]2CCN(C(=O)OC(C)(C)C)C2)C(C)(C)C)cc1]

To a solution of (R)-1-(t-butoxycarbonyl)-3-pyrrolidinecarboxylic acid (246 mg) and Reference Example compound 5 (500 mg) in N,N-dimethylformamide (6.9 mL) was added N,N-diisopropylethylamine (0.899 mL), and HATU (593 mg) was added under ice-cooling, and the mixture was allowed to naturally warm to room temperature and stirred for 65 hr. Water was added to the reaction solution and the mixture was extracted with ethyl acetate, and the extract was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=98:2-93:7) to give the title compound (521 mg) as a pale-yellow solid. MS (ESI) m/z: 642.7 [M+H]$^+$ (109-2) methyl [(6S)-4-{4'-[(3R)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrrolidine-1-carbonyl][1,1'-biphenyl]-4-yl}-2,3,9-trimethyl-6H-thieno[3,2-f][1,2,4]triazolo[4,3-a][1,4]diazepin-6-yl]acetate (Example Compound 109)

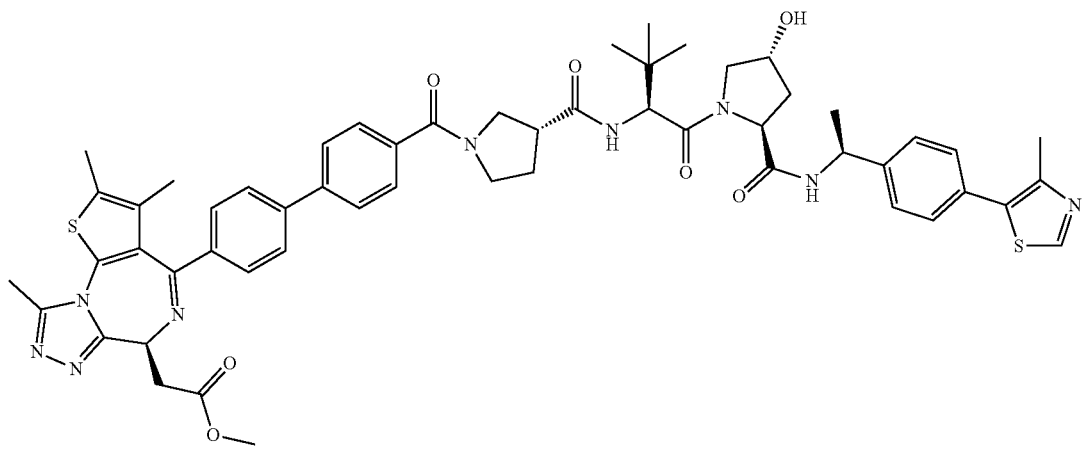 [SMILES: COC(=O)C[C@@H]1N=C(c2ccc(-c3ccc(C(=O)N4CC[C@@H](C(=O)N[C@H](C(=O)N5C[C@H](O)C[C@H]5C(=O)N[C@@H](C)c5ccc(-c6scnc6C)cc5)C(C)(C)C)C4)cc3)cc2)c2c(sc(C)c2C)-n2c(C)nnc21]

To a solution of Example compound 109-1 (150 mg) and Example compound 90-1 (139 mg) in N,N-dimethylformamide (2.8 mL) was added N,N-diisopropylethylamine (0.240 mL), and HATU (158 mg) was added under ice-cooling, and the mixture was allowed to naturally warm to room temperature and stirred for 15 hr. To the reaction solution was added water and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=99:1-95:5). The obtained solid was suspension washed with diethyl ether, collected by filtration and dried under reduced pressure to give the title compound (204 mg) as a white solid. MS (ESI) m/z: 1022.7 [M−H]⁻

Example 110

(110-1) methyl (4-{4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)acetate (Example Compound 110)

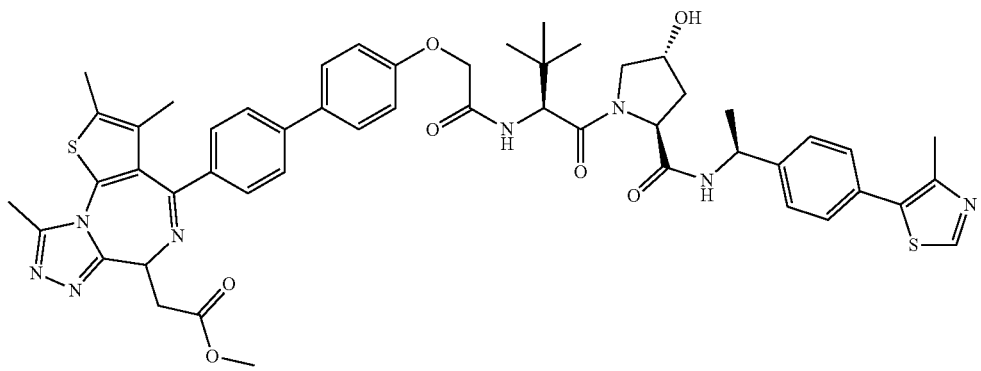 [SMILES: COC(=O)CC1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

By reaction and treatment in the same manner as in Example 15 (15-1)-(15-3) and using Reference Example compound 13 instead of Reference Example compound 1, the title compound was obtained as a yellow solid. MS (ESI) m/z: 957.5 [M+H]⁺

Example 111

(111-1) methyl (4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl)acetate (Example Compound 111)

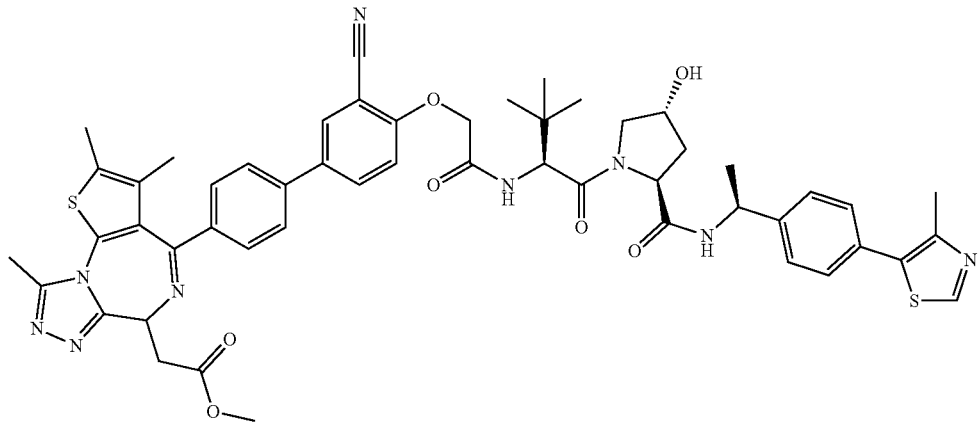 [SMILES: COC(=O)CC1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

By reaction and treatment in the same manner as in Example 9 (9-3)-(9-5) and using Reference Example compound 13 instead of Reference Example compound 1, the title compound was obtained as a yellow solid. MS (ESI) m/z: 982.4 [M+H]$^+$

Example 112

(112-1) methyl {(6S)-4-[2'-fluoro-3'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 112)

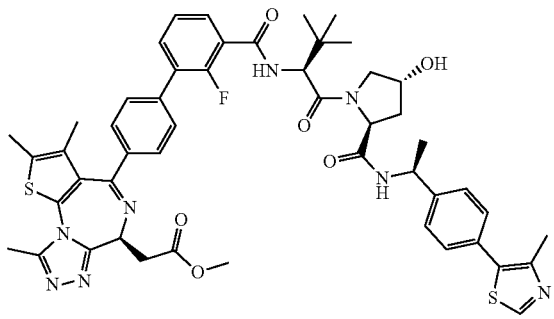

By reaction and treatment in the same manner as in Example 106 (106-1)-(106-2) and using 3-bromo-2-fluorobenzoic acid instead of 3-bromo-4-fluorobenzoic acid, the title compound was obtained as a yellow solid.
MS (ESI) m/z: 945.5 [M+H]$^+$

Example 113

(113-1) 6-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyridine-2-carboxamide (Example Compound 113-1)

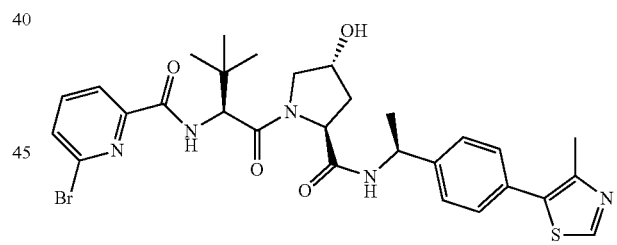

To a solution of 6-bromopicolinic acid (300 mg), Reference Example compound 5 (714 mg), N,N-dimethylformamide (5.0 mL) and N,N-diisopropylethylamine (0.771 mL) was added, under ice-cooling, HATU (1.01 g), and the mixture was stirred at room temperature for 18 hr. The reaction mixture was diluted with ethyl acetate, washed successively with saturated aqueous sodium hydrogen carbonate, water and saturated brine, dried over anhydrous sodium sulfate and filtered. The solvent was evaporated under reduced pressure. To the precipitated solid was added diethyl ether and, after ultrasonic suspension washing, the solid was collected by filtration to give the title compound (680 mg) as a white solid.

MS (ESI) m/z: 628.4, 630.3 [M+H]$^+$ (113-2) methyl [(6S)-4-{4-[6-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-2-yl]phenyl}-2,3,9-trimethyl-6H-thieno[3,2-f][1,2,4]triazolo[4,3-a][1,4]diazepin-6-yl]acetate (Example Compound 113)

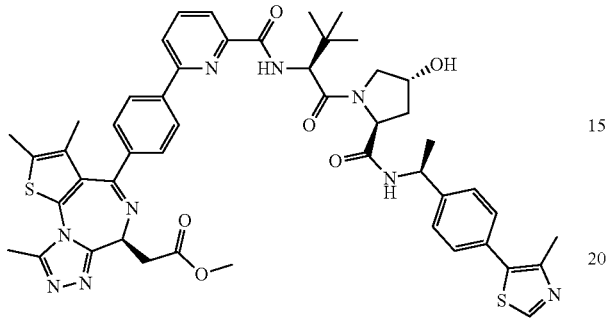

To a solution of Example compound 113-1 (270 mg) and Reference Example compound 3 (240 mg) in tetrahydrofuran (4.3 mL) were added palladium acetate (10 mg), S-phos (35 mg), potassium fluoride (75 mg) and water (0.028 mL), and the mixture was stirred with heating under reflux for 40 hr. The reaction mixture was diluted with chloroform, insoluble material was filtered off through diatomaceous earth, and the filtrate was concentrated under reduced pressure. To the obtained residue was added saturated aqueous sodium hydrogen carbonate, and the mixture was extracted with chloroform, and the extract was dried over anhydrous sodium sulfate and filtered. The solvent was evaporated under reduced pressure. The obtained residue was purified by silica gel column chromatography (chloroform:methanol=100:0-93:7) and NH silica gel column chromatography (ethyl acetate:methanol=100:0-90:10) to give the title compound (83 mg) as a white solid.

MS (ESI) m/z: 928.5 [M+H]$^+$

Example 114

(114-1) t-butyl 4-[5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-2-yl]piperazine-1-carboxylate (Example Compound 114-1)

By reaction and treatment in the same manner as in Example 97 (97-2) and using 6-(4-(t-butoxycarbonyl)-1-piperazinyl)nicotinic acid instead of Example compound 97-1, the title compound was obtained as a white solid.

MS (ESI) m/z: 734.8 [M+H]$^+$ (114-2) N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-6-(piperazin-1-yl)pyridine-3-carboxamide (Example Compound 114-2)

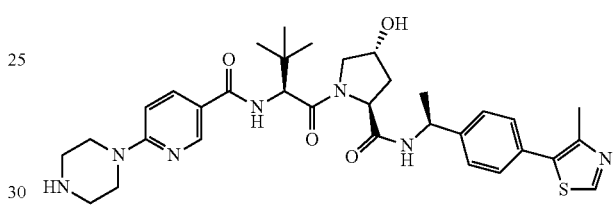

To a solution of Example compound 114-1 (370 mg) in chloroform (2 mL) was added trifluoroacetic acid (1 mL) and the mixture was stirred at room temperature for 3 hr. The reaction mixture was concentrated under reduced pressure, saturated aqueous sodium hydrogen carbonate, chloroform were added to the residue and the mixture was stirred. The aqueous layer was removed by Phase Separator and the organic layer was concentrated under reduced pressure to give the target compound (301 mg) as a yellow solid. MS (ESI) m/z: 634.3 [M+H]$^+$

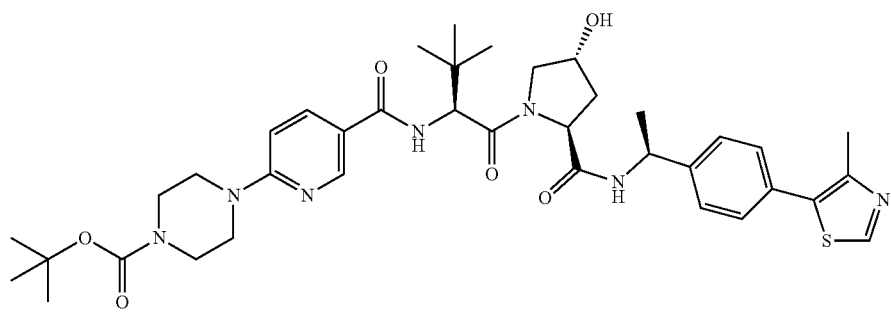 [SMILES: Cc1ncsc1-c1ccc([C@H](C)NC(=O)[C@@H]2C[C@@H](O)CN2C(=O)[C@@H](NC(=O)c2ccc(N3CCN(C(=O)OC(C)(C)C)CC3)nc2)C(C)(C)C)cc1]

(114-3) methyl [(6S)-4-(4-{4-[5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-2-yl]piperazin-1-yl}phenyl)-2,3,9-trimethyl-6H-thieno[3,2-f][1,2,4]triazolo[4,3-a][1,4]diazepin-6-yl]acetate (Example Compound 114)

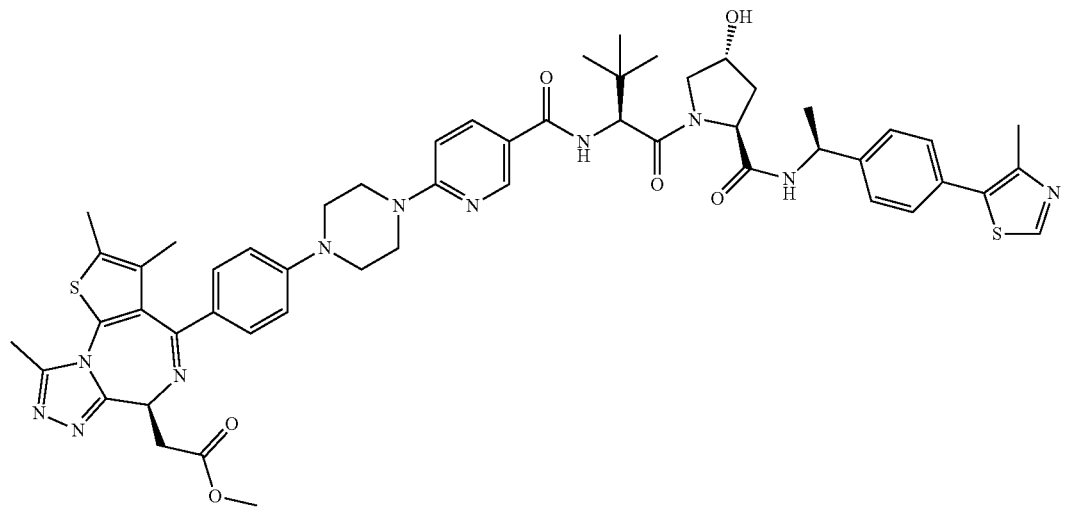 [SMILES: COC(=O)C[C@@H]1N=C(c2ccc(N3CCN(c4ccc(C(=O)N[C@H](C(=O)N5C[C@H](O)C[C@H]5C(=O)N[C@@H](C)c5ccc(-c6scnc6C)cc5)C(C)(C)C)cn4)CC3)cc2)c2c(sc(C)c2C)-n2c(C)nnc21]

By reaction and treatment in the same manner as in Example 98 (98-3) and using Example compound 114-2 instead of Example compound 98-2, the title compound was obtained as a yellow solid. MS (ESI) m/z: 1012.9 [M+H]⁺

Example 115

(115-1) benzyl 3-[4-(t-butoxycarbonyl)phenoxy]pyrrolidine-1-carboxylate (Example Compound 115-1)

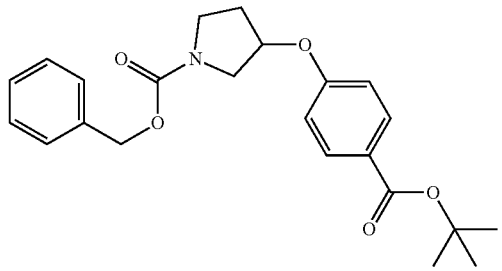 [SMILES: CC(C)(C)OC(=O)c1ccc(OC2CCN(C(=O)OCc3ccccc3)C2)cc1]

Under an argon stream, a solution of t-butyl 4-hydroxybenzoate (500 mg), 1-(benzyloxycarbonyl)-3-pyrrolidinol (683 mg) and triphenylphosphine (1.01 g) in tetrahydrofuran (5 mL) was cooled to 0° C., bis(2-methoxyethyl) azodicarboxylate (905 mg) was added and the mixture was stirred at room temperature for 3 hr. Water was added to the reaction mixture and the mixture was stirred and extracted twice with ethyl acetate. The organic layer was washed with water and concentrated under reduced pressure. The residue was purified by NH silica gel column chromatography (ethyl acetate:hexane=0:100-30:70) to give the title compound (607 mg) as a colorless viscous compound. MS (ESI) m/z: 398.4 [M+H]⁺

(115-2) t-butyl 4-[(pyrrolidin-3-yl)oxy]benzoate (Example Compound 115-2)

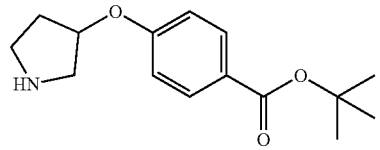 [SMILES: CC(C)(C)OC(=O)c1ccc(OC2CCNC2)cc1]

To a solution of Example compound 115-1 (607 mg) in ethanol (4 mL)-tetrahydrofuran (4 mL) was added 10% palladium carbon (200 mg) and, after hydrogen substitution, the mixture was stirred at room temperature for 5 hr. Using ethyl acetate, the reaction mixture was filtered through celite and the filtrate was concentrated under reduced pressure. The residue was purified by NH silica gel column chromatography (methanol:ethyl acetate=0:100-10:90) to give the title compound (266 mg) as a white solid. MS (ESI) m/z: 264.3 [M+H]⁺

(115-3) t-butyl 4-[(1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrrolidin-3-yl)oxy]benzoate (Example Compound 115-3)

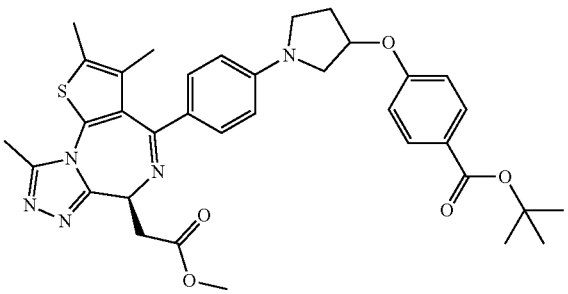 [SMILES: COC(=O)C[C@@H]1N=C(c2ccc(N3CCC(Oc4ccc(C(=O)OC(C)(C)C)cc4)C3)cc2)c2c(sc(C)c2C)-n2c(C)nnc21]

Under an argon stream, compound 115-2 (266 mg), Reference Example compound 1 (400 mg), tris(dibenzylideneacetone)dipalladium(0) (88 mg), t-BuXphos (82 mg), potassium phosphate (614 mg) were heated under reflux in tetrahydrofuran (5 mL) solvent for 26 hr. Using ethyl acetate, the reaction mixture was filtered through diatomaceous earth, and the filtrate was concentrated under reduced pressure. The residue was purified by silica gel column chromatography (methanol:chloroform=0:100-4:96) to give the title compound (460 mg) as a yellow solid. MS (ESI) m/z: 642.3 [M+H]$^+$ (115-4) methyl [(6S)-4-(4-{3-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)phenoxy]pyrrolidin-1-yl}phenyl)-2,3,9-trimethyl-6H-thieno[3,2-f][1,2,4]triazolo[4,3-a][1,4]diazepin-6-yl]acetate (Example Compound 115)

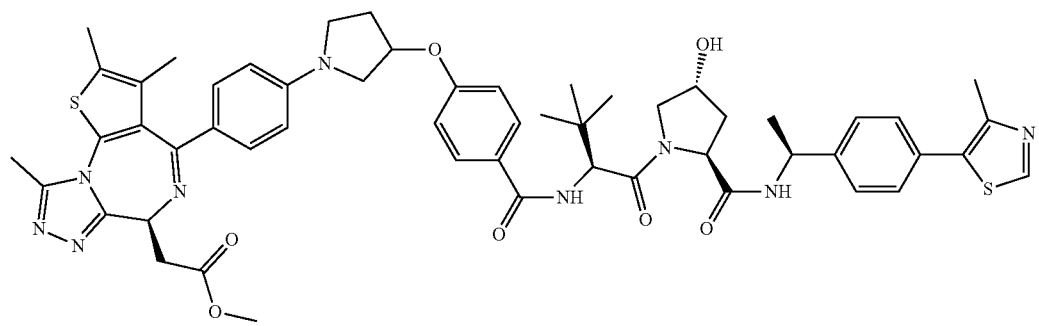 [SMILES: COC(=O)C[C@@H]1N=C(c2ccc(N3CCC(Oc4ccc(C(=O)N[C@H](C(=O)N5C[C@H](O)C[C@H]5C(=O)N[C@@H](C)c5ccc(-c6scnc6C)cc5)C(C)(C)C)cc4)C3)cc2)c2c(sc(C)c2C)-n2c(C)nnc21]

To a solution of Example compound 115-3 (460 mg) in chloroform (1 mL) was added trifluoroacetic acid (1 mL) and the mixture was stirred at room temperature for 3 hr. The reaction mixture was concentrated under reduced pressure and azeotropically distilled 2 times with toluene. The residue was dissolved in N,N-dimethylformamide (5 mL), and Reference Example compound 5 (413 mg), N,N-diisopropylethylamine (0.619 mL), HATU (327 mg) were added and the mixture was stirred at room temperature for 20 hr. To the reaction mixture was added saturated aqueous sodium hydrogen carbonate and the mixture was stirred and extracted twice with ethyl acetate. The organic layer was washed twice with water and concentrated under reduced pressure. The residue was purified by silica gel column chromatography (methanol:chloroform=0:100-7:93) and NH silica gel column chromatography (methanol:chloroform=0:100-2:98) to give the title compound (467 mg) as a yellow solid.

MS (ESI) m/z: 1012.5 [M+H]$^+$

Example 116

(116-1) 4-[(6S)-2,3,6,9-tetramethyl-6H-thieno[3,2-f][1,2,4]triazolo[4,3-a][1,4]diazepin-4-yl]phenol (Example Compound 116-1)

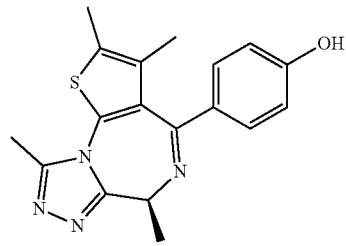 [SMILES: Cc1sc2c(c1C)C(c1ccc(O)cc1)=N[C@@H](C)c1nnc(C)n1-2]

To a solution of Reference Example compound 12 (1.00 g) in dioxane (10 mL) were added potassium hydroxide (1.8 mL, 8 mol/L), [2-(2-aminophenyl)phenyl)]-methylsulfonyloxy-palladium; dicyclohexyl-[3,6-dimethoxy-2-(2,4,6-triisopropylphenyl)phenyl]phosphate (127 mg) and the mixture was stirred at 120° C. for 1 hr under microwave radiation. To the reaction solution was added 1N hydrochloric acid and the mixture was extracted with chloroform. To the aqueous layer was added 4N aqueous sodium hydroxide solution and the mixture was extracted with chloroform. The organic layer was dried over anhydrous sodium sulfate. The solvent was evaporated under reduced pressure. The residue was purified by silica gel column chromatography (chloroform:methanol=100:0-90:10) to give the title compound (904 mg) as a colorless solid.

MS (ESI) m/z: 339.2 [M+H]$^+$ (116-2) methyl {4-[(6S)-2,3,6,9-tetramethyl-6H-thieno[3,2-f] [1,2,4]triazolo[4,3-a][1,4]diazepin-4-yl]phenoxy}acetate (Example Compound 116-2)

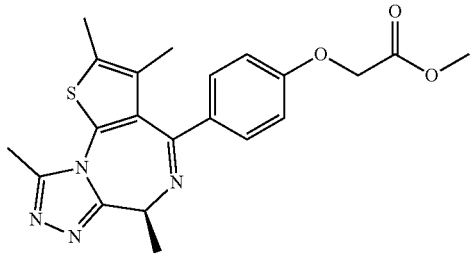

To a solution of Example compound 116-1 (400 mg) in N,N-dimethylformamide (5.9 mL) were added cesium carbonate (770 mg) and methyl bromoacetate (271 mg) and the mixture was stirred at room temperature for 1 hr. To the reaction solution were added water and ethyl acetate for partitioning and the aqueous layer was further extracted with ethyl acetate. The organic layers were collected, washed with water:saturated brine=1:1 and saturated brine, and dried over anhydrous sodium sulfate. The solvent was evaporated under reduced pressure. The residue was purified by silica gel column chromatography (chloroform:methanol=100:0-90:10) to give the title compound (453 mg) as a pale-brown powder. MS (ESI) m/z: 411.2 [M+H]$^+$ (116-3) (2S,4R)-1-[(2S)-3,3-dimethyl-2-(2-{4-[(6S)-2,3,6,9-tetramethyl-6H-thieno[3,2-f][1,2,4]triazolo[4,3-a] [1,4]diazepin-4-yl]phenoxy}acetamido)butanoyl]-4-hydroxy-N-{(1S)-1-[4-(4-methyl-1,3-thiazol-5-yl)phenyl]ethyl}pyrrolidine-2-carboxamide (Example Compound 116)

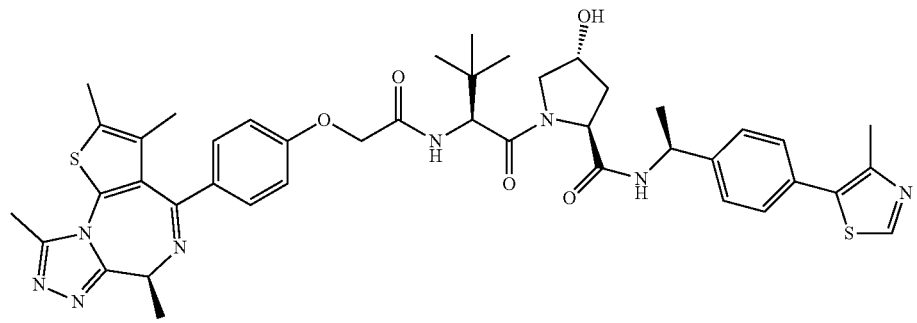 [SMILES: Cc1ncsc1-c1ccc([C@H](C)NC(=O)[C@@H]2C[C@@H](O)CN2C(=O)[C@@H](NC(=O)COc2ccc(C3=N[C@@H](C)c4nnc(C)n4-c4sc(C)c(C)c43)cc2)C(C)(C)C)cc1]

To a solution of Example compound 116-2 (213 mg) in methanol (2.0 mL) was added, under ice-cooling, sodium hydroxide (166 mg), and the mixture was allowed to naturally warm to room temperature and stirred for 2.5 hr. The reaction solution was concentrated under reduced pressure and azeotropically distilled twice with toluene. To a solution of the obtained residue (283 mg) and Reference Example compound 5 (274.6 mg) in N,N-dimethylformamide (5.2 mL) was added N,N-diisopropylethylamine (0.449 mL), and HATU (296 mg) was added under ice-cooling, and the mixture was allowed to naturally warm to room temperature and stirred for 2.5 hr. To the reaction solution was added water and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=95:5-85:15), and then by silica gel column chromatography (chloroform:methanol=99:1-95:5). The obtained solid was suspension washed with diethyl ether, collected by filtration and dried under reduced pressure to give the title compound (232 mg) as a white solid. MS (ESI) m/z: 821.5 [M−H]$^-$ Example 117

(117-1) t-butyl [cis-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclobutyl]carbamate (Example Compound 117-1)

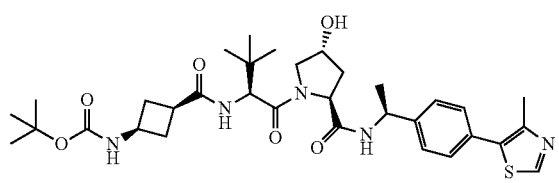 [SMILES: Cc1ncsc1-c1ccc([C@H](C)NC(=O)[C@@H]2C[C@@H](O)CN2C(=O)[C@@H](NC(=O)[C@H]2C[C@@H](NC(=O)OC(C)(C)C)C2)C(C)(C)C)cc1]

Reference Example compound 5 (400 mg) and cis-3-(t-butoxycarbonylamino)cyclobutanecarboxylic acid (197 mg) were dissolved in N,N-dimethylformamide (8.3 mL), N,N-diisopropylethylamine (0.43 mL) and HATU (475 mg) were added under ice-cooling and the mixture was stirred at room temperature for 16 hr. To the reaction mixture was added ice water, saturated aqueous sodium hydrogen carbonate to quench the reaction, ethyl acetate and saturated brine were added and the organic layer was extracted. The aqueous layer was extracted twice with ethyl acetate, and the organic layers were collected and washed twice with saturated brine:water=1:1, and washed with saturated brine. After drying over anhydrous sodium sulfate, the solvent was evaporated under reduced pressure, and the residue was purified by silica gel column chromatography (chloroform:methanol=100:0-95:5) to give the title compound (490 mg) as a white solid.

MS (ESI) m/z: 642.5 [M+H]$^+$ (117-2) methyl [(6S)-4-(4'-{[cis-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclobutyl]carbamoyl}[1,1'-biphenyl]-4-yl)-2,3,9-trimethyl-6H-thieno[3,2-f][1,2,4]triazolo[4,3-a] [1,4]diazepin-6-yl]acetate (Example Compound 117)

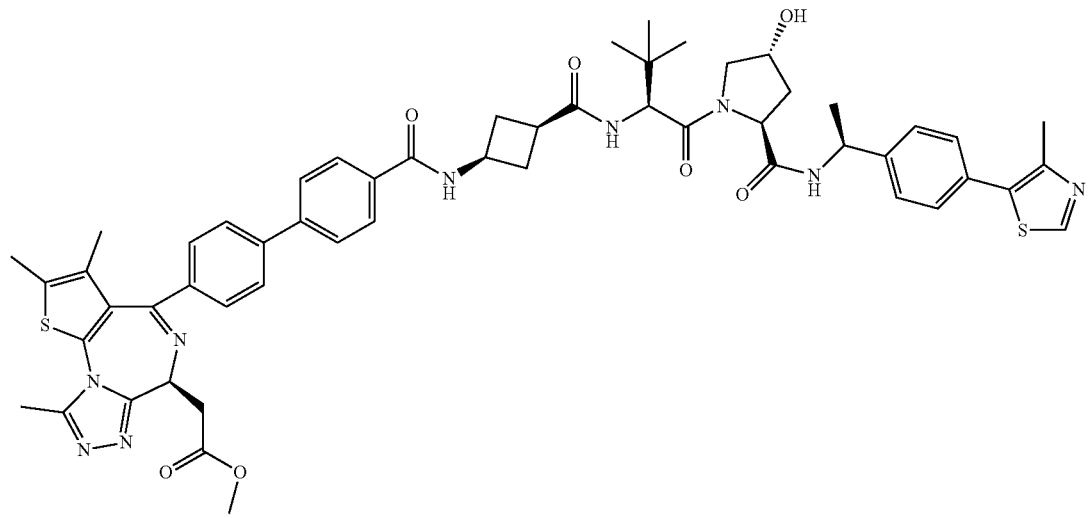 [SMILES: COC(=O)C[C@@H]1N=C(c2ccc(-c3ccc(C(=O)N[C@H]4C[C@@H](C(=O)N[C@H](C(=O)N5C[C@H](O)C[C@H]5C(=O)N[C@@H](C)c5ccc(-c6scnc6C)cc5)C(C)(C)C)C4)cc3)cc2)c2c(sc(C)c2C)-n2c(C)nnc21]

Example compound 117-1 (485 mg) was dissolved in N,N-dimethylformamide (5.0 mL), 4 M hydrogen chloride/1,4-dioxane solution was added and the mixture was stirred at room temperature for 1 hr. The reaction mixture was concentrated. 1,4-Dioxane was added and the mixture was concentrated under reduced pressure, and this operation was performed twice. The concentrate was dried under reduced pressure at 60° C. To the residue was added N,N-dimethylformamide (10.2 mL) and the mixture was stirred. Under ice-cooling, N,N-diisopropylethylamine (3.9 mL), Example compound 90-1 (342 mg), HATU (430 mg) were added and the mixture was stirred at room temperature for 2 hr. Furthermore, N,N-diisopropylethylamine (0.78 mL), HATU (90 mg) were added under ice-cooling and the mixture was stirred for 14 hr. Under ice-cooling, to the reaction mixture were added ethyl acetate, saturated aqueous sodium hydrogen carbonate, water and the mixture was stirred. Saturated brine:water=1:1 was added and the organic layer was extracted. The aqueous layer was extracted twice with ethyl acetate, and the organic layers were collected and washed twice with saturated brine:water=1:1 and washed with saturated brine. After drying over anhydrous sodium sulfate, the solvent was evaporated under reduced pressure, and the residue was purified by NH silica gel column chromatography (ethyl acetate:methanol=100:0-80:20), silica gel column chromatography (ethyl acetate:methanol=100:0-80:20), and then preparative HPLC (10 mM aqueous ammonium carbonate solution-acetonitrile) to give the title compound (240 mg) as a white solid. MS (ESI) m/z: 1024.5 [M+H]+

Example 118

(118-1) methyl [(6S)-4-(4'-{[(trans-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclobutyl]carbamoyl}[1,1'-biphenyl]-4-yl)-2,3,9-trimethyl-6H-thieno[3,2-f][1,2,4]triazolo[4,3-a] [1,4]diazepin-6-yl]acetate (Example Compound 118)

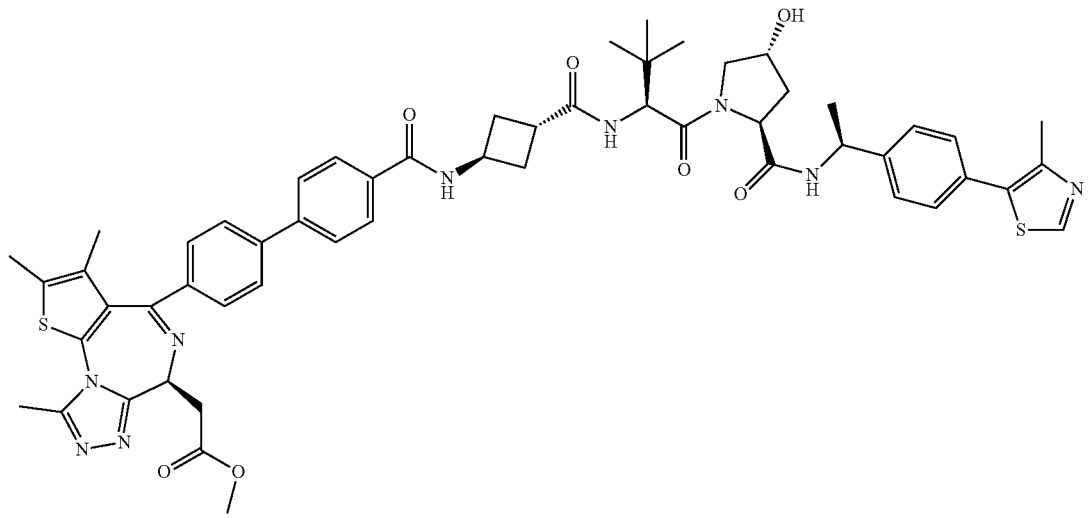 [SMILES: COC(=O)C[C@@H]1N=C(c2ccc(-c3ccc(C(=O)N[C@H]4C[C@H](C(=O)N[C@H](C(=O)N5C[C@H](O)C[C@H]5C(=O)N[C@@H](C)c5ccc(-c6scnc6C)cc5)C(C)(C)C)C4)cc3)cc2)c2c(sc(C)c2C)-n2c(C)nnc21]

By reaction and treatment in the same manner as in Example 117 (117-1)-(117-2) and using trans-3-(t-butoxycarbonylamino)cyclobutanecarboxylic acid instead of cis-3-(t-butoxycarbonylamino)cyclobutanecarboxylic acid, the title compound was obtained as a white solid.

MS (ESI) m/z: 1024.5 [M+H]$^+$

Example 119

(119-1) 5-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyridine-2-carboxamide (Example Compound 119-1)

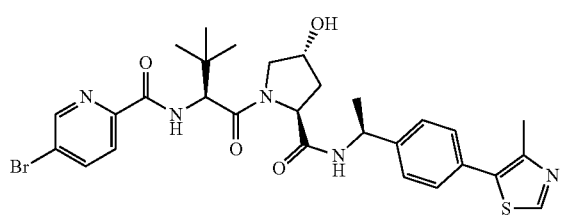 [SMILES: Cc1ncsc1-c1ccc([C@H](C)NC(=O)[C@@H]2C[C@@H](O)CN2C(=O)[C@@H](NC(=O)c2ccc(Br)cn2)C(C)(C)C)cc1]

By reaction and treatment in the same manner as in Example 97 (97-2) and using 5-bromopicolinic acid instead of Example compound 97-1, the title compound was obtained as a white solid. MS (ESI) m/z: 628.2, 630.2 [M+H]$^+$ (119-2) methyl [(6S)-4-{4-[6-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-3-yl]phenyl}-2,3,9-trimethyl-6H-thieno[3,2-f][1,2,4]triazolo[4,3-a][1,4]diazepin-6-yl]acetate (Example Compound 119)

By reaction and treatment in the same manner as in Example 101 (101-2) and using Example compound 119-1 instead of Example compound 101-1, the title compound was obtained as a white solid. MS (ESI) m/z: 928.4 [M+H]$^+$ Example 120

(120-1) 5-chloro-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyrazine-2-carboxamide (Example Compound 120-1)

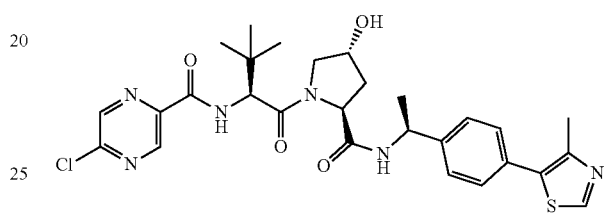

5-Chloropyrazine 2-carboxylic acid (119 mg) and Reference Example compound 5 (300 mg), N,N-diisopropylethylamine (0.324 mL) and HATU (285 mg) were stirred in N,N-dimethylformamide (5 mL) at room temperature for 5 hr. Water was added to the reaction mixture and the mixture was stirred and extracted twice with ethyl acetate. The organic layer was washed twice with water and concentrated under reduced pressure. The residue was purified by NH silica gel column chromatography (methanol:chloroform=10:90) to give the title compound (308 mg) as a white solid. MS (ESI) m/z: 585.2, 587.2 [M+H]$^+$

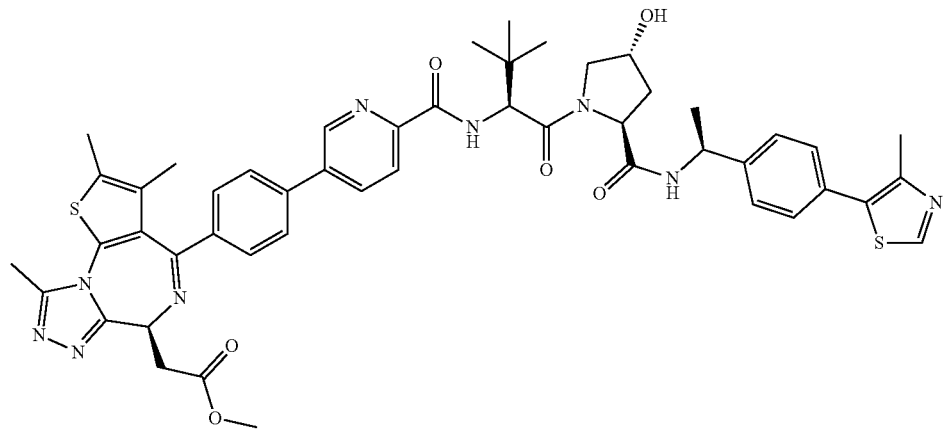 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)nc3)cc2)c2c(sc(C)c2C)-n2c(C)nnc21]

(120-2) t-butyl 4-{4-[(6S)-6-(2-methoxy-2-oxo-ethyl)-2,3,9-trimethyl-6H-thieno[3,2-f][1,2,4]triazolo[4,3-a][1,4]diazepin-4-yl]phenyl}piperazine-1-carboxylate (Example Compound 120-2)

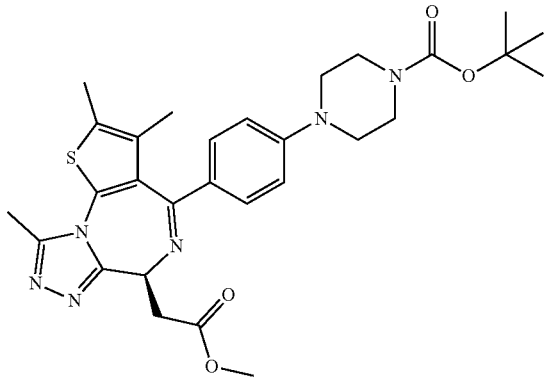 [SMILES: COC(=O)C[C@@H]1N=C(c2ccc(N3CCN(C(=O)OC(C)(C)C)CC3)cc2)c2c(sc(C)c2C)-n2c(C)nnc21]

Under an argon stream, Reference Example compound 1 (400 mg), 1-(t-butoxycarbonyl)-piperazine (216 mg), tris(dibenzylideneacetone)dipalladium(0) (44 mg), t-BuXphos (41 mg) and potassium phosphate (614 mg) were stirred in 1,2-dimethoxyethane (5 mL) solvent at 70° C. for 19 hr. Using ethyl acetate, the reaction mixture was filtered through diatomaceous earth and the filtrate was concentrated under reduced pressure. The residue was purified by silica gel column chromatography (methanol:chloroform=0:100-5:95) to give the title compound (314 mg) as a yellow solid.
MS (ESI) m/z: 565.6 [M+H]$^+$ (120-3) methyl {(6S)-2,3,9-trimethyl-4-[4-(piperazin-1-yl)phenyl]-6H-thieno[3,2-f][1,2,4]triazolo[4,3-a][1,4]diazepin-6-yl}acetate hydrochloride (Example Compound 120-3)

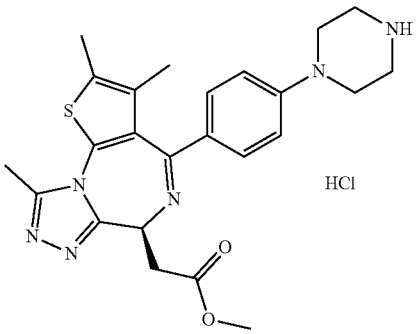 [SMILES: COC(=O)C[C@@H]1N=C(c2ccc(N3CCNCC3)cc2)c2c(sc(C)c2C)-n2c(C)nnc21 ; Cl]

To a solution of Example compound 120-2 (314 mg) in methanol (1 mL) was added 4 M hydrogen chloride/ethyl acetate solution (2 mL) and the mixture was stirred at room temperature for 4 hr. The reaction mixture was concentrated under reduced pressure to give the title compound (301 mg) as an orange solid.
MS (ESI) m/z: 465.4 [M+H]$^+$ (120-4) methyl [(6S)-4-(4-{4-[5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrazin-2-yl]piperazin-1-yl}phenyl)-2,3,9-trimethyl-6H-thieno[3,2-f][1,2,4]triazolo[4,3-a][1,4]diazepin-6-yl]acetate (Example Compound 120)

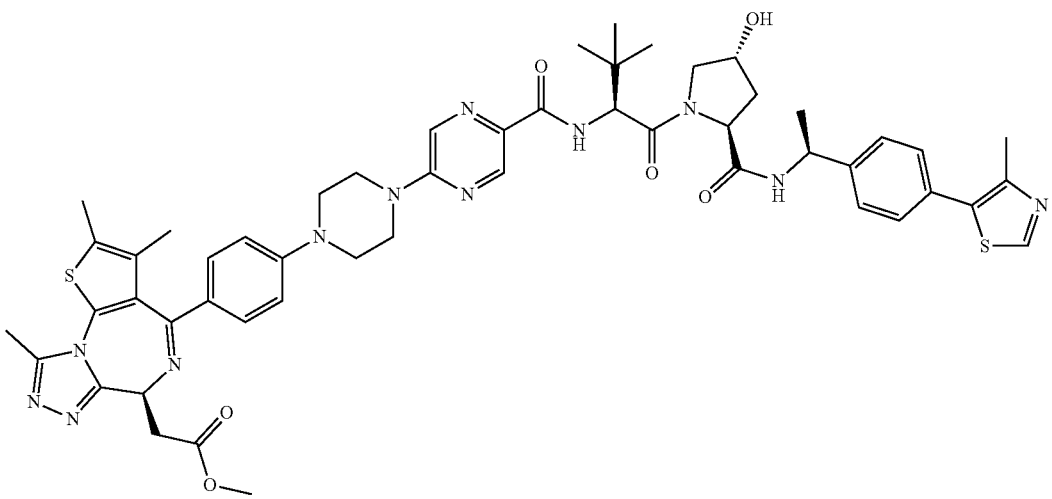 [SMILES: COC(=O)C[C@@H]1N=C(c2ccc(N3CCN(c4cnc(C(=O)N[C@H](C(=O)N5C[C@H](O)C[C@H]5C(=O)N[C@@H](C)c5ccc(-c6scnc6C)cc5)C(C)(C)C)cn4)CC3)cc2)c2c(sc(C)c2C)-n2c(C)nnc21]

Example compound 120-1 (144 mg), Example compound 120-3 (124 mg) and N,N-diisopropylethylamine (0.103 mL) were heated under reflux in tetrahydrofuran (5 mL) solvent for 12 hr. To the reaction mixture was added saturated aqueous sodium hydrogen carbonate and the mixture was stirred. Using ethyl acetate, the mixture was filtered through diatomaceous earth and the filtrate was concentrated under reduced pressure. The residue was purified by silica gel column chromatography (methanol:chloroform=0:100-5:95) to give the title compound (135 mg) as a yellow solid.
MS (ESI) m/z: 1013.4 [M+H]$^+$

Example 121

(121-1) methyl [(6S)-4-{4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)piperidin-1-yl]phenyl}-2,3,9-trimethyl-6H-thieno[3,2-f][1,2,4]triazolo[4,3-a][1,4]diazepin-6-yl]acetate (Example Compound 121)

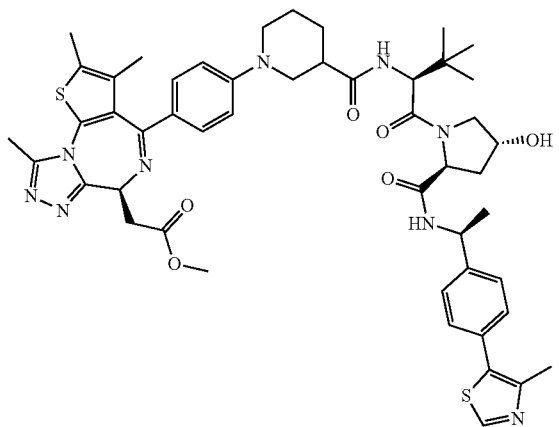

By reaction and treatment in the same manner as in Example 98 (98-3)-(98-4) and using t-butyl nipecotate hydrochloride instead of Example compound 98-2, the title compound was obtained as a yellow solid.

MS (ESI) m/z: 934.4 [M+H]$^+$

Example 122

(122-1) (2S,4R)-1-{(2S)-2-[2-(4-bromophenoxy)(difluoro)acetamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 122-1)

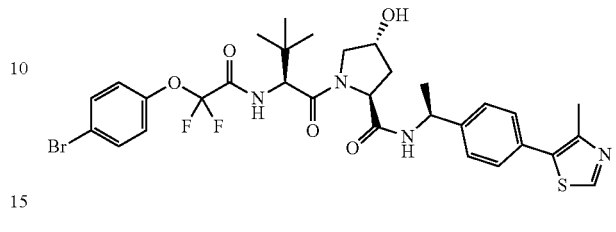

2-(4-Bromophenoxy)-2,2-difluoroacetic acid (200 mg), Reference Example compound 5 (300 mg), N,N-diisopropylethylamine (0.325 mL) and HATU (285 mg) were stirred in N,N-dimethylformamide (5 mL) at room temperature for 24 hr. Water was added to the reaction mixture and the mixture was stirred and extracted twice with ethyl acetate. The organic layer was washed twice with water and concentrated under reduced pressure. The residue was purified by silica gel column chromatography (methanol:chloroform=0:100-5:95) to give the title compound (214 mg) as a white solid.

MS (ESI) m/z: 693.1, 695.1 [M+H]$^+$ (122-2) methyl [(6S)-4-{4'-[1,1-difluoro-2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate (Example Compound 122)

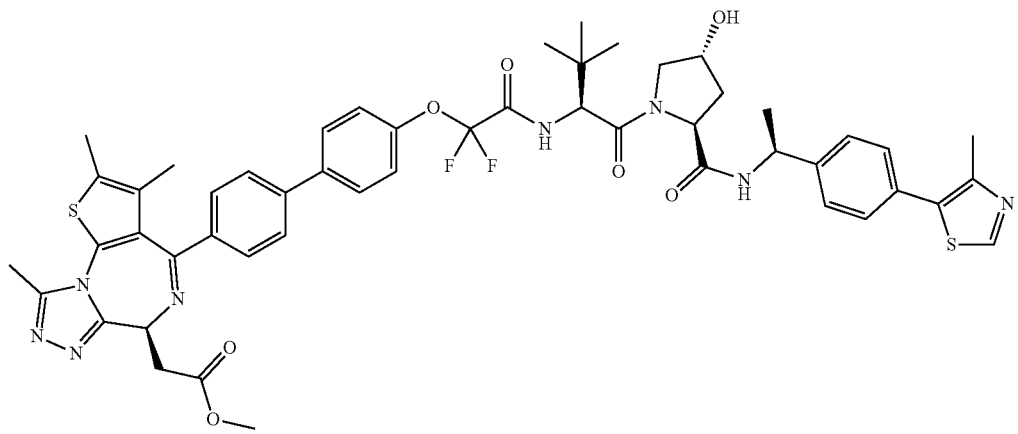 [SMILES: COC(=O)C[C@@H]1N=C(c2ccc(-c3ccc(OC(F)(F)C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

Under an argon stream, Example compound 122-1 (214 mg), Reference Example compound 3 (150 mg), palladium acetate (6.7 mg), S-phos (24 mg), potassium fluoride (52 mg) and water (19 µL) were heated under reflux in tetrahydrofuran (5 mL) solvent for 8 hr. Using ethyl acetate, the reaction mixture was filtered through diatomaceous earth and the filtrate was concentrated under reduced pressure. The residue was purified by silica gel column chromatography (methanol:chloroform=0:100-5:95) and NH silica gel column chromatography (methanol:chloroform=0:100-2:98) to give the title compound (93 mg) as a white solid. MS (ESI) m/z: 993.4 [M+H]$^+$

Example 123

(123-1) t-butyl 4-{4-[(6S)-2,3,6,9-tetramethyl-6H-thieno[3,2-f] [1,2,4]triazolo[4,3-a][1,4]diazepin-4-yl]phenoxy}butanoate (Example Compound 123-1)

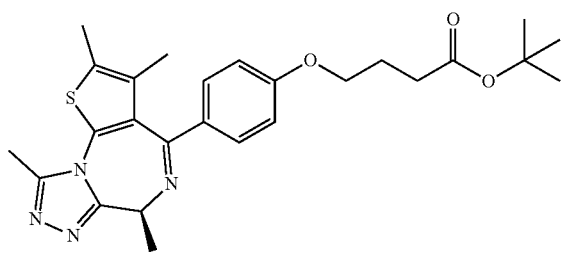 [SMILES: Cc1sc2c(c1C)C(c1ccc(OCCCC(=O)OC(C)(C)C)cc1)=N[C@@H](C)c1nnc(C)n1-2]

To a solution of Example compound 116-1 (500 mg) in N,N-dimethylformamide (4.9 mL) was added cesium carbonate (530 mg) and the mixture was stirred for 10 min. t-Butyl-4-bromobutanoate (330 mg) was added dropwise over 5 min, and the mixture was stirred at room temperature for 1 hr. The reaction solution was heated to 70° C. and further stirred for 1 hr. To the reaction solution were added saturated aqueous ammonium chloride solution, water and the mixture was extracted with ethyl acetate. The organic layer was washed with water and saturated brine, and dried over anhydrous sodium sulfate. The solvent was evaporated under reduced pressure. The residue was purified by silica gel column chromatography (chloroform:methanol=99:1-97:3) to give the title compound (633 mg) as a pale-brown powder. MS (ESI) m/z: 481.4 [M+H]$^+$ (123-2) (2S,4R)-1-[(2S)-3,3-dimethyl-2-(4-{4-[(6S)-2,3,6,9-tetramethyl-6H-thieno[3,2-f][1,2,4]triazolo[4,3-a] [1,4]diazepin-4-yl]phenoxy}butanamido) butanoyl]-4-hydroxy-N-{(1S)-1-[4-(4-methyl-1,3-thiazol-5-yl)phenyl]ethyl}pyrrolidine-2-carboxamide (Example Compound 123)

To a solution of Example compound 123-1 (213 mg) in dichloromethane (2.0 mL) was added dropwise, under ice-cooling, trifluoroacetic acid (2.0 mL), and the mixture was allowed to naturally warm to room temperature and stirred for 2.0 hr. The reaction solution was concentrated under reduced pressure and azeotropically distilled twice with toluene. To the obtained residue were added ethyl acetate and saturated aqueous sodium hydrogen carbonate and the mixture was vigorously stirred at room temperature for 30 min and partitioned. The aqueous layer was acidified with 1N hydrochloric acid, extracted with chloroform, and the extract was washed with water, saturated aqueous sodium hydrogen carbonate and saturated brine. The organic layer was dried over anhydrous sodium sulfate and the filtrate was concentrated under reduced pressure and dried. To a solution of the obtained residue (350 mg) and Reference Example compound 5 (230 mg) in N,N-dimethylformamide (4.8 mL) was added N,N-diisopropylethylamine (0.414 mL), and HATU (273 mg) was added under ice-cooling, and the mixture was allowed to naturally warm to room temperature and stirred for 38 hr. To the reaction solution was added water and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by NH silica gel column chromatography (ethyl acetate:methanol=93:7-80:20), and then by silica gel column chromatography (chloroform:methanol=98:2-93:7). The obtained solid was suspension washed with diethyl ether, collected by filtration and dried under reduced pressure to give the title compound (106 mg) as a white solid. MS (ESI) m/z: 851.6 [M+H]$^+$

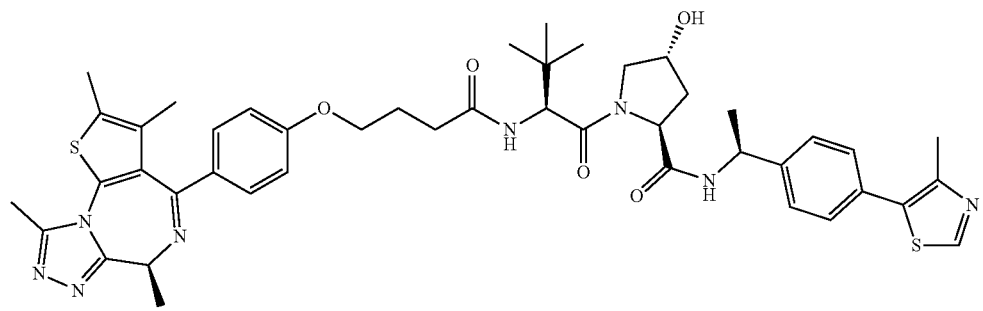 [SMILES: Cc1ncsc1-c1ccc([C@H](C)NC(=O)[C@@H]2C[C@@H](O)CN2C(=O)[C@@H](NC(=O)CCCOc2ccc(C3=N[C@@H](C)c4nnc(C)n4-c4sc(C)c(C)c43)cc2)C(C)(C)C)cc1]

Example 124

(124-1) methyl [(6S)-4-{4-[(3R)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)piperidin-1-yl]phenyl}-2,3,9-trimethyl-6H-thieno[3,2-f][1,2,4]triazolo[4,3-a][1,4]diazepin-6-yl]acetate or methyl [(6S)-4-{4-[(3S)-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)piperidin-1-yl]phenyl}-2,3,9-trimethyl-6H-thieno[3,2-f][1,2,4]triazolo[4,3-a][1,4]diazepin-6-yl]acetate (Example Compound 124)

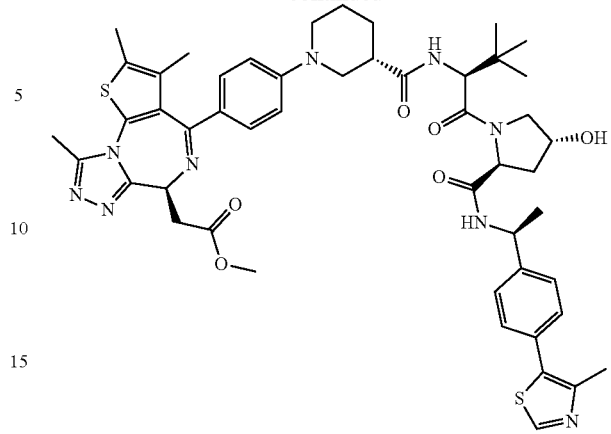

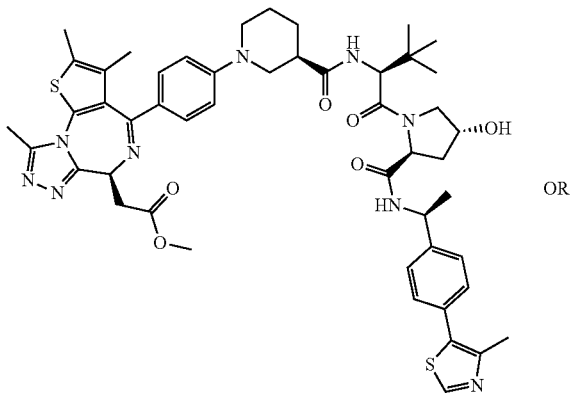

OR

Example compound 121 (233 mg) was resolved by a chiral column [CHIRALPAK ID (30*250), methanol:acetonitrile:diethylamine=60:40:0.1, flow 20 mL/min, recycle once] (retention time: 13 min and 21 min). The fractions obtained first (retention time: 13 min) were collected to give the title compound as a yellow solid.

MS (ESI) m/z: 934.9 [M+H]$^+$

Example 125

(125-1) methyl [(6S)-4-(4'-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl](methyl)carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 125)

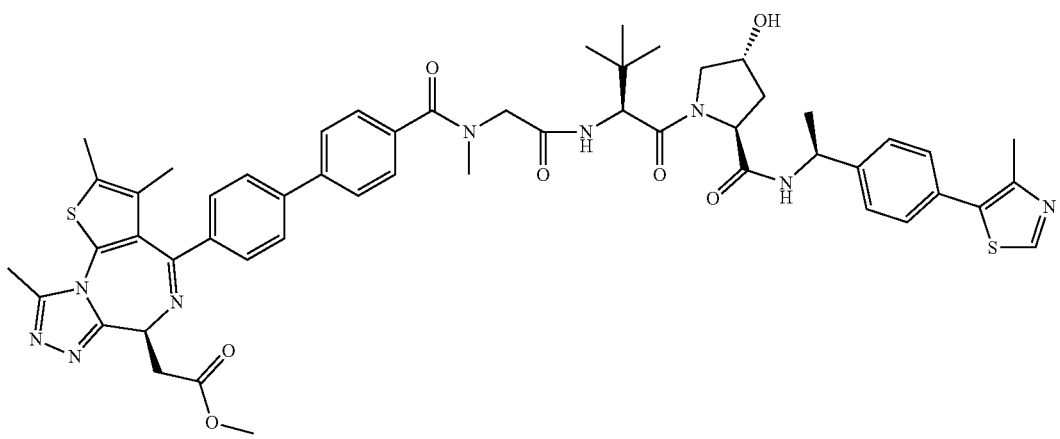 [SMILES: COC(=O)C[C@@H]1N=C(c2ccc(-c3ccc(C(=O)N(C)CC(=O)N[C@H](C(=O)N4C[C@H](O)C[C@H]4C(=O)N[C@@H](C)c4ccc(-c5scnc5C)cc4)C(C)(C)C)cc3)cc2)c2c(sc(C)c2C)-n2c(C)nnc21]

By reaction and treatment in the same manner as in Example 90 (90-2)-(90-3) and using N-methyl-N-(t-butoxycarbonyl)-glycine instead of N-(t-butoxycarbonyl)-glycine, a white title compound was obtained. MS (ESI) m/z: 998.5 [M+H]$^+$ Example 126 and Example 127

(126-1) and (127-1) methyl [(6S)-4-(4-{(3R)-3-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)phenoxy]pyrrolidin-1-yl}phenyl)-2,3,9-trimethyl-6H-thieno[3,2-f][1,2,4]triazolo[4,3-a][1,4]diazepin-6-yl]acetate and methyl [(6S)-4-(4-{(3S)-3-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)phenoxy]pyrrolidin-1-yl}phenyl)-2,3,9-trimethyl-6H-thieno[3,2-f][1,2,4]triazolo[4,3-a][1,4]diazepin-6-yl]acetate

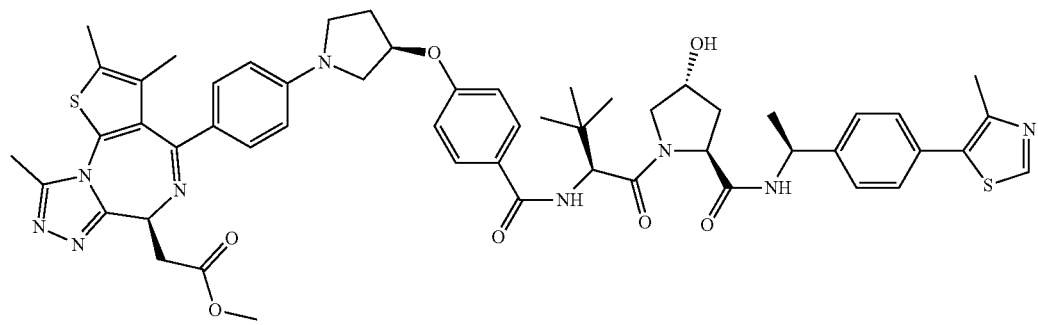

AND

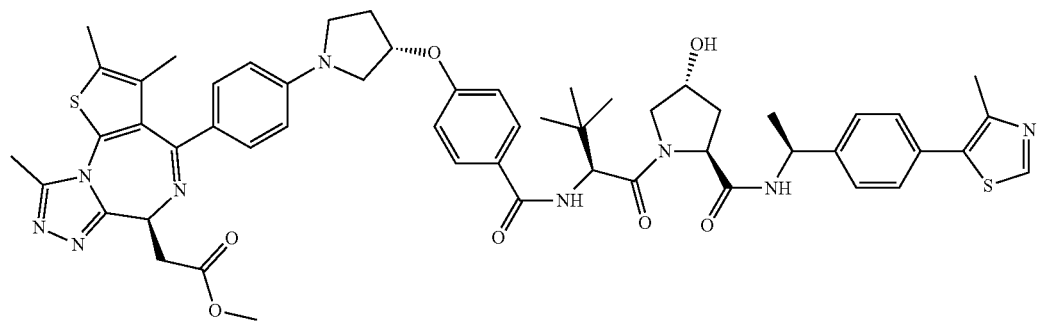

Example compound 115 (422 mg) was resolved by a chiral column [CHIRALPAK IA (30*250), ethanol:tetrahydrofuran:diethylamine=60:40:0.1] and purified by silica gel column chromatography (methanol:chloroform=0:100-5:95) to give the both compounds (compound having shorter retention time, 202 mg (MS (ESI) m/z: 1012.4 [M+H]$^+$, Example compound 126) and compound having longer retention time, 188 mg (MS (ESI) m/z: 1012.4 [M+H]$^+$, Example compound 127)) as yellow solids.

Example 128

(128-1) t-butyl 4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)phenoxy]piperidine-1-carboxylate (Example Compound 128-1)

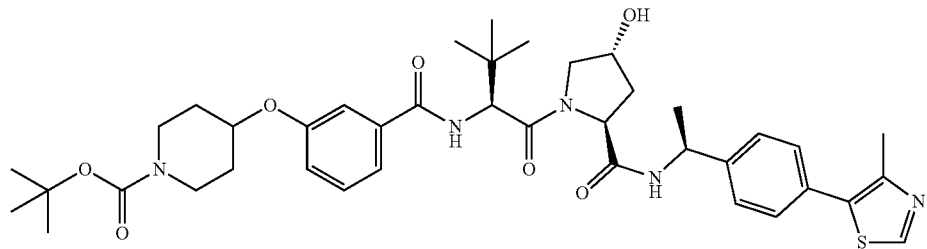 [SMILES: Cc1ncsc1-c1ccc([C@H](C)NC(=O)[C@@H]2C[C@@H](O)CN2C(=O)[C@@H](NC(=O)c2cccc(OC3CCN(C(=O)OC(C)(C)C)CC3)c2)C(C)(C)C)cc1]

By reaction and treatment in the same manner as in Example 97 (97-2) and using 1-(t-butoxycarbonyl)-4-(3-carboxyphenoxy)piperidine instead of Example compound 97-1, the title compound was obtained as a white solid.

MS (ESI) m/z: 748.4 [M+H]$^+$ (128-2) (2S,4R)-1-[(2S)-3,3-dimethyl-2-{3-[(piperidin-4-yl)oxy]benzamido}butanoyl]-4-hydroxy-N-{(1S)-1-[4-(4-methyl-1,3-thiazol-5-yl)phenyl]ethyl}pyrrolidine-2-carboxamide (Example Compound 128-2)

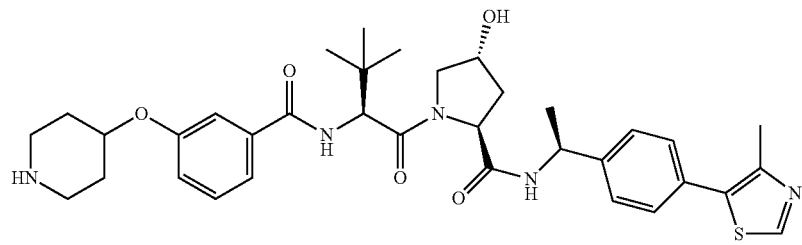 [SMILES: Cc1ncsc1-c1ccc([C@H](C)NC(=O)[C@@H]2C[C@@H](O)CN2C(=O)[C@@H](NC(=O)c2cccc(OC3CCNCC3)c2)C(C)(C)C)cc1]

By reaction and treatment in the same manner as in Example 114 (114-2) and using Example compound 128-1 instead of Example compound 114-1, the title compound was obtained as a pale-yellow solid. MS (ESI) m/z: 648.7 [M+H]$^+$ (128-3) methyl [(6S)-4-(4-{4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)phenoxy]piperidin-1-yl}phenyl)-2,3,9-trimethyl-6H-thieno[3,2-f][1,2,4]triazolo[4,3-a][1,4]diazepin-6-yl]acetate (Example Compound 128)

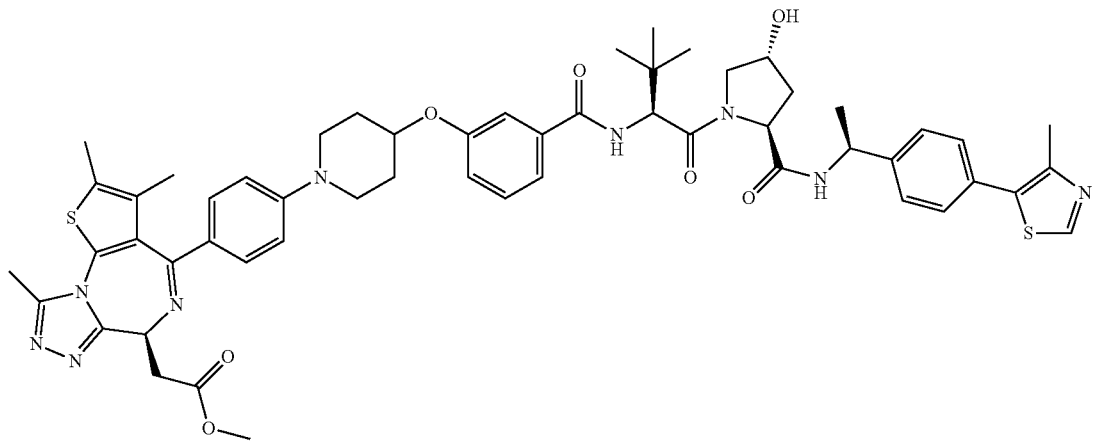 [SMILES: COC(=O)C[C@@H]1N=C(c2ccc(N3CCC(Oc4cccc(C(=O)N[C@H](C(=O)N5C[C@H](O)C[C@H]5C(=O)N[C@@H](C)c5ccc(-c6scnc6C)cc5)C(C)(C)C)c4)CC3)cc2)c2c(sc(C)c2C)-n2c(C)nnc21]

By reaction and treatment in the same manner as in Example 98 (98-3) and using Example compound 128-2 instead of Example compound 98-2, the title compound was obtained as a yellow solid. MS (ESI) m/z: 1026.5 [M+H]⁺

Example 129

(129-1) (2S,4R)-1-{(2S)-2-[3-(5-bromopyridin-2-yl)propanamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 129-1)

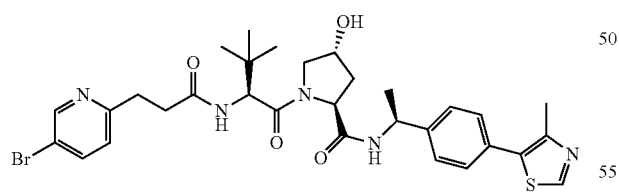

By reaction and treatment in the same manner as in Example 97 (97-2) and using 3-(5-bromo-2-pyridinyl)propionic acid instead of Example compound 97-1, the title compound was obtained as a white solid. MS (ESI) m/z: 656.2, 658.2 [M+H]⁺

(129-2) methyl [(6S)-4-(4-{6-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl]pyridin-3-yl}phenyl)-2,3,9-trimethyl-6H-thieno[3,2-f][1,2,4]triazolo[4,3-a][1,4]diazepin-6-yl]acetate (Example Compound 129)

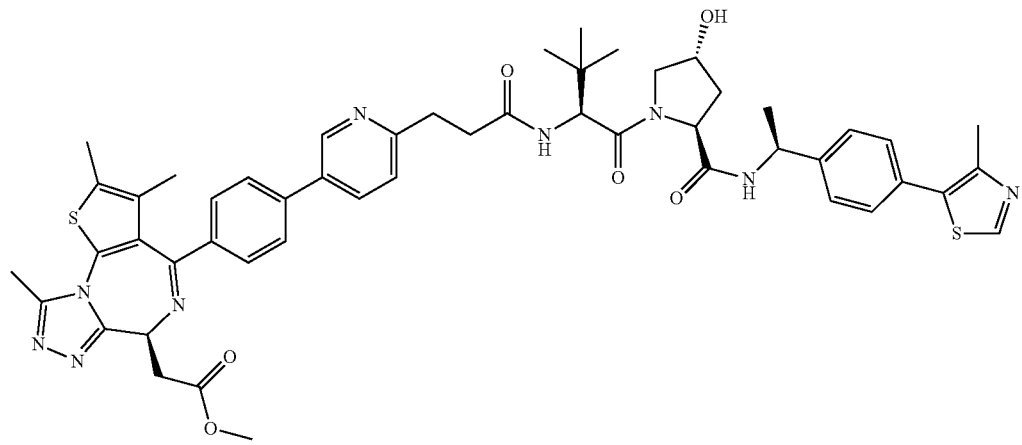 [SMILES: COC(=O)C[C@@H]1N=C(c2ccc(-c3ccc(CCC(=O)N[C@H](C(=O)N4C[C@H](O)C[C@H]4C(=O)N[C@@H](C)c4ccc(-c5scnc5C)cc4)C(C)(C)C)nc3)cc2)c2c(sc(C)c2C)-n2c(C)nnc21]

By reaction and treatment in the same manner as in Example 101 (101-2) and using Example compound 129-1 instead of Example compound 101-1, the title compound was obtained as a white solid. MS (ESI) m/z: 956.4 [M+H]⁺

Example 130

(130-1) benzyl 1,2,3,4-tetrahydroquinoline-6-carboxylate (Example Compound 130-1)

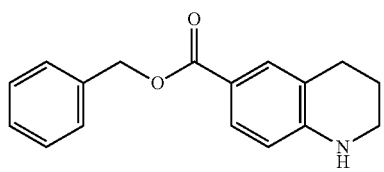 [SMILES: O=C(OCc1ccccc1)c1ccc2c(c1)CCCN2]

To a solution of 1,2,3,4-tetrahydroquinoline-6-carboxylic acid (1 g) in N,N-dimethylformamide (28 mL) were added potassium carbonate (3.9 g), benzyl bromide (0.709 mL) and the mixture was stirred at room temperature for 1 hr. Water was added to the reaction mixture and the mixture was stirred and extracted 3 times with ethyl acetate. The organic layers were collected and washed with water, dried over sodium sulfate, filtered and concentrated under reduced pressure. The residue was purified by silica gel column chromatography (ethyl acetate:hexane=30:70-40:60) to give the title compound (1.13 g) as a pale-yellow oil. MS (ESI) m/z: 268.1 [M+H]⁺

(130-2) benzyl 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1,2,3,4-tetrahydroquinoline-6-carboxylate (Example compound 130-2)

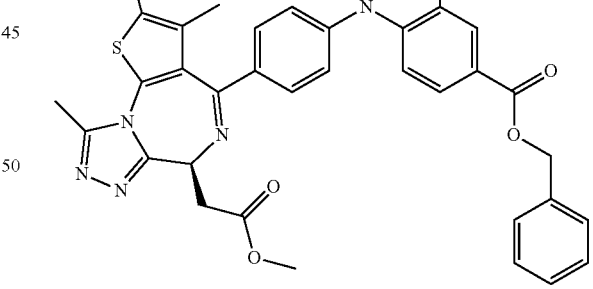

By reaction and treatment in the same manner as in Example 81 (81-1) and using Example compound 130-1 instead of 3-(t-butoxycarbonyl)pyrrolidine, the title compound was obtained as a pale-yellow solid. MS (ESI) m/z: 646.2 [M+H]⁺

(130-3) 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1,2,3,4-tetrahydroquinoline-6-carboxylic acid (Example Compound 130-3)

By reaction and treatment in the same manner as in Example 80 (80-5) and using Example compound 130-3 instead of Example compound 80-4, the title compound was obtained as a pale-yellow solid. MS (ESI) m/z: 982.4 [M+H]+

Example 131

(131-1) t-butyl 3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]piperidine-1-carboxylate (Example Compound 131-1)

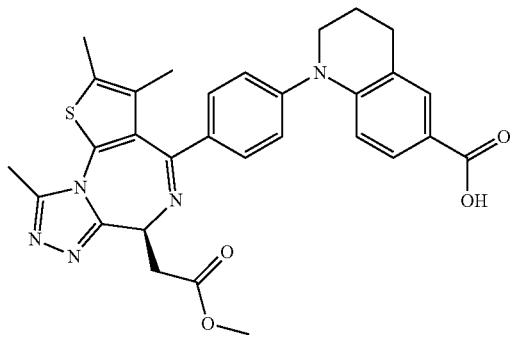 [SMILES: COC(=O)C[C@@H]1N=C(c2ccc(N3CCCc4cc(C(=O)O)ccc43)cc2)c2c(sc(C)c2C)-n2c(C)nnc21]

To a solution of Example compound 130-2 (96.6 mg) in ethanol (3 mL) was added 10% palladium carbon (50 mg) and, after hydrogen substitution, the mixture was stirred at room temperature for 8 hr. Using methanol, the reaction mixture was filtered through celite and the filtrate was concentrated under reduced pressure. The residue was purified by silica gel column chromatography (methanol:chloroform=0:100-4:96) to give the title compound (95.3 mg) as a pale-yellow solid.

MS (ESI) m/z: 556.2 [M+H]+

(130-4) methyl [(6S)-4-{4-[6-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3,4-dihydroquinolin-1(2H)-yl]phenyl}-2,3,9-trimethyl-6H-thieno[3,2-f][1,2,4]triazolo[4,3-a][1,4]diazepin-6-yl]acetate (Example Compound 130)

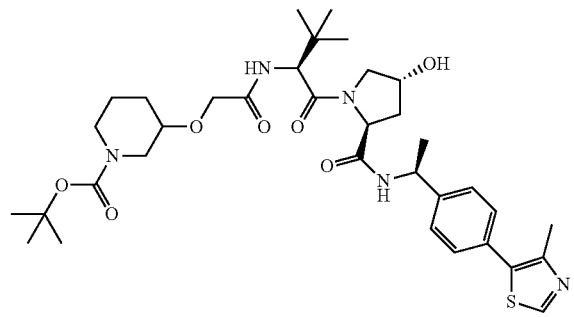

By reaction and treatment in the same manner as in Example 97 (97-2) and using N-(t-butoxycarbonyl)-3-carboxymethoxypiperidine instead of Example compound 97-1, the title compound was obtained as a white solid.

MS (ESI) m/z: 686.3 [M+H]+

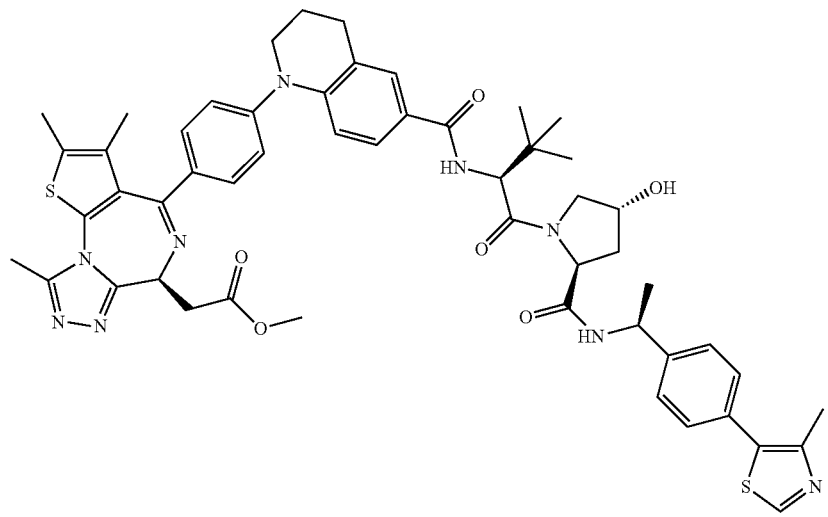

(131-2) (2S,4R)-1-[(2S)-3,3-dimethyl-2-{2-[(piperidin-3-yl)oxy]acetamido}butanoyl]-4-hydroxy-N-{(1S)-1-[4-(4-methyl-1,3-thiazol-5-yl)phenyl]ethyl}pyrrolidine-2-carboxamide (Example Compound 131-2)

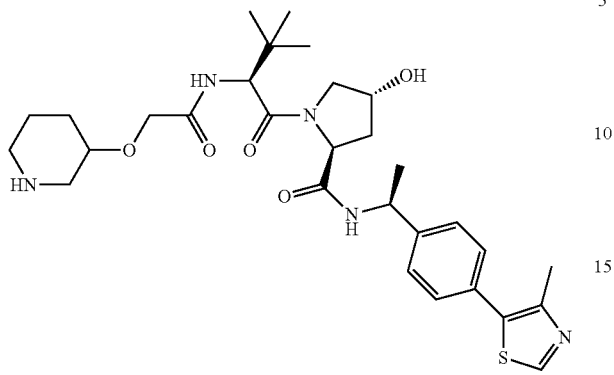

By reaction and treatment in the same manner as in Example 114 (114-2) and using Example compound 131-1 instead of Example compound 114-1, the title compound was obtained as a white solid. MS (ESI) m/z: 586.6 [M+H]$^+$ (131-3) methyl [(6S)-4-(4-{3-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]piperidin-1-yl}phenyl)-2,3,9-trimethyl-6H-thieno[3,2-f][1,2,4]triazolo[4,3-a][1,4]diazepin-6-yl]acetate (Example Compound 131)

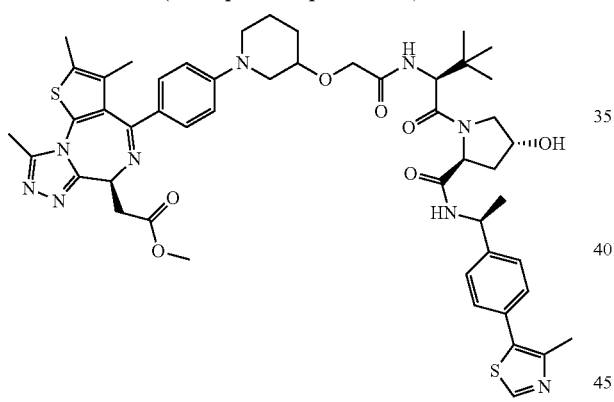

By reaction and treatment in the same manner as in Example 98 (98-3) and using Example compound 131-2 instead of Example compound 98-2, the title compound was obtained as a yellow solid. MS (ESI) m/z: 964.4 [M+H]$^+$ Example 132

(132-1) t-butyl (7-bromo-1-oxo-3,4-dihydroisoquinolin-2(1H)-yl)acetate (Example Compound 132-1)

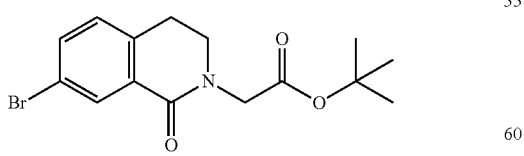

By reaction and treatment in the same manner as in Example 63 (63-1) and using 7-bromo-3,4-dihydro-1-isoquinolinone instead of 5-bromo-2-fluoropyridine, and t-butyl bromoacetate instead of t-butyl glycolate, the title compound was obtained as a white solid. MS (ESI) m/z: 340.1, 342.0 [M+H]$^+$ (132-2) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1-oxo-1,2,3,4-tetrahydroisoquinolin-7-yl}phenyl)-2,3,9-trimethyl-6H-thieno[3,2-f][1,2,4]triazolo[4,3-a][1,4]diazepin-6-yl]acetate (Example Compound 132)

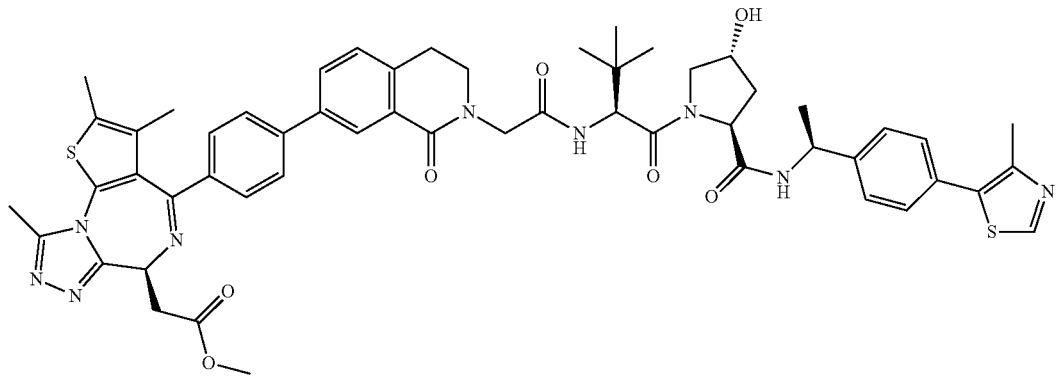 [SMILES: COC(=O)C[C@@H]1N=C(c2ccc(-c3ccc4c(c3)C(=O)N(CC(=O)N[C@H](C(=O)N3C[C@H](O)C[C@H]3C(=O)N[C@@H](C)c3ccc(-c5scnc5C)cc3)C(C)(C)C)CC4)cc2)c2c(sc(C)c2C)-n2c(C)nnc21]

By reaction and treatment in the same manner as in Example 100 (100-2)-(100-3) and using Example compound 132-1 instead of Example compound 100-1, the title compound was obtained as a white solid. MS (ESI) m/z: 1010.4 [M+H]+

Example 133

(133-1) 1-(t-butoxycarbonyl)-2,3-dihydro-1H-indole-6-carboxylic acid (Example Compound 133-1)

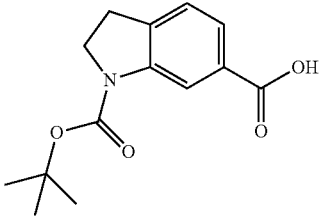 [SMILES: CC(C)(C)OC(=O)N1CCc2ccc(C(=O)O)cc21]

To a solution of 6-indoline methyl ester (500 mg) in tetrahydrofuran (9.4 mL), methanol (4 mL) were added triethylamine (0.43 mL) and di-t-butyl dicarbonate (739 mg), and the mixture was stirred at room temperature for 3 hr. The reaction mixture was concentrated under reduced pressure, and the residue was dissolved in 1,2-dimethoxyethane (15 mL) and methanol (15 mL), 4 M aqueous lithium hydroxide solution (2.1 mL) and water (10 mL) were added and the mixture was stirred at room temperature for 22 hr. The reaction mixture was concentrated under reduced pressure, and the aqueous layer was washed with ethyl acetate. To the aqueous layer was added 1N hydrochloric acid, and the mixture was extracted 3 times with ethyl acetate. The organic layers were collected, washed with saturated brine, dried over sodium sulfate and filtered. The filtrate was concentrated under reduced pressure to give the title compound (560 mg) as a pale-yellow solid.

MS (ESI) m/z: 262.1 [M−H]+

(133-2) N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-2,3-dihydro-1H-indole-6-carboxamide (Example Compound 133-2)

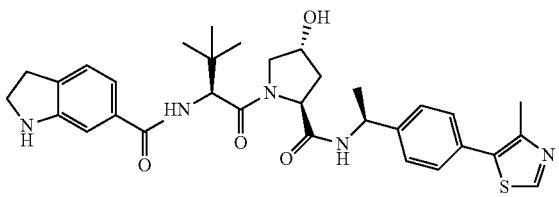 [SMILES: Cc1ncsc1-c1ccc([C@H](C)NC(=O)[C@@H]2C[C@@H](O)CN2C(=O)[C@@H](NC(=O)c2ccc3c(c2)NCC3)C(C)(C)C)cc1]

Example compound 133-1 (200 mg) was dissolved in N,N-dimethylformamide (4 mL), and Reference Example compound 5 (452 mg), HATU (347 mg) and N,N-diisopropylethylamine (0.394 mL) were added and the mixture was stirred at room temperature for 4 hr. Water was added to the reaction mixture and the mixture was stirred. The precipitate was collected by filtration. To a solution of the obtained solid in dichloromethane (10 mL) was added trifluoroacetic acid (1 mL) and the mixture was stirred at room temperature for 14 hr. To the reaction mixture was added saturated aqueous sodium hydrogen carbonate and the mixture was stirred for 2 hr and extracted 3 times with ethyl acetate. The organic layers were collected, dried over sodium sulfate, filtered and concentrated under reduced pressure. The residue was purified by silica gel column chromatography (methanol:chloroform=0:100-4:96) to give the title compound (360 mg) as a pale-yellow solid. MS (ESI) m/z: 590.3 [M+H]+

(133-3) methyl [(6S)-4-{4-[6-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-2,3-dihydro-1H-indol-1-yl]phenyl}-2,3,9-trimethyl-6H-thieno[3,2-f][1,2,4]triazolo[4,3-a][1,4]diazepin-6-yl]acetate (Example Compound 133)

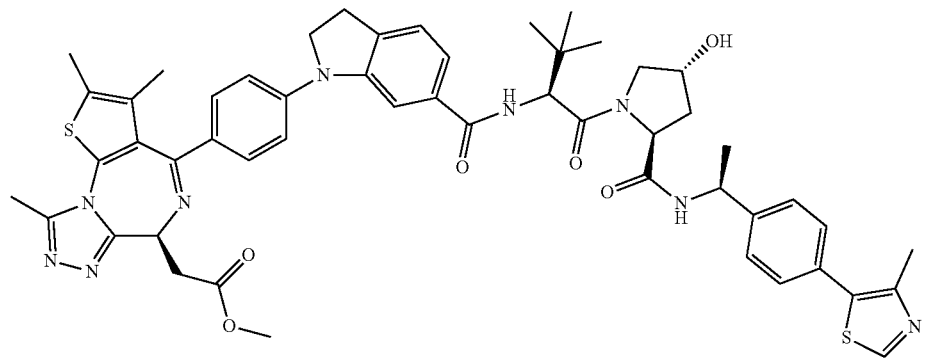 [SMILES: COC(=O)C[C@@H]1N=C(c2ccc(N3CCc4ccc(C(=O)N[C@H](C(=O)N5C[C@H](O)C[C@H]5C(=O)N[C@@H](C)c5ccc(-c6scnc6C)cc5)C(C)(C)C)cc43)cc2)c2c(sc(C)c2C)-n2c(C)nnc21]

By reaction and treatment in the same manner as in Example 81 (81-1) and using Example compound 133-2 instead of 3-(t-butoxycarbonyl)pyrrolidine, the title compound was obtained as an orange powder. MS (ESI) m/z: 968.4 [M+H]$^+$ Example 134

(134-1) t-butyl (5-bromo-3,4-dihydroisoquinolin-2(1H)-yl)acetate (Example Compound 134-1)

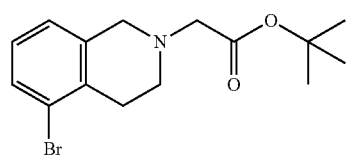 [SMILES: CC(C)(C)OC(=O)CN1CCc2c(Br)cccc2C1]

To a solution of 5-bromo-1,2,3,4-tetrahydroisoquinoline hydrochloride (500 mg) in acetonitrile (5 mL), N,N-dimethylformamide (10 mL) were added potassium carbonate (556 mg) and t-butyl bromoacetate (0.332 mL), and the mixture was stirred at room temperature for 22 hr. Water was added to the reaction mixture and the mixture was stirred and extracted twice with ethyl acetate. The organic layers were collected, dried over sodium sulfate, filtered and concentrated under reduced pressure. The residue was purified by silica gel column chromatography (ethyl acetate:hexane=0:100-20:80) to give the title compound (570 mg) as a colorless oil. MS (ESI) m/z: 326.1, 328.0 [M+H]$^+$ (134-2) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1,2,3,4-tetrahydroisoquinolin-5-yl}phenyl)-2,3,9-trimethyl-6H-thieno[3,2-f][1,2,4]triazolo[4,3-a][1,4]diazepin-6-yl]acetate (Example Compound 134)

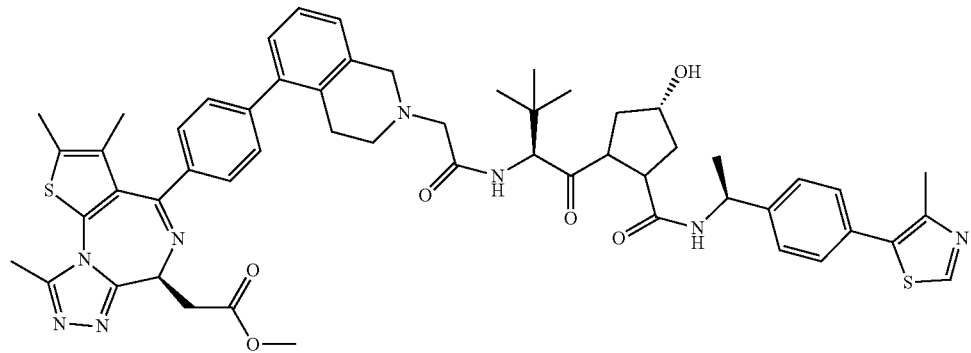 [SMILES: COC(=O)C[C@@H]1N=C(c2ccc(-c3cccc4c3CCN(CC(=O)N[C@H](C(=O)C3C[C@H](O)CC3C(=O)N[C@@H](C)c3ccc(-c5scnc5C)cc3)C(C)(C)C)C4)cc2)c2c(sc(C)c2C)-n2c(C)nnc21]

By reaction and treatment in the same manner as in Example 100 (100-2)-(100-3) and using Example compound 134-instead of Example compound 100-1, the title compound was obtained as a white solid. MS (ESI) m/z: 996.4 [M+H]⁺

Example 135

(135-1) methyl 3-{[(5-bromopyridin-2-yl)oxy]methyl}bicyclo[1.1.1]pentane-1-carboxylate (Example Compound 135-1)

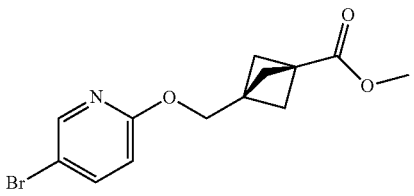 [SMILES: COC(=O)[C@]12C[C@](COc3ccc(Br)cn3)(C1)C2]

A solution of 5-bromo-2-fluoropyridine (0.300 mL), methyl 1-(hydroxymethyl)bicyclo[1,1,1]pentane-3-carboxylate (500 mg) in N,N-dimethylformamide (5 mL) was cooled to 0° C., sodium hydride (60%, 129 mg) was added and the mixture was stirred for 5 hr while allowing the mixture to naturally warm to room temperature. Water was added to the reaction mixture and the mixture was stirred and extracted twice with ethyl acetate. The organic layer was washed twice with water and concentrated under reduced pressure. The residue was purified by silica gel column chromatography (chloroform:hexane=0:100-70:30) to give the title compound (123 mg) as a colorless viscous compound. MS (ESI) m/z: 312.2, 314.2 [M+H]⁺

(135-2) (2S,4R)-1-{(2S)-2-[(3-{[(5-bromopyridin-2-yl)oxy]methyl}bicyclo[1.1.1]pentane-1-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 135-2)

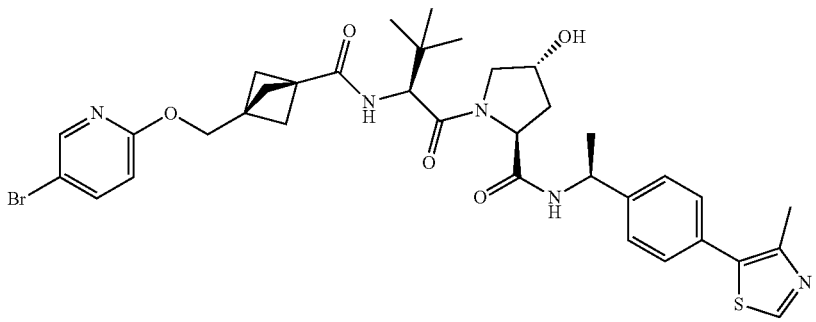 [SMILES: Cc1ncsc1-c1ccc([C@H](C)NC(=O)[C@@H]2C[C@@H](O)CN2C(=O)[C@@H](NC(=O)[C@]23C[C@](COc4ccc(Br)cn4)(C2)C3)C(C)(C)C)cc1]

To a solution of Example compound 135-1 (123 mg) in 1,2-dimethoxyethane (3 mL) was added 4 M aqueous lithium hydroxide solution (0.295 mL) and the mixture was stirred at room temperature for 4 hr. To the reaction mixture were added 1N hydrochloric acid, chloroform and the mixture was stirred. The aqueous layer was removed by Phase Separator and the organic layer was concentrated under reduced pressure. The residue was dissolved in N,N-dimethylformamide (5 mL), and Reference Example compound 5 (189 mg), N,N-diisopropylethylamine (0.340 mL), HATU (179 mg) were added, and the mixture was stirred at room temperature for 18 hr. Water was added to the reaction mixture, the mixture was stirred, and the resulting solid was collected by filtration. The solid was suspension washed in water and dried to give the title compound (273 mg) as a beige solid. MS (ESI) m/z: 724.2, 726.2 [M+H]+

(135-3) methyl {(6S)-4-[4-(6-{[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)bicyclo[1.1.1]pentan-1-yl]methoxy}pyridin-3-yl)phenyl]-2,3,9-trimethyl-6H-thieno[3,2-f] [1,2,4]triazolo[4,3-a][1,4]diazepin-6-yl}acetate (Example Compound 135)

Under an argon stream, a solution of t-butyl glycolate (611 mg) in N,N-dimethylformamide (15 mL) was cooled to 0° C., sodium hydride (60%, 185 mg) was added and the mixture was stirred at the same temperature for 30 min. Then, 2,5-dibromopyrazine (1.00 g) was added and the mixture was stirred for 4 hr while allowing the mixture to naturally warm to room temperature. Water was added to the reaction mixture and the mixture was stirred and extracted twice with ethyl acetate. The organic layer was washed twice with water and concentrated under reduced pressure. The residue was purified by silica gel column chromatography (ethyl acetate:hexane=0:100-15:85) to give the title compound (874 mg) as a white solid.

MS (ESI) m/z: 289.0, 291.0 [M+H]+

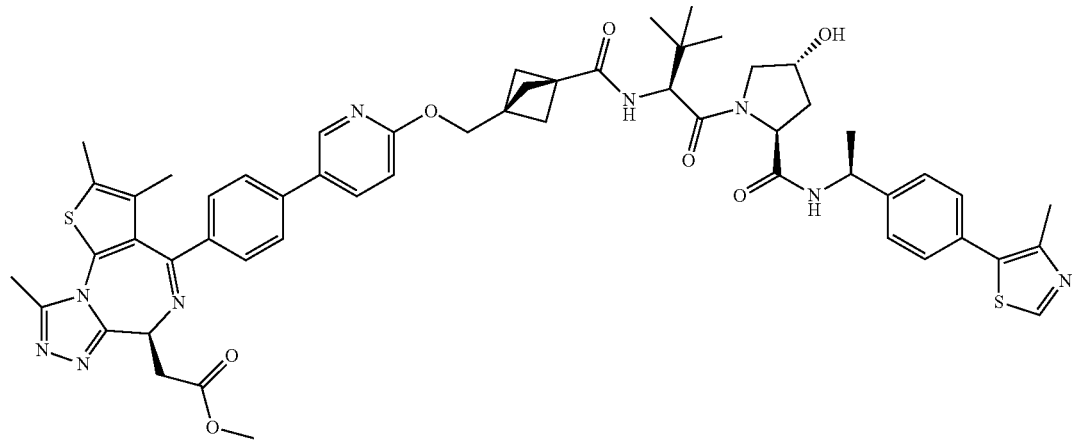 [SMILES: COC(=O)C[C@@H]1N=C(c2ccc(-c3ccc(OC[C@]45C[C@](C(=O)N[C@H](C(=O)N6C[C@H](O)C[C@H]6C(=O)N[C@@H](C)c6ccc(-c7scnc7C)cc6)C(C)(C)C)(C4)C5)nc3)cc2)c2c(sc(C)c2C)-n2c(C)nnc21]

Under an argon stream, Example compound 135-2 (273 mg), Reference Example compound 3 (170 mg), palladium acetate (7.5 mg), S-phos (28 mg), potassium fluoride (59 mg) and water (22 µL) were heated under reflux in tetrahydrofuran (5 mL) solvent for 5 hr. Using chloroform, the reaction mixture was filtered through diatomaceous earth, and the filtrate was concentrated under reduced pressure. The residue was purified by silica gel column chromatography (methanol:chloroform=0:100-5:95) and NH silica gel column chromatography (methanol:chloroform=0:100-2:98) and re-purified by silica gel column chromatography (methanol:chloroform=4:96) to give the title compound (214 mg) as a white solid. MS (ESI) m/z: 1024.4 [M+H]+

Example 136

(136-1) t-butyl [(5-bromopyrazin-2-yl)oxy]acetate (Example Compound 136-1)

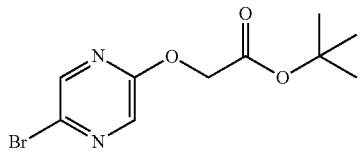 [SMILES: CC(C)(C)OC(=O)COc1cnc(Br)cn1]

(136-2) [(5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrazin-2-yl)oxy]acetic acid hydrochloride (Example Compound 136-2)

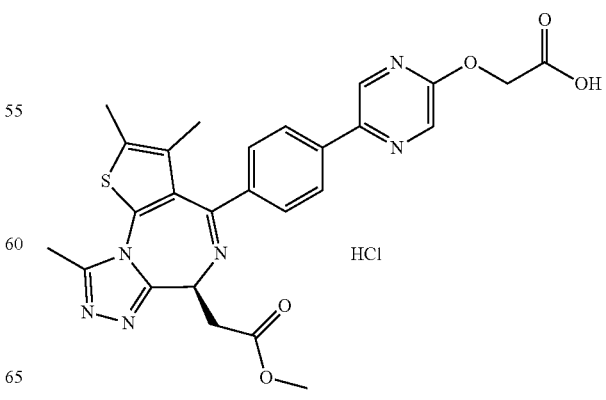

Under an argon stream, Example compound 136-1 (274 mg), Reference Example compound 3 (400 mg), palladium acetate (18 mg), S-phos (65 mg), potassium fluoride (138 mg) and water (51 µL) were heated under reflux in tetrahydrofuran (5 mL) solvent for 8 hr. Using chloroform, the reaction mixture was filtered through diatomaceous earth, and the filtrate was concentrated under reduced pressure. The residue was purified by silica gel column chromatography (methanol:chloroform=0:100-4:96) to give a pale-yellow viscous compound. The obtained viscous compound was dissolved in chloroform (1 mL), trifluoroacetic acid (1 mL) was added and the mixture was stirred at room temperature for 2 hr. The reaction mixture was concentrated under reduced pressure, and azeotropically distilled with toluene. To the residue was slowly added saturated aqueous sodium hydrogen carbonate to set to pH9 and the mixture was washed twice with ethyl acetate. The aqueous layer was set to pH4 with 1N hydrochloric acid and extracted twice with ethyl acetate. The organic layer was concentrated under reduced pressure to give the title compound (99 mg) as a yellow solid.

MS (ESI) m/z: 533.1 [M+H]$^+$ (136-3) methyl [(6S)-4-(4-{5-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]pyrazin-2-yl}phenyl)-2,3,9-trimethyl-6H-thieno[3,2-f][1,2,4]triazolo[4,3-a][1,4]diazepin-6-yl]acetate (Example Compound 136)

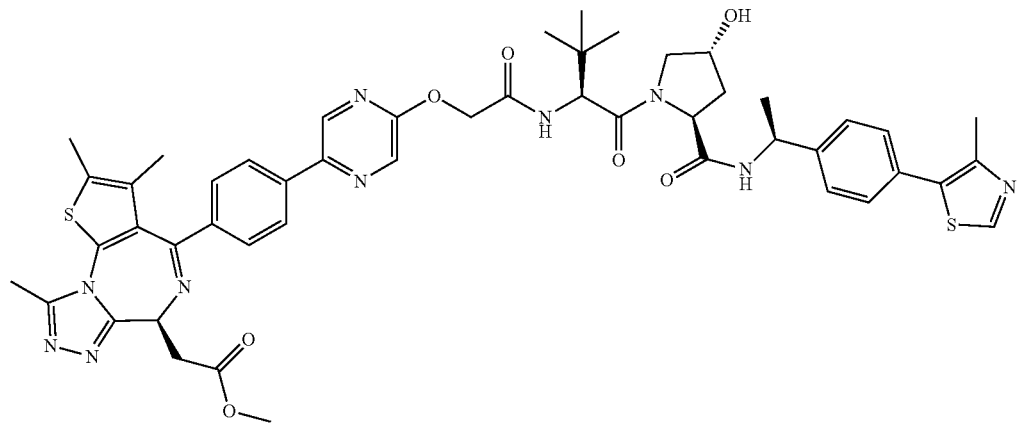 [SMILES: COC(=O)C[C@@H]1N=C(c2ccc(-c3cnc(OCC(=O)N[C@H](C(=O)N4C[C@H](O)C[C@H]4C(=O)N[C@@H](C)c4ccc(-c5scnc5C)cc4)C(C)(C)C)cn3)cc2)c2c(sc(C)c2C)-n2c(C)nnc21]

Example compound 136-2 (99 mg) and Reference Example compound 5 (101 mg), N,N-diisopropylethylamine (0.151 mL) and HATU (80 mg) were stirred in N,N-dimethylformamide (5 mL) at room temperature for 14 hr. Water was added to the reaction mixture and the mixture was stirred and extracted twice with ethyl acetate. The organic layer was washed twice with water and concentrated under reduced pressure. The residue was purified by silica gel column chromatography (methanol:chloroform=0:100-5:95) to give the title compound (125 mg) as a white solid. MS (ESI) m/z: 959.4 [M+H]$^+$ Example 137

(137-1) t-butyl 3-{4-[(6S)-2,3,6,9-tetramethyl-6H-thieno[3,2-f] [1,2,4]triazolo[4,3-a][1,4]diazepin-4-yl]phenoxy}propanoate (Example Compound 137-1)

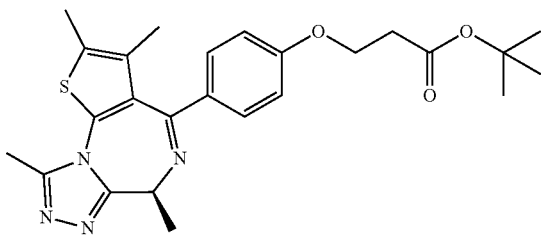 [SMILES: Cc1sc2c(c1C)C(c1ccc(OCCC(=O)OC(C)(C)C)cc1)=N[C@@H](C)c1nnc(C)n1-2]

To a mixed solution of Example compound 116-1 (500 mg), t-butyl-3-hydroxy-propanoate (324 mg) and triphenylphosphine (620 mg) in tetrahydrofuran (14.8 mL) was added dropwise diisopropyl azodicarboxylate (0.86 mL), and the mixture was stirred at room temperature for 27 hr. The reaction solution was concentrated under reduced pressure to evaporate tetrahydrofuran, water was added, and the mixture was extracted with ethyl acetate. The organic layer was washed with saturated aqueous sodium hydrogen carbonate and saturated brine, and dried over anhydrous sodium sulfate. The solvent was evaporated under reduced pressure. The residue was purified by silica gel column chromatography (chloroform:methanol=99:1-94:6) to give the title compound (169 mg) as a yellow ocher powder. MS (ESI) m/z: 467.4 [M+H]$^+$ (137-2) (2S,4R)-1-[(2S)-3,3-dimethyl-2-(3-{4-[(6S)-2,3,6,9-tetramethyl-6H-thieno[3,2-f][1,2,4]triazolo[4,3-a][1,4] diazepin-4-yl] phenoxy}propanamido)butanoyl]-4-hydroxy-N-{(1S)-1-[4-(4-methyl-1,3-thiazol-5-yl)phenyl] ethyl}pyrrolidine-2-carboxamide (Example Compound 137)

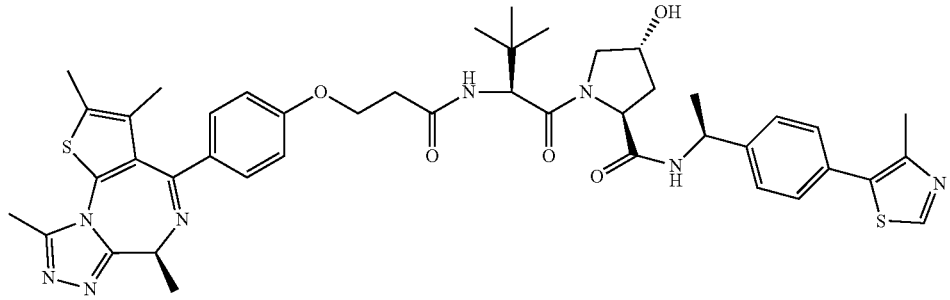 [SMILES: Cc1ncsc1-c1ccc([C@H](C)NC(=O)[C@@H]2C[C@@H](O)CN2C(=O)[C@@H](NC(=O)CCOc2ccc(C3=N[C@@H](C)c4nnc(C)n4-c4sc(C)c(C)c43)cc2)C(C)(C)C)cc1]

To a solution of Example compound 137-1 (166 mg) in dichloromethane (2.0 mL) was added dropwise, under ice-cooling, trifluoroacetic acid (2.0 mL), and the mixture was allowed to naturally warm to room temperature and stirred for 14 hr. The reaction solution was concentrated under reduced pressure and azeotropically distilled twice with toluene. To a solution of the obtained residue (203 mg) and Reference Example compound 5 (171.1 mg) in N,N-dimethylformamide (3.6 mL) was added N,N-diisopropylethylamine (0.308 mL), and HATU (203 mg) was added under ice-cooling, and the mixture was allowed to naturally warm to room temperature and stirred for 67 hr. To the reaction solution was added water and the mixture was extracted with chloroform. The organic layer was washed with water, saturated aqueous sodium hydrogen carbonate and saturated brine, and dried over anhydrous sodium sulfate. The solvent was evaporated under reduced pressure. The residue was purified by silica gel column chromatography (chloroform:methanol=97:3-92:8-90:10-85:15). The obtained solid was suspension washed with diethyl ether, collected by filtration and dried under reduced pressure to give the title compound (106 mg) as a white solid. MS (ESI) m/z: 837.5 [M+H]$^+$ Example 138

(138-1) t-butyl [2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]carbamate (Example Compound 138-1)

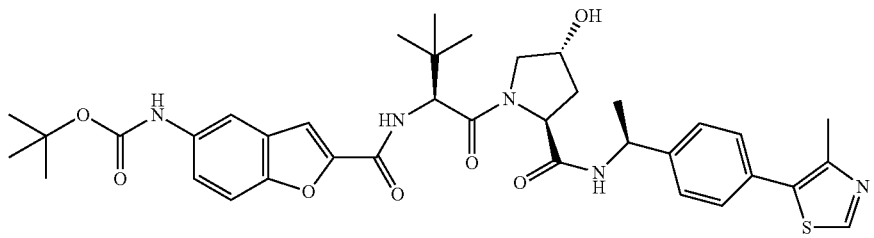 [SMILES: Cc1ncsc1-c1ccc([C@H](C)NC(=O)[C@@H]2C[C@@H](O)CN2C(=O)[C@@H](NC(=O)c2cc3cc(NC(=O)OC(C)(C)C)ccc3o2)C(C)(C)C)cc1]

To a solution of 5-aminobenzofuran-2-carboxylic acid (300 mg) in tetrahydrofuran (3 mL), water (3 mL) were added triethylamine (0.26 mL) and di-t-butyl dicarbonate (406 mg), and the mixture was stirred at room temperature for 16 hr. To the reaction mixture were added chloroform and water, the aqueous layer was removed by Phase Separator, and the organic layer was concentrated under reduced pressure. The residue was dissolved in N,N-dimethylformamide (17 mL), Reference Example compound 5 (896 mg), HATU (966 mg), N,N-diisopropylethylamine (0.879 mL) were added and the mixture was stirred at room temperature for 1 hr. Water was added to the reaction mixture is and the mixture was stirred. The precipitate was collected by filtration and the obtained solid was purified by silica gel column chromatography (methanol:chloroform=0:100-4:96) to give the title compound (643 mg) as a pale-yellow solid.

MS (ESI) m/z: 704.7 [M+H]$^+$ (138-2) (2S,4R)-1-{(2S)-2-[(5-amino-1-benzofuran-2-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide hydrochloride (Example Compound 138-2)

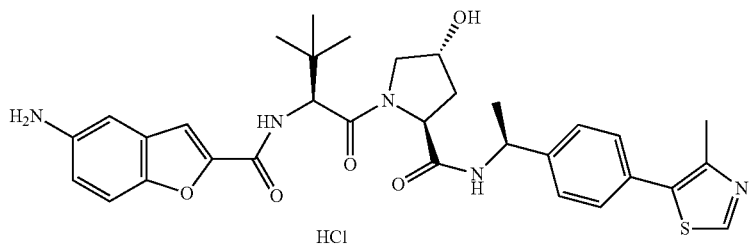 [SMILES: Cc1ncsc1-c1ccc([C@H](C)NC(=O)[C@@H]2C[C@@H](O)CN2C(=O)[C@@H](NC(=O)c2cc3cc(N)ccc3o2)C(C)(C)C)cc1 ; Cl]

To a solution of Example compound 138-1 (643 mg) in methanol (2 mL), ethanol (2 mL) was added 4 M hydrogen chloride/ethyl acetate solution (5 mL) and the mixture was stirred for 2 hr. The reaction mixture was concentrated under reduced pressure to give the title compound (715 mg) as a pale-yellow solid. MS (ESI) m/z: 604.3 $[M+H]^+$ (138-3) methyl [(6S)-4-{4-[3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]carbamoyl}pyrrolidin-1-yl]phenyl}-2,3,9-trimethyl-6H-thieno[3,2-f][1,2,4]triazolo[4,3-a][1,4]diazepin-6-yl]acetate (Example Compound 138-3)

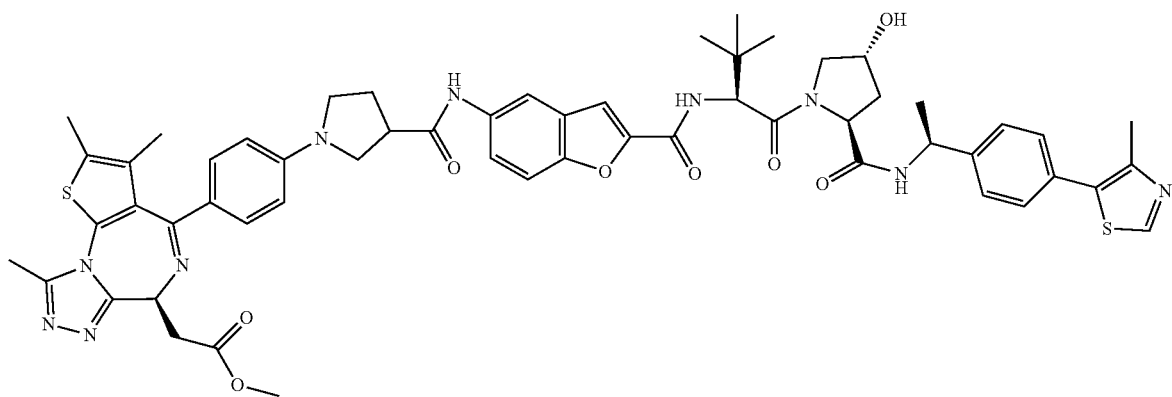 [SMILES: COC(=O)C[C@@H]1N=C(c2ccc(N3CCC(C(=O)Nc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

To a solution of Example compound 81-1 (600 mg) in chloroform (4 mL) was added, under ice-cooling, trifluoroacetic acid (2 mL), and the mixture was stirred at room temperature for 22 hr. The reaction mixture was diluted with chloroform and the solvent was evaporated under reduced pressure. To the residue was added toluene and the mixture was concentrated under reduced pressure. This operation was performed twice to give an orange viscous compound (1.1 g). The obtained viscous compound (311 mg) was dissolved in N,N-dimethylformamide (2 mL), compound 138-2 (328 mg), N,N-diisopropylethylamine (0.890 mL), HATU (584 mg) were added and the mixture was stirred at room temperature for 21 hr. Water was added to the reaction mixture and the mixture was stirred. The precipitate was collected by filtration and the obtained solid was purified by NH silica gel column chromatography (methanol:chloroform=0:100-4:96) and silica gel column chromatography (methanol:chloroform=0:100-10:90) to give the title compound as an orange powder.
MS (ESI) m/z: 1079.4 $[M+H]^+$ (138-4) methyl [(6S)-4-{4-[(3S)-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]carbamoyl}pyrrolidin-1-yl]phenyl}-2,3,9-trimethyl-6H-thieno[3,2-f][1,2,4]triazolo[4,3-a][1,4]diazepin-6-yl]acetate (Example Compound 138)

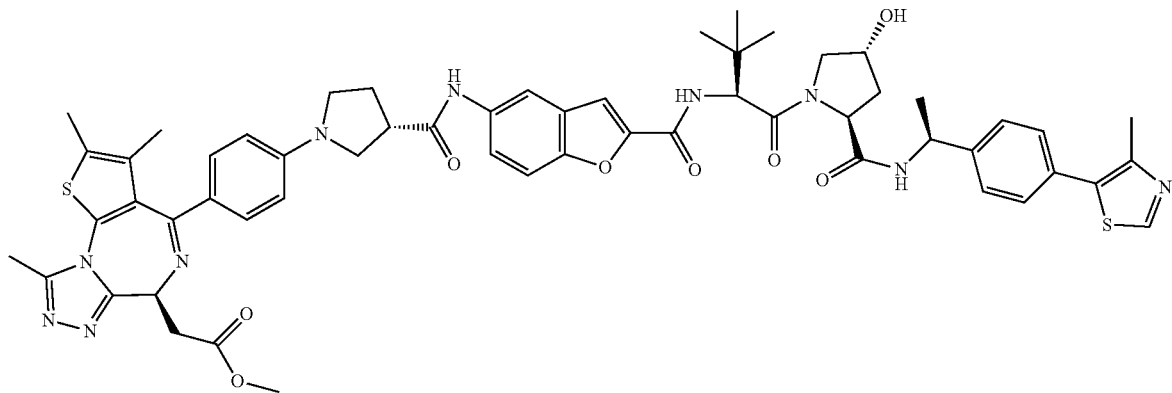 [SMILES: COC(=O)C[C@@H]1N=C(c2ccc(N3CC[C@H](C(=O)Nc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

Example compound 138-3 (135 mg) was resolved by a chiral column [CHIRALPAK IC (30*250), ethanol:methanol:tetrahydrofuran:diethylamine=40:40:20:0.1]. The fraction obtained later was purified by NH silica gel column chromatography (methanol:chloroform=0:100-5:95) to give the title compound (50 mg) as a yellow powder.

MS (ESI) m/z: 1079.4 [M+H]$^+$

Example 139

(139-1) methyl [(6S)-4-{4-[(3R)-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]carbamoyl}pyrrolidin-1-yl]phenyl}-2,3,9-trimethyl-6H-thieno[3,2-f][1,2,4]triazolo[4,3-a][1,4]diazepin-6-yl]acetate (Example Compound 139)

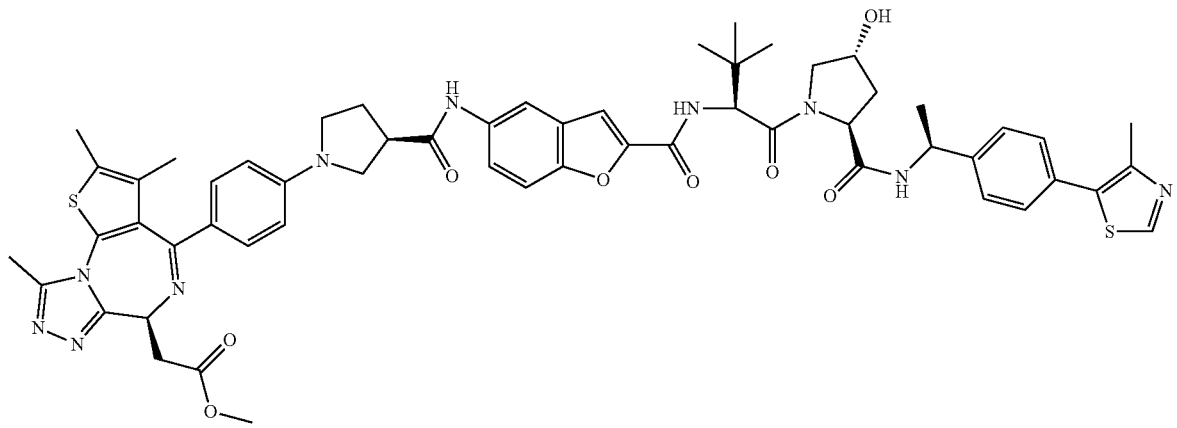 [SMILES: COC(=O)C[C@@H]1N=C(c2ccc(N3CC[C@@H](C(=O)Nc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

Example compound 138-3 (135 mg) was resolved by a chiral column [CHIRALPAK IC (30*250), ethanol:methanol:tetrahydrofuran:diethylamine=40:40:20:0.1]. The fraction obtained earlier was purified by NH silica gel column chromatography (methanol:chloroform=0:100-5:95) to give the title compound (46 mg) as a yellow powder.

MS (ESI) m/z: 1079.4 [M+H]$^+$

Example 140

(140-1) (2S,4R)-1-{(2S)-2-[(5-{2-[(azetidine-3-carbonyl)amino]ethoxy}-1-benzofuran-2-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 140-1)

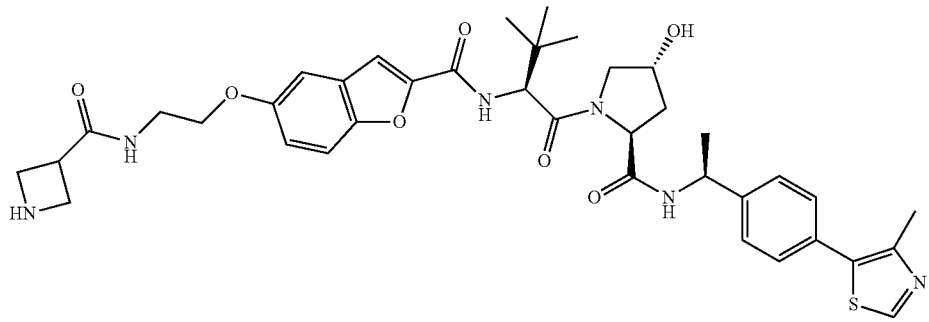 [SMILES: Cc1ncsc1-c1ccc([C@H](C)NC(=O)[C@@H]2C[C@@H](O)CN2C(=O)[C@@H](NC(=O)c2cc3cc(OCCNC(=O)C4CNC4)ccc3o2)C(C)(C)C)cc1]

By reaction and treatment in the same manner as in Example 133 (133-2) and using N-(t-butoxycarbonyl)-azetidine-3-carboxylic acid instead of Example compound 133-1, and Example compound 42-1 instead of Reference Example compound 5, the title compound was obtained as a pale-yellow powder.
MS (ESI) m/z: 731.3 [M+H]+

(140-2) methyl [(6S)-4-(4-{3-[(2-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}ethyl)carbamoyl]azetidin-1-yl}phenyl)-2,3,9-trimethyl-6H-thieno[3,2-f][1,2,4]triazolo[4,3-a][1,4]diazepin-6-yl]acetate (Example Compound 140)

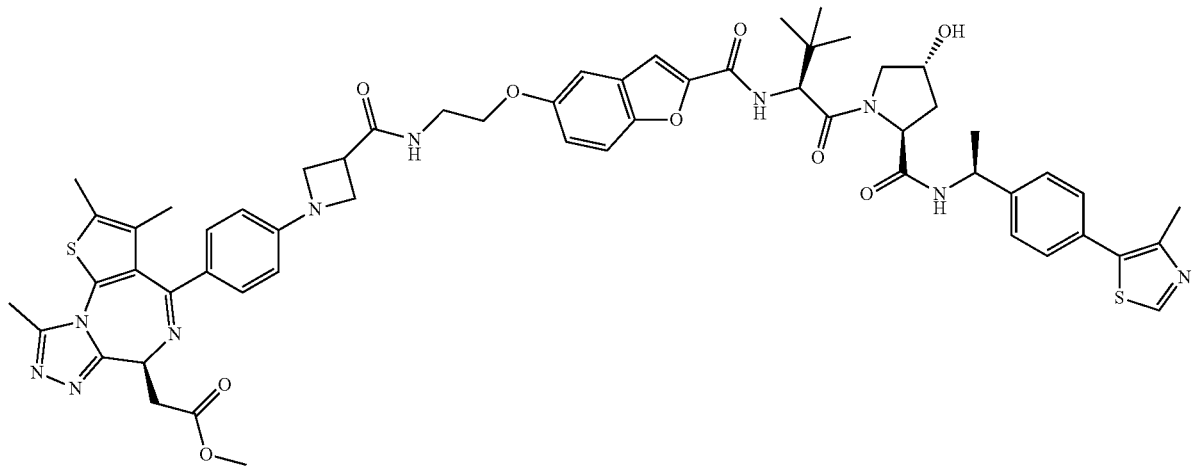 [SMILES: COC(=O)C[C@@H]1N=C(c2ccc(N3CC(C(=O)NCCOc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

By reaction and treatment in the same manner as in Example 81 (81-1) and using Example compound 140-1 instead of 3-(t-butoxycarbonyl)pyrrolidine, the title compound was obtained as a white solid. MS (ESI) m/z: 1109.3 [M+H]+

Example 141

(141-1) [5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)thiophen-2-yl]boronic acid (Example Compound 141-1)

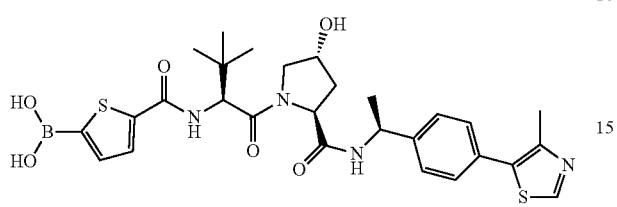

5-Carboxythiophene-2-boronic acid pinacol ester (190 mg) and Reference Example compound 5 (300 mg), N,N-diisopropylethylamine (0.325 mL) and HATU (285 mg) were stirred in N,N-dimethylformamide (5 mL) at room temperature for 15 hr. Water was added to the reaction mixture and the mixture was stirred and extracted 3 times with ethyl acetate. The organic layer was washed twice with water and concentrated under reduced pressure. Then, chloroform was added to the aqueous layer and the mixture was extracted 3 times and the extract was concentrated under reduced pressure. The obtained solids were combined, and small amounts of chloroform and diisopropyl ether were added to suspend and wash the solids. The solids were dried under reduced pressure to give a white solid (449 mg) containing the title compound. MS (ESI) m/z: 599.2 [M+H]$^+$ (141-2) methyl [(6S)-4-{4-[5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)thiophen-2-yl]phenyl}-2,3,9-trimethyl-6H-thieno[3,2-f][1,2,4]triazolo[4,3-a][1,4]diazepin-6-yl]acetate (Example Compound 141)

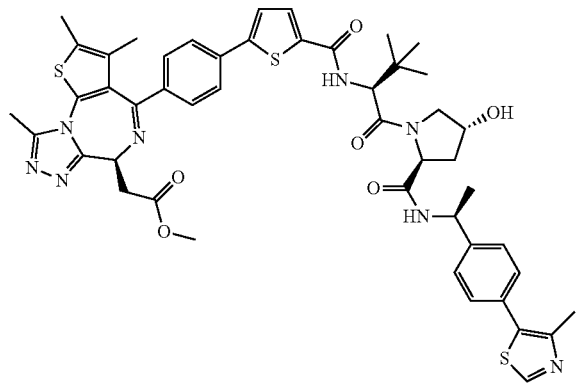

Under an argon stream, Example compound 141-1 (449 mg), Reference Example compound 1 (200 mg), palladium acetate (11 mg), S-phos (40 mg), potassium fluoride (84 mg) and water (0.031 mL) were heated under reflux in tetrahydrofuran (5 mL) solvent for 24 hr. Using chloroform, the reaction mixture was filtered through diatomaceous earth, and the filtrate was concentrated under reduced pressure. The residue was purified by NH silica gel column chromatography (methanol:chloroform=0:100-2:98) and silica gel column chromatography (methanol:ethyl acetate=0:100-10:90) to give the title compound (57 mg) as a white solid.

MS (ESI) m/z: 933.9 [M+H]$^+$

Example 142

(142-1) 5-{[1-(t-butoxycarbonyl)pyrrolidin-3-yl]oxy}-1-benzofuran-2-carboxylic acid (Example Compound 142-1)

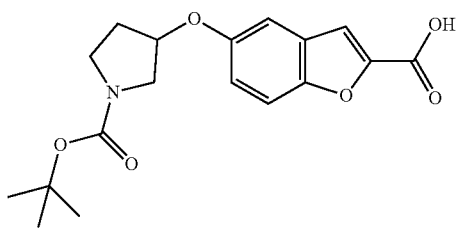 [SMILES: CC(C)(C)OC(=O)N1CCC(Oc2ccc3oc(C(=O)O)cc3c2)C1]

Under an argon stream, a solution of Example compound 25-2 (305 mg), 1-(t-butoxycarbonyl)-3-pyrrolidinol (356 mg) and triphenylphosphine (500 mg) in tetrahydrofuran (8 mL) was cooled to 0° C., 40% diisopropyl azodicarboxylate/toluene solution (1 mL) was added and the mixture was stirred at room temperature for 18 hr. Water was added to the reaction mixture and the mixture was stirred and extracted 3 times with ethyl acetate. The organic layer was washed with saturated brine and dried over sodium sulfate, filtered and the filtrate was concentrated under reduced pressure. The residue was purified by silica gel column chromatography (ethyl acetate:hexane=20:80-40:60). To a suspension of the obtained compound in 1,2-dimethoxyethane (10 mL) were added 4 M aqueous lithium hydroxide solution (1.2 mL), water (6 mL) and the mixture was stirred at room temperature for 18 hr. The reaction mixture was partitioned between water and ethyl acetate, 1N hydrochloric acid was added to the aqueous layer and the mixture was extracted 3 times with ethyl acetate. The organic layers were collected, dried over sodium sulfate, filtered and the filtrate was concentrated under reduced pressure to give the title compound (464 mg) as a white solid.

MS (ESI) m/Z: 364.1 [M−H]$^-$ (142-2) (2S,4R)-1-[(2S)-3,3-dimethyl-2-({5-[(pyrrolidin-3-yl)oxy]-1-benzofuran-2-carbonyl}amino)butanoyl]-4-hydroxy-N-{(1S)-1-[4-(4-methyl-1,3-thiazol-5-yl)phenyl]ethyl}pyrrolidine-2-carboxamide (Example Compound 142-2)

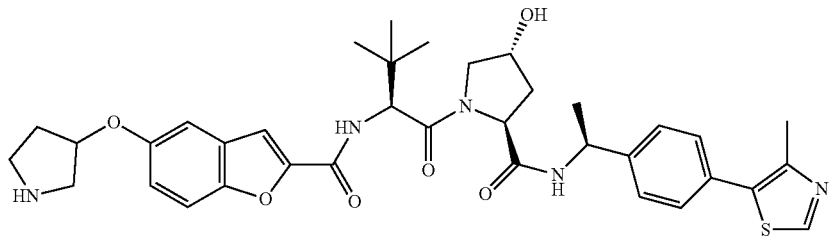 [SMILES: Cc1ncsc1-c1ccc([C@H](C)NC(=O)[C@@H]2C[C@@H](O)CN2C(=O)[C@@H](NC(=O)c2cc3cc(OC4CCNC4)ccc3o2)C(C)(C)C)cc1]

Example compound 142-1 (200 mg) was dissolved in N,N-dimethylformamide (2 mL), and Reference Example compound 5 (305 mg), HATU (328 mg) and N,N-diisopropylethylamine (0.3 mL) were added and the mixture was stirred at room temperature for 1 hr. Water was added to the reaction mixture and the mixture was stirred. The precipitate was collected by filtration. To a solution of the obtained solid in dichloromethane (2 mL) was added trifluoroacetic acid (1 mL) and the mixture was stirred at room temperature for 2 hr. The reaction mixture was concentrated, saturated aqueous sodium hydrogen carbonate was added to the residue and the mixture was extracted 3 times with chloroform. The organic layers were collected, dried over sodium sulfate, filtered and concentrated under reduced pressure. The residue was purified by silica gel column chromatography (methanol:ethyl acetate=10:90-20:80) to give the title compound (228 mg) as a pale-yellow powder.

MS (ESI) m/z: 674.3 [M+H]$^+$ (142-3) methyl [(6S)-4-{4-[3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}pyrrolidin-1-yl]phenyl}-2,3,9-trimethyl-6H-thieno[3,2-f][1,2,4]triazolo[4,3-a][1,4]diazepin-6-yl]acetate (Example Compound 142-3)

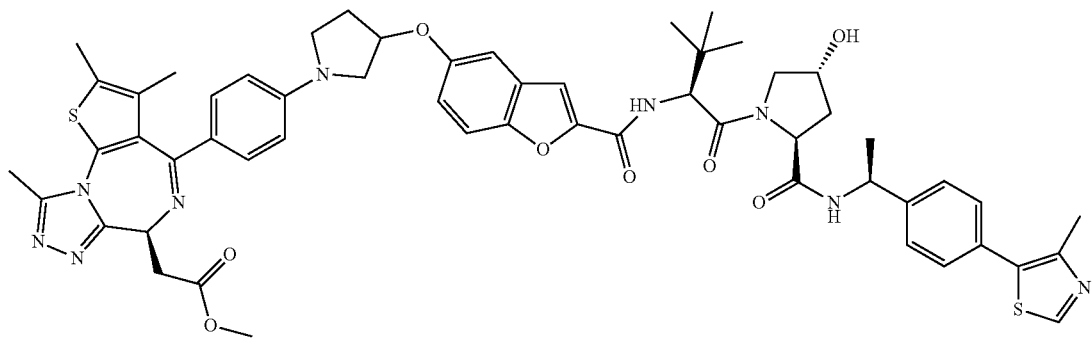 [SMILES: COC(=O)C[C@@H]1N=C(c2ccc(N3CCC(Oc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

Under an argon stream, Example compound 142-2 (228 mg), Reference Example compound 1 (120 mg), tris(dibenzylideneacetone)dipalladium(0) (26.5 mg), t-BuXphos (24.6 mg) and potassium phosphate (184 mg) were heated under reflux in tetrahydrofuran (3 mL) solvent for 6 hr. Using ethyl acetate, the reaction mixture was filtered through diatomaceous earth, and the filtrate was concentrated under reduced pressure. The residue was purified by silica gel column chromatography (methanol:chloroform=0:100-2:98) to give the title compound (229 mg) as a yellow solid. MS (ESI) m/z: 1052.4 [M+H]$^+$ (142-4) methyl [(6S)-4-{4-[(3R)-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}pyrrolidin-1-yl]phenyl}-2,3,9-trimethyl-6H-thieno[3,2-f][1,2,4]triazolo[4,3-a][1,4]diazepin-6-yl]acetate (Example Compound 142)

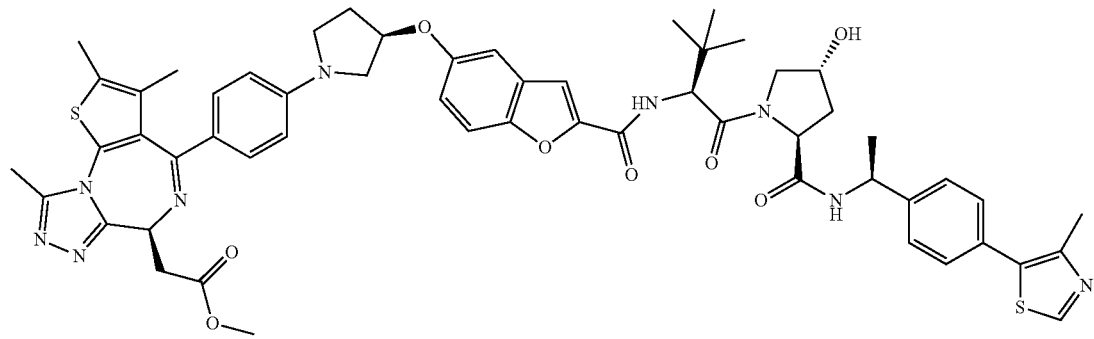 [SMILES: COC(=O)C[C@@H]1N=C(c2ccc(N3CC[C@@H](Oc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

Example compound 142-3 (225 mg) was resolved by a chiral column [CHIRALPAK ID (30*250), ethanol:tetrahydrofuran:diethylamine=77:23:0.1]. The fraction obtained earlier was purified by silica gel column chromatography (methanol:chloroform=0:100-5:95) to give the title compound (47 mg) as a yellow solid.
MS (ESI) m/z: 1052.4 [M+H]$^+$ Example 143

(143-1) methyl [(6S)-4-{4-[(3S)-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}pyrrolidin-1-yl]phenyl}-2,3,9-trimethyl-6H-thieno[3,2-f][1,2,4]triazolo[4,3-a][1,4]diazepin-6-yl]acetate (Example Compound 143)

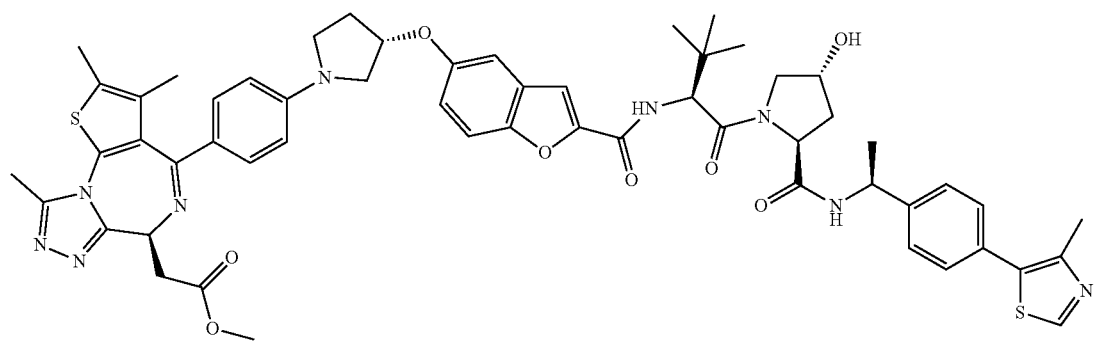 [SMILES: COC(=O)C[C@@H]1N=C(c2ccc(N3CC[C@H](Oc4ccc5oc(C(=O)N[C@H](C(=O)N6C[C@H](O)C[C@H]6C(=O)N[C@@H](C)c6ccc(-c7scnc7C)cc6)C(C)(C)C)cc5c4)C3)cc2)c2c(sc(C)c2C)-n2c(C)nnc21]

Example compound 142-3 (225 mg) was resolved by a chiral column [CHIRALPAK ID (30*250), ethanol:tetrahydrofuran:diethylamine=77:23:0.1]. The fraction obtained later was purified by silica gel column chromatography (methanol:chloroform=0:100-5:95) to give the title compound (52 mg) as a yellow solid. MS (ESI) m/z: 1052.3 [M+H]$^+$

Example 144

(144-1) t-butyl (4-bromo-1H-indazol-1-yl)acetate (Example Compound 144-1A) and t-butyl (4-bromo-2H-indazol-2-yl)acetate (Example Compound 144-1B)

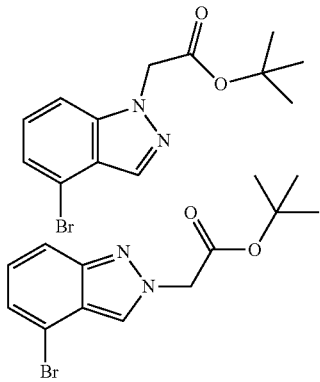

4-Bromo-1H-indazole (1.00 g) was dissolved in N,N-dimethylformamide (25 mL), t-butyl bromoacetate (0.94 mL) and potassium carbonate (1.18 g) were added and the mixture was stirred at 100° C. for 3 hr. To the reaction mixture was added ice water and the mixture was stirred. Hexane:ethyl acetate=1:1 was added and the organic layer was extracted. The aqueous layer was extracted again with hexane:ethyl acetate=1:1 and the organic layers were collected and washed twice with water, washed with saturated brine, and dried over anhydrous sodium sulfate. The solvent was evaporated under reduced pressure. The residue was purified by silica gel column chromatography (hexane:ethyl acetate=90:10-80:20) to give the title compound (Example compound 144-1A, 508 mg), (Example compound 144-1B, 289 mg) each as a yellow white solid.

MS (ESI) m/z: 311.1 [M+H]$^+$ (Example compound 144-1A), MS (ESI) m/z: 311.1 [M+H]$^+$ (Example compound 144-1B)

(144-2) methyl [(6S)-4-(4-{1-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1H-indazol-4-yl}phenyl)-2,3,9-trimethyl-6H-thieno[3,2-f][1,2,4]triazolo[4,3-a][1,4]diazepin-6-yl]acetate (Example Compound 144)

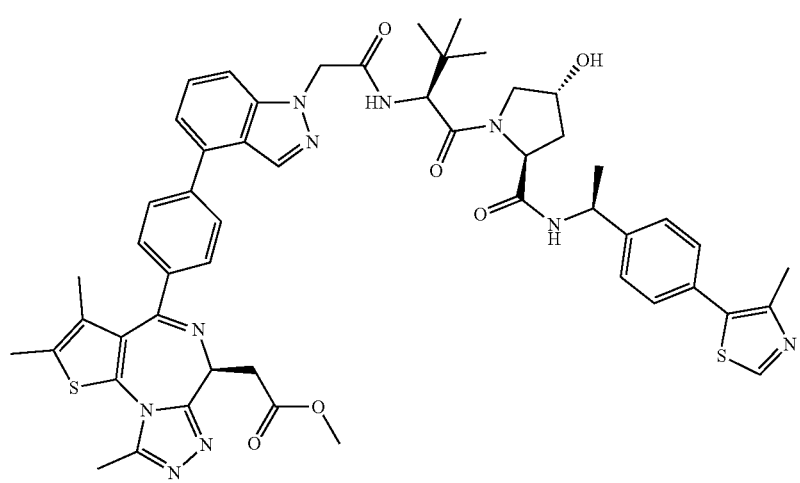 [SMILES: COC(=O)C[C@@H]1N=C(c2ccc(-c3cccc4c3cnn4CC(=O)N[C@H](C(=O)N3C[C@H](O)C[C@H]3C(=O)N[C@@H](C)c3ccc(-c4scnc4C)cc3)C(C)(C)C)cc2)c2c(sc(C)c2C)-n2c(C)nnc21]

By reaction and treatment in the same manner as in Example 52 (52-1)-(52-3) and using Example compound 144-1A instead of 4-bromo-3-chlorophenol, the title compound was obtained as a yellow-white solid. MS (ESI) m/z: 981.4 [M+H]$^+$

Example 145

(145-1) t-butyl (7-bromo-2H-indazol-2-yl)acetate (Example Compound 145-1)

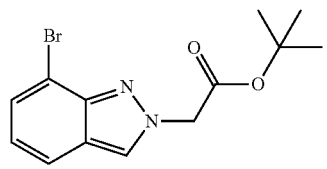 [SMILES: CC(C)(C)OC(=O)Cn1cc2cccc(Br)c2n1]

7-Bromo-1H-indazole (0.93 g) was dissolved in N,N-dimethylformamide (25 mL), and t-butyl bromoacetate (0.89 mL) and potassium carbonate (1.08 g) were added and the mixture was stirred at 100° C. for 4 hr. To the reaction mixture was added ice water, and the mixture was stirred. Hexane:ethyl acetate=1:1 was added and the organic layer was extracted. The aqueous layer was extracted again with hexane:ethyl acetate=1:1 and the organic layers were collected and washed twice with water, washed with saturated brine and dried over anhydrous sodium sulfate. The solvent was evaporated under reduced pressure. The residue was purified by silica gel column chromatography (hexane:ethyl acetate=95:5-75:25) to give the title compound (1.04 g) as a yellow solid.

MS (ESI) m/z: 311.1 [M+H]$^+$ (145-2) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-2H-indazol-7-yl}phenyl)-2,3,9-trimethyl-6H-thieno[3,2-f][1,2,4]triazolo[4,3-a][1,4]diazepin-6-yl]acetate (Example Compound 145)

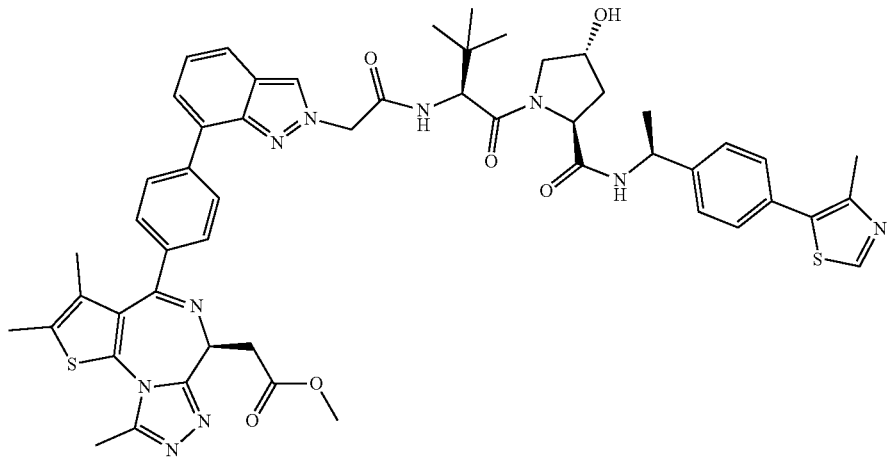

By reaction and treatment in the same manner as in Example 52 (52-1)-(52-3) and using Example compound 145-1 instead of 4-bromo-3-chlorophenol, the title compound was obtained as a yellow solid. MS (ESI) m/z: 981.5 [M+H]+

Example 146

(146-1) t-butyl (7-bromo-2-oxo-3,4-dihydroquinolin-1(2H)-yl)acetate (Example Compound 146-1)

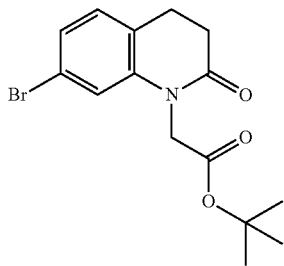 [SMILES: CC(C)(C)OC(=O)CN1C(=O)CCc2ccc(Br)cc21]

7-Bromo-3,4-dihydro-1H-quinolin-2-one (500 mg) was dissolved in tetrahydrofuran (15 mL), and sodium hydride (60%, 80 mg) was added under ice-cooling. After stirring for 10 min, t-butyl bromoacetate (0.58 mL) was added and the mixture was stirred at room temperature for 17 hr. To the reaction mixture were added saturated aqueous ammonium chloride solution and water and the mixture was extracted with ethyl acetate. The organic layer was washed with saturated aqueous sodium hydrogen carbonate and saturated brine and dried over anhydrous sodium sulfate, and the solvent was evaporated under reduced pressure. The residue was purified by silica gel column chromatography (hexane:ethyl acetate=95:5-75:25) to give the title compound (879 mg) as a white solid. ¹H NMR (400 MHz, CDCl₃) δppm 1.47 (9H, s), 2.69 (2H, m), 2.90 (2H, m), 4.54 (2H, s), 6.88 (1H, d, J=2.1 Hz), 7.04 (1H, d, J=7.7 Hz), 7.14 (1H, dd, J=7.7, 2.1 Hz)

(146-2) methyl [(6S)-4-{4-[1-(2-t-butoxy-2-oxoethyl)-2-oxo-1,2,3,4-tetrahydroquinolin-7-yl]phenyl}-2,3,9-trimethyl-6H-thieno[3,2-f][1,2,4]triazolo[4,3-a][1,4]diazepin-6-yl]acetate (Example Compound 146-2)

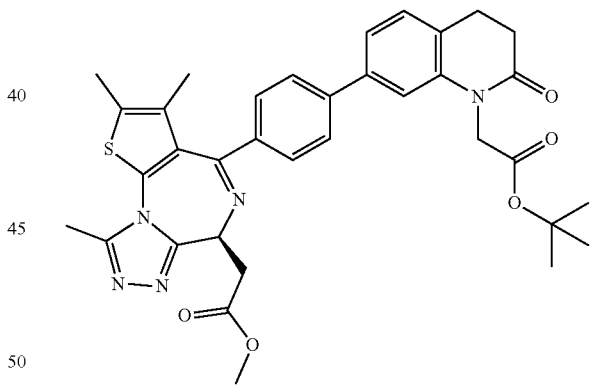

To a mixture of Reference Example compound 3 (162 mg), Example compound 146-1 (128 mg), potassium fluoride (55 mg), S-phos (39 mg), palladium acetate (14 mg) in tetrahydrofuran (6.0 mL) was added water (20 μL) and the mixture was stirred at 85° C. for 18 hr. To the reaction mixture were added ice water and saturated brine and the mixture was extracted with chloroform. The aqueous layer was extracted 3 times with chloroform. The organic layers were collected, dried over anhydrous sodium sulfate, and the solvent was evaporated under reduced pressure. The residue was purified by silica gel column chromatography (chloroform:methanol=100:0-96:4) to give a crudely purified title compound (196 mg) as a yellow solid.

MS (ESI) m/z: 640.4 [M+H]+

(146-3) methyl [(6S)-4-(4-{1-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-2-oxo-1,2,3,4-tetrahydroquinolin-7-yl}phenyl)-2,3,9-trimethyl-6H-thieno[3,2-f] [1,2,4]triazolo[4,3-a][1,4]diazepin-6-yl]acetate (Example Compound 146)

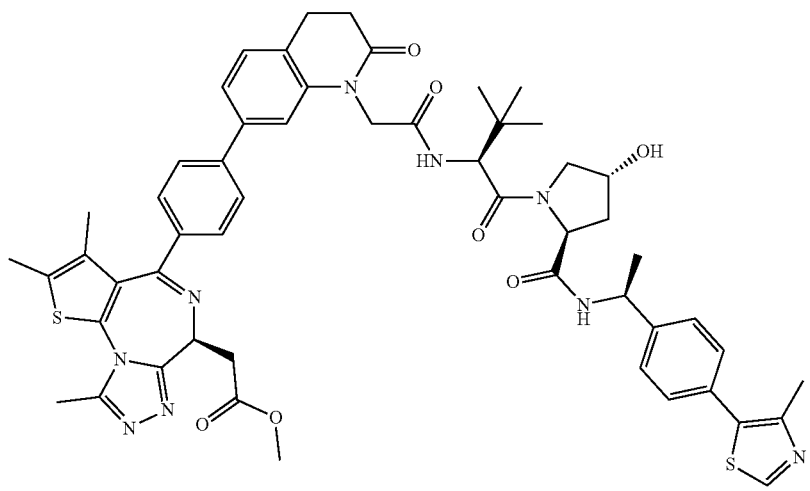

Example compound 146-2 (190 mg) was dissolved in dichloromethane (2.0 mL), trifluoroacetic acid (2.0 mL) was added under ice-cooling and the mixture was stirred at room temperature for 3 hr. To the reaction mixture was added toluene and toluene was evaporated under reduced pressure. This was repeated 3 times and the mixture was dried under reduced pressure at 60° C. The residue was dissolved in N,N-dimethylformamide (3.0 mL), N,N-diisopropylethylamine (0.26 mL), Reference Example compound 5 (172 mg), HATU (182 mg) were added under ice-cooling and the mixture was stirred at room temperature for 16 hr. To the reaction mixture were added ice water and saturated brine and the mixture was extracted with chloroform. The aqueous layer was extracted twice with chloroform. The organic layers were collected and, after drying over anhydrous sodium sulfate, the solvent was evaporated under reduced pressure, and the residue was purified by NH silica gel column chromatography (ethyl acetate:methanol=100:0-80:20), silica gel column chromatography (ethyl acetate:methanol=100:0-80:20) to give the title compound (128 mg) as a white solid.

MS (ESI) m/z: 1010.4 [M+H]+

Example 147

(147-1) t-butyl (8-bromo-3,4-dihydroisoquinolin-2(1H)-yl)acetate (Example Compound 147-1)

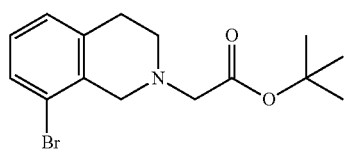 [SMILES: CC(C)(C)OC(=O)CN1CCc2cccc(Br)c2C1]

t-Butyl 8-bromo-3,4-dihydro-1H-isoquinoline-2-carboxylate (300 mg) was dissolved in dichloromethane (3.0 mL), trifluoroacetic acid (2.0 mL) was added under ice-cooling and the mixture was stirred at room temperature for 1 hr. To the reaction mixture was added toluene and toluene was evaporated under reduced pressure. This was repeated 3 times and the mixture was dried under reduced pressure at 60° C. The residue was dissolved in acetonitrile (5.0 mL) and t-butyl bromoacetate (0.25 mL) and cesium carbonate (470 mg) were added and the mixture was stirred at 80° C. for 1 hr. To the reaction mixture were added ice water and saturated brine and the mixture was extracted with ethyl acetate, and the extract was washed with saturated brine, and dried over anhydrous sodium sulfate. The solvent was evaporated under reduced pressure, and the residue was purified by silica gel column chromatography (hexane:ethyl acetate=100:0-80:20) to give the title compound (190 mg) as a pale-yellow oil. MS (ESI) m/z: 326.1 [M+H]+

(147-2) methyl [(6S)-4-{4-[2-(2-t-butoxy-2-oxoethyl)-1,2,3,4-tetrahydroisoquinolin-8-yl]phenyl}-2,3,9-trimethyl-6H-thieno[3,2-f][1,2,4]triazolo[4,3-a][1,4]diazepin-6-yl]acetate (Example Compound 147-2)

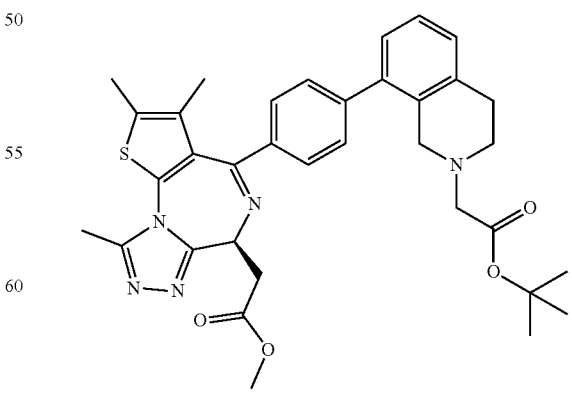

To a mixture of Reference Example compound 3 (243 mg), Example compound 147-1 (190 mg), potassium fluoride (80 mg), S-phos (59 mg) and palladium acetate (22 mg) in tetrahydrofuran (6.0 mL) was added water (30 μL) and the mixture was stirred at 85° C. for 18 hr. To the reaction mixture were added ice water and saturated brine and the mixture was extracted with chloroform, and the aqueous layer was extracted 3 times with chloroform. The organic layers were collected, dried over anhydrous sodium sulfate, and the solvent was evaporated under reduced pressure. The residue was purified by silica gel column chromatography (chloroform:methanol=100:0-95:5) to give a crudely purified title compound (220 mg) as a yellow solid. MS (ESI) m/z: 626.4 [M+1-1]⁺

(147-3) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1,2,3,4-tetrahydroisoquinolin-8-yl}phenyl)-2,3,9-trimethyl-6H-thieno[3,2-f] [1,2,4]triazolo[4,3-a][1,4]diazepin-6-yl]acetate (Example Compound 147)

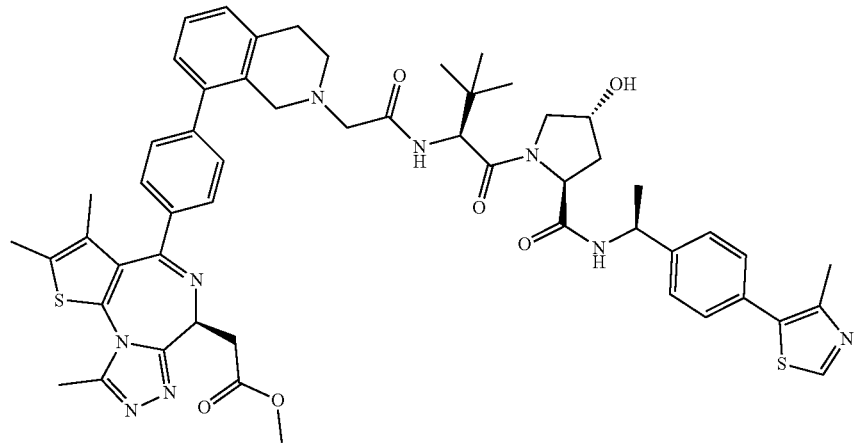 [SMILES: COC(=O)C[C@@H]1N=C(c2ccc(-c3cccc4c3CN(CC(=O)N[C@H](C(=O)N3C[C@H](O)C[C@H]3C(=O)N[C@@H](C)c3ccc(-c5scnc5C)cc3)C(C)(C)C)CC4)cc2)c2c(sc(C)c2C)-n2c(C)nnc21]

Example compound 147-2 (210 mg) was dissolved in dichloromethane (2.0 mL), trifluoroacetic acid (2.0 mL) was added under ice-cooling and the mixture was stirred at room temperature for 3 hr. To the reaction mixture was added toluene and toluene was evaporated under reduced pressure. This was repeated 3 times and the mixture was dried under reduced pressure at 60° C. The residue was dissolved in N,N-dimethylformamide (3.0 mL), N,N-diisopropylethylamine (0.44 mL), Reference Example compound 5 (195 mg), HATU (207 mg) were added under ice-cooling and the mixture was stirred at room temperature for 16 hr. To the reaction mixture were added ice water and saturated brine and the mixture was extracted with chloroform. The aqueous layer was extracted twice with chloroform. The organic layers were collected and, after drying over anhydrous sodium sulfate, the solvent was evaporated under reduced pressure, and the residue was purified by NH silica gel column chromatography (ethyl acetate:methanol=100:0-80:20), silica gel column chromatography (ethyl acetate:methanol=100:0-80:20) to give the title compound (142 mg) as a white solid.

MS (ESI) m/z: 996.5 [M+H]⁺

Example 148

(148-1) methyl [(6S)-4-{4-[4-(hydroxymethyl)piperidin-1-yl]phenyl}-2,3,9-trimethyl-6H-thieno[3,2-f][1,2,4]triazolo[4,3-a] [1,4]diazepin-6-yl]acetate (Example Compound 148-1)

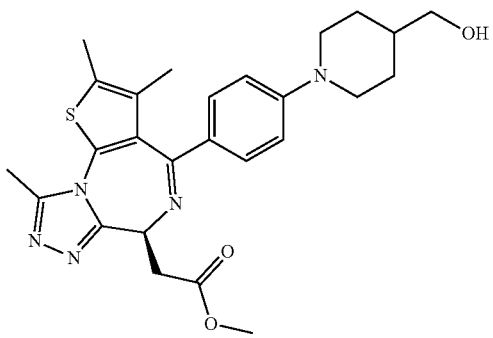 [SMILES: COC(=O)C[C@@H]1N=C(c2ccc(N3CCC(CO)CC3)cc2)c2c(sc(C)c2C)-n2c(C)nnc21]

A mixture of 4-piperidinylmethanol (333 mg), Reference Example compound 1 (500 mg), tris(dibenzylideneacetone)dipalladium(0) (110 mg), t-BuXphos (102 mg), potassium phosphate (767 mg) and tetrahydrofuran (12.0 mL) was stirred at 80° C. for 1 hr. The insoluble material in the reaction mixture was filtered off through diatomaceous earth, water was added to the filtrate, and the mixture was extracted with chloroform, and the extract was dried over anhydrous sodium sulfate and filtered. The solvent was evaporated under reduced pressure. The obtained residue was purified by silica gel column chromatography (chloroform:methanol=98:2-95:5) to give the title compound (425 mg) as a yellow solid. MS (ESI) m/z: 494.3 [M+H]⁺

383

(148-2) methyl {(6S)-4-[4-(4-formylpiperidin-1-yl)phenyl]-2,3,9-trimethyl-6H-thieno[3,2-f][1,2,4]triazolo[4,3-a][1,4]diazepin-6-yl}acetate (Example Compound 148-2)

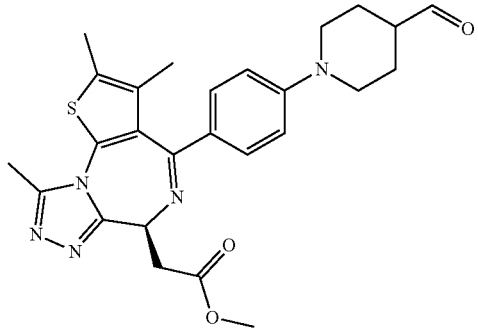 [SMILES: COC(=O)C[C@@H]1N=C(c2ccc(N3CCC(C=O)CC3)cc2)c2c(sc(C)c2C)-n2c(C)nnc21]

To a solution of Example compound 148-1 (200 mg) in dichloromethane (4.0 mL) was added 1,1,1-triacetoxy-1,1-dihydro-1,2-benziodoxol-3-(1H)-one (Dess-Martin reagent, 206 mg), and the mixture was stirred at room temperature for 30 min. The reaction mixture was concentrated, saturated aqueous sodium hydrogen carbonate and saturated aqueous sodium thiosulfate solution were added to the residue, and the mixture was extracted with ethyl acetate, and the extract was washed with saturated aqueous sodium hydrogen carbonate, dried over anhydrous sodium sulfate and filtered. The solvent was evaporated under reduced pressure. The obtained residue was purified by silica gel column chromatography (chloroform:methanol=100:0-95:5) to give the title compound (173 mg) as a yellow solid. MS (ESI) m/z: 492.3 [M+H]+

384

(148-3) 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}piperidine-4-carboxylic acid (Example Compound 148-3)

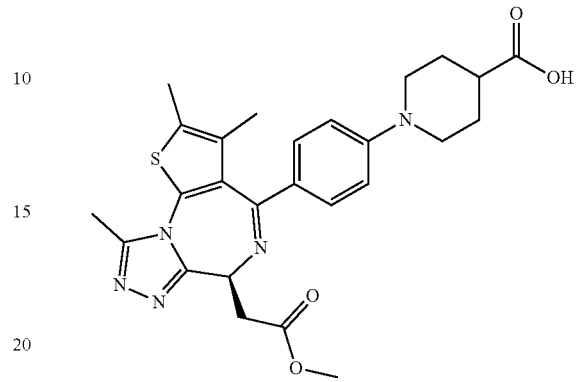

To a solution of Example compound 148-2 (170 mg) and 2-methyl-but-2-ene (0.088 mL) in acetonitrile (3.0 mL) was added a solution of sodium chlorite (59 mg) and sodium dihydrogen phosphate (62 mg) in water (1.0 mL), and the mixture was stirred at room temperature for 30 min. To the reaction mixture were added a solution of sodium chlorite (12 mg) and sodium dihydrogen phosphate (12 mg) in water (0.5 mL), 2-methyl-but-2-ene (0.022 mL), and the mixture was further stirred for 30 min. The reaction mixture was concentrated, water was added to the residue and the mixture was extracted with ethyl acetate, and the extract was dried over anhydrous sodium sulfate and filtered. The solvent was evaporated under reduced pressure. The obtained residue was purified by silica gel column chromatography (chloroform:methanol=100:0-90:10) to give the title compound (173 mg) as a yellow solid.

MS (ESI) m/z: 508.3 [M+H]+

(148-4) methyl {(6S)-4-[4-(4-{[cis-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamoyl}piperidin-1-yl)phenyl]-2,3,9-trimethyl-6H-thieno[3,2-f][1,2,4]triazolo[4,3-a][1,4]diazepin-6-yl}acetate (Example Compound 148)

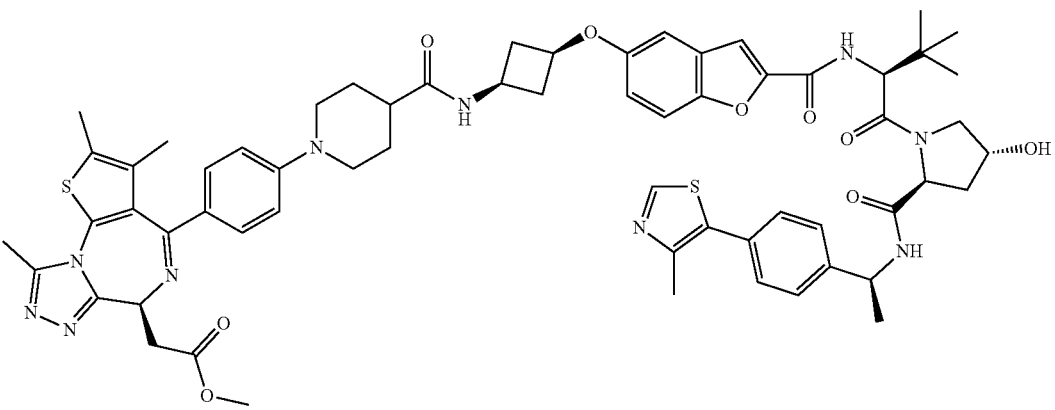 [SMILES: COC(=O)C[C@@H]1N=C(c2ccc(N3CCC(C(=O)N[C@H]4C[C@@H](Oc5ccc6oc(C(=O)N[C@H](C(=O)N7C[C@H](O)C[C@H]7C(=O)N[C@@H](C)c7ccc(-c8scnc8C)cc7)C(C)(C)C)cc6c5)C4)CC3)cc2)c2c(sc(C)c2C)-n2c(C)nnc21]

To a solution of Example compound 148-3 (50 mg), Example compound 83-5 66 mg), N,N-dimethylformamide (1.0 mL) and N,N-diisopropylethylamine (0.085 mL) was added, under ice-cooling, HATU (75 mg) and the mixture was stirred at room temperature for 3 hr. Under ice-cooling, to the reaction mixture was added saturated aqueous sodium hydrogen carbonate, and the mixture was extracted with chloroform. The organic layers were combined and washed with water and the solvent was evaporated under reduced pressure. The obtained residue was purified by silica gel column chromatography (chloroform:methanol=100:0-90:10) and NH silica gel column chromatography (ethyl acetate:methanol=100:0-88:12) to give the title compound (56 mg) as a yellow solid. MS (ESI) m/z: 1161.6 [M–H]⁻

Example 149

(149-1) (2S,4R)-1-{(2S)-2-[(5-{[trans-3-aminocyclobutyl]oxy}-1-benzofuran-2-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 149-1)

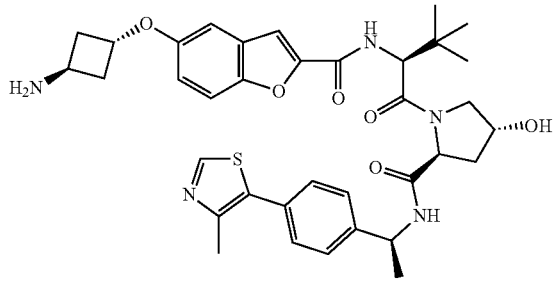 [SMILES: Cc1ncsc1-c1ccc([C@H](C)NC(=O)[C@@H]2C[C@@H](O)CN2C(=O)[C@@H](NC(=O)c2cc3cc(O[C@H]4C[C@H](N)C4)ccc3o2)C(C)(C)C)cc1]

By reaction and treatment in the same manner as in Example 83 (83-1)-(83-4), (42-1) and using cis-t-butyl 3-hydroxycyclobutylcarbamate instead of trans-t-butyl 3-hydroxycyclobutylcarbamate, the title compound was obtained as a pale-yellow solid. MS (ESI) m/z: 674.7 [M+H]⁺

(149-2) methyl {(6S)-4-[4-(4-{[trans-3-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-5-yl]oxy}cyclobutyl]carbamoyl}piperidin-1-yl)phenyl]-2,3,9-trimethyl-6H-thieno[3,2-f][1,2,4]triazolo[4,3-a][1,4]diazepin-6-yl}acetate (Example Compound 149)

To a solution of Example compound 148-3 (50 mg), Example compound 149-1 (66 mg), N,N-dimethylformamide (3.0 mL) and N,N-diisopropylethylamine (0.085 mL) was added, under ice-cooling, HATU (75 mg) and the mixture was stirred at room temperature for 1 hr. Under ice-cooling, saturated aqueous sodium hydrogen carbonate was added to the reaction mixture and the mixture was extracted with chloroform. The organic layer was combined and washed with water, and the solvent was evaporated under reduced pressure. The obtained residue was purified by NH silica gel column chromatography (ethyl acetate:methanol=100:0-88:12) to give the title compound (99 mg) as a yellow solid.
MS (ESI) m/z: 1161.6 [M–H]⁻

Example 150

(150-1) benzyl 1,2,3,4-tetrahydroquinoline-7-carboxylate (Example Compound 150-1)

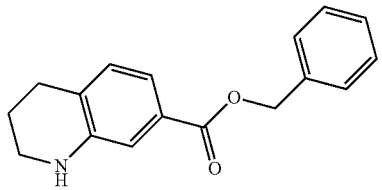

Methyl 1,2,3,4-tetrahydroquinoline-7-carboxylate (480 mg) was dissolved in tetrahydrofuran (25 mL), 2.0 M aqueous lithium hydroxide solution (6.3 mL) and methanol (12.6 mL) were added and the mixture was stirred at room temperature for 17 hr. 2.0 M Aqueous lithium hydroxide solution (6.3 mL), methanol (6.0 mL) were added and the mixture was stirred at room temperature for 6 hr. Again, 2.0 M aqueous lithium hydroxide solution (2.5 mL) was added and the mixture was stirred at room temperature for 2 hr. The reaction mixture was concentrated under reduced pressure, toluene was added and toluene was evaporated under reduced pressure. This was repeated two times, and the mixture was dried under reduced pressure at 60° C. The residue was dissolved in N,N-dimethylformamide (12.6 mL) and the insoluble material was filtered off, benzyl alcohol (0.78 mL), N,N-diisopropylethylamine (1.3 mL), HATU (1.91 g) were added and the mixture was stirred at room

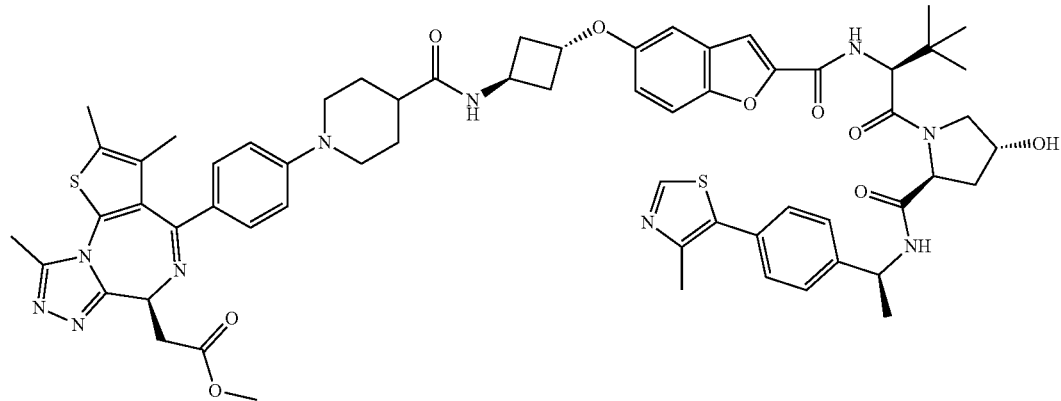 [SMILES: COC(=O)C[C@@H]1N=C(c2ccc(N3CCC(C(=O)N[C@H]4C[C@H](Oc5ccc6oc(C(=O)N[C@H](C(=O)N7C[C@H](O)C[C@H]7C(=O)N[C@@H](C)c7ccc(-c8scnc8C)cc7)C(C)(C)C)cc6c5)C4)CC3)cc2)c2c(sc(C)c2C)-n2c(C)nnc21]

temperature for 24 hr. To the reaction mixture were added water and saturated brine and the mixture was extracted with ethyl acetate, and the extract was washed 3 times with water, and washed with saturated brine. After drying over anhydrous sodium sulfate, the solvent was evaporated under reduced pressure, and the residue was purified by silica gel column chromatography (hexane:ethyl acetate=95:5–60:40) to give triazolo[4,5-b]pyridin-3-yl 1,2,3,4-tetrahydroquinoline-7-carboxylate as a crudely purified form (417 mg). This was dissolved in tetrahydrofuran (20 mL), benzyl alcohol was added and the mixture was stirred at 85° C. for 16 hr. Under ice-cooling, sodium hydride (60%, 90 mg) was added and the mixture was stirred at room temperature for 1 hr. To the reaction mixture was added ice water and the mixture was extracted with ethyl acetate, and the extract was washed with saturated brine, dried over anhydrous sodium sulfate. The solvent was evaporated under reduced pressure, and the residue was purified by silica gel column chromatography (hexane:ethyl acetate=100:0-95:5) and then by silica gel column chromatography (chloroform:methanol=100:0-99:1) to give the title compound (350 mg) as a yellow-white solid.

MS (ESI) m/z: 268.1 [M+1-1]$^+$ (150-2) benzyl 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1,2,3,4-tetrahydroquinoline-7-carboxylate (Example Compound 150-2)

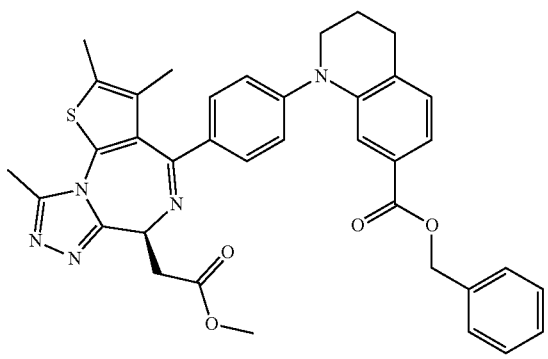 [SMILES: COC(=O)C[C@@H]1N=C(c2ccc(N3CCCc4ccc(C(=O)OCc5ccccc5)cc43)cc2)c2c(sc(C)c2C)-n2c(C)nnc21]

A mixture of Reference Example compound 1 (500 mg), Example compound 150-1 (340 mg), tris(dibenzylideneacetone)dipalladium(0) (44 mg), 2-di-t-butylphosphino-2',4',6'-triisopropylbiphenyl (41 mg), potassium phosphate (765 mg) in tetrahydrofuran (6.0 mL) was stirred at 85° C. for 64 hr. To the reaction mixture were added ice water and saturated brine and the mixture was extracted with chloroform, and the aqueous layer was extracted 3 times with chloroform. The organic layers were collected, dried over anhydrous sodium sulfate, and the solvent was evaporated under reduced pressure. The residue was purified by silica gel column chromatography (chloroform:methanol=100:0-95:5) to give a crudely purified title compound (265 mg) as a brown solid. MS (ESI) m/z: 646.4 [M+H]$^+$ (150-3) methyl [(6S)-4-{4-[7-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3,4-dihydroquinolin-1(2H)-yl]phenyl}-2,3,9-trimethyl-6H-thieno[3,2-f][1,2,4]triazolo[4,3-a][1,4]diazepin-6-yl]acetate (Example Compound 150)

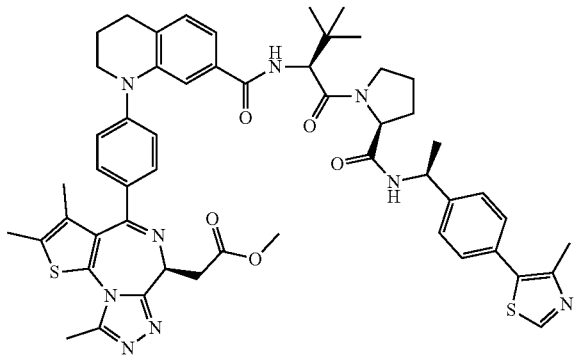

Example compound 150-2 (210 mg) was dissolved in methanol (4.0 mL), 10% palladium carbon (33 mg) was added and the mixture was stirred under a hydrogen atmosphere for 14 hr. Furthermore, 10% palladium carbon (33 mg) was added and the mixture was stirred under a hydrogen atmosphere for 4 hr. The reaction mixture was filtered through diatomaceous earth, and the solvent was evaporated under reduced pressure and the residue was dried under reduced pressure at 60° C. The residue was dissolved in N,N-dimethylformamide (4.0 mL), N,N-diisopropylethylamine (0.35 mL), Reference Example compound 5 (233 mg), HATU (230 mg) were added under ice-cooling and the mixture was stirred at room temperature for 1 hr. To the reaction mixture was added ice water and the mixture was stirred. Water and saturated brine were added and the mixture was extracted with chloroform. The aqueous layer was extracted twice with chloroform, and the organic layers were collected. After drying over anhydrous sodium sulfate, the solvent was evaporated under reduced pressure, and the residue was purified by NH silica gel column chromatography (ethyl acetate:methanol=100:0-80:20), silica gel column chromatography (ethyl acetate:methanol=100:0-80:20) to give the title compound (68 mg) as a yellow solid.

MS (ESI) m/z: 982.5 [M+H]$^+$

Example 151

(151-1) benzyl [(2,3-dihydro-1H-indol-5-yl)oxy] acetate trifluoroacetate (Example Compound 151-1)

(151-2) methyl [(6S)-4-(4-{5-[2-(benzyloxy)-2-oxo-ethoxy]-2,3-dihydro-1H-indol-1-yl}phenyl)-2,3,9-trimethyl-6H-thieno[3,2-f] [1,2,4]triazolo[4,3-a][1,4]diazepin-6-yl]acetate (Example Compound 151-2)

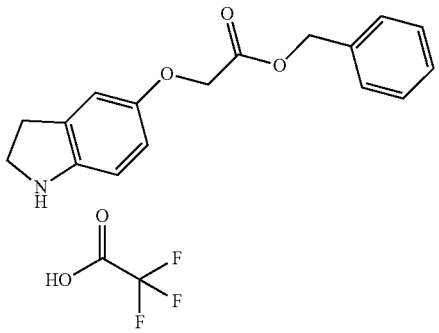

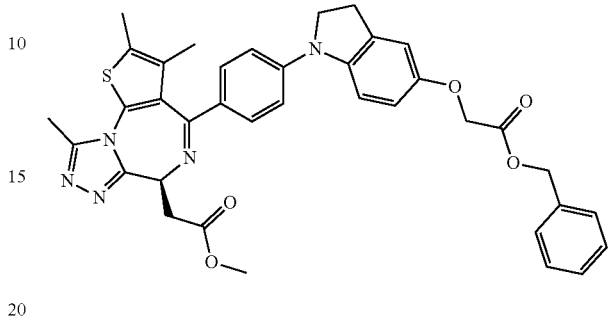

t-Butyl 5-hydroxyindoline-1-carboxylate (300 mg) was suspended in acetonitrile (6.4 mL), benzyl bromoacetate (0.30 mL) and cesium carbonate (500 mg) were added and the mixture was stirred at 80° C. for 2 hr. The reaction mixture was allowed to cool, ice water was added, and the mixture was extracted with ethyl acetate. The aqueous layer was extracted with ethyl acetate, and the organic layers were collected and washed with saturated brine, and dried over anhydrous sodium sulfate. The solvent was evaporated under reduced pressure. The residue was dissolved in dichloromethane (3.0 mL), trifluoroacetic acid (1.5 mL) was added under ice-cooling and the mixture was stirred at room temperature for 3 hr. To the reaction mixture was added toluene and toluene was evaporated under reduced pressure. This was repeated 3 times, and the residue was purified by silica gel column chromatography (chloroform:methanol=100:0-85:15) to give the title compound (494 mg) as a brown solid. MS (ESI) m/z: 284.1 [M+H]⁺

Reference Example compound 1 (300 mg), Example compound 151-1 (250 mg), tris(dibenzylideneacetone)dipalladium(0) (33 mg), 2-di-t-butylphosphino-2',4',6'-triisopropylbiphenyl (33 mg) and potassium phosphate (460 mg) were added to tetrahydrofuran (6.0 mL) and the mixture was stirred at 85° C. for 16 hr. To the reaction mixture were added ice water and saturated brine, water and the mixture was extracted with chloroform, and the aqueous layer was extracted twice with chloroform. The organic layers were collected, dried over anhydrous sodium sulfate, and the solvent was evaporated under reduced pressure. The residue was purified by silica gel column chromatography (chloroform:methanol=100:0-95:5) to give the title compound as a crudely purified red viscous compound (285 mg). MS (ESI) m/z: 662.4 [M+H]⁺

(151-3) methyl [(6S)-4-(4-{5-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy]-2,3-dihydro-1H-indol-1-yl}phenyl)-2,3,9-trimethyl-6H-thieno[3,2-f][1,2,4]triazolo[4,3-a] [1,4]diazepin-6-yl]acetate (Example Compound 151)

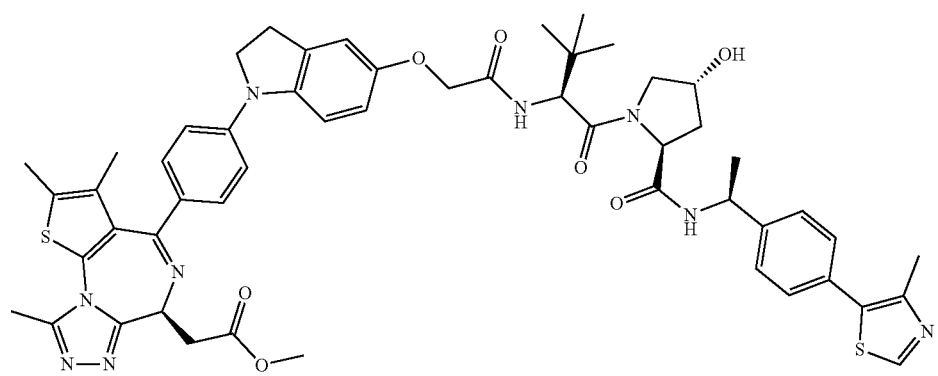 [SMILES: COC(=O)C[C@@H]1N=C(c2ccc(N3CCc4cc(OCC(=O)N[C@H](C(=O)N5C[C@H](O)C[C@H]5C(=O)N[C@@H](C)c5ccc(-c6scnc6C)cc5)C(C)(C)C)ccc43)cc2)c2c(sc(C)c2C)-n2c(C)nnc21]

Example compound 151-2 (280 mg) was dissolved in methanol (4.0 mL), 10% palladium carbon (33 mg) was added and the mixture was stirred under a hydrogen atmosphere for 16 hr. The reaction mixture was filtered through diatomaceous earth, the solvent was evaporated under reduced pressure and the residue was dried under reduced pressure at 60° C. The residue was dissolved in N,N-dimethylformamide (4.0 mL), and N,N-diisopropylethylamine (0.22 mL), Reference Example compound 5 (244 mg), HATU (262 mg) were added under ice-cooling and the mixture was stirred at room temperature for 2 hr. To the reaction mixture was added ice water and the mixture was stirred. Saturated brine was added and the mixture was extracted with chloroform. The aqueous layer was extracted twice with chloroform, and the organic layers were collected and dried over anhydrous sodium sulfate. The solvent was evaporated under reduced pressure, and the residue was purified by NH silica gel column chromatography (ethyl acetate:methanol=100:0-80:20), silica gel column chromatography (ethyl acetate:methanol=100:0-80:20) to give the title compound (240 mg) as a yellow solid. MS (ESI) m/z: 998.5 [M+H]$^+$ Example 152

(152-1) methyl [(6S)-4-{4-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)piperidin-1-yl]phenyl}-2,3,9-trimethyl-6H-thieno[3,2-f][1,2,4]triazolo[4,3-a][1,4]diazepin-6-yl]acetate (Example Compound 152)

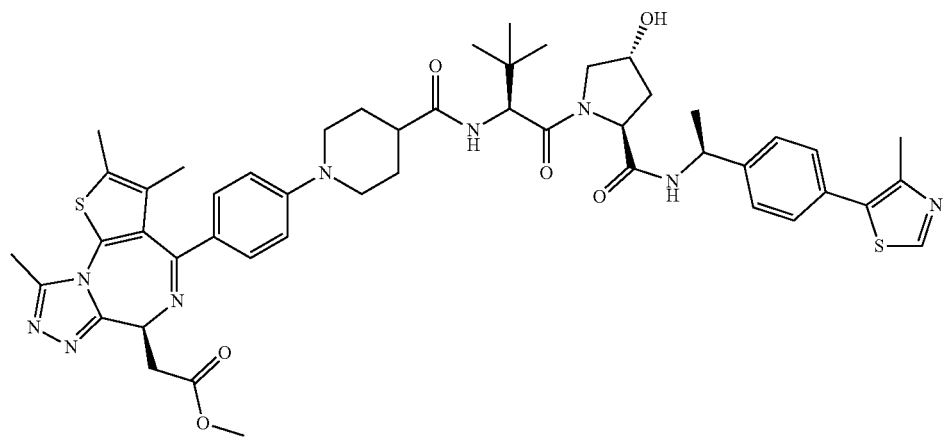 [SMILES: COC(=O)C[C@@H]1N=C(c2ccc(N3CCC(C(=O)N[C@H](C(=O)N4C[C@H](O)C[C@H]4C(=O)N[C@@H](C)c4ccc(-c5scnc5C)cc4)C(C)(C)C)CC3)cc2)c2c(sc(C)c2C)-n2c(C)nnc21]

By reaction and treatment in the same manner as in Example 97 (97-1)-(97-2) and using t-butyl isonipecotate hydrochloride instead of t-butyl 2-(4-piperidyl)acetate, the title compound was obtained as a yellow solid.
MS (ESI) m/z: 934.4 [M+H]$^+$ Example 153

(153-1) t-butyl 1-{4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carbonyl}piperidine-4-carboxylate (Example Compound 153-1)

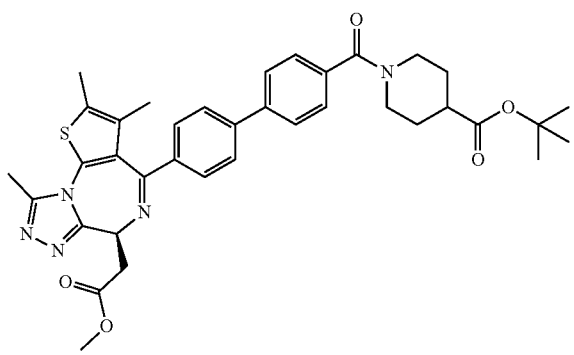 [SMILES: COC(=O)C[C@@H]1N=C(c2ccc(-c3ccc(C(=O)N4CCC(C(=O)OC(C)(C)C)CC4)cc3)cc2)c2c(sc(C)c2C)-n2c(C)nnc21]

Reference Example compound 90-1 (120 mg) and t-butyl piperidine-4-carboxylate hydrochloride (65 mg) were dissolved in N,N-dimethylformamide (2.4 mL), N,N-diisopropylethylamine (0.21 mL) and HATU (170 mg) were added under ice-cooling and the mixture was stirred at room temperature for 16 hr. To the reaction mixture were added ice water, saturated aqueous sodium hydrogen carbonate, ethyl acetate and the mixture was stirred. The organic layer was extracted. The aqueous layer was to extracted twice with ethyl acetate and the organic layers were collected and washed twice with saturated brine:water=1:1, and washed with saturated brine. After drying over anhydrous sodium sulfate, the solvent was evaporated under reduced pressure, and the residue was purified by silica gel column chromatography (chloroform:methanol=100:0-95:5) to give the title compound (160 mg) as a pale-yellow solid.
MS (ESI) m/z: 668.5 [M+H]$^+$

393

(153-2) methyl [(6S)-4-{4'-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)piperidine-1-carbonyl][1,1'-biphenyl]-4-yl}-2,3,9-trimethyl-6H-thieno[3,2-f][1,2,4]triazolo[4,3-a] [1,4]diazepin-6-yl]acetate (Example Compound 153)

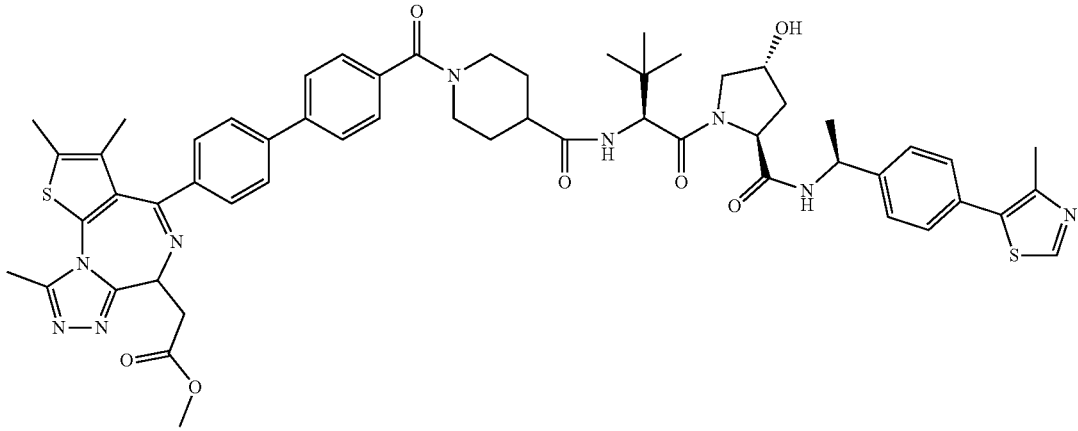 [SMILES: COC(=O)CC1N=C(c2ccc(-c3ccc(C(=O)N4CCC(C(=O)N[C@H](C(=O)N5C[C@H](O)C[C@H]5C(=O)N[C@@H](C)c5ccc(-c6scnc6C)cc5)C(C)(C)C)CC4)cc3)cc2)c2c(sc(C)c2C)-n2c(C)nnc21]

Example compound 153-1 (150 mg) was dissolved in dichloromethane (1.5 mL), trifluoroacetic acid (1.5 mL) was added under ice-cooling and the mixture was stirred at room temperature for 3 hr. To the reaction mixture was added toluene and the mixture was concentrated under reduced pressure. This was repeated 3 times and the residue was dried under reduced pressure at 60° C. The residue was dissolved in N,N-dimethylformamide (2.2 mL), N,N-diisopropylethylamine (0.19 mL), Reference Example compound 5 (130 mg), HATU (155 mg) were added under ice-cooling and the mixture was stirred at room temperature for 2 hr. To the reaction mixture were added ethyl acetate, water, saturated aqueous sodium hydrogen carbonate and the mixture was stirred. The organic layer was extracted and the aqueous layer was extracted twice with ethyl acetate. The organic layers were collected, washed twice with saturated brine:water=1:1 and washed with saturated brine, and dried over anhydrous sodium sulfate. The solvent was evaporated under reduced pressure, and the residue was purified by NH silica gel column chromatography (ethyl acetate:methanol=100:0-80:20), silica gel column chromatography (ethyl acetate:methanol=100:0-80:20) to give the title compound (187 mg) as a yellow-white solid. MS (ESI) m/z: 1038.4 [M+H]$^+$ Example 154

(154-1) t-butyl [4-bromo-2-(hydroxymethyl)phenoxy]acetate (Example Compound 154-1)

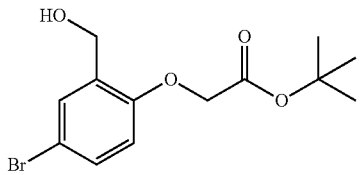 [SMILES: CC(C)(C)OC(=O)COc1ccc(Br)cc1CO]

394

To a solution of 4-bromo-2-(hydroxymethyl)phenol (500 mg) in N,N-dimethylformamide (10 mL) were added potassium carbonate (681 mg), t-butyl bromoacetate (0.41 mL) and the mixture was stirred at room temperature for 16 hr. Water was added to the reaction mixture and the mixture was stirred and extracted twice with ethyl acetate. The organic layers were collected and washed twice with water. Using ethyl acetate, they were passed through Phase Separator. The filtrate was concentrated under reduced pressure to give the title compound (754 mg) as a colorless oil. MS (ESI) m/z: 317.0, 319.0 [M+H]$^+$ (154-2) methyl {(6S)-4-[4'-(2-t-butoxy-2-oxoethoxy)-3'-(hydroxymethyl)[1,1'-biphenyl]-4-yl]-2,3,9-trimethyl-6H-thieno[3,2-f][1,2,4]triazolo[4,3-a][1,4]diazepin-6-yl}acetate (Example Compound 154-2)

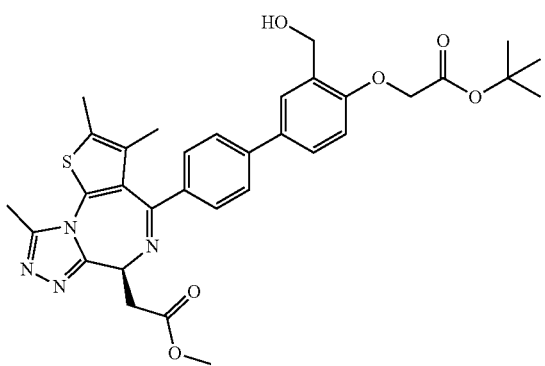 [SMILES: COC(=O)C[C@@H]1N=C(c2ccc(-c3ccc(OCC(=O)OC(C)(C)C)c(CO)c3)cc2)c2c(sc(C)c2C)-n2c(C)nnc21]

Under an argon stream, Example compound 154-1 (207 mg), Reference Example compound 3 (300 mg), palladium acetate (13 mg), S-phos (49 mg), potassium fluoride (103 mg) and water (0.038 mL) were heated under reflux in tetrahydrofuran (3 mL) solvent for 4 hr. Using ethyl acetate, the reaction mixture was filtered through diatomaceous earth, and the filtrate was concentrated under reduced pressure. The residue was purified by silica gel column chromatography (methanol:ethyl acetate=0:100-10:90) to give the title compound (224 mg) as a white solid. MS (ESI) m/z: 617.2 [M+H]$^+$ (154-3) methyl [(6S)-4-{3'-(hydroxymethyl)-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl] acetate (Example Compound 154)

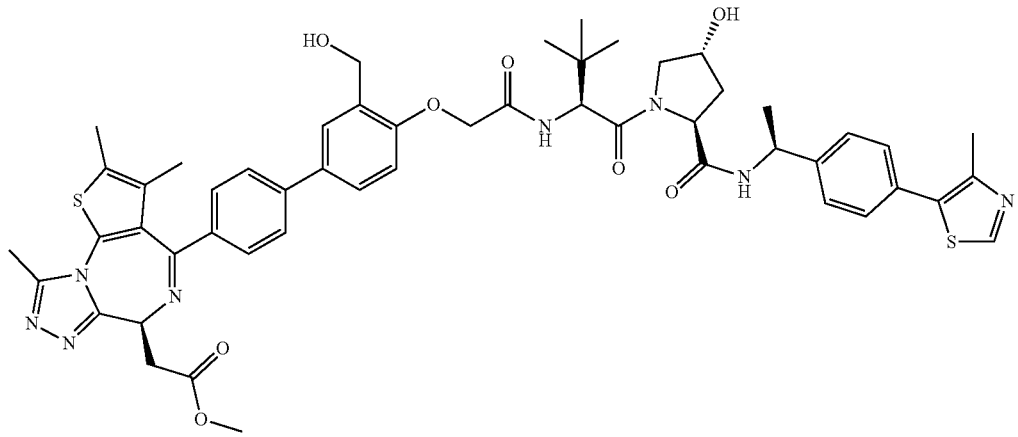 [SMILES: COC(=O)C[C@@H]1N=C(c2ccc(-c3ccc(OCC(=O)N[C@H](C(=O)N4C[C@H](O)C[C@H]4C(=O)N[C@@H](C)c4ccc(-c5scnc5C)cc4)C(C)(C)C)c(CO)c3)cc2)c2c(sc(C)c2C)-n2c(C)nnc21]

To a solution of Example compound 154-2 (224 mg) in chloroform (4 mL) was added trifluoroacetic acid (2 mL) and the mixture was stirred at room temperature for 16 hr. The reaction mixture was concentrated under reduced pressure, and azeotropically distilled 2 times with toluene. The residue was dissolved in N,N-dimethylformamide (4 mL), Reference Example compound 5 (192 mg), N,N-diisopropylethylamine (0.630 mL), HATU (152 mg) were added and the mixture was stirred at room temperature for 2 hr. Water was added to the reaction mixture and the mixture was stirred. The precipitate was collected by filtration and the obtained solid was purified by NH silica gel column chromatography (methanol:chloroform=0:100-5:95) and is silica gel column chromatography (methanol:ethyl acetate=0:100-5:95) to give the title compound (87.5 mg) as a pale-yellow solid. MS (ESI) m/z: 987.4 [M+H]+

Example 155

(155-1) benzyl 4-[4-(t-butoxycarbonyl)phenoxy]piperidine-1-carboxylate (Example Compound 155-1)

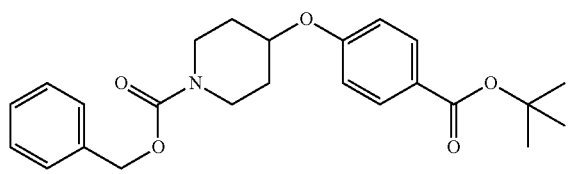 [SMILES: CC(C)(C)OC(=O)c1ccc(OC2CCN(C(=O)OCc3ccccc3)CC2)cc1]

Under an argon stream, a solution of t-butyl 4-hydroxybenzoate (497 mg), benzyl 4-hydroxy-1-piperidinecarboxylate (723 mg) and triphenylphosphine (1.01 g) in tetrahydrofuran (5 mL) was cooled to 0° C., bis(2-methoxyethyl)azodicarboxylate (899 mg) was added and the mixture was stirred at room temperature for 5 hr. Water was added to the reaction mixture and the mixture was stirred and extracted twice with ethyl acetate. The organic layer was washed with water and concentrated under reduced pressure. The residue was purified by NH silica gel column chromatography (ethyl acetate:hexane=0:100-25:75) to give the title compound (660 mg) as a white solid. MS (ESI) m/z: 412.2 [M+H]+

(155-2) t-butyl 4-[(piperidin-4-yl)oxy]benzoate (Example Compound 155-2)

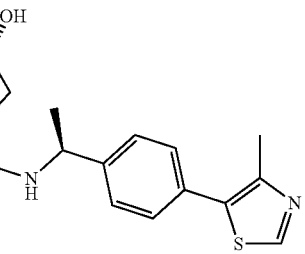

To a solution of Example compound 155-1 (660 mg) in ethanol (5 mL)-tetrahydrofuran (5 mL) was added 10% palladium carbon (200 mg) and, after hydrogen substitution, the mixture was stirred at room temperature for 7 hr. The reaction mixture was filtered through diatomaceous earth, and the filtrate was concentrated under reduced pressure. The residue was purified by NH silica gel column chromatography (methanol:chloroform=0:100-2:98) to give the title compound (379 mg) as a white solid. MS (ESI) m/z: 278.1 [M+H]+

(155-3) 4-[(1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}piperidin-4-yl)oxy]benzoic acid hydrochloride (Example Compound 155-3)

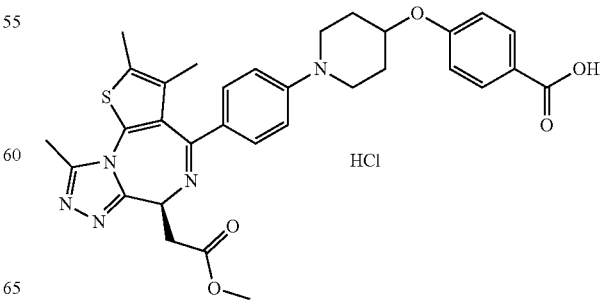

Under an argon stream, Reference Example compound 1 (450 mg), Example compound 155-2 (379 mg), tris(dibenzylideneacetone)dipalladium(0) (50 mg), t-BuXphos (46 mg) and potassium phosphate (691 mg) were stirred in 1,2-dimethoxyethane (5 mL) solvent at 70° C. for 7 hr. Tris(dibenzylideneacetone)dipalladium(0) (50 mg), t-BuXphos (46 mg) were added and the mixture was further stirred at 70° C. for 16 hr. Using ethyl acetate, the reaction mixture was filtered through diatomaceous earth, and the filtrate was concentrated under reduced pressure. The residue was purified by silica gel column chromatography (methanol:chloroform=0:100-5:95) to give a yellow solid. The solid was dissolved in chloroform (1 mL), trifluoroacetic acid (1 mL) was added and the mixture was stirred at room temperature for 4 hr. The reaction mixture was concentrated under reduced pressure, and azeotropically distilled twice with toluene. The residue was dissolved in ethyl acetate, and saturated aqueous sodium hydrogen carbonate was slowly added to set to pH9. The organic layer was removed by partitioning and the aqueous layer was set to pH4 with 1N hydrochloric acid and extracted 3 times with chloroform. The organic layer was concentrated under reduced pressure to give the title compound (347 mg) as a yellow solid.

MS (ESI) m/z: 600.2 [M+H]$^+$ (155-4) methyl [(6S)-4-(4-{4-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)phenoxy]piperidin-1-yl}phenyl)-2,3,9-trimethyl-6H-thieno[3,2-f][1,2,4]triazolo[4,3-a][1,4]diazepin-6-yl]acetate (Example Compound 155)

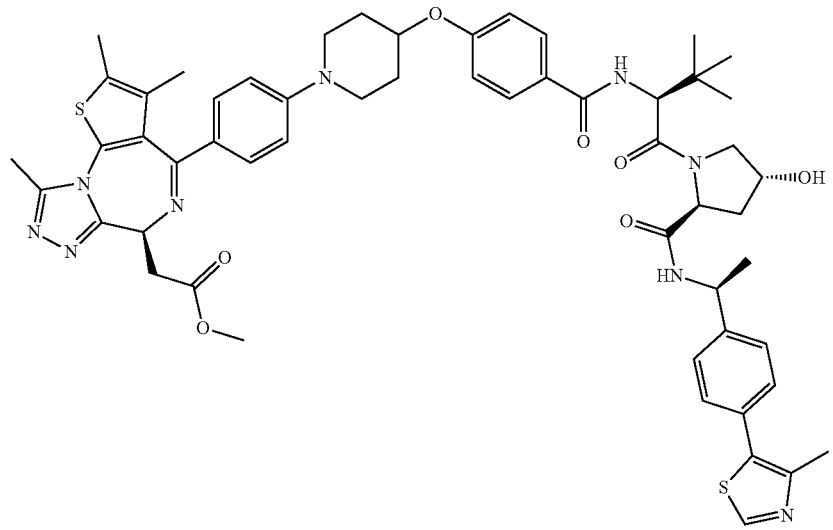

Example compound 155-3 (347 mg) and Reference Example compound 5 (314 mg), N,N-diisopropylethylamine (0.283 mL) and HATU (249 mg) were stirred in N,N-dimethylformamide (5 mL) at room temperature for 6 hr. To the reaction mixture was added saturated aqueous sodium hydrogen carbonate and the mixture was stirred and extracted twice with ethyl acetate. The organic layer was washed twice with water and concentrated under reduced pressure. The residue was purified by silica gel column chromatography (methanol:chloroform=0:100-5:95) and NH silica gel column chromatography (methanol:chloroform=0:100-2:98) and successively purified by preparative HPLC (10 mM aqueous ammonium carbonate solution-acetonitrile=40:60-70:30) to give the title compound (180 mg) as a yellow solid.

MS (ESI) m/z: 1026.4 [M+H]$^+$

Example 156

(156-1) benzyl 4-(3-t-butoxy-3-oxopropoxy)piperidine-1-carboxylate (Example Compound 156-1)

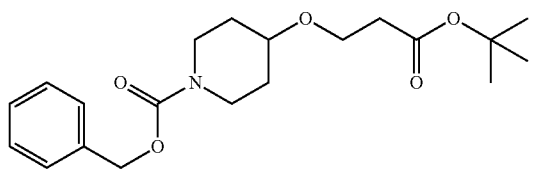 [SMILES: CC(C)(C)OC(=O)CCOC1CCN(C(=O)OCc2ccccc2)CC1]

Benzyl 4-hydroxy-1-piperidinecarboxylate (1.00 g), t-butyl acrylate (0.931 mL) and potassium t-butoxide (48 mg) were heated under reflux in 1,2-dimethoxyethane (5 mL) solvent for 16 hr. Using ethyl acetate, the reaction mixture was filtered, and the filtrate was concentrated under reduced pressure. The residue was purified by silica gel column chromatography (ethyl acetate:hexane=0:100-30:70) to give the title compound (648 mg) as a colorless viscous compound. MS (ESI) m/z: 364.4 [M+H]$^+$ (156-2) methyl [(6S)-4-(4-{4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropoxy]piperidin-1-yl}phenyl)-2,3,9-trimethyl-6H-thieno[3,2-f][1,2,4]triazolo[4,3-a][1,4]diazepin-6-yl]acetate (Example Compound 156)

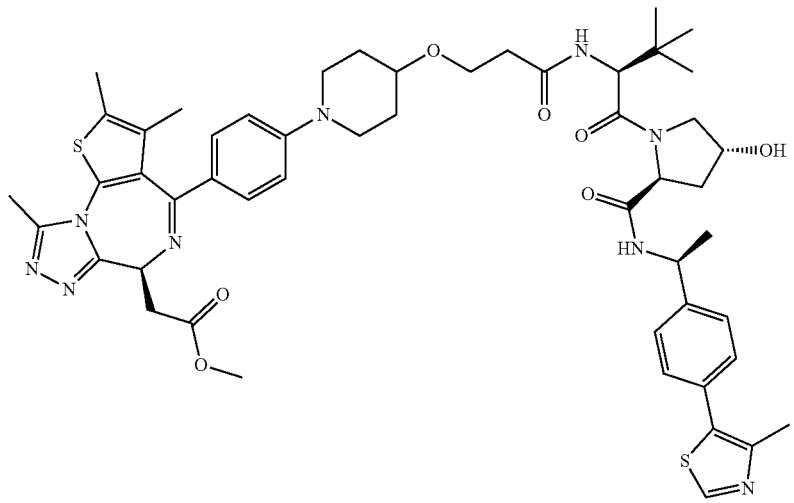

By reaction and treatment in the same manner as in Example 98 (98-2)-(98-4) and using Example compound 156-1 instead of Example compound 98-1, the title compound was obtained as a yellow solid. MS (ESI) m/z: 978.5 [M+H]⁺

Example 157

(157-1) (2S,4R)-1-[(2S)-2-(4-bromo-2-chlorobenzamido)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 157-1)

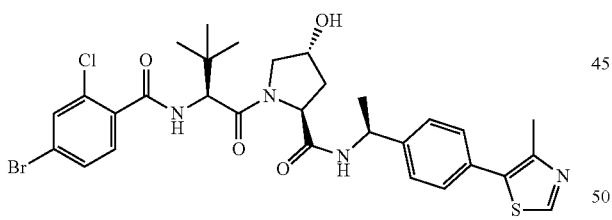

Reference Example compound 5 (200 mg), 4-bromo-2-chlorobenzoic acid (119 mg) were dissolved in N,N-dimethylformamide (4.2 mL), N,N-diisopropylethylamine (0.26 mL) and HATU (290 mg) were added under ice-cooling and the mixture was stirred at room temperature for 2 hr. To the reaction mixture were added ice water, saturated aqueous sodium hydrogen carbonate, ethyl acetate and the mixture was stirred. The organic layer was extracted and the aqueous layer was washed twice with ethyl acetate. The organic layers were collected, washed twice with saturated aqueous sodium hydrogen carbonate and saturated brine:water=1:1, washed with saturated brine, and dried over anhydrous sodium sulfate. The solvent was evaporated under reduced pressure, and the residue was purified by silica gel column chromatography (chloroform:methanol=100:0-95:5) to give the title compound (245 mg) as a pale-yellow solid. MS (ESI) m/z: 661.3 [M+H]⁺

(157-2) methyl {(6S)-4-[3'-chloro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 157)

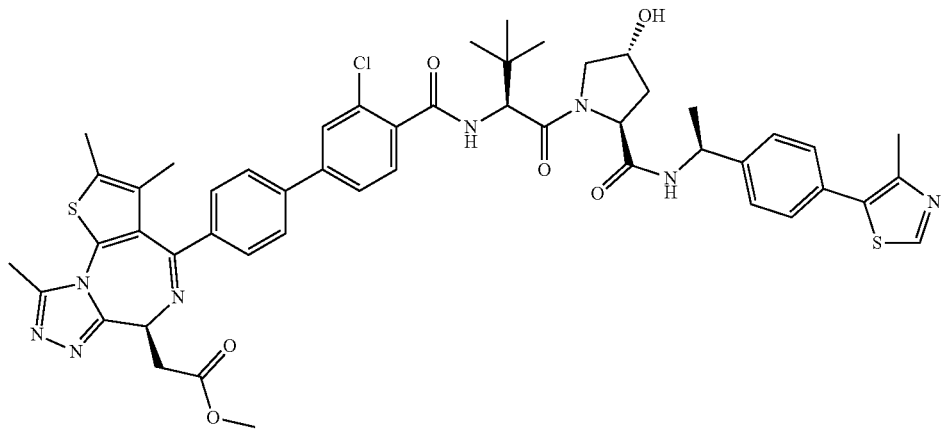 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(Cl)c3)cc2)c2c(sc(C)c2C)-n2c(C)nnc21]

Example compound 157-1 (240 mg) was dissolved in tetrahydrofuran (7.2 mL), and Reference Example compound 3 (280 mg), potassium fluoride (65 mg), S-phos (45 mg), palladium acetate (17 mg) and water (24 μL) were added and the mixture was stirred at 85° C. for 15 hr. Furthermore, potassium fluoride (65 mg), S-phos (45 mg), palladium acetate (17 mg), water (24 μL) were added and the mixture was stirred at 85° C. for 6 hr. To the reaction mixture were added chloroform and water, the organic layer was extracted, and the aqueous layer was extracted twice with chloroform. The organic layers were collected, washed with saturated brine and dried over anhydrous sodium sulfate. The solvent was evaporated under reduced pressure. The residue was purified by NH silica gel column chromatography (ethyl acetate:methanol=100:0-85:15), silica gel column chromatography (ethyl acetate:methanol=100:0-85:15), and then by silica gel column chromatography (chloroform:methanol=100:0-95:95), NH silica gel column chromatography (ethyl acetate:methanol=100:0-95:5) to give the title compound (110 mg) as a white solid.

MS (ESI) m/z: 961.4 [M+H]$^+$

Example 158

(158-1) methyl {(6S)-4-[4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3'-(trifluoromethyl)[1,1'-biphenyl]-4-yl]-2,3,9-trimethyl-6H-thieno[3,2-f][1,2,4]triazolo[4,3-a][1,4]diazepin-6-yl}acetate (Example Compound 158)

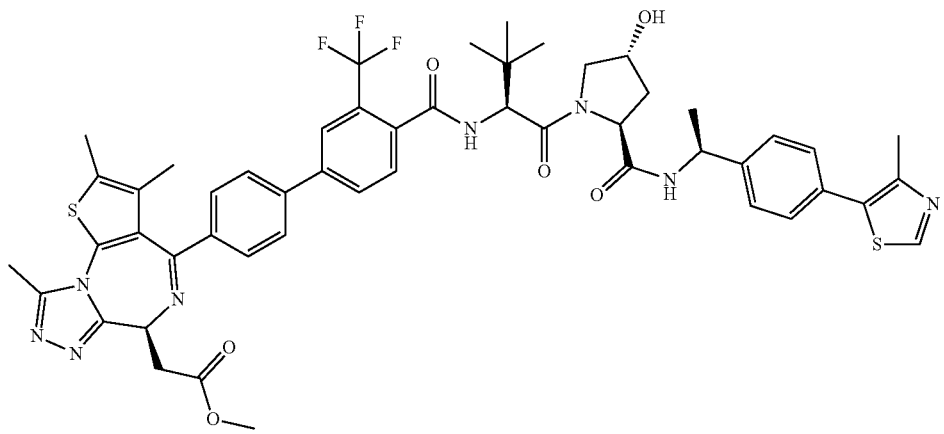 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(C(F)(F)F)c3)cc2)c2c(sc(C)c2C)-n2c(C)nnc21]

By reaction and treatment in the same manner as in Example 157 (157-1)-(157-2) and using 4-bromo-2-(trifluoromethyl)benzoic acid instead of 4-bromo-2-chlorobenzoic acid, the title compound was obtained as a white solid. MS (ESI) m/z: 995.4 [M+H]+

Example 159

(159-1) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-2H-indazol-4-yl}phenyl)-2,3,9-trimethyl-6H-thieno[3,2-f][1,2,4]triazolo[4,3-a][1,4]diazepin-6-yl]acetate (Example Compound 159)

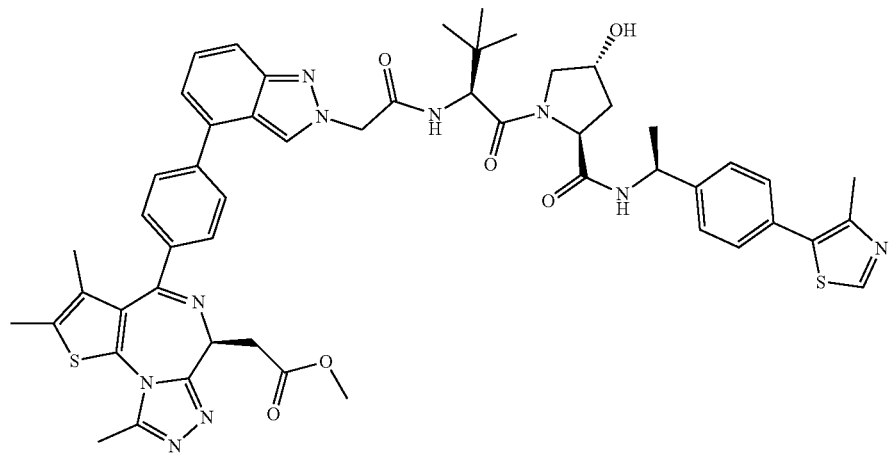 [SMILES: COC(=O)C[C@@H]1N=C(c2ccc(-c3cccc4nn(CC(=O)N[C@H](C(=O)N5C[C@H](O)C[C@H]5C(=O)N[C@@H](C)c5ccc(-c6scnc6C)cc5)C(C)(C)C)cc34)cc2)c2c(sc(C)c2C)-n2c(C)nnc21]

By reaction and treatment in the same manner as in Example 52 (52-1)-(52-3) and using Example compound 144-1B instead of 4-bromo-3-chlorophenol, the title compound was obtained as a yellow solid. MS (ESI) m/z: 981.4 [M+H]+

Example 160

(160-1) t-butyl (8-bromo-1-oxo-3,4-dihydroisoquinolin-2(1H)-yl)acetate (Example Compound 160-1)

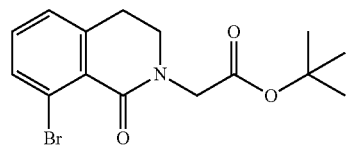 [SMILES: CC(C)(C)OC(=O)CN1CCc2cccc(Br)c2C1=O]

8-Bromo-3,4-dihydro-2H-isoquinolin-1-one (300 mg) was dissolved in N,N-dimethylformamide (15 mL), sodium hydride (60%, 40 mg) was added under ice-cooling and the mixture was stirred at the same temperature for 20 min. After stirring, t-butyl bromoacetate (0.25 mL) was added and the mixture was stirred at room temperature for 2 hr. Under ice-cooling, sodium hydride (60%, 14 mg), t-butyl bromoacetate (78 μL) were added and the mixture was stirred at room temperature for 1 hr. Under ice-cooling, saturated aqueous ammonium chloride solution was added to the reaction mixture and the mixture was stirred. Ethyl acetate, water were added and the organic layer was extracted. The aqueous layer was extracted with ethyl acetate, and the organic layers were collected and washed with water and saturated brine:water=1:1 and saturated brine and dried over anhydrous sodium sulfate. The solvent was evaporated under reduced pressure. The residue was purified by silica gel column chromatography (hexane:ethyl acetate=95:5-70:30) to give the title compound (430 mg) as a pale-yellow solid.

MS (ESI) m/z: 340.1

(160-2) methyl [(6S)-4-(4-{2-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]-1-oxo-1,2,3,4-tetrahydroisoquinolin-8-yl}phenyl)-2,3,9-trimethyl-6H-thieno[3,2-f][1,2,4]triazolo[4,3-a][1,4]diazepin-6-yl]acetate (Example Compound 160)

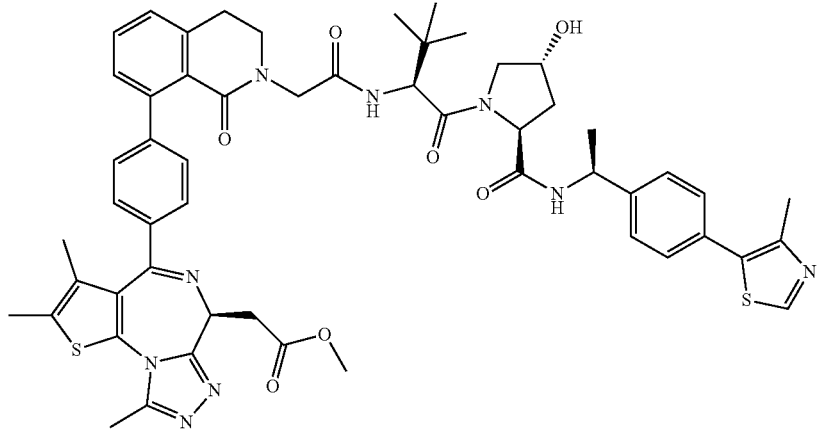 [SMILES: COC(=O)C[C@@H]1N=C(c2ccc(-c3cccc4c3C(=O)N(CC(=O)N[C@H](C(=O)N3C[C@H](O)C[C@H]3C(=O)N[C@@H](C)c3ccc(-c5scnc5C)cc3)C(C)(C)C)CC4)cc2)c2c(sc(C)c2C)-n2c(C)nnc21]

By reaction and treatment in the same manner as in Example 147 (147-2)-(147-3) and using Example compound 160-1 instead of Example compound 147-1, the title compound was obtained (84 mg) as a yellow-white solid.
MS (ESI) m/z: 1010.5 [M+H]+

Example 161

(161-1) tert-butyl 7-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3,4-dihydroisoquinoline-2(1H)-carboxylate (Example Compound 161-1)

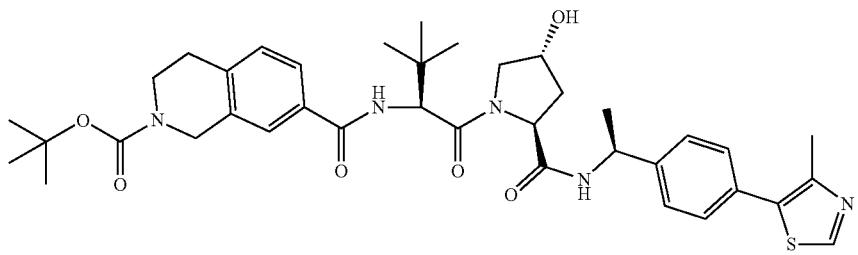 [SMILES: Cc1ncsc1-c1ccc([C@H](C)NC(=O)[C@@H]2C[C@@H](O)CN2C(=O)[C@@H](NC(=O)c2ccc3c(c2)CN(C(=O)OC(C)(C)C)CC3)C(C)(C)C)cc1]

To a suspension of 1,2,3,4-tetrahydroisoquinoline-7-carboxylic acid (500 mg) in N,N-dimethylformamide (14.0 mL) were added N,N-diisopropylethylamine (0.59 mL), 4-dimethylaminopyridine (70 mg) and di-t-butyl dicarbonate (926 mg) and the mixture was stirred at room temperature for 16 hr. Toluene was added and the mixture was concentrated under reduced pressure. This was repeated 3 times, and the residue was dried over anhydrous sodium sulfate and filtered. To the obtained residue were added N,N-diisopropylethylamine (2.44 mL), Reference Example compound 5 (1.63 g), HATU (3.22 g) under ice-cooling, and the mixture was stirred at room temperature for 64 hr. To the reaction mixture was added ice water and the mixture was stirred. Saturated brine was added and the mixture was extracted 4 times with chloroform. The organic layers were collected, dried over anhydrous sodium sulfate, filtered, and the solvent was evaporated under reduced pressure. The residue was purified by silica gel column chromatography (chloroform:methanol=100:0-99:1) to give the title compound (310 mg) as a yellow-white solid. MS (ESI) m/z: 704.5 [M+H]+

(161-2) N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-1,2,3,4-tetrahydroisoquinoline-7-carboxamide (Example Compound 161-2)

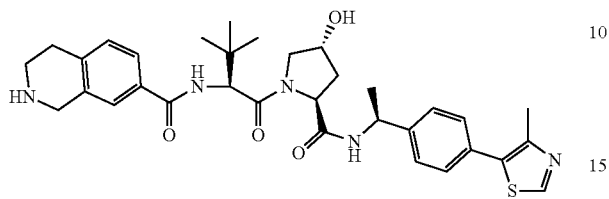

To a solution of Example compound 161-1 (310 mg) in dichloromethane (5.0 mL) was added, under ice-cooling, trifluoroacetic acid (5.0 mL) and the mixture was stirred at room temperature for 1 hr. The reaction mixture was added dropwise to saturated aqueous sodium hydrogen carbonate, water under ice-cooling, chloroform was added and the mixture was stirred. The organic layer was extracted. The aqueous layer was extracted again with chloroform and the organic layers were collected, dried over anhydrous sodium sulfate and filtered. The solvent was evaporated under reduced pressure and dried under reduced pressure to give the title compound (265 mg) as a crudely purified yellow solid. MS (ESI) m/z: 604.4 [M+H]$^+$ (161-3) methyl [(6S)-4-{4-[7-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3,4-dihydroisoquinolin-2(1H)-yl]phenyl}-2,3,9-trimethyl-6H-thieno[3,2-f][1,2,4]triazolo[4,3-a] [1,4]diazepin-6-yl]acetate (Example Compound 161)

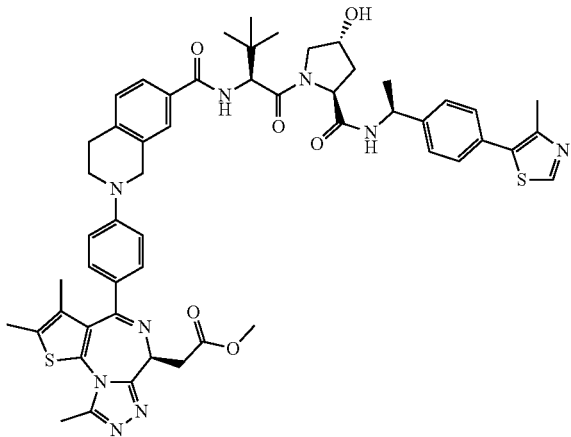 [SMILES: COC(=O)C[C@@H]1N=C(c2ccc(N3CCc4ccc(C(=O)N[C@H](C(=O)N5C[C@H](O)C[C@H]5C(=O)N[C@@H](C)c5ccc(-c6scnc6C)cc5)C(C)(C)C)cc4C3)cc2)c2c(sc(C)c2C)-n2c(C)nnc21]

By reaction and treatment in the same manner as in Example 98 (98-3) and using Example compound 161-2 instead of Example compound 98-2, the title compound was obtained as a yellow-white solid. MS (ESI) m/z: 982.5 [M+H]$^+$ Example 162

(162-1) methyl cis-3-[(5-bromopyridin-2-yl)oxy]cyclobutane-1-carboxylate (Example Compound 162-1), and, methyl trans-3-[(5-bromopyridin-2-yl)oxy]cyclobutane-1-carboxylate (Example Compound 162-2)

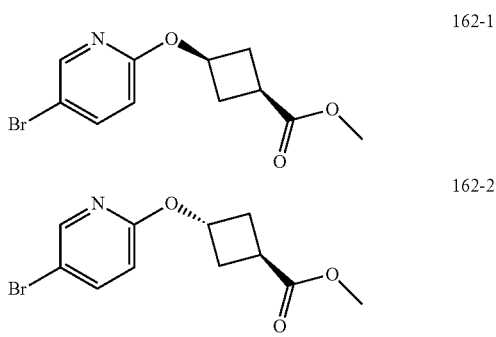

By reaction and treatment in the same manner as in Example 135 (135-1) and using methyl 3-hydroxycyclobutanecarboxylate instead of methyl 1-(hydroxymethyl)bicyclo[1,1,1]pentane-3-carboxylate, the title compound was obtained. Example compound 162-1: white solid, MS (ESI) m/z: 286.0, 288.0 [M+H]$^+$. Example compound 162-2: colorless viscous compound, MS (ESI) m/z: 286.0, 288.0 [M+H]$^+$ (162-2) methyl {(6S)-4-[4-(6-{[cis-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclobutyl]oxy}pyridin-3-yl)phenyl]-2,3,9-trimethyl-6H-thieno[3,2-f][1,2,4]triazolo[4,3-a] [1,4]diazepin-6-yl}acetate (Example Compound 162)

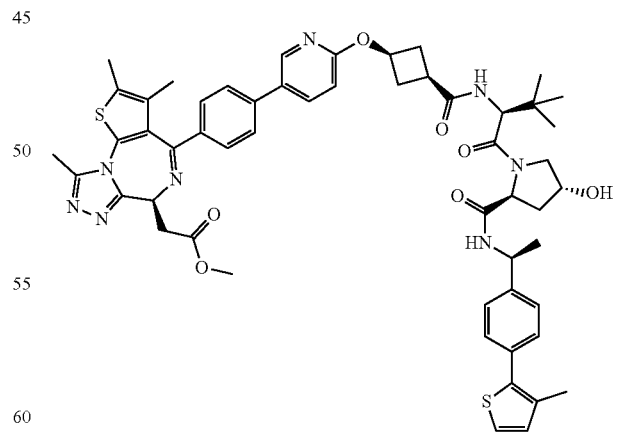

By reaction and treatment in the same manner as in Example 135 (135-2)-(135-3) and using Example compound 162-1 instead of Example compound 135-1, the title compound was obtained as a white solid. MS (ESI) m/z: 998.9 [M+H]$^+$

Example 163

(163-1) methyl [(5-bromopyridin-2-yl)(tert-butoxycarbonyl)amino]acetate (Example Compound 163-1)

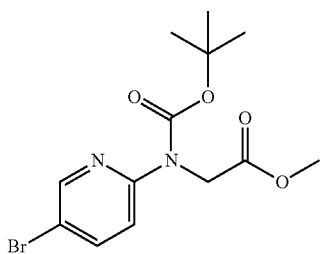 [SMILES: COC(=O)CN(C(=O)OC(C)(C)C)c1ccc(Br)cn1]

2-(Boc-amino)-5-bromopyridine (1.00 g), sodium hydride (60%, 161 mg) were stirred in N,N-dimethylformamide (5.0 mL) solvent at 0° C. for 10 min, t-butyl bromoacetate (0.506 mL) was added and the mixture was stirred for 5 hr while allowing the mixture to naturally warm to room temperature. Water was added to the reaction mixture, and the mixture was extracted twice with ethyl acetate, and the organic layer was washed twice with water and concentrated under reduced pressure. The residue was purified by silica gel column chromatography (chloroform:hexane=30: 70-100:0) to give the title compound (1.22 g) as a colorless viscous compound.

MS (ESI) m/z: 345.1, 347.0 [M+H]$^+$ (163-2) methyl [(5-bromopyridin-2-yl)amino]acetate (Example Compound 163-2)

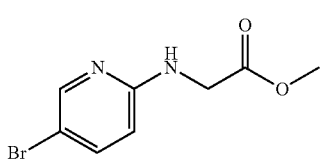

By reaction and treatment in the same manner as in Example 114 (114-2) and using Example compound 163-1 instead of Example compound 114-1, the title compound was obtained as a white solid. MS (ESI) m/z: 244.9, 246.9 [M+H]$^+$ (163-3) methyl {(6S)-4-[4-(6-{[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethyl]amino}pyridin-3-yl)phenyl]-2,3,9-trimethyl-6H-thieno[3,2-f][1,2,4]triazolo[4,3-a][1,4]diazepin-6-yl}acetate (Example Compound 163)

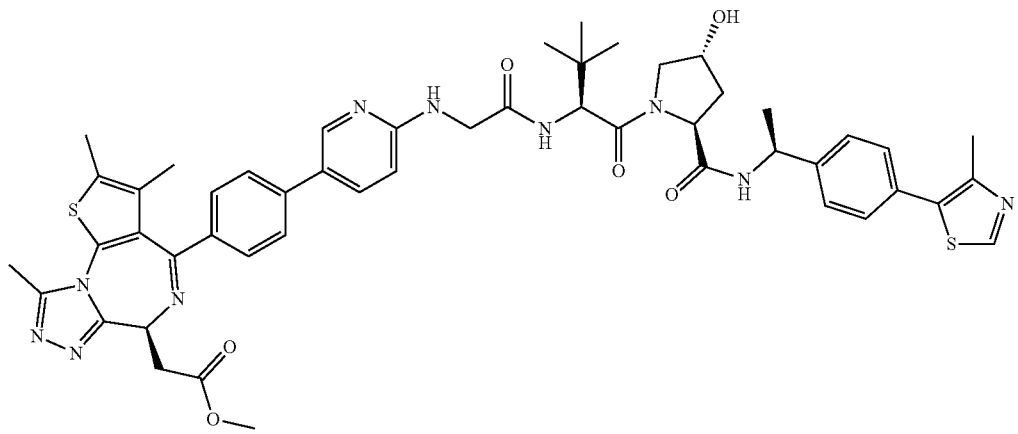 [SMILES: COC(=O)C[C@@H]1N=C(c2ccc(-c3ccc(NCC(=O)N[C@H](C(=O)N4C[C@H](O)C[C@H]4C(=O)N[C@@H](C)c4ccc(-c5scnc5C)cc4)C(C)(C)C)nc3)cc2)c2c(sc(C)c2C)-n2c(C)nnc21]

By reaction and treatment in the same manner as in Example 135 (135-2)-(135-3) and using Example compound 163-2 instead of Example compound 135-1, the title compound was obtained as a pale-yellow solid. MS (ESI) m/z: 957.4 [M+H]$^+$

Example 164

(164-1) (2S,4R)-1-{(2S)-2-[(6-bromo-1-benzofuran-2-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 164-1)

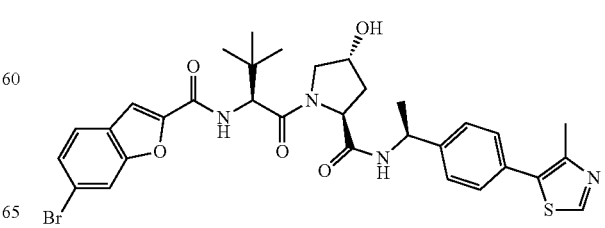

By reaction and treatment in the same manner as in Example 97 (97-2) and using 6-bromobenzofuran-2-carboxylic acid instead of Example compound 97-1, the title compound was obtained as a pale-yellow solid. MS (ESI) m/z: 667.1, 669.1 [M+H]+

(164-2) methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1-benzofuran-6-yl]phenyl}-2,3,9-trimethyl-6H-thieno[3,2-f][1,2,4]triazolo[4,3-a][1,4]diazepin-6-yl]acetate (Example Compound 164)

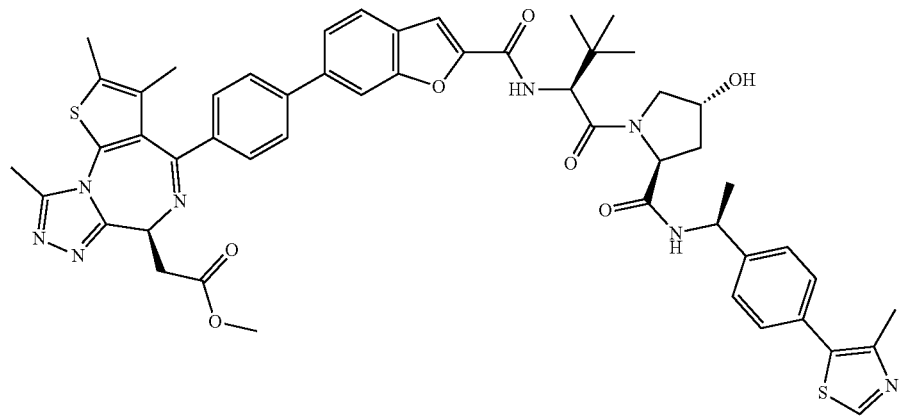

By reaction and treatment in the same manner as in Example 101 (101-2) and using Example compound 164-1 instead of Example compound 101-1, the title compound was obtained as a white solid. MS (ESI) m/z: 967.9 [M+H]+

Example 165

(165-1) methyl {(6S)-4-[4-(6-{[trans-3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclobutyl]oxy}pyridin-3-yl)phenyl]-2,3,9-trimethyl-6H-thieno[3,2-f][1,2,4]triazolo[4,3-a][1,4]diazepin-6-yl}acetate (Example Compound 165)

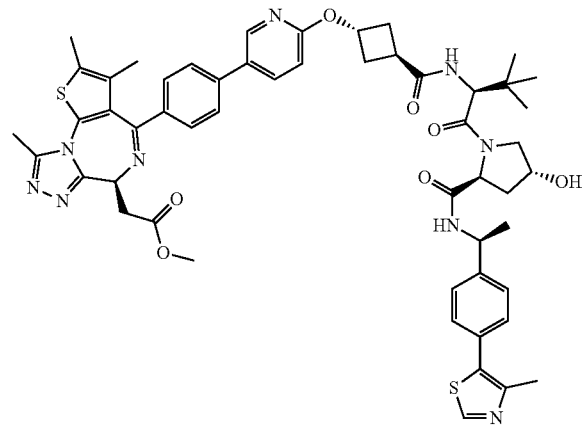 [SMILES: COC(=O)C[C@@H]1N=C(c2ccc(-c3ccc(O[C@H]4C[C@H](C(=O)N[C@H](C(=O)N5C[C@H](O)C[C@H]5C(=O)N[C@@H](C)c5ccc(-c6scnc6C)cc5)C(C)(C)C)C4)nc3)cc2)c2c(sc(C)c2C)-n2c(C)nnc21]

By reaction and treatment in the same manner as in Example 135 (135-2)-(135-3) and using Example compound 162-2 instead of Example compound 135-1, the title compound was obtained as a white solid. MS (ESI) m/z: 998.4 [M+H]+

Example 166

(166-1) tert-butyl 6-bromopyridine-3-carboxylate (Example Compound 166-1)

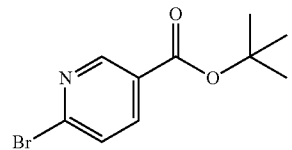

6-Bromonicotinic acid (1.00 g), N,N-dimethylformamide di-t-butylacetal (4.74 mL) were heated under reflux in toluene (5 mL) for 10 hr. To the reaction mixture was added saturated aqueous sodium hydrogen carbonate, and the mixture was extracted twice with ethyl acetate. The organic layer was washed twice with water and concentrated under reduced pressure. The residue was purified by silica gel column chromatography (chloroform:hexane=30:70-70:30) to give the title compound (745 mg) as a white solid. MS (ESI) m/z: 258.1, 260.1 [M+H]+

(166-2) methyl [(6S)-4-{4-[5-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-2-yl]phenyl}-2,3,9-trimethyl-6H-thieno[3,2-f][1,2,4]triazolo[4,3-a][1,4]diazepin-6-yl]acetate (Example Compound 166)

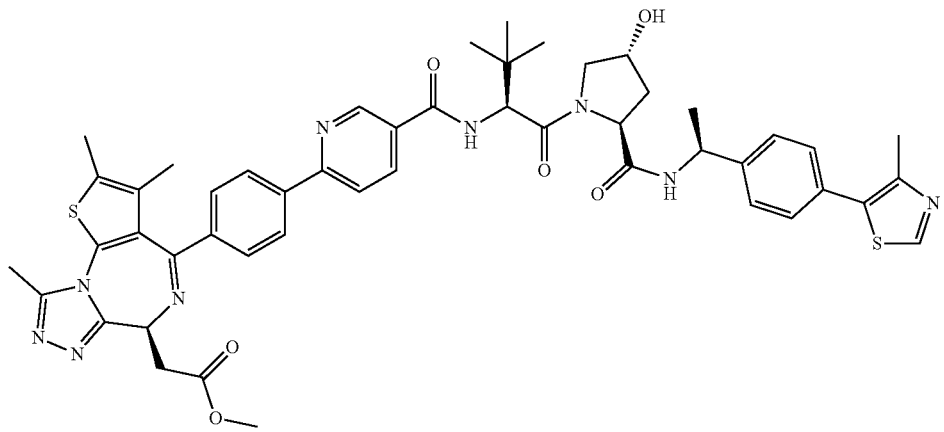 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cn3)cc2)c2c(sc(C)c2C)-n2c(C)nnc21]

By reaction and treatment in the same manner as in Example 136 (136-2)-(136-3) and using Example compound 166-1 instead of Example compound 136-1, the title compound was obtained as a white solid. MS (ESI) m/z: 928.4 [M+H]$^+$ Example 167

(167-1) 6-chloro-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}pyrazine-2-carboxamide (Example Compound 167-1)

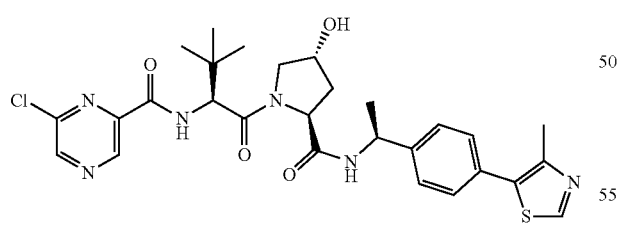

By reaction and treatment in the same manner as in Example 97 (97-2) and using 6-chloropyrazine-2-carboxylic acid instead of Example compound 97-1, the title compound was obtained as a white solid. MS (ESI) m/z: 585.2, 587.2 [M+H]$^+$ (167-2) methyl [(6S)-4-{4-[6-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyrazin-2-yl]phenyl}-2,3,9-trimethyl-6H-thieno[3,2-f][1,2,4]triazolo[4,3-a][1,4]diazepin-6-yl]acetate (Example Compound 167)

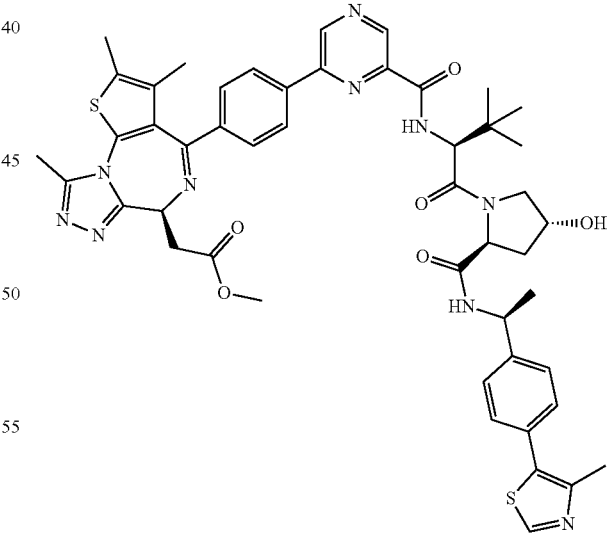

By reaction and treatment in the same manner as in Example 101 (101-2) and using Example compound 167-1 instead of Example compound 101-1, the title compound was obtained as a white solid. MS (ESI) m/z: 929.8 [M+H]$^+$

Example 168

168-1) (2S,4R)-1-[(2S)-2-(4-bromo-2-methoxyben-
zamido)-3,3-dimethylbutanoyl]-4-hydroxy-N-{(1S)-
1-[4-(4-methyl-1,3-thiazol-5-yl)phenyl]
ethyl}pyrrolidine-2-carboxamide (Example
Compound 168-1)

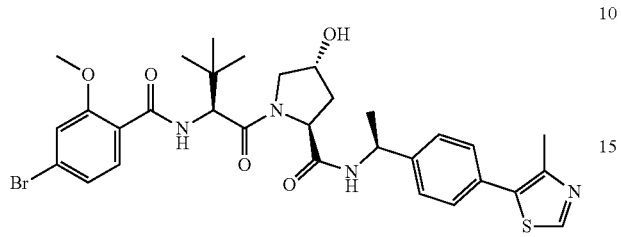

By reaction and treatment in the same manner as in Example 157 (157-1) and using 4-bromo-2-methoxybenzoic acid instead of 4-bromo-2-chlorobenzoic acid, the title compound was obtained as a white solid. MS (ESI) m/z: 657.3, 659.3 [M+H]$^+$ (168-2) methyl {(6S)-4-[4'-({(2S)-1-[(2S,4R)-4-
hydroxy-2-({(1S)-1-[4-(4-methyl-1,3-thiazol-5-yl)
phenyl]ethyl}carbamoyl)pyrrolidin-1-yl]-3,3-dim-
ethyl-1-oxobutan-2-yl}carbamoyl)-3'-methoxy[1,1'-
biphenyl]-4-yl]-2,3,9-trimethyl-6H-thieno[3,2-f][1,2,
4]triazolo[4,3-a][1,4]diazepin-6-yl}acetate (Example
Compound 168)

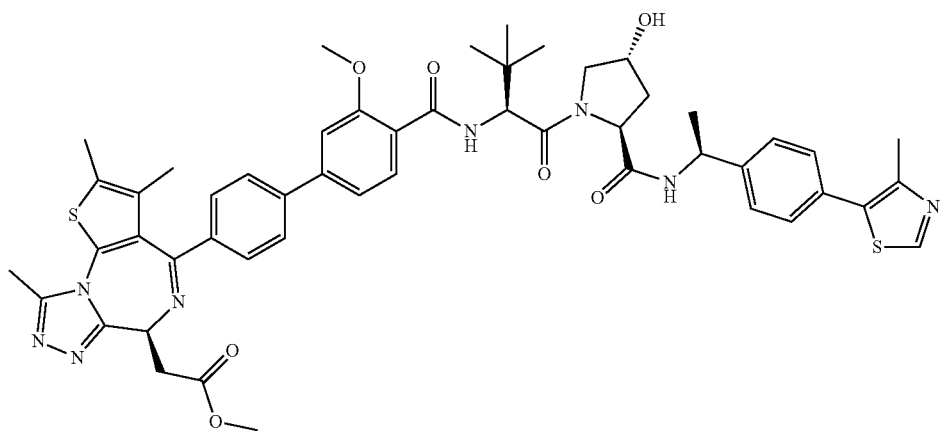 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(OC)c3)cc2)c2c(sc(C)c2C)-n2c(C)nnc21]

By reaction and treatment in the same manner as in Example 157 (157-2) and using Example compound 168-1 instead of Example compound 157-1, the title compound was obtained as a white solid. MS (ESI) m/z: 957.3 [M+H]$^+$ Example 169

(169-1) methyl {(6S)-4-[2'-chloro-4'-({(2S)-1-[(2S, 4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 169)

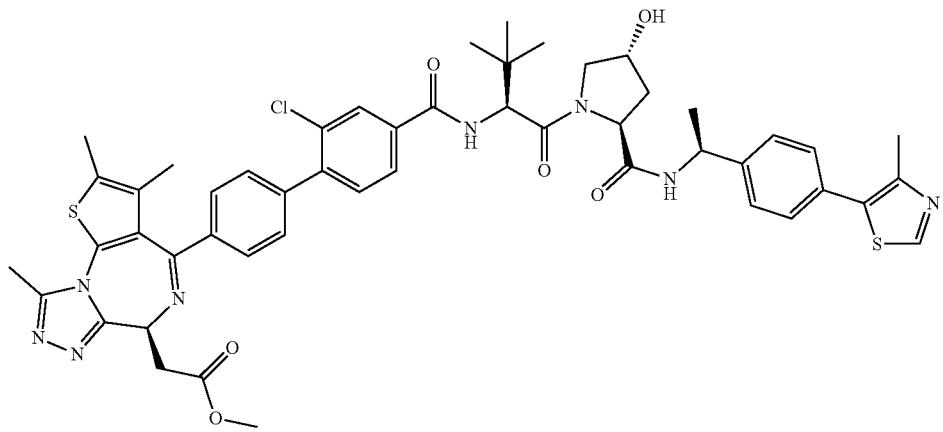

By reaction and treatment in the same manner as in Example 157 (157-1)-(157-2) and using 4-bromo-3-chlorobenzoic acid instead of 4-bromo-2-chlorobenzoic acid, the title compound was obtained as a white solid. MS (ESI) m/z: 961.3 [M+H]+

Example 170

(170-1) methyl {(6S)-4-[2'-hydroxy-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 170)

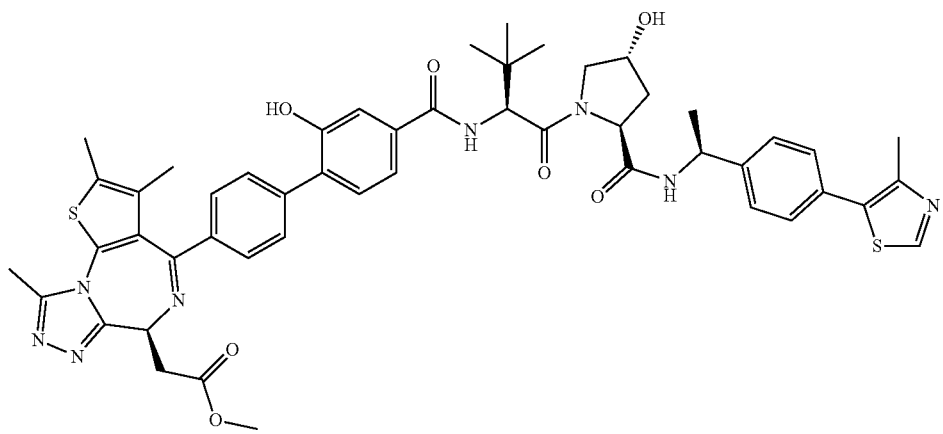 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cc3Cl)cc2)c2c(sc(C)c2C)-n2c(C)nnc21]

By reaction and treatment in the same manner as in Example 157 (157-1)-(157-2) and using 4-bromo-3-hydroxybenzoic acid instead of 4-bromo-2-chlorobenzoic acid, the title compound was obtained as a white solid. MS (ESI) m/z: 943.3 [M+H]+

Example 171

(171-1) 5-bromo-N-{(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}-1,3-benzoxazole-2-carboxamide (Example Compound 171-1)

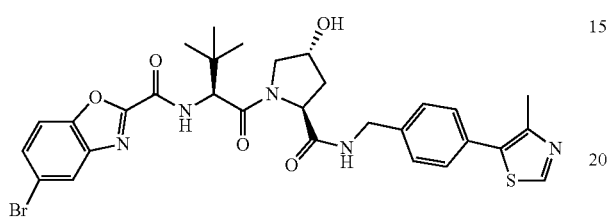

By reaction and treatment in the same manner as in Example 61 (61-4) and using 5-bromo-1,3-benzoxazole-2-carboxylic acid instead of Example compound 61-3, the title compound was obtained as a white solid.

MS (ESI) m/z: 654.1, 656.1 [M+H]$^+$ (171-2) methyl [(6S)-4-{4-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}carbamoyl)-1,3-benzoxazol-5-yl]phenyl}-2,3,9-trimethyl-6H-thieno[3,2-f][1,2,4]triazolo[4,3-a][1,4]diazepin-6-yl]acetate (Example Compound 171)

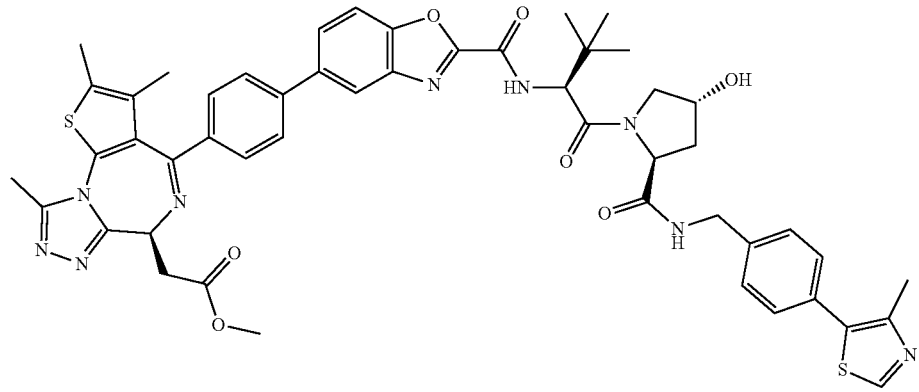 [SMILES: COC(=O)C[C@@H]1N=C(c2ccc(-c3ccc4oc(C(=O)N[C@H](C(=O)N5C[C@H](O)C[C@H]5C(=O)NCc5ccc(-c6scnc6C)cc5)C(C)(C)C)nc4c3)cc2)c2c(sc(C)c2C)-n2c(C)nnc21]

By reaction and treatment in the same manner as in Example 101 (101-2) and using Example compound 171-1 instead of Example compound 101-1, the title compound was obtained as a white powder. MS (ESI) m/z: 954.4 [M+H]$^+$

Example 172

(172-1) 1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1H-pyrazole-3-carboxylic acid hydrochloride (Example Compound 172-1)

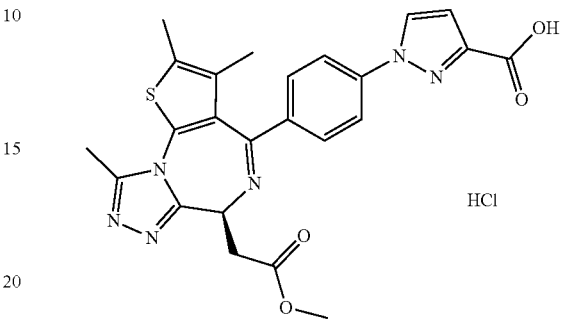

Reference Example compound 3 (400 mg), copper(II) acetate (144 mg), t-butyl pyrazole-3-carboxylate (146 mg), triethylamine (0.549 mL) were stirred in dichloromethane (5.0 mL) solvent at room temperature for 17 hr, and heated under reflux for 26 hr. Using chloroform, the reaction mixture was filtered through diatomaceous earth, and the filtrate was concentrated under reduced pressure. The residue was purified by NH silica gel column chromatography (ethyl acetate:hexane=50:50-90:10) to give a pale-yellow solid. The obtained solid was dissolved in chloroform (1.0 mL), trifluoroacetic acid (1.0 mL) was added and the mixture was stirred at room temperature for 15 hr. The reaction mixture was concentrated under reduced pressure, and azeotropically distilled with toluene. Saturated aqueous sodium hydrogen carbonate was added to set to pH9 and the mixture was washed twice with ethyl acetate. The aqueous layer was set to pH4 with 1N hydrochloric acid and extracted twice with ethyl acetate. The organic layer was concentrated under reduced pressure to give the title compound (114 mg) as a yellow viscous compound. MS (ESI) m/z: 491.1 [M+H]$^+$ (172-2) methyl [(6S)-4-{4-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1H-pyrazol-1-yl]phenyl}-2,3,9-trimethyl-6H-thieno[3,2-f][1,2,4]triazolo[4,3-a][1,4]diazepin-6-yl]acetate (Example Compound 172)

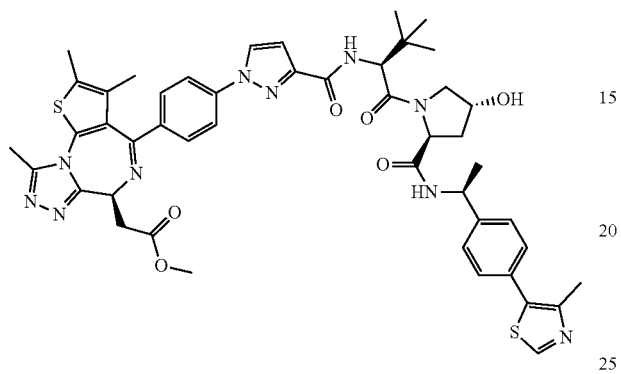

By reaction and treatment in the same manner as in Example 97 (97-2) and using Example compound 172-1 instead of Example compound 97-1, the title compound was obtained as a white solid. MS (ESI) m/z: 917.3 [M+H]$^+$ Example 173

(173-1) methyl {(6S)-4-[2',3'-difluoro-5'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 173)

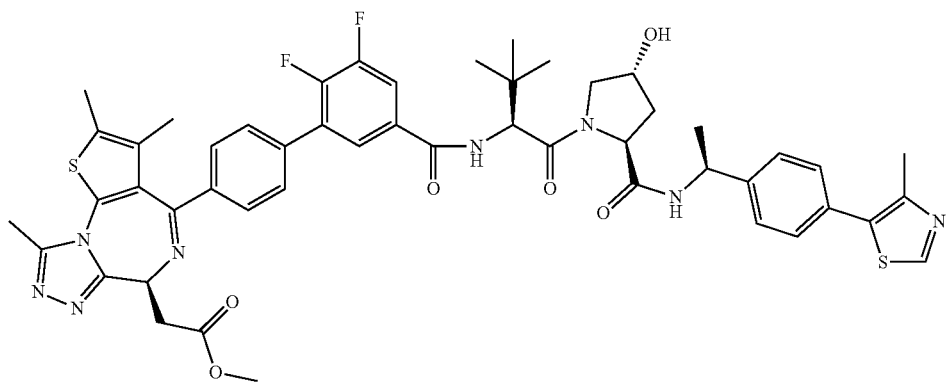 [SMILES: COC(=O)C[C@@H]1N=C(c2ccc(-c3cc(C(=O)N[C@H](C(=O)N4C[C@H](O)C[C@H]4C(=O)N[C@@H](C)c4ccc(-c5scnc5C)cc4)C(C)(C)C)cc(F)c3F)cc2)c2c(sc(C)c2C)-n2c(C)nnc21]

By reaction and treatment in the same manner as in Example 106 (106-1)-(106-2) and using 3-bromo-4,5-difluorobenzoic acid instead of 3-bromo-4-fluorobenzoic acid, the title compound was obtained as a white solid.

MS (ESI) m/z: 963.6 [M+H]$^+$

Example 174

(174-1) methyl {(6S)-4-[2',6'-difluoro-3'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 174)

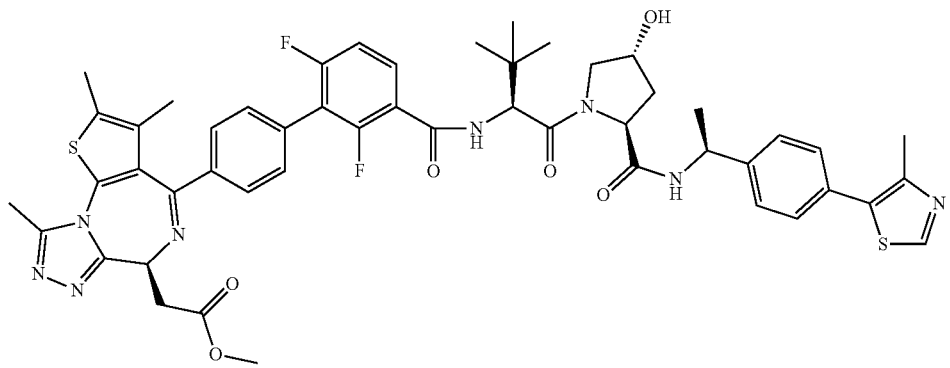 [SMILES: COC(=O)C[C@@H]1N=C(c2ccc(-c3c(F)ccc(C(=O)N[C@H](C(=O)N4C[C@H](O)C[C@H]4C(=O)N[C@@H](C)c4ccc(-c5scnc5C)cc4)C(C)(C)C)c3F)cc2)c2c(sc(C)c2C)-n2c(C)nnc21]

By reaction and treatment in the same manner as in Example 106 (106-1)-(106-2) and using 3-bromo-2,4-difluorobenzoic acid instead of 3-bromo-4-fluorobenzoic acid, the title compound was obtained as a white solid.
MS (ESI) m/z: 963.6 [M+H]⁺

Example 175

(175-1) methyl {(6S)-4-[2',5'-difluoro-3'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 175)

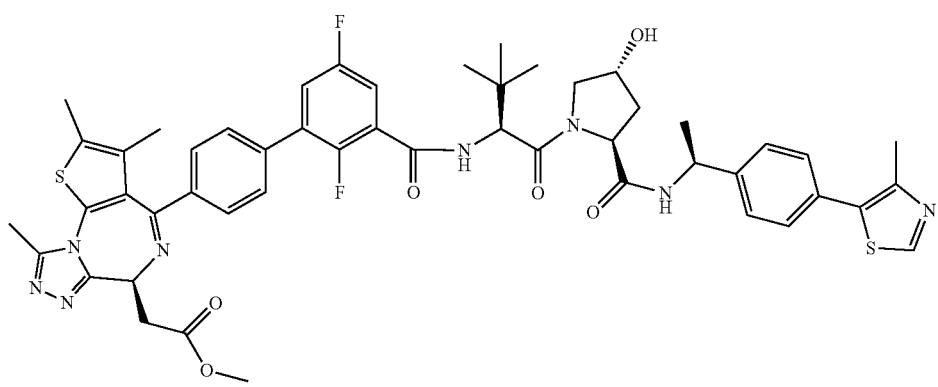 [SMILES: COC(=O)C[C@@H]1N=C(c2ccc(-c3cc(F)cc(C(=O)N[C@H](C(=O)N4C[C@H](O)C[C@H]4C(=O)N[C@@H](C)c4ccc(-c5scnc5C)cc4)C(C)(C)C)c3F)cc2)c2c(sc(C)c2C)-n2c(C)nnc21]

By reaction and treatment in the same manner as in Example 106 (106-1)-(106-2) and using 3-bromo-2,5-difluorobenzoic acid instead of 3-bromo-4-fluorobenzoic acid, the title compound was obtained as a white solid.
MS (ESI) m/z: 963.6 [M+H]⁺

Example 176

(176-1) methyl {(6S)-4-[2',3'-difluoro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 176)

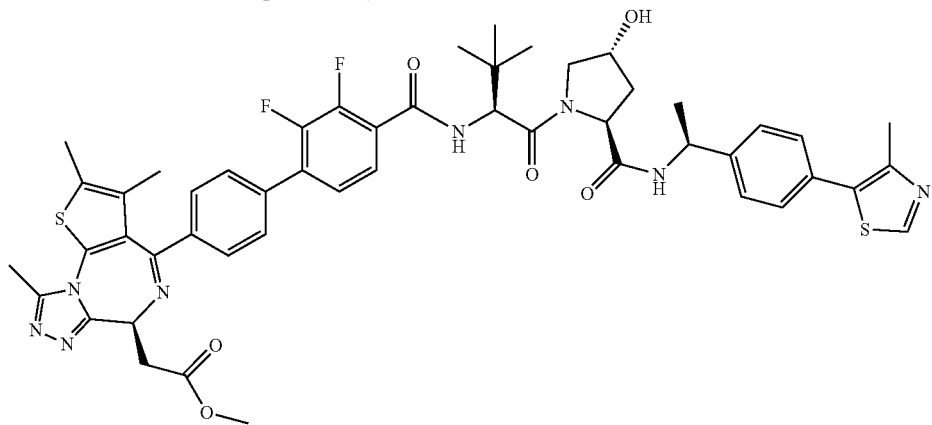 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(F)c3F)cc2)c2c(sc(C)c2C)-n2c(C)nnc21]

By reaction and treatment in the same manner as in Example 106 (106-1)-(106-2) and using 3-bromo-2,3-difluorobenzoic acid instead of 3-bromo-4-fluorobenzoic acid, the title compound was obtained as a white solid.
MS (ESI) m/z: 963.6 [M+H]$^+$ Example 177

(177-1) methyl [(6S)-4-(4-{4-[6-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)pyridin-2-yl]piperazin-1-yl}phenyl)-2,3,9-trimethyl-6H-thieno[3,2-f][1,2,4]triazolo[4,3-a] [1,4]diazepin-6-yl]acetate (Example Compound 177)

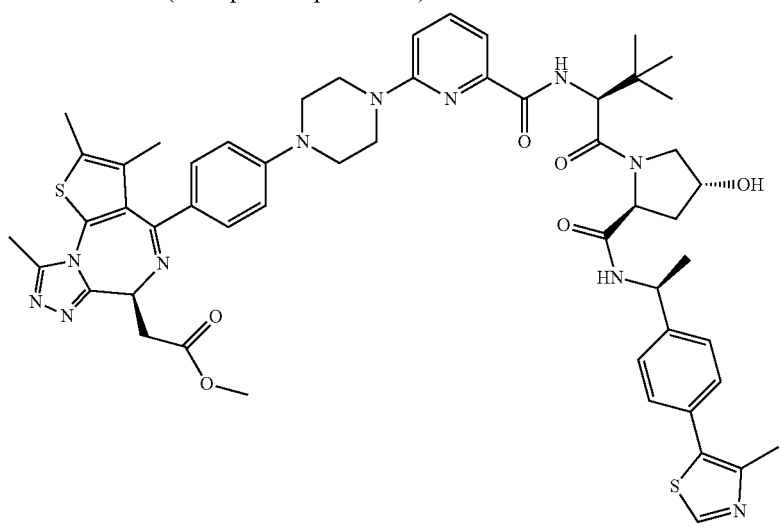

By reaction and treatment in the same manner as in Example 98 (98-3)-(98-4) and using t-butyl 6-(1-piperazinyl)picolinate instead of Example compound 98-2, the is title compound was obtained as a yellow powder.
MS (ESI) m/z: 1012.4 [M+H]$^+$

Example 178

(178-1) methyl [(6S)-4-{2'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate
(Example Compound 178)

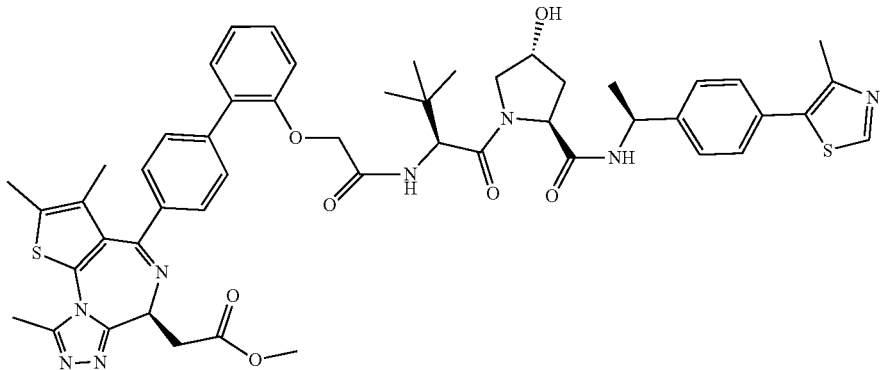 [SMILES: COC(=O)C[C@@H]1N=C(c2ccc(-c3ccccc3OCC(=O)N[C@H](C(=O)N3C[C@H](O)C[C@H]3C(=O)N[C@@H](C)c3ccc(-c4scnc4C)cc3)C(C)(C)C)cc2)c2c(sc(C)c2C)-n2c(C)nnc21]

By reaction and treatment in the same manner as in Example 51 (51-1)-(51-4) and using 2-bromophenol instead of 3-bromobenzyl alcohol, the title compound was obtained as a white solid. MS (ESI) m/z: 957.4 [M+H]$^+$

Example 179

(179-1) 5-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-1,3-benzothiazole-2-carboxamide
(Example Compound 179-1)

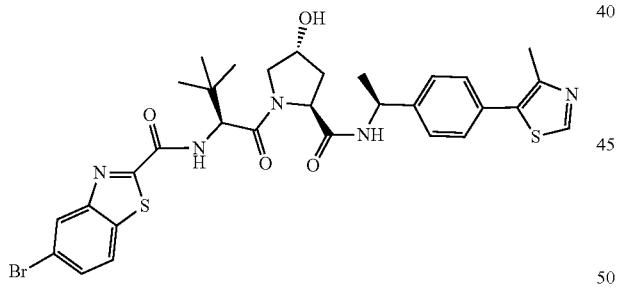

To a solution of methyl 5-bromo-1,3-benzothiazole-2-carboxylate (200 mg) in 1,2-dimethoxyethane (3.0 mL), water (3.0 mL) was added aqueous lithium hydroxide solution (0.55 mL, 4.0 mol/L), and the mixture was stirred at room temperature for 1.5 hr. To the reaction mixture was added ice water, 1N hydrochloric acid was added to adjust to pH3-4 and the mixture was stirred. The precipitate was collected by filtration. The precipitate was dissolved in N,N-dimethylformamide (3.0 mL), and Reference Example compound 5 (389 mg), N,N-diisopropylethylamine (0.38 mL), HATU (727 mg) were added and the mixture was stirred at room temperature for 24 hr. Water was added to the reaction mixture and the mixture was stirred. The precipitate was collected by filtration. The obtained solid was purified by silica gel column chromatography (methanol:chloroform=0:100-5:95) to give the title compound (206 mg) as a pale-yellow solid. MS (ESI) m/z: 684.1, 686.1 [M+H]$^+$ (179-2) methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzothiazol-5-yl]phenyl}-2,3,9-trimethyl-6H-thieno[3,2-f][1,2,4]triazolo[4,3-a][1,4]diazepin-6-yl]acetate (Example Compound 179)

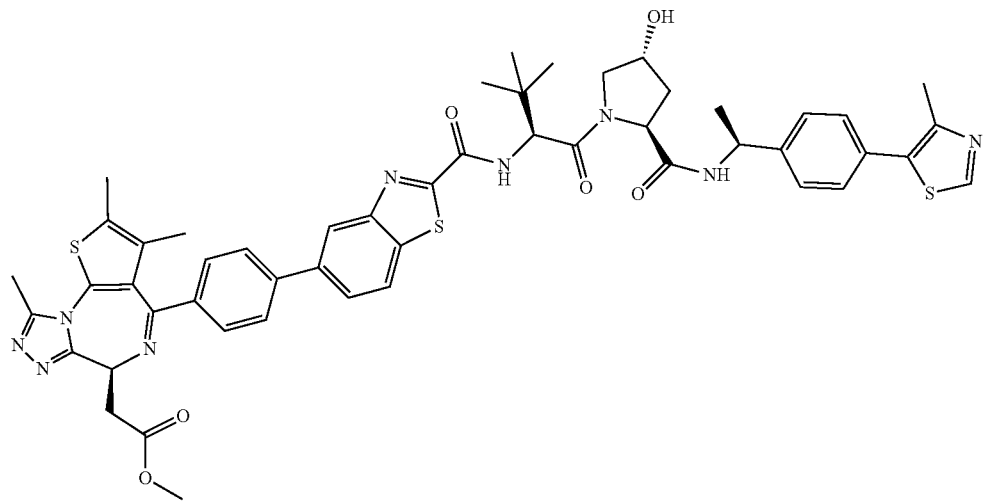 [SMILES: COC(=O)C[C@@H]1N=C(c2ccc(-c3ccc4sc(C(=O)N[C@H](C(=O)N5C[C@H](O)C[C@H]5C(=O)N[C@@H](C)c5ccc(-c6scnc6C)cc5)C(C)(C)C)nc4c3)cc2)c2c(sc(C)c2C)-n2c(C)nnc21]

By reaction and treatment in the same manner as in Example 100 (100-2) and using Example compound 179-1 instead of Example compound 100-1, the title compound was obtained as a white solid. MS (ESI) m/z: 984.3 [M+H]$^+$ Example 180

(180-1) 6-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-1,3-benzothiazole-2-carboxamide (Example Compound 180-1)

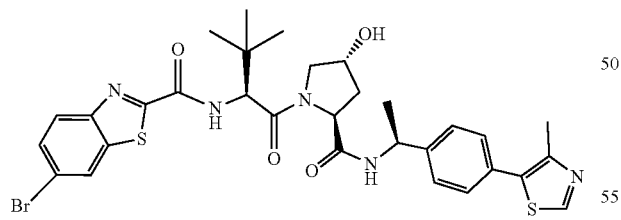

By reaction and treatment in the same manner as in Example 179 (179-1) and using methyl 6-bromo-1,3-benzothiazole-2-carboxylate instead of methyl 5-bromo-1,3-benzothiazole-2-carboxylate, the title compound was obtained as a pale-yellow solid. MS (ESI) m/z: 684.1, 686.1 [M+H]$^+$ (180-2) methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzothiazol-6-yl]phenyl}-2,3,9-trimethyl-6H-thieno[3,2-f][1,2,4]triazolo[4,3-a][1,4]diazepin-6-yl]acetate (Example Compound 180)

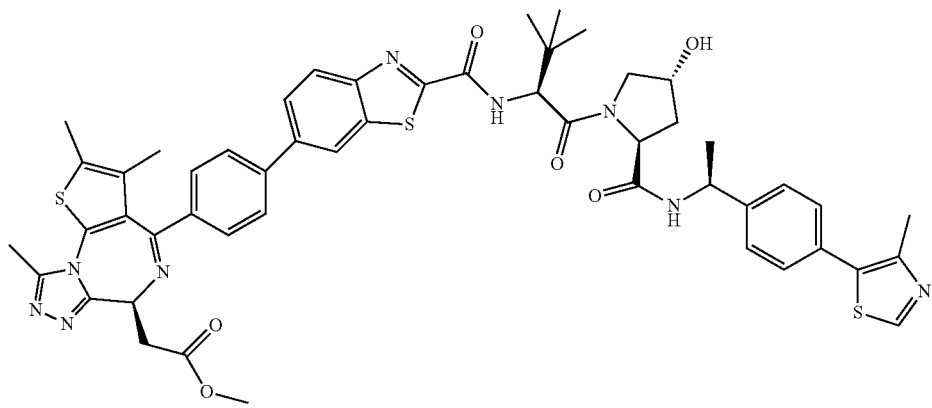 [SMILES: COC(=O)C[C@@H]1N=C(c2ccc(-c3ccc4nc(C(=O)N[C@H](C(=O)N5C[C@H](O)C[C@H]5C(=O)N[C@@H](C)c5ccc(-c6scnc6C)cc5)C(C)(C)C)oc4c3)cc2)c2c(sc(C)c2C)-n2c(C)nnc21]

By reaction and treatment in the same manner as in Example 100 (100-2) and using Example compound 180-1 instead of Example compound 100-1, the title compound was obtained as a white solid. MS (ESI) m/z: 984.3 [M+H]$^+$ Example 181

(181-1) 6-bromo-N-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}-1,3-benzoxazole-2-carboxamide (Example Compound 181-1)

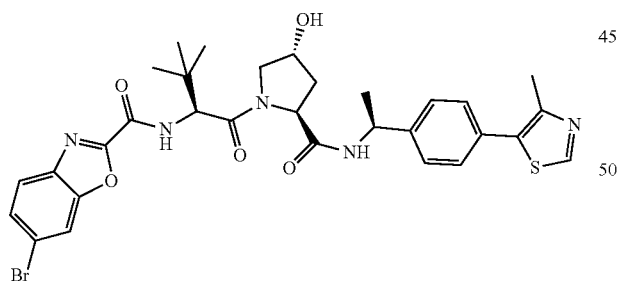

6-Bromo-1,3-benzoxazole-2-carboxylic acid (200 mg) was dissolved in N,N-dimethylformamide (3.0 mL), and Reference Example compound 5 (437 mg), N,N-diisopropylethylamine (0.43 mL), HATU (503 mg) were added and the mixture was stirred at room temperature for 5 hr. Water was added to the reaction mixture and the mixture was stirred. The precipitate was collected by filtration. The obtained solid was purified by silica gel column chromatography (methanol:chloroform=0:100-5:95) to give the title compound (230 mg) as an orange solid.

MS (ESI) m/z: 668.2, 670.2 [M+H]$^+$ (181-2) methyl [(6S)-4-{4-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzoxazol-6-yl]phenyl}-2,3,9-trimethyl-6H-thieno[3,2-f][1,2,4]triazolo[4,3-a][1,4]diazepin-6-yl]acetate (Example Compound 181)

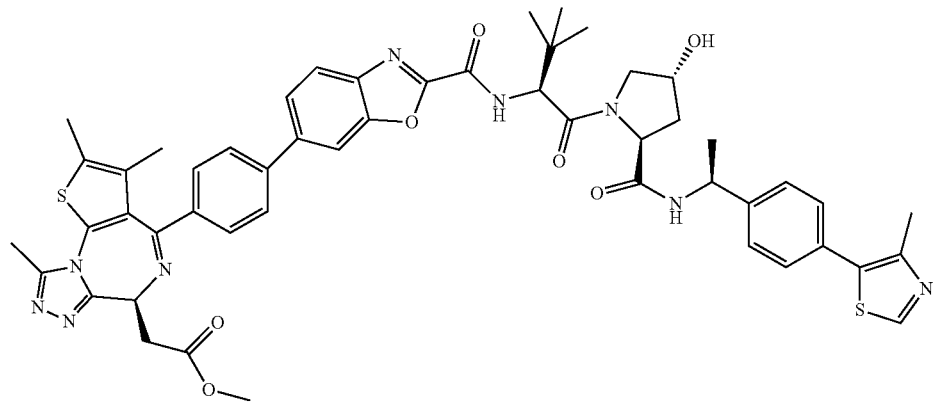

By reaction and treatment in the same manner as in Example 100 (100-2) and using Example compound 181-1 instead of Example compound 100-1, the title compound was obtained as a white solid. MS (ESI) m/z: 968.2 [M+H]$^+$ Example 182

(182-1) methyl {(6S)-4-[3'-cyano-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 182)

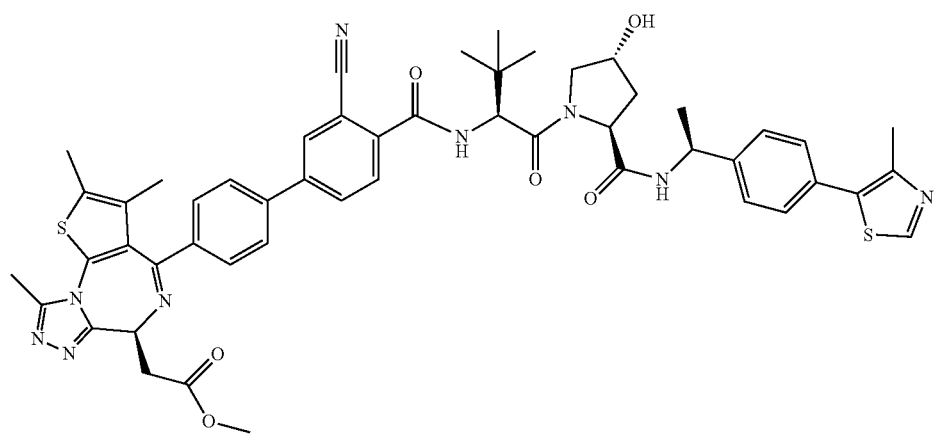 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(C#N)c3)cc2)c2c(sc(C)c2C)-n2c(C)nnc21]

By reaction and treatment in the same manner as in Example 157 (157-1)-(157-2) and using 4-bromo-2-cyanobenzoic acid instead of 4-bromo-2-chlorobenzoic acid, the title compound was obtained as a white solid. MS (ESI) m/z: 952.3 [M+H]$^+$

Example 183

(183-1) methyl {(6S)-4-[4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-3'-methyl[1,1'-biphenyl]-4-yl]-2,3,9-trimethyl-6H-thieno[3,2-f][1,2,4]triazolo[4,3-a][1,4]diazepin-6-yl}acetate (Example Compound 183)

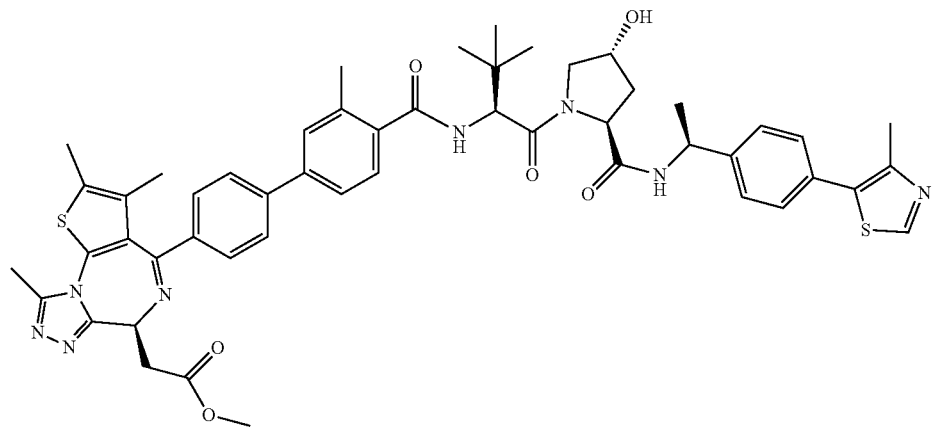 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)c(C)c3)cc2)c2c(sc(C)c2C)-n2c(C)nnc21]

By reaction and treatment in the same manner as in Example 157 (157-1)-(157-2) and using 4-bromo-2-methylbenzoic acid instead of 4-bromo-2-chlorobenzoic acid, the title compound was obtained as a white solid. MS (ESI) m/z: 941.4 [M+H]$^+$

Example 184

(184-1) methyl {(6S)-4-[4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-2'-methyl[1,1'-biphenyl]-4-yl]-2,3,9-trimethyl-6H-thieno[3,2-f][1,2,4]triazolo[4,3-a][1,4]diazepin-6-yl}acetate (Example Compound 184)

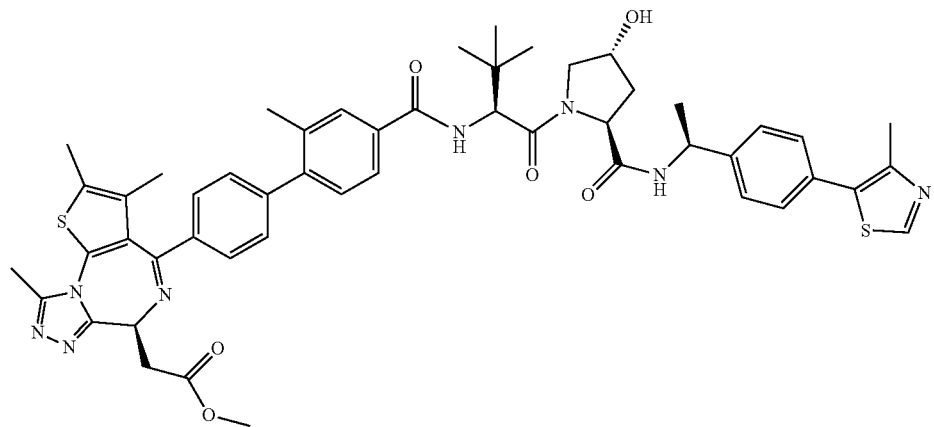 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cc3C)cc2)c2c(sc(C)c2C)-n2c(C)nnc21]

By reaction and treatment in the same manner as in Example 157 (157-1)-(157-2) and using 4-bromo-3-methylbenzoic acid instead of 4-bromo-2-chlorobenzoic acid, the title compound was obtained as a white solid. MS (ESI) m/z: 941.4 [M+H]$^+$

Example 185

(185-1) (6S)-4-(3-bromophenyl)-2,3,6,9-tetramethyl-6H-thieno[3,2-f][1,2,4]triazolo[4,3-a][1,4]diazepine (Example Compound 185-1)

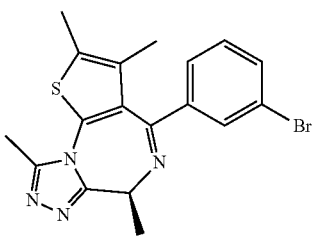 [SMILES: Cc1sc2c(c1C)C(c1cccc(Br)c1)=N[C@@H](C)c1nnc(C)n1-2]

By reaction and treatment in the same manner as in Reference Example 4 (4-1)-(4-4) and using 3-(3-bromophenyl)-3-oxopropanenitrile instead of 3-(4-bromophenyl)-3-oxopropanenitrile, the title compound was obtained as a yellow solid. MS (ESI) m/z: 401.1, 403.1 [M+H]+

(185-2) tert-butyl 3'-[(6S)-2,3,6,9-tetramethyl-6H-thieno[3,2-f] [1,2,4]triazolo[4,3-a][1,4]diazepin-4-yl][1,1'-biphenyl]-3-carboxylate (Example Compound 185-2)

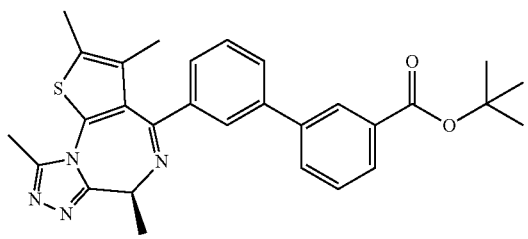 [SMILES: Cc1sc2c(c1C)C(c1cccc(-c3cccc(C(=O)OC(C)(C)C)c3)c1)=N[C@@H](C)c1nnc(C)n1-2]

By reaction and treatment in the same manner as in Reference Example Reference Example 11 and using (3-t-butoxycarbonylphenyl)boronic acid instead of t-butyl 4-(4,4,5,5-tetramethyl-1,3,2-dioxaborolan-2-yl)benzoate, the title compound was obtained as a pale-yellow solid.
MS (ESI) m/z: 499.4 [M+H]+

(185-3) (2S,4R)-1-[(2S)-3,3-dimethyl-2-({3'-[(6S)-2,3,6,9-tetramethyl-6H-thieno [3,2-f][1,2,4] triazolo [4,3-a] [1,4] diazepin-4-yl][1,1'-biphenyl]-4-carbonyl}amino)butanoyl]-4-hydroxy-N-{(1S)-1-[4-(4-methyl-1,3-thiazol-5-yl)phenyl]ethyl}pyrrolidine-2-carboxamide (Example Compound 185)

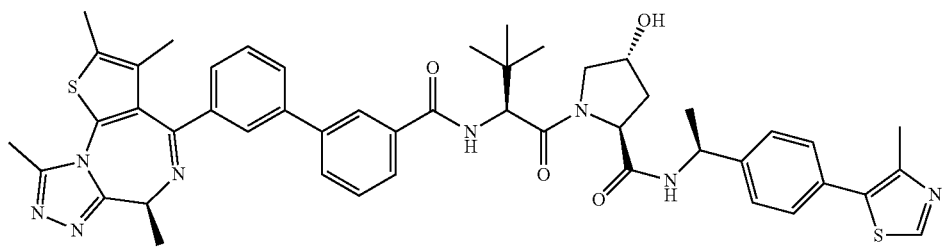 [SMILES: Cc1ncsc1-c1ccc([C@H](C)NC(=O)[C@@H]2C[C@@H](O)CN2C(=O)[C@@H](NC(=O)c2cccc(-c3cccc(C4=N[C@@H](C)c5nnc(C)n5-c5sc(C)c(C)c54)c3)c2)C(C)(C)C)cc1]

By reaction and treatment in the same manner as in Example 43 (43-1) and using Example compound 185-1 instead of Reference Example compound 11, the title compound was obtained as a white solid. MS (ESI) m/z: 869.6 [M+H]+

Example 186

(186-1) (2S,4R)-1-[(2S)-3,3-dimethyl-2-({3'-[(6S)-2,3,6,9-tetramethyl-6H-thieno[3,2-f][1,2,4]triazolo[4,3-a] [1,4]diazepin-4-yl][1,1'-biphenyl]-4-carbonyl}amino)butanoyl]-4-hydroxy-N-{(1S)-1-[4-(4-methyl-1,3-thiazol-5-yl)phenyl]ethyl}pyrrolidine-2-carboxamide (Example Compound 186)

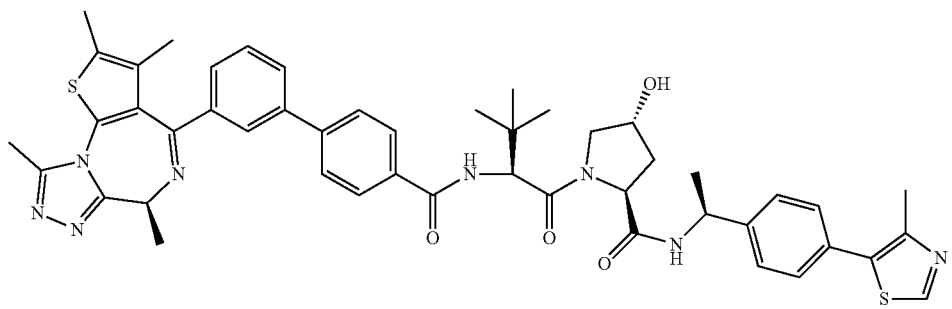 [SMILES: Cc1ncsc1-c1ccc([C@H](C)NC(=O)[C@@H]2C[C@@H](O)CN2C(=O)[C@@H](NC(=O)c2ccc(-c3cccc(C4=N[C@@H](C)c5nnc(C)n5-c5sc(C)c(C)c54)c3)cc2)C(C)(C)C)cc1]

By reaction and treatment in the same manner as in Reference Example 11 and using (4-t-butoxycarbonylphenyl)boronic acid instead of t-butyl 4-(4,4,5,5-tetramethyl-1,3,2-dioxaborolan-2-yl)benzoate, and by reaction and treatment in the same manner as in Example 43 (43-1) and using the obtained compound, the title compound was obtained as a white solid. MS (ESI) m/z: 869.6 [M+H]+

Example 187

(187-1) methyl {(6S)-4-[2'-cyano-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 187)

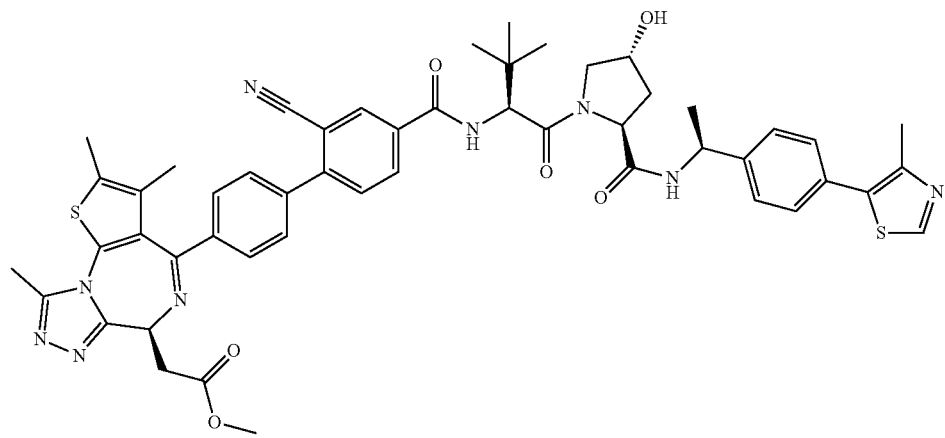 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cc3C#N)cc2)c2c(sc(C)c2C)-n2c(C)nnc21]

By reaction and treatment in the same manner as in Example 157 (157-1)-(157-2) and using 4-bromo-3-cyanobenzoic acid instead of 4-bromo-2-chlorobenzoic acid, the title compound was obtained as a white solid. MS (ESI) m/z: 952.4 [M+H]+

Example 188

(188-1) (2S,4R)-1-{(2S)-2-[3-(5-bromothiophen-2-yl)propanamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 188-1)

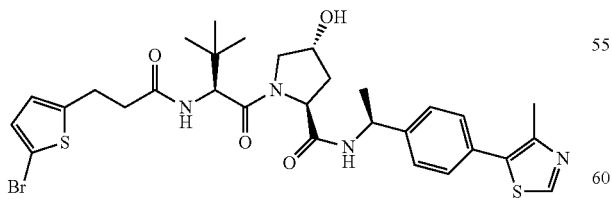

By reaction and treatment in the same manner as in Example 181 (181-1) and using 3-(5-bromo-2-thienyl)propanoic acid instead of 6-bromo-1,3-benzoxazole-2-carboxylic acid, the title compound was obtained as a white solid. MS (ESI) m/z: 661.2, 663.2 [M+H]+

(188-2) methyl [(6S)-4-(4-{5-[3-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-3-oxopropyl]thiophen-2-yl}phenyl)-2,3,9-trimethyl-6H-thieno[3,2-f][1,2,4]triazolo[4,3-a][1,4]diazepin-6-yl]acetate (Example Compound 188)

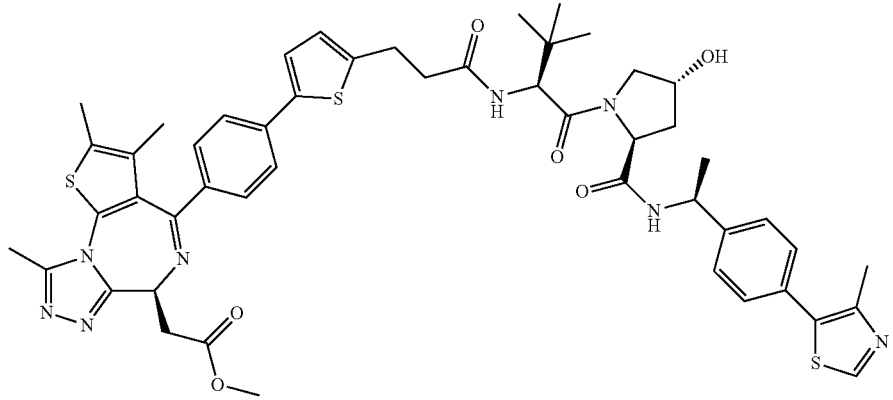 [SMILES: COC(=O)C[C@@H]1N=C(c2ccc(-c3ccc(CCC(=O)N[C@H](C(=O)N4C[C@H](O)C[C@H]4C(=O)N[C@@H](C)c4ccc(-c5scnc5C)cc4)C(C)(C)C)s3)cc2)c2c(sc(C)c2C)-n2c(C)nnc21]

By reaction and treatment in the same manner as in Example 100 (100-2) and using Example compound 188-1 instead of Example compound 100-1, the title compound was obtained as a white solid. MS (ESI) m/z: 961.5 [M+H]$^+$ Example 189

(189-1) methyl {(6S)-4-[2'-fluoro-4'-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}carbamoyl) [1,1'-biphenyl]-4-yl]-2,3,9-trimethyl-6H-thieno [3,2-f][1,2,4] triazolo [4,3-a][1,4] diazepin-6-yl}acetate (Example Compound 189)

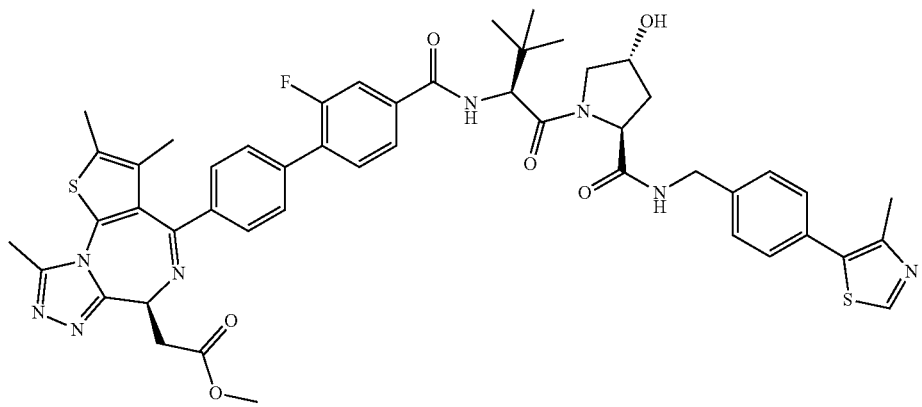 [SMILES: COC(=O)C[C@@H]1N=C(c2ccc(-c3ccc(C(=O)N[C@H](C(=O)N4C[C@H](O)C[C@H]4C(=O)NCc4ccc(-c5scnc5C)cc4)C(C)(C)C)cc3F)cc2)c2c(sc(C)c2C)-n2c(C)nnc21]

By reaction and treatment in the same manner as in Example 62 (62-2) and using Reference Example compound 6 instead of Reference Example compound 5, the title compound was obtained as a white solid. MS (ESI) m/z: 931.4 [M+H]$^+$

Example 190

(190-1) methyl {(6S)-4-[3'-chloro-4'-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 190)

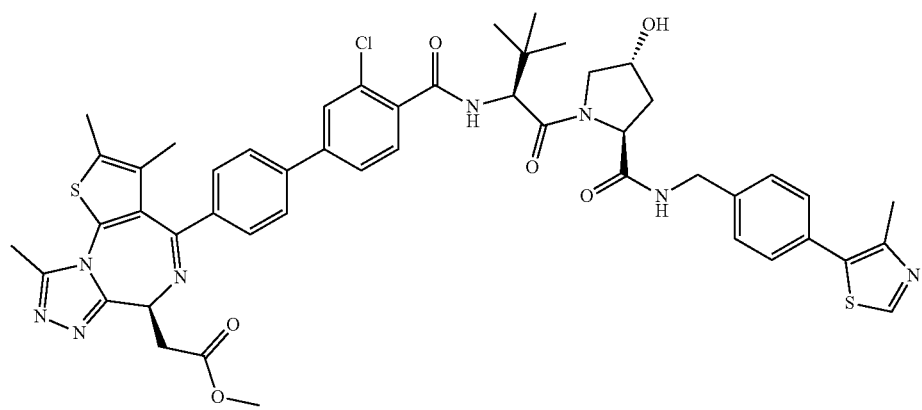 [SMILES: COC(=O)C[C@@H]1N=C(c2ccc(-c3ccc(C(=O)N[C@H](C(=O)N4C[C@H](O)C[C@H]4C(=O)NCc4ccc(-c5scnc5C)cc4)C(C)(C)C)c(Cl)c3)cc2)c2c(sc(C)c2C)-n2c(C)nnc21]

By reaction and treatment in the same manner as in Example 94 (94-1)-(94-3) and using Reference Example compound 3 instead of Reference Example compound 2, and t-butyl 4-bromo-2-chloro-benzoate instead of t-butyl 4-bromo-2-fluoro-benzoate, and Reference Example compound 6 instead of Reference Example compound 5, the title compound was obtained as a white solid. MS (ESI) m/z: 947.3 [M+H]$^+$

Example 191

(191-1) 4-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}butanoic acid (Example Compound 191-1)

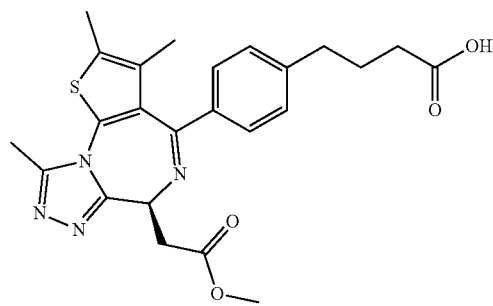 [SMILES: COC(=O)C[C@@H]1N=C(c2ccc(CCCC(=O)O)cc2)c2c(sc(C)c2C)-n2c(C)nnc21]

To a solution of Reference Example compound 1 (250 mg) in 1,4-dioxane (3.0 mL) were added tert-butyl 3-butenoate (0.29 mL), tris(dibenzylideneacetone)dipalladium(0) (55 mg), tri-tert-butylphosphonium tetrafluoroborate (70 mg), N,N-dicyclohexylmethylamine (0.39 mL), and the mixture was stirred under reflux for 24 hr. Furthermore, t-butyl 3-butenoate (0.20 mL), tris(dibenzylideneacetone)dipalladium(0) (110 mg), tri-tert-butylphosphonium tetrafluoroborate (105 mg), N,N-dicyclohexylmethylamine (0.26 mL) were added, and the mixture was stirred with heating under reflux for 8 hr. To the reaction solution were added saturated aqueous ammonium chloride solution and water and the mixture was extracted with ethyl acetate. The organic layer was washed with saturated brine, dried over anhydrous sodium sulfate, filtered, and the filtrate was concentrated under reduced pressure. The residue was purified by silica gel column chromatography (hexane:ethyl acetate=40:60-0:100). The obtained compound was dissolved in methanol (5 mL), 10% palladium carbon (30 mg) was added and, after hydrogen substitution, the mixture was stirred at room temperature for 3.5 hr. The reaction mixture was filtered through diatomaceous earth using chloroform, and the filtrate was concentrated under reduced pressure. The residue was dissolved in dichloromethane (4 mL), trifluoroacetic acid (2 mL) was added and the mixture was stirred at room temperature for 2.5 hr. The reaction mixture was concentrated under reduced pressure, and the residue was dissolved in toluene, saturated aqueous sodium hydrogen carbonate and water were added and the mixture was partitioned. The aqueous layer was acidified with 1N hydrochloric acid and the mixture was extracted with chloroform. The organic layer was washed with saturated brine, dried over anhydrous sodium sulfate, filtered, and the filtrate was concentrated under reduced pressure to give the title compound (96 mg) as a pale-yellow viscous compound. MS (ESI) m/z: 467.5 [M+H]$^+$ (191-2) methyl [(6S)-4-{4-[4-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-4-oxobutyl]phenyl}-2,3,9-trimethyl-6H-thieno[3,2-f][1,2,4]triazolo[4,3-a][1,4]diazepin-6-yl]acetate (Example Compound 191)

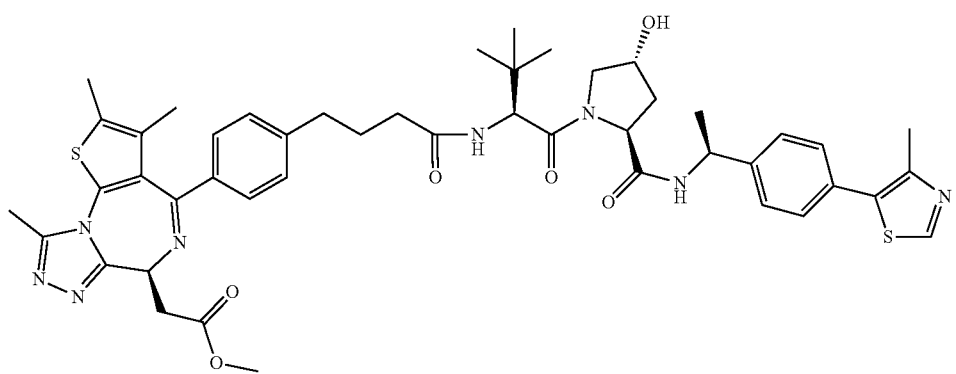 [SMILES: COC(=O)C[C@@H]1N=C(c2ccc(CCCC(=O)N[C@H](C(=O)N3C[C@H](O)C[C@H]3C(=O)N[C@@H](C)c3ccc(-c4scnc4C)cc3)C(C)(C)C)cc2)c2c(sc(C)c2C)-n2c(C)nnc21]

To a solution of Example compound 191-1 (96 mg) and Reference Example compound 5 (99 mg) in N,N-dimethylformamide (2.0 mL) was added N,N-diisopropylethylamine (0.089 mL), and HATU (94 mg) was added, and the mixture was stirred at room temperature for 15 hr. To the reaction solution was added methanol (1.0 mL), and the mixture was purified by preparative HPLC (10 mM aqueous ammonium carbonate solution-acetonitrile) and further purified by silica gel column chromatography (ethyl acetate:methanol=90:10-80:20) to give the title compound (72 mg) as a white powder.
MS (ESI) m/z: 893.8 [M+H]$^+$ Example 192

(192-1) 5-{4-[(6S)-2,3,6,9-tetramethyl-6H-thieno[3,2-f] [1,2,4]triazolo[4,3-a][1,4]diazepin-4-yl]phenyl}pentanoic acid (Example Compound 192-1)

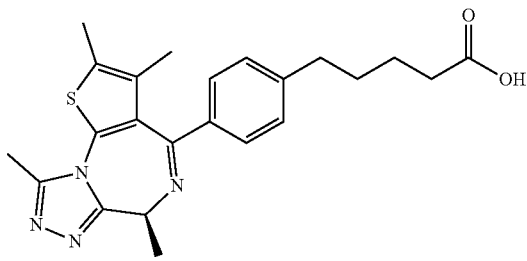 [SMILES: Cc1sc2c(c1C)C(c1ccc(CCCCC(=O)O)cc1)=N[C@@H](C)c1nnc(C)n1-2]

To a solution of Reference Example compound 4 (400 mg) in 1,4-dioxane (3.5 mL) were added 4-pentenoic acid (0.20 mL), tris(dibenzylideneacetone)dipalladium(0) (46 mg), tri-tert-butylphosphonium tetrafluoroborate (58 mg), N,N-dicyclohexylmethylamine (0.64 mL), and the mixture was stirred with heating at 80° C. for 4 hr. The reaction solution was diluted with toluene, and saturated aqueous sodium hydrogen carbonate and water were added. After partitioning, the aqueous layer was acidified with 1N hydrochloric acid and the mixture was extracted with chloroform. The organic layer was washed with saturated brine, dried over anhydrous sodium sulfate, filtered, and the filtrate was concentrated under reduced pressure. The residue was dissolved in ethanol (10.0 mL), 10% palladium carbon (80 mg) was added and, after hydrogen substitution, the mixture was stirred at room temperature for 15 hr. The reaction mixture was filtered through diatomaceous earth using chloroform, and the filtrate was concentrated under reduced pressure. The residue was purified by silica gel column chromatography (chloroform:methanol=99:1-90:10) to give a crude title compound (495 mg) as a white powder.
MS (ESI) m/z: 423.2 [M+H]$^+$ (192-2) (2S,4R)-1-{(2S)-3,3-dimethyl-2-[(5-{4-[(6S)-2,3,6,9-tetramethyl-6H-thieno[3,2-f][1,2,4]triazolo[4,3-a] [1,4]diazepin-4-yl]phenyl}pentanoyl)amino]butanoyl}-4-hydroxy-N-{(1S)-1-[4-(4-methyl-1,3-thiazol-5-yl)phenyl]ethyl}pyrrolidine-2-carboxamide (Example Compound 192)

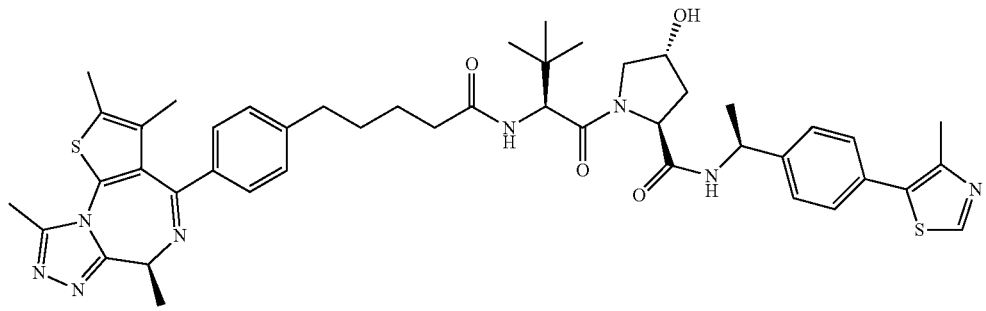 [SMILES: Cc1ncsc1-c1ccc([C@H](C)NC(=O)[C@@H]2C[C@@H](O)CN2C(=O)[C@@H](NC(=O)CCCCc2ccc(C3=N[C@@H](C)c4nnc(C)n4-c4sc(C)c(C)c43)cc2)C(C)(C)C)cc1]

To a solution of Example compound 192-1 (70 mg) and Reference Example compound 5 (81 mg) in N,N-dimethylformamide (2.0 mL) was added N,N-diisopropylethylamine (0.083 mL), and HATU (79 mg) was added, and the mixture was stirred at room is temperature for 5 hr. To the reaction solution was added methanol (1.0 mL) and the mixture was purified by preparative HPLC (10 mM aqueous ammonium carbonate solution-acetonitrile) to give the title compound (57 mg) as a milky white solid.

MS (ESI) m/z: 849.8 [M+H]$^+$

Example 193

(193-1) (2S,4R)-1-{(2S)-3,3-dimethyl-2-[(6-{4-[(6S)-2,3,6,9-tetramethyl-6H-thieno[3,2-f][1,2,4]triazolo[4,3-a] [1,4]diazepin-4-yl]phenyl}hexanoyl)amino]butanoyl}-4-hydroxy-N-{(1S)-1-[4-(4-methyl-1,3-thiazol-5-yl)phenyl]ethyl}pyrrolidine-2-carboxamide (Example Compound 193)

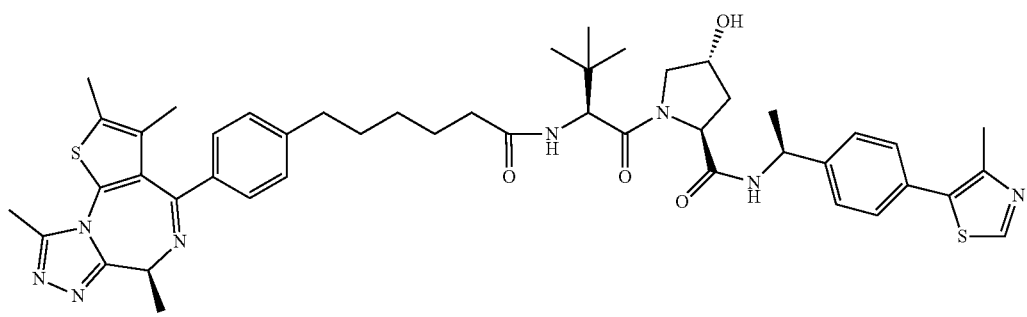 [SMILES: Cc1ncsc1-c1ccc([C@H](C)NC(=O)[C@@H]2C[C@@H](O)CN2C(=O)[C@@H](NC(=O)CCCCCc2ccc(C3=N[C@@H](C)c4nnc(C)n4-c4sc(C)c(C)c43)cc2)C(C)(C)C)cc1]

By reaction and treatment in the same manner as in Example 192 (192-1)-(192-2) and using 5-hexenoic acid instead of 4-pentenoic acid, the title compound was obtained as a white powder. MS (ESI) m/z: 863.8 [M+H]$^+$

Example 194

(194-1) (2S,4R)-1-{(2S)-3,3-dimethyl-2-[(7-{4-[(6S)-2,3,6,9-tetramethyl-6H-thieno[3,2-f][1,2,4]triazolo[4,3-a][1,4]diazepin-4-yl]phenyl}heptanoyl)amino]butanoyl}-4-hydroxy-N-{(1S)-1-[4-(4-methyl-1,3-thiazol-5-yl)phenyl]ethyl}pyrrolidine-2-carboxamide (Example Compound 194)

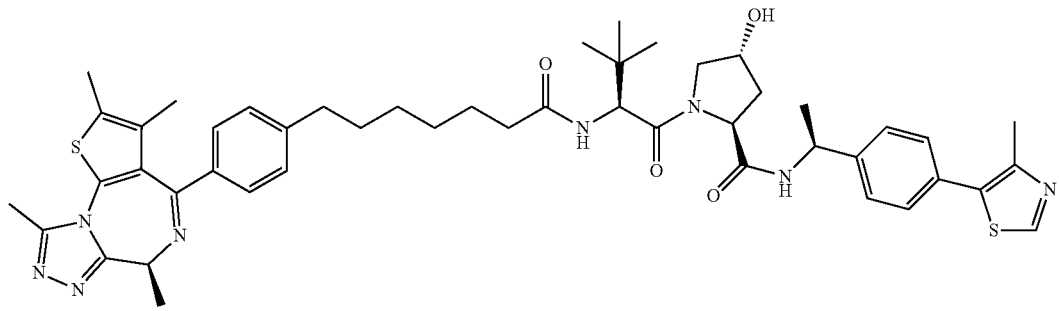 [SMILES: Cc1ncsc1-c1ccc([C@H](C)NC(=O)[C@@H]2C[C@@H](O)CN2C(=O)[C@@H](NC(=O)CCCCCCc2ccc(C3=N[C@@H](C)c4nnc(C)n4-c4sc(C)c(C)c43)cc2)C(C)(C)C)cc1]

By reaction and treatment in the same manner as in Example 192 (192-1)-(192-2) and using 6-heptenoic acid instead of 4-pentenoic acid, the title compound was obtained as a white powder. MS (ESI) m/z: 877.8 [M+H]+

Example 195

(195-1) (2S,4R)-1-{(2S)-3,3-dimethyl-2-[(9-{4-[(6S)-2,3,6,9-tetramethyl-6H-thieno[3,2-f][1,2,4]triazolo[4,3-a][1,4]diazepin-4-yl]phenyl}nonanoyl)amino]butanoyl}-4-hydroxy-N-{(1S)-1-[4-(4-methyl-1,3-thiazol-5-yl)phenyl]ethyl}pyrrolidine-2-carboxamide (Example Compound 195)

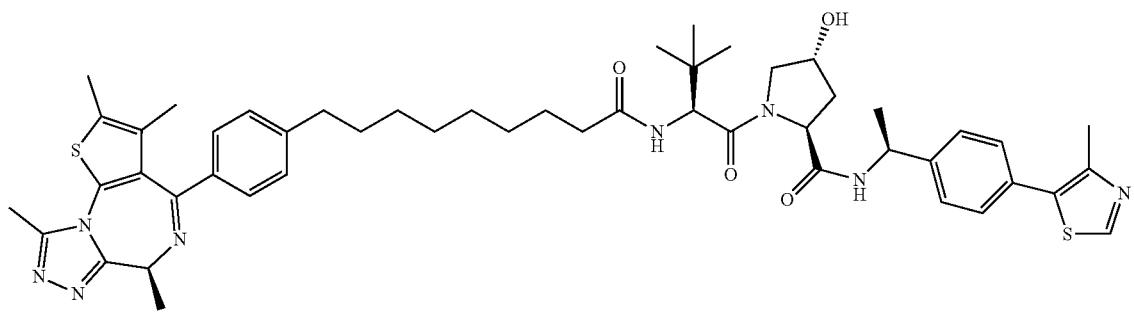 [SMILES: Cc1ncsc1-c1ccc([C@H](C)NC(=O)[C@@H]2C[C@@H](O)CN2C(=O)[C@@H](NC(=O)CCCCCCCCc2ccc(C3=N[C@@H](C)c4nnc(C)n4-c4sc(C)c(C)c43)cc2)C(C)(C)C)cc1]

By reaction and treatment in the same manner as in Example 192 (192-1)-(192-2) and using 8-nonenoic acid instead of 4-pentenoic acid, the title compound was obtained as a white powder. MS (ESI) m/z: 905.8 [M+H]+

Example 196

(196-1) methyl 1-[(4-bromophenyl)methoxy]cyclopropane-1-carboxylate (Example Compound 196-1)

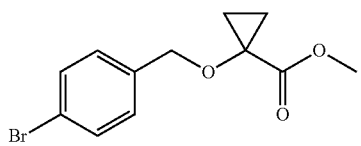 [SMILES: COC(=O)C1(OCc2ccc(Br)cc2)CC1]

To a mixture of methyl 1-hydroxycyclopropanecarboxylate (1.00 g), 4-bromobenzyl bromide (2.37 g) in N,N-dimethylformamide (25.0 mL) was added sodium hydride (60%, 362 mg), and the mixture was stirred at room temperature for 20 hr. The reaction mixture was acidified with 0.1N hydrochloric acid and extracted with ethyl acetate. The organic layer was washed successively with water and saturated brine, dried over anhydrous sodium sulfate, filtered and concentrated under reduced pressure. The residue was azeotropically distilled with toluene and purified by silica gel column chromatography (hexane:ethyl acetate=95:5-85:15) to give the title compound (2.06 g) as a colorless oil. MS (ESI) m/z: 285.2, 287.2 [M+H]+

(196-2) (2S,4R)-1-[(2S)-2-({1-[(4-bromophenyl)methoxy]cyclopropane-1-carbonyl}amino)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 196-2)

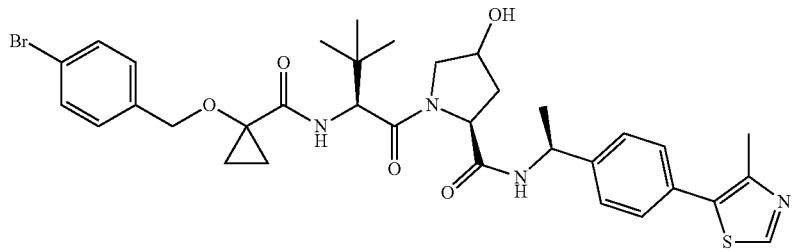 [SMILES: Cc1ncsc1-c1ccc([C@H](C)NC(=O)[C@@H]2CC(O)CN2C(=O)[C@@H](NC(=O)C2(OCc3ccc(Br)cc3)CC2)C(C)(C)C)cc1]

To a solution of Example compound 196-1 (0.32 g) in tetrahydrofuran (3.0 mL), methanol (3.0 mL) was added 4N aqueous sodium hydroxide solution (1.5 mL), and the mixture was stirred at room temperature for 4 hr. The reaction mixture was acidified with 0.5N hydrochloric acid and concentrated under reduced pressure. The resulting solid was suspension washed with water. The obtained compound was dissolved in N,N-dimethylformamide (4.0 mL), and N,N-diisopropylethylamine (0.65 mL), Reference Example compound 5 (450 mg) were added. HATU (462 mg) was added and the mixture was stirred at room temperature for 6 hr. Water was added to the reaction mixture and the mixture was extracted with ethyl acetate. The organic layer was washed successively with water and saturated brine, dried over anhydrous sodium sulfate, filtered and concentrated under reduced pressure. The residue was azeotropically distilled with toluene and purified by silica gel column chromatography (chloroform:methanol=99:1-93:7) to give the title compound (563 mg) as a white powder.
MS (ESI) m/z: 697.6, 699.6 [M+H]$^+$

(196-3) (2S,4R)-1-{(2S)-3,3-dimethyl-2-[(1-{[4-(4,4,5,5-tetramethyl-1,3,2-dioxaborolan-2-yl)phenyl]methoxy}cyclopropane-1-carbonyl)amino]butanoyl}-4-hydroxy-N-{(1S)-1-[4-(4-methyl-1,3-thiazol-5-yl)phenyl]ethyl}pyrrolidine-2-carboxamide (Example Compound 196-3)

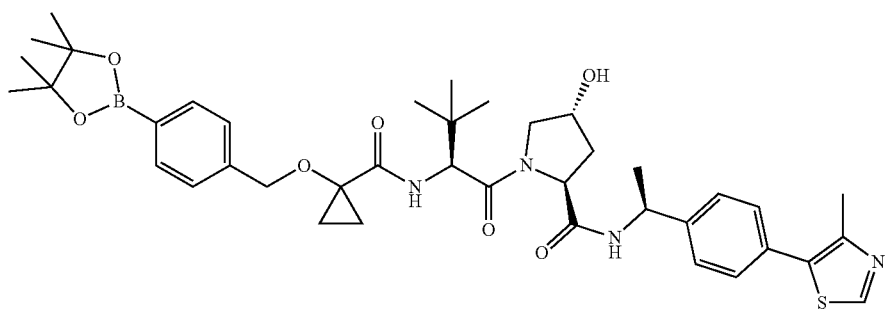 [SMILES: Cc1ncsc1-c1ccc([C@H](C)NC(=O)[C@@H]2C[C@@H](O)CN2C(=O)[C@@H](NC(=O)C2(OCc3ccc(B4OC(C)(C)C(C)(C)O4)cc3)CC2)C(C)(C)C)cc1]

A mixture of Example compound 196-2 (130 mg), bis(pinacolato)diboron (70 mg), potassium acetate (54 mg), 1,1'-bis(diphenylphosphino)ferrocene-palladium(II) dichloride dichloromethane complex (30 mg) and 1,4-dioxane (3.0 mL) was stirred with heating at 100° C. for 4 hr. Bis(pinacolato)diboron (70 mg), 1,1'-bis(diphenylphosphino)ferrocene-palladium(II) dichloride dichloromethane complex (30 mg) were added, and the mixture was stirred with heating at 100° C. for 5 hr. Water was added to the reaction mixture, and the mixture was extracted with ethyl acetate. The organic layer was washed with saturated brine, dried over anhydrous sodium sulfate, filtered and concentrated under reduced pressure. The residue was purified by silica gel column chromatography (ethyl acetate:methanol=99:1-90:10) to give the title compound (116 mg) as a pale-brown oil. MS (ESI) m/z: 745.7 [M+H]$^+$

(196-4) tert-butyl 2-acetamido-4,5-dimethylthiophene-3-carboxylate (Example Compound 196-4)

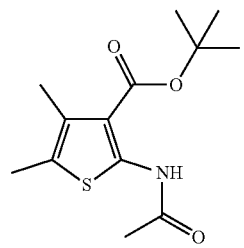 [SMILES: CC(=O)Nc1sc(C)c(C)c1C(=O)OC(C)(C)C]

To a mixed solution of t-butyl 2-amino-4,5-dimethylthiophene-3-carboxylate (14.0 g) in tetrahydrofuran (100 mL) and pyridine (14.9 mL) was added dropwise a solution of acetyl chloride (5.67 mL) in tetrahydrofuran (125 mL) under ice-cooling and the mixture was stirred under ice-cooling for 2 hr. The reaction mixture was concentrated under reduced pressure, water was added and the mixture was extracted 3 times with chloroform. The organic layer was concentrated under reduced pressure, and the resulting solid was suspension washed with diethyl ether and dried to give the title compound (13.3 g) as a white solid. MS (ESI) m/z: 270.1 [M+H]+

(196-5) tert-butyl 2-(3-{(1S)-1-[(tert-butoxycarbonyl)amino]ethyl}-5-methyl-4H-1,2,4-triazol-4-yl)-4,5-dimethylthiophene-3-carboxylate (Example Compound 196-5)

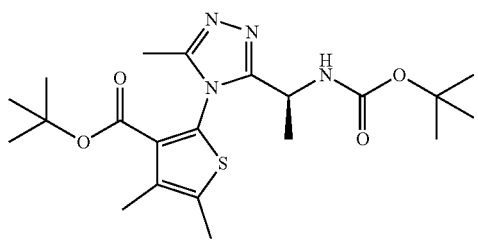 [SMILES: Cc1sc(-n2c(C)nnc2[C@H](C)NC(=O)OC(C)(C)C)c(C(=O)OC(C)(C)C)c1C]

A mixture of Example compound 196-4 (6.00 g) and Lawesson reagent (5.41 g) in 1,4-dioxane (60.0 mL) was divided into 3 batches. Under microwave radiation, the mixture was stirred with heating at 100° C. for 3 hr. The reaction mixture was concentrated under reduced pressure and the resulting solid was suspension washed with a mixture of diisopropyl ether:chloroform=8:1 and dried. The obtained compound was dissolved in tetrahydrofuran (130 mL), hydrazine monohydrate (3.32 mL) was added, and the mixture was stirred at room temperature for 1.5 hr. Water was added to the reaction mixture, and the mixture was extracted 3 times with ethyl acetate. The organic layer was washed with aqueous sodium hypochlorite solution, dried over anhydrous sodium sulfate, filtered and concentrated under reduced pressure to give an intermediate. A reaction mixture of a solution of N-(t-butoxycarbonyl)-L-alanine (8.62 g), N-methylmorpholine (6.26 mL) in tetrahydrofuran (130 mL) and isobutyl chloroformate (5.91 mL), which was prepared separately, was added dropwise to a solution of the above-mentioned intermediate in tetrahydrofuran (65.0 mL), and the mixture was stirred at room temperature for 2 hr. The reaction mixture was concentrated under reduced pressure, dissolved in chloroform, and washed with water. The organic layer was dried over anhydrous sodium sulfate, filtered and concentrated under reduced pressure. The residue was dissolved in 2-propanol (195 mL), and the mixture was stirred at 120° C. for 21 hr. The reaction mixture was concentrated under reduced pressure, and the residue was purified by silica gel column chromatography (chloroform:methanol) to give the title compound (9.04 g) as a pale-yellow oil. MS (ESI) m/z: 437.3 [M+H]+

(196-6) (6S)-2,3,6,9-tetramethyl-5,6-dihydro-4H-thieno[3,2-f] [1,2,4]triazolo[4,3-a][1,4]diazepin-4-one (Example Compound 196-6)

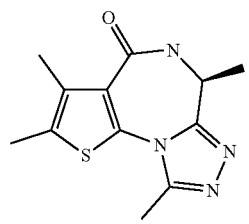

To a solution of Example compound 196-5 9.00 g) in 1,4-dioxane (90.0 mL) was added 4 M hydrogen chloride/dioxane solution (52.0 mL), and the mixture was stirred with heating at 60° C. for 2.5 hr. The reaction mixture was concentrated under reduced pressure, and the resulting solid was suspension washed with ethyl acetate. The obtained solid was dissolved in N,N-dimethylformamide (206 mL) and N,N-diisopropylethylamine (8.91 mL). HATU (11.8 g) was added and the mixture was stirred at room temperature for 1.5 hr. To the reaction mixture was added saturated aqueous sodium hydrogen carbonate, and the mixture was extracted with chloroform. The organic layer was dried over anhydrous sodium sulfate, filtered, concentrated under reduced pressure, and azeotropically distilled with toluene. The residue was purified by silica gel column chromatography (chloroform:methanol) and the obtained solid was suspension washed with diisopropyl ether and dried to give the title compound (3.72 g) as a pale-yellow solid.

MS (ESI) m/z: 263.1 [M+H]+

(196-7) (6S)-4-chloro-2,3,6,9-tetramethyl-6H-thieno[3,2-f] [1,2,4]triazolo[4,3-a][1,4]diazepine (Example Compound 196-7)

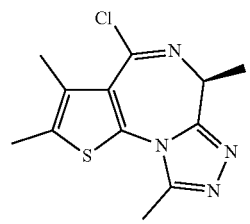

A suspension of Example compound 196-6 (3.00 g) in phosphorus oxychloride (25.0 mL) was stirred with heating at 105° C. for 3 hr. The reaction mixture was concentrated under reduced pressure and azeotropically distilled with toluene. The residue was dissolved in dichloromethane, and washed successively with saturated aqueous sodium hydrogen carbonate and saturated brine. The organic layer was dried over anhydrous sodium sulfate, filtered and concentrated. The residue was purified by silica gel column chromatography (chloroform:methanol) and the obtained solid was suspension washed with diethyl ether to give the title compound (1.78 g) as a pale-brown solid. MS (ESI) m/z: 281.1, 283.1 [M+H]+

(196-8) (2S,4R)-1-[(2S)-3,3-dimethyl-2-{[1-({4-[(6S)-2,3,6,9-tetramethyl-6H-thieno[3,2-f][1,2,4]triazolo[4,3-a] [1,4]diazepin-4-yl]phenyl}methoxy)cyclopropane-1-carbonyl]amino}butanoyl]-4-hydroxy-N-{(1S)-1-[4-(4-methyl-1,3-thiazol-5-yl)phenyl]ethyl}pyrrolidine-2-carboxamide (Example Compound 196)

By reaction and treatment in the same manner as in Example 207 (207-1)-(207-2) and using Example compound 191 instead of Example compound 62, the title compound was obtained as a white powder. MS (ESI) m/z: 906.7 [M+H]$^+$

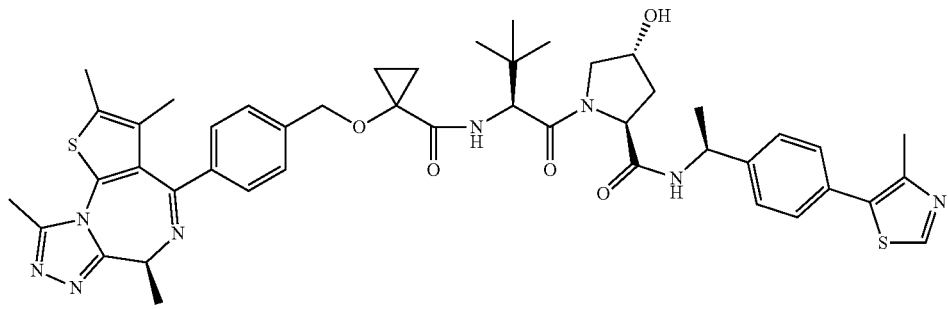 [SMILES: Cc1ncsc1-c1ccc([C@H](C)NC(=O)[C@@H]2C[C@@H](O)CN2C(=O)[C@@H](NC(=O)C2(OCc3ccc(C4=N[C@@H](C)c5nnc(C)n5-c5sc(C)c(C)c54)cc3)CC2)C(C)(C)C)cc1]

A mixture of Example compound 196-3 (112 mg), Example compound 196-7 (52 mg), potassium phosphate (91 mg), 1,2-dimethoxyethane (2.5 mL), water (0.21 mL), tetrakis(triphenylphosphine)palladium(0) (41 mg) was stirred at 85° C. for 3 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by silica gel column chromatography (chloroform:methanol=99:1-90:10) to give the title compound (97 mg) as a white powder.

MS (ESI) m/z: 863.7 [M+H]$^+$

Example 197

(197-1) (2S,4R)-1-{(2S)-2-[4-(4-{(6S)-6-[2-(dimethylamino)-2-oxoethyl]-2,3,9-trimethyl-6H-thieno[3,2-f][1,2,4]triazolo[4,3-a] [1,4]diazepin-4-yl}phenyl)butanamido]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 197)

Example 198

(198-1) ethyl 3-{4-[(6S)-2,3,6,9-tetramethyl-6H-thieno[3,2-f] [1,2,4]triazolo[4,3-a][1,4]diazepin-4-yl]phenyl}prop-2-ynoate (Example Compound 198-1)

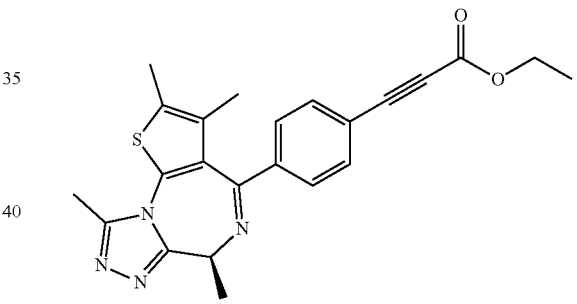

A mixture of ethyl 3-[4-(4,4,5,5-tetramethyl-1,3,2-dioxaborolan-2-yl)phenyl]propiolate (130 mg) described in WO 2017/085198, Example compound 196-7 (134 mg), potas-

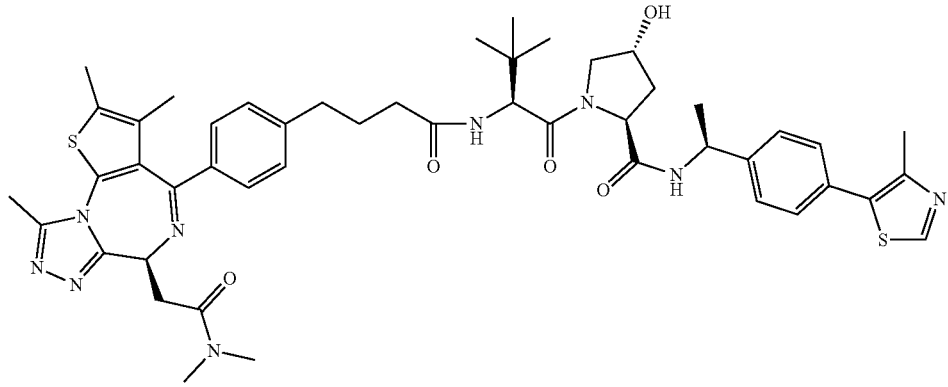 [SMILES: Cc1ncsc1-c1ccc([C@H](C)NC(=O)[C@@H]2C[C@@H](O)CN2C(=O)[C@@H](NC(=O)CCCc2ccc(C3=N[C@@H](CC(=O)N(C)C)c4nnc(C)n4-c4sc(C)c(C)c43)cc2)C(C)(C)C)cc1]

sium phosphate (184 mg), 1,2-dimethoxyethane (4.5 mL), water (0.43 mL), tetrakis(triphenylphosphine)palladium(0) (100 mg) was stirred at 85° C. for 2 hr. Water was added to the reaction mixture and the mixture was extracted with chloroform. The organic layer was washed with saturated brine, dried over anhydrous sodium sulfate, filtered, and the filtrate was concentrated under reduced pressure. The residue was purified by silica gel column chromatography (ethyl acetate:methanol=99:1-90:10) to give the title compound (68 mg) as a pale-yellow oil. MS (ESI) m/z: 419.3 [M+H]$^+$ (198-2) (2S,4R)-1-{(2S)-3,3-dimethyl-2-[(3-{4-[(6S)-2,3,6,9-tetramethyl-6H-thieno[3,2-f][1,2,4]triazolo[4,3-a] [1,4]diazepin-4-yl]phenyl}prop-2-ynoyl)amino]butanoyl}-4-hydroxy-N-{(1S)-1-[4-(4-methyl-1,3-thiazol-5-yl)phenyl]ethyl}pyrrolidine-2-carboxamide (Example Compound 198)

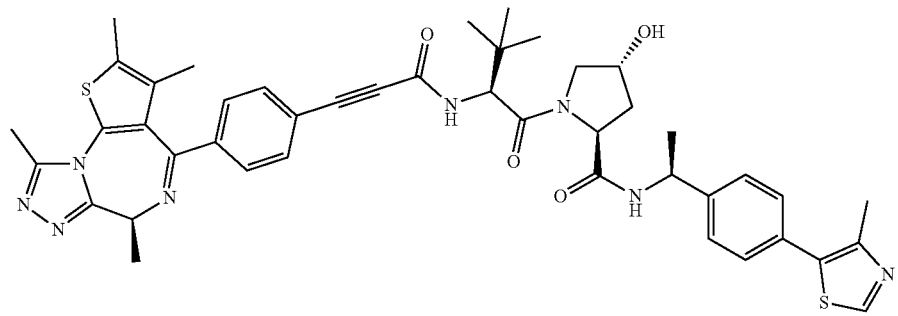 [SMILES: Cc1ncsc1-c1ccc([C@H](C)NC(=O)[C@@H]2C[C@@H](O)CN2C(=O)[C@@H](NC(=O)C#Cc2ccc(C3=N[C@@H](C)c4nnc(C)n4-c4sc(C)c(C)c43)cc2)C(C)(C)C)cc1]

To a solution of Example compound 198-1 (65 mg) in tetrahydrofuran (1.5 mL), methanol (1.5 mL) was added 2 M aqueous lithium hydroxide solution (1.0 mL), and the mixture was stirred at room temperature for 2 hr. The reaction mixture was acidified with 0.5N hydrochloric acid and extracted with chloroform. The organic layer was washed with saturated brine, dried over anhydrous sodium sulfate, filtered, and the filtrate was concentrated under reduced pressure. The obtained residue was dissolved in N,N-dimethylformamide (1.5 mL), and N,N-diisopropylethylamine (0.075 mL), Reference Example compound 5 (104 mg) were added. HATU (78 mg) was added and the mixture was stirred at room temperature for 14 hr. To the reaction solution was added methanol (1.0 mL) and the mixture was purified by preparative HPLC (10 mM aqueous ammonium carbonate solution-acetonitrile) and further purified by preparative HPLC (0.05% aqueous trifluoroacetic acid solution-0.05% acetonitrile solution of trifluoroacetic acid) to give the title compound (43 mg) as a white powder. MS (ESI) m/z: 817.7 [M+H]$^+$ Example 199

(199-1) 1-[(prop-2-en-1-yl)oxy]cyclopropane-1-carboxylic acid (Example Compound 199-1)

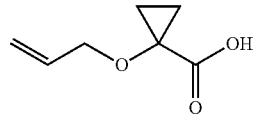

To a mixture of methyl 1-hydroxycyclopropanecarboxylate (400 mg), allyl bromide (0.36 mL) in N,N-dimethylformamide (8.0 mL) was added sodium hydride (60%, 145 mg), and the mixture was stirred at room temperature for 3 days. The reaction mixture was acidified with 0.1N hydrochloric acid and the mixture was extracted with diethyl ether. The organic layer was washed successively with water and saturated brine, dried over anhydrous sodium sulfate, filtered and concentrated under reduced pressure. The obtained residue was dissolved in tetrahydrofuran (8.0 mL) and methanol (8.0 mL), 4N aqueous sodium hydroxide solution (4.0 mL) was added, and the mixture was stirred at room temperature for 8 hr. The reaction mixture was washed with diisopropyl ether and the aqueous layer was acidified with 2N hydrochloric acid. The mixture was extracted with chloroform. The organic layer was washed with saturated brine, dried over anhydrous magnesium sulfate, filtered, and the filtrate was concentrated under reduced pressure to give the title compound as a pink oil. MS (ESI) m/z: 141.0 [M−H]$^-$ (199-2) (2S,4R)-1-[(2S)-3,3-dimethyl-2-{[1-(3-{4-[(6S)-2,3,6,9-tetramethyl-6H-thieno[3,2-f][1,2,4]triazolo[4,3-a] [1,4]diazepin-4-yl]phenyl}propoxy)cyclopropane-1-carbonyl]amino}butanoyl]-4-hydroxy-N-{(1S)-1-[4-(4-methyl-1,3-thiazol-5-yl)phenyl]ethyl}pyrrolidine-2-carboxamide (Example Compound 199)

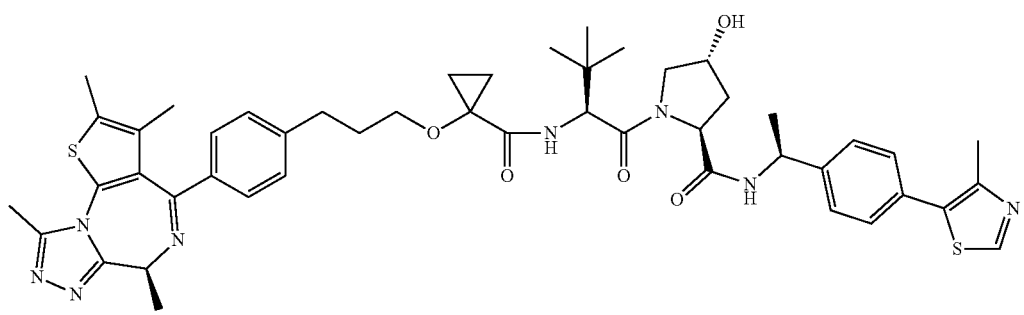 [SMILES: Cc1ncsc1-c1ccc([C@H](C)NC(=O)[C@@H]2C[C@@H](O)CN2C(=O)[C@@H](NC(=O)C2(OCCCc3ccc(C4=N[C@@H](C)c5nnc(C)n5-c5sc(C)c(C)c54)cc3)CC2)C(C)(C)C)cc1]

By reaction and treatment in the same manner as in Example 192 (192-1)-(192-2) and using Example compound 199-1 instead of 4-pentenoic acid, the title compound was obtained as a white powder. MS (ESI) m/z: 891.7 [M+H]$^+$ Example 200

(200-1) (4S)-6-(4-bromophenyl)-1,4-dimethyl-8,9-dihydro-4H,7H-cyclopenta[4,5]thieno[3,2-f][1,2,4]triazolo[4,3-a] [1,4]diazepine (Example Compound 200-1)

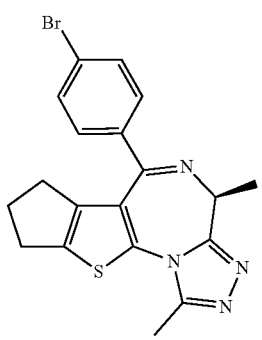 [SMILES: Cc1nnc2n1-c1sc3c(c1C(c1ccc(Br)cc1)=N[C@H]2C)CCC3]

By reaction and treatment in the same manner as in Reference Example 4 (4-1)-(4-4) and using cyclopentanone instead of ethyl methyl ketone, the title compound was obtained as a white powder. MS (ESI) m/z: 413.2, 415.2 [M+H]$^+$ (200-2) methyl 4'-[(4S)-1,4-dimethyl-8,9-dihydro-4H,7H-cyclopenta[4,5]thieno[3,2-f][1,2,4]triazolo[4,3-a] [1,4] diazepin-6-yl][1,1'-biphenyl]-4-carboxylate (Example Compound 200-2)

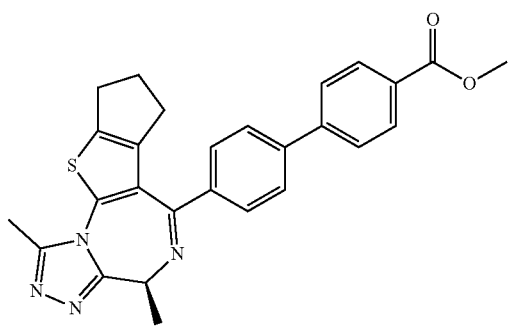

A mixture of Example compound 200-1 (150 mg), (4-methoxycarbonylphenyl)boronic acid (78 mg), sodium carbonate (77 mg), 1,4-dioxane (3.0 mL), water (1.0 mL) and 2-dicyclohexylphosphino-2',4',6'-triisopropylbiphenyl aminobiphenyl palladium chloride precatalyst (14 mg) was stirred with heating at 100° C. for 20 min under microwave radiation. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by NH silica gel column chromatography (hexane:ethyl acetate=80:20-0:100) to give the title compound (169 mg) as a pale-yellow powder.

MS (ESI) m/z: 469.4 [M+H]$^+$

461

(200-3) 4'-[(4S)-1,4-dimethyl-8,9-dihydro-4H,7H-cyclopenta[4,5]thieno[3,2-f][1,2,4]triazolo[4,3-a][1,4]diazepin-6-yl][1,1'-biphenyl]-4-carboxylic acid (Example Compound 200-3)

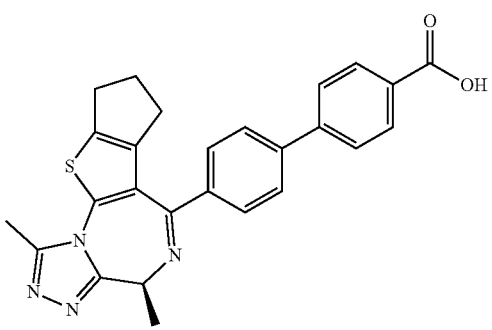 [SMILES: Cc1nnc2n1-c1sc3c(c1C(c1ccc(-c4ccc(C(=O)O)cc4)cc1)=N[C@H]2C)CCC3]

To a solution of Example compound 200-2 (162 mg) in tetrahydrofuran (1.0 mL), ethanol (3.5 mL) was added 1N aqueous sodium hydroxide solution (3.5 mL) and the mixture was stirred at room temperature for 16 hr. The reaction mixture was acidified with 1N hydrochloric acid and the resulting precipitate was collected by filtration to give the title compound (145 mg) as a pale-yellow solid.
MS (ESI) m/z: 455.4 [M+H]$^+$ (200-4) (2S,4R)-1-[(2S)-2-({4'-[(4S)-1,4-dimethyl-8,9-dihydro-4H,7H-cyclopenta[4,5]thieno[3,2-f][1,2,4]triazolo[4,3-a][1,4]diazepin-6-yl][1,1'-biphenyl]-4-carbonyl}amino)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 200)

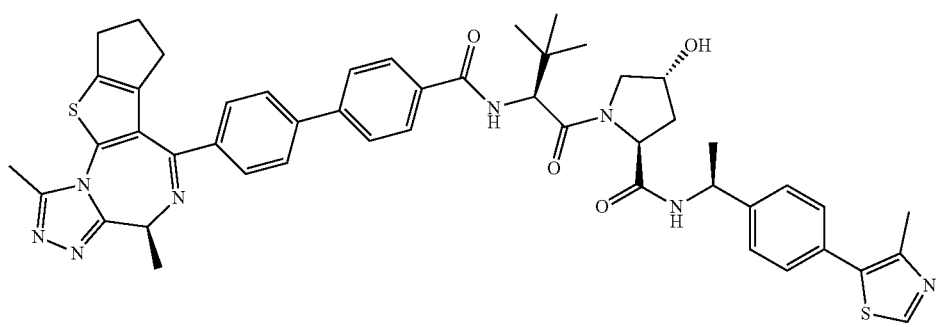 [SMILES: Cc1ncsc1-c1ccc([C@H](C)NC(=O)[C@@H]2C[C@@H](O)CN2C(=O)[C@@H](NC(=O)c2ccc(-c3ccc(C4=N[C@@H](C)c5nnc(C)n5-c5sc6c(c54)CCC6)cc3)cc2)C(C)(C)C)cc1]

To a solution of Example compound 200-3 (30 mg) in N,N-dimethylformamide (1.3 mL) were added Reference Example compound 5 (48 mg), N,N-diisopropylethylamine (0.034 mL) and HATU (50 mg) was added and the mixture was stirred at room temperature for 18 hr. To the reaction solution was added methanol (1.0 mL) and the mixture was purified by preparative HPLC (10 mM aqueous ammonium carbonate solution-acetonitrile) to give the title compound (45 mg) as a white powder.
MS (ESI) m/z: 881.7 [M+H]$^+$

462

Example 201

(201-1) tert-butyl (2E)-3-{4-[(6S)-2,3,6,9-tetramethyl-6H-thieno[3,2-f][1,2,4]triazolo[4,3-a][1,4]diazepin-4-yl]phenyl}prop-2-enoate (Example Compound 201-1)

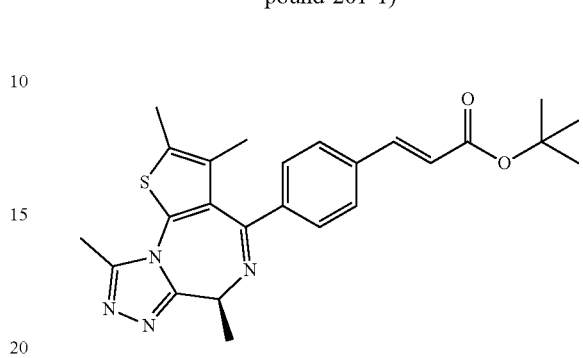

To a solution of Reference Example compound 4 (1.00 g) in 1,4-dioxane (5.0 mL) were added tert-butyl acrylate (0.91 mL), tris(dibenzylideneacetone)dipalladium(0) (57 mg), tri-tert-butylphosphonium tetrafluoroborate (72 mg), N,N-dicyclohexylmethylamine (1.1 mL), and the mixture was stirred with heating at 80° C. for 3 hr. Furthermore, tert-butyl acrylate (0.37 mL), tris(dibenzylideneacetone)dipalladium (0) (57 mg), tri-tert-butylphosphonium tetrafluoroborate (72 mg), N,N-dicyclohexylmethylamine (0.53 mL) were added and the mixture was stirred at 100° C. for 2 hr under microwave radiation. The reaction mixture was filtered through celite using acetonitrile, and the filtrate was concentrated under reduced pressure. The residue was purified by silica gel column chromatography (ethyl acetate:methanol=100:0-90:10) and further purified by NH silica gel column chromatography (hexane:ethyl acetate=80:20-50:50) to give the title compound (1.41 g) as a pale-yellow viscous compound.
MS (ESI) m/z: 449.4 [M+H]$^+$ (201-2) (2S,4R)-1-[(2S)-3,3-dimethyl-2-{[(2E)-3-{4-[(6S)-2,3,6,9-tetramethyl-6H-thieno[3,2-f][1,2,4]triazolo[4,3-a] [1,4]diazepin-4-yl]phenyl}prop-2-enoyl]amino}butanoyl]-4-hydroxy-N-{(1S)-1-[4-(4-methyl-1,3-thiazol-5-yl)phenyl]ethyl}pyrrolidine-2-carboxamide (Example Compound 201)

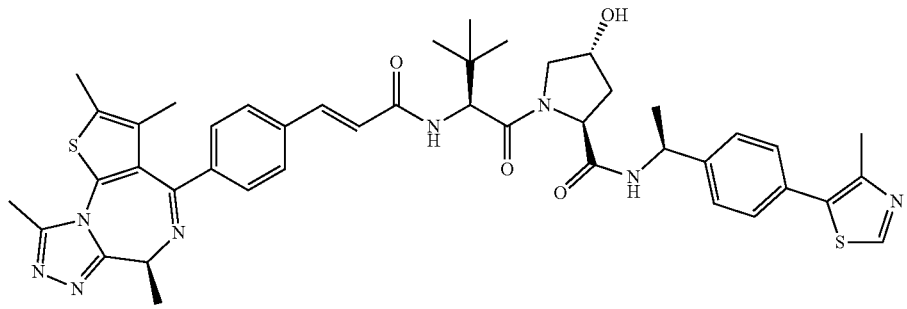 [SMILES: Cc1ncsc1-c1ccc([C@H](C)NC(=O)[C@@H]2C[C@@H](O)CN2C(=O)[C@@H](NC(=O)/C=C/c2ccc(C3=N[C@@H](C)c4nnc(C)n4-c4sc(C)c(C)c43)cc2)C(C)(C)C)cc1]

To a solution of Example compound 201-1 (85 mg) in dichloromethane (2.5 mL) was added trifluoroacetic acid (1.0 mL) and the mixture was stirred at room temperature for 3 hr. The reaction mixture was concentrated under reduced pressure and azeotropically distilled with toluene. The residue was dissolved in N,N-dimethylformamide (2.0 mL), Reference Example compound 5 (119 mg), HATU (130 mg), N,N-diisopropylethylamine (0.33 mL) were added and the mixture was stirred at room temperature for 18 hr. To the reaction solution was added methanol (1.0 mL) and the mixture was purified by preparative HPLC (10 mM aqueous ammonium carbonate solution-acetonitrile) to give the title compound (85 mg) as a white powder.

MS (ESI) m/z: 819.6 [M+H]+

Example 202

(202-1) 3-{4-[(6S)-2,3,6,9-tetramethyl-6H-thieno[3,2-f] [1,2,4]triazolo[4,3-a][1,4]diazepin-4-yl]phenyl}propanoic acid (Example Compound 202-1)

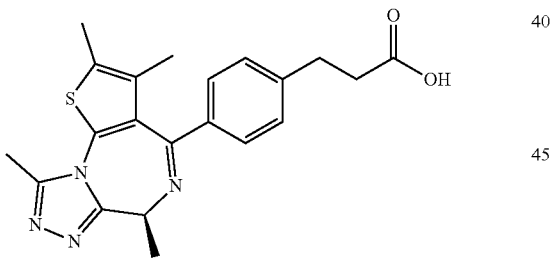

To a solution of Example compound 201-1 (500 mg) in ethanol (5.0 mL) was added 10% palladium carbon (60 mg) and, after hydrogen substitution, the mixture was stirred at room temperature for 5 days. The reaction mixture was filtered through diatomaceous earth using chloroform, and the filtrate was concentrated under reduced pressure. The residue was dissolved in dichloromethane (4.0 mL), trifluoroacetic acid (2.0 mL) was added and the mixture was stirred at room temperature for 2 hr. The reaction mixture was concentrated under reduced pressure and azeotropically distilled with toluene. The residue was dissolved in chloroform, 1N aqueous sodium hydroxide solution was slowly added to set to pH4, and the mixture was extracted with chloroform. The organic layer was washed with saturated aqueous ammonium chloride solution and saturated brine, dried over anhydrous sodium sulfate, filtered, and the filtrate was concentrated under reduced pressure to give the title compound (440 mg) as a pale-yellow viscous compound. MS (ESI) m/z: 395.3 [M+H]+

(202-2) (2S,4R)-1-[(2S)-3,3-dimethyl-2-(3-{4-[(6S)-2,3,6,9-tetramethyl-6H-thieno[3,2-f][1,2,4]triazolo[4,3-a] [1,4]diazepin-4-yl]phenyl}propanamido)butanoyl]-4-hydroxy-N-{(1S)-1-[4-(4-methyl-1,3-thiazol-5-yl)phenyl]ethyl}pyrrolidine-2-carboxamide (Example Compound 202)

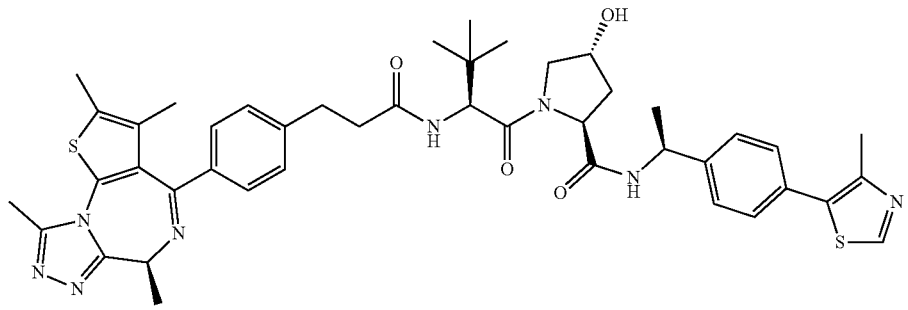 [SMILES: Cc1ncsc1-c1ccc([C@H](C)NC(=O)[C@@H]2C[C@@H](O)CN2C(=O)[C@@H](NC(=O)CCc2ccc(C3=N[C@@H](C)c4nnc(C)n4-c4sc(C)c(C)c43)cc2)C(C)(C)C)cc1]

To a solution of Example compound 202-1 (95 mg) and Reference Example compound 5 (136 mg) in N,N-dimethylformamide (2.0 mL) was added N,N-diisopropylethylamine (0.19 mL). HATU (148 mg) was added and the mixture was stirred at room temperature for 15 hr. To the reaction solution was added methanol (1.0 mL) and the mixture was purified by preparative HPLC (10 mM aqueous ammonium carbonate solution-acetonitrile) to give the title compound (125 mg) as a white powder. MS (ESI) m/z: 821.6 [M+H]⁺

Example 203

(203-1) (2S,4R)-1-[(2S)-2-({2',3-difluoro-4'-[(6S)-2,3,6,9-tetramethyl-6H-thieno[3,2-f][1,2,4]triazolo[4,3-a] [1,4]diazepin-4-yl][1,1'-biphenyl]-4-carbonyl}amino)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 203)

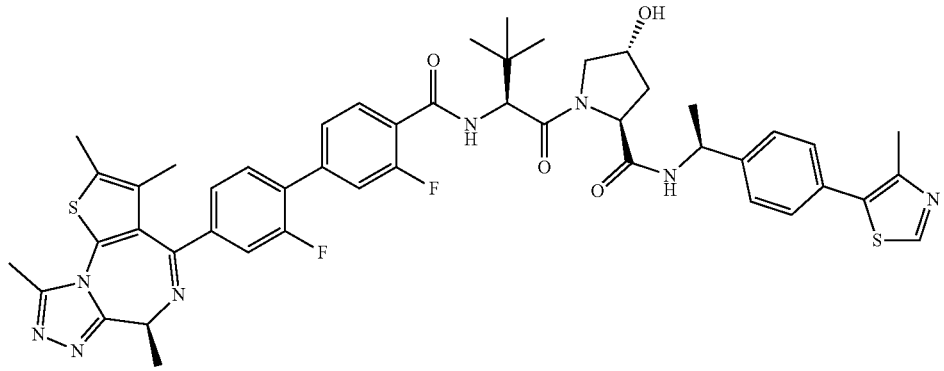 [SMILES: Cc1ncsc1-c1ccc([C@H](C)NC(=O)[C@@H]2C[C@@H](O)CN2C(=O)[C@@H](NC(=O)c2ccc(-c3ccc(C4=N[C@@H](C)c5nnc(C)n5-c5sc(C)c(C)c54)cc3F)cc2F)C(C)(C)C)cc1]

A mixture of (4-chloro-2-fluorophenyl)boronic acid (225 mg), t-butyl 4-bromo-2-fluorobenzoate (426 mg), potassium carbonate (446 mg), 1,2-dimethoxyethane (7.0 mL), water (1.6 mL), tetrakis(triphenylphosphine)palladium(0) (149 mg) was stirred with heating at 90° C. for 2 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by silica gel column chromatography (hexane:ethyl acetate=95:5-90:10). The obtained compound was dissolved in 1,4-dioxane (4.0 mL), and bis(pinacolato)diboron (136 mg), potassium acetate (70 mg), 2-dicyclohexylphosphino-2',4',6'-triisopropylbiphenyl aminobiphenyl palladium methanesulfonate precatalyst (15 mg) were added, and the mixture was stirred with heating at 95° C. for 2 hr. To the reaction mixture were added Example compound 196-7 (151 mg), potassium phosphate (228 mg), water (0.60 mL), tetrakis(triphenylphosphine)palladium(0) (103 mg), and the mixture was stirred with heating at 80° C. for 2 hr. Furthermore, tetrakis(triphenylphosphine)palladium(0) (62 mg) was added, and the mixture was stirred with heating at 80° C. for 2 hr. To the reaction mixture was added ethyl acetate and the insoluble material was filtered off through diatomaceous earth. Water was added and the mixture was extracted with ethyl acetate. The organic layer was washed with saturated brine, dried over anhydrous sodium sulfate, filtered, and the filtrate was concentrated under reduced pressure. The residue was purified by silica gel column chromatography (ethyl acetate:methanol=100:0-90:10). The obtained compound was dissolved in dichloromethane (2.0 mL), trifluoroacetic acid (0.80 mL) was added, and the mixture was stirred at room temperature for 5 hr. The reaction mixture was concentrated and azeotropically distilled with toluene. The obtained residue was dissolved in N,N-dimethylformamide (2.0 mL) and N,N-diisopropylethylamine (0.29 mL), and Reference Example compound 5 (122 mg), HATU (128 mg) were added and the mixture was stirred at room temperature for 4 days. To the reaction solution was added methanol (1.0 mL) and the mixture was purified by preparative HPLC (10 mM aqueous ammonium carbonate solution-acetonitrile) to give the title compound (67 mg) as a white powder. MS (ESI) m/z: 905.7 [M+H]⁺

Example 204

(204-1) 5-chloro-2-fluoro-4'-[(6S)-2,3,6,9-tetramethyl-6H-thieno[3,2-f][1,2,4]triazolo[4,3-a][1,4]diazepin-4-yl][1,1'-biphenyl]-4-carboxylic acid (Example Compound 204-1)

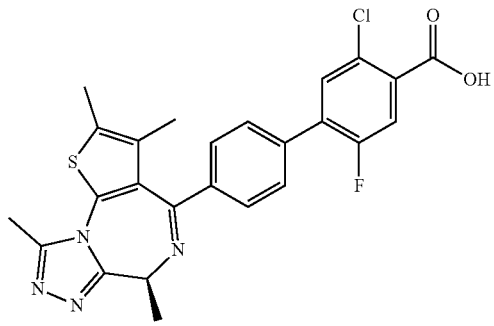 [SMILES: Cc1sc2c(c1C)C(c1ccc(-c3cc(Cl)c(C(=O)O)cc3F)cc1)=N[C@@H](C)c1nnc(C)n1-2]

A mixture of Reference Example compound 4 (370 mg), t-butyl 2-chloro-5-fluoro-4-(4,4,5,5-tetramethyl-1,3,2-dioxaborolan-2-yl)benzoate (330 mg), potassium phosphate (587 mg), 1,4-dioxane (5.0 mL), water (1.1 mL), 2-dicyclohexylphosphino-2'-6'-dimethoxybiphenyl aminobiphenyl palladium chloride precatalyst (66 mg) and S-phos (38 mg) was stirred with heating at 75° C. for 4 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by NH silica gel column chromatography (hexane:ethyl acetate=85:15-45:55). The obtained compound was dissolved in dichloromethane (4.0 mL), trifluoroacetic acid (1.5 mL) was added, and the mixture was stirred at room temperature for 2.5 hr. The reaction mixture was concentrated under reduced pressure, and the residue was dissolved in 1 M aqueous sodium carbonate solution and washed with toluene. The aqueous layer was acidified with 2N hydrochloric acid and the resulting precipitate was collected by filtration to give the title compound (310 mg) as a white solid.
MS (ESI) m/z: 495.3, 497.3 [M+H]⁺

(204-2) (2S,4R)-1-[(2S)-2-({5-chloro-2-fluoro-4'-[(6S)-2,3,6,9-tetramethyl-6H-thieno[3,2-f][1,2,4]triazolo[4,3-a] [1,4]diazepin-4-yl][1,1'-biphenyl]-4-carbonyl}amino)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 204)

To a solution of Example compound 204-1 (65 mg) and Reference Example compound 5 (95 mg) in N,N-dimethylformamide (1.5 mL) was added N,N-diisopropylethylamine (0.091 mL). HATU (100 mg) was added and the mixture was stirred at room temperature for 18 hr. To the reaction solution was added methanol (1.0 mL) and the mixture was purified by preparative HPLC (10 mM aqueous ammonium carbonate solution-acetonitrile) to give the title compound (54 mg) as a white powder.
MS (ESI) m/z: 921.6, 923.6 [M+H]⁺

Example 205

(205-1) [(6S)-4-(4-chlorophenyl)-2,3,9-trimethyl-6H-thieno[3,2-f] [1,2,4]triazolo[4,3-a][1,4]diazepin-6-yl]acetonitrile (Example Compound 205-1)

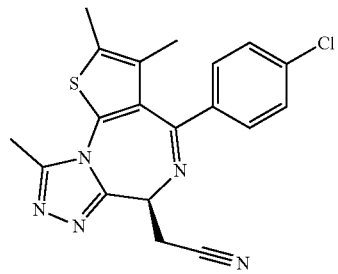

To a solution of (6S)-4-(4-chlorophenyl)-2,3,9-trimethyl-6H-thieno[3,2-f][1,2,4]triazolo[4,3-a][1,4]diazepine-6-acetic acid (500 mg) in N,N-dimethylformamide (6.0 mL) was added 28% aqueous ammonia (0.30 mL). 1-Hydroxy-7-azabenzotriazole (HOAt) (170 mg), 1-(3-dimethylaminopropyl)-3-ethylcarbodiimide hydrochloride (WSCI) (311 mg) were added, and the mixture was stirred at room temperature for 5 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was dissolved in tetrahydrofuran (18.0 mL) and N,N-diisopropylethylamine (0.85 mL). Trifluoroacetic anhydride (0.34 mL) was added and the mixture was stirred at room temperature for 3 hr. N,N-diisopropylethylamine (0.43 mL), trifluoroacetic anhydride (0.17 mL) were further added and the mixture was stirred at room temperature for 16 hr. Water was added to the reaction mixture and the mixture was extracted with ethyl acetate. The organic layer was washed with saturated brine, dried over anhydrous sodium sulfate, fil-

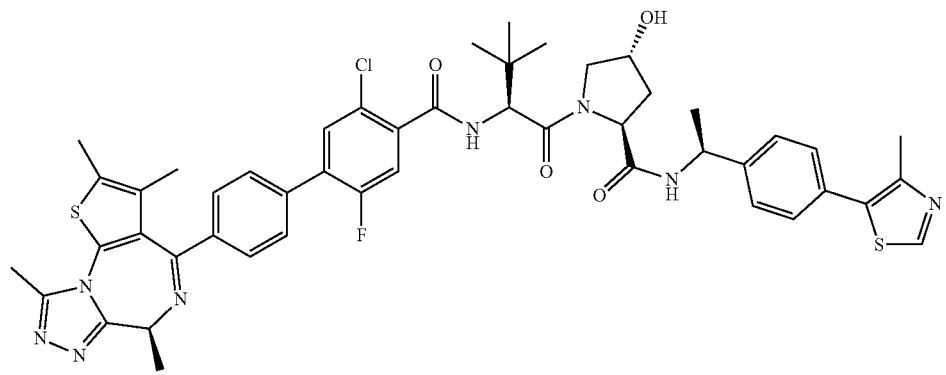 [SMILES: Cc1ncsc1-c1ccc([C@H](C)NC(=O)[C@@H]2C[C@@H](O)CN2C(=O)[C@@H](NC(=O)c2cc(F)c(-c3ccc(C4=N[C@@H](C)c5nnc(C)n5-c5sc(C)c(C)c54)cc3)cc2Cl)C(C)(C)C)cc1]

tered, and the filtrate was concentrated under reduced pressure. The residue was purified by NH silica gel column chromatography (ethyl acetate) to give the title compound (255 mg) as a milky white powder. MS (ESI) m/z: 382.2, 384.2 [M+H]+

(205-2) tert-butyl 4'-[(6S)-6-(cyanomethyl)-2,3,9-trimethyl-6H-thieno[3,2-f][1,2,4]triazolo[4,3-a][1,4]diazepin-4-yl][1,1'-biphenyl]-4-carboxylate (Example Compound 205-2)

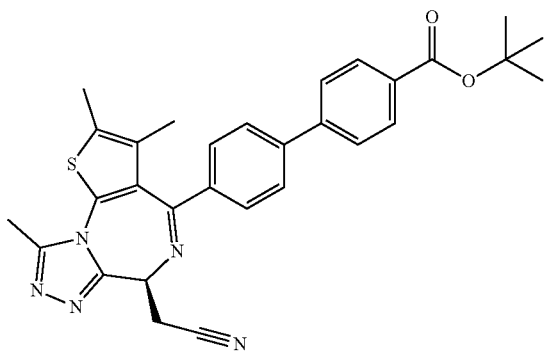 [SMILES: Cc1sc2c(c1C)C(c1ccc(-c3ccc(C(=O)OC(C)(C)C)cc3)cc1)=N[C@@H](CC#N)c1nnc(C)n1-2]

A mixture of Example compound 205-1 (114 mg), t-butyl 4-(4,4,5,5-tetramethyl-1,3,2-dioxaborolan-2-yl)benzoate (227 mg), potassium carbonate (124 mg), tetrahydrofuran (3.0 mL), water (0.80 mL), 2-dicyclohexylphosphino-2'-6'-dimethoxybiphenyl aminobiphenyl palladium chloride precatalyst (22 mg), S-phos (12 mg) was stirred with heating under reflux for 3 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by silica gel column chromatography (chloroform:methanol=99:1-90:10) to give the title compound (165 mg) as a gray powder. MS (ESI) m/z: 524.4 [M+H]+

(205-3) (2S,4R)-1-[(2S)-2-({4'-[(6S)-6-(cyanomethyl)-2,3,9-trimethyl-6H-thieno[3,2-f][1,2,4]triazolo[4,3-a][1,4]diazepin-4-yl][1,1'-biphenyl]-4-carbonyl}amino)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 205)

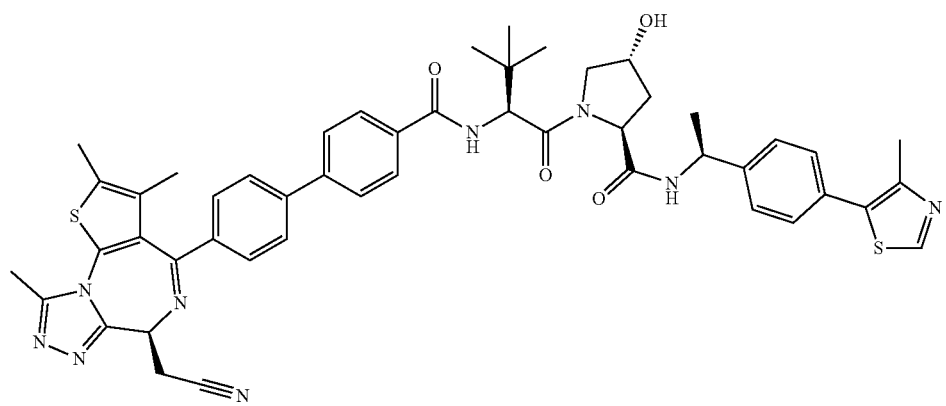 [SMILES: Cc1ncsc1-c1ccc([C@H](C)NC(=O)[C@@H]2C[C@@H](O)CN2C(=O)[C@@H](NC(=O)c2ccc(-c3ccc(C4=N[C@@H](CC#N)c5nnc(C)n5-c5sc(C)c(C)c54)cc3)cc2)C(C)(C)C)cc1]

To a solution of Example compound 205-2 (80 mg) in dichloromethane (3.0 mL) was added trifluoroacetic acid (1.0 mL) and the mixture was stirred at room temperature for 2 hr. The reaction mixture was concentrated under reduced pressure, and azeotropically distilled with toluene. The obtained residue was dissolved in N,N-dimethylformamide (1.5 mL), and N,N-diisopropylethylamine (0.22 mL), Reference Example compound 5 (92 mg) were added. HATU (96 mg) was added and the mixture was stirred at room temperature for 15 hr. To the reaction solution was added methanol (1.0 mL) and the mixture was purified by preparative HPLC (10 mM aqueous ammonium carbonate solution-acetonitrile) to give the title compound (92 mg) as a milky white powder. MS (ESI) m/z: 894.7 [M+H]+

Example 206

(206-1) (2S,4R)-1-{(2S)-2-[(2-fluoro-4'-{(6S)-2,3,9-trimethyl-6-[2-(methylamino)-2-oxoethyl]-6H-thieno[3,2-f] [1,2,4]triazolo[4,3-a][1,4]diazepin-4-yl}[1,1'-biphenyl]-4-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 206)

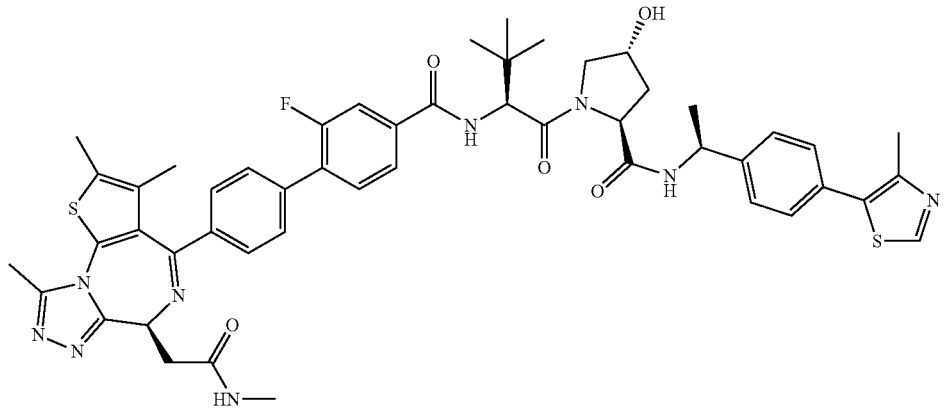 [SMILES: CNC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cc3F)cc2)c2c(sc(C)c2C)-n2c(C)nnc21]

By reaction and treatment in the same manner as in Example 207 (207-1)-(207-2) and using 2 M tetrahydrofuran solution of methylamine instead of 2 M tetrahydrofuran solution of dimethylamine, the title compound was obtained as a white powder. MS (ESI) m/z: 944.4 [M+H]$^+$ Example 207

(207-1) {(6S)-4-[2'-fluoro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetic acid (Example Compound 207-1)

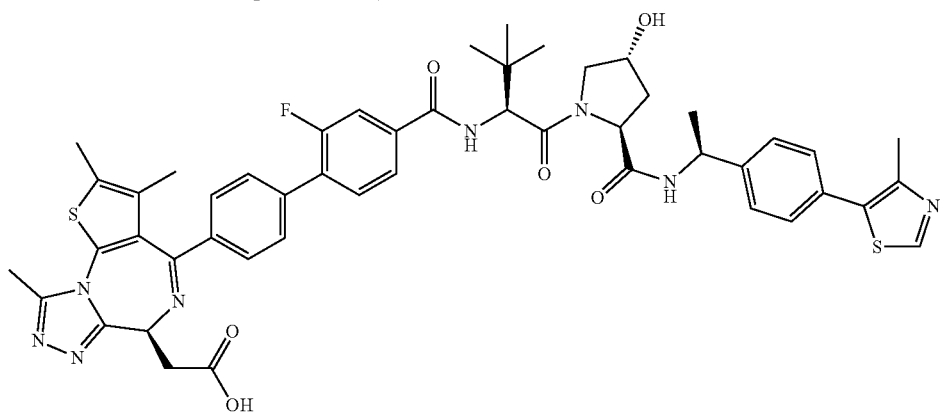 [SMILES: Cc1ncsc1-c1ccc([C@H](C)NC(=O)[C@@H]2C[C@@H](O)CN2C(=O)[C@@H](NC(=O)c2ccc(-c3ccc(C4=N[C@@H](CC(=O)O)c5nnc(C)n5-c5sc(C)c(C)c54)cc3)c(F)c2)C(C)(C)C)cc1]

To a solution of Example compound 62 (698 mg) in tetrahydrofuran (3.5 mL) and methanol (3.5 mL) was added 2 M aqueous lithium hydroxide solution (1.5 mL) and the mixture was stirred at room temperature for 1 hr. The reaction mixture was acidified with 0.5N hydrochloric acid under ice-cooling and the mixture was extracted with chloroform. The organic layer was washed with saturated brine, dried over anhydrous sodium sulfate, filtered, and the filtrate was concentrated under reduced pressure to give the title compound (750 mg) as a crude white powder. MS (ESI) m/z: 931.6 [M+H]$^+$ (207-2) (2S,4R)-1-{(2S)-2-[(4'-{(6S)-6-[2-(dimethylamino)-2-oxoethyl]-2,3,9-trimethyl-6H-thieno[3,2-f][1,2,4]triazolo[4,3-a][1,4]diazepin-4-yl}-2-fluoro [1,1'-biphenyl]-4-carbonyl)amino]-3,3-dimethylbutanoyl}-4-hydroxy-N-{(1S)-1-[4-(4-methyl-1,3-thiazol-5-yl)phenyl]ethyl}pyrrolidine-2-carboxamide (Example Compound 207)

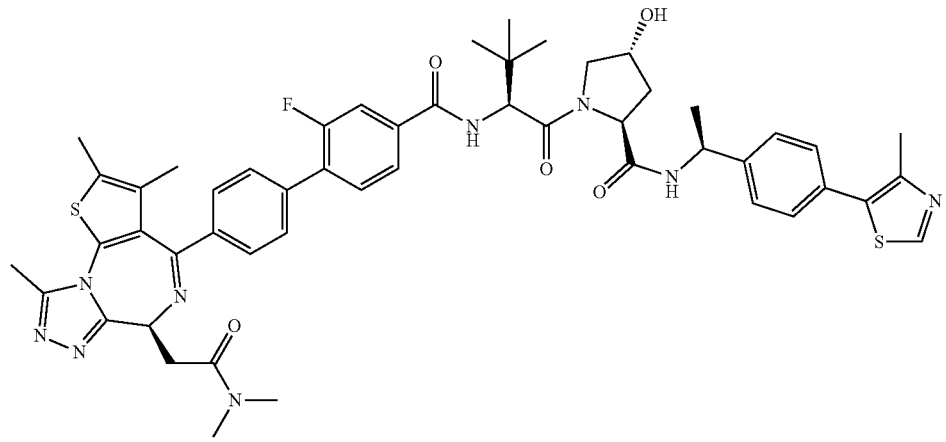 [SMILES: Cc1ncsc1-c1ccc([C@H](C)NC(=O)[C@@H]2C[C@@H](O)CN2C(=O)[C@@H](NC(=O)c2ccc(-c3ccc(C4=N[C@@H](CC(=O)N(C)C)c5nnc(C)n5-c5sc(C)c(C)c54)cc3)c(F)c2)C(C)(C)C)cc1]

To a solution of Example compound 207-1 (90 mg) in methanol (1.5 mL) was added 2 M tetrahydrofuran solution (0.11 mL) of dimethylamine. 4-(4,6-Dimethoxy[1.3.5]triazin-2-yl)-4-methylmorpholinium chloride hydrate (DMT-MM) (115 mg) was added, and the mixture was stirred at room temperature for 19 hr. Water was added to the reaction solution and the mixture was extracted with chloroform. The organic layer was concentrated under reduced pressure. The residue was purified by preparative HPLC (10 mM aqueous ammonium carbonate solution-acetonitrile) to give the title compound (73 mg) as a white powder. MS (ESI) m/z: 958.4 [M+H]$^+$ Example 208

(208-1) 2-[(6S)-4-(4-chlorophenyl)-2,3,9-trimethyl-6H-thieno[3,2-f][1,2,4]triazolo[4,3-a][1,4]diazepin-6-yl]-N-phenylacetamide (Example Compound 208-1)

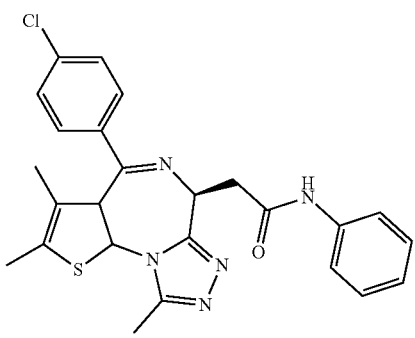 [SMILES: CC1=C(C)C2C(c3ccc(Cl)cc3)=N[C@@H](CC(=O)Nc3ccccc3)c3nnc(C)n3C2S1]

To a solution of (S)-4-(4-chlorophenyl)-2,3,9-trimethyl-6H-thieno[3,2-f][1,2,4]triazolo[4,3-a][1,4]diazepine-6-acetic acid (4.0 g) in tetrahydrofuran (20.0 mL) were added triethylamine (1.50 mL), pivaloyl chloride (1.30 mL) under ice-cooling, and the mixture was stirred at the same temperature for 0.5 hr. To the reaction mixture was added aniline (0.96 mL), and the mixture was stirred at room temperature for 5 hr. Water was added to the reaction mixture, and the mixture was extracted with ethyl acetate, and the extract was washed with saturated brine, dried over anhydrous sodium sulfate and filtered. The solvent was evaporated under reduced pressure. The obtained residue was purified by NH silica gel column chromatography (hexane:ethyl acetate) to give the title compound (4.95 g) as a white solid.
MS (ESI) m/z: 476.0, 478.0 [M+H]$^+$ (208-2) 2-[(6S)-4-(4-hydroxyphenyl)-2,3,9-trimethyl-6H-thieno[3,2-f][1,2,4]triazolo[4,3-a][1,4]diazepin-6-yl]-N-phenylacetamide (Example Compound 208-2)

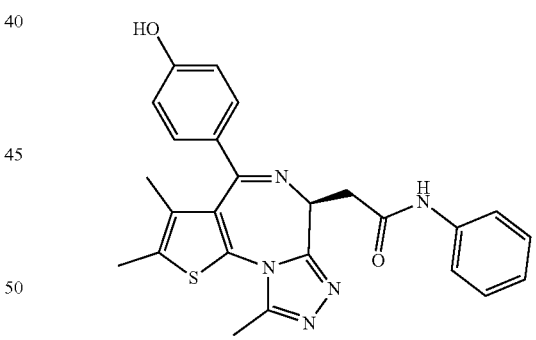

A mixture of Example compound 208-1 (503 mg), [(2-di-tert-butylphosphino-3,6-dimethoxy-2',4',6'-triisopropyl-1,1'-biphenyl)-2-(2'-amino-1,1'-biphenyl)]palladium(II) methanesulfonate (180 mg), potassium phosphate (342 mg), water (0.48 mL) in tetrahydrofuran (4.3 mL) was stirred with heating at 80° C. for 2 hr under microwave irradiation. Water was added to the reaction mixture and the mixture was extracted with chloroform. The organic layers were collected, dried over anhydrous sodium sulfate, and the solvent was evaporated under reduced pressure. The residue was purified by silica gel column chromatography (chloroform:methanol=100:0-93:7) to give a crudely purified title compound (330 mg) as a yellow solid. MS (ESI) m/z: 458.3 [M+H]$^+$ (208-3) tert-butyl (3-{4-[(6S)-6-(2-anilino-2-oxo-ethyl)-2,3,9-trimethyl-6H-thieno[3,2-f][1,2,4]triazolo[4,3-a][1,4]diazepin-4-yl]phenoxy}propoxy)acetate (Example Compound 208-3)

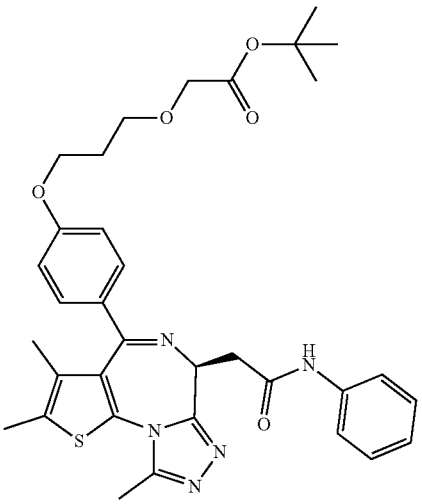 [SMILES: Cc1sc2c(c1C)C(c1ccc(OCCCOCC(=O)OC(C)(C)C)cc1)=N[C@@H](CC(=O)Nc1ccccc1)c1nnc(C)n1-2]

To a mixture of Example compound 208-2 (50 mg), potassium carbonate (20 mg), N,N-dimethylformamide (1.5 mL) was added tert-butyl 2-[3-(p-tolylsulfonyloxy)propoxy]acetate (45 mg) and the mixture was stirred at 70° C. for 3.5 hr. Water was added to the reaction mixture, and the mixture was extracted twice with ethyl acetate. The combined organic layer was washed 3 times with water and one time with saturated brine, dried over anhydrous sodium sulfate and filtered. The solvent was evaporated under reduced pressure. The obtained residue was purified by NH silica gel column chromatography (ethyl acetate:methanol=100:0-95:5) to give the title compound (56 mg) as a white solid. MS (ESI) m/z: 630.5 [M+H]$^+$ (208-4) (3-{4-[(6S)-6-(2-anilino-2-oxoethyl)-2,3,9-trimethyl-6H-thieno[3,2-f][1,2,4]triazolo[4,3-a][1,4]diazepin-4-yl]phenoxy}propoxy)acetic acid (Example Compound 208-4)

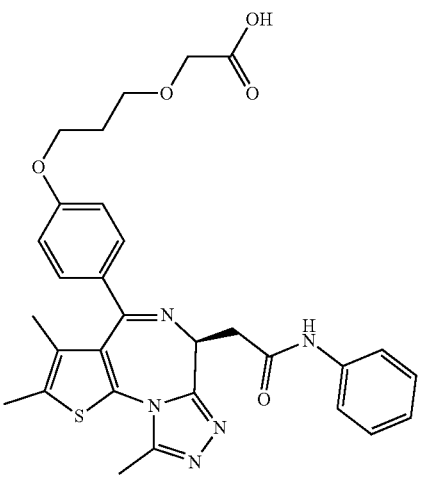 [SMILES: Cc1sc2c(c1C)C(c1ccc(OCCCOCC(=O)O)cc1)=N[C@@H](CC(=O)Nc1ccccc1)c1nnc(C)n1-2]

To a solution of Example compound 208-4 (54 mg) in dichloromethane (1.0 mL) was added trifluoroacetic acid (0.25 mL) under ice-cooling, and the mixture was stirred at room temperature for 3.5 hr. The reaction mixture was concentrated under reduced pressure, and an operation to add toluene to the residue and concentrate the mixture was performed twice. The residue was dissolved in ethyl acetate, water and saturated aqueous sodium hydrogen carbonate were added. The organic layer was separated and further extracted with water and saturated aqueous sodium hydrogen carbonate. The obtained aqueous layers were combined, acidified with 5% aqueous citric acid solution and extracted twice with ethyl acetate. The obtained organic layers were combined, washed successively with water and saturated brine, dried over anhydrous sodium sulfate and filtered. The filtrate was concentrated under reduced pressure and dried under reduced pressure to give the title compound (45 mg) as a pale-yellow solid.

MS (ESI) m/z: 574.2 [M+H]$^+$ (208-5) (2S,4R)-1-{(2S)-2-[2-(3-{4-[(6S)-6-(2-anilino-2-oxoethyl)-2,3,9-trimethyl-6H-thieno[3,2-f][1,2,4]triazolo[4,3-a] [1,4]diazepin-4-yl]phenoxy}propoxy)acetamido]-3,3-dimethylbutanoyl}-4-hydroxy-N-{[4-(4-methyl-1,3-thiazol-5-yl)phenyl]methyl}pyrrolidine-2-carboxamide (Example Compound 208)

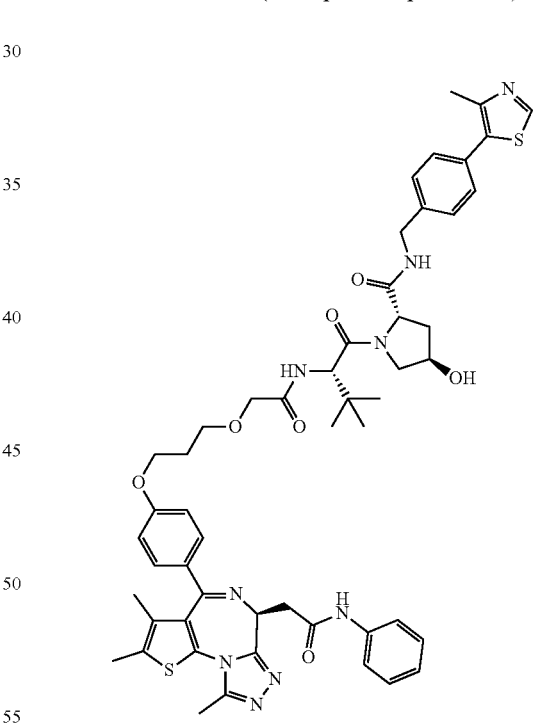

To a solution of Example compound 208-4 (23 mg), Reference Example compound 6 (19 mg) in tetrahydrofuran (2.0 mL), water (0.4 mL), N,N-diisopropylethylamine (0.015 mL) was added DMT-MM (17 mg) under ice-cooling, and the mixture was stirred at room temperature for 17 hr. To the reaction mixture were added saturated aqueous sodium hydrogen carbonate and water and the mixture was extracted twice with ethyl acetate. The obtained organic layers were combined, washed with saturated brine, 5% citric acid water (aqueous layer pH=3-4). The obtained organic layer was washed twice with saturated brine, dried over anhydrous sodium sulfate and filtered. The solvent was evaporated under reduced pressure. The residue was purified by silica gel column chromatography (chloroform:methanol=100:0-90:10) to give the title compound (22 mg) as a white powder. MS (ESI) m/z: 986.5 [M+H]+

Example 209

(209-1) tert-butyl 4'-[(6S)-2-(hydroxymethyl)-6-(2-methoxy-2-oxoethyl)-3,9-dimethyl-6H-thieno[3,2-f][1,2,4]triazolo[4,3-a] [1,4]diazepin-4-yl][1,1'-biphenyl]-4-carboxylate (Example compound 209-1)

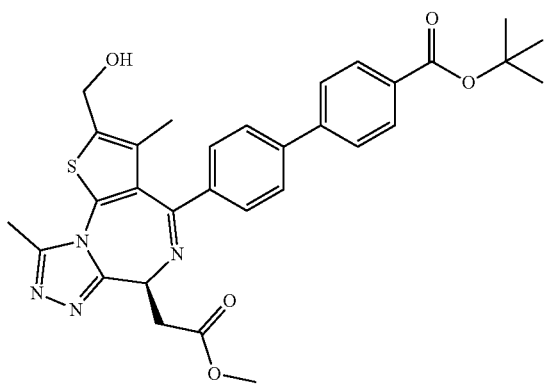 [SMILES: COC(=O)C[C@@H]1N=C(c2ccc(-c3ccc(C(=O)OC(C)(C)C)cc3)cc2)c2c(sc(CO)c2C)-n2c(C)nnc21]

A mixture of methyl [(6S)-4-(4-chlorophenyl)-2-(hydroxymethyl)-3,9-dimethyl-6H-thieno[3,2-f] [1,2,4]triazolo[4,3-a][1,4]diazepin-6-yl]acetate (500 mg) described in WO 2006/129623, (4-t-butoxycarbonylphenyl)boronic acid (386 mg), potassium phosphate (616 mg), tetrahydrofuran (5.0 mL), water (0.52 mL), 2-dicyclohexylphosphino-2'-6'-dimethoxybiphenyl aminobiphenyl palladium chloride precatalyst (42 mg), S-phos (24 mg) was stirred with heating under reflux for 3 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by NH silica gel column chromatography (ethyl acetate:methanol=99:1-90:10) to give the title compound (610 mg) as a milky white solid.

MS (ESI) m/z: 573.2 [M+H]+

(209-2) methyl {(6S)-2-(hydroxymethyl)-4-[4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-3,9-dimethyl-6H-thieno[3,2-f][1,2,4]triazolo[4,3-a][1,4]diazepin-6-yl}acetate (Example Compound 209)

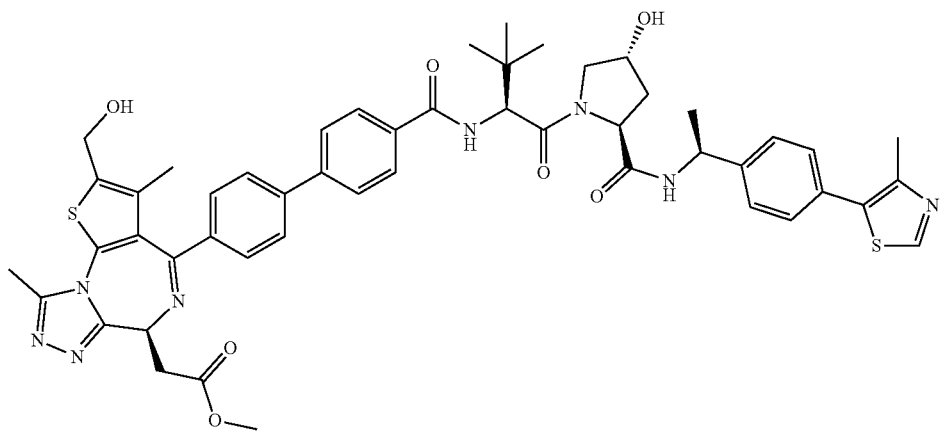 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)(C)C)cc3)cc2)c2c(sc(CO)c2C)-n2c(C)nnc21]

To a solution of Example compound 209-1 (80 mg) in dichloromethane (2.5 mL) was added trifluoroacetic acid (1.0 mL) and the mixture was stirred at room temperature for 2 hr. The reaction mixture was concentrated under reduced pressure and azeotropically distilled with toluene. The obtained residue was dissolved in N,N-dimethylformamide (1.5 mL), and N,N-diisopropylethylamine (0.24 mL), Reference Example compound 5 (86 mg) were added. HATU (78 mg) was added and the mixture was stirred at room temperature for 2 hr. To the reaction solution was added methanol (1.0 mL) and the mixture was purified by preparative HPLC (10 mM aqueous ammonium carbonate solution-acetonitrile) to give the title compound (94 mg) as a milky white powder. MS (ESI) m/z: 943.7 [M+H]+

Example 210

(210-1) tert-butyl (2S,4R)-4-hydroxy-2-({(1S)-1-[4-(4-methyl-1,3-thiazol-5-yl)phenyl]ethyl}carbamoyl)pyrrolidine-1-carboxylate (Example Compound 210-1)

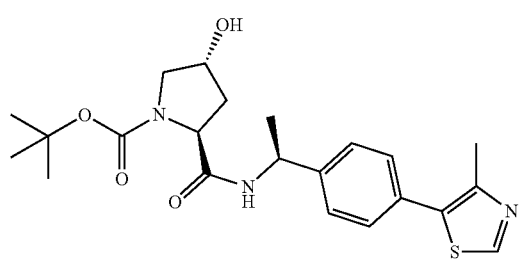 [SMILES: Cc1ncsc1-c1ccc([C@H](C)NC(=O)[C@@H]2C[C@@H](O)CN2C(=O)OC(C)(C)C)cc1]

To a mixture of Reference Example compound 5-3 (944 mg), (2S,4R)-1-t-butoxycarbonyl-4-hydroxypyrrolidine-2-carboxylic acid (1.0 g) in N,N-dimethylformamide (22.0 mL) were added N,N-diisopropylethylamine (2.99 mL) and HATU (1.97 g) and the mixture was stirred at room temperature for 1.5 hr. Water was added to the reaction mixture, and the mixture was extracted with ethyl acetate. The organic layer was washed with saturated brine, dried over anhydrous magnesium sulfate, filtered and concentrated under reduced pressure. The residue was purified by silica gel column chromatography (ethyl acetate:methanol=100:0-90:10) to give the title compound (2.02 g) as a brown crude oil. MS (ESI) m/z: 432.3 [M+H]+

(210-2) (2S,4R)-4-hydroxy-N-{(1S)-1-[4-(4-methyl-1,3-thiazol-5-yl)phenyl]ethyl}pyrrolidine-2-carboxamide hydrochloride (Example Compound 210-2)

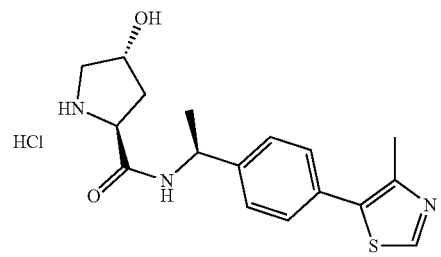 [SMILES: Cl ; Cc1ncsc1-c1ccc([C@H](C)NC(=O)[C@@H]2C[C@@H](O)CN2)cc1]

To a mixed solution of Example compound 210-1 (2.02 g) in dichloromethane (4.0 mL), methanol (6.0 mL) was added 4 M hydrogen chloride/dioxane solution (4.3 mL) and the mixture was stirred at room temperature for 6 hr. The reaction mixture was concentrated under reduced pressure and azeotropically distilled with toluene. To the residue was added hexane and the mixture was concentrated under reduced pressure. The obtained solid was suspension washed with diethyl ether to give the title compound (1.33 g) as a pale-brown powder.

MS (ESI) m/z: 332.4 [M+H]+

(210-3) methyl {(6S)-4-[4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3-methyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 210)

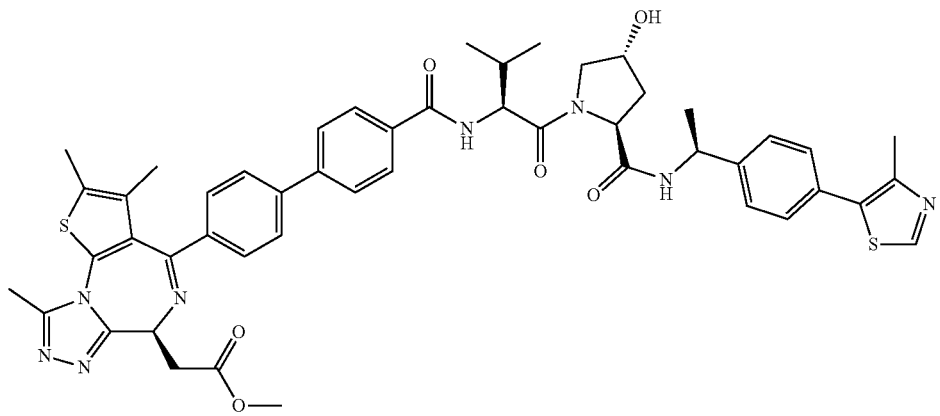 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)C(C)C)cc3)cc2)c2c(sc(C)c2C)-n2c(C)nnc21]

481

To a mixture of Example compound 210-2 (100 mg), N-(t-butoxycarbonyl)-L-valine (71 mg), N,N-dimethylformamide (2.5 mL) were added N,N-diisopropylethylamine (0.19 mL) and HATU (155 mg) and the mixture was stirred at room temperature for 1 hr. Water was added to the reaction mixture, and the mixture was extracted with ethyl acetate. The organic layer was washed with saturated brine, dried over anhydrous sodium sulfate, filtered and concentrated under reduced pressure. The obtained residue was dissolved in dichloromethane (4.0 mL), trifluoroacetic acid (2.0 mL) was added and the mixture was stirred at room temperature for 2 hr. The reaction mixture was concentrated under reduced pressure and azeotropically distilled with toluene. The residue was dissolved in N,N-dimethylformamide (2.0 mL), and N,N-diisopropylethylamine (0.38 mL), Example compound 90-1 (163 mg), HATU (207 mg) were added and the mixture was stirred at room temperature for 4 hr. To the reaction solution was added methanol (2.0 mL) and the mixture was purified by preparative HPLC (10 mM aqueous ammonium carbonate solution-acetonitrile) to give the title compound (150 mg) as a pale-yellow powder.

MS (ESI) m/z: 913.4 [M+H]$^+$

Example 211

(211-1) methyl {(6S)-4-[4'-({(1S)-2-[(2S,4R)-4-hydroxy-2-({(1S)-1-[4-(4-methyl-1,3-thiazol-5-yl)phenyl]ethyl}carbamoyl)pyrrolidin-1-yl]-2-oxo-1-phenylethyl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 211)

482 under reduced pressure. The obtained residue was dissolved in dichloromethane (4.0 mL), trifluoroacetic acid (2.0 mL) was added and the mixture was stirred at room temperature for 2 hr. The reaction mixture was concentrated under reduced pressure and azeotropically distilled with toluene. The residue was dissolved in N,N-dimethylformamide (2.0 mL), and N,N-diisopropylethylamine (0.38 mL), Example compound 90-1 (163 mg), HATU (207 mg) were added and the mixture was stirred at room temperature for 4 hr. To the reaction solution was added methanol (2.0 mL) and the mixture was purified by preparative HPLC (10 mM aqueous ammonium carbonate solution-acetonitrile) to give the title compound (88 mg) as a pale-yellow powder.

MS (ESI) m/z: 947.4 [M+H]$^+$

Example 212

(212-1) tert-butyl (2S)-2-(5-bromo-1-oxo-1,3-dihydro-2H-isoindol-2-yl)-3-methylbutanoate (Example Compound 212-1)

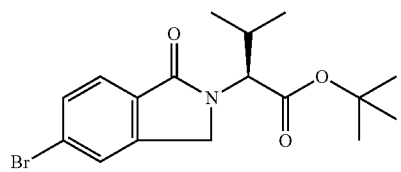

To a solution of 4-bromo-2-bromomethylbenzoic acid (1.00 g) in toluene (10.0 mL) were added t-butyl L-valinate (1.02 g) and N,N-diisopropylethylamine (1.1 mL), and the mixture was stirred with heating under reflux for 17 hr.

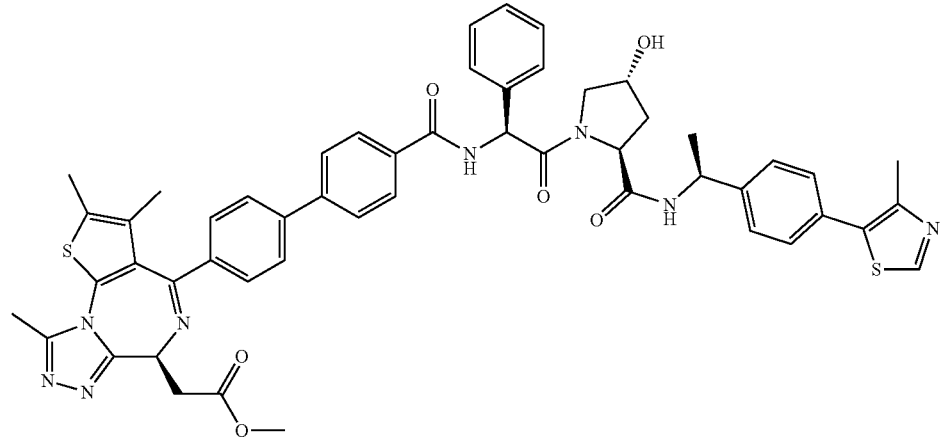 [SMILES: COC(=O)C[C@@H]1N=C(c2ccc(-c3ccc(C(=O)N[C@H](C(=O)N4C[C@H](O)C[C@H]4C(=O)N[C@@H](C)c4ccc(-c5scnc5C)cc4)c4ccccc4)cc3)cc2)c2c(sc(C)c2C)-n2c(C)nnc21]

To a mixture of Example compound 210-2 (100 mg), N-(t-butoxycarbonyl)-L-2-phenylglycine (82 mg), acetonitrile (5.0 mL) were added N,N-diisopropylethylamine (0.19 mL), HATU (155 mg), and the mixture was stirred at room temperature for 1 hr. Water was added to the reaction mixture, and the mixture was extracted with ethyl acetate. The organic layer was washed with saturated brine, dried over anhydrous sodium sulfate, filtered and concentrated Water was added to the reaction mixture, and the mixture was extracted with ethyl acetate. The organic layer was washed with saturated brine, dried over anhydrous sodium sulfate, filtered and concentrated under reduced pressure. The obtained solid was suspension washed with diisopropyl ether to give the title compound (828 mg) as a milky white powder.

MS (ESI) m/z: 368.3, 370.3 [M+H]$^+$ (212-2) tert-butyl (2S)-2-(5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1-oxo-1,3-dihydro-2H-isoindol-2-yl)-3-methylbutanoate (Example Compound 212-2)

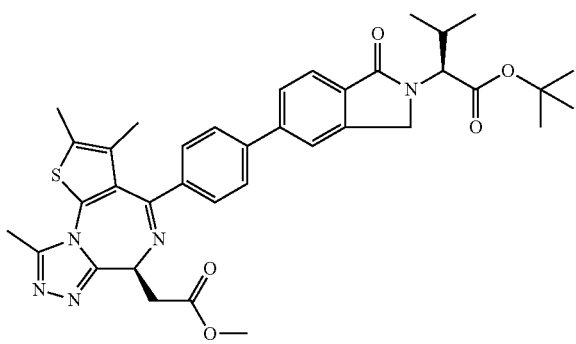 [SMILES: COC(=O)C[C@@H]1N=C(c2ccc(-c3ccc4c(c3)CN([C@H](C(=O)OC(C)(C)C)C(C)C)C4=O)cc2)c2c(sc(C)c2C)-n2c(C)nnc21]

To a solution of Example compound 212-1 (117 mg) in tetrahydrofuran (3.0 mL) were added Reference Example compound 3 (193 mg), tetrakis(triphenylphosphine)palladium(0) (37 mg), potassium phosphate (203 mg) and water (0.70 mL) and the mixture was stirred with heating under reflux for 2 hr. Furthermore, tetrakis(triphenylphosphine)palladium(0) (37 mg) was added and the mixture was stirred with heating under reflux for 2 hr. Water was added to the reaction mixture, and the mixture was extracted with ethyl acetate. The organic layer was washed with saturated brine, dried over anhydrous sodium sulfate, filtered and concentrated under reduced pressure. The residue was purified by NH silica gel column chromatography (hexane:ethyl acetate=50:50-0:100) and further purified by silica gel column chromatography (ethyl acetate:methanol=99:1-90:10) to give the title compound (125 mg) as a white solid.

MS (ESI) m/z: 668.3 [M+H]+

(212-3) methyl {(6S)-4-[4-(2-{(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3-methyl-1-oxobutan-2-yl}-1-oxo-2,3-dihydro-1H-isoindol-5-yl)phenyl]-2,3,9-trimethyl-6H-thieno[3,2-f][1,2,4]triazolo[4,3-a][1,4]diazepin-6-yl}acetate (Example Compound 212)

To a solution of Example compound 212-2 (60 mg) in dichloromethane (1.5 mL) was added trifluoroacetic acid (0.60 mL) and the mixture was stirred at room temperature for 2 hr. The reaction mixture was concentrated under reduced pressure and azeotropically distilled with toluene. The residue was dissolved in N,N-dimethylformamide (1.0 mL), and N,N-diisopropylethylamine (0.15 mL), Example compound 210-2 (48 mg), HATU (50 mg) were added and the mixture was stirred at room temperature for 2.5 hr. To the reaction solution was added methanol (1.0 mL) and the mixture was purified by preparative HPLC (10 mM aqueous ammonium carbonate solution-acetonitrile) to give the title compound (70 mg) as a milky white solid.

MS (ESI) m/z: 925.4 [M+H]+

Example 213

(213-1) [(6S)-4-(4-chlorophenyl)-3,6,9-trimethyl-6H-thieno[3,2-f] [1,2,4]triazolo[4,3-a][1,4]diazepin-2-yl]methyl acetate (Example Compound 213-1)

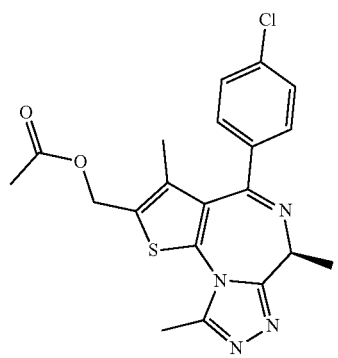

To a mixture of Reference Example compound 12 (1.00 g), manganese(III) acetate dihydrate (1.88 g), acetic acid (9.6 mL) and acetic anhydride (5.3 mL) was added concentrated sulfuric acid (1.50 mL) and the mixture was stirred at room temperature for 1 day. The reaction mixture was added to ice water and the mixture was extracted with ethyl acetate. The organic layer was washed with 1N aqueous sodium hydroxide solution, dried over anhydrous sodium sulfate, filtered and concentrated under reduced pressure. The resi-

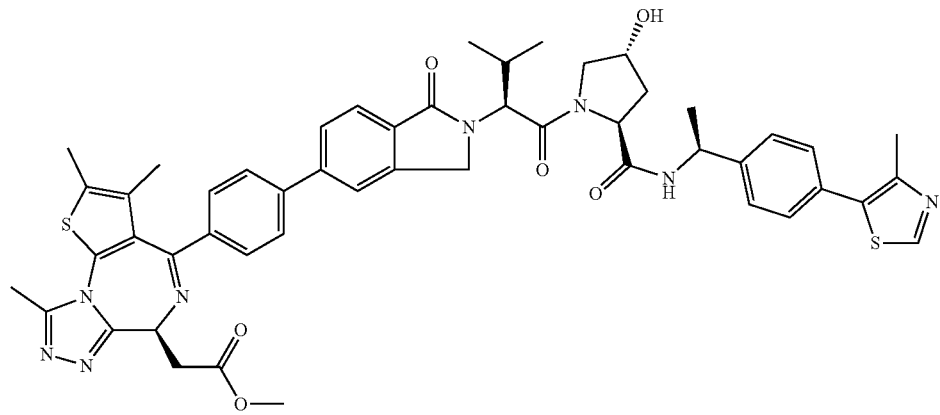 [SMILES: COC(=O)C[C@@H]1N=C(c2ccc(-c3ccc4c(c3)CN([C@H](C(=O)N3C[C@H](O)C[C@H]3C(=O)N[C@@H](C)c3ccc(-c5scnc5C)cc3)C(C)C)C4=O)cc2)c2c(sc(C)c2C)-n2c(C)nnc21]

due was purified by silica gel column chromatography (ethyl acetate:methanol=100:0-90:10) to give the title compound (802 mg) as a white powder.

MS (ESI) m/z: 415.2, 417.2 [M+H]+

(213-2) (6S)-4-(4-chlorophenyl)-3,6,9-trimethyl-6H-thieno[3,2-f] [1,2,4]triazolo[4,3-a][1,4]diazepine-2-carbaldehyde (Example Compound 213-2)

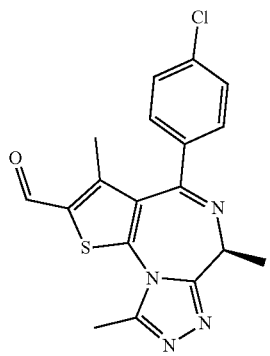 [SMILES: Cc1c(C=O)sc2c1C(c1ccc(Cl)cc1)=N[C@@H](C)c1nnc(C)n1-2]

To a solution of Example compound 213-1 (500 mg) in methanol (5.0 mL) was added 1N aqueous sodium hydroxide solution (5.0 mL) and the mixture was stirred at room temperature for 2 hr. To the reaction mixture was added saturated aqueous ammonium chloride solution and the mixture was extracted with chloroform and the extract was concentrated under reduced pressure. The obtained residue was dissolved in dichloromethane (12.0 mL), manganese dioxide (1.05 g) was added and the mixture was stirred at room temperature for 1 day. Furthermore, manganese dioxide (1.05 g) was added and the mixture was stirred at room temperature for 3 hr. The reaction mixture was filtered through diatomaceous earth and the filtrate was concentrated under reduced pressure to give the title compound (394 mg) as a yellow powder.

MS (ESI) m/z: 371.2, 373.2 [M+H]+

(213-3) (6S)-4-(4-chlorophenyl)-3,6,9-trimethyl-6H-thieno[3,2-f] [1,2,4]triazolo[4,3-a][1,4]diazepine-2-carbonitrile (Example Compound 213-3)

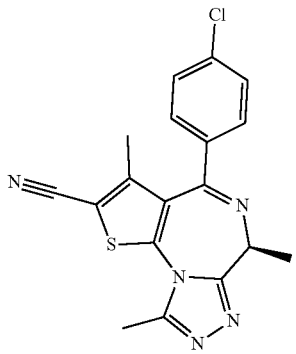 [SMILES: Cc1c(C#N)sc2c1C(c1ccc(Cl)cc1)=N[C@@H](C)c1nnc(C)n1-2]

To a solution of Example compound 213-2 (394 mg) in dimethyl sulfoxide (5.3 mL) was added hydroxyamine hydrochloride (111 mg), and the mixture was stirred with heating at 90° C. for 5 hr. The reaction mixture was added to water and the resulting precipitate was collected by filtration and washed with water to give the title compound (160 mg) as a pale-yellow powder. MS (ESI) m/z: 368.2, 370.2 [M+H]+

(213-4) (2S,4R)-1-[(2S)-2-({4'-[(6S)-2-cyano-3,6,9-trimethyl-6H-thieno[3,2-f][1,2,4]triazolo[4,3-a][1,4] diazepin-4-yl][1,1'-biphenyl]-4-carbonyl}amino)-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 213)

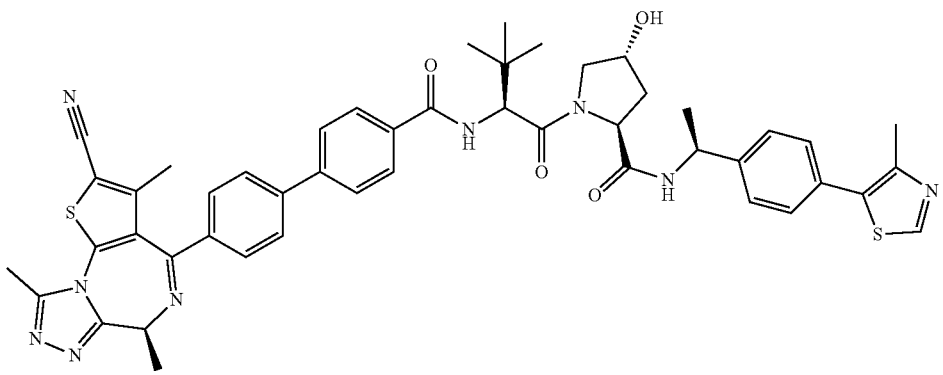 [SMILES: Cc1ncsc1-c1ccc([C@H](C)NC(=O)[C@@H]2C[C@@H](O)CN2C(=O)[C@@H](NC(=O)c2ccc(-c3ccc(C4=N[C@@H](C)c5nnc(C)n5-c5sc(C#N)c(C)c54)cc3)cc2)C(C)(C)C)cc1]

By reaction and treatment in the same manner as in Example 209 (209-1)-(209-2) and using Example compound 213-2 instead of methyl [(6S)-4-(4-chlorophenyl)-2-(hydroxymethyl)-3,9-dimethyl-6H-thieno[3,2-f][1,2,4]triazolo [4,3-a] [1,4]diazepin-6-yl]acetate, the title compound was obtained as a white powder. MS (ESI) m/z: 880.4 [M+H]+

Example 214

(214-1) tert-butyl {(2S)-1-[(2S,4R)-2-{[(4-chlorophenyl)methyl]carbamoyl}-4-hydroxypyrrolidin-1-yl]-3,3-dimethyl-1-oxobutan-2-yl}carbamate (Example Compound 214-1)

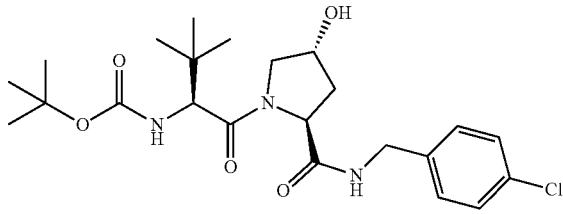 [SMILES: CC(C)(C)OC(=O)N[C@H](C(=O)N1C[C@H](O)C[C@H]1C(=O)NCc1ccc(Cl)cc1)C(C)(C)C]

(2S,4R)—N-[(4-chlorophenyl)methyl]-4-hydroxypyrrolidine-2-carboxamide hydrochloride (190 mg) described in WO 2015/000867 was added to a mixed solution of (2S)-2-(t-butoxycarbonylamino)-3,3-dimethyl-butanoic acid (196 mg), N,N-diisopropylethylamine (0.88 mL), HATU (322 mg) in N,N-dimethylformamide (8.0 mL), which was prepared separately, and the mixture was stirred at room temperature for 1.5 hr. Water was added to the reaction mixture and the mixture was extracted with ethyl acetate. The organic layer was washed with saturated brine, dried over anhydrous sodium sulfate, filtered and concentrated under reduced pressure. The residue was purified by preparative HPLC (10 mM aqueous ammonium carbonate solution-acetonitrile) to give the title compound (200 mg) as a white solid. MS (ESI) m/z: 468.5 [M+H]$^+$ (214-2) methyl {(6S)-4-[4'-({(2S)-1-[(2S,4R)-2-{[(4-chlorophenyl)methyl]carbamoyl}-4-hydroxy-pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 214)

To a solution of Example compound 214-1 (45 mg) in dichloromethane (1.4 mL) was added trifluoroacetic acid (0.60 mL) and the mixture was stirred at room temperature for 2 hr. The reaction mixture was concentrated under reduced pressure and azeotropically distilled with toluene. The residue was dissolved in N,N-dimethylformamide (1.5 mL), and N,N-diisopropylethylamine (0.13 mL), Example compound 90-1 (63 mg), HATU (73 mg) were added and the mixture was stirred at room temperature for 3 hr. To the reaction solution was added methanol (1.0 mL) and the mixture was purified by preparative HPLC (10 mM aqueous ammonium carbonate solution-acetonitrile) to give the title compound (49 mg) as a white powder.

MS (ESI) m/z: 850.6, 852.6 [M+H]$^+$

Example 215

(215-1) (2S,4R)-1-[(2S)-2-amino-3,3-dimethylbutanoyl]-4-hydroxy-N-{(1R)-2-hydroxy-1-[4-(4-methyl-1,3-thiazol-5-yl)phenyl]ethyl}pyrrolidine-2-carboxamide hydrochloride (Example Compound 215-1)

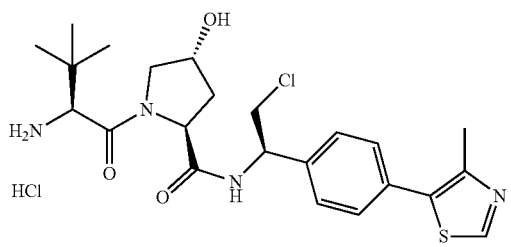

To a solution of tert-butyl {(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3,3-dimethyl-1-oxobutan-2-yl}carbamate (235 mg) described in WO 2017/030814 in 1,4-dioxane (2.3 mL) was added 4 M hydrogen chloride/dioxane solution (2.3 mL), and the mixture was stirred at room temperature overnight. The reaction mixture was concentrated under reduced pressure and azeotropically distilled with toluene to give the title compound (209 mg) as a pale-yellow solid. MS (ESI) m/z: 461.5 [M+H]$^+$

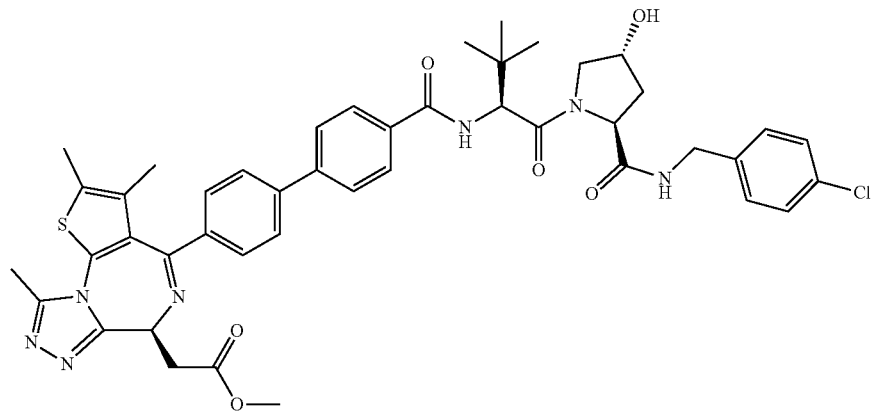 [SMILES: COC(=O)C[C@@H]1N=C(c2ccc(-c3ccc(C(=O)N[C@H](C(=O)N4C[C@H](O)C[C@H]4C(=O)NCc4ccc(Cl)cc4)C(C)(C)C)cc3)cc2)c2c(sc(C)c2C)-n2c(C)nnc21]

(215-2) methyl {(6S)-4-[4'-({(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3,3-dimethyl-1-oxobutan-2-yl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 215)

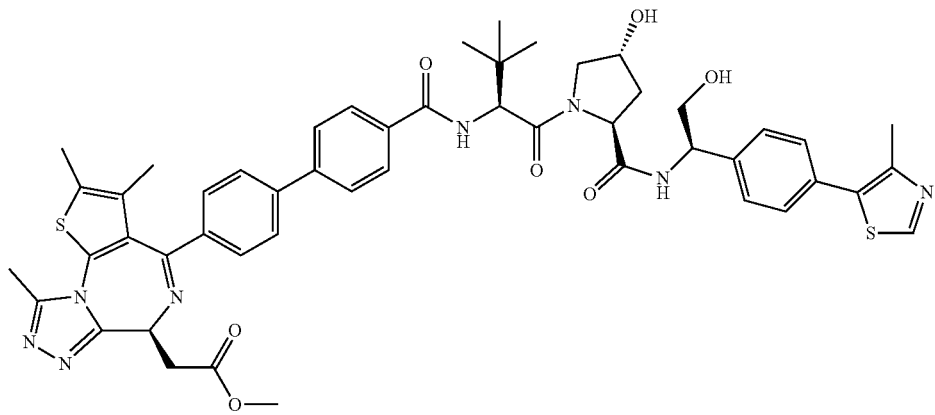 [SMILES: COC(=O)C[C@@H]1N=C(c2ccc(-c3ccc(C(=O)N[C@H](C(=O)N4C[C@H](O)C[C@H]4C(=O)N[C@@H](CO)c4ccc(-c5scnc5C)cc4)C(C)(C)C)cc3)cc2)c2c(sc(C)c2C)-n2c(C)nnc21]

To a solution of Example compound 215-1 (35 mg) in N,N-dimethylformamide (1.5 mL) were added N,N-diisopropylethylamine (0.061 mL), Example compound 90-1 (53 mg) and HATU (54 mg) and the mixture was stirred at room temperature for 2 hr. To the reaction solution was added methanol (1.0 mL) and the mixture was purified by preparative HPLC (10 mM aqueous ammonium carbonate solution-acetonitrile) to give the title compound (27 mg) as a milky white powder. MS (ESI) m/z: 943.8 [M+H]+

Example 216

(216-1) ethyl 2-[4-(4-bromophenyl)-1H-pyrazol-1-yl]-3-methylbutanoate (Example Compound 216-1)

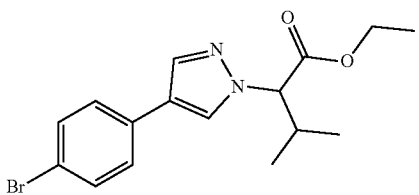

To a solution of 4-(4-bromophenyl)-1H-pyrazole (1.00 g) in acetonitrile (25.0 mL) were added ethyl 2-bromo-3-methylbutanoate (1.41 g) and cesium carbonate (2.92 g), and the mixture was stirred with heating at 80° C. for 16 hr. Insoluble material was filtered off from the reaction mixture and the filtrate was concentrated under reduced pressure. The residue was purified by silica gel column chromatography (hexane:ethyl acetate=90:10-75:25) to give the title compound (1.60 g) as a pale-yellow oil. MS (ESI) m/z: 351.2, 353.2 [M+H]+

(216-2) ((2S,4R)-1-{2-[4-(4-bromophenyl)-1H-pyrazol-1-yl]-3-methylbutanoyl}-4-hydroxy-N-{(1S)-1-[4-(4-methyl-1,3-thiazol-5-yl)phenyl]ethyl}pyrrolidine-2-carboxamide (Example Compound 216-2), and (2S,4R)-1-{2-[4-(4-bromophenyl)-1H-pyrazol-1-yl]-3-methylbutanoyl}-4-hydroxy-N-{(1S)-1-[4-(4-methyl-1,3-thiazol-5-yl)phenyl]ethyl}pyrrolidine-2-carboxamide (Example Compound 216-3)

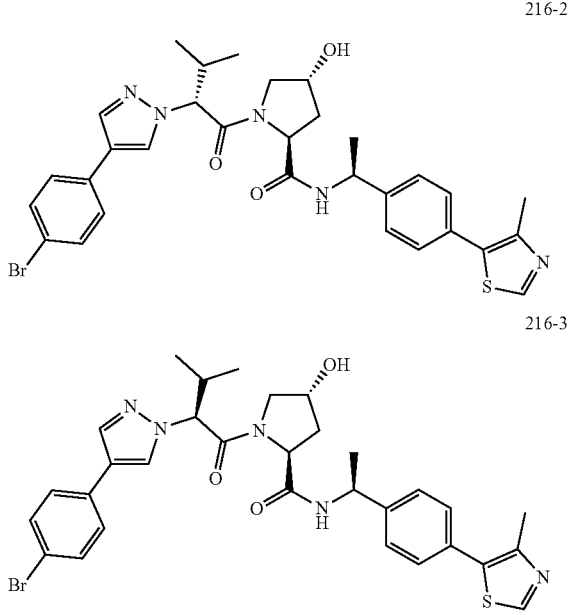

To a solution of Example compound 216-1 (300 mg) in tetrahydrofuran (2.0 mL), methanol (2.0 mL) was added 4N aqueous sodium hydroxide solution (1.0 mL), and the mixture was stirred at room temperature for 2 hr. The reaction mixture was acidified with 0.5N hydrochloric acid and extracted with chloroform. The organic layer was washed with saturated brine, dried over anhydrous sodium sulfate, filtered and concentrated under reduced pressure. The obtained residue was dissolved in N,N-dimethylformamide (3.0 mL), and N,N-diisopropylethylamine (0.49 mL), Example compound 210-2 (284 mg) were added. HATU (432 mg) was added and the mixture was stirred at room temperature for 13 hr. Water was added to the reaction mixture and the mixture was extracted with ethyl acetate. The organic layer was washed successively with water and saturated brine, dried over anhydrous sodium sulfate, filtered and concentrated under reduced pressure. The residue was azeotropically distilled with toluene and purified by silica gel column chromatography (chloroform:methanol=99:1-93:7) to give Example compound 216-2 (235 mg, white powder; single compound but isopropyl group moiety is sterically unknown) MS (ESI) m/z: 636.1, 638.1 [M+H]$^+$, and Example compound 216-3 (200 mg, colorless oil; single compound but isopropyl group moiety is sterically unknown) MS (ESI) m/z: 636.1, 638.1 [M+H]$^+$.

(216-3) methyl {(6S)-4-[4'-(1-{1-[(2S,4R)-4-hydroxy-2-({(1S)-1-[4-(4-methyl-1,3-thiazol-5-yl)phenyl]ethyl}carbamoyl)pyrrolidin-1-yl]-3-methyl-1-oxobutan-2-yl}-1H-pyrazol-4-yl)[1,1'-biphenyl]-4-yl]-2,3,9-trimethyl-6H-thieno[3,2-f][1,2,4]triazolo[4,3-a][1,4]diazepin-6-yl}acetate (Example Compound 216)

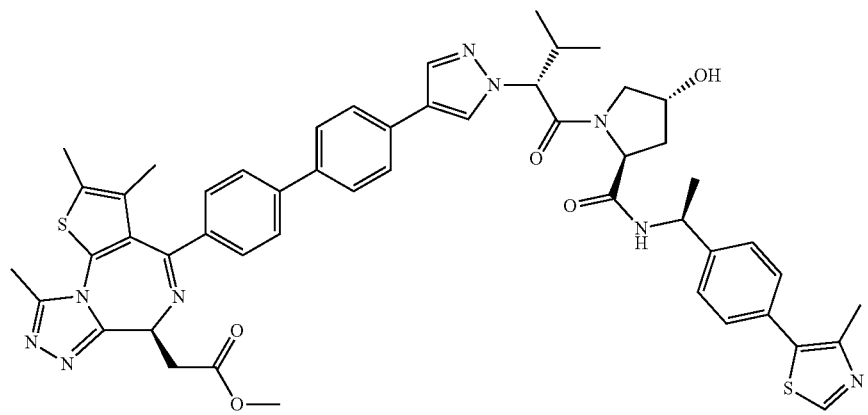

A mixture of Example compound 216-2 (95 mg), Reference Example compound 3 (123 mg), 1,1'-bis(diphenylphosphino)ferrocene-palladium(II) dichloride dichloromethane complex (22 mg), potassium carbonate (74 mg), tetrahydrofuran (3.0 mL) and water (0.25 mL) was stirred with heating under reflux for 4 hr. Reference Example compound 3 (82 mg), 1,1'-bis(diphenylphosphino)ferrocene-palladium(II) dichloride dichloromethane complex (22 mg) were further added and the mixture was stirred with heating under reflux for 3 hr. Water was added to the reaction mixture, and the mixture was extracted with ethyl acetate. The organic layer was washed with saturated brine, dried over anhydrous sodium sulfate, filtered and concentrated under reduced pressure. The residue was purified by silica gel column chromatography (chloroform:methanol=95:5-89:11) and further purified by preparative HPLC (10 mM aqueous ammonium carbonate solution-acetonitrile) to give the title compound (65 mg; single compound but isopropyl group moiety is sterically unknown) as a white powder. MS (ESI) m/z: 936.7 [M+H]$^+$

Example 217

(217-1) methyl {(6S)-4-[4'-(1-{1-[(2S,4R)-4-hydroxy-2-({(1S)-1-[4-(4-methyl-1,3-thiazol-5-yl)phenyl]ethyl}carbamoyl)pyrrolidin-1-yl]-3-methyl-1-oxobutan-2-yl}-1H-pyrazol-4-yl)[1,1'-biphenyl]-4-yl]-2,3,9-trimethyl-6H-thieno[3,2-f][1,2,4]triazolo[4,3-a][1,4]diazepin-6-yl}acetate (Example Compound 217)

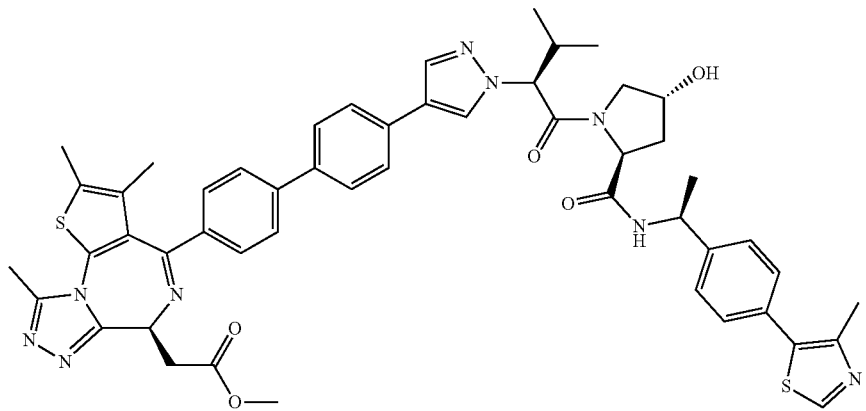

By reaction and treatment in the same manner as in Example 216 and using Example compound 216-3 instead of Example compound 216-2, the title compound (single compound but isopropyl group moiety is sterically unknown) was obtained as a white powder. MS (ESI) m/z: 936.7 [M+H]⁺

Example 218

(218-1) methyl {(6S)-4-[4'-({(2S)-1-[(2S,4R)-4-hydroxy-2-({[4-(4-methyl-1,3-oxazol-5-yl)phenyl]methyl}carbamoyl) pyrrolidin-1-yl]-3,3-dimethyl-1-oxobutan-2-yl}carbamoyl) [1,1'-biphenyl]-4-yl]-2,3,9-trimethyl-6H-thieno [3,2-f][1,2,4] triazolo [4,3-a] [1,4] diazepin-6-yl}acetate (Example Compound 218)

To a solution of (2S,4R)-1-[(2S)-2-amino-3,3-dimethylbutanoyl]-4-hydroxy-N-{[4-(4-methyl-1,3-oxazol-5-yl)phenyl]methyl}pyrrolidine-2-carboxamide hydrochloride (250 mg) described in WO 2016/118666 in tetrahydrofuran (0.8 mL) were added 4 M hydrogen chloride/methanol solution (0.8 mL) and methanol (0.4 mL), and the mixture was stirred at room temperature for 2 hr. The reaction mixture was concentrated under reduced pressure, and the residue was dissolved in methanol, diluted with tetrahydrofuran and ethyl acetate and concentrated under reduced pressure again to give a deprotected form (220 mg). The deprotected form (70 mg) was dissolved in N,N-dimethylformamide (1.5 mL), and N,N-diisopropylethylamine (0.095 mL), Example compound 90-1 (82 mg), HATU (78 mg) were added and the mixture was stirred at room temperature for 2.5 hr. To the reaction solution was added methanol (1.0 mL) and the mixture was purified by preparative HPLC (10 mM aqueous ammonium carbonate solution-acetonitrile) to give the title compound (54 mg) as milky white powder. MS (ESI) m/z: 897.7 [M+H]⁺

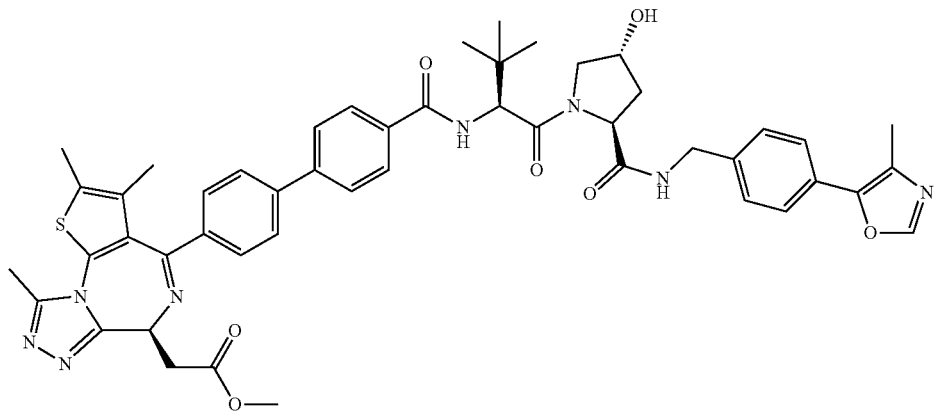 [SMILES: COC(=O)C[C@@H]1N=C(c2ccc(-c3ccc(C(=O)N[C@H](C(=O)N4C[C@H](O)C[C@H]4C(=O)NCc4ccc(-c5ocnc5C)cc4)C(C)(C)C)cc3)cc2)c2c(sc(C)c2C)-n2c(C)nnc21]

Example 219

(219-1) ethyl 5-(4-{[(tert-butoxycarbonyl)amino]methyl}phenyl)-1,3-thiazole-4-carboxylate (Example Compound 219-1)

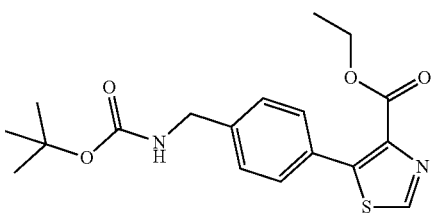 [SMILES: CCOC(=O)c1ncsc1-c1ccc(CNC(=O)OC(C)(C)C)cc1]

By reaction and treatment of t-butyl N-[(4-bromophenyl)methyl] carbamate and ethyl 1,3-thiazole-4-carboxylate in the same manner as in obtaining Compound 17b described in Chem. Eur. J. 2011, 17, 14450, the title compound was obtained as a brown oil. MS (ESI) m/z: 363.3 [M+H]$^+$

(219-2) ethyl 5-[4-({[(2S,4R)-1-{(2S)-2-[(tert-butoxycarbonyl)amino]-3,3-dimethylbutanoyl}-4-hydroxypyrrolidine-2-carbonyl]amino}methyl)phenyl]-1,3-thiazole-4-carboxylate (Example Compound 219-2)

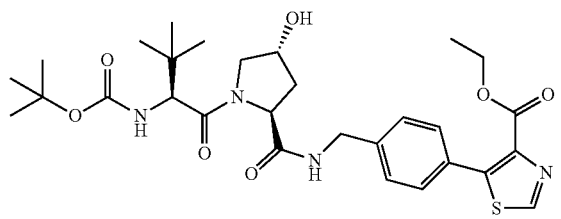 [SMILES: CCOC(=O)c1ncsc1-c1ccc(CNC(=O)[C@@H]2C[C@@H](O)CN2C(=O)[C@@H](NC(=O)OC(C)(C)C)C(C)(C)C)cc1]

To a solution of Example compound 219-1 (125 mg) in dichloromethane (2.5 mL) was added trifluoroacetic acid (1.0 mL) and the mixture was stirred at room temperature for 2 hr. The reaction mixture was concentrated under reduced pressure and azeotropically distilled with toluene. The obtained residue was dissolved in N,N-dimethylformamide (2.0 mL), and N,N-diisopropylethylamine (0.55 mL), (2S,4R)-1-(t-butoxycarbonyl)-4-hydroxyproline 99 mg), HATU (163 mg) were added, and the mixture was stirred at room temperature for 2 hr. To the reaction mixture was added saturated aqueous sodium hydrogen carbonate, and the mixture was extracted with ethyl acetate. The organic layer was washed with saturated brine, dried over anhydrous sodium sulfate, filtered and concentrated under reduced pressure. The obtained residue was dissolved in dichloromethane (3.0 mL), trifluoroacetic acid (1.5 mL) solution was added and the mixture was stirred at room temperature for 2 hr. The reaction mixture was concentrated under reduced pressure and azeotropically distilled with toluene. The obtained residue was dissolved in N,N-dimethylformamide (2.0 mL), and N,N-diisopropylethylamine (0.82 mL), (2S)-2-(t-butoxycarbonylamino)-3,3-dimethyl-butanoic acid (147 mg), HATU (241 mg) were added, and the reaction mixture was stirred at room temperature for 15 hr. Water was added to the reaction mixture, and the mixture was extracted with ethyl acetate. The organic layer was washed with saturated brine, dried over anhydrous sodium sulfate, filtered and concentrated under reduced pressure. The residue was purified by silica gel column chromatography (chloroform:methanol=99:1-95:5) to give the title compound (195 mg) as a pale-yellow oil. MS (ESI) m/z: 589.5 [M+H]$^+$

(219-3) ethyl 5-{4-[({(2S,4R)-4-hydroxy-1-[(2S)-2-({4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carbonyl}amino)-3,3-dimethylbutanoyl]pyrrolidine-2-carbonyl}amino)methyl]phenyl}-1,3-thiazole-4-carboxylate (Example Compound 219)

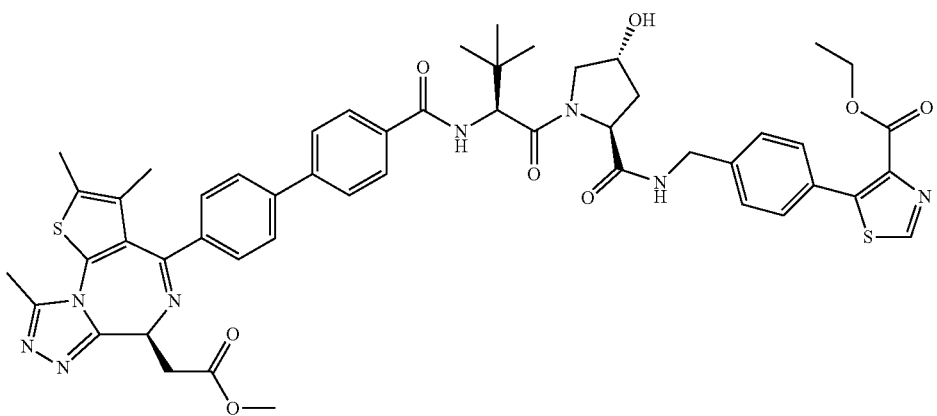 [SMILES: CCOC(=O)c1ncsc1-c1ccc(CNC(=O)[C@@H]2C[C@@H](O)CN2C(=O)[C@@H](NC(=O)c2ccc(-c3ccc(C4=N[C@@H](CC(=O)OC)c5nnc(C)n5-c5sc(C)c(C)c54)cc3)cc2)C(C)(C)C)cc1]

To a solution of Example compound 219-2 (60 mg) in dichloromethane (2.5 mL) was added trifluoroacetic acid (1.0 mL) and the mixture was stirred at room temperature for 2 hr. The reaction mixture was concentrated under reduced pressure and azeotropically distilled with toluene. The residue was dissolved in N,N-dimethylformamide (1.5 mL), and N,N-diisopropylethylamine (0.26 mL), Example compound 90-1 (55 mg), HATU (57 mg) were added and the mixture was stirred at room temperature for 2 hr. To the reaction solution was added methanol (1.0 mL) and the mixture was purified by preparative HPLC (10 mM aqueous ammonium carbonate solution-acetonitrile) to give the title compound (60 mg) as a white powder.

MS (ESI) m/z: 971.7 [M+H]$^+$

Example 220

(220-1) tert-butyl ({4-[4-(hydroxymethyl)-1,3-thiazol-5-yl]phenyl}methyl)carbamate (Example Compound 220-1)

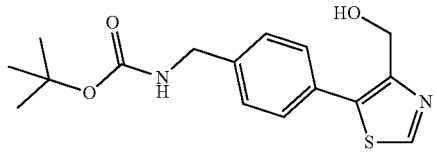 [SMILES: CC(C)(C)OC(=O)NCc1ccc(-c2scnc2CO)cc1]

To a solution of Example compound 219-1 (180 mg) in tetrahydrofuran (4.0 mL) were added a solution (2 M) (2.1 mL) of lithium borohydride in tetrahydrofuran and methanol (1.0 mL) under ice-cooling and the mixture was stirred for 3.5 hr while allowing the mixture to warm to room temperature. To the reaction mixture were added saturated aqueous ammonium chloride solution and saturated brine and the mixture was extracted with chloroform. The organic layer was washed with saturated brine, dried over sodium sulfate, filtered and concentrated under reduced pressure to give the title compound (160 mg) as a brown powder. MS (ESI) m/z: 321.3 [M+H]$^+$ (220-2) (2S,4R)-1-[(2S)-2-amino-3,3-dimethylbutanoyl]-4-hydroxy-N-({4-[4-(hydroxymethyl)-1,3-thiazol-5-yl]phenyl}methyl)pyrrolidine-2-carboxamide (Example Compound 220-2)

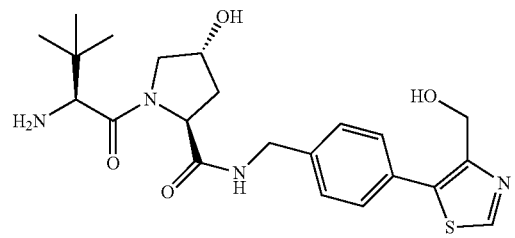 [SMILES: CC(C)(C)[C@H](N)C(=O)N1C[C@H](O)C[C@H]1C(=O)NCc1ccc(-c2scnc2CO)cc1]

To a solution of Example compound 220-1 (160 mg) in dichloromethane (3.5 mL) was added trifluoroacetic acid (1.5 mL) and the mixture was stirred at room temperature for 2 hr. The reaction mixture was concentrated under reduced pressure and azeotropically distilled with toluene. The obtained residue was dissolved in N,N-dimethylformamide (2.5 mL), and N,N-diisopropylethylamine (1.2 mL), (2S,4R)-1-(t-butoxycarbonyl)-4-hydroxyproline 149 mg), HATU (245 mg) were added, and the mixture was stirred at room temperature for 3 hr. To the reaction mixture was added saturated aqueous sodium hydrogen carbonate and the mixture was extracted with ethyl acetate. The organic layer was washed with saturated brine, dried over anhydrous sodium sulfate, filtered and concentrated under reduced pressure. The obtained residue was dissolved in dichloromethane (4.0 mL), trifluoroacetic acid (2.0 mL) solution was added and the mixture was stirred at room temperature for 4 hr. The reaction mixture was concentrated under reduced pressure and azeotropically distilled with toluene. The obtained residue was dissolved in N,N-dimethylformamide (2.5 mL), and N,N-diisopropylethylamine (0.80 mL), (2S)-2-(t-butoxycarbonylamino)-3,3-dimethyl-butanoic acid (159 mg), HATU (349 mg) were added, and the reaction mixture was stirred at room temperature for 3 hr. Furthermore, N,N-diisopropylethylamine (0.80 mL), (2S)-2-(t-butoxycarbonylamino)-3,3-dimethyl-butanoic acid (159 mg), HATU (262 mg) were added, and the reaction mixture was stirred at room temperature for 16 hr. To the reaction mixture were added water and saturated aqueous sodium hydrogen carbonate, and the mixture was extracted with ethyl acetate. The organic layer was washed with saturated brine, dried over anhydrous sodium sulfate, filtered and concentrated under reduced pressure. The residue was purified by silica gel column chromatography (chloroform:methanol=99:1-99:10). The obtained compound was dissolved in dichloromethane (2.0 mL), trifluoroacetic acid (2.0 mL) solution was added and the mixture was stirred at room temperature for 2 hr. The reaction mixture was concentrated under reduced pressure and azeotropically distilled with toluene. The residue was purified by preparative HPLC (10 mM aqueous ammonium carbonate solution-acetonitrile) to give the title compound (25 mg) as a pale-yellow oil.

MS (ESI) m/z: 447.3 [M+H]$^+$ (220-3) methyl [(6S)-4-(4'-{[(2S)-1-{(2S,4R)-4-hydroxy-2-[({4-[4-(hydroxymethyl)-1,3-thiazol-5-yl]phenyl}methyl)carbamoyl]pyrrolidin-1-yl}-3,3-dimethyl-1-oxobutan-2-yl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 220)

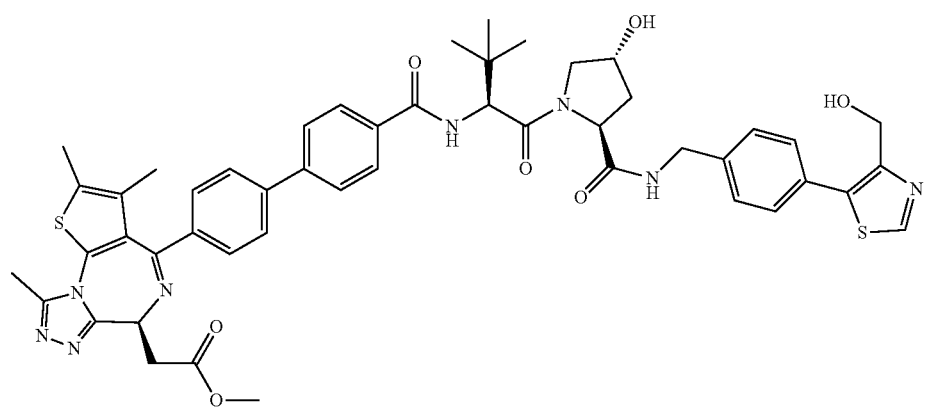 [SMILES: COC(=O)C[C@@H]1N=C(c2ccc(-c3ccc(C(=O)N[C@H](C(=O)N4C[C@H](O)C[C@H]4C(=O)NCc4ccc(-c5scnc5CO)cc4)C(C)(C)C)cc3)cc2)c2c(sc(C)c2C)-n2c(C)nnc21]

To a solution of Example compound 220-2 (20 mg) in N,N-dimethylformamide (1.0 mL) were added N,N-diisopropylethylamine (0.027 mL), Example compound 90-1 (29 mg) and HATU (26 mg) and the mixture was stirred at room temperature for 15 hr. To the reaction solution was added methanol (1.0 mL) and the mixture was purified by preparative HPLC (10 mM aqueous ammonium carbonate solution-acetonitrile) to give the title compound (12 mg) as a white viscous compound. MS (ESI) m/z: 929.7 [M+H]$^+$ Example 221

(221-1) methyl [(6S)-4-(4-hydroxyphenyl)-2-3,9-trimethyl-6H-thieno[3,2-f][1,2,4]triazolo[4,3-a][1,4]diazepin-6-yl]acetate (Example Compound 221-1)

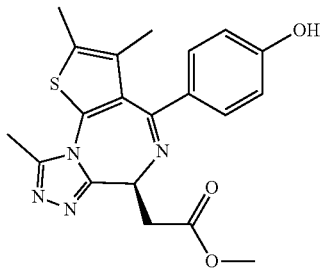 [SMILES: COC(=O)C[C@@H]1N=C(c2ccc(O)cc2)c2c(sc(C)c2C)-n2c(C)nnc21]

Methyl (S)-{4-(4-aminophenyl)-2,3,9-trimethyl-6H-thieno[3,2-f][1,2,4]triazolo[4,3-a][1,4]diazepin-6-yl}acetate (1.58 g) was dissolved in 35% sulfuric acid (4 mi) and the mixture was cooled to −5° C. To the reaction mixture was added sodium nitrite (352 mg) aqueous solution (4 mL) and the mixture was stirred at 0° C. for 30 min. A small amount of urea was added and the mixture was further stirred at 0° C. for 30 min. To the reaction mixture were added copper(II) nitrate 3 hydrate (15 g) aqueous solution (140 mL), copper (I) oxide (520 mg) and the mixture was stirred at 10° C. for 1 hr. The mixture was extracted with chloroform-methanol, and the organic layer was washed with saturated brine and concentrated under reduced pressure. The residue was purified by silica gel column chromatography and recrystallized from hexane-ethyl acetate to give the title compound (379 mg) as a white solid.

MS (ESI) m/z: 397.4 [M+H]$^+$ (221-2) methyl [(6S)-4-(4-{3-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}amino)-2-oxoethoxy]propoxy}phenyl)-2,3,9-trimethyl-6H-thieno[3,2-f][1,2,4]triazolo[4,3-a][1,4]diazepin-6-yl]acetate (Example Compound 221)

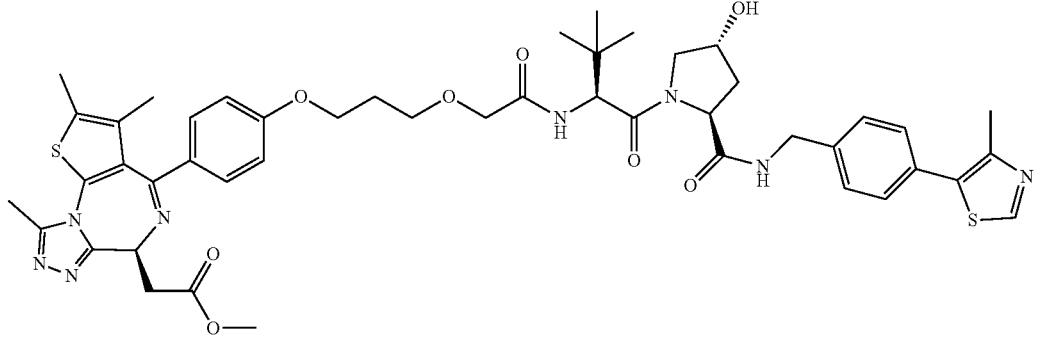 [SMILES: COC(=O)C[C@@H]1N=C(c2ccc(OCCCOCC(=O)N[C@H](C(=O)N3C[C@H](O)C[C@H]3C(=O)NCc3ccc(-c4scnc4C)cc3)C(C)(C)C)cc2)c2c(sc(C)c2C)-n2c(C)nnc21]

By reaction and treatment in the same manner as in Example 208 (208-3)-(208-5) and using Example compound 221-1 instead of Example compound 208-2, the title compound was obtained as a white solid. MS (ESI) m/z: 925.5 [M+H]$^+$ Example 222

(222-1) (2S,4R)-1-{(2S)-3,3-dimethyl-2-[2-(3-{4-[(6S)-2,3,6,9-tetramethyl-6H-thieno[3,2-f][1,2,4]triazolo[4,3-a] [1,4]diazepin-4-yl]phenoxy}propoxy)acetamido]butanoyl}-4-hydroxy-N-{[4-(4-methyl-1,3-thiazol-5-yl)phenyl]methyl}pyrrolidine-2-carboxamide (Example Compound 222)

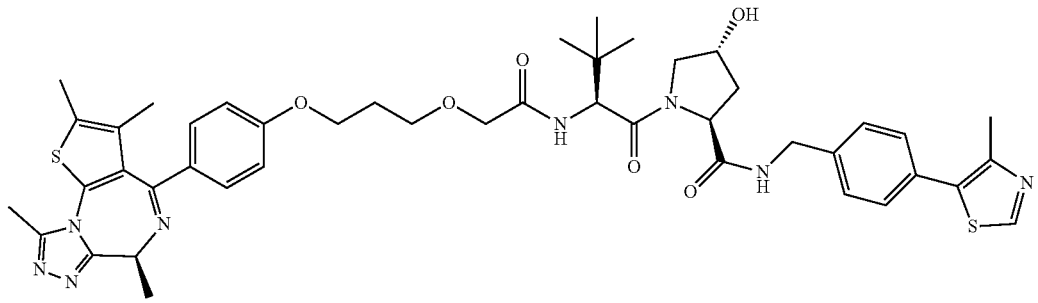 [SMILES: Cc1ncsc1-c1ccc(CNC(=O)[C@@H]2C[C@@H](O)CN2C(=O)[C@@H](NC(=O)COCCCOc2ccc(C3=N[C@@H](C)c4nnc(C)n4-c4sc(C)c(C)c43)cc2)C(C)(C)C)cc1]

By reaction and treatment in the same manner as in Example 208 (208-3)-(208-5) and using Example compound 116-1 instead of Example compound 208-2, the title compound was obtained as a white solid. MS (ESI) m/z: 867.4 [M+H]$^+$ Example 223

(223-1) (2S,4R)-1-[(2S)-2-{[cis-2-(4-bromophenyl)cyclopropane-1-carbonyl]amino}-3,3-dimethylbutanoyl]-4-hydroxy-N-{(1S)-1-[4-(4-methyl-1,3-thiazol-5-yl)phenyl]ethyl}pyrrolidine-2-carboxamide (Example Compound 223-1)

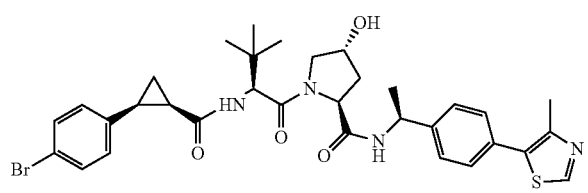 [SMILES: Cc1ncsc1-c1ccc([C@H](C)NC(=O)[C@@H]2C[C@@H](O)CN2C(=O)[C@@H](NC(=O)[C@@H]2C[C@@H]2c2ccc(Br)cc2)C(C)(C)C)cc1]

Ethyl cis-2-(4-bromophenyl)cyclopropanecarboxylate (150 mg) was dissolved in tetrahydrofuran (5.6 mL), and ethanol (2.8 mL), 1N aqueous sodium hydroxide solution (2.8 mL) were added and the mixture was stirred at room temperature for 15 hr. To the reaction mixture were added 1N hydrochloric acid, chloroform under ice-cooling, and the mixture was stirred. The organic layer was extracted and the aqueous layer was extracted twice with chloroform. The organic layers were collected, washed with saturated brine and dried over anhydrous sodium sulfate. The solvent was evaporated under reduced pressure. The residue was dried under reduced pressure, dissolved in N,N-dimethylformamide (5.6 mL) and N,N-diisopropylethylamine (0.29 mL), Reference Example compound 5 (322 mg), HATU (318 mg) were added under ice-cooling and the mixture was stirred at room temperature for 15 hr. To the reaction mixture were added ice water, ethyl acetate and the mixture was stirred. Water, saturated brine and ethyl acetate were added and the organic layer was extracted. The aqueous layer was extracted with ethyl acetate, and the organic layers were collected and washed twice with saturated brine:water=1:1, and washed with saturated brine. After drying over anhydrous sodium sulfate, the solvent was evaporated under reduced pressure, and the residue was purified by silica gel column chromatography (chloroform:methanol=100:0-96:4) and then purified by silica gel column chromatography (ethyl acetate:methanol=100:0-90:10) to give the title compound (86 mg) as a white solid.

MS (ESI) m/z: 665.4 [M–H]$^-$ (223-2) methyl [(6S)-4-{4'-[cis-2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclopropyl][1,1'-biphenyl]-4-yl}-2,3,9-trimethyl-6H-thieno[3,2-f][1,2,4]triazolo[4,3-a] [1,4]diazepin-6-yl]acetate (Example Compound 223)

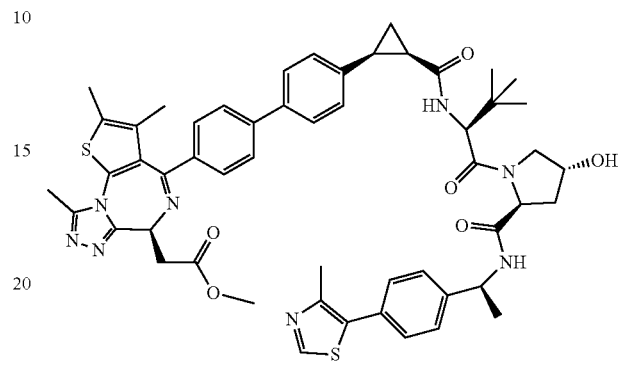

Example compound 223-1 (85 mg) was dissolved in tetrahydrofuran (2.4 mL), and water (0.0083 mL), palladium acetate (3.1 mg), S-phos (12 mg), potassium fluoride (24 mg) and Reference Example compound 2 (14 mg) were added and the mixture was stirred at 75° C. for 5 hr. Furthermore, water (0.0083 mL), palladium acetate (3.1 mg), S-phos (12 mg), potassium fluoride (24 mg), Reference Example compound 2 (40 mg), tetrahydrofuran (2.4 mL) were added and the mixture was stirred at 75° C. for 6 hr. The insoluble material in the reaction mixture was filtered off through diatomaceous earth. Chloroform and water were added and the organic layer was extracted, washed with saturated brine, and dried over anhydrous sodium sulfate. The solvent was evaporated under reduced pressure. The residue was purified by NH silica gel column chromatography (ethyl acetate:methanol=100:0-85:15) and silica gel column chromatography (ethyl acetate:methanol=100:0-85:15) to give the title compound (17.7 mg) as a yellow solid. MS (ESI) m/z: 967.5 [M+H]$^+$ Example 224

(224-1) methyl [(6S)-4-{4'-[trans-2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)cyclopropyl][1,1'-biphenyl]-4-yl}-2,3,9-trimethyl-6H-thieno[3,2-f][1,2,4]triazolo[4,3-a] [1,4]diazepin-6-yl]acetate (Example Compound 224)

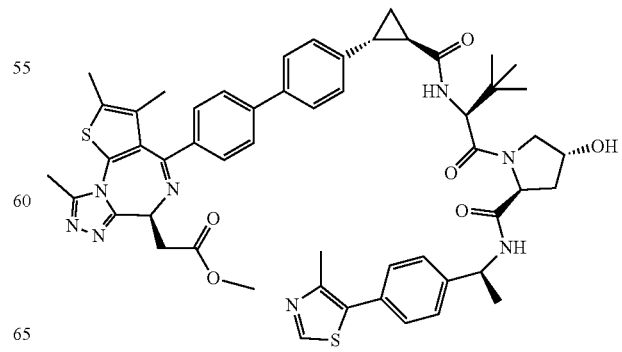

By reaction and treatment in the same manner as in Example 223 (223-1)-(223-2) and using ethyl trans-2-(4-bromophenyl)cyclopropanecarboxylate instead of ethyl cis-2-(4-bromophenyl)cyclopropanecarboxylate, the title compound was obtained as a yellow solid. MS (ESI) m/z: 967.5 [M+H]$^+$ Experimental Example 1

Cytotoxic Action on Cancer Cells

The cytotoxic action of the compound of the present invention against human cancer cells was evaluated in vitro. In this experiment, (+)-JQ1 (Nature volume 468, pages 1067-1073 (23 Dec. 2010)) known to have an inhibitory activity on the binding of BRD4 protein and a ligand therefor was used as a positive control drug. Respective cells were suspended in 10% FBS/RPMI1640, seeded in a 96 well plate and cultured at 5% $CO_2$, 37° C. overnight. A test compound dissolved in DMSO was diluted with 10% FBS/RPMI1640 and added and the cells were further cultured for 96 hr. After culturing, the viable cell number was measured using a cell number measurement WST-8 kit (Kishida Chemical Co., Ltd.). As a control, the measurement was performed under conditions free of the test compound. The cytotoxic activity of the compound of the present invention against human prostate cancer LNCaP cells is shown in $IC_{50}$ value in Table 1. The $IC_{50}$ value is a concentration of the compound showing 50% cell survival rate when the cell survival rate thereof under compound untreated condition is 100%. It was calculated from the straight line connecting the cell survival rate at two points enclosing the 50% cell survival rate and the compound concentration. In addition, the cytotoxic activity against respective cancer cells of human acute myeloid leukemia MV-4-11 cell, human chronic myeloid leukemia K562 cell, human multiple myeloma MM.1S cell, human diffuse large B-cell lymphoma SU-DHL-6 cell, human T-cell leukemia Jurkat cells, human Burkitt lymphoma Raji cell, human castration-resistant prostate cancer PC-3 cell, human ovarian cancer A2780 cell, human bladder cancer 5637 cell, human breast cancer ZR-75-1 cell, human triple negative breast cancer MDA-MB-231 cell, human uterine sarcoma MES-SA cell, human gastric cancer SNU-16 cell, human non-small cell lung cancer NCI-H1975 cell, human small cell lung cancer NCI-H82 cell, human large cell lung cancer NCI-H460 cell, human colorectal cancer HCT116 cell, human glioma U-87 MG cell, human pancreatic cancer AsPC-1 cell, and human liver cancer Hep G2 cell is shown in $IC_{50}$ value in Table 2. The compound of the present invention showed a strong cytotoxic action on the cancer cells.

TABLE 1

| Example compound No. | LNCaP cytotoxic activity: $IC_{50}$ (nmol/L) |
| --- | --- |
| 5 | 1.2 |
| 8 | 0.68 |
| 9 | 0.16 |
| 15 | 0.083 |
| 16 | 0.29 |
| 27 | 0.064 |
| 28 | 0.044 |
| 30 | 0.99 |
| 31 | 0.039 |
| 33 | 0.26 |
| 34 | 0.72 |
| 35 | 3.9 |
| 39 | 0.071 |
| 45 | 0.32 |
| 47 | 0.42 |
| 49 | 0.12 |
| 50 | 0.25 |
| 53 | 0.20 |
| 60 | 0.12 |
| 61 | 0.17 |
| 62 | 0.26 |
| 63 | 0.037 |
| 67 | 0.47 |
| 68 | 0.52 |
| 69 | 0.33 |
| 75 | 0.39 |
| 91 | 0.54 |
| 94 | 0.29 |
| 100 | 0.67 |
| 101 | 0.059 |
| 106 | 0.58 |
| 113 | 0.096 |
| 122 | 0.40 |
| 138 | 0.24 |
| 141 | 0.38 |
| 142 | 0.30 |
| 146 | 0.44 |
| 147 | 0.34 |
| 151 | 0.058 |
| 154 | 0.45 |
| 157 | 0.40 |
| 161 | 0.22 |
| 162 | 0.37 |
| 164 | 0.077 |
| 165 | 0.26 |
| 167 | 0.14 |
| 171 | 0.080 |
| 172 | 0.36 |
| 173 | 0.53 |
| 174 | 0.37 |
| 175 | 0.30 |
| 176 | 0.39 |
| 177 | 0.36 |
| 178 | 0.68 |
| 179 | 0.21 |
| 181 | 0.037 |
| 183 | 1.5 |
| 188 | 0.042 |
| 189 | 0.17 |
| 190 | 0.13 |
| 192 | 0.46 |
| 193 | 0.30 |
| 194 | 0.17 |
| 198 | 0.061 |
| 199 | 0.64 |
| 200 | 0.38 |
| 201 | 0.34 |
| 204 | 0.32 |
| 206 | 0.68 |
| 207 | 0.43 |
| 209 | 0.24 |
| 210 | 0.29 |
| 215 | 0.31 |
| 218 | 0.37 |
| 219 | 0.52 |
| 220 | 0.92 |
| (+)-JQ1 | 19000 |

TABLE 2

| cell line | Example compound 8 | Example compound 9 | Example compound 142 | Example compound 157 |
|---|---|---|---|---|
| MV-4-11 | 0.15 | 0.015 | 0.041 | 0.029 |
| K562 | 5.2 | 2.2 | 2.1 | 1.2 |
| MM.1S | 0.24 | 0.14 | 0.23 | 0.081 |
| SU-DHL-6 | 2.1 | 0.57 | 0.93 | 0.39 |
| Jurkat | 4.3 | 1.2 | 0.36 | 0.46 |
| Raji | 5.7 | 1.9 | 0.71 | 0.59 |
| P0-3 | 2.5 | 1.0 | 0.34 | 0.41 |
| A2780 | 0.36 | 0.16 | 0.27 | 0.15 |
| 5637 | 2.1 | 0.45 | 0.34 | 0.33 |
| ZR-75-1 | 4.2 | 0.96 | 0.49 | 2.0 |
| MDA-MB-231 | 14 | 5.7 | 0.98 | 1.8 |
| MES-SA | 21 | 2.6 | 1.6 | 1.7 |
| SNU-16 | 17 | 3.0 | 0.55 | 1.2 |
| NCI-H1975 | 20 | 3.7 | 1.8 | 2.2 |
| NCI-H82 | 35 | 15 | 5.9 | 4.5 |
| NCI-H460 | 75 | 24 | 11 | 23 |
| HCT116 | 37 | 4.7 | 3.9 | 4.5 |
| U-87 MG | 25 | 9.1 | 4.0 | 18 |
| AsPC-1 | 81 | 30 | 5.7 | 23 |
| Hep G2 | 48 | 33 | 7.4 | 12 | cytotoxic activity: IC$_{50}$ (nmol/L)

Experimental Example 2

BET Protein Degradation inducing Action in Cancer Cells

The degradation inducing action of the compound of the present invention on BET proteins (BRD2, BRD3, BRD4) in cancer cells and accompanying decrease in the c-MYC expression level m were evaluated in vitro using human prostate cancer LNCaP cells. LNCaP cells were suspended in 10% FBS/RPMI1640, seeded in a 6 well plate and cultured at 5% CO$_2$, 37° C. overnight. A test compound dissolved in DMSO was diluted with 10% FBS/RPMI1640 and added and the cells were further cultured for 6 hr. After culturing, the cells were lysed in a solubilizing solution (10 mM Tris-HCl, pH 7.4, 0.1% NP-40, 0.1% sodium deoxycholate, 0.1% SDS, 0.15 M NaCl, 1 mM EDTA, 10 μg/mL aprotinin). The solution was electrophoresed and proteins in acrylamide gel were transferred to Immobilon PVDF membrane using a semi-dry transfer device. After transfer, the membrane was blocked and immersed in a primary antibody (Anti-BRD2 antibody:Abcam, Anti-BRD3 antibody:Abcam, Anti-Brd4 antibody:Abcam, c-MYC Antibody:Cell Signaling Technology, Anti-β-Actin antibody:Sigma-Aldrich) solution at 4° C. overnight. After immersing in a secondary antibody solution for 1 hr, the object protein on the membrane was detected using ECL Prime Western Blotting Detection System or ECL Select Western Blotting Detection System (GE Healthcare). As a result, as shown in FIG. 1, the compound of the present invention induced degradation of BET protein in the cancer cells.

Experimental Example 3

BRD4 Protein Degradation inducing Action in Cancer Cells

The degradation inducing action of the compound of the present invention on BRD4 protein in cancer cells was evaluated in vitro using human prostate cancer LNCaP cells. LNCaP cells were suspended in 10% FBS/RPMI1640, seeded in a 96 well Cell carrier plate (Perkin Elmer) and cultured at 5% CO$_2$, 37° C. overnight. A test compound dissolved in DMSO was diluted with 10% FBS/RPMI1640 and added and the cells were further cultured for 6 hr. After culturing, the cells were immobilized with 4% para-formaldehyde/PBS and further subjected to a permeation treatment with 0.25% Triton X-100/PBS. Thereafter, the cells were blocked with 10% BSA/PBS, a solution containing Anti-Brd4 antibody (Abcam) or Anti-BRD4 (Sigma-Aldrich) as the primary antibody was added and the cells were incubated at 4° C. overnight. Thereafter, as the secondary antibody, a solution containing secondary antibody A shown below was added to Example compounds 1-190, 223 and 224, and a solution containing secondary antibody B shown below was added to Example compounds 191-222, and 0.5 μg/mL Hoechst 33342 (Sigma-Aldrich) and 14 μM Acti-Stain 555 Fluorescent Phalloidin (Cytoskeleton) were further added. After incubation for 1 hr, BRD4 protein amount was measured by Operetta (Perkin Elmer) as fluorescence intensity.

Secondary Antibody A

Anti-Rabbit IgG(H+L), F(ab')$_2$ Fragment (Alexa Fluor 488 Conjugate) (Cell Signaling Technology), fluorescence intensity was measured at excitation: 495 nm, emission: 519 nm.

Secondary Antibody B

Goat anti-Rabbit IgG(H+L) Cross-Adserbed Secondary Antibody (Alexa Fluor 546) (Thermo Fisher Scientific) fluorescence intensity was measured at excitation: 560 nm, emission: 572 nm.

The BRD4 protein degradation inducing activity of the compound of the present invention in LNCaP cells is shown in DC$_{50}$ value in Table 3. The DC$_{50}$ value is a concentration of the compound showing 50% fluorescence intensity when the fluorescence intensity thereof under compound untreated condition is 100%. It was calculated from the straight line connecting the fluorescence intensity at two points enclosing the 50% fluorescence intensity and the compound concentration. The compound of the present invention induced degradation of BRD4 protein in the cancer cells at a concentration showing a cell proliferation suppressive action.

TABLE 3

| Example compound No. | BRD4 protein degradation inducing activity: DC$_{50}$ (nmol/L) |
|---|---|
| 5 | 0.52 |
| 8 | 0.41 |
| 9 | 0.15 |
| 15 | 0.066 |
| 16 | 0.53 |
| 27 | 0.085 |
| 28 | 0.023 |
| 30 | 0.43 |
| 31 | 0.062 |
| 33 | 0.38 |
| 34 | 0.098 |
| 35 | 0.66 |
| 39 | 0.013 |
| 45 | 0.051 |
| 47 | 0.45 |
| 49 | 0.24 |
| 50 | 0.61 |
| 53 | 0.091 |
| 60 | 0.74 |
| 61 | 0.81 |
| 62 | 0.24 |
| 63 | 0.11 |
| 67 | 0.55 |
| 68 | 0.46 |
| 69 | 0.15 |
| 75 | 0.75 |
| 91 | 0.77 |
| 94 | 0.64 |
| 100 | 0.21 |

TABLE 3-continued

| Example compound No. | BRD4 protein degradation inducing activity: $DC_{50}$ (nmol/L) |
|---|---|
| 101 | 0.052 |
| 106 | 0.60 |
| 113 | 0.075 |
| 122 | 0.097 |
| 138 | 0.62 |
| 141 | 0.72 |
| 142 | 0.72 |
| 146 | 0.46 |
| 147 | 0.28 |
| 151 | 0.042 |
| 154 | 0.42 |
| 157 | 0.38 |
| 161 | 0.075 |
| 162 | 0.30 |
| 164 | 0.066 |
| 165 | 0.041 |
| 167 | 0.28 |
| 171 | 0.16 |
| 172 | 0.37 |
| 173 | 0.53 |
| 174 | 0.31 |
| 175 | 0.50 |
| 176 | 0.44 |
| 177 | 0.23 |
| 178 | 0.80 |
| 179 | 0.11 |
| 181 | 0.031 |
| 183 | 0.93 |
| 188 | 0.26 |
| 189 | 0.44 |
| 190 | 0.17 |
| 192 | 0.77 |
| 193 | 0.62 |
| 194 | 0.23 |
| 198 | 0.058 |
| 199 | 0.55 |
| 200 | 0.66 |
| 201 | 0.37 |
| 204 | 0.51 |
| 206 | 0.73 |
| 207 | 0.62 |
| 209 | 0.32 |
| 210 | 0.26 |
| 215 | 0.33 |
| 218 | 0.41 |
| 219 | 0.52 |
| 220 | 0.92 |

Experimental Example 4

Inhibitory Action on Binding of BRD4 Protein and Ligand

Test Method 1

The inhibitory action of the compound of the present invention on the binding of BRD4 protein and a ligand thereof was evaluated by the time-resolved fluorescence resonance energy transfer (TR-FRET) method using BRD4 bromodomain 1 TR-FRET Assay Kit (Cayman). In this experiment, (+)-JQ1 known to have an inhibitory activity on the binding of BRD4 protein and a ligand therefor was used as a positive control drug. A test compound dissolved in DMSO was diluted with TR-FRET Assay Buffer, added to a 384 well black plate, BRD4 bromodomain 1 Europium Chelete was further added and the cells were incubated at room temperature for 15 min. Thereafter, BRD4 bromodomain 1 Ligand/APC Acceptor Mixture was added and the cells were incubated at room temperature for 1 hr. The binding amount of the BRD4 protein and ligand was measured as fluorescence intensity (excitation: 340 nm/emission: 620 nm and excitation: 340 nm/emission: 670 nm).

The BRD4 protein inhibitory activity of the compound of the present invention is shown in $IC_{50}$ value (concentration of compound that inhibits 50% of the binding of BRD4 protein and ligand) in Table 4-1. The $IC_{50}$ value is a concentration of the compound showing 50% fluorescence intensity when the fluorescence intensity thereof under compound untreated condition is 100%. It was calculated from the straight line connecting the degradation rate at two points enclosing the 50% fluorescence intensity and the compound concentration. The compound of the present invention showed a strong inhibitory action on the binding of BRD4 protein and ligand.

TABLE 4-1

| Example compound No. | BRD4 protein inhibitory activity: $IC_{50}$ (nmol/L) |
|---|---|
| 8 | 82 |
| 9 | 47 |
| (+)-JQ1 | 7400 |

Test Method 2

The inhibitory action of the compound of the present invention on the binding of BRD4 protein and a ligand thereof (acetylated histone H4) was evaluated by the time-resolved fluorescence resonance energy transfer (TR-FRET) method using EPIgeneous™ Binding Domain Kit A (Cisbio), BRD4-1 (GST) (Reaction Biology Corp) and [Lys(Ac)5/8/12/16]-Histone H4(1-21)-GGK (Biotin) (Eurogentec). In this experiment, (+)-JQ1 known to have an inhibitory activity on the binding of BRD4 protein and acetylated histone H4 therefor was used as a positive control drug. A test compound dissolved DMSO was diluted with attached Diluent Buffer, added to a 384 well white plate, and BRD4-1 (GST) and [Lys(Ac)5/8/12/16]-Histone H4(1-21)-GGK (Biotin) were further added. Thereafter, Streptavidin-d2 conjugate and Anti-GST-$Eu^{3+}$ Cryptate Conjugate were added and the cells were incubated at room temperature for 3 hr. The binding amount of the BRD4 protein and acetylated histone H4 was measured as the fluorescence intensity (excitation: 314 nm/emission: 620 nm and excitation: 314 nm/emission: 665 nm). The BRD4 protein inhibitory activity of the compound of the present invention is shown in $IC_{50}$ value (concentration of compound that inhibits 50% of the binding of BRD4 protein and acetylated histone H4) in Table 4-2. The $IC_{50}$ value is a concentration of the compound showing 50% fluorescence intensity when the fluorescence intensity thereof under compound untreated condition is 100%. It was calculated from the straight line connecting the degradation rate at two points enclosing the 50% fluorescence intensity and the compound concentration. The compound of the present invention showed a strong inhibitory action on the binding of BRD4 protein and ligand.

TABLE 4-2

| Example compound No. | BRD4 protein inhibitory activity: $IC_{50}$ (nmol/L) |
|---|---|
| 142 | 110 |
| 157 | 61 |
| (+)-JQ1 | 550 |

Experimental Example 5

Antitumor Effect in Human Acute Myeloid Leukemia MV-4-11 Cell Transplanted Mouse The in vivo antitumor effect of the compound of the present invention was studied using human acute myeloid leukemia MV-4-11 cell transplanted mouse. MV-4-11 cells were subcutaneously transplanted into the inguinal region of male, 6-week-old BALB/c nude mouse ($5 \times 10^6$ cells/mouse). The compound of the present invention was administered into the tail vein on days 1, 5, 9, 13 from the time point when the assumed tumor volume determined from $1/2ab^2$ (a is major axis and b is minor axis of tumor) reached about 100 mm$^3$ (day 1). The control group was administered with a solvent, 10% hydroxypropyl-β-cyclodextrin solution. On day 15, the tumor was isolated, the weight was measured, and the tumor growth inhibitory rate IR (%) was calculated by the following formula.

tumor growth inhibitory rate IR (%)=(1−tumor weight of administration group/tumor weight of nonadministration control group)×100

Figure 2:
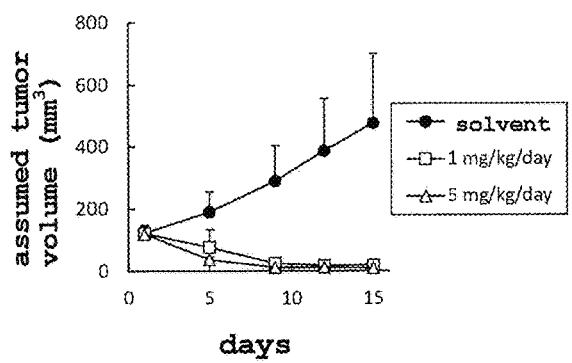
FIG. 2 shows an antitumor effect of the compound of the present invention in mouse transplanted with human acute myeloid leukemia MV-4-11 cells.
Figure 2:
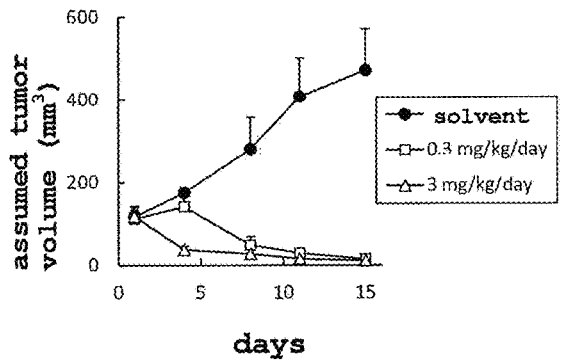
Figure 2:
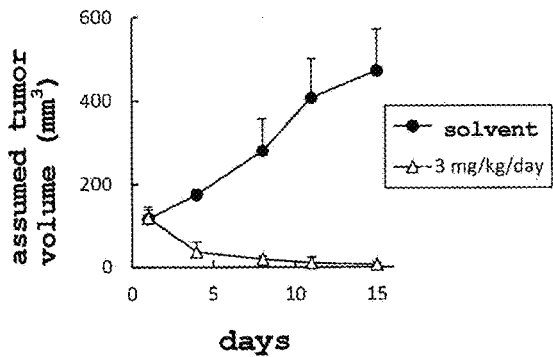
Figure 2:
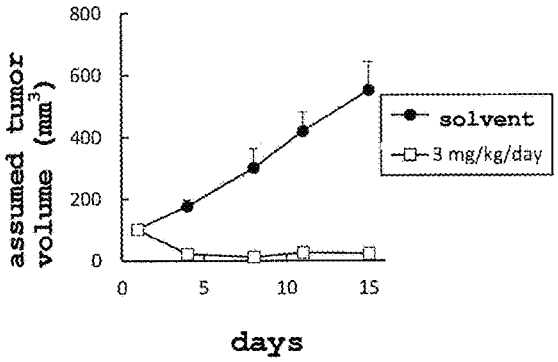
Figure 2:
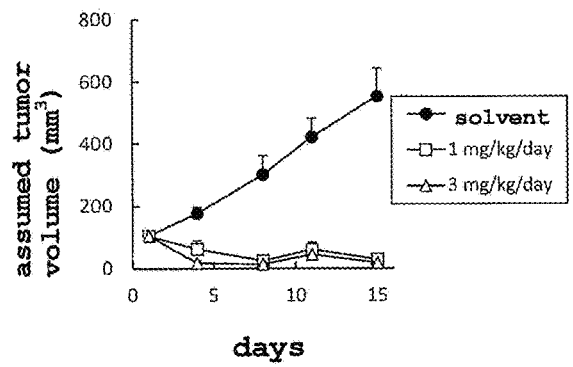

As a result, as shown in Table 5 and FIG. 2, it was demonstrated that the compound of the present invention exhibits an antitumor effect in human acute myeloid leukemia MV-4-11 cell transplanted mouse.

TABLE 5

| Example compound No. | dose (mg/kg/day) | tumor growth inhibitory rate (%) |
|---|---|---|
| 9 | 1 | 98.5* |
|  | 5 | 98.4* |
| 31 | 0.3 | 95.6* |
| 61 | 3 | 97.2* |
| 62 | 0.3 | 95.6* |
|  | 3 | 97.4* |
| 67 | 3 | 97.7* |
| 94 | 3 | 98.2* |
| 101 | 3 | 98.2* |
| 138 | 1 | 97.8* |
|  | 3 | 98.6* |
| 142 | 3 | 97.4* |
| 157 | 1 | 95.5* |
|  | 3 | 98.2* |

*P < 0.001; significant difference from solvent administration group (Dunnett's test)

Experimental Example 6

Figure 3:
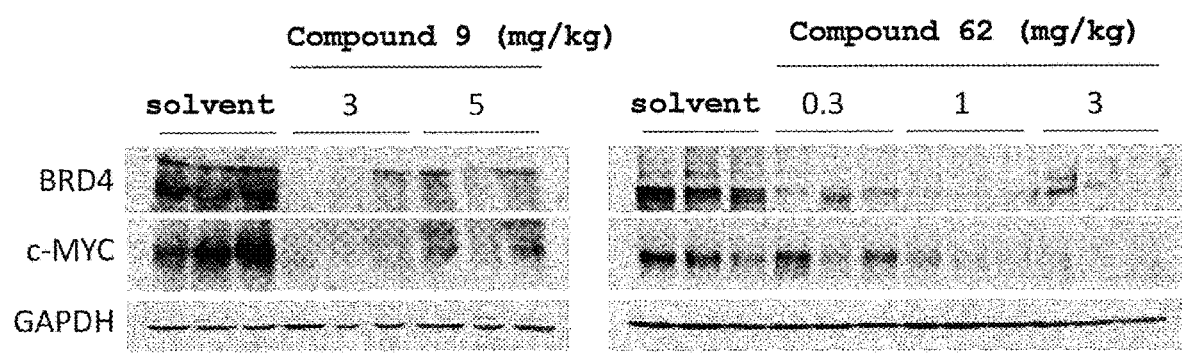
FIG. 3 shows a degrading BRD4 protein action of the compound of the present invention in human acute myeloid leukemia MV-4-11 cell transplanted tumor.

BRD4 Protein Degradation inducing Action in Human Acute Myeloid Leukemia MV-4-11 Cell Transplanted Tumor The compound of the present invention was evaluated for a BRD4 protein degradation inducing action in the tumor and an accompanying c-MYC expression suppressive action by using, as an index, variation of the expression level of BRD4 protein and c-MYC protein in the tumor after administration of the compound to the human acute myeloid leukemia MV-4-11 cell transplanted mouse. MV-4-11 cells were subcutaneously transplanted into the inguinal region of male, 6-week-old BALE/c nude mouse ($5 \times 10^6$ cells/mouse). When the assumed tumor volume reached 80-100 mm$^3$, the compound of the present invention was administered into the tail vein. The control group was administered with a solvent, 10% hydroxypropyl-β-cyclodextrin solution. At 4 hr after the administration, the tumor was isolated from the mouse and immersed in RNAlater (Thermo Fisher Scientific). The isolated tumor was lysed in a solubilizing solution (10 mM Tris-HCl, pH 7.4, 0.1% NP-40, 0.1% sodium deoxycholate, 0.1% SDS, 0.15 M NaCl, 1 mM EDTA, 10 μg/mL aprotinin). The solution was electrophoresed and proteins in acrylamide gel were transferred to Immobilon PVDF membrane using a semi-dry transfer device. After transfer, the membrane was blocked and immersed in a primary antibody (Anti-Brd4 antibody:Abcam, c-MYC Antibody:Cell Signaling Technology, GAPDH Monoclonal Antibody:Thermo Fisher Scientific) solution at 4° C. overnight. After immersing in a secondary antibody solution for 1 hr, the object protein on the membrane was detected using ECL Prime eastern Blotting Detection System or ECL Select Western Blotting Detection System (GE Healthcare). As a result, as shown in FIG. 3, the compound of the present invention induced degradation of BRD4 protein in the tumor and accompanying decrease in the c-MYC expression level.

INDUSTRIAL APPLICABILITY

The compound of the present invention can be utilized as an anticancer agent, a BET protein degradation inducer or a BET protein inhibitor.

This application is based on patent application No. 2018-127896 filed in Japan, the contents of which are encompassed in full herein.

The invention claimed is:

1. A compound represented by the following formula (I)

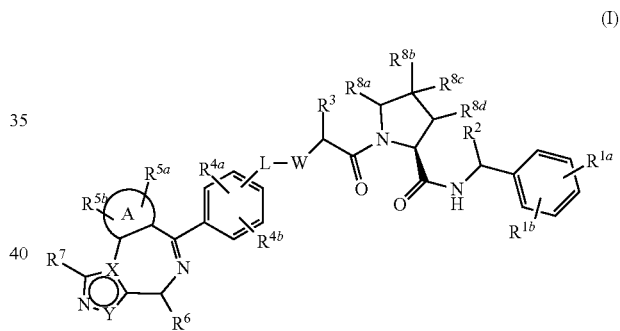

(I)

wherein

A is any of the following formula (Aa), (Ab) and (Ac)

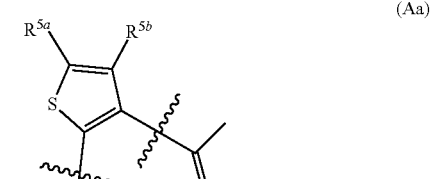

(Aa)

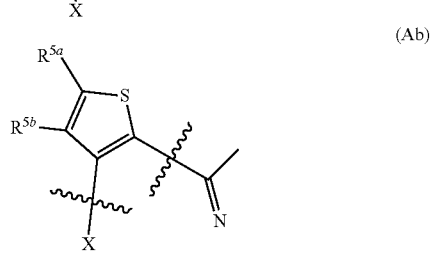

(Ab)

511

-continued

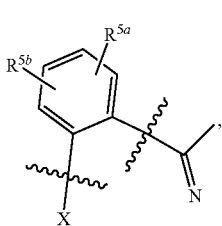

(Ac)

$R^{1a}$ and $R^{1b}$ are the same or different and each is independently
a hydrogen atom,
a halogen atom,
cyano,
hydroxy,
mercapto,
nitro,
—N($R^{11}$)($R^{12}$),
—COOH,
unsubstituted or substituted alkyl having 1-6 carbon atoms,
unsubstituted or substituted cycloalkyl having 3-6 carbon atoms,
unsubstituted or substituted alkyl having 1-6 carbon atoms-O—,
unsubstituted or substituted cycloalkyl having 3-6 carbon atoms-O—,
unsubstituted or substituted alkyl having 1-6 carbon atoms-S—,
unsubstituted or substituted cycloalkyl having 3-6 carbon atoms-S—,
unsubstituted or substituted alkyl having 1-6 carbon atoms-O-CO—,
unsubstituted or substituted cycloalkyl having 3-6 carbon atoms-O-CO—,
unsubstituted or substituted alkyl having 1-6 carbon atoms-N($R^{13}$)—CO—,
unsubstituted or substituted cycloalkyl having 3-6 carbon atoms-N($R^{13}$)—CO—,
unsubstituted or substituted alkyl having 1-6 carbon atoms-CO—N($R^{13}$)—,
unsubstituted or substituted cycloalkyl having 3-6 carbon atoms-CO—N($R^{13}$)—,
unsubstituted or substituted alkyl having 1-6 carbon atoms-N($R^{13}$)—$SO_2$—,
unsubstituted or substituted cycloalkyl having 3-6 carbon atoms-N($R^{13}$)—$SO_2$—,
unsubstituted or substituted alkyl having 1-6 carbon atoms-$SO_2$—N($R^{13}$)—,
unsubstituted or substituted cycloalkyl having 3-6 carbon atoms-$SO_2$—N($R^{13}$)—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms,
$R^2$ is
a hydrogen atom,
unsubstituted or substituted alkyl having 1-6 carbon atoms or
unsubstituted or substituted cycloalkyl having 3-6 carbon atoms,

512

$R^3$ is
a hydrogen atom,
unsubstituted or substituted alkyl having 1-6 carbon atoms,
unsubstituted or substituted cycloalkyl having 3-6 carbon atoms,
unsubstituted or substituted aryl having 6-10 carbon atoms or
unsubstituted or substituted heteroaryl having 1 to 6 hetero atoms selected from a nitrogen atom, an oxygen atom and a sulfur atom and containing 5 to 10 ring-constituting atoms,
$R^{4a}$ and $R^{4b}$ are the same or different and each is independently
a hydrogen atom,
a halogen atom,
cyano,
hydroxy,
mercapto,
nitro,
—N($R^{41}$)($R^{42}$),
—COOH,
unsubstituted or substituted alkyl having 1-6 carbon atoms,
unsubstituted or substituted cycloalkyl having 3-6 carbon atoms,
unsubstituted or substituted alkenyl having 2-6 carbon atoms,
unsubstituted or substituted alkynyl having 2-6 carbon atoms,
unsubstituted or substituted arylalkyl having 7-16 carbon atoms,
unsubstituted or substituted alkyl having 1-6 carbon atoms-O—,
unsubstituted or substituted cycloalkyl having 3-6 carbon atoms-O—,
unsubstituted or substituted alkyl having 1-6 carbon atoms-S—,
unsubstituted or substituted cycloalkyl having 3-6 carbon atoms-S—,
unsubstituted or substituted arylalkyl having 7-16 carbon atoms-O—,
unsubstituted or substituted alkyl having 1-6 carbon atoms-O-CO—,
unsubstituted or substituted cycloalkyl having 3-6 carbon atoms-O-CO—,
unsubstituted or substituted alkyl having 1-6 carbon atoms-N($R^{43}$)—CO—,
unsubstituted or substituted cycloalkyl having 3-6 carbon atoms-N($R^{43}$)—CO—,
unsubstituted or substituted alkyl having 1-6 carbon atoms-CO—N($R^{43}$)—,
unsubstituted or substituted cycloalkyl having 3-6 carbon atoms-CO—N($R^{43}$)—,
unsubstituted or substituted alkyl having 1-6 carbon atoms-N($R^{43}$)—$SO_2$—,
unsubstituted or substituted cycloalkyl having 3-6 carbon atoms-N($R^{43}$)—$SO_2$—,
unsubstituted or substituted alkyl having 1-6 carbon atoms-$SO_2$—N($R^{43}$)—,
unsubstituted or substituted cycloalkyl having 3-6 carbon atoms-$SO_2$—N($R^{43}$)—,
unsubstituted or substituted alkyl having 1-6 carbon atoms-CO-O—,
unsubstituted or substituted cycloalkyl having 3-6 carbon atoms-CO-O—,
unsubstituted or substituted alkyl having 1-6 carbon atoms-$SO_2$—, unsubstituted or substituted cycloalkyl having 3-6 carbon atoms-$SO_2$—,
unsubstituted or substituted alkyl having 1-6 carbon atoms-O—CO—N($R^{43}$)—,
unsubstituted or substituted cycloalkyl having 3-6 carbon atoms-O—CO—N($R^{43}$)—,
unsubstituted or substituted alkyl having 1-6 carbon atoms-N($R^{43}$)—CO—N($R^{44}$)—,
unsubstituted or substituted cycloalkyl having 3-6 carbon atoms-N($R^{43}$)—CO—N($R^{44}$)—,
unsubstituted or substituted alkyl having 1-6 carbon atoms-N($R^{43}$)—$SO_2$—N($R^{44}$)—,
unsubstituted or substituted cycloalkyl having 3-6 carbon atoms-N($R^{43}$)—$SO_2$—N($R^{44}$)—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, $R^{5a}$ and $R^{5b}$ are the same or different and each is independently
a hydrogen atom,
a halogen atom,
cyano,
unsubstituted or substituted alkyl having 1-6 carbon atoms,
unsubstituted or substituted cycloalkyl having 3-6 carbon atoms,
unsubstituted or substituted alkyl having 1-6 carbon atoms-O—,
unsubstituted or substituted cycloalkyl having 3-6 carbon atoms-O—,
unsubstituted or substituted aryl having 6-10 carbon atoms or
unsubstituted or substituted heteroaryl having 1 to 6 hetero atoms selected from a nitrogen atom, an oxygen atom and a sulfur atom and containing 5 to 10 ring-constituting atoms, or $R^{5a}$ and $R^{5b}$ are joined to show
—$CH_2$—$CH_2$—$CH_2$—,
—$CH_2$—$CH_2$—$CH_2$—$CH_2$- or
—$CH_2$—$CH_2$—$CH_2$—$CH_2$—$CH_2$— and form a fused ring with adjacent ring A, $R^6$ is
hydroxy,
unsubstituted or substituted alkyl having 1-6 carbon atoms,
unsubstituted or substituted cycloalkyl having 3-6 carbon atoms,
—$(CH_2)_k$—CO—$OR^{61}$,
—$(CH_2)_m$—CO—N($R^{62}$)($R^{63}$),
—$(CH_2)_n$—$R^{64}$,
—N($R^{65}$)—CO—$OR^{66}$,
—N($R^{65}$)—CO—N($R^{67}$)($R^{68}$),
—N($R^{65}$)—CO—$R^{69}$ or
—N($R^{610}$)($R^{611}$),
k, m and n are each an integer of 1-4,
$R^{62}$, $R^{63}$, $R^{67}$ and $R^{68}$ are the same or different and each is independently a hydrogen atom,
unsubstituted or substituted alkyl having 1-6 carbon atoms,
unsubstituted or substituted alkyl having 1-6 carbon atoms-O-unsubstituted or substituted alkyl having 1-6 carbon atoms,
unsubstituted or substituted cycloalkyl having 3-6 carbon atoms,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, or
$R^{62}$ and $R^{63}$ or $R^{67}$ and $R^{68}$ show, together with the adjacent nitrogen atom, the following formula

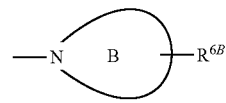

wherein ring B is an aziridine ring, an azetidine ring, a pyrrolidine ring, a piperidine ring or a morpholine ring, $R^{6B}$ is a hydrogen atom, a halogen atom, cyano, hydroxy, unsubstituted or substituted alkyl having 1-6 carbon atoms or unsubstituted or substituted alkyl having 1-6 carbon atoms-O—, $R^{64}$ is
unsubstituted or substituted aryl having 6-10 carbon atoms or
unsubstituted or substituted heteroaryl having 1 to 6 hetero atoms selected from a nitrogen atom, an oxygen atom and a sulfur atom and containing 5 to 10 ring-constituting atoms, $R^7$ is
a hydrogen atom,
unsubstituted or substituted alkyl having 1-6 carbon atoms or
unsubstituted or substituted cycloalkyl having 3-6 carbon atoms, $R^{8a}$ is
a hydrogen atom or
unsubstituted or substituted alkyl having 1-3 carbon atoms, $R^{8b}$, $R^{8c}$ and $R^{8d}$ are the same or different and each is independently
a hydrogen atom,
a halogen atom,
hydroxy,
amino,
unsubstituted or substituted alkyl having 1-3 carbon atoms or
unsubstituted or substituted alkyl having 1-3 carbon atoms-O—, L is absent or a group obtained by freely selecting and combining 1-50 from
—C($R^{L1}$)($R^{L2}$)—,
—C($R^{L3}$)=C($R^{L4}$)—,
—C≡C—,
—O—,
—S—,
—N($R^{L5}$)—,
—SO—,
—$SO_2$—,
—CO-O—,
—CO—N($R^{L6}$)—, —$SO_2$—$N(R^{L6})$—,
—$N(R^{L6})$—CO—O—,
—$N(R^{L6})$—CO—$N(R^{L7})$—,
—$N(R^{L6})$—$SO_2$—$N(R^{L7})$—,
—$N(R^{L6})$—C(=N—CN)—$N(R^{L7})$—,
—$N(R^{L6})$—C(=CH—$NO_2$)—$N(R^{L7})$—, and

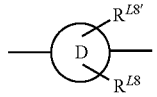

the number of ring D is 5 at maximum, and all or one part of L does not show —O—O—, —S—S—, —$N(R^{L5})$—$N(R^{L5})$—, —O—S—, —S—O—, —O—$N(R^{L5})$—, —$N(R^{L5})$—O—, —S—$N(R^{L5})$— or —$N(R^{L5})$—S—, ring D is
cycloalkane having 3-6 carbon atoms,
optionally partially reduced aromatic hydrocarbon having 6-10 carbon atoms,
a hetero ring having 1-6 hetero atoms selected from a nitrogen atom, an oxygen atom and a sulfur atom and containing 3 to 10 ring-constituting atoms,
a bicyclo ring having 4-12 carbon atoms,
a bicyclohetero ring having 1-6 hetero atoms selected from a nitrogen atom, an oxygen atom and a sulfur atom and containing 4 to 12 ring-constituting atoms,
a spiro ring having 6-12 carbon atoms, or
a spirohetero ring having 1-6 hetero atoms selected from a nitrogen atom, an oxygen atom and a sulfur atom and containing 6 to 12 ring-constituting atoms, $R^{L1}$, $R^{L2}$, $R^{L8}$ and $R^{L8'}$ are the same or different and each is independently
a hydrogen atom,
a halogen atom,
cyano,
hydroxy,
mercapto,
nitro,
—$N(R^{La})(R^{Lb})$,
—COOH,
oxo, provided that when $R^{L1}$ is oxo, then $R^{L2}$ is absent,
thioxo, provided that when $R^{L1}$ is thioxo, then $R^{L2}$ is absent,
unsubstituted or substituted alkyl having 1-6 carbon atoms,
unsubstituted or substituted cycloalkyl having 3-6 carbon atoms,
unsubstituted or substituted alkenyl having 2-6 carbon atoms,
unsubstituted or substituted alkynyl having 2-6 carbon atoms,
unsubstituted or substituted arylalkyl having 7-16 carbon atoms,
unsubstituted or substituted alkyl having 1-6 carbon atoms-O—,
unsubstituted or substituted cycloalkyl having 3-6 carbon atoms-O—,
unsubstituted or substituted alkyl having 1-6 carbon atoms-S—,
unsubstituted or substituted cycloalkyl having 3-6 carbon atoms-S—,
unsubstituted or substituted arylalkyl having 7-16 carbon atoms-O—,
unsubstituted or substituted alkyl having 1-6 carbon atoms-O-CO—,
unsubstituted or substituted cycloalkyl having 3-6 carbon atoms-O-CO—,
unsubstituted or substituted alkyl having 1-6 carbon atoms-$N(R^{Lc})$—CO—,
unsubstituted or substituted cycloalkyl having 3-6 carbon atoms-$N(R^{Lc})$—CO—,
unsubstituted or substituted alkyl having 1-6 carbon atoms-CO—$N(R^{Lc})$—,
unsubstituted or substituted cycloalkyl having 3-6 carbon atoms-CO—$N(R^{Lc})$—,
unsubstituted or substituted alkyl having 1-6 carbon atoms-$N(R^{Lc})$—$SO_2$—,
unsubstituted or substituted cycloalkyl having 3-6 carbon atoms-$N(R^{Lc})$—$SO_2$—,
unsubstituted or substituted alkyl having 1-6 carbon atoms-$SO_2$—$N(R^{Lc})$—,
unsubstituted or substituted cycloalkyl having 3-6 carbon atoms-$SO_2$—$N(R^{Lc})$—,
unsubstituted or substituted alkyl having 1-6 carbon atoms-CO-O—,
unsubstituted or substituted cycloalkyl having 3-6 carbon atoms-CO-O—,
unsubstituted or substituted alkyl having 1-6 carbon atoms-$SO_2$—,
unsubstituted or substituted cycloalkyl having 3-6 carbon atoms-$SO_2$—,
unsubstituted or substituted alkyl having 1-6 carbon atoms-O—CO—$N(R^{Lc})$—,
unsubstituted or substituted cycloalkyl having 3-6 carbon atoms-O—CO—$N(R^{Lc})$—,
unsubstituted or substituted alkyl having 1-6 carbon atoms-$N(R^{Lc})$—CO—$N(R^{Ld})$—,
unsubstituted or substituted cycloalkyl having 3-6 carbon atoms-$N(R^{Lc})$—CO—$N(R^{Ld})$—,
unsubstituted or substituted alkyl having 1-6 carbon atoms-$N(R^{Lc})$—$SO_2$—$N(R^{Ld})$—,
unsubstituted or substituted cycloalkyl having 3-6 carbon atoms-$N(R^{Lc})$—$SO_2$—$N(R^{Ld})$—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, and further, $R^{L1}$ and $R^{L2}$ are optionally joined to show
—$CH_2$—$CH_2$—, —$CH_2$—$CH_2$—$CH_2$—, —$CH_2$—$CH_2$—$CH_2$—$CH_2$— or —$CH_2$—$CH_2$—$CH_2$—$CH_2$—$CH_2$—, $R^{L3}$ and $R^{L4}$ are the same or different and each is independently
a hydrogen atom,
a halogen atom
cyano,
—COOH,
unsubstituted or substituted alkyl having 1-6 carbon atoms,
unsubstituted or substituted cycloalkyl having 3-6 carbon atoms,
unsubstituted or substituted alkenyl having 2-6 carbon atoms,
unsubstituted or substituted arylalkyl having 7-16 carbon atoms,
unsubstituted or substituted alkyl having 1-6 carbon atoms-O-CO—, unsubstituted or substituted cycloalkyl having 3-6 carbon atoms-O-CO—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, $R^{L5}$ is
a hydrogen atom,
unsubstituted or substituted alkyl having 1-6 carbon atoms,
unsubstituted or substituted cycloalkyl having 3-6 carbon atoms,
unsubstituted or substituted arylalkyl having 7-16 carbon atoms,
unsubstituted or substituted alkyl having 1-6 carbon atoms-O-CO—,
unsubstituted or substituted cycloalkyl having 3-6 carbon atoms-O-CO—,
unsubstituted or substituted alkyl having 1-6 carbon atoms-N($R^{Lc}$)—CO—,
unsubstituted or substituted cycloalkyl having 3-6 carbon atoms-N($R^{Lc}$)—CO—,
unsubstituted or substituted alkyl having 1-6 carbon atoms-N($R^{Lc}$)—SO$_2$—,
unsubstituted or substituted cycloalkyl having 3-6 carbon atoms-N($R^{Lc}$)—SO$_2$—,
unsubstituted or substituted alkyl having 1-6 carbon atoms-SO$_2$—,
unsubstituted or substituted cycloalkyl having 3-6 carbon atoms-SO$_2$—,
unsubstituted or substituted alkyl having 1-6 carbon atoms-CO—,
unsubstituted or substituted cycloalkyl having 3-6 carbon atoms-CO—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, W is any of the following formula (Wa), (Wb), (Wc), (Wd) and (We)

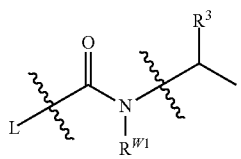
(Wa)

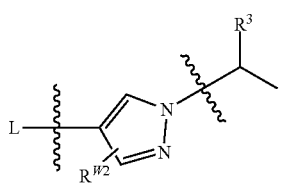
(Wb)

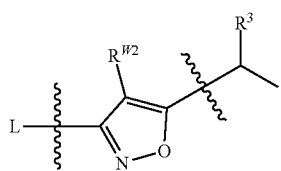
(Wc)

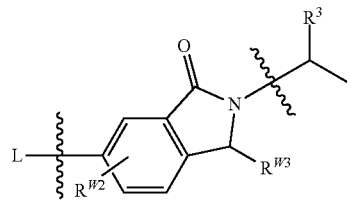
(Wd)

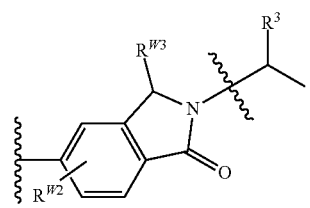
(We)

X and Y are:
X is a nitrogen atom and Y is a nitrogen atom, or X is a carbon atom and Y is an oxygen atom, $R^{W2}$ is
a hydrogen atom,
a halogen atom,
cyano,
hydroxy,
unsubstituted or substituted alkyl having 1-6 carbon atoms,
unsubstituted or substituted cycloalkyl having 3-6 carbon atoms,
unsubstituted or substituted alkyl having 1-6 carbon atoms-O— or
unsubstituted or substituted cycloalkyl having 3-6 carbon atoms-O—, $R^{11}$, $R^{12}$, $R^{13}$, $R^{41}$, $R^{42}$, $R^{43}$, $R^{44}$, $R^{61}$, $R^{65}$, $R^{66}$, $R^{610}$, $R^{611}$, $R^{L6}$, $R^{L7}$, $R^{La}$, $R^{Lb}$, $R^{Lc}$, $R^{Ld}$, $R^{W1}$ and $R^{W3}$ are the same or different and each is independently
a hydrogen atom,
unsubstituted or substituted alkyl having 1-6 carbon atoms or
unsubstituted or substituted cycloalkyl having 3-6 carbon atoms, $R^{69}$ is
unsubstituted or substituted alkyl having 1-6 carbon atoms or
unsubstituted or substituted cycloalkyl having 3-6 carbon atoms, when alkyl having 1-6 carbon atoms, cycloalkyl having 3-6 carbon atoms, alkenyl having 2-6 carbon atoms and alkynyl having 2-6 carbon atoms are substituted, they are substituted by one or two or more groups selected from a halogen atom, cyano, hydroxy and alkyl having 1-6 carbon atoms-O—, when aryl having 6-10 carbon atoms; a heterocyclic group having 1 to 6 hetero atoms selected from a nitrogen atom, an oxygen atom and a sulfur atom and containing 3 to 10 ring-constituting atoms; heteroaryl having 1 to 6 hetero atoms selected from a nitrogen atom, an oxygen atom and a sulfur atom and containing 5 to 10 ring-constituting atoms; and arylalkyl having 7-16 carbon atoms are substituted, they are substituted by one or two or more groups selected from a halogen atom, cyano, hydroxy, alkyl having 1-6 carbon atoms, cycloalkyl having 3-6 carbon atoms, alkyl having 1-6 carbon atoms-O- and cycloalkyl having 3-6 carbon atoms-O—, or a pharmacologically acceptable salt thereof.

2. The compound according to claim 1, wherein $R^{L1}$, $R^{L2}$, $R^{L8}$ and $R^{L8'}$ are the same or different and each is independently
a hydrogen atom,
a halogen atom,
cyano,
hydroxy,
mercapto,
nitro,
$N(R^{La})(R^{Lb})$,
—COOH,
oxo, provided that when $R^{L1}$ is oxo, then $R^{L2}$ is absent,
thioxo, provided that when $R^{L1}$ is thioxo, then $R^{L2}$ is absent,
unsubstituted or substituted alkyl having 1-6 carbon atoms,
unsubstituted or substituted cycloalkyl having 3-6 carbon atoms,
unsubstituted or substituted alkenyl having 2-6 carbon atoms,
unsubstituted or substituted alkynyl having 2-6 carbon atoms,
unsubstituted or substituted arylalkyl having 7-16 carbon atoms,
unsubstituted or substituted alkyl having 1-6 carbon atoms-O—,
unsubstituted or substituted cycloalkyl having 3-6 carbon atoms-O—,
unsubstituted or substituted alkyl having 1-6 carbon atoms-S—,
unsubstituted or substituted cycloalkyl having 3-6 carbon atoms-S—,
unsubstituted or substituted arylalkyl having 7-16 carbon atoms-O—,
unsubstituted or substituted alkyl having 1-6 carbon atoms-O-CO—,
unsubstituted or substituted cycloalkyl having 3-6 carbon atoms-O-CO—,
unsubstituted or substituted alkyl having 1-6 carbon atoms-N($R^{Lc}$)—CO—,
unsubstituted or substituted cycloalkyl having 3-6 carbon atoms-N($R^{Lc}$)—CO—,
unsubstituted or substituted alkyl having 1-6 carbon atoms-CO—N($R^{Lc}$)—,
unsubstituted or substituted cycloalkyl having 3-6 carbon atoms-CO—N($R^{Lc}$)—,
unsubstituted or substituted alkyl having 1-6 carbon atoms-N($R^{Lc}$)—SO$_2$—,
unsubstituted or substituted cycloalkyl having 3-6 carbon atoms-N($R^{Lc}$)—SO$_2$—,
unsubstituted or substituted alkyl having 1-6 carbon atoms-SO$_2$—N($R^{Lc}$)—,
unsubstituted or substituted cycloalkyl having 3-6 carbon atoms-SO$_2$—N($R^{Lc}$)—,
unsubstituted or substituted alkyl having 1-6 carbon atoms-CO-O—,
unsubstituted or substituted cycloalkyl having 3-6 carbon atoms-CO-O—,
unsubstituted or substituted alkyl having 1-6 carbon atoms-SO$_2$—,
unsubstituted or substituted cycloalkyl having 3-6 carbon atoms-SO$_2$—,
unsubstituted or substituted alkyl having 1-6 carbon atoms-O—CO—N($R^{Lc}$)—,
unsubstituted or substituted cycloalkyl having 3-6 carbon atoms-O—CO—N($R^{Lc}$)—,
unsubstituted or substituted alkyl having 1-6 carbon atoms-N($R^{Lc}$)—CO—N($R^{Ld}$)—,
unsubstituted or substituted cycloalkyl having 3-6 carbon atoms-N($R^{Lc}$)—CO—N($R^{Ld}$)—,
unsubstituted or substituted alkyl having 1-6 carbon atoms-N($R^{Lc}$)—SO$_2$—N($R^{Ld}$)—,
unsubstituted or substituted cycloalkyl having 3-6 carbon atoms-N($R^{Lc}$)—SO$_2$—N($R^{Ld}$)—,
unsubstituted or substituted aryl having 6-10 carbon atoms or
an unsubstituted or substituted heterocyclic group having 1 to 6 hetero atoms selected from a nitrogen atom, an oxygen atom and a sulfur atom and containing 3 to 10 ring-constituting atoms, or a pharmacologically acceptable salt thereof.

3. The compound according to claim 1, wherein A is

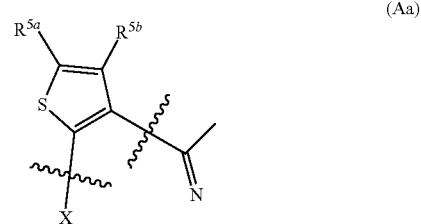

(Aa)

or a pharmacologically acceptable salt thereof.

4. The compound according to claim 1, wherein X and Y are nitrogen atoms, or a pharmacologically acceptable salt thereof.

5. The compound according to claim 1, wherein W is

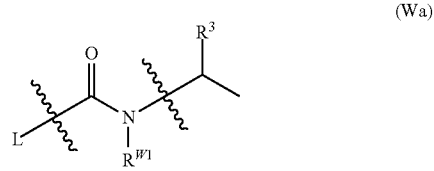

(Wa)

or a pharmacologically acceptable salt thereof.

6. The compound according to claim 1, wherein L is

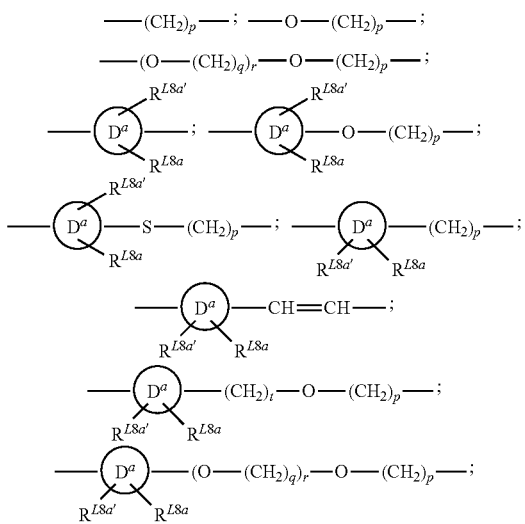

-continued

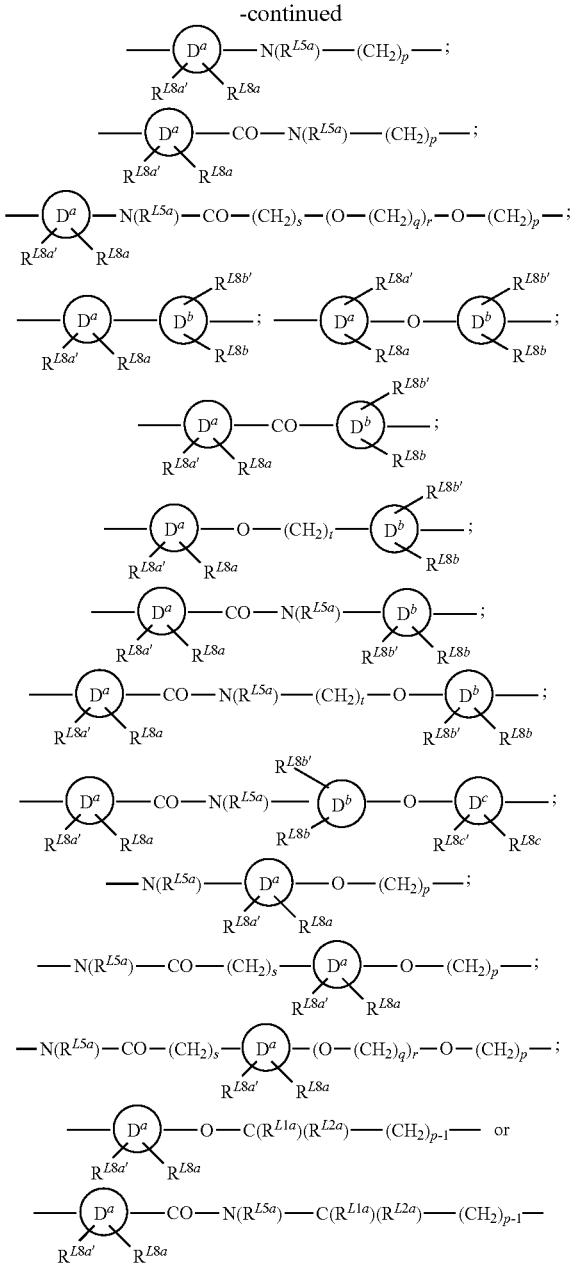

wherein
p and t are each an integer of 1-6,
q and s are each an integer of 1-4,
r is an integer of 1-7,
ring $D^a$, ring $D^b$ and ring $D^c$ are the same or different and each is independently cycloalkane having 3-6 carbon atoms, benzene, naphthalene, dihydronaphthalene, tetrahydronaphthalene, azetidine, pyrrole, dihydropyrrole, pyrrolidine, furan, dihydrofuran, tetrahydrofuran, thiophene, dihydrothiophene, tetrahydrothiophene, pyridine, dihydropyridine, tetrahydropyridine, piperidine, pyran, dihydropyran, tetrahydropyran, thiopyran, dihydrothiopyran, tetrahydrothiopyran, pyrazole, dihydropyrazole, tetrahydropyrazole, imidazole, dihydroimidazole, tetrahydroimidazole, isoxazole, dihydroisoxazole, tetrahydroisoxazole, oxazole, dihydrooxazole, tetrahydrooxazole, isothiazole, dihydroisothiazole, tetrahydroisothiazole, thiazole, dihydrothiazole, tetrahydrothiazole, pyridazine, dihydropyridazine, tetrahydropyridazine, hexahydropyridazine, pyrimidine, dihydropyrimidine, tetrahydropyrimidine, hexahydropyrimidine, pyrazine, dihydropyrazine, tetrahydropyrazine, piperazine, oxazine, dihydrooxazine, tetrahydrooxazine, thiazine, dihydrothiazine, tetrahydrothiazine, benzopyrrole, dihydrobenzopyrrole, benzopyrrolidine, benzofuran, dihydrobenzofuran, benzothiophene, dihydrobenzothiophene, benzopyridine, dihydrobenzopyridine, benzopiperidine, benzopyran, dihydrobenzopyran, benzothiopyran, dihydrobenzothiopyran, benzopyrazole, dihydrobenzopyrazole, benzimidazole, dihydrobenzimidazole, benzisoxazole, dihydrobenzisoxazole, benzoxazole, dihydrobenzoxazole, benzisothiazole, dihydrobenzisothiazole, benzothiazole, dihydrobenzothiazole, benzopyridazine, dihydrobenzopyridazine, tetrahydrobenzopyridazine, benzopyrimidine, dihydrobenzopyrimidine, tetrahydrobenzopyrimidine, benzopyrazine, dihydrobenzopyrazine, benzopiperazine, benzoxazine, dihydrobenzoxazine, benzothiazine, dihydrobenzothiazine or a bicyclo ring having 4-12 carbon atoms, $R^{L1a}$ is unsubstituted or substituted alkyl having 1-6 carbon atoms or a halogen atom, $R^{L2a}$ is a hydrogen atom, unsubstituted or substituted alkyl having 1-6 carbon atoms or a halogen atom, $R^{L5a}$ is a hydrogen atom or unsubstituted or substituted alkyl having 1-6 carbon atoms, $R^{L8a}$, $R^{L8a'}$, $R^{L8b}$, $R^{L8b'}$, $R^{L8c}$ and $R^{L8c'}$ are the same or different and each is independently a hydrogen atom, a halogen atom, cyano, oxo, unsubstituted or substituted alkyl having 1-6 carbon atoms or unsubstituted or substituted alkyl having 1-6 carbon atoms-O—, or a pharmacologically acceptable salt thereof.

7. The compound according to claim 1, wherein L is

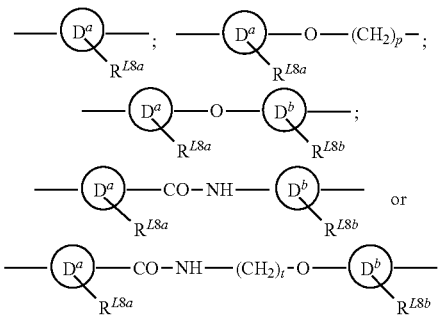

wherein
p and t are each an integer of 1-6,
ring $D^a$ and ring $D^b$ are the same or different and each is independently benzene, pyrrolidine, benzofuran, benzoxazole or benzothiazole,
$R^{L8a}$ and $R^{L8b}$ are the same or different and each is independently a hydrogen atom, a halogen atom or cyano,
or a pharmacologically acceptable salt thereof.

8. The compound according to claim 1, wherein $R^{1a}$ is unsubstituted or substituted heteroaryl having 1 to 6 hetero atoms selected from a nitrogen atom, an oxygen atom and a sulfur atom and containing 5 to 10 ring-constituting atoms, or a pharmacologically acceptable salt thereof.

9. The compound according to claim 1, wherein $R^{1b}$ is a hydrogen atom, or a pharmacologically acceptable salt thereof.

10. The compound according to claim 1, wherein $R^2$ is a hydrogen atom or unsubstituted or substituted alkyl having 1-6 carbon atoms, or a pharmacologically acceptable salt thereof.

11. The compound according to claim 1, wherein $R^3$ is unsubstituted or substituted alkyl having 1-6 carbon atoms, or a pharmacologically acceptable salt thereof.

12. The compound according to claim 1, wherein $R^{4a}$ and $R^{4b}$ are each a hydrogen atom, or a pharmacologically acceptable salt thereof.

13. The compound according to claim 1, wherein $R^{5a}$ and $R^{5b}$ are the same or different and each is independently unsubstituted or substituted alkyl having 1-6 carbon atoms, or a pharmacologically acceptable salt thereof.

14. The compound according to claim 1, wherein $R^6$ is —$(CH_2)_k$—CO—$OR^{61}$, or a pharmacologically acceptable salt thereof.

15. The compound according to claim 1, wherein $R^7$ is unsubstituted or substituted alkyl having 1-6 carbon atoms, or a pharmacologically acceptable salt thereof.

16. The compound according to claim 1, wherein $R^{8a}$, $R^{8c}$ and $R^{8d}$ are each a hydrogen atom, or a pharmacologically acceptable salt thereof.

17. The compound according to claim 1, wherein $R^{8b}$ is hydroxy, or a pharmacologically acceptable salt thereof.

18. Methyl [(6S)-4-{3'-cyano-4'-[2-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{4'-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}amino)-2-oxoethoxy][1,1'-biphenyl]-4-yl}-2,3,9-trimethyl-6H-thieno[3,2-f][1,2,4]triazolo[4,3-a][1,4] diazepin-6-yl] acetate, methyl {(6S)-4-[2'-fluoro-4'-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl) [1,1'-biphenyl]-4-yl]-2,3,9-trimethyl-6H-thieno[3,2-f][1,2,4]triazolo[4,3-a][1,4] diazepin-6-yl}acetate, methyl [(6S)-4-(4-{(3R)-3-[(2-{[2-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-1-benzofuran-5-yl] oxy}ethyl)carbamoyl]pyrrolidin-1-yl}phenyl)-2,3,9-trimethyl-6H-thieno[3,2-f][1,2,4]triazolo[4,3-a][1,4] diazepin-6-yl] acetate, methyl {(6S)-4-[3'-fluoro-4'-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl) [1,1'-biphenyl]-4-yl]-2,3,9-trimethyl-6H-thieno[3,2-f][1,2,4]triazolo[4,3-a][1,4]diazepin-6-yl}acetate, methyl [(6S)-4-{4-[(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl)-1,3-benzoxazol-5-yl]phenyl}-2,3,9-trimethyl-6H-thieno[3,2-f][1,2,4]triazolo[4,3-a][1,4]diazepin-6-yl]acetate, methyl [(6S)-4-{4-[(3S)-3-{[2-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-1-benzofuran-5-yl]carbamoyl}pyrrolidin-1-yl]phenyl]-2,3,9-trimethyl-6H-thieno[3,2-f][1,2,4]triazolo[4,3-a][1,4]diazepin-6-yl]acetate, methyl [(6S)-4-{4-[(3R)-3-{[2-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-1-benzofuran-5-yl] oxy}pyrrolidin-1-yl]phenyl]-2,3,9-trimethyl-6H-thieno[3,2-f][1,2,4]triazolo[4,3-a][1,4]diazepin-6-yl] acetate, methyl {(6S)-4-[3'-chloro-4'-({(2S)-1-[(2S,4R)-4-hydroxy-2-({(1S)-1-[4-(4-methyl-1,3-thiazol-5-yl)phenyl]ethyl}carbamoyl)pyrrolidin-1-yl]-3,3-dimethyl-1-oxobutan-2-yl}carbamoyl) [1,1'-biphenyl]-4-yl]-2,3,9-trimethyl-6H-thieno[3,2-f][1,2,4]triazolo[4,3-a][1,4] diazepin-6-yl}acetate, methyl [(6S)-4-{4-[7-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-3,4-dihydroisoquinolin-2 (1H)-yl]phenyl]-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-1-benzofuran-6-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl}carbamoyl)-1,3-benzoxazol-5-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-1,3-benzothiazol-5-yl]phenyl}-2,3,9-trimethyl-6H-thieno[3,2-f][1,2,4]triazolo[4,3-a][1,4]diazepin-6-yl]acetate, methyl [(6S)-4-{4-[2-({(2S)-1-[(2S,4R)-4-hydroxy-2-({(1S)-1-[4-(4-methyl-1,3-thiazol-5-yl)phenyl] ethyl}carbamoyl)pyrrolidin-1-yl]-3,3-dimethyl-1-oxobutan-2-yl}carbamoyl)-1,3-benzoxazol-6-yl]phenyl}-2,3,9-trimethyl-6H-thieno[3,2-f][1,2,4]triazolo[4,3-a][1,4]diazepin-6-yl]acetate or (2S,4R)-1-{(2S)-3,3-dimethyl-2-[(3-{4-[(6S)-2,3,6,9-tetramethyl-6H-thieno[3,2-f][1,2,4]triazolo[4,3-a][1,4]diazepin-4-yl]phenyl}prop-2-ynoyl)amino]butanoyl}-4-hydroxy-N-{(1S)-1-[4-(4-methyl-1,3-thiazol-5-yl)phenyl]ethyl}pyrrolidine-2-carboxamide, or a pharmacologically acceptable salt thereof.

19. A pharmaceutical composition comprising the compound according to claim 1 or a pharmacologically acceptable salt thereof and a pharmaceutically acceptable additive.

20. A method for treating cancer comprising administering an effective amount of the compound according to claim 1 or a pharmacologically acceptable salt thereof to a subject in need thereof, thereby treating cancer in the subject, wherein the cancer is gastric cancer, ovarian cancer, lung cancer, liver cancer, urothelial cancer, testicular cancer, skin cancer, prostate cancer, breast cancer, colorectal cancer, or leukemia.

21. A method for treating cancer comprising administering an effective amount of the compound according to claim 1 or a pharmacologically acceptable salt thereof to a subject in need thereof, thereby treating cancer in the subject, wherein the cancer is acute myeloid leukemia, chronic myeloid leukemia, multiple myeloma, diffuse large B-cell lymphoma, adult T-cell leukemia/lymphoma, Burkitt lymphoma, bladder cancer, uterine sarcoma, glioma, or pancreatic cancer.

22. A method for degrading BET protein comprising administering an effective amount of the compound according to claim 1 or a pharmacologically acceptable salt thereof to a subject in need thereof, thereby degrading BET protein in the subject.

23. A method for degrading BRD4 protein comprising administering an effective amount of the compound according to claim 1 or a pharmacologically acceptable salt thereof to a subject in need thereof, thereby degrading BRD4 protein in the subject.

24. A method of inhibiting BET protein comprising administering an effective amount of the compound according to claim 1 or a pharmacologically acceptable salt thereof to a subject in need thereof, thereby inhibiting BET protein in the subject.

25. A method of inhibiting BRD4 protein comprising administering an effective amount of the compound according to claim 1 or a pharmacologically acceptable salt thereof to a subject in need thereof, thereby inhibiting BET protein in the subject.

* * * * *